US011028181B2

(12) United States Patent
Eavarone et al.

(10) Patent No.: US 11,028,181 B2
(45) Date of Patent: Jun. 8, 2021

(54) GLYCAN-INTERACTING COMPOUNDS AND METHODS OF USE

(71) Applicant: Seagen Inc., Bothell, WA (US)

(72) Inventors: David A. Eavarone, North Quincy, MA (US); Jillian M. Prendergast, Maynard, MA (US); Jeffrey Behrens, Newton, MA (US)

(73) Assignee: Seagen Inc., Bothell, WA (US)

( * ) Notice: Subject to any disclaimer, the term of this patent is extended or adjusted under 35 U.S.C. 154(b) by 253 days.

(21) Appl. No.: 15/775,410

(22) PCT Filed: Nov. 10, 2016

(86) PCT No.: PCT/US2016/061427
§ 371 (c)(1),
(2) Date: May 11, 2018

(87) PCT Pub. No.: WO2017/083582
PCT Pub. Date: May 18, 2017

(65) Prior Publication Data
US 2018/0327509 A1 Nov. 15, 2018

Related U.S. Application Data

(60) Provisional application No. 62/254,278, filed on Nov. 12, 2015, provisional application No. 62/274,572, filed on Jan. 4, 2016, provisional application No. 62/287,666, filed on Jan. 27, 2016, provisional application No. 62/293,989, filed on Feb. 11, 2016, provisional application No. 62/345,515, filed on Jun. 3, 2016, provisional application No. 62/382,835, filed on Sep. 2, 2016.

(51) Int. Cl.
C07K 16/30 (2006.01)
A61K 47/68 (2017.01)
A61K 39/00 (2006.01)

(52) U.S. Cl.
CPC ...... *C07K 16/3084* (2013.01); *A61K 47/6803* (2017.08); *A61K 47/6817* (2017.08); *A61K 47/6851* (2017.08); *C07K 16/3092* (2013.01); *A61K 2039/505* (2013.01); *A61K 2039/572* (2013.01); *C07K 2317/24* (2013.01); *C07K 2317/33* (2013.01); *C07K 2317/56* (2013.01); *C07K 2317/565* (2013.01); *C07K 2317/567* (2013.01); *C07K 2317/73* (2013.01); *C07K 2317/77* (2013.01); *C07K 2317/92* (2013.01)

(58) Field of Classification Search
CPC ........ A61K 2039/505; A61K 2039/572; A61K 47/6803; A61K 47/6817; A61K 47/6851; C07K 16/3084; C07K 16/309; C07K 2317/24; C07K 2317/33; C07K 2317/56; C07K 2317/565; C07K 2317/567
See application file for complete search history.

(56) References Cited

U.S. PATENT DOCUMENTS

| | | |
|---|---|---|
| 4,179,337 A | 12/1979 | Davis |
| 4,301,144 A | 11/1981 | Iwashita |
| 4,444,887 A | 4/1984 | Hoffmann |
| 4,474,893 A | 10/1984 | Reading |
| 4,485,045 A | 11/1984 | Regen |
| 4,496,689 A | 1/1985 | Mitra |
| 4,544,545 A | 10/1985 | Ryan |
| 4,640,835 A | 2/1987 | Shimizu |
| 4,670,417 A | 6/1987 | Iwasaki |
| 4,695,198 A | 9/1987 | Goodacre |
| 4,714,681 A | 12/1987 | Reading |
| 4,716,111 A | 12/1987 | Osband |
| 4,791,192 A | 12/1988 | Nakagawa |
| 4,816,397 A | 3/1989 | Boss |
| 4,816,567 A | 3/1989 | Cabilly |
| 4,900,727 A | 2/1990 | Kattige |
| 4,925,648 A | 5/1990 | Hansen |
| 4,946,778 A | 8/1990 | Ladner |
| 4,965,198 A | 10/1990 | Yamasaki |
| 4,975,369 A | 12/1990 | Beavers |
| 4,978,745 A | 12/1990 | Schoemaker |
| 5,013,556 A | 5/1991 | Woodle |
| 5,045,532 A | 9/1991 | Della Valle |
| 5,059,680 A | 10/1991 | Davis |
| 5,091,513 A | 2/1992 | Huston |
| 5,158,886 A | 10/1992 | Kawamura |

(Continued)

FOREIGN PATENT DOCUMENTS

| | | |
|---|---|---|
| EP | 0239400 | 4/1989 |
| EP | 0316818 | 5/1989 |

(Continued)

OTHER PUBLICATIONS

Reichert & Valge-Archer, Nat. Rev. Drug Disc,. 6:349-356 (Year: 2007).*
Eavarone et al., PLoS ONE 13(7):e0201314 (Year: 2018).*
Ishida, A. et al., 2008.Mucin-induced apoptosis of monocyte-derived dendritic cells during maturation Proteomics. 8: 3342-9.
Itzkowitz, S.H. et al., Sialosyl-Tn. A novel mucin antigen associated with prognosis in colorectal cancer patients. Cancer. Nov. 1, 1990;66(9):1960-6.
Jandus, C. et al., 2014. Interactions between Siglec-7/9 receptors and ligands influence NK cell-dependent tumor Immunosurveillance. JCI. pii: 65899.

(Continued)

*Primary Examiner* — Jessica H Roark
(74) *Attorney, Agent, or Firm* — McNeill Baur PLLC

(57) ABSTRACT

The present invention provides glycan-interacting antibodies and methods for producing glycan-interacting antibodies useful in the treatment and prevention of human disease, including cancer. Such glycan-interacting antibodies include humanized antibodies, derivatives and fragments thereof as well as related compositions and kits. Methods of using glycan-interacting antibodies for treatment and diagnosis are included.

93 Claims, 5 Drawing Sheets

Specification includes a Sequence Listing.

(56) References Cited

U.S. PATENT DOCUMENTS

| | | | |
|---|---|---|---|
| 5,208,020 | A | 5/1993 | Chari |
| 5,225,539 | A | 7/1993 | Winter |
| 5,258,498 | A | 11/1993 | Huston |
| 5,403,484 | A | 4/1995 | Ladner |
| 5,413,923 | A | 5/1995 | Kucherlapati |
| 5,427,908 | A | 6/1995 | Dower |
| 5,475,092 | A | 12/1995 | Chari |
| 5,516,637 | A | 5/1996 | Huang |
| 5,530,101 | A | 6/1996 | Queen |
| 5,565,332 | A | 10/1996 | Hoogenboom |
| 5,571,698 | A | 11/1996 | Ladner |
| 5,573,920 | A | 11/1996 | Randle |
| 5,580,717 | A | 12/1996 | Dower |
| 5,585,089 | A | 12/1996 | Queen |
| 5,585,499 | A | 12/1996 | Chari |
| 5,601,819 | A | 2/1997 | Wong |
| 5,625,126 | A | 4/1997 | Lonberg |
| 5,633,425 | A | 5/1997 | Lonberg |
| 5,658,727 | A | 8/1997 | Barbas |
| 5,693,761 | A | 12/1997 | Queen |
| 5,693,762 | A | 12/1997 | Queen |
| 5,698,426 | A | 12/1997 | Huse |
| 5,710,038 | A | 1/1998 | Mes-Masson |
| 5,733,743 | A | 3/1998 | Johnson |
| 5,733,920 | A | 3/1998 | Mansuri |
| 5,750,753 | A | 5/1998 | Kimae |
| 5,780,225 | A | 7/1998 | Wigler |
| 5,786,464 | A | 7/1998 | Seed |
| 5,807,715 | A | 9/1998 | Morrison |
| 5,811,510 | A | 9/1998 | Papisov |
| 5,821,047 | A | 10/1998 | Garrard |
| 5,846,545 | A | 12/1998 | Chari |
| 5,849,733 | A | 12/1998 | Kim |
| 5,863,990 | A | 1/1999 | Papisov |
| 5,902,725 | A | 5/1999 | Robbins |
| 5,919,652 | A | 7/1999 | Pang |
| 5,932,448 | A | 8/1999 | Tso |
| 5,939,598 | A | 8/1999 | Kucherlapati |
| 5,951,983 | A | 9/1999 | Bazin |
| 5,958,398 | A | 9/1999 | Papisov |
| 5,969,108 | A | 10/1999 | McCafferty |
| 6,075,181 | A | 6/2000 | Kucherlapati |
| 6,114,148 | A | 9/2000 | Seed |
| 6,114,598 | A | 9/2000 | Kucherlapati |
| 6,180,370 | B1 | 1/2001 | Queen |
| 6,300,129 | B1 | 10/2001 | Lonberg |
| 6,348,584 | B1 | 2/2002 | Hodgson |
| 6,673,901 | B2 | 1/2004 | Koide |
| 6,852,533 | B1 | 2/2005 | Rafii |
| 6,872,868 | B1 | 3/2005 | Wagner |
| 6,936,612 | B2 | 8/2005 | Barvian |
| 7,119,200 | B2 | 10/2006 | Guzi |
| 7,208,489 | B2 | 4/2007 | Barvian |
| 7,345,171 | B2 | 3/2008 | Beylin |
| 7,456,168 | B2 | 11/2008 | Barvian |
| 7,569,390 | B1 | 8/2009 | Eric |
| 7,608,453 | B2 | 10/2009 | Cattaneo |
| 7,682,794 | B2 | 3/2010 | Varki |
| 7,749,225 | B2 | 7/2010 | Chappuis |
| 7,820,797 | B2 | 10/2010 | Boons |
| 7,855,211 | B2 | 12/2010 | Coates |
| 7,863,278 | B2 | 1/2011 | Beylin |
| 7,884,054 | B2 | 2/2011 | Zhou |
| 7,897,347 | B2 | 3/2011 | Tse |
| 7,994,100 | B2 | 8/2011 | Ventresca |
| 8,084,219 | B2 | 12/2011 | Varki |
| 8,232,448 | B2 | 7/2012 | Varki |
| 8,298,773 | B2 | 10/2012 | Vuskovic |
| 8,399,625 | B1 | 3/2013 | Escher |
| 8,440,798 | B2 | 5/2013 | Clausen |
| 8,506,966 | B2 | 8/2013 | Podda |
| 8,524,214 | B2 | 9/2013 | Yurkovetskiy |
| 8,541,231 | B2 | 9/2013 | Varki |
| 8,685,383 | B2 | 4/2014 | Yurkovetskiy |
| 8,685,980 | B2 | 4/2014 | Besong |
| 8,808,679 | B2 | 8/2014 | Yurkovetskiy |
| 8,980,311 | B2 | 3/2015 | Ingale |
| 9,193,732 | B2 | 11/2015 | Calienni |
| 9,254,339 | B2 | 2/2016 | Yurkovetskiy |
| 9,273,142 | B2 | 3/2016 | Ghaderi |
| 9,423,401 | B2 | 8/2016 | Varki |
| 9,555,112 | B2 | 1/2017 | Bodyak |
| 9,718,888 | B2 | 8/2017 | Magliery |
| 9,879,087 | B2 | 1/2018 | DeSander et al. |
| 2002/0012660 | A1 | 1/2002 | Colman |
| 2002/0192231 | A1 | 12/2002 | Zhu |
| 2003/0104402 | A1 | 6/2003 | Zauderer |
| 2003/0108548 | A1 | 6/2003 | Bluestone et al. |
| 2003/0212027 | A1 | 11/2003 | Barbera-Guillem et al. |
| 2003/0235850 | A1 | 12/2003 | Cattaneo |
| 2004/0047891 | A1 | 3/2004 | Glozman |
| 2004/0115740 | A1 | 6/2004 | Benson |
| 2005/0084903 | A1 | 4/2005 | Kim |
| 2005/0272107 | A1 | 12/2005 | Rabbitts |
| 2005/0276800 | A1 | 12/2005 | Rabbitts |
| 2005/0288492 | A1 | 12/2005 | Rabbitts |
| 2006/0034834 | A1 | 2/2006 | Marasco |
| 2007/0048314 | A1 | 3/2007 | Dai et al. |
| 2007/0059769 | A1 | 3/2007 | Blixt |
| 2007/0089178 | A1 | 4/2007 | Zhu |
| 2007/0116727 | A1 | 5/2007 | Hakomori et al. |
| 2007/0265170 | A1 | 11/2007 | Blixt et al. |
| 2007/0275409 | A1 | 11/2007 | Varki et al. |
| 2008/0019968 | A1 | 1/2008 | Blixt et al. |
| 2008/0166805 | A1 | 7/2008 | Varki |
| 2008/0193453 | A1 | 8/2008 | Monterio et al. |
| 2008/0253963 | A1 | 10/2008 | Morin et al. |
| 2008/0279847 | A1 | 11/2008 | Hong |
| 2009/0041783 | A1 | 2/2009 | Takayama |
| 2009/0099073 | A1 | 4/2009 | Rosen |
| 2009/0196916 | A1 | 8/2009 | Ingale |
| 2009/0221803 | A1 | 9/2009 | Dall'Acqua et al. |
| 2009/0280116 | A1 | 11/2009 | Smith |
| 2009/0280128 | A1 | 11/2009 | Kamogawa et al. |
| 2009/0326203 | A1 | 12/2009 | Adams et al. |
| 2010/0009424 | A1 | 1/2010 | Forde |
| 2010/0034825 | A1 | 2/2010 | Clausen et al. |
| 2010/0075344 | A1 | 3/2010 | Vuskovic et al. |
| 2010/0104572 | A1 | 4/2010 | Luria |
| 2010/0143939 | A1 | 6/2010 | Rabbitts |
| 2010/0178292 | A1 | 7/2010 | Wang |
| 2010/0196983 | A1 | 8/2010 | Yang |
| 2010/0221770 | A1 | 9/2010 | Varki |
| 2010/0272707 | A1 | 10/2010 | Bay |
| 2010/0278818 | A1 | 11/2010 | Hubert-Haddad |
| 2010/0292095 | A1 | 11/2010 | Laukkanen |
| 2010/0293624 | A1 | 11/2010 | Varki |
| 2011/0081356 | A1 | 4/2011 | Tahara et al. |
| 2011/0135570 | A1 | 6/2011 | Janatpour |
| 2011/0143373 | A1 | 6/2011 | Hirvonen et al. |
| 2011/0177614 | A1 | 7/2011 | Varki |
| 2011/0195921 | A1 | 8/2011 | Varki |
| 2012/0027813 | A1 | 2/2012 | Podda |
| 2012/0039984 | A1 | 2/2012 | Boons |
| 2012/0045816 | A1 | 2/2012 | Ghaderi |
| 2012/0114652 | A1 | 5/2012 | Elvin et al. |
| 2012/0142903 | A1 | 6/2012 | Varki |
| 2012/0164068 | A1 | 6/2012 | Hudson et al. |
| 2012/0177664 | A1 | 7/2012 | Yokoseki |
| 2013/0011868 | A1 | 1/2013 | Hosaka |
| 2013/0017200 | A1 | 1/2013 | Scheer et al. |
| 2013/0039991 | A1 | 2/2013 | Varki |
| 2013/0108624 | A1 | 5/2013 | Wang |
| 2013/0177579 | A1 | 7/2013 | Lin et al. |
| 2013/0236486 | A1 | 9/2013 | Boons |
| 2014/0005069 | A1 | 1/2014 | Yang |
| 2014/0106449 | A1 | 4/2014 | June |
| 2014/0113979 | A1 | 4/2014 | Varki et al. |
| 2014/0178365 | A1 | 6/2014 | Ghaderi et al. |
| 2015/0314008 | A1 | 11/2015 | Yurkovetskiy |
| 2015/0368349 | A1 | 12/2015 | Gonzalez |
| 2016/0022829 | A1 | 1/2016 | Yurkovetskiy |
| 2016/0130356 | A1 | 5/2016 | DeSander et al. |
| 2016/0220696 | A1 | 8/2016 | Yurkovetskiy |

(56) References Cited

U.S. PATENT DOCUMENTS

| | | |
|---|---|---|
| 2017/0305950 A1 | 10/2017 | Silva et al. |
| 2017/0306046 A1 | 10/2017 | daSilva et al. |
| 2018/0037663 A1 | 2/2018 | Magliery |
| 2018/0280504 A1 | 10/2018 | Silva et al. |
| 2018/0327509 A1 | 11/2018 | Eavarone et al. |
| 2019/0031780 A1 | 1/2019 | Eavarone et al. |
| 2019/0276541 A1 | 9/2019 | Eavarone et al. |
| 2020/0000932 A1* | 1/2020 | Dransfield ............. A61K 38/08 |
| 2020/0041517 A1 | 2/2020 | Eavarone et al. |
| 2020/0247902 A1* | 8/2020 | Prendergast ..... G01N 33/57492 |
| 2020/0276306 A1 | 9/2020 | da Silva et al. |
| 2021/0011021 A1 | 1/2021 | da Silva et al. |
| 2021/0017213 A1 | 1/2021 | da Silva et al. |

FOREIGN PATENT DOCUMENTS

| | | |
|---|---|---|
| EP | 0313244 | 8/1990 |
| EP | 0404097 A2 | 12/1990 |
| EP | 0404097 | 10/1991 |
| EP | 0519596 | 12/1992 |
| EP | 0316818 B1 | 5/1993 |
| EP | 0592106 | 4/1994 |
| EP | 0592106 A1 | 4/1994 |
| EP | 2287202 | 2/2011 |
| EP | 2422811 | 2/2012 |
| EP | 2565268 | 3/2013 |
| EP | 2703485 | 3/2014 |
| EP | 2703485 A1 | 3/2014 |
| EP | 3091032 A1 | 11/2016 |
| EP | 3218005 A4 | 9/2018 |
| WO | 1990002809 | 3/1990 |
| WO | 1991000360 | 1/1991 |
| WO | 1991009967 | 7/1991 |
| WO | 1991010737 | 7/1991 |
| WO | 1991010741 | 7/1991 |
| WO | 1991019739 | 12/1991 |
| WO | 1992001047 | 1/1992 |
| WO | 1992005793 | 4/1992 |
| WO | 1992008802 | 5/1992 |
| WO | 1992018619 | 10/1992 |
| WO | 1993011161 | 6/1993 |
| WO | 1993011236 | 6/1993 |
| WO | 1993017715 | 9/1993 |
| WO | 1995015982 | 6/1995 |
| WO | 1995020401 | 8/1995 |
| WO | 1995015982 A3 | 12/1995 |
| WO | 1996033735 | 10/1996 |
| WO | 1996034096 | 10/1996 |
| WO | 1998016654 | 4/1998 |
| WO | 1998024893 | 6/1998 |
| WO | 1998046645 | 10/1998 |
| WO | 1998050433 | 11/1998 |
| WO | 1998050433 A3 | 2/1999 |
| WO | 1999014353 | 3/1999 |
| WO | 1998046645 A3 | 4/1999 |
| WO | 2000023573 | 4/2000 |
| WO | 2000054057 | 9/2000 |
| WO | 2001040276 | 6/2001 |
| WO | 2001043778 | 6/2001 |
| WO | 2002035237 | 5/2002 |
| WO | 2002077029 | 10/2002 |
| WO | 2002086096 | 10/2002 |
| WO | 2002086505 | 10/2002 |
| WO | 2002088334 | 11/2002 |
| WO | 2002088351 | 11/2002 |
| WO | 2003008451 | 1/2003 |
| WO | 2003014960 | 2/2003 |
| WO | 2003016329 A2 | 2/2003 |
| WO | 2003040185 | 5/2003 |
| WO | 2003062415 | 7/2003 |
| WO | 2003077945 | 9/2003 |
| WO | 2003086276 | 10/2003 |
| WO | 2003086276 A2 | 10/2003 |
| WO | 2003095641 | 11/2003 |
| WO | 2003097697 | 11/2003 |
| WO | 2003062415 A3 | 6/2004 |
| WO | 2004046185 | 6/2004 |
| WO | 2004046186 | 6/2004 |
| WO | 2004046187 | 6/2004 |
| WO | 2004046188 | 6/2004 |
| WO | 2004046189 | 6/2004 |
| WO | 2004046192 | 6/2004 |
| WO | 2004099775 | 11/2004 |
| WO | 2003097697 A3 | 12/2004 |
| WO | 2005010485 | 2/2005 |
| WO | 2005033303 | 4/2005 |
| WO | 2005088310 | 9/2005 |
| WO | 2006002382 | 1/2006 |
| WO | 2006002382 A3 | 10/2006 |
| WO | 2006133356 | 12/2006 |
| WO | 2007059298 | 5/2007 |
| WO | 2008040362 | 4/2008 |
| WO | 2008070363 | 6/2008 |
| WO | 2009018438 | 2/2009 |
| WO | 2008040362 A3 | 3/2009 |
| WO | 2009035494 | 3/2009 |
| WO | 2009035494 A3 | 4/2009 |
| WO | 2009060129 A1 | 5/2009 |
| WO | 2009091826 | 7/2009 |
| WO | 2010004432 | 1/2010 |
| WO | 2010030666 | 3/2010 |
| WO | 2010065818 | 6/2010 |
| WO | 2011003896 | 1/2011 |
| WO | 2011041093 | 4/2011 |
| WO | 2011088385 | 7/2011 |
| WO | 2011089004 A1 | 7/2011 |
| WO | 2012007167 | 1/2012 |
| WO | 2012009474 A1 | 1/2012 |
| WO | 2012048332 | 4/2012 |
| WO | 2012079000 | 6/2012 |
| WO | 2012094627 A2 | 7/2012 |
| WO | 2012106465 A2 | 8/2012 |
| WO | 2013023251 | 2/2013 |
| WO | 2013033420 | 3/2013 |
| WO | 2013040557 | 3/2013 |
| WO | 2013055404 | 4/2013 |
| WO | 2013074916 | 5/2013 |
| WO | 2013092001 | 6/2013 |
| WO | 2013126712 | 8/2013 |
| WO | 2013138795 | 9/2013 |
| WO | 2013151649 | 10/2013 |
| WO | 2014028560 | 2/2014 |
| WO | 2014030780 | 2/2014 |
| WO | 2014039513 | 3/2014 |
| WO | 2014055771 | 4/2014 |
| WO | 2014105810 A1 | 7/2014 |
| WO | 2014106639 | 7/2014 |
| WO | 2014144357 | 9/2014 |
| WO | 2014144573 | 9/2014 |
| WO | 2015048748 A1 | 4/2015 |
| WO | 2015054600 | 4/2015 |
| WO | 2015134488 A1 | 9/2015 |
| WO | 2015159076 A1 | 10/2015 |
| WO | 2016033284 A1 | 3/2016 |
| WO | 2016057916 | 4/2016 |
| WO | 2016057916 A1 | 4/2016 |
| WO | 2016077526 A1 | 5/2016 |
| WO | 2016077526 A1 | 5/2016 |
| WO | 2016090034 A2 | 6/2016 |
| WO | 2016149368 A1 | 9/2016 |
| WO | 2016201240 A1 | 12/2016 |
| WO | 2017083582 A1 | 5/2017 |
| WO | 2018094143 A1 | 5/2018 |
| WO | 2018094144 A1 | 5/2018 |
| WO | 2015054600 A2 | 5/2019 |

OTHER PUBLICATIONS

Jass, J.R. et al., Distribution of sialosyl Tn and Tn antigens within normal and malignant colorectal epithelium. J Pathol. Jun. 1995;176(2):143-9.

Johannes, L. et al., Clathrin-dependent or not: is it still the question? Traffic. Jul. 2002;3(7):443-51.

(56) References Cited

OTHER PUBLICATIONS

Johnson, G. et al., 2000,Kabat Database and its applications: 30 years after the first variability plot Nucleic Acids Res. 28(1): 214-8.
Ju, T. and Cummings, R. D. (2002) a unique molecular chaperone Cosme required for activity of the mammalian.
Ju, T. et al., Protein glycosylation: chaperone mutation in Tn syndrome. Nature. Oct. 27, 2005;437(7063):1252.
Julien et al., Glycobiology, 2006, 16, 54-64.
Julien S. et al. Sialyl-Tn in Cancer: (How) Did We Miss the Target? Biomolecules 2012, 2, 435-466.
Julien S. et al. Stable expression of sialyl-Tn antigen in T47-D cells induces a decrease of cell adhesion and an increase of cell migration Breast Cancer Research and Treatment (2005) 90: 77-84.
Julien, S. et al., 2001. Expression of Sialyl-Tn antigen in breast cancer cells transfected with the human CMP-Neu5Ac:GalNAc a2,6-sialyltransferase (ST6GalNAc 1) cDNA. Glycoconjugate Journal 18, 883-93.
Parkin, D. M. et al. (2001) "Cancer burden in the year 2000. The global picture," European Journal of Cancer 37, Supplement 8(0), 4-66.
Julien, S. et al., Sialyl-Tn vaccine induces antibody-mediated tumour protection in a relevant murine model. Br J Cancer. Jun. 2, 2009;100(11):1746-54.
Juneja, L R. et al. Large-scale preparation of sialic acid from chalaza and egg-yolk membrane. Carbohydr. Res. vol. 214, 1991, pp. 179-186.
"Karim, M., et al. 2006. Is sialic acid in milk food for the brain? CAB Reviews: Perspectives in Agriculture, Veterinary Science, Nutrition, and Natural Resources 1 (018 ):1-11."
Karlen, P. et al., Sialyl-Tn antigen as a marker of colon cancer risk in ulcerative colitis: relation to dysplasia and DNA aneuploidy. Gastroenterology. Dec. 1998;115(6):1395-404.
Karsten and Goletz, SpringerPlus, 2013, 2, 301.
Kasai N et al: "Preparation and specificity of avian anti-GM2(NeuGc) ganglioside antiserum", Biochemical and Biophysical Research Communications, Academic Press Inc. Orlando, FL, US, vol. 129, No. 2, Jun. 14, 1985 (Jun. 14, 1985) , pp. 334-341.
Kawachi, et al. ""Heterophile Hanganutziu-Deicher Antigen in Ganglioside Fractions of Human Melanoma Tissues."" International Archives of Allergy and Immunology, 85(3):381-383 (1988). -.
Kawai T. et al., Quantitative determination of N-glycolylneuraminic acid expression in human cancerous tissues and avian lymphoma cell lines as a tumor-associated sialic acid by gas chromatography-mass spectrometry. Cancer Res. vol. 51, 1991, pp. 1242-1246.
"Kawano, T. et al. (1995) ""Molecular Cloning of Cytidine Monophospho-N-Acetylneuraminic Acid Hydroxylase. Regulation of Species- and Tissue-Specific Expression of N-Glycolylneuraminic Acid,"" Journal of Biological Chemistry 270(27), 16458-16463."
Kayser, H. et al., Biosynthesis of a nonphysiological sialic acid in different rat organs, using N-propanoyl-D-hexosamines as precursors. J Biol. Chem. vol. 267, 1992, pp. 16934-16938.
Kettleborough, C.A. et al., Isolation of tumor cell-specific single-chain Fv from immunized mice using phage-antibody libraries and the re-construction of whole antibodies from these antibody fragments. Eur J Immunol. Apr. 1994;24(4):952-8.
Kilgore, B.R. et al., Comparability and monitoring immunogenic N-linked oligosaccharides from recombinant monoclonal antibodies from two different cell lines using HPLC with fluorescence detection and mass spectrometry. Methods Mol Biol. 2008;446:333-46.
Kim, Y.G. et al., Hybrid restriction enzymes: zinc finger fusions to Fok I cleavage domain. Proc Natl Acad Sci U S A. Feb. 6, 1996;93(3):1156-60.
Kinney et al., Cancer,1997, 80, 2240-2249.
Kirkeby, S. et al., MUC1 and the simple mucin-type antigens: Tn and Sialyl-Tn are differently expressed in salivary gland acini and ducts from the submandibular gland, the vestibular folds, and the soft palate. Arch Oral Biol. Nov. 2010;55(11):830-41.
Klein, A. et al., New sialic acids from biological sources identified by a comprehensive and sensitive approach: liquid chromatography-electrospray ionization-mass spectrometry (LC-ESI-MS) of SIA quinoxalinones. Glycobiology vol. 7, 1997, pp. 421-432.
Cavadas, V. et al. (2010) "Prostate Cancer Prevention Trial and European Randomized Study of Screening for Prostate Cancer Risk Calculators: A Performance Comparison in a Contemporary Screened Cohort," European Urology 58(4), 551-558.
Raedle, J. et al. (1998) "Clinical evaluation of autoantibodies to p53 protein in patients with chronic liver disease and hepatocellular carcinoma," European Journal of Cancer 34(8), 1198-1203.
Kobayashi et al.,(1991) Journal of clinical oncology: official journal of the American Society of Clinical Oncology, 9, 983-987.
Kohler, G. et al., Continuous cultures of fused cells secreting antibody of predefined specificity. Nature. Aug. 7, 1975;256(5517):495-7.
Kostelny, S.A. et al., Formation of a bispecific antibody by the use of leucine zippers. J Immunol. Mar. 1, 1992;148(5):1547-53).
Kozbor, D. et al., A human hybrid myeloma for production of human monoclonal antibodies. J Immunol. Dec. 1984;133(6):3001-5.
Kozutsumi, Y. et al., Participation of cytochrome b5 in CMP-N-acetylneuraminic acid hydroxylation in mouse liver cytosol. J Biochem. vol. 108, 1990, pp. 704-706.
Lee, J.-O., et al. Production of N-acetylneuraminic acid from N-acetylglucosamine and pyruvate using recombinant human renin binding protein and sialic acid aldolase in one pot 2004. Enzyme and Microbial Technology 35(2-3):121-125.
Lefranc, M.P. et al., 2005, Immunome Res. 1:3.
Leth-Larsen et al., Molecular medicine, 2012, 18, 1109-1121.
Lewartowska Aleksandra et al: "Ganglioside reactive antibodies of IgG and IgM class in sera of patients with differentiated thyroid cancer", Immunology Letters, vol. 80, No. 2, Feb. 1, 2002 (Feb. 1, 2002), pp. 129-132.
Liang, D. et al., 2012. BMC Cancer. 12: 201.
Ransohoff, D. F. (2004) "Rules of evidence for cancer molecular-marker discovery and validation," Nature Reviews Cancer 4(4), 309-314.
Lobo et al., 2007, 23, 675-699.
"Lofling, J. C. et al. (2009) ""A dietary non-human sialic acid may facilitate hemolytic-uremic syndrome,"" Kidney International 76(2), 140-144."
Lonberg, N. et al., Human antibodies from transgenic mice. Int Rev Immunol. 1995;13(1):65-93.
"Lowe and Marth, ""A Genetic Approach to Mammalian Glycan Function."" Annu Rev Biochem, 72:643-691 (2003)."
MacCallum et al. (J. Mol. Biol. Oct. 11, 1996; 262 (5): 732-745).
Maccioni, H.J. et al., Organization of the synthesis of glycolipid oligosaccharides in the Golgi complex. FEBS Lett. Jun. 6, 2011;585(11):1691-8.
Mack et al, Proc. Natl. Acad. Sci., 92: 7021-7025, 1995.
Malphettes, L. et al., Highly efficient deletion of FUT8 in CHO cell lines using zinc-finger nucleases yields cells that produce completely nonfucosylated antibodies. Biotechnol Bioeng. Aug. 1, 2010;106(5):774-83.
Sing et al., "ROCR: visualizing classifier performance in R", Bioinformatics, 21(20), pp. 3940-3941 (2005).
Singer et al., "Targeting BACE1 with siRNAs ameliorates Alzheimer disease neuropathology in a transgenic model", Nature Neuroscience, 8(10), pp. 1343-1349 (2005).
Song et al., "A Sialylated Glycan Microarray Reveals Novel Interactions of Modified Sialic Acids with Proteins and Viruses", Journal of Biological Chemistry, vol. 286, No. 36 pp. 31610-31622 (Jul. 12, 2011).
Starbuck et al. Eradicating ovarian cancer stem cells by targeting the tumor-associated carbohydrate antigen sialyl Tn. Gynecologic Oncology 2015, 139(3):590, 3 pages.
Tiscornia et al., "Production and purification of lentiviral vectors", Nature Protocols, 1 (1), pp. 241-245 (2006).
Winkler et al., "Changing the antigen binding specificity by single point mutations of an anti-p24 (HIV-1) antibody," J. Immunol., 165(8), pp. 4505-4514 (Oct. 15, 2000).
Written Opinion in related International Application No. PCT/US2011/021387, dated Oct. 6, 2011 (5 pages).

(56) References Cited

OTHER PUBLICATIONS

Thompson I.M. et al. (2005) "Operating characteristics of prostate-specific antigen in men with an initial psa level of 3.0 ng/mlor lower," JAMA: The Journal of the American Medical Association 294(1), 66-70.
Ohage and Steipe, 1999, J. Mol. Biol. 291:1119-1128.
Ohage et al., 1999, J. Mol. Biol. 291:1129-1134.
Ohno, S. et al, Expression of Tn and sialyl-Tn antigens in endometrial cancer: its relationship with tumor-produced cyclooxygenase-2, tumor-infiltrated lymphocytes and patient prognosis. Anticancer Res. Nov.-Dec. 2006;26(6A):4047-53.
Padlan, E.A., A possible procedure for reducing the immunogenicity of antibody variable domains while preserving their ligand-binding properties. Mol Immunol. Apr.-May 1991;28(4-5):489-98.
"Padler-Karavani, V. et al (2008) Diversity in specificity, abundance and composition of anti-Neu5Gc antibodies in normal humans: Potential implications for disease, Glycobiology 18(10), 818-830."
Panowski, S. et al., 2014. mAbs 6:1, 34-45.
Park J.G. et al., 1990. Cancer Res. 50: 2773-80.
"Pearce, O. M. et al. (2010) ""Chemo-enzymatic synthesis of the carbohydrate antigen N-glycolylneuraminic acid from glucose,"" Carbohydrate Research 345(9), 1225-1229."
Pershad, K. et al., 2010. Protein Engineering Design and Selection. 23:279-88.
Varki, A "N-glycolylneuraminic acid deficiency in humans", Biochimie 83 (2001) 615-622.
Persic, L. et al., An integrated vector system for the eukaryotic expression of antibodies or their fragments after selection from phage display libraries. Gene. Mar. 10, 1997;187(1):9-18.
Petterson et al. (J. Immunol. Jun. 15, 1999; 162 (12): 7031-7040).
"Phelps, C. J. et al., ""Production of Alpha 1,3-Galactosyltransferase-Deficient Pigs."" Science, 299(5605):411-414 (2003)."
Pinho, S. et al., Biological significance of cancer-associated sialyl-Tn antigen: modulation of malignant phenotype in gastric carcinoma cells. Cancer Lett. May 8, 2007;249(2):157-70.
Porteus, M.H. et al., Chimeric nucleases stimulate gene targeting in human cells. Science. May 2, 2003;300(5620):763.
Proba et al., 1998, J. Mol. Biol. 275:245-253.
Rabu et al.,. Future oncology, 2012, 8, 943-960.
Richardson et al., 1998, Gene Ther. 5:635-44.
Conze, T. et al. (2010) "MUC2 mucin is a major carrier of the cancer-associated sialyl-Tn antigen in intestinal metaplasia and gastric carcinomas," Glycobiology 20(2), 199-206.
Varki, A. (2009) "Multiple changes in sialic acid biology during human evolution," Glycoconjugate Journal 26(3), 231-245.
Riechmann, L. et al., Reshaping human antibodies for therapy. Nature. Mar. 24, 1988;332(6162):323-7.
Riethmuller, G. 2012. Cancer Immunity. 12:12-18.
Roguska, M.A. et al., Humanization of murine monoclonal antibodies through variable domain resurfacing. Proc Natl Acad Sci U S A. Feb. 1, 1994;91(3):969-73.
Rozema et al., Dynamic PolyConjugates for targeted in vivo delivery of siRNA to hepatocytes Proc Natl Acad Sci U S A. 2007 104:12982-12887.
Rudikoff et al. (Proc. Natl. Acad. Sci. USA. 1982; 79: 1979-1983).
Sato et al. Frequent occurrence of pre-existing alpha 2→8-linked disialic and oligosialic acids with chain lengths up to 7 Sia residues in mammalian brain glycoproteins. Prevalence revealed by highly sensitive chemical methods and anti-di-, oligo-, and poly-Sia antibodies specific for defined chain lengths. J. Bioi. Chem. 2000 vol. 276, p. 15422-15431.
Sato, Chihiro et al., "Carbohydrates, Lipids, and Other Natural Products: Identification of Oligo-N-Glycolylneuraminic Acid Residues in Mammal-derived Glycoprotiens by a Newly Developed Immunochemical Reagent and Biochemical Methods", J. Biol. Chern. 1998, 273:2575-2582.
Schaefer, W. et al., 2011. PNAS. 108(27):11187-92.
"Schauer, R. et al. (2009) ""Low incidence of N-glycolylneuraminic acid in birds and reptiles and its absence in the platypus,"" Carbohydrate Research 344(12), 1494-1500."

Schauer, R. Adv. Carbohydr. Chem. Biochem. vol. 40, 1982, pp. 131-234.
Schofield, D. et al., 2007. Genome Biol. 8, R254.
Schultz et al., Cancer metastasis reviews, 2012, 31, 501-518.
Schwarzkopf, et al., ""Sialylation Is Essential for Early Development in Mice."" Proc Natl Acad Sci U S A, 99(8):5267-5270 (2002).
Sen et al., Infection Immunity, 2006, 74(3):2177-86.
"Sewell R. et al. (2006) The ST6GalNAc-I Sialyltransferase Localizes throughout the Golgi and Is Responsible for the Synthesis of the Tumor-associated Sialyl-Tn O-Glycan in Human Breast Cancer, Journal of Biological Chemistry 281(6), 3586-3594."
Shaw, L. et al. (1988) "The biosynthesis of N-glycoloylneuraminic acid occurs by hydroxylation of the CMP-glycoside of N-acetylneuraminic acid," Biological Chemistry Hoppe-Seyler 369(6), 477-486.
Varki, A. et al. (2009) Glycosylation Changes in Cancer, in Essentials of Glycobiology. Ch 44, pp. 617-632, Cold Spring Harbor Laboratory Press, Cold Spring Harbor, New York.
Shaw, L. et al. (1994) ""CMP-N-acetylneuraminic acid hydroxylase from mouse liver and pig submandibular glands,"" European Journal of Biochemistry 219(3), 1001-1011.
Sherwood, J.K. et al., Controlled antibody delivery systems Nature Biotechnology 10, 1446-1449 (1992).
Shi, W-X. et al., 1996. J of Biol Chem. 271(49): 31526-32.
Shu, L. et al., Secretion of a single-gene-encoded immunoglobulin from myeloma cells. Proc Natl Acad Sci U S A. Sep. 1, 1993;90(17):7995-9.
Siegel et al., Cancer statistics, 2013. CA: a cancer journal for clinicians 63, 11-30.
Siegwart et al., Combinatorial synthesis of chemically diverse core-shell nanoparticles for intracellular delivery Proc Natl Acad Sci U S A. 2011 108:12996-13001.
Sjoberg, Eric R.; L D. Powell; A Klein; and A Varki; "Natural Ligands of the B Cell Adhesion Molecule CD22j3 can be Masked by 9-0-Acetylation of Sialic Acids"; The Journal of Cell Biology; Jul. 1994; Voo. 126, No. 2., pp. 549-562.
Weiss, J. M. et at. (2007) Immunotherapy of Cancer by IL-12-based Cytokine Combinations. Expert Opinion on Biological Therapy 7(11), 1705-1721.
Skerra, A. et al., Assembly of a functional immunoglobulin Fv fragment in *Escherichia coli*. Science. May 20, 1988;240(4855):1038-41.
Sonnenburg, Justin L.; H. van Halbeek; and A Varki ""Characterization of the Acid Stability of Glycosidically Linked Neuraminic Acid""; The Journal of Biological Chemistry; May 17, 2002; vol. 277, No. 20, pp. 17502-17510.
Stancoviski et al. (Proceeding of the National Academy of Science USA. 1991; 88: 8691-8695).
Stanley and Ioffe, "Glycosyltransferase Mutants: Key to New Insights in Glycobiology." FASEB J, 9(14):1436-1444 (1995).
International Search Report and Written Opinion received in PCT/US2015/060287 dated Mar. 31, 2016.
International Search Report and Written Opinion received in PCT/US2013/029240 dated Jun. 21, 2013.
Beatson, R. et al. (2015). The Breast Cancer-Associated Glycoforms of MUC1, MUC1-Tn and sialyl-Tn, Are Expressed in COSMC Wild-Type Cells and Bind the C-Type Lectin MGL. PLoS One 10, e0125994.
Gao, H. et al. (2015). High-throughput screening using patient-derived tumor xenografts to predict clinical trial drug response. Nat. Med. advance on.
Hinrichs, M.(2015). Antibody Drug Conjugates: Nonclinical Safety Considerations. AAPS J. 17, 1055-1064.
Hofmann, B. T. et al. (2015) COSMC knockdown mediated aberrant O-glycosylation promotes oncogenic properties in pancreatic cancer. Mol. Cancer 14, 1-15.
Loureiro, L. et al. (2015). Challenges in Antibody Development against Tn and Sialyl-Tn Antigens. Biomolecules 5, 1783-1809.
Yu, H. et al. (2007) "Efficient chemoenzymatic synthesis of biotinylated human serum albumin-sialoglycoside conjugates containing O-acetylated sialic acids," Organic & Biomolecular Chemistry 5(15), 2458-2463.

(56) References Cited

OTHER PUBLICATIONS

Ozaki, H. et al. (2012) Enhancement of metastatic ability by ectopic expression of ST6GalNAcl on a gastric cancer cell line in a mouse model. Clin. Exp. Metastasis 29, 229-38.
Saber, H. et al. (2015). An FDA oncology analysis of antibody-drug conjugates. Regul. Toxicol. Pharmacol. 71, 444-452.
Vacchelli, E. et al. (2015). Trial watch: Tumor-targeting monoclonal antibodies for oncological indications. Oncoimmunology 4, e985940.
Ang JE, et al. (2013) Efficacy of chemotherapy in BRCA1/2 mutation carrier ovarian cancer in the setting of PARP Inhibitor resistance: a multi-institutional study. Clin Cancer Res; 19:5485-93.
Armstrong DK, et al. (2006) Intraperitoneal cisplatin and paclitaxel in ovarian cancer. N Engl J Med. 354(1), 34-43.
Berns EM & Bowtell DD. (2012) The changing view of high-grade serous ovarian cancer. Cancer Res. 72, 2701-4.
Ceccaldi R, et al. (2015) A unique subset of epithelial ovarian cancers with platinum sensitivity and PARP inhibitor resistance. Cancer Res; 75:628-34.
Choi YE, et al. (2016) Platinum and PARP Inhibitor Resistance Due to Overexpression of MicroRNA-622 in BRCA1-Mutant Ovarian Cancer. Cell Rep; 14:429-39.
Cohen JG, et al. (2014) In 2014, can we do better than CA125 in the early detection of ovarian cancer? World J. Biol. Chem. 5, 286-300.
Coleman RL. (2016) Ovarian cancer in 2015: Insights into strategies for optimizing ovarian cancer care. Nat Rev Clin Oncol. 13(2), 71-2.
Diaz, S. L. et al. (2009) "Sensitive and Specific Detection of the Non-Human Sialic Acid N-Glycolylneuraminic Acid in Human Tissues and Biotherapeutic Products," PLoS One 4(1), e4241.
Ghaderi, D. et al. (2010) "Implications of the presence of N-glycolylneuraminic acid in recombinant therapeutic glycoproteins," Nature Biotechnology 28(8), 863-867.
Cooke SL & Brenton JD. (2011) Evolution of platinum resistance in high-grade serous ovarian cancer. Lancet Oncol; 12:1169-74.
Curley MD, et al. (2009) CD133 expression defines a tumor initiating cell population in primary human ovarian cancer. Stem Cells; 27:2875-83.
Curley MD, et al. (2011) Evidence for cancer stem cells contributing to the pathogenesis of ovarian cancer. Front Biosci (Landmark Ed); 16:368-92.
Curry Jm, et al. (2013) The use of a novel MUC1 antibody to identify cancer stem cells and circulating MUC1 in mice and patients with pancreatic cancer. J Surg Oncol; 107:713-22.
Davidson B, et al. (2000) Expression of carbohydrate antigens in advanced-stage ovarian carcinomas and their metastases—A clinicopathologic study. Gynecol Oncol; 77:35-43.
De Goeij Be & Lambert JM. (2016) New developments for antibody-drug conjugate-based therapeutic approaches. Curr Opin Immunol; 40:14-23.
Dearnley DD & McMeekin DS. (2006) Consolidation therapy in ovarian cancer: where do we stand? Curr Opin Obstet Gynecol; 18:3-7.
Di C & Zhao Y. (2015) Multiple drug resistance due to resistance to stem cells and stem cell treatment progress in cancer (Review). Exp Ther Med; 9:289-93.
Federici, MF. et al. (1999) Selection of carbohydrate antigens in human epithelial ovarian cancers as targets for immunotherapy: serous and mucinous tumors exhibit distinctive patterns of expression. Int J Cancer. Apr. 12;81(2):193-8.
Glavey, SV. (2015) The cancer glycome: carbohydrates as mediators of metastasis. Blood Rev. July;29(4):269-79.
TangvoranuntakuL P. et al. (2003) Human uptake and incorporation of an immunogenic nonhuman dietary sialic acid. Proceedings of the National Academy of Sciences 100(21) 12045-12050.
Kulkarni-Datar K, et al. (2013) Ovarian tumor initiating cell populations persist following paclitaxel and carboplatin chemotherapy treatment in vivo. Cancer Lett; 339:237-46.
Li X, et al (2015) Prognostic value of cancer stem cell marker CD133 expression in pancreatic ductal adenocarcinoma (PDAC): a systematic review and meta-analysis. Int J Clin Exp Pathol; 8:12084-92.

Liu JF, et al. (2014) PARP inhibitors in ovarian cancer: current status and future promise. Gynecol Oncol; 133:362-9.
Long H, et al. (2015) CD133+ ovarian cancer stem-like cells promote non-stem cancer cell metastasis via CCL5 Induced epithelial-mesenchymal transition. Oncotarget; 6:5846-59.
Markman M. (2003) Rationale for maintenance or consolidation therapy in ovarian cancer. Clin Adv Hematol Oncol; 1:176-8.
Ozga M, et al. (2015) A systematic review of ovarian cancer and fear of recurrence. Palliat Support Care. 13(6), 1771-80.
Ozols RF, et al. (2003) Phase III trial of carboplatin and paclitaxel compared with cisplatin and paclitaxel in patients with optimally resected stage III ovarian cancer: a Gynecologic Oncology Group study. J Clin Oncol. 21(17), 3194-200.
Pinato DJ, et al. (2013) Evolving concepts in the management of drug resistant ovarian cancer: dose dense chemotherapy and the reversal of clinical platinum resistance. Cancer Treat Rev; 39:153-60.
Ricci F, et al. (2013) ALDH enzymatic activity and CD133 positivity and response to chemotherapy in ovarian cancer patients. Am J Cancer Res; 3:221-9.
Sabbatini P. (2009) Consolidation therapy in ovarian cancer: a clinical update. Int J Gynecol Cancer; 19 Suppl 2:S35-9.
Candefjord, S. et al. (2009) "Technologies for localization and diagnosis of prostate cancer," Journal of Medical Engineering & Technology 33(8), 585-603.
Thapa R & Wilson GD. (2016) The Importance of CD44 as a Stem Cell Biomarker and Therapeutic Target in Cancer. Stem Cells Int; 2016:2087204.
De Visser, K E. et al. (2005) De novo carcinogenesis promoted by chronic inflammation is B lymphocyte dependent. Cancer Cell 7(5), 411-423.
Desmetz, C. et al. (2009) "Humoral response to cancer as a tool for biomarker discovery," Journal of Proteomics 72(6), 982-988.
Jolles, S. et al. (2005) "Clinical uses of intravenous immunoglobulin," Clinical & Experimental Immunology 142(1), 1-11.
Mechref, Y. et al. (2009) "Quantitative Serum Glycomics of Esophageal Adenocarcinoma and Other Esophageal Disease Onsets," Journal of Proteome Research 8(6), 2656-2666.
Nossov, V. et al. (2008) "The early detection of ovarian cancer: from traditional methods to proteomics. Can we really do better than serum CA-125?," American Journal of Obstetrics and Gynecology 199(3), 215-223.
Drake, P. M. et al. (2010) "Sweetening the Pot: Adding Glycosylation to the Biomarker Discovery Equation," Clinical Chemistry 56(2), 223-236.
Uygur-Bayramicli, O. et al. (2007) "Type 2 diabetes mellitus and CA 19-9 levels," World Journal of Gastroenterology 13(40), 5357-5359.
Biocca, Neuberger and Cattaneo EMBO J. 9: 101-108, 1990.
Bork et al, 2009, Increasing the Sialylation of Therapeutic Glycoproteins: The Potential of the Sialic Acid Biosynthetic Pathway. Journal of Pharmaceutical Sciences. 98(10):3499-508.
Bradbury, A.R. et al., Beyond natural antibodies: the power of in vitro display technologies. Nat Biotechnol. Mar. 2011;29(3):245-54.
Brinkmann, U. et al., Phage display of disulfide-stabilized Fv fragments. J Immunol Methods. May 11, 1995;182(1):41-50.
Brinkman-Van der Linden, E.C. et al., New aspects of siglec binding specificities, including the significance of fucosylation and of the sialyl-Tn epitope. Sialic acid-binding immunoglobulin superfamily lectins. J Biol Chem. Mar. 24, 2000;275(12):8625-32.
Brockhausen, I. et al., Pathways of mucin O-glycosylation in normal and malignant rat colonic epithelial cells reveal a mechanism for cancer-associated Sialyl-Tn antigen expression. Biol Chem. Feb. 2001;382(2):219-32.
Kjeldsen, T. et al. (1988) "Preparation and Characterization of Monoclonal Antibodies Directed to the Tumor-associated O-linked Sialosyl-2?6 ?-N-Acetylgalactosaminyl (Sialosyl-Tn) Epitope," Cancer Research 48(8), 2214-2220.
Burgos-Ojeda et al., Cancer letters, 2012, 322, 1-7.
Caldas et al. (Mol. Immunol. May 2003; 39 (15): 941-952).
Cao, Y. et al., Immunodetection of epithelial mucin (MUC1, MUC3) and mucin-associated glycotopes (TF, Tn, and sialosyl-Tn) in benign

(56) References Cited

OTHER PUBLICATIONS and malignant lesions of colonic epithelium: apolar localization corresponds to malignant transformation. Virchows Arch. Sep. 1997;431(3):159-66.
Carlson, D. M. et al. (1968) ""Structures and Immunochemical Properties of Oligosaccharides Isolated from Pig Submaxillary Mucins,"" Journal of Biological Chemistry 243(3), 616-626.
Caron et al., Intracellular delivery of a Tat-eGFP fusion protein into muscle cells Mol. Ther. 3(3):310-8 (2001).
Carr, et al. "A Mouse IgG1 Monoclonal Antibody Specific for N-Glycolyl Gm3 Ganglioside Recognized Breast and Melanoma Tumors." Hybridoma, 19(3):241-247 (2000).
Carrascal, M.A., et al.,(2014). Molecular Oncology.Sialyl Tn-expressing bladder cancer cells induce a tolerogenic phenotype in innate and adaptive immune cells 8(3): 753-65.
Carroll, D., Progress and prospects: zinc-finger nucleases as gene therapy agents. Gene Ther. Nov. 2008;15(22):1463-8.
Casadesus, A.V. et al., 2013. Glycoconj J. 30(7):687-99.
Kobata, A. and Amano, J. (2005) "Altered glycosylation of proteins produced by malignant cells, and application for the diagnosis and immunotherapyof tumours," Immunology & Cell Biology 83(4), 429-439.
Casset et al. (Biochem. Biophys. Res. Commun. Jul. 18, 2003; 307 (1): 198-205).
Cathomen, T. et al., Zinc-finger nucleases: the next generation emerges. Mol Ther. Jul. 2008;16(7):1200-7.
Cazet et al., Breast cancer research: BCR, 2010, 12,204.
Chang et al. (Structure. Jan. 7, 2014; 22 (1): 9-21).
Chao, G. et al., Isolating and engineering human antibodies using yeast surface display. Nat Protoc. 2006;1(2):755-68.
Cheever, M.A. et al., The prioritization of cancer antigens: a national cancer institute pilot project for the acceleration of translational research. Clin Cancer Res. Sep. 1, 2009;15(17):5323-37.
Chen et al., 1994, Proc. Natl. Acad. Sci. USA, 91: 5932-5936.
Chen et al., Journal of proteome research, 2013, 12, 1408-1418.
Chen, X. et al., Advances in the biology and chemistry of sialic acids. ACS Chem Biol. Feb. 19, 2010;5(2):163-76.
Chenu, et al. "Reduction of CMP-N-Acetylneuraminic Acid Hydroxylase Activity in Engineered Chinese Hamster Ovary Cells Using an Antisense-RNA Strategy." Biochim Biophys Acta, 1622(2):133-144 (2003).
Li, C. et al. (2008) "Pancreatic Cancer Serum Detection Using a Lectin/Glyco-Antibody Array Method," Journal of Proteome Research 8(2), 483-492.
Chien et al. (Proc. Natl. Acad. Sci. USA. Jul. 1989; 86 (14): 5532-5536).
Chothia and Lesk, J. Mol. Biol. 196, 901 (1987).
Chothia et al., Nature 342, 877 (1989).
Chou, et al. "A Mutation in Human Cmp-Sialic Acid Hydroxylase Occurred after the Homo-Pan Divergence." Proceedings of the National Academy of Sciences, 95(20):11751-11756 (1998).
Chou, et al. ""Inactivation of Cmp-N-Acetylneuraminic Acid Hydroxylase Occurred Prior to Brain Expansion During Human Evolution."" Proc Natl Acad Sci U S A, 99(18):11736-11741 (2002).
Chu et al.,CpG Oligodeoxynucleotides Act as Adjuvants for Pneumococcal Polysaccharide-Protein Conjugate Vaccines and Enhance Antipolysaccharide Immunoglobulin G2a (IgG2a) and IgG3 Antibodies, Infection Immunity 2000, vol. 68(3):1450-6.
Chung, C.H. et al., Cetuximab-induced anaphylaxis and IgE specific for galactose-alpha-1,3-galactose. N Engl J Med. Mar. 13, 2008;358(11):1109-17.
Cohen, et al., Characterization of a new intrabody directed against the N-terminal region of human p53. 1998, Oncogene 17:2445-56.
Bardor, M. et al., Mechanism of uptake and incorporation of the non-human sialic acid N-glycolylneuraminic acid into human cells. J Biol Chem. 2005. 280: 4228-4237.
Ludwig, J. A. and Weinstein, J. N. (2005) "Biomarkers in Cancer Staging, Prognosis and Treatment Selection," Nature Reviews Cancer 5(11), 845-856.

Colby et al., Potent inhibition of huntingtin aggregation and cytotoxicity by a disulfide bond-free single domain intracellular antibody. Proc. Natl. Acad. Sci. U.S.A. 101 : 17616-21 , 2004.
Colcher, D.A spectrum of monoclonal antibodies reactive with human mammary tumor cells. et al., 1981. PNAS. 78(5):3199-203.
Collins, Brian E.; T. J. Fralich; S. Itonori; Y. Ichiawa; and R. L. Schnaar; ""Conversion of cellular sialic acid expression from N-acetyl- to N-glycolylneuraminic acid using a synthetic precursor, N-glycolylmannosamine pentaacetate: inhibition of myelin-associated glycoprotein binding to neural cells"" Glycobiology; 2000, vol. 10, No. 1, pp. 11-20.
Cronican et al., Potent delivery of functional proteins into Mammalian cells in vitro and in vivo using a supercharged protein ACS Chem. Biol. 2010 5:747-752.
Curry et al., Journal of surgical oncology,2013, 107, 713-722.
Dai, et al., ""Targeted Disruption of the Alpha1,3-Galactosyltransferase Gene in Cloned Pigs." Nat Biotechnol, 20(3):251-255 (2002)."
Daugherty, et al., Formulation and delivery issues for monoclonal antibody therapeutics. Adv Drug Deliv Rev. Aug. 7, 2006;58(5-6):686-706.
Davis et al. Evidence of RNAi in humans from systemically administered siRNA via targeted nanoparticles Nature 2010 464:1067-1070.
Malykh, Y. N. et al. (2001) "N-Glycolylneuraminic acid in human tumours," Biochimie 83(7), 623-634.
Davis, M.E. The first targeted delivery of siRNA in humans via a self-assembling, cyclodextrin polymer-based nanoparticle: from concept to clinic Mol Pharm. 2009 6:659-668.
De Pascalis et al. (J. Immunol. 2002; 169 (6): 3076-3084).
Der Maur et al., 2002, J. Biol. Chem. 277:45075-85.
Schröder, F. H. et al. (2009) "Screening and Prostate-Cancer Mortality in a Randomized European Study," New England Journal of Medicine 360(13), 1320-1328.
"Manimala, J. et al., Carbohydrate Array Analysis of Anti-Tn Antibodies and Lectins Reveals Unexpected Specificities: Implications for Diagnostic and Vaccine Development ChemBioChem 2005, 6, 2229-2241".
Marasco et al., 1993. Design, intracellular expression, and activity of a human anti-human immunodeficiency virus type 1 gpl20 single-chain antibody. Proc. Natl. Acad. Sci. USA, 90: 7889-7893.
Marasco, 1995. Intracellular antibodies (intrabodies) as research reagents and therapeutic molecules for gene therapy. Immunotech, 1: 1-19.
Marasco.(1997). Intrabodies: turning the humoral immune system outside in for intracellular immunization Gene Ther. 4:11-15, 1997.
Mariuzza et al. (Annu. Rev. Biophys. Biophys. Chem. 1987; 16: 139-159).
"Marquina, Gilda; H. Waki; L. E. Fernandez; K. Kon; A Carr; 0. Valiente; R. Perez; and S. Ando; "Gangliosides Expressed in Human Breast Cancer"; Cancer Research; Nov. 15, 1996; 56; pp. 5165-5171".
Soussi, T. (2000) "p53 Antibodies in the Sera of Patients with Various Types of Cancer: A Review," Cancer Research 60(7), 1777-1788.
Martin et al. Abstract #4182, Blood, (Nov. 16, 2004) vol. 104, No. 11, Part 2, pp. 132B. Meeting Info.: 46th Annual Meeting of the American-Society-of-Hematology. San Diego, CA, USA. Dec. 4-7, 2004.
Martin, F.J. et al., Irreversible coupling of immunoglobulin fragments to preformed vesicles. An improved method for liposome targeting. J Biol Chem. Jan. 10, 1982;257(1):286-8.
Martin. L. T. et al. (2002) Genetically Altered Mice with Different Sialyl transferase Deficiencies Show Tissue-specific Alterations in Sialylation and Sialic Acid 9-O-Acetylation, Journal of Biological Chemistry 277(36).
Marvin, J.S. et al., 2005. Acta Pharmacologica Sinica. 26(6):649-58.
Massignani, et al., Cellular delivery of antibodies: effective targeted subcellular imaging and new therapeutic tool. Nature Proceedings, May 2010.
Matsuda, F. et al., 1998. The Complete Nucleotide Sequence of the Human Immunoglobulin Heavy Chain Variable Region Locus The Journal of Experimental Medicine. 188(11); 2151-62.
McCafferty, et al., 1990. Nature. 348:552-4.

(56) References Cited

OTHER PUBLICATIONS

McCann et al., PloS one, 2011,6, e28077.
Srivastava, S. and Gopal-Srivastava, R. (2002) "Biomarkers in Cancer Screening: A Public Health Perspective," The Journal of Nutrition 132(8), 2471S-2475S.
McDevitt et al. (Cancer Res. Nov. 1, 2000; 60: 6095-6100).
McNaughton et al., Mammalian cell penetration, siRNA transfection, and DNA transfection by supercharged proteins Proc. Natl. Acad. Sci. USA 2009 106:6111-6116.
Medema et al., Nature cell biology, 2013, 15, 338-344.
Meng, X. et al., Targeted gene inactivation in zebrafish using engineered zinc-finger nucleases. Nat Biotechnol. Jun. 2008;26(6):695-701.
Merrick, J. M.et al., Characterization of the Hanganutziu-Deicher (serum-sickness) antigen as gangliosides containing n-glycolylneuraminic acid. Int. Arch. Allergy Appl. Immunol. vol. 57, 1978, pp. 477-480.
Meunier, L. et al., 2010. Transl Oncol. 3(4): 230-8.
Mhashilkar et al., 2002, Gene Ther. 9:307-19.
Mhashilkar, et al., 1995, EMBO J. 14: 1542-51.
Miersch, S. et al., Synthetic antibodies: Concepts, potential and practical considerations. Methods. Aug. 2012;57(4):486-98.
Miles et al., The oncologist, 2011, 16, 1092-1100.
Morito T et al. 1986. "Studies on Hanganutziu-Deicher antigens-antibodies. I. Hanganutziu-Deicher antibodies of IgG class in liver diseases", International Archives of Allergy and Applied Immunology. 81(3):204-208.
Morrison, S.L., Transfectomas provide novel chimeric antibodies. Science. Sep. 20, 1985;229(4719):1202-7.
Mortezai, N. et al., 2013. Glycobiology. 23(7):844-52.
Motoo, Y. et al., Serum sialyl-Tn antigen levels in patients with digestive cancers. Oncology. 1991;48(4):321-6.
"Muchmore, Elaine et al, American Journal of Physical Anthropology 107:187-198 (1998); A Structural Difference Between the Cell Surfaces of Humans and the Great Apes."
Muchmore, E. et al., Biosynthesis of N-glycolyneuraminic acid. The primary site of hydroxylation of N-acetylneuraminic acid is the cytosolic sugar nucleotide pool. J Biol. Chem vol. 264, 1989, pp. 20216-20223.
Mukherjee, K. et al., 2008. J Cell Biochem. 105: 724-34.
Mukherjee, K. et al., 2009. Biol Chem. 390: 325-35.
Muraro, R. et al., 1988. Cancer Res. 48: 4588-96.
Taylor, R. E. et al. (2010) "Novel mechanism for the generation of human xeno-autoantibodies against the nonhuman sialic acid N-glycolylneuraminic acid," The Journal of Experimental Medicine 207(8), 1637-1646.
Naor et al., Seminars in cancer biology, 2008, 18, 260-267.
Negi et al., Journal of drug targeting,2012, 20, 561-573.
Nelson, A. L., MAbs.Jan.-Feb. 2010;2(1):77-83.
"Nelson, H. D. et al (2009) Screening for Breast Cancer: An Update for the U.S. Preventive Services Task Force, Annals of Internal Medicine 151(10), 727-737."
Newman and Bettinger, Gene therapy progress and prospects: ultrasound for gene transfer Gene Ther. 2007 14:465-475.
Newsom-Davis, T. et al., Enhanced Immune Recognition of Cryptic Glycan Markers in Human Tumors Cancer Res 2009;69:2018-2025.
Nikoloudis, D. et al., 2014. complete,multi-level conformational clustering of antibody complementarity-determining regions. PeerJ. 2:e456.
"Nogueira, L. et aL (2009) Prostatic specific antigen for prostate cancer detection. International Braz j urol 35(5), 521-529."
"Nohle, U. et al. (1982) ""Uptake, metabolism and excretion of orally and intravenously administered, 14C- and 3H-labeled N-acetylneuraminic acid mixture in the mouse and rat,"" Hoppe-Seylers Zeitschriftfur Physiologische Chemie 362(11), 1495-1506."
"Nohle, U. et al. (1982) ""Uptake, Metabolism and Excretion of Orally and Intravenously Administered, Double-Labeled N-Glycoloylneuraminic Acid and Single-Labeled 2-Deoxy-2,3-dehydro-N-acetylneuraminic Acid in Mouse and Rat,"" European Journal of Biochemistry 126(3), 543-548."

Nollau, P. et al., 2013. J Histochem Cytochem. 61(3):199-205.
"Oetke, Cornelia; S. Hinderlich; R. Brossmer; W. Reutter; M. Pawlita; and 0. T. Keppler; ""Evidence for efficient uptake and incorporation of sialic acid by eukaryotic cells"""; Eur. J. Biochem.; 2001; 265; pp. 4553-4561".
Ogata, S. et al., Tumor-associated sialylated antigens are constitutively expressed in normal human colonic mucosa. Cancer Res. May 1, 1995;55(9):1869-74.
Adams et al., "Monoclonal antibody therapy of cancer", Nature Biotechnology, 23(9), pp. 1147-1157 (2005).
Anti-STn Antibody, SBH Sciences, https://www.sbhsciences.com/Anti_STn.asp, 1 page, 2019.
Blixt et al. Analysis of Tn antigenicity with a panel of new IgM and IgG1 monoclonal antibodies raised against leukemic cells. Glicobiology 2012, vol. 22, No. 4, pp. 529-542 (2012).
Brinkman-Van Der Linden et al., "Loss of N-Glycolylneuraminic Acid in Human Evoluation", J Biol Chem., 275(12), pp. 8633-8640 (Mar. 24, 2000).
Campbell et al. High-throughput profiling of anti-glycan humoral responses to SIV vaccination and challenge. PLOS ONE, 2013, vol. 8, Issue. 9, pp. 1-12 (2013).
Cao et al., "Thomsen-Friedenreich-related carbohydrate antigens in normal adult human tissues: a systematic and comparative study", Histochemistry and Cell Biology, 106(2), pp. 197-207 (1996).
Cholleti et al., "Automated Motif Discovery from Glycan Array Data", OMICS A Journal of Integrative Biology, 16(10) pp. 497-512 (2012).
Chun-Chi et al., "Integrative disease classification based on cross-platform microarray data", BMC Bioinformatics, 10, pp. 1-8 (2009).
Desmetz et al., "Identifying autoantibody signatures in cancer: a promising challenge", Expert Review of Proteomics, 6(4), pp. 377-386 (2009).
Emens, L.A. "Breast Cancer Immunobiology Driving Immunotherapy:Vaccines and Immune Checkpoint Blockade" Expert Review of Anticancer Therapy, vol. 12, pp. 1597-1611 (Dec. 1, 2012).
European Search Report in related EP Application No. EP 13 18 4707, dated Jun. 2, 2014 (13 pages).
Extended European Search Report dated May 17, 2017, received in EP Application No. 14852277.4 (12 pages).
Extended European Search Report in related EP Application No. EP 11 73 3477, dated Jun. 25, 2013 (12 pages).
Extended European Search Report dated Jul. 11, 2018 in correspondence European Patent Application No. 15848503.7 (14 pages).
Fawcett, T. "ROC Graphs: Notes and Practical Considerations for Data Mining Researchers", Intelligent Enterprise Technologies Laboratory, (HP Laboratories Palo Alto), pp. 1-27 (2004).
Hakomori, S., "Tumor Malignancy Defined by Aberrant Glycosylation and Sphingo(glyco)lipid Metabolism," Cancer Research, 56, pp. 5309-5318, Dec. 1, 1996.
Hawkins, D. M., "The Problem of Overfitting", Journal of Chemical Information and Computer Sciences, 44(1), pp. 1-12 (2003).
Hirakawa et al., "Novel Anti-carbohydrate Antibodies Reveal the Cooperative Function of Sulfated N- andO-Glycans in Lymphocyte Homing", Journal of Biological Chemistry, vol. 285, No. 52, 7, pp. 40864-40878 (Oct. 2010).
Imai et al. "Immunohistochemical expression of T, Tn and sialyl-Tn antigens and clinical outcome in human breast carcinoma", Anti-cancer Research, 21(2B), pp. 1327-1334 (2001).
International Preliminary Report on Patentability in related International Application No. PCT/US2011/021387, dated Jul. 26, 2012 (6 pages).
International Search Report in related International Application No. PCT/US2011/021387, dated Oct. 6, 2011 (5 pages).
International Search Report and Written Opinion dated Jun. 9, 2017 in Application No. PCT/US2017/015301, dated Jun. 9, 2017 (13 pages).
International Search Report and Written Opinion for corresponding PCT Application No. PCT/US2017/062155, dated Apr. 17, 2018 (12 pages).
International Search Report and Written Opinion for corresponding PCT Application No. PCT/US2017/062156 dated Feb. 20, 2018 (15 pages).

(56) References Cited

OTHER PUBLICATIONS

International Search Report and Written Opinion received in PCT/US2016/036907 dated Sep. 7, 2016 (9 pages).
Keshab D Pant et al: "Immunohistochemical Examination of Anti-STn Monoclonal Antibodies LLU9B4, B72.3, and B35.2 for Their Potential use as Tumor Markers", Digestive Diseases and Sciences, Kluwer Academic Publishers—Plenum Publishers, NE, vol. 53, No. 8, Feb. 26, 2008, pp. 2189-2194.
Kim et al. "Combination of Cancer Immunotherapy with Clinically Available Drugs that can Block Immunosupressive Cells", Immunological Investigations, vol. 43, pp. 517-534 (Aug. 1, 2014).
Kim et al., "Implication of Aberrant Glycosylation in Cancer and Use of Lectin for Cancer Biomarker Discovery", Protein & Peptide Letters, 16(5), pp. 499-507 (2009).
Kobayashi et al., Clinical Evaluation of Circulating Serum Sialyl Tn Antigen Levels in Patients with Epithelial Ovarian Cancer, Journal of clinical oncology: official journal of the American Society of Clinical Oncology, 9:983-987, (1991).
Koda et al., "Application of Tyramide Signal Amplification for Detection of N-Glycolylneuraminic Acid in Human Hepatocellular Carcinoma", Int J Clin Oneal, 8(5), pp. 317-321 (2003).
Marcos et al., "Role of the Human ST6GalNAc-I and ST6GalNAc-II in the Synthesis of the Cancer-Associated Sialyl-Tn Antigen," Cancer Research, 64, pp. 7050-7057, Oct. 1, 2004.
Munkley, J. "The Role of Sialyl-Tn in Cancer" International Journal of Molecular Sciences, vol. 17, pp. 1-9 (Feb. 24, 2016).
O'Boyle et al., "Immunization of Colorectal Cancer Patients with Modified Ovine Submaxillary Gland Mucin and Adjuvants Induces IgM and IgG Antibodies to Sialylated Tn[1]", Cancer Resarch, 52, pp. 5663-5667 (1992).
Oppmann et al., "Novel p19 Protein Engages IL-12p40 to Form a Cytokine, IL-23, with Biological Activities Similar as Well as Distinct from IL-12", Immunity, 13(5), pp. 715-725 (2000).
Ostrand-Rosenberg, S., "Immune surveillance: a balance between protumor and antitumor immunity", Current Opinion in Genetics & Development, 18(1), pp. 11-18 (2008).
Oza e al. Olaparib combined with chemotherapy for recurrent platinum-sensitive ovarian cancer: a randomised phase 2 trial. Lancet Oncol. 2015, 16(1):87-97; Abstract, p. 91, Fig 2 and its legend.
Padler-Karavani et al. Cross-comparison of protein recognition of sialic acid diversity on two novel sialoglycan microarrays. J BC 2012, vol. 287, No. 27, pp. 22593-22608 (2012).
Partial Supplementary European Search Report for corresponding European Application No. 15848503.7 dated Apr. 10, 2018 (6 pages).
Petterson et al., "CD47 signals T cell death," J. Immunol., 162(12), pp. 7031-7040 (Jun. 15, 1999).
Pitot, H. C., "The Language of Oncology", Fundamentals of Oncology (Dekker, M., Ed.), pp. 15-28, New York, (1978).
Porter et al., "Chimeric Antigen Receptor-Modified T Cells in Chronic Lymphoid Leukemia", The New England Journal of Medicine, pp. 725-733 (Aug. 25, 2011).
Prehn et al., "The flip side of immune surveillance: immune dependency", Immunological Reviews, 222(1), pp. 341-356 (2008).
Prendergast et al. "Novel Anti-Aialyl-Tn Monoclonal Antibodies and Antibody-Drug Conjugates (ADCs) Demonstrate Tumor Specificity in Vitro and in Vivo Antitumor Efficacy" Poster, Proceedings of the American Association for Cancer Research Annual Meeting 2017, Cancer Research, vol. 77, suppl. 13, 1, pp. 1-13 (Apr. 1, 2017).
Rho et al., "Discovery of sialyl Lewis A and Lewis X modified protein cancer biomarkers using high density antibody array",. J Proteomics; 96:291-9 (2014).
Rho et al., "High-throughput screening for native autoantigen-autoantibody complexes using antibody microarrays", J Proteome Res. May 3, 2013;12(5):2311-20 (2013).
Ricardo et al., "Detection of glyco-mucin profiles improves specificity of MUC16 and MUC1 biomarkers in ovarian serous tumours", Mol Oncol. 9(2), 503-12 (2015).

Rudd et al., "Glycosylation changes on serum glycoproteins in ovarian cancer may contribute to disease pathogenesis", Disease Markers, 25(415), pp. 219-232 (2008).
Sato et al., "Carbohydrates, Lipids, and Other Natural Products: Identification of Oligo-N-Glycolylneuraminic Acid Residues in Mammal-derived Glycoprotiens by a Newly Developed Immunochemical Reagent and Biochemical Methods", J Biol Chem., 273, pp. 2575-2582 (1998).
Schultz et al., "Application of phage display to high throughput antibody generation and characterization," Cancer metastasis reviews, 31, pp. 501-518 (2012).
Schwarz et al., "A new kind of carhohydrate array, its use for profiling antiglycan antibodies, and the discovery of a novel human cellulose-binding antibody", Glycobiology, Oxford Univ. Press, US, vol. 13, No. 11 pp. 749-754 (Nov. 2003).
Steentoft, C. et al., Mining the O-glycoproteome using zinc-finger nuclease-glycoengineered SimpleCell lines. Nat Methds. Oct. 9, 2011;8(11):977-82.
Steinberger et al., 2000, Proc. Natl. Acad. Sci. USA 97:805-810.
Strohl, W.R. Therapeutic Antibody Engineering. Woodhead Publishing, Philadelphia PA. 2012. Ch. 3, p. 47-54.
Studnicka, G.M. et al., Human-engineered monoclonal antibodies retain full specific binding activity by preserving non-CDR complementarity-modulating residues. Protein Eng. Jun. 1994;7(6):805-14.
Takahashi et al. Immunoglobulin G3 Monoclonal Antibody Directed to Tn Antigen(Tumor-associated alpha-N-Acetylgalactasaminyl Epitope) That Does Not Cross-React with Blood Group A Antigen, Cancer Res 1988;48:4361-4367.
Wu, X. et al. (2004) "A New Homobifunctional p-Nitro Phenyl Ester Coupling Reagent for the Preparation of Neoglycoproteins," Organic Letters 6(24), 4407-4410.
Takematsu, H. et al., (1994) "Reaction Mechanism Underlying CMP-N-Acetylneuraminic Acid Hydroxylation in Mouse Liver: Formation of a Ternary Complex of Cytochrome b5, CMP-N-Acetylneuraminic Acid, and a Hydroxylation Enzyme," J. Biochem. (Tokyo) 115(3), 381-386.
Takeshita et al. (Leukemia. Jul. 2009; 23 (7): 1329-36).
Tan, H. T. et al. (2009) "Serum autoantibodies as biomarkers for early cancer detection," FEBS Journal 276(23), 6880-6904.
Toda, M. et al., 2008. Biochem Biophys Res Commun. 372(1):45-50.
Townsend, J.A. et al., High-frequency modification of plant genes using engineered zinc-finger nucleases. Nature. May 21, 2009;459(7245):442-5.
Traving and Schauer "Structure, Function and Metabolism of Sialic Acids." Cell Mol Life Sci, 54(12):1330-1349 (1998).
Tso, P. et al. (1986) "Formation and transport of chylomicrons by enterocytes to the lymphatics," American Journal of Physiology 250(6 Pt 1), G715-726.
Tutt, A. et al., Trispecific F(ab')3 derivatives that use cooperative signaling via the TCR/CD3 complex and CD2 to activate and redirect resting cytotoxic T cells. J Immunol. Jul. 1, 1991;147(1):60-9.
Tzanakakis, et al., "Determination and Distribution of N-Acetyl- and N-Glycolylneuraminic Acids in Culture Media and Cell-Associated Glycoconjugates from Human Malignant Mesothelioma and Adenocarcinoma Cells." Biomed Chromatogr, 20(5):434-439 (2006).
Vajdos et al. (J. Mol. Biol. Jul. 5, 2002; 320 (2): 415-428).
Wu. C.-Y. et al. (2009) New development of glycan arrays, Organic & Biomolecular Chemistry 7(11), 2247-2254.
Vamecq, J. et al., Studies on the metabolism of glycolyl-CoA. Biochem. Cell Biol. vol. 68, 1990, pp. 846-851.
Vamecq, J.et al., Subcellular distribution of glycolyltransferases in rodent liver and their significance in special reference to the synthesis of N-glycolyneuraminic acid. J Biochem vol. 111, 1992, pp. 579-583.
Van Vliet, SJ. et al., 2008. J Immunol. 181(5):3148-55.
Van Vliet, SJ., 2007. Amsterdam: Vrije Universiteit. p. 1-232.
Varki "Sialic Acids in Human Health and Disease." Trends Mol Med, 14(8):351-360 (2008).

(56) References Cited

OTHER PUBLICATIONS

Varki, A. "Loss of N-Glycolylneuraminic Acid in Humans: Mechanisms, Consequences, and Implications for Hominid Evolution" Yearbook of Physical Anthropology 44:54-69 (2001).
Varki, A. et al. (2009) in Essentials of Glycobiology (Varki, A., et al., Eds.), Ch. 14, pp. 199-218, Cold Spring Harbor Laboratory Press, Cold Spring Harbor, NY.
Varki, A. et al., The release and purification of sialic acids from glycoconjugates: methods to minimize the loss and migration of O-acetyl groups. Anal. Biochem. vol. 137, 1984, pp. 236-247.
Varki, A., Glycan-based interactions involving vertebrate sialic-acid-recognizing proteins, Nature 2007 446:1023-1029.
Varki, Ajit; ""Sialic acids such as ligands in recognition phenomena"" The FASEB Journal; Mar. 1997; vol. 111 pp. 248-255.
Varki, N.M. et al., Biomedical differences between human and nonhuman hominids: potential roles for uniquely human aspects of sialic acid biology. Annu Rev Pathol. 2011. 6: 365-393.
Vazquez, A. M. et al., Generation of a murine monoclonal antibody specific for N-glycolylneuraminic acid-containing gangliosides that also recognizes sulfated glycolipids. Hybridoma vol. 14, 1995, pp. 551-556.
Von Mensdorff-Pouilly, S., et al. Reactivity of natural and induced human antibodies to MUC1 mucin with MUC1 peptides and n-acetylgalactosamine (GalNAc) peptides Int J Cancer. Jun. 1, 2000;86(5):702-12.
Wang, B. et al. (2001) ""Concentration and distribution of sialic acid in human milk and infant formulas,"" American Journal of Clinical Nutrition 74(4), 510-515.
Wang, B. et al. (2007) ""Dietary sialic acid supplementation improves learning and memory in piglets,"" American Journal of Clinical Nutrition 85(2), 561-569.
Wang, D., N-glycan Cryptic Antigens as Active Immunological Targets in Prostate Cancer Patients J Proteomics Bioinform vol. 5(4): 090-095 (2012)—090.
Warren, L. 1963. The Distribution of Sialic Acids in Nature. Comp. Biochem. Physiol. 10: 153-71.
Wheeler et al., 2003, FASEB J. 17: 1733-5.
Wirtz and Steipe, 1999, Protein Sci. 8:2245-2250.
Wong, N.S. et al, 2010. An Investigation of Intracellular Glycosylation Activities in CHO Cells: Effects of Nucleotide Sugar Precursor Feeding. Biotechnology and Bioengineering. 107(2):321-36.
Wood, A.J. et al., Targeted genome editing across species using ZFNs and TALENs. Science. Jul. 15, 2011;333(6040):307.
Wright, et al., "Piscine Islet Xenotransplantation." ILAR J, 45(3):314-323 (2004).
Wu, T.T. et al., 1970, JEM, 132(2):211-50.
Yin, J. et al., Hypoxic culture induces expression of sialin, a sialic acid transporter, and cancer-associated gangliosides containing non-human sialic acid on human cancer cells. Cancer Res. Mar. 15, 2006;66(6):2937-45.
Yu et al. (PLoS One. 2012; 7 (3): e33340; pp. 1-15).
Yu, H. et al. (2006) Highly Efficient Chemoenzymatic Synthesis of Naturally Occurring and Non-Natural a-2,6-Linked Sialosides: A P. damsela a-2,6-Sialyltransferase with Extremely Flexible Donor-Substrate Specificity, Angewandte Chemie International Edition 45(24), 3938-3944.
Zhang et al., Cancer research, 2008, 68, 4311-4320.
Zhu et al. Anti-N-glycolylneuraminic acid antibodies identified in healthy human serum. Xenotransplantation. 2002 vol. 9: 376-81.
Zhu et al., 1999. Extended half-life and elevated steady-state level of a single-chain Fv intrabody are critical for specific intracellular retargeting of its antigen, caspase-7. J. Immunol. Methods 231:207-222.
Zoller, Cancer, 2011, 11, 254-267.
International Search Report and Written Opinion received in PCT/US2014/060079 dated Mar. 27, 2015.
International Search Report and Written Opinion received in PCT/US2015/054877 dated Feb. 9, 2016.
International Search Report and Written Opinion received in PCT/US2015/054936 dated Feb. 4, 2016.

Tamura et al. "RNAi-mediated gene silencing of ST6GalNAc I suppresses the metastatic potential in gastric cancer cells," Gastric Cancer, Dec. 23, 2014 (Dec. 23, 2014), vol. 19, Iss. 1, pp. 85-97. entire document.
Yu et al. "Silencing of ST6GalNAc I suppresses the proliferation, migration and invasion of hepatocarcinoma cells thourgh PI3K/AKT/NF-κB pathway," Tumor Biology, May 27, 2016 (May 27, 2016), vol. 37, Iss. 9, pp. 12213-12221. entire document.
Barrow et al. "Suppression of Core 1 Gal-Transferase Is Associated with Reduction of TF and Reciprocal Increase of Tn, sialyl-Tn and Core 3 Glycans in Human Colon Cancer Cells," PLoS One, Mar. 25, 2013 (Mar. 25, 2013), vol. 8, Iss. 3, e59792, pp. 106. entire document.
International Search Report & Written Opinion dated Apr. 14, 2017 in co-pending application No. PCT/US2016/061427, entitled Glycan-Interacting Compounds and Methods of Use.
Gao et al., "Identification of Cancer Stem-like Side Population Cells in Ovarian Cancer Cell Line OVCAR-3," Ultrastructual Pathology, 33, pp. 175-181 (2009).
Han et al., "A2780 human ovarian cancer cells with acquired paclitaxel resistance display cancer stem cell properties," Oncology Letters 6; pp. 1295-1298 (2013).
Ota et al., "Antitumor effect of monoclonal antibody-carboplatin conjugates in nude mice bearing human ovarian cncer cells," Int J Clin Oncol, 4, pp. 236-240 (1999).
Quiles et al., "Synthesis and Preliminary Biological Evaluation of High-Drug-Load-Paclitaxel-Antibody Conjugates for Tumor-Targeted Chemotherapy," J. Med. Chem. 53, pp. 586-594 (2010).
Andreu P; Johansson M; Affara NI et al: 'FcRgamma activation regulates inflammation-associated squamous carcinogenesis' Cancer Cell vol. 17, 2010, pp. 121-134.
Finn, O. J. (2008) "Cancer Immunology," New England Journal of Medicine 358(25), 2704-2715.
Burger RA, et al. (2011) Incorporation of bevacizumab in the primary treatment of ovarian cancer. N Engl J Med; 365:2473-83.
Cazet A, et al. (2010) Consequences of the expression of sialylated antigens in breast cancer. Carbohydr Res. 345(10), 1377-83.
Chothia, C. et al. (1992) Structural repertoire of the human VH segments. J Mol Biol. Oct. 5;227(3):799-817.
Christiansen, M. N. et al. (2014). Cell surface protein glycosylation in cancer. Proteomics 14, 525-46.
Fuster MM & Esko JD. (2005) The sweet and sour of cancer: glycans as novel therapeutic targets. Nat Rev Cancer. July;5(7):526-42.
Hakomori S. (2001) Tumor-associated carbohydrate antigens defining tumor malignancy: basis for development of anti-cancer vaccines. Adv Exp Med Biol 491, 369-402.
Hauselmann, I.(2014). Altered Tumor-Cell Glycosylation Promotes Metastasis. Front. Oncol. 4, 28.
Holmberg LA & Sandmaier BM. (2004) Vaccination with Theratope (STn-KLH) as treatment for breast cancer. Expert Rev Vaccines; 3:655-63.
Imada T, et al. (1999) Sialyl Tn antigen expression is associated with the prognosis of patients with advanced colorectal cancer. Hepatogastroenterology 46, 208-14.
Ju T, et al. (2014) The Cosmc connection to the Tn antigen in cancer. Cancer Biomark; 14:63-81.
Greene, K. L. et al. (2009) "Prostate Specific Antigen Best Practice Statement: 2009 Update," The Journal of Urology 182(5), 2232-2241.
Ju, T. et al. (2013).Tn and SialylTn antigens, Aberrant O-glycomics as Human Disease Markers. Proteomics Clin Appl 1-26. doi:10.1002/prca.201300024.1).
Katari, R. S., et al. (1990) Characterization of the shed form of the human tumor-associated glycoprotein (TAG-72) from serous effusions of patients with different types of carcinomas. Cancer Res. 50, 4885-90.
Padler-Karavani, V. (2014) Cancer Lett. Sep. 28;352(1):102-12.
Reddish, M. a et al. (1997) Specificities of anti-sialyl-Tn and anti-Tn monoclonal antibodies generated using novel clustered synthetic glycopeptide epitopes. Glycoconj. J. 14, 549-60.
Sedlacek, HH. et al. (1977) Neuraminidase and tumor immunotherapy. Klin Wochenschr. Mar. 1;55(5):199-214.

(56) References Cited

OTHER PUBLICATIONS

Gupta, D. and Lis, C. (2009) "Role of CA125 in predicting ovarian cancer survival—a review of the epidemiological literature," Journal of Ovarian Research 2(1), 13.
Zhang B, et al. (2011) An overview of biomarkers for the ovarian cancer diagnosis. Eur. J. Obstet. Gynecol. Reprod. Biol. 158, 119-23.
Cao Y et al. (2008) Expression of CD175 (Tn), CD175s (sialosyl-Tn) and CD176 (Thomsen-Friedenreich antigen) on malignant human hematopoietic cells. Int J Cancer Jul. 1, 2008;123(1):89-99.
Pant KD et al. (2008) Immunohistochemical examination of anti-STn monoclonal antibodies LLU9B4, B723, and B35.2 for their potential use as tumor markers. Dig Dis Sci. Aug. 2008;53(8):2189-94.
Carrascal, M.A. et al. (2014) Mol. Oncol.S1574-7891(14)00047-7.
Hara, S. et al. (1986) "Highly sensitive determination of N-acetyl- and N- glycolylneuraminic acids in human serum and urine and rat serum by reversed-phase liquid chromatography with fluorescence detection," Journal of chromatography A 377, 111-119.
Varki, A. (2010) ""Uniquely human evolution of sialic acid genetics and biology,"" Proceedings of the National Academy of Sciences 107(Supplement 2), 8939-8946.
Yu, H. et al. (2005) A Multifunctional Pasteurella multocida Sialyltransferase: A Powerful Powerful Tool for the Synthesis of Sialoside Libraries, Journal of the American Chemical Society 127(50), 17618-17619.
Yu, H. et al. (2006) One-pot three-enzyme chemoenzymatic approach to the synthesis of sialosides containing natural and non-natural functionalities. Nature Protocols 1(5), 2485-2492.
Johansen, E. et al. (2009) "A Lectin HPLC Method to Enrich Selectively-glycosylated Peptides from Complex Biological Samples," Journal of Visualized Experiments(32), 1398.
Perez, H. L. et al. (2014) Antibody-drug conjugates: current status and future directions. Drug Discov. Today 19, 869-881.
Krishn, S. R. et al. (2017) Mucins and associated O-glycans based immunoprofile for stratification of colorectal polyps: clinical implication for improved colon surveillance. Oncotarget 1-2. doi:10.18632/oncotarget.1234.
Reis CA et al (1999) Intestinal metaplasia of human stomach displays distinct patterns of mucin (MUC1, MUC2, MUC5AC, and MUC6) expression. Cancer Res. Mar. 1, 1999;59(5):1003-7.
Schlom, J. et al. (1989) Tumor targeting with monoclonal antibody B72.3. Int. J. Rad. Appl. Instrum. B. 16, 137-42.
Schlom, J. et al. (1990) Tumor targeting with monoclonal antibody B72.3: experimental and clinical results. Cancer Treat Res. 51, 313-35.
Tiller et al. (2013) A fully synthetic human Fab antibody library based on fixed VH/VL framework pairings with favorable biophysical properties. mAbs 5(3): 445-470.
Zhang, S. et al. (1995) Immune sera and monoclonal antibodies define two configurations for the sialyl Tn tumor antigen. Cancer Res. 55, 3364-8.
Acres et al., Expert review of vaccines,2005, 4, 493-502.
Alderson, K.L. et al., J Biomed Biotechnol. 2011. 2011:379123.
Ju, T. et al. (2008) "Human Tumor Antigens Tn and Sialyl Tn Arise from Mutations in Cosmc," Cancer Research 68(6), 1636-1646.
Allavena, P. et al., Clin Dev Immunol. 2010;2010:547179.
Al-Lazikani, B. et al., 1997, J. Mol. Biol. 273(4):927-48.
Ames, R.S. et al., Conversion of murine Fabs isolated from a combinatorial phage display library to full length immunoglobulins. J Immunol Methods. Aug. 18, 1995;184(2):177-86.
Angata, T. et al. (2002) "Chemical Diversity in the Sialic Acids and Related α-Keto Acids: An Evolutionary Perspective," Chemical Reviews 102(2), 439-470.
Arafat et al., 2000, Cancer Gene Ther. 7:1250-6.
Asaoka, H. et al. "Two chicken monoclonal antibodies specific for heterophil Hanganutziu-Deicher antigens." Immunol. Lett vol. 32, 1992, pp. 91-96.
Bapat, S. A. (2010) Human ovarian cancer stem cells. Reproduction 140, 33-41.

Benoit et al., Synthesis of folate-functionalized RAFT polymers for targeted siRNA delivery Biomacromolecules. 2011 12:2708-2714.
Bergfeld, A. K. et al. (2012) ""Metabolism of Vertebrate Amino Sugars with N-Glycolyl Groups: Elucidating the Intracellular Fate of the Non-Human Sialic Acid N-Glycolylneuraminic Acid,"" Journal of Biological Chemistry 287(34), 28865-28881.
Kim, Y. and Varki, A. (1997) "Perspectives on the significance of altered glycosylation of glycoproteins in cancer," Glycoconjugate Journal 14(5), 569-576.
Bernard et al. (Human Immunol. 1986; 17: 388-405).
Bibikova, M. et al., Enhancing gene targeting with designed zinc finger nucleases. Science. May 2, 2003;300(5620):764.
Van Leeuwen, P. J. et al. (2010) "Prostate cancer mortality in screen and cliically detected prostate cancer: Estimating the screening benefit," European Journal of Cancer 46(2), 377-383.
Hedlund, M. et al. (2008) "Evidence for a human-specific mechanism for diet and antibody-mediated inflammation in carcinoma progression," Proceedings of the National Academy of Sciences 105(48), 18936-18941.
Du, J. et al. (2009) "Metabolic glycoengineering: Sialic acid and beyond," Glycobiology 19(12), 1382-1401.
Yonezawa. S. et al. (1992) Sialosyl-Tn antigen. Its distribution in normal human tissues and expression in adenocarcinomas., American journal of clinical pathology 98(2), 167-174.
Liu, C.C. et al. (2009) "Integrative disease classification based on cross-platform microarray data," BMC Bioinformatics 10 Suppl 1:S25.
Saldova, R. et al., 'Glycosylation changes on serum glycoproteins in ovarian cancer may contribute to disease pathogenesis' Dis Markers vol. 25, 2008, pp. 219-232.
An, H. J . et al. (2009) Glycomics and disease markers. Current Opinion in Chemical Biology 13(5-6), 601-607.
Oyelaran O; Mcshane LM; Dodd L; Gildersleeve JC: 'Profiling human serum antibodies with a carbohydrate antigen microarray' J Proteome Res. vol. 8, 2009, pp. 4301-4310.
Naito, Y. et al., 2007. Germinal center marker GL7 probes activation-dependent repression of N-glycolylneuraminic acid, a sialic acid species involved in the negative modulation of B-cell activation. Mol Cell Biol. Apr. 2007;27(8):3008-22.
De Leén, J. et al. (2008) "Differential influence of the tumour-specific non-human sialic acid containing GM3 ganglioside on CD4+CD25? effector and naturally occurring CD4+CD25+ regulatory T cells function," International Immunology 20(4), 591-600.
Dube, D. H. and Bertozzi, C. R. (2005) "Glycans in cancer and inflammation—potential for therapeutics and diagnostics," Nature Reviews Drug Discovery 4(6), 477-488.
Devine, P. L. et al. (1991) "The Breast Tumor-associated Epitope Defined by Monoclonal Antibody 3E1.2 Is an O-linked Mucin Carbohydrate Containing N-Glycolylneuraminic Acid," Cancer Research 51(21), 5826-5836.
Díaz, A. et al., (2003) "Immune responses in breast cancer patients immunized with an anti-idiotype antibody mimicking NeuGc-containing gangliosides," Clin. Immunol. 107(2), 80-89.
Inoue, S. et al., (2010) "Extensive enrichment ofN-glycolylneuraminic acid in extracellular sialoglycoproteins abundantly synthesized and secreted by human cancer cells," Glycobiology 20(6), 752-762.
Kim, G. E. et al. (2002) "Aberrant expression of MUC5AC and MUC6 gastric mucins and sialyl Tn antigen in intraepithelial neoplasms of the pancreas," Gastroenterology 123(4), 1052-1060.
Kobayashi, H. et al. (1992) "Serum sialyl Tn as an independent predictor of poor prognosis in patients with epithelial ovarian cancer," Journal of Clinical Oncology 10(1), 95-101.
Ogata, S. et al. (1998) "Different modes of sialyl-Tn expression during malignant transformation of human colonic mucosa," Glycoconjugate Journal 15(1), 29-35.
Slovin, S. F. et al. (2005) "Carbohydrate vaccines as immunotherapy for cancer," Immunology & Cell Biology 83(4), 418-428.
Stacker, S. A. et al., (1985) "A new breast carcinoma antigen defined by a monoclonal antibody," J. Natl. Cancer Inst. 75(5), 801-811.
Ferris, R. L. et al. (2010) "Tumor Antigen-Targeted, Monoclonal Antibody-Based Immunotherapy: Clinical Response, Cellular Immunity, and Immunoescape," Journal of Clinical Oncology 28(28), 4390-4399.

(56) References Cited

OTHER PUBLICATIONS

Zhang, D.Y. et al. (2009) "Proteomics, pathway array and signaling network-based medicine in cancer," Cell Division 4(1), 20.
Padler-Karavani, V. et al., Human xeno-autoantibodies against a non-human sialic acid serve as novel serum biomarkers and immunotherapeutics in cancer Cancer Res. May 1, 2011;71(9):3352-63.
Andergassen, U. et al.(2015). Glycosyltransferases as Markers for Early Tumorigenesis. Biomed Res. Int. 792672.
Büll, C. et al. (2014) Sialic acids sweeten a tumors life. Cancer Res. Jun. 15;74(12):3199-204.
Extended European Search Report dated Jul. 17, 2019 in corresponding European Patent Application No. 16865044.8.
International Search Report and Written Opinion received in PCT/US2018/020562 dated Jun. 27, 2018.
First Examiner's Report dated Feb. 19, 2018 in corresponding Canadian Patent Application No. 2,967,595.
Partial Supplementary European Search Report dated May 7, 2018 in corresponding European Patent Application No. 15859152.9.
Ola Blixt: "Glycan Microarray Analysis of Tumor-Associates Antibodies" In: Paul Kosma (edit.): "Anticharbohydrate Antibodies", Nov. 27, 2011 (Nov. 27, 2011), Springer-Verlag, Wien, XP002780306, ISBN: 978-3-7091-0869-7, pp. 290-293.
K Meetze et al: "The discovery and development of potent and specific anti-SialylTn antibodies for the treatment of solid tumors (479)", European Journal of Cancer, vol. 50, No. suppl. 6, Nov. 1, 2014 (Nov. 1, 2014), p. 156, XP055365195.
Braun D P et al "Aromatase inhibitors increase the sensitivity of human tumor cells to monocyte-mediated, antibody-dependent cellular cytotoxicity", American Journal of Surgery, Paul Hoeber, New York, NY, US, vol. 190, No. 4, Oct. 1, 2005 (Oct. 1, 2005), pp. 570-571.
Welinder Charlotte et al: "A new murine IgG1 anti-Tn monoclonal antibody with in vivo anti-tumor activity.", Glycobiology Aug. 2011, vol. 21, No. 8, Aug. 2011 (Aug. 2011), pp. 1097-1107.
Jillian M. Prendergast et al: "Novel anti-Sialyl-Tn monoclonal antibodies and antibody-drig conjugates demonstrate tumor specificity and anti-tumor activity", MABS, Feb. 22, 2017 (Feb. 22, 2017), pp. 1-13.
Kirkeby S et al: "MUC1 and the simple mucin-type antigens: Tn and Sialyl-Tn are differently expressed in salivary gland acini and ducts from the submandibular gland, the vestibular folds, and the soft palate", Archives of Oral Biology, Pergamon Press, Oxford, GB, vol. 55, No. 11, Nov. 1, 2010 (Nov. 1, 2010), pp. 830-841.
Extended European Search Report dated Aug. 16, 2018 in corresponding European Patent Application No. 15859152.9.
Deshayes et al., Cell-penetrating peptides: tools for intracellular delivery of therapeutics. Cell. Mol. Life Sci. 62(16):1839-49 (2005).
Dharmawardhane, S. et al., Regulation of macropinocytosis by p21-activated kinase-1. Mol Biol Cell. Oct. 2000;11(10):3341-52.
Doyon, Y. et al., Heritable targeted gene disruption in zebrafish using designed zinc-finger nucleases. Nat Biotechnol. Jun. 2008;26(6):702-8.
Eckhardt, A. E. et al. (1997) ""The Complete cDNA Sequence and Structural Polymorphism of the Polypeptide Chain of Porcine Submaxillary Mucin,"" Journal of Biological Chemistry 272(52), 33204-33210.
Edwards, B.M. et al., 2003. JMB. 334: 103-18.
El-Andaloussi et al., Cell-penetrating peptides: mechanisms and applications Curr. Pharm. Des. 11(28):3597-611 (2003).
Marcial, V. A. (1977) "Carcinoma of the cervix. Present status and future," Cancer 39(Supplement S2), 945-958.
Engelmann et al., Cancer research, 2008, 68, 2419-2426.
Eppstein, D.A. et al., Biological activity of liposome-encapsulated murine interferon gamma is mediated by a cell membrane receptor. Proc Natl Acad Sci U S A Jun. 1985;82(11):3688-92.
Ferreira et al., Molecular oncology, 2013, 7, 719-731.
Finney, et al., J. Immunology, 2004, 172:104-113.
Foster et al., Cancer letters, 2013, 338, 147-157.
Fujii, Y. et al., Specificities of human heterophilic Hanganutziu and Deicher (H-D) antibodies and avian antisera against H-D antigen-active glycosphingolipids. Mol. Immunol. vol. 19, 1982, pp. 87-94.
Furukawa, K. et al., Analysis of the expression of N-glycolylneuraminic acid-containing gangliosides in cells and issues using two human monoclonal antibodies. J Biol. Chem. vol. 263, 1988, pp. 18507-18512.
Geurts, A.M. et al., Knockout rats via embryo microinjection of zinc-tinger nucleases. Science. Jul. 24, 2009;325(5939):433.
Ghaderi et al. "Production platforms for biotherapeutic glycoproteins. Occurrence, impact, and challaenges of non-human sialyation," Biotechnology and Genetic Engineering Reviews, Apr. 15, 2013 (Apr. 15, 2013), vol. 26, pp. 147-176.
Gill et al., Proceedings of the National Academy of Sciences of the United States of America 2013, 110, E3152-3161.
Gillies, S.D. et al., High-level expression of chimeric antibodies using adapted cDNA variable region cassettes. J Immunol Methods. Dec. 20, 1989;125(1-2):191-202.
Giusti et al. (Proc. Natl. Acad. Sci. USA. May 1987; 84 (9): 2926-2930).
20 Goodman, M. The genomic record of Humankind's evolutionary roots. Am. J. Hum. Genet. vol. 64, 1999, pp. 31-39.
Graille, M.G. et al., 2000. Crystal structure of a *Staphylococcus aureus* protein A domain complexed with the Fab fragment of a human IgM antibody: Structural basis for recognition of B-cell receptors and superantigen activity. PNAS. 97(10): 5399-404.
Gupta et al., Nature medicine, 2009, 15, 1010-1012.
Gussow et al. (Methods in Enzymology. 1991; 203: 99-121).
Hamilton, T.C. et al., 1983. Cancer Res. 43: 5379-89.
Hassanzadeh, et al., 1998, FEBS Lett. 437:81-6.
Hayakawa, T. et al. (2001) ""Alu-mediated inactivation of the human CMP-N-acetylneuraminic acid hydroxylase gene,"" Proceedings of the National Academy of Sciences 98(20), 11399-11404.
Nelson, A. E. et al. (2009) "Population screening and early detection of ovarian cancer in asymptomatic women," Australian & New Zealand Journal of Obstetrics & Gynaecology 49(5), 448-450.
Hedlund, M. et al. (2007) ""N-Glycolylneuraminic Acid Deficiency in Mice: Implications for Human Biology and Evolution,"" Molecular and Cellular Biology 27(12), 4340-4346.
Heimburg-Molinaro, J. et al., Cancer vaccines and carbohydrate epitopes. Vaccine. Nov. 8, 2011;29(48):8802-26.
"Heiskanen, et al., N-Glycolylneuraminic Acid Xenoantigen Contamination of Human b202 (2007)."
Henry et al. (Cancer Res. Nov. 1, 2004; 64: 7995-8001).
"Higashi, et al. ""Detection of Gangliosides as N-Glycolylneuraminic Acid-Specific Tumor-Associated Hanganutziu-Deicher Antigen in Human Retinoblastoma Cells."" Jpn J Cancer Res, 79(8):952-956 (1988)."
Higashi, H. et al., Antigen of "serum sickness" type of heterophile antibodies in human sera: indentification as gangliosides with N-glycolylneuraminic acid. Biochem. Biophys. Res. Comm. vol, 79, 1977, pp. 388-395.
Hligashi, H. et al., Characterization of N-glycolylneuraminic acid-containing gangliosides as tumor-associated Hanganutziu-Deicher antigen in human colon cancer.. Cancer Res. Aug. 1985;45(8):3796-802.
Hirabayashi Y et al: "A new method for purification of anti-glycosphingolipid antibody. Avian anti-hematoside (NeuGc) antibody" Journal of Biochemistry, Japanese Biochemical Society OUP, Tokyo; JP, vol. 94, No. 1, Jul. 1, 1983 (Jul. 1, 1983), pp. 327-330.
Hirabayashi Y et al: "Occurrence of Tumor-Associated Ganglioside Antigens With Hanganutziu-Deicher Antigenic Activity on Human Melanomas" Japanese Journal of Cancer Research, Japanese Cancer Association, Tokyo, JP, vol. 78, No. 6, Jan. 1, 1987 (Jan. 1, 1987), pp. 614-620, XP008127779 ISSN: 0910-5050.
Hirabayashi, et al. "Specific Expression of Unusual Gm2 Ganglioside with Hanganutziu-Deicher Antigen Activity on Human Colon Cancers." 78(3):251-260 (1987).
Hojman, Basic principles and clinical advancements of muscle electrotransfer Curr Gene Ther. 2010 10:128-138.
Hollinger et al., Diabodies: Small bivalent and bispecific antibody fragments. Proc. Natl. Acad. Sci. USA, 90:6444-6448 (1993).
Holm et al. (Mol. Immunol. Feb. 2007; 44 (6): 1075-1084).

(56) References Cited

OTHER PUBLICATIONS

Honegger, A. and Pluckthun, A. 2001. J. Mol. Biol. 309(3):657-70.
"Hong and Stanley, ""Lec3 Chinese Hamster Ovary Mutants Lack UDP-N-Acetylglucosamine 2-Epimerase Activity Because of Mutations in the Epimerase Domain of the Gne Gene."" J Biol Chem, 278(52):53045-53054 (2003)."
Nguyen, D. H. et al. (2005) "Effects of Natural Human Antibodies against a Nonhuman Sialic Acid That Metabolically Incorporates into Activated and Malignant Immune Cells," The Journal of Immunology 175(1), 228-236.
Hossler et al, Glycobiology, vol. 19, No. 9, pp. 936-949, 2009, Optimal and consistent protein glycosylation in mammalian cell culture.
Huston, J.S. et al., Protein engineering of single-chain Fv analogs and fusion proteins. Methods Enzymol. 1991;203:46-88.
Hwang, K.J. et al., Hepatic uptake and degradation of unilamellar sphingomyelincholesterol liposomes: a kinetic study. Proc Natl Acad Sci U S A. Jul. 1980;77(7):4030-4.
Ibrahim et al., Journal of clinical oncology: official journal of the American Society of Clinical Oncology, 2004, 22, 2547.
Ibrahim, N.K. et al., 2013. 4(7): 577-584.
Ikehara, Y. et al., Cloning and expression of a human gene encoding an N-acetylgalactosamine-alpha2,6-sialyltransferase (ST6GalNAc I): a candidate for synthesis of cancer-associated sialyl-Tn antigens. Glycobiology. Nov. 1999;9(11):1213-24.
Irie, A. et al: "The Molecular Basis for the Absence of N-Glycolylneuraminic Acid in Humans", Journal of Biological Chemistry, vol. 273, No. 25, Jun. 19, 1998 (Jun. 19, 1998), pp. 15866-15871.
An et al., "A Novel Anti-STn Monoclonal Antibody 3P9 Inhibits Human Xenografted Colorectal Carcinomas," J Immunother, vol. 36, No. 1 pp. 20-28 (2013).
Eavarone et al., "Novel Humanized anti-Sialyl-Tn, anti-CD3 bispecific antibodies demostrate tumor and T-cell specificity for immune activation at the tumor site," Cancer Research, vol. 77, No. Suppl. 13, p. 3640, Jul. 2017, and Annual Meeting of the AACR, Washington DC on Apr. 1-5, 2017.
Eaverone et al., "Abstract LB-221: Novel anti-Sialyl-Tn monoclonal antibodies and antibody-drug conjugates (ADCs) demonstrate tumor specificity, unique sequence homology and in vitro and in vivo antitumor efficacy," AACR 107 4nnual Meeting 2016, Apr. 16-20, 2016, New Orleans, LA, AACR; Cancer Res 2016, vol. 76, 14 Suppl (4 pages).
Extended European Search Report for European Application No. 17871763.3, dated May 29, 2020 (9 pages).
Extended European Search Report in European Application No. 17872341.7, dated May 27, 2020 (8 pages).
Numa et al., "Tissue Expression of Siayl Tn Antigen in Gynecologic Tumors," J. Obstet. Gynacol. vol. 21, No. 4 pp. 385-389 (1995).
Prendergast et al: "Abstract 36: Novel anti-Sialyl-Tn monoclonal antibodies and antibody-drug conjugates (ADCs) demonstrate tumor specificity in vitro and in vivo antitumor efficacy," AACR Annual Meeting 2017, Apr. 1-5, 2017, Washington, DC., AACR, vol. 77, Issue 13 Supplement (4 pages).
Shi et al., "Sialyl-Tn 1 Polysaccharide A1 as an Entirely Carbohydrate Immunogen: Synthesis and Immunological Evaluation," Journal of American Chemical Society, vol. 138, No. 43, pp. 14264-14272 (Oct. 21, 2016).
Examiner's Report dated Mar. 8, 2019 in corresponding Canadian Patent Application No. 2,967,595.
Partial Supplementary European Search Report for corresponding European Application No. 16865044.8 dated May 3, 2019 entitled "Glycan-Interacting Compounds and Methods of Use".
Al-Alem et al., "Abstract LB-229: Utilizing a novel highly specific sialyl-Tn ELISA as a diagnostic for ovarian cancer," Cancer Research, vol. 79, Issue 13 supplement, Jul. 2019 (2 pages).
Amon et al., "A combined computational experimental approach to define the structural origin of antibody recognition of sialyl-Tn, a tumor associatedcarbohydrate antigen," Scientific Reports, 8:107086, Feb. 2018 (12 pages).

Brinkman-Van der Linden et al., "CD33/Siglec-3 Binding Specificity, Expression Pattern, and Consequences of Gene Deletion in Mice," Molecular and Cellular Biology, vol. 23, No. 12, Jun. 2003, p. 4199-4206 (8 pages).
Dransfield et al., "Abstract B28: Targeting the tumor-associated carbohydrate antigen STn with humanized anti-Sialyl-Tn monoclonal antibody-drug conjugates inhibits ovarian cancer tumor growth in vitro and in vivo," Clinical Cancer Research, vol. 24, Issue 15 supplement, Aug. 2018 (2 pages).
Dransfield, et al. Abstract B114: Humanized anti-Sialyl-Tn monoclonal antibody-drug conjugates inhibit tumor growth in vitro and invivo. Molecular Cancer Therapeutics, Jan. 1, 2018, vol. 17, Issue 1 Supplement (2 pages).
Eavarone et al. "Abstract 5625: Myeloid derived suppressor cells (MDSCs) express Sialyl Tn (STn) and are a therapeutic target for anti-STn antibody drug conjugates," Cancer Research, vol. 78, Issue 13 supplement, Jul. 2018 (2 pages).
Eavarone et al., "Abstract 3640: Novel humanized anti-Sialyl-Tn, anti-CD3 bispecific antibodies demonstrate tumor and T-cell specificity for immuneactivation at the tumor site," Cancer Research, vol. 77, Issue 13 supplement, Jul. 2017 (2 pages).
Jimeno et al., "Poster 478 Pharmacological disruption of the Astrocytic Elevated Gene-1 (AEG1) in anticancer Intervention: PB0412_3 (PB03) as a first-in-class AEG1 interacting agent," Poster Session—Molecular Targeted Agents II, European Journal of Cancer, 50(6):156, Nov. 21, 2014 (1 page).
Kim et al., Abstract: "Session III: Translational Research/Basic Science—I Tetrathiomolybdate mediates the degradation of hypoxia-inducible,factor-1α," Abstracts, Gynecologic Oncology 139 (2015) (1 page).
Kristo et al., Abstract e24279: "Tumor associated carbohydrate antigens in prostatic adenocarcinoma (PAC): Correlation of sialyl-Tn with malignant phenotype," Journal of Clinical Oncology, 36, No. 15 supplemental, Jun. 1, 2018 (2 pages).
Padler-Karavani et al., "Abstract 67: Expression and antigenicity of tumor-associated Neu5Gc-containing O-glycans in human carcinomas," Conference Abstracts, Joint Meeting of the Society for Glycobiology & American Society for Matrix Biology, Glycobiology, vol. 22, Issue 11, p. 1542, Nov. 1, 2012 (1 page).
Padler-Karavani et al., "Expression of the tumor-associated antigen Neu5Gc-Sialyl-Tn in human carcinomas," J Immunol May 1, 2012, 188 (1 Supplement) 74.6 (2 pages).
Patel et al., "OB-BP1/Siglec-6, A Leptin- and Sialic Acid-Binding Protein of the Immunoglobulin Superfamily," The Journal of Biological Chemistry, vol. 274, No. 32, Issue 6, pp. 22729-22738, Apr. 9, 1999 (10 pages).
Prendergast et al., "Novel anti-Sialyl-Tn monoclonal antibodies and antibody-drug conjugates demonstrate tumor specificity and anti-tumor activity," Mabs, vol. 9, No. 4, pp. 615-627; 2017 (13 pages).
Prendergast et al., Abstract 183: "Novel anti-Sialyl-Tn monoclonal antibodies and antibody drug conjugates (ADCs) target a cancer stem cell population and demonstrate in vitro and in vivo anti-tumor efficacy," Program and Abstracts for 2016 Annual Meeting of the Society for Glycobiology, Glycobiology, vol. 26, Issue 12, p. 1499, Dec. 1, 2016 (1 page).
Rueda et al., "Abstract MIP-071: Targeting a Chemoresistant Ovariancancer Cell Population Via the Carbohydrate Antigensialyl Tn," Clinical Cancer Research, vol. 23, Issue 11, Jun. 2017 (2 pages).
Starbuck et al., "Treatment of ovarian cancer by targeting the tumor stem cell associated carbohydrate antigen, Sialyl-Thomsen-nouveau," Oncotarget, 2018, vol. 9, (No. 33), pp: 23289-23305 (17 pages).
Agarwal et al., "Site-Specific Antibody-Drug Conjugates: The Nexus of Biorthogonal Chemistry, Protein Engineering, and Drug Development," Bioconjugate Chem., 2015, 26, 176-192 (17 pages).
Dorywalska et al., "Effect of Attachment Site on Stability of Cleavable Antibody Drug Conjugates," Bioconjugate Chem., 2015, 26, 650-659 (10 pages).
McCombs et al., "Antibody Drug Conjugates: Design and Selection of Linker, Payload and Conjugation Chemistry," The AAPS Journal, vol. 17, No. 2, Mar. 2015, 339-351 (13 pages).

(56) References Cited

OTHER PUBLICATIONS

Partial Extended Search Report issued in European Patent Application No. 18760528.2, dated Mar. 16, 2021 (21 pages).

* cited by examiner

STn Binding Specificity (Group 1)

Detected epitope (largest ellipse)

STn Binding Specificity (Group 2)

Detected epitope (largest ellipse)

STn Binding Specificity (Group 3)

Detected epitope (largest ellipse)

STn Binding Specificity (Group 4)

Detected epitope (largest ellipse)

Fig. 2

Variable domain

| FR1 | CDR1 | FR2 | CDR2 | FR3 | CDR3 | FR4 |

FR = Framework region
CDR = Complimentarity determining region

SEQUENCE LISTING

```
<160> NUMBER OF SEQ ID NOS: 266

<210> SEQ ID NO 1
<211> LENGTH: 115
<212> TYPE: PRT
<213> ORGANISM: Mus sp.

<400> SEQUENCE: 1

Gln Val Gln Leu Leu Gln Tyr Asp Ala Glu Leu Val Lys Pro Gly Gly
1               5                   10                  15

Ser Val Lys Ile Ser Cys Lys Ala Ser Gly Tyr Thr Phe Thr Asp His
            20                  25                  30

Ala Ile His Trp Val Lys Gln Lys Pro Glu Gln Gly Leu Glu Trp Ile
        35                  40                  45

Gly Tyr Phe Ser Pro Gly Asn Asp Asp Ile Lys Tyr Ser Glu Lys Phe
    50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Lys Arg Ser Ile Thr Thr Pro Tyr Trp Gly Gln Gly Thr Leu Val Thr
            100                 105                 110

Val Ser Ala
        115

<210> SEQ ID NO 2
<211> LENGTH: 106
<212> TYPE: PRT
<213> ORGANISM: Mus sp.

<400> SEQUENCE: 2

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Tyr Lys Val Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Asp Gln Ser Tyr Pro Tyr
                85                  90                  95

Thr Phe Gly Gly Gly Thr Lys Leu Lys Lys
```

<210> SEQ ID NO 3
<211> LENGTH: 115
<212> TYPE: PRT
<213> ORGANISM: Mus sp.

<400> SEQUENCE: 3

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Lys Pro Glu Gln Gly Leu Glu Trp Ile
        35                  40                  45

Gly Tyr Ile Ser Pro Gly Asn Asp Asp Ile Lys Tyr Asn Glu Lys Phe
    50                  55                  60

Lys Gly Lys Ala Thr Leu Thr Ala Asp Lys Ser Ser Thr Ala Tyr
65                  70                  75                  80

Met Gln Leu Asn Ser Leu Thr Ser Glu Asp Ser Ala Val Tyr Phe Cys
                85                  90                  95

Lys Arg Ser Ile Thr Thr Ser Tyr Trp Gly Gln Gly Thr Leu Val Thr
            100                 105                 110

Val Ser Ala
        115

<210> SEQ ID NO 4
<211> LENGTH: 108
<212> TYPE: PRT
<213> ORGANISM: Mus sp.

<400> SEQUENCE: 4

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Ile Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys Arg
            100                 105

<210> SEQ ID NO 5
<211> LENGTH: 115
<212> TYPE: PRT
<213> ORGANISM: Mus sp.

<400> SEQUENCE: 5

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Lys Pro Glu Gln Gly Leu Glu Trp Ile
        35                  40                  45

```
Gly Tyr Val Ser Pro Gly Asn Gly Asp Ile Lys Tyr Asn Glu Lys Phe
        50                  55                  60

Lys Gly Lys Ala Thr Leu Thr Ala Asp Lys Ser Ser Thr Ala Tyr
65                  70                  75                  80

Met Gln Leu Asn Ser Leu Thr Ser Glu Asp Ser Ala Val Tyr Phe Cys
                85                  90                  95

Lys Arg Ser Leu Ile Gly Asp Tyr Trp Gly Gln Gly Thr Thr Leu Thr
                100                 105                 110

Val Ser Ser
        115

<210> SEQ ID NO 6
<211> LENGTH: 107
<212> TYPE: PRT
<213> ORGANISM: Mus sp.

<400> SEQUENCE: 6

Asp Ile Val Met Thr Gln Ser Gln Lys Phe Met Ser Ser Val Gly
1               5                   10                  15

Asp Arg Val Thr Ile Thr Cys Lys Ala Ser Gln Asn Val Gly Thr Ala
                20                  25                  30

Val Ala Trp Tyr Gln Gln Lys Pro Gly Gln Ser Pro Lys Phe Leu Ile
            35                  40                  45

Tyr Ser Ala Ser Asn Arg Tyr Thr Gly Val Pro Asp Arg Phe Thr Gly
        50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Ser Ser Tyr Arg Leu
                85                  90                  95

Thr Phe Gly Gly Gly Thr Lys Leu Glu Ile Lys
                100                 105

<210> SEQ ID NO 7
<211> LENGTH: 115
<212> TYPE: PRT
<213> ORGANISM: Mus sp.

<400> SEQUENCE: 7

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
                20                  25                  30

Ala Ile His Trp Val Lys Gln Lys Pro Glu Gln Gly Leu Glu Trp Ile
            35                  40                  45

Gly Tyr Leu Ser Pro Gly Asn Asp Asp Ile Lys Tyr Ser Glu Lys Phe
        50                  55                  60

Lys Asp Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Lys Arg Ser Ile Gly Gly Asp His Trp Gly Gln Gly Thr Thr Leu Thr
                100                 105                 110

Val Ser Ser
        115

<210> SEQ ID NO 8
```

```
<211> LENGTH: 108
<212> TYPE: PRT
<213> ORGANISM: Mus sp.

<400> SEQUENCE: 8

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Asn Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
50                  55                  60

Ser Gly Ser Gly Thr Gly Phe Thr Leu Thr Ile Gly Ser Leu Gln Pro
65                  70                  75                  80

Glu Asp Ile Ala Thr Tyr Tyr Cys Gln Gln Gly Gln Ser Tyr Pro Phe
                85                  90                  95

Thr Phe Gly Gly Gly Thr Lys Leu Glu Ile Lys Arg
            100                 105

<210> SEQ ID NO 9
<211> LENGTH: 115
<212> TYPE: PRT
<213> ORGANISM: Mus sp.

<400> SEQUENCE: 9

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Lys Pro Glu Gln Gly Leu Glu Trp Ile
        35                  40                  45

Gly Tyr Ile Ser Pro Gly Asn Gly Asp Ile Lys Tyr Asn Glu Lys Phe
50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Gln Arg Gln Leu Gly Gly Tyr Trp Gly Gln Gly Thr Thr Leu Thr
            100                 105                 110

Val Ser Ser
        115

<210> SEQ ID NO 10
<211> LENGTH: 113
<212> TYPE: PRT
<213> ORGANISM: Mus sp.

<400> SEQUENCE: 10

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Tyr Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
50                  55                  60
```

-continued

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr His Val Pro Tyr Thr Phe Gly Gly Gly Thr Lys Leu Glu Ile Lys
            100                 105                 110

Arg

<210> SEQ ID NO 11
<211> LENGTH: 115
<212> TYPE: PRT
<213> ORGANISM: Mus sp.

<400> SEQUENCE: 11

Gln Val Gln Leu Gln Gln Ser Asp Ala Glu Leu Gly Lys Pro Gly Ala
1               5                   10                  15

Ser Val Lys Ile Ser Cys Lys Ala Ser Gly Tyr Thr Phe Ser Asp His
                20                  25                  30

Ala Ile His Trp Val Lys Gln Lys Pro Glu Gln Gly Leu Glu Trp Ile
            35                  40                  45

Gly Tyr Ile Ser Pro Gly Asn Asp Asp Ile Lys Tyr Asn Glu Lys Phe
50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Glu Arg Ser Met Ile Gly Val Tyr Trp Gly Gln Gly Thr Leu Val Thr
            100                 105                 110

Val Ser Ala
        115

<210> SEQ ID NO 12
<211> LENGTH: 112
<212> TYPE: PRT
<213> ORGANISM: Mus sp.

<400> SEQUENCE: 12

Asp Val Val Met Thr Gln Thr Pro Leu Ser Leu Thr Val Ser Leu Gly
1               5                   10                  15

Asp Gln Ala Ser Ile Ser Cys Arg Phe Ser Gln Ser Leu Val Gln Ser
                20                  25                  30

Asn Gly Asn Thr Tyr Leu Gln Trp Tyr Leu Gln Lys Pro Gly Gln Ser
            35                  40                  45

Pro Lys Leu Leu Ile Tyr Lys Val Ser Asn Arg Phe Cys Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ala Pro Leu Thr Phe Gly Ala Gly Thr Lys Leu Glu Leu Lys
            100                 105                 110

<210> SEQ ID NO 13
<211> LENGTH: 114
<212> TYPE: PRT
<213> ORGANISM: Mus sp.

<400> SEQUENCE: 13

Gln Val Gln Leu Gln Gln Ser Asp Ala Glu Leu Val Lys Pro Gly Ala
1               5                   10                  15

Ser Val Lys Ile Ser Cys Lys Thr Ser Gly Tyr Thr Phe Thr Asp His
            20                  25                  30

Ala Ile His Trp Val Lys Gln Lys Pro Glu Gln Gly Leu Glu Trp Ile
            35                  40                  45

Gly Tyr Ile Ser Pro Gly Asn Gly Asp Ile Lys Tyr Asn Glu Lys Phe
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Pro Glu Asp Ser Ala Val Tyr Phe Cys
                85                  90                  95

Lys Ile Ser Tyr Tyr Gly Ile Trp Gly Gln Gly Thr Thr Leu Thr Val
            100                 105                 110

Ser Ser

<210> SEQ ID NO 14
<211> LENGTH: 107
<212> TYPE: PRT
<213> ORGANISM: Mus sp.

<400> SEQUENCE: 14

Asp Ile Gln Met Thr Gln Ser Pro Ala Ser Leu Ser Val Ser Val Gly
1               5                   10                  15

Glu Ser Val Thr Ile Thr Cys Arg Leu Ser Glu Asp Ile Tyr Ser Asn
            20                  25                  30

Leu Ala Trp Phe Gln Gln Arg Pro Gly Lys Ser Pro Gln Leu Leu Val
            35                  40                  45

Tyr Lys Ala Thr Asn Leu Ala Asp Gly Val Pro Ser Arg Phe Ser Gly
        50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Phe Trp Gly Thr Pro Phe
                85                  90                  95

Thr Phe Gly Ser Gly Thr Lys Val Glu Ile Lys
            100                 105

<210> SEQ ID NO 15
<211> LENGTH: 114
<212> TYPE: PRT
<213> ORGANISM: Mus sp.

<400> SEQUENCE: 15

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Lys Pro Glu Gln Gly Leu Glu Trp Ile
            35                  40                  45

Gly Tyr Phe Ser Pro Gly Asn Asp Asp Ile Lys Tyr Asn Glu Lys Phe
        50                  55                  60

Lys Val Lys Ala Thr Leu Thr Ala Asp Lys Ser Ser Ser Thr Ala Tyr
65                  70                  75                  80

Met Gln Leu Thr Ser Leu Thr Ser Glu Asp Ser Ala Val Tyr Phe Cys
                85                  90                  95

Lys Arg Ser Tyr Tyr Gly Asp Trp Gly Gln Gly Thr Thr Leu Thr Val
                100                 105                 110
Ser Ser

<210> SEQ ID NO 16
<211> LENGTH: 107
<212> TYPE: PRT
<213> ORGANISM: Mus sp.

<400> SEQUENCE: 16

Asp Ile Gln Met Thr Gln Ser Pro Ala Ser Leu Ser Val Ser Val Gly
1               5                   10                  15
Glu Thr Val Thr Ile Thr Cys Arg Ala Ser Glu Asn Ile Tyr Ser His
            20                  25                  30
Leu Ala Trp Tyr Gln Gln Lys Gln Gly Lys Ser Pro Gln Leu Leu Val
        35                  40                  45
Tyr Gly Ala Thr Asn Leu Ala Asp Gly Val Pro Ser Arg Phe Ser Gly
    50                  55                  60
Ser Gly Ser Gly Thr Gln Phe Ser Leu Lys Ile His Ser Leu Gln Ser
65                  70                  75                  80
Glu Asp Phe Gly Ser Tyr Tyr Cys Gln His Phe Trp Gly Ala Pro Phe
                85                  90                  95
Thr Phe Gly Ser Gly Thr Lys Leu Glu Ile Lys
            100                 105

<210> SEQ ID NO 17
<211> LENGTH: 115
<212> TYPE: PRT
<213> ORGANISM: Mus sp.

<400> SEQUENCE: 17

Gln Ile Gln Leu Gln Gln Ser Asp Ala Glu Leu Val Lys Pro Gly Thr
1               5                   10                  15
Ser Val Lys Met Ser Cys Lys Ala Ser Gly Tyr Thr Phe Thr Asp His
            20                  25                  30
Ala Ile His Trp Val Lys Gln Lys Pro Glu Gln Gly Leu Glu Trp Ile
        35                  40                  45
Gly Tyr Phe Ser Pro Gly Asn Asp Asp Ile Lys Tyr Asn Val Lys Phe
    50                  55                  60
Lys Gly Lys Ala Thr Leu Thr Ala Asp Lys Ser Ser Ser Thr Ala Tyr
65                  70                  75                  80
Met Gln Leu Asn Ser Leu Thr Ser Glu Asp Ser Ala Val Tyr Phe Cys
                85                  90                  95
Ser Val Gly Tyr Ala Leu Asp Tyr Trp Gly Leu Gly Thr Thr Leu Thr
            100                 105                 110
Val Ser Ser
        115

<210> SEQ ID NO 18
<211> LENGTH: 108
<212> TYPE: PRT
<213> ORGANISM: Mus sp.

<400> SEQUENCE: 18

Asn Ile Val Met Thr Gln Ser Pro Lys Ser Met Ser Met Ser Val Gly
1               5                   10                  15
Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
                35                  40                  45

Tyr Gly Ala Ser Asn Arg Tyr Thr Gly Val Pro Asp Arg Phe Thr Gly
            50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys Arg
                100                 105

<210> SEQ ID NO 19
<211> LENGTH: 115
<212> TYPE: PRT
<213> ORGANISM: Mus sp.

<400> SEQUENCE: 19

Gln Val Gln Leu Gln Gln Ser Asp Ala Glu Leu Val Lys Pro Gly Thr
1               5                   10                  15

Thr Val Lys Ile Ser Cys Lys Ala Ser Gly Tyr Thr Phe Thr Asp His
                20                  25                  30

Ala Ile His Trp Val Lys Glu Lys Pro Glu Gln Gly Leu Glu Trp Ile
            35                  40                  45

Gly Tyr Ile Ser Pro Gly Asn Asp Asp Ile Lys Tyr Ser Glu Lys Phe
        50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Asp Asp Ser Ala Val Tyr Phe Cys
                85                  90                  95

Lys Arg Ser Leu Ser Thr Pro Tyr Trp Gly Gln Gly Thr Leu Val Thr
                100                 105                 110

Val Ser Ala
        115

<210> SEQ ID NO 20
<211> LENGTH: 114
<212> TYPE: PRT
<213> ORGANISM: Mus sp.

<400> SEQUENCE: 20

Asp Ile Val Met Thr Gln Ser Pro Ser Ser Leu Thr Val Thr Ala Gly
1               5                   10                  15

Glu Lys Val Thr Met Ser Cys Arg Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Tyr Thr Phe Gly Gly Gly Thr Lys Leu Glu Ile
                100                 105                 110

Lys Arg

<210> SEQ ID NO 21
<211> LENGTH: 114
<212> TYPE: PRT
<213> ORGANISM: Mus sp.

<400> SEQUENCE: 21

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Met Gln Met Pro Glu Gln Gly Leu Glu Trp Ile
        35                  40                  45

Gly Tyr Ile Ser Pro Gly Asn Gly Asp Val Lys Tyr Ser Glu Arg Phe
    50                  55                  60

Lys Gly Arg Ala Thr Leu Thr Ala Asp Lys Ser Ser Ser Ser Ala Tyr
65                  70                  75                  80

Met Gln Leu Asn Ser Leu Thr Ser Glu Asp Ser Ala Val Tyr Phe Cys
                85                  90                  95

Lys Arg Ser Leu Ser Thr Pro Tyr Trp Gly Gln Gly Thr Leu Val Thr
            100                 105                 110

Val Ser

<210> SEQ ID NO 22
<211> LENGTH: 114
<212> TYPE: PRT
<213> ORGANISM: Mus sp.

<400> SEQUENCE: 22

Asp Ile Val Met Thr Gln Ser Pro Ser Ser Leu Thr Val Thr Ala Gly
1               5                   10                  15

Glu Arg Val Thr Met Ser Cys Lys Ser Ser Gln Ser Leu Leu Asn Ser
            20                  25                  30

Gly Asn Gln Lys Ser Tyr Leu Thr Trp Tyr Gln Gln Lys Pro Gly Gln
        35                  40                  45

Pro Pro Lys Leu Leu Ile Ser Trp Ala Ser Thr Arg Asp Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Ser
                85                  90                  95

Asp Tyr Ser Tyr Pro Tyr Thr Phe Gly Gly Gly Thr Lys Leu Glu Ile
            100                 105                 110

Lys Arg

<210> SEQ ID NO 23
<211> LENGTH: 115
<212> TYPE: PRT
<213> ORGANISM: Mus sp.
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (111)..(111)
<223> OTHER INFORMATION: Any amino acid

<400> SEQUENCE: 23

Gln Val Gln Leu Gln Gln Ser Asp Xaa Glu Leu Val Lys Pro Gly Ala

```
                     1               5                  10                   15
            Ser Val Lys Ile Ser Cys Lys Ala Ser Gly Tyr Thr Phe Thr Asp His
                             20                  25                  30
            Ala Ile His Trp Val Lys Gln Lys Pro Glu Gln Gly Leu Glu Trp Ile
                             35                  40                  45
            Gly Tyr Phe Ser Pro Gly Asn Asp Asp Ile Lys Tyr Asn Glu Lys Phe
                         50                  55                  60
            Arg Gly Lys Ala Thr Leu Thr Ala Asp Lys Ser Ser Ser Thr Ala Tyr
             65                  70                  75                  80
            Met Gln Leu Asn Ser Leu Ser Ser Asp Ser Ala Val Tyr Phe Cys
                             85                  90                  95
            Lys Arg Ser Leu Ser Thr Pro Tyr Trp Gly Gln Gly Thr Leu Xaa Thr
                            100                 105                 110
            Val Ser Ala
                    115

<210> SEQ ID NO 24
<211> LENGTH: 114
<212> TYPE: PRT
<213> ORGANISM: Mus sp.

<400> SEQUENCE: 24

Asp Ile Val Met Thr Gln Ser Pro Ser Ser Leu Thr Val Thr Ala Gly
             1               5                  10                  15
            Glu Lys Val Thr Met Ser Cys Lys Ser Ser Gln Ser Leu Leu Asn Arg
                             20                  25                  30
            Gly Asn His Lys Asn Tyr Leu Thr Trp Tyr Arg Gln Lys Pro Gly Leu
                             35                  40                  45
            Pro Pro Lys Leu Leu Ile Tyr Trp Ala Ser Thr Arg Glu Ser Gly Val
                         50                  55                  60
            Pro Asp Arg Phe Thr Gly Ser Gly Ser Gly Thr Asp Phe Ala Leu Thr
             65                  70                  75                  80
            Ile Ser Ser Val Gln Ala Glu Asp Leu Ala Val Tyr Tyr Cys Gln Asn
                             85                  90                  95
            Asp Tyr Thr Tyr Pro Tyr Thr Phe Gly Gly Gly Thr Lys Leu Glu Ile
                            100                 105                 110
            Lys Arg

<210> SEQ ID NO 25
<211> LENGTH: 115
<212> TYPE: PRT
<213> ORGANISM: Mus sp.

<400> SEQUENCE: 25

Gln Val Gln Leu Gln Gln Ser Asp Ala Glu Leu Val Lys Pro Gly Ala
             1               5                  10                  15
            Ser Met Lys Ile Ser Cys Lys Ala Ser Gly Tyr Thr Phe Thr Asp His
                             20                  25                  30
            Ala Ile His Trp Val Lys Gln Lys Pro Glu Gln Gly Leu Glu Trp Ile
                             35                  40                  45
            Gly Tyr Ile Ser Pro Gly Asn Gly Asp Ile Lys Tyr Asn Glu Lys Phe
                         50                  55                  60
            Lys Val Lys Ala Thr Leu Thr Ala Asp Lys Ser Ser Ser Thr Ala Tyr
             65                  70                  75                  80
            Met Gln Leu Asn Ser Leu Thr Ser Glu Asp Ser Ala Val Tyr Phe Cys
                             85                  90                  95
```

```
Lys Arg Ser Ile Thr Thr Pro Tyr Trp Gly Gln Gly Thr Leu Val Thr
                100                 105                 110

Val Ser Ala
        115

<210> SEQ ID NO 26
<211> LENGTH: 114
<212> TYPE: PRT
<213> ORGANISM: Mus sp.

<400> SEQUENCE: 26

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Lys Thr Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Asn
                85                  90                  95

Asp Tyr Ser Tyr Pro Tyr Thr Phe Gly Gly Gly Thr Lys Leu Glu Ile
                100                 105                 110

Lys Arg

<210> SEQ ID NO 27
<211> LENGTH: 115
<212> TYPE: PRT
<213> ORGANISM: Mus sp.

<400> SEQUENCE: 27

Gln Val Gln Leu Gln Gln Ser Asp Ala Glu Leu Val Lys Pro Gly Ala
1               5                   10                  15

Ser Val Lys Ile Ser Cys Lys Thr Ser Gly Tyr Thr Phe Thr Asp His
            20                  25                  30

Ala Ile His Trp Val Lys Gln Lys Pro Glu Gln Gly Leu Glu Trp Ile
        35                  40                  45

Gly Tyr Ile Ser Pro Gly Asn Asp Asp Ile Lys Tyr Thr Glu Lys Phe
    50                  55                  60

Lys Gly Lys Val Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Lys Arg Ser Ile Thr Thr Pro Tyr Trp Gly Gln Gly Thr Leu Val Thr
                100                 105                 110

Val Ser Ala
        115

<210> SEQ ID NO 28
<211> LENGTH: 115
<212> TYPE: PRT
<213> ORGANISM: Mus sp.

<400> SEQUENCE: 28

Gln Val Gln Leu Gln Gln Ser Asp Ala Glu Leu Val Lys Pro Gly Ala
```

```
            1               5                  10                  15
        Ser Val Lys Ile Ser Cys Lys Ala Ser Gly Tyr Thr Phe Thr Asp His
                        20                  25                  30

Ala Ile His Trp Val Lys Gln Lys Pro Glu Gln Gly Leu Glu Trp Ile
                        35                  40                  45

Gly Tyr Ile Ser Pro Gly Asn Gly Asp Ile Lys Tyr Asp Glu Lys Phe
                        50                  55                  60

Lys Gly Lys Ala Thr Leu Thr Ala Asp Lys Ser Ser Ser Thr Ala Tyr
         65                  70                  75                  80

Met Gln Leu Asn Ser Leu Thr Ser Glu Asp Ser Ala Val Tyr Phe Cys
                        85                  90                  95

Lys Arg Ser Ile Thr Thr Ser Tyr Trp Gly Gln Gly Thr Leu Val Thr
                        100                 105                 110

Val Ser Ala
                115

<210> SEQ ID NO 29
<211> LENGTH: 115
<212> TYPE: PRT
<213> ORGANISM: Mus sp.

<400> SEQUENCE: 29

Gln Val Gln Leu Gln Gln Ser Asp Ala Glu Leu Val Lys Pro Gly Ala
        1               5                  10                  15

Ser Val Lys Ile Ser Cys Lys Ala Ser Gly Tyr Thr Phe Thr Asp His
                        20                  25                  30

Ala Ile His Trp Val Lys Gln Lys Pro Glu Gln Gly Leu Glu Trp Ile
                        35                  40                  45

Gly Tyr Ile Ser Pro Gly Asn Asp Asp Ile Lys Tyr Asn Glu Lys Phe
                        50                  55                  60

Lys Gly Lys Ala Thr Leu Thr Ala Asp Lys Ser Ser Ser Thr Ala Tyr
         65                  70                  75                  80

Met Gln Leu Asn Ser Leu Thr Ser Glu Asp Ser Ala Val Phe Phe Cys
                        85                  90                  95

Lys Arg Ser Ile Thr Thr Ser Tyr Trp Gly Gln Gly Thr Leu Val Thr
                        100                 105                 110

Val Ser Ala
                115

<210> SEQ ID NO 30
<211> LENGTH: 115
<212> TYPE: PRT
<213> ORGANISM: Mus sp.

<400> SEQUENCE: 30

Gln Val Gln Leu Gln Gln Ser Asp Ala Glu Leu Val Lys Pro Gly Ala
        1               5                  10                  15

Ser Val Lys Ile Ser Cys Lys Ala Ser Gly Tyr Ile Phe Thr Asp His
                        20                  25                  30

Ala Ile His Trp Val Lys Gln Lys Pro Glu Gln Gly Leu Glu Trp Ile
                        35                  40                  45

Gly Tyr Ile Ser Pro Gly Asn Gly Asp Ile Lys Tyr Asn Glu Lys Phe
                        50                  55                  60

Lys Gly Lys Ala Thr Leu Thr Ala Asp Lys Ser Ser Ser Thr Ala Tyr
         65                  70                  75                  80

Met His Leu Asn Ser Leu Thr Ser Glu Asp Ser Ala Val Tyr Phe Cys
```

85                  90                  95

Lys Arg Ser Ile Thr Thr Ser Tyr Trp Gly Gln Gly Thr Leu Val Thr
                100                 105                 110

Val Ser Ala
        115

<210> SEQ ID NO 31
<211> LENGTH: 108
<212> TYPE: PRT
<213> ORGANISM: Mus sp.

<400> SEQUENCE: 31

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln His Ile Asn Phe Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Leu Pro
65                  70                  75                  80

Glu Asp Val Ala Thr Tyr Tyr Cys Gln Gln Asp Gln Ser Tyr Pro Tyr
                85                  90                  95

Met Phe Gly Gly Gly Thr Lys Leu Glu Ile Lys Arg
                100                 105

<210> SEQ ID NO 32
<211> LENGTH: 115
<212> TYPE: PRT
<213> ORGANISM: Mus sp.

<400> SEQUENCE: 32

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Lys Pro Glu Gln Gly Leu Glu Trp Ile
        35                  40                  45

Gly Tyr Ile Ser Pro Gly Asn Asp Asp Ile Lys Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Leu Leu Asn Ser Leu Thr Ser Glu Asp Ser Ala Val Tyr Phe Cys
                85                  90                  95

Lys Arg Ser Ile Thr Thr Ser Tyr Trp Gly Gln Gly Thr Leu Val Thr
                100                 105                 110

Val Ser Ala
        115

<210> SEQ ID NO 33
<211> LENGTH: 115
<212> TYPE: PRT
<213> ORGANISM: Mus sp.

<400> SEQUENCE: 33

Gln Val Gln Leu Gln Gln Ser Asp Ala Glu Leu Val Lys Pro Gly Ala
1               5                   10                  15

```
Ser Val Lys Ile Ser Cys Lys Ala Ser Gly Tyr Thr Phe Thr Asp His
            20                  25                  30

Ala Ile His Trp Val Lys Gln Lys Pro Glu Gln Gly Leu Glu Trp Ile
            35                  40                  45

Gly Tyr Ile Ser Pro Gly Asn Gly Asp Ile Lys Tyr Asn Glu Lys Phe
50                          55                  60

Lys Gly Lys Ala Thr Leu Thr Ala Asp Thr Ser Ser Thr Thr Ala Tyr
65                  70                  75                  80

Met Gln Leu Asn Ser Leu Thr Ser Glu Asp Ser Ala Met Tyr Phe Cys
                85                  90                  95

Lys Arg Ser Ile Thr Thr Ser Tyr Trp Gly Gln Gly Thr Leu Val Thr
                100                 105                 110

Val Ser Ala
        115

<210> SEQ ID NO 34
<211> LENGTH: 107
<212> TYPE: PRT
<213> ORGANISM: Mus sp.

<400> SEQUENCE: 34

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Ser Trp Tyr Gln Gln Lys Pro Gly Asn Ile Pro Lys Leu Leu Ile
            35                  40                  45

Tyr Lys Ala Ser Asn Leu Tyr Thr Gly Val Pro Ser Arg Phe Ser Gly
50                  55                  60

Ser Gly Ser Gly Thr Gly Phe Thr Leu Thr Ile Ser Ser Leu Gln Pro
65                  70                  75                  80

Glu Asp Val Ala Thr Tyr Tyr Cys Gln His Asp Gln Ser Tyr Pro Tyr
                85                  90                  95

Thr Phe Gly Gly Gly Thr Lys Leu Glu Ile Lys
                100                 105

<210> SEQ ID NO 35
<211> LENGTH: 115
<212> TYPE: PRT
<213> ORGANISM: Mus sp.

<400> SEQUENCE: 35

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Ile Phe Thr Asp His
            20                  25                  30

Ala Ile His Trp Val Lys Gln Lys Pro Glu Gln Gly Leu Glu Trp Ile
            35                  40                  45

Gly Tyr Ile Ser Pro Gly Asn Gly Asp Ile Lys Tyr Ile Glu Lys Phe
50                  55                  60

Arg Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Lys Arg Ser Leu Ser Thr Pro Tyr Trp Gly Gln Gly Thr Leu Val Thr
                100                 105                 110
```

Val Ser Ala
    115

<210> SEQ ID NO 36
<211> LENGTH: 110
<212> TYPE: PRT
<213> ORGANISM: Mus sp.

<400> SEQUENCE: 36

Asn Ile Leu Met Thr Gln Ser Pro Lys Ser Met Ser Met Ser Val Gly
1               5                   10                  15

Glu Arg Val Thr Leu Thr Cys Lys Ala Ser Glu Asn Val Val Asn Tyr
            20                  25                  30

Val Ser Trp Tyr Gln Gln Lys Pro Glu Gln Ser Pro Lys Leu Leu Ile
        35                  40                  45

Phe Gly Ala Ser Asn Arg Tyr Ser Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Ser Lys Trp Ile Thr Ser Tyr
                85                  90                  95

Pro Tyr Thr Phe Gly Gly Gly Thr Lys Leu Glu Ile Lys Arg
            100                 105                 110

<210> SEQ ID NO 37
<211> LENGTH: 109
<212> TYPE: PRT
<213> ORGANISM: Mus sp.

<400> SEQUENCE: 37

Asn Ile Leu Met Thr Gln Ser Pro Lys Ser Met Ser Met Ser Val Gly
1               5                   10                  15

Glu Arg Val Thr Leu Thr Cys Lys Ala Ser Glu Asn Val Val Asn Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Ser Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Ala Arg Val Thr Ser Tyr Pro
                85                  90                  95

Tyr Thr Phe Gly Gly Gly Thr Lys Leu Glu Ile Lys Arg
            100                 105

<210> SEQ ID NO 38
<211> LENGTH: 115
<212> TYPE: PRT
<213> ORGANISM: Mus sp.

<400> SEQUENCE: 38

Gln Val Gln Leu Gln Gln Ser Asp Ala Glu Leu Val Lys Pro Gly Thr
1               5                   10                  15

Ser Val Lys Ile Ser Cys Arg Ala Ser Gly Tyr Thr Phe Thr Asp His
            20                  25                  30

Ala Ile His Trp Val Lys Gln Lys Pro Glu Gln Gly Leu Glu Trp Ile
        35                  40                  45

```
Gly Tyr Ile Ser Pro Gly Asn Gly Asp Ile Lys Tyr Asn Glu Lys Phe
        50                  55                  60

Lys Gly Lys Ala Thr Leu Thr Ala Asp Lys Ser Ser Thr Ala Tyr
65                  70                  75                  80

Met Gln Leu Asn Ser Leu Thr Ser Asp Asp Ser Ala Val Tyr Phe Cys
                85                  90                  95

Lys Arg Ser Ile Thr Thr Pro Tyr Trp Gly Gln Gly Thr Thr Leu Thr
                100                 105                 110

Val Ser Ser
        115

<210> SEQ ID NO 39
<211> LENGTH: 105
<212> TYPE: PRT
<213> ORGANISM: Mus sp.

<400> SEQUENCE: 39

Ser Phe Val Met Thr Gln Thr Pro Lys Phe Leu Leu Val Ser Ala Gly
1               5                   10                  15

Asp Arg Val Thr Ile Thr Cys Lys Ala Ser Gln Ser Val Asn Asn Asn
                20                  25                  30

Val Ala Trp Tyr Gln Gln Lys Pro Gly Gln Ser Pro Lys Gln Leu Ile
            35                  40                  45

Tyr Tyr Ala Ser Asn Arg Tyr Thr Gly Val Pro Asp Arg Phe Thr Gly
        50                  55                  60

Ser Gly Tyr Gly Thr Asp Phe Thr Phe Thr Ile Tyr Thr Val Gln Ala
65                  70                  75                  80

Glu Asp Leu Ala Val Tyr Phe Cys Gln Gln Gly Tyr Ser Ser Pro Trp
                85                  90                  95

Thr Phe Gly Gly Gly Thr Lys Leu Lys
            100                 105

<210> SEQ ID NO 40
<211> LENGTH: 116
<212> TYPE: PRT
<213> ORGANISM: Mus sp.

<400> SEQUENCE: 40

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
                20                  25                  30

Ala Ile His Trp Val Lys Gln Lys Pro Glu Gln Gly Leu Asp Trp Ile
            35                  40                  45

Gly Tyr Ile Ser Pro Gly Asn Gly Asp Ile Lys Tyr Asn Glu Lys Phe
        50                  55                  60

Lys Asp Lys Val Thr Leu Thr Ala Asp Lys Ser Ser Ser Thr Ala Cys
65                  70                  75                  80

Met His Leu Asn Ser Leu Thr Ser Glu Asp Ser Ala Val Tyr Phe Cys
                85                  90                  95

Lys Arg Ser Leu Leu Ala Leu Asp Tyr Trp Gly Gln Gly Thr Thr Leu
                100                 105                 110

Thr Val Ser Ser
            115

<210> SEQ ID NO 41
<211> LENGTH: 107
```

```
<212> TYPE: PRT
<213> ORGANISM: Mus sp.

<400> SEQUENCE: 41

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Asn
            20                  25                  30

Ile Ala Trp Tyr Gln Gln Lys Pro Gly Arg Ser Pro Lys Val Leu Ile
        35                  40                  45

Tyr Ser Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Thr Asp Tyr Phe Cys Gln Gln Tyr Ser Ser Phe Pro Leu
                85                  90                  95

Thr Phe Gly Val Gly Thr Lys Leu Glu Leu Lys
            100                 105

<210> SEQ ID NO 42
<211> LENGTH: 116
<212> TYPE: PRT
<213> ORGANISM: Mus sp.

<400> SEQUENCE: 42

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Lys Pro Glu Gln Gly Leu Asp Trp Ile
        35                  40                  45

Gly Tyr Ile Ser Pro Gly Asn Gly Asp Ile Lys Tyr Asn Glu Lys Phe
    50                  55                  60

Lys Asp Lys Val Thr Leu Thr Ala Asp Lys Ser Ser Ser Thr Ala Ser
65                  70                  75                  80

Met His Leu Asn Ser Leu Thr Ser Glu Asp Ser Ala Val Tyr Phe Cys
                85                  90                  95

Lys Arg Ser Leu Leu Ala Leu Asp Tyr Trp Gly Gln Gly Thr Thr Leu
            100                 105                 110

Thr Val Ser Ser
        115

<210> SEQ ID NO 43
<211> LENGTH: 12
<212> TYPE: PRT
<213> ORGANISM: Mus sp.

<400> SEQUENCE: 43

Gly Tyr Thr Phe Thr Asp His Ala Ile His Trp Val
1               5                   10

<210> SEQ ID NO 44
<211> LENGTH: 12
<212> TYPE: PRT
<213> ORGANISM: Mus sp.

<400> SEQUENCE: 44

Gly Tyr Thr Phe Ser Asp His Ala Ile His Trp Val
1               5                   10
```

```
<210> SEQ ID NO 45
<211> LENGTH: 12
<212> TYPE: PRT
<213> ORGANISM: Mus sp.

<400> SEQUENCE: 45

Gly Tyr Ile Phe Thr Asp His Ala Ile His Trp Val
1               5                   10

<210> SEQ ID NO 46
<211> LENGTH: 10
<212> TYPE: PRT
<213> ORGANISM: Mus sp.

<400> SEQUENCE: 46

Phe Ser Pro Gly Asn Asp Asp Ile Lys Tyr
1               5                   10

<210> SEQ ID NO 47
<211> LENGTH: 10
<212> TYPE: PRT
<213> ORGANISM: Mus sp.

<400> SEQUENCE: 47

Ile Ser Pro Gly Asn Gly Asp Ile Lys Tyr
1               5                   10

<210> SEQ ID NO 48
<211> LENGTH: 10
<212> TYPE: PRT
<213> ORGANISM: Mus sp.

<400> SEQUENCE: 48

Leu Ser Pro Gly Asn Asp Asp Ile Lys Tyr
1               5                   10

<210> SEQ ID NO 49
<211> LENGTH: 10
<212> TYPE: PRT
<213> ORGANISM: Mus sp.

<400> SEQUENCE: 49

Val Ser Pro Gly Asn Gly Asp Ile Lys Tyr
1               5                   10

<210> SEQ ID NO 50
<211> LENGTH: 10
<212> TYPE: PRT
<213> ORGANISM: Mus sp.

<400> SEQUENCE: 50

Ile Ser Pro Gly Asn Gly Asp Val Lys Tyr
1               5                   10

<210> SEQ ID NO 51
<211> LENGTH: 10
<212> TYPE: PRT
<213> ORGANISM: Mus sp.

<400> SEQUENCE: 51

Ile Ser Pro Gly Asn Asp Asp Ile Lys Tyr
1               5                   10
```

<210> SEQ ID NO 52
<211> LENGTH: 8
<212> TYPE: PRT
<213> ORGANISM: Mus sp.

<400> SEQUENCE: 52

Ser Val Gly Tyr Ala Leu Asp Tyr
1               5

<210> SEQ ID NO 53
<211> LENGTH: 7
<212> TYPE: PRT
<213> ORGANISM: Mus sp.

<400> SEQUENCE: 53

Lys Ile Ser Tyr Tyr Gly Ile
1               5

<210> SEQ ID NO 54
<211> LENGTH: 7
<212> TYPE: PRT
<213> ORGANISM: Mus sp.

<400> SEQUENCE: 54

Lys Arg Ser Tyr Tyr Gly Asp
1               5

<210> SEQ ID NO 55
<211> LENGTH: 8
<212> TYPE: PRT
<213> ORGANISM: Mus sp.

<400> SEQUENCE: 55

Lys Arg Ser Ile Gly Gly Asp His
1               5

<210> SEQ ID NO 56
<211> LENGTH: 8
<212> TYPE: PRT
<213> ORGANISM: Mus sp.

<400> SEQUENCE: 56

Gln Arg Gln Leu Gly Gln Gly Tyr
1               5

<210> SEQ ID NO 57
<211> LENGTH: 8
<212> TYPE: PRT
<213> ORGANISM: Mus sp.

<400> SEQUENCE: 57

Lys Arg Ser Leu Ile Gly Asp Tyr
1               5

<210> SEQ ID NO 58
<211> LENGTH: 8
<212> TYPE: PRT
<213> ORGANISM: Mus sp.

<400> SEQUENCE: 58

Lys Arg Ser Leu Ser Thr Pro Tyr
1               5

<210> SEQ ID NO 59
<211> LENGTH: 8

```
<212> TYPE: PRT
<213> ORGANISM: Mus sp.

<400> SEQUENCE: 59

Lys Arg Ser Ile Thr Thr Pro Tyr
1               5

<210> SEQ ID NO 60
<211> LENGTH: 8
<212> TYPE: PRT
<213> ORGANISM: Mus sp.

<400> SEQUENCE: 60

Glu Arg Ser Met Ile Gly Val Tyr
1               5

<210> SEQ ID NO 61
<211> LENGTH: 8
<212> TYPE: PRT
<213> ORGANISM: Mus sp.

<400> SEQUENCE: 61

Lys Arg Ser Ile Thr Thr Ser Tyr
1               5

<210> SEQ ID NO 62
<211> LENGTH: 6
<212> TYPE: PRT
<213> ORGANISM: Mus sp.

<400> SEQUENCE: 62

Glu Asn Val Val Thr Tyr
1               5

<210> SEQ ID NO 63
<211> LENGTH: 6
<212> TYPE: PRT
<213> ORGANISM: Mus sp.

<400> SEQUENCE: 63

Glu Asp Ile Tyr Ser Asn
1               5

<210> SEQ ID NO 64
<211> LENGTH: 6
<212> TYPE: PRT
<213> ORGANISM: Mus sp.

<400> SEQUENCE: 64

Glu Asn Ile Tyr Ser His
1               5

<210> SEQ ID NO 65
<211> LENGTH: 6
<212> TYPE: PRT
<213> ORGANISM: Mus sp.

<400> SEQUENCE: 65

Gln Asn Ile Asn Val Trp
1               5

<210> SEQ ID NO 66
<211> LENGTH: 11
<212> TYPE: PRT
<213> ORGANISM: Mus sp.
```

<400> SEQUENCE: 66

Gln Ser Leu Val His Ser Tyr Gly Asn Thr Tyr
1               5                   10

<210> SEQ ID NO 67
<211> LENGTH: 6
<212> TYPE: PRT
<213> ORGANISM: Mus sp.

<400> SEQUENCE: 67

Gln Asn Val Gly Thr Ala
1               5

<210> SEQ ID NO 68
<211> LENGTH: 12
<212> TYPE: PRT
<213> ORGANISM: Mus sp.

<400> SEQUENCE: 68

Gln Ser Leu Leu Asn Ser Gly Asn Gln Lys Ser Tyr
1               5                   10

<210> SEQ ID NO 69
<211> LENGTH: 6
<212> TYPE: PRT
<213> ORGANISM: Mus sp.

<400> SEQUENCE: 69

Gln Ser Val Asn Asn Asn
1               5

<210> SEQ ID NO 70
<211> LENGTH: 12
<212> TYPE: PRT
<213> ORGANISM: Mus sp.

<400> SEQUENCE: 70

Gln Ser Leu Leu Asn Arg Gly Asn His Lys Asn Tyr
1               5                   10

<210> SEQ ID NO 71
<211> LENGTH: 11
<212> TYPE: PRT
<213> ORGANISM: Mus sp.

<400> SEQUENCE: 71

Gln Ser Leu Val Gln Ser Asn Gly Asn Thr Tyr
1               5                   10

<210> SEQ ID NO 72
<211> LENGTH: 6
<212> TYPE: PRT
<213> ORGANISM: Mus sp.

<400> SEQUENCE: 72

Glu Asn Val Val Asn Tyr
1               5

<210> SEQ ID NO 73
<211> LENGTH: 12
<212> TYPE: PRT
<213> ORGANISM: Mus sp.

<400> SEQUENCE: 73

Gln Ser Leu Leu Asn Ser Gly Lys Thr Lys Asn Tyr
1               5                   10

<210> SEQ ID NO 74
<211> LENGTH: 6
<212> TYPE: PRT
<213> ORGANISM: Mus sp.

<400> SEQUENCE: 74

Gln His Ile Asn Phe Trp
1               5

<210> SEQ ID NO 75
<211> LENGTH: 6
<212> TYPE: PRT
<213> ORGANISM: Mus sp.

<400> SEQUENCE: 75

Glu Asn Val Val Ile Tyr
1               5

<210> SEQ ID NO 76
<211> LENGTH: 12
<212> TYPE: PRT
<213> ORGANISM: Mus sp.

<400> SEQUENCE: 76

Gln Ser Leu Leu Asn Ser Gly Asn Gln Lys Asn Tyr
1               5                   10

<210> SEQ ID NO 77
<211> LENGTH: 7
<212> TYPE: PRT
<213> ORGANISM: Mus sp.

<400> SEQUENCE: 77

Gly Ala Ser Asn Arg Tyr Thr
1               5

<210> SEQ ID NO 78
<211> LENGTH: 7
<212> TYPE: PRT
<213> ORGANISM: Mus sp.

<400> SEQUENCE: 78

Lys Ala Thr Asn Leu Ala Asp
1               5

<210> SEQ ID NO 79
<211> LENGTH: 7
<212> TYPE: PRT
<213> ORGANISM: Mus sp.

<400> SEQUENCE: 79

Gly Ala Thr Asn Leu Ala Asp
1               5

<210> SEQ ID NO 80
<211> LENGTH: 7
<212> TYPE: PRT
<213> ORGANISM: Mus sp.

<400> SEQUENCE: 80

Lys Ala Ser Asn Leu His Thr

```
<210> SEQ ID NO 81
<211> LENGTH: 7
<212> TYPE: PRT
<213> ORGANISM: Mus sp.

<400> SEQUENCE: 81

Lys Val Ser Asn Arg Phe Ser
1               5

<210> SEQ ID NO 82
<211> LENGTH: 7
<212> TYPE: PRT
<213> ORGANISM: Mus sp.

<400> SEQUENCE: 82

Ser Ala Ser Asn Arg Tyr Thr
1               5

<210> SEQ ID NO 83
<211> LENGTH: 7
<212> TYPE: PRT
<213> ORGANISM: Mus sp.

<400> SEQUENCE: 83

Trp Ala Ser Thr Arg Asp Ser
1               5

<210> SEQ ID NO 84
<211> LENGTH: 7
<212> TYPE: PRT
<213> ORGANISM: Mus sp.

<400> SEQUENCE: 84

Tyr Ala Ser Asn Arg Tyr Thr
1               5

<210> SEQ ID NO 85
<211> LENGTH: 7
<212> TYPE: PRT
<213> ORGANISM: Mus sp.

<400> SEQUENCE: 85

Trp Ala Ser Thr Arg Glu Ser
1               5

<210> SEQ ID NO 86
<211> LENGTH: 7
<212> TYPE: PRT
<213> ORGANISM: Mus sp.

<400> SEQUENCE: 86

Lys Val Ser Asn Arg Phe Cys
1               5

<210> SEQ ID NO 87
<211> LENGTH: 7
<212> TYPE: PRT
<213> ORGANISM: Mus sp.

<400> SEQUENCE: 87

Gly Ala Ser Asn Arg Tyr Ser
1               5
```

```
<210> SEQ ID NO 88
<211> LENGTH: 7
<212> TYPE: PRT
<213> ORGANISM: Mus sp.

<400> SEQUENCE: 88

Lys Val Ser Asn Leu His Thr
1               5

<210> SEQ ID NO 89
<211> LENGTH: 9
<212> TYPE: PRT
<213> ORGANISM: Mus sp.

<400> SEQUENCE: 89

Gly Gln Gly Tyr Ser Tyr Pro Tyr Thr
1               5

<210> SEQ ID NO 90
<211> LENGTH: 9
<212> TYPE: PRT
<213> ORGANISM: Mus sp.

<400> SEQUENCE: 90

Gln His Phe Trp Gly Thr Pro Phe Thr
1               5

<210> SEQ ID NO 91
<211> LENGTH: 9
<212> TYPE: PRT
<213> ORGANISM: Mus sp.

<400> SEQUENCE: 91

Gln His Phe Trp Gly Ala Pro Phe Thr
1               5

<210> SEQ ID NO 92
<211> LENGTH: 9
<212> TYPE: PRT
<213> ORGANISM: Mus sp.

<400> SEQUENCE: 92

Gln Gln Gly Gln Ser Tyr Pro Phe Thr
1               5

<210> SEQ ID NO 93
<211> LENGTH: 9
<212> TYPE: PRT
<213> ORGANISM: Mus sp.

<400> SEQUENCE: 93

Ser Gln Asn Thr His Val Pro Tyr Thr
1               5

<210> SEQ ID NO 94
<211> LENGTH: 9
<212> TYPE: PRT
<213> ORGANISM: Mus sp.

<400> SEQUENCE: 94

Gln Gln Tyr Ser Ser Tyr Arg Leu Thr
1               5

<210> SEQ ID NO 95
```

```
<211> LENGTH: 9
<212> TYPE: PRT
<213> ORGANISM: Mus sp.

<400> SEQUENCE: 95

Gln Ser Asp Tyr Ser Tyr Pro Tyr Thr
1               5

<210> SEQ ID NO 96
<211> LENGTH: 9
<212> TYPE: PRT
<213> ORGANISM: Mus sp.

<400> SEQUENCE: 96

Gln Gln Gly Tyr Ser Ser Pro Trp Thr
1               5

<210> SEQ ID NO 97
<211> LENGTH: 9
<212> TYPE: PRT
<213> ORGANISM: Mus sp.

<400> SEQUENCE: 97

Gln Asn Asp Tyr Thr Tyr Pro Tyr Thr
1               5

<210> SEQ ID NO 98
<211> LENGTH: 9
<212> TYPE: PRT
<213> ORGANISM: Mus sp.

<400> SEQUENCE: 98

Ser Gln Ser Thr His Ala Pro Leu Thr
1               5

<210> SEQ ID NO 99
<211> LENGTH: 11
<212> TYPE: PRT
<213> ORGANISM: Mus sp.

<400> SEQUENCE: 99

Gly Ser Lys Trp Ile Thr Ser Tyr Pro Tyr Thr
1               5                   10

<210> SEQ ID NO 100
<211> LENGTH: 10
<212> TYPE: PRT
<213> ORGANISM: Mus sp.

<400> SEQUENCE: 100

Gly Ala Arg Val Thr Ser Tyr Pro Tyr Thr
1               5                   10

<210> SEQ ID NO 101
<211> LENGTH: 9
<212> TYPE: PRT
<213> ORGANISM: Mus sp.

<400> SEQUENCE: 101

Gln Gln Asp Gln Ser Tyr Pro Tyr Thr
1               5

<210> SEQ ID NO 102
<211> LENGTH: 9
<212> TYPE: PRT
```

```
<213> ORGANISM: Mus sp.

<400> SEQUENCE: 102

Lys Asn Asp Tyr Ser Tyr Pro Tyr Thr
 1               5

<210> SEQ ID NO 103
<211> LENGTH: 9
<212> TYPE: PRT
<213> ORGANISM: Mus sp.

<400> SEQUENCE: 103

Gln Gln Asp Gln Ser Tyr Pro Tyr Met
 1               5

<210> SEQ ID NO 104
<211> LENGTH: 9
<212> TYPE: PRT
<213> ORGANISM: Mus sp.

<400> SEQUENCE: 104

Gln Asn Asp Tyr Ser Tyr Pro Tyr Thr
 1               5

<210> SEQ ID NO 105
<211> LENGTH: 10
<212> TYPE: PRT
<213> ORGANISM: Mus sp.

<400> SEQUENCE: 105

Gly Tyr Thr Phe Thr Asp His Ala Ile His
 1               5                  10

<210> SEQ ID NO 106
<211> LENGTH: 10
<212> TYPE: PRT
<213> ORGANISM: Mus sp.

<400> SEQUENCE: 106

Gly Tyr Ile Phe Thr Asp His Ala Ile His
 1               5                  10

<210> SEQ ID NO 107
<211> LENGTH: 17
<212> TYPE: PRT
<213> ORGANISM: Mus sp.

<400> SEQUENCE: 107

Tyr Ile Ser Pro Gly Asn Gly Asp Ile Lys Tyr Asn Glu Lys Phe Lys
 1               5                  10                  15

Gly

<210> SEQ ID NO 108
<211> LENGTH: 17
<212> TYPE: PRT
<213> ORGANISM: Mus sp.

<400> SEQUENCE: 108

Tyr Phe Ser Pro Gly Asn Asp Asp Ile Lys Tyr Asn Glu Lys Phe Arg
 1               5                  10                  15

Gly

<210> SEQ ID NO 109
```

```
<211> LENGTH: 17
<212> TYPE: PRT
<213> ORGANISM: Mus sp.

<400> SEQUENCE: 109

Tyr Phe Ser Pro Gly Asn Asp Asp Ile Lys Tyr Asn Glu Lys Phe Lys
1               5                   10                  15

Val

<210> SEQ ID NO 110
<211> LENGTH: 17
<212> TYPE: PRT
<213> ORGANISM: Mus sp.

<400> SEQUENCE: 110

Tyr Ile Ser Pro Gly Asn Gly Asp Ile Lys Tyr Asn Glu Lys Phe Lys
1               5                   10                  15

Val

<210> SEQ ID NO 111
<211> LENGTH: 17
<212> TYPE: PRT
<213> ORGANISM: Mus sp.

<400> SEQUENCE: 111

Tyr Ile Ser Pro Gly Asn Gly Asp Ile Lys Tyr Asn Glu Lys Phe Lys
1               5                   10                  15

Asp

<210> SEQ ID NO 112
<211> LENGTH: 17
<212> TYPE: PRT
<213> ORGANISM: Mus sp.

<400> SEQUENCE: 112

Tyr Phe Ser Pro Gly Asn Asp Asp Phe Lys Tyr Asn Glu Lys Phe Lys
1               5                   10                  15

Gly

<210> SEQ ID NO 113
<211> LENGTH: 17
<212> TYPE: PRT
<213> ORGANISM: Mus sp.

<400> SEQUENCE: 113

Tyr Ile Ser Pro Gly Asn Asp Asp Ile Lys Tyr Asn Glu Lys Phe Lys
1               5                   10                  15

Gly

<210> SEQ ID NO 114
<211> LENGTH: 6
<212> TYPE: PRT
<213> ORGANISM: Mus sp.

<400> SEQUENCE: 114

Ser Ile Thr Thr Ser Tyr
1               5

<210> SEQ ID NO 115
<211> LENGTH: 6
<212> TYPE: PRT
<213> ORGANISM: Mus sp.
```

<400> SEQUENCE: 115

Ser Leu Ser Thr Pro Tyr
1               5

<210> SEQ ID NO 116
<211> LENGTH: 5
<212> TYPE: PRT
<213> ORGANISM: Mus sp.

<400> SEQUENCE: 116

Ser Tyr Tyr Gly Asp
1               5

<210> SEQ ID NO 117
<211> LENGTH: 6
<212> TYPE: PRT
<213> ORGANISM: Mus sp.

<400> SEQUENCE: 117

Ser Ile Thr Thr Pro Tyr
1               5

<210> SEQ ID NO 118
<211> LENGTH: 7
<212> TYPE: PRT
<213> ORGANISM: Mus sp.

<400> SEQUENCE: 118

Ser Leu Leu Ala Leu Asp Tyr
1               5

<210> SEQ ID NO 119
<211> LENGTH: 6
<212> TYPE: PRT
<213> ORGANISM: Mus sp.

<400> SEQUENCE: 119

Ser Leu Asn Met Ala Tyr
1               5

<210> SEQ ID NO 120
<211> LENGTH: 5
<212> TYPE: PRT
<213> ORGANISM: Mus sp.

<400> SEQUENCE: 120

Ser Tyr Tyr Gly His
1               5

<210> SEQ ID NO 121
<211> LENGTH: 11
<212> TYPE: PRT
<213> ORGANISM: Mus sp.

<400> SEQUENCE: 121

Lys Ala Ser Glu Asn Val Val Thr Tyr Val Ser
1               5                   10

<210> SEQ ID NO 122
<211> LENGTH: 11
<212> TYPE: PRT
<213> ORGANISM: Mus sp.

<400> SEQUENCE: 122

```
His Ala Ser Gln His Ile Asn Phe Trp Leu Ser
1               5                   10

<210> SEQ ID NO 123
<211> LENGTH: 17
<212> TYPE: PRT
<213> ORGANISM: Mus sp.

<400> SEQUENCE: 123

Lys Ser Ser Gln Ser Leu Leu Asn Arg Gly Asn His Lys Asn Tyr Leu
1               5                   10                  15

Thr

<210> SEQ ID NO 124
<211> LENGTH: 11
<212> TYPE: PRT
<213> ORGANISM: Mus sp.

<400> SEQUENCE: 124

Arg Ala Ser Glu Asn Ile Tyr Ser His Leu Ala
1               5                   10

<210> SEQ ID NO 125
<211> LENGTH: 17
<212> TYPE: PRT
<213> ORGANISM: Mus sp.

<400> SEQUENCE: 125

Lys Ser Ser Gln Ser Leu Leu Asn Ser Gly Lys Thr Lys Asn Tyr Leu
1               5                   10                  15

Thr

<210> SEQ ID NO 126
<211> LENGTH: 11
<212> TYPE: PRT
<213> ORGANISM: Mus sp.

<400> SEQUENCE: 126

Lys Ala Ser Gln Ser Val Asn Asn Asn Val Ala
1               5                   10

<210> SEQ ID NO 127
<211> LENGTH: 11
<212> TYPE: PRT
<213> ORGANISM: Mus sp.

<400> SEQUENCE: 127

Lys Ala Ser Gln Asp Val Gly Thr Asn Ile Ala
1               5                   10

<210> SEQ ID NO 128
<211> LENGTH: 17
<212> TYPE: PRT
<213> ORGANISM: Mus sp.

<400> SEQUENCE: 128

Lys Ser Ser Gln Ser Leu Leu Tyr Ser Gly Asn Gln Lys Asn Tyr Leu
1               5                   10                  15

Ala

<210> SEQ ID NO 129
<211> LENGTH: 11
```

```
<212> TYPE: PRT
<213> ORGANISM: Mus sp.

<400> SEQUENCE: 129

Arg Ala Ser Glu Asn Ile Tyr Ser Asn Leu Ala
1               5                   10

<210> SEQ ID NO 130
<211> LENGTH: 7
<212> TYPE: PRT
<213> ORGANISM: Mus sp.

<400> SEQUENCE: 130

Ser Ala Ser Thr Arg His Thr
1               5

<210> SEQ ID NO 131
<211> LENGTH: 7
<212> TYPE: PRT
<213> ORGANISM: Mus sp.

<400> SEQUENCE: 131

Trp Ala Ser Ala Arg Glu Ser
1               5

<210> SEQ ID NO 132
<211> LENGTH: 7
<212> TYPE: PRT
<213> ORGANISM: Mus sp.

<400> SEQUENCE: 132

Ala Ala Thr Asn Leu Ala Asp
1               5

<210> SEQ ID NO 133
<211> LENGTH: 9
<212> TYPE: PRT
<213> ORGANISM: Mus sp.

<400> SEQUENCE: 133

Gln Gln Tyr Ser Ser Phe Pro Leu Thr
1               5

<210> SEQ ID NO 134
<211> LENGTH: 9
<212> TYPE: PRT
<213> ORGANISM: Mus sp.

<400> SEQUENCE: 134

Gln Gln Tyr Tyr Ser Tyr Pro Leu Thr
1               5

<210> SEQ ID NO 135
<211> LENGTH: 9
<212> TYPE: PRT
<213> ORGANISM: Mus sp.

<400> SEQUENCE: 135

Gln His Phe Trp Gly Thr Pro Tyr Thr
1               5

<210> SEQ ID NO 136
<211> LENGTH: 10
<212> TYPE: PRT
<213> ORGANISM: Mus sp.
```

<400> SEQUENCE: 136

Gly Tyr Thr Phe Ser Asp His Ala Ile His
1               5                   10

<210> SEQ ID NO 137
<211> LENGTH: 17
<212> TYPE: PRT
<213> ORGANISM: Mus sp.

<400> SEQUENCE: 137

Tyr Ile Ser Pro Gly Asn Gly Asp Val Lys Tyr Ser Glu Arg Phe Lys
1               5                   10                  15

Gly

<210> SEQ ID NO 138
<211> LENGTH: 17
<212> TYPE: PRT
<213> ORGANISM: Mus sp.

<400> SEQUENCE: 138

Tyr Phe Ser Pro Gly Asn Asp Asp Ile Lys Tyr Ser Glu Lys Phe Lys
1               5                   10                  15

Gly

<210> SEQ ID NO 139
<211> LENGTH: 17
<212> TYPE: PRT
<213> ORGANISM: Mus sp.

<400> SEQUENCE: 139

Tyr Ile Ser Pro Gly Asn Gly Asp Ile Lys Tyr Asp Glu Lys Phe Lys
1               5                   10                  15

Gly

<210> SEQ ID NO 140
<211> LENGTH: 6
<212> TYPE: PRT
<213> ORGANISM: Mus sp.

<400> SEQUENCE: 140

Gln Leu Gly Gln Gly Tyr
1               5

<210> SEQ ID NO 141
<211> LENGTH: 6
<212> TYPE: PRT
<213> ORGANISM: Mus sp.

<400> SEQUENCE: 141

Ser Met Ile Gly Val Tyr
1               5

<210> SEQ ID NO 142
<211> LENGTH: 11
<212> TYPE: PRT
<213> ORGANISM: Mus sp.

<400> SEQUENCE: 142

His Ala Ser Gln Asn Ile Asn Val Trp Leu Ser
1               5                   10

<210> SEQ ID NO 143
<211> LENGTH: 17
<212> TYPE: PRT
<213> ORGANISM: Mus sp.

<400> SEQUENCE: 143

Lys Ser Ser Gln Ser Leu Leu Asn Ser Gly Asn Gln Lys Ser Tyr Leu
1               5                   10                  15
Thr

<210> SEQ ID NO 144
<211> LENGTH: 11
<212> TYPE: PRT
<213> ORGANISM: Mus sp.

<400> SEQUENCE: 144

Lys Ala Ser Glu Asn Val Val Ile Tyr Val Ser
1               5                   10

<210> SEQ ID NO 145
<211> LENGTH: 16
<212> TYPE: PRT
<213> ORGANISM: Mus sp.

<400> SEQUENCE: 145

Arg Ser Ser Gln Ser Leu Val His Ser Tyr Gly Asn Thr Tyr Leu His
1               5                   10                  15

<210> SEQ ID NO 146
<211> LENGTH: 16
<212> TYPE: PRT
<213> ORGANISM: Mus sp.

<400> SEQUENCE: 146

Arg Phe Ser Gln Ser Leu Val Gln Ser Asn Gly Asn Thr Tyr Leu Gln
1               5                   10                  15

<210> SEQ ID NO 147
<211> LENGTH: 7
<212> TYPE: PRT
<213> ORGANISM: Mus sp.

<400> SEQUENCE: 147

Lys Ala Ser Asn Leu Tyr Thr
1               5

<210> SEQ ID NO 148
<211> LENGTH: 9
<212> TYPE: PRT
<213> ORGANISM: Mus sp.

<400> SEQUENCE: 148

Gln His Asp Gln Ser Tyr Pro Thr Tyr
1               5

<210> SEQ ID NO 149
<211> LENGTH: 345
<212> TYPE: DNA
<213> ORGANISM: Mus sp.

<400> SEQUENCE: 149
caggttcagt tgctgcagta tgacgctgag ttggtgaaac ctggggggtc agtgaagata      60
tcgtgcaagg cctctggcta caccttcact gaccatgcta ttcactgggt gaagcagaag     120

```
cctgaacagg gcctggaatg gattggatat ttttctcccg gaaatgatga tattaagtac      180
agtgagaagt tcaagggcaa ggccacactg actgcagaca agtcctccag cactgcctac      240
atgcagctca acagcctgac atctgaggat tctgcagtgt atttctgtaa aagatccatt      300
actacgcctt actggggcca agggactctg gtcactgtct ctgca                     345
```

```
<210> SEQ ID NO 150
<211> LENGTH: 319
<212> TYPE: DNA
<213> ORGANISM: Mus sp.

<400> SEQUENCE: 150
gacatccaga tgaaccagtc tccatccagt ctgtctgcat cccttggaga cacaattacc      60
atcacttgcc atgccagtca gaacattaat gtttggttaa ctggtacca gcagaaacca      120 ggaaatattc ctaaactatt gatctataag gtttccaact tgcacacagg cgtcccatca      180
aggtttagtg gcagtggatc tggaacaggt ttcacattaa ccatcagcag cctgcagcct      240
gaagacattg ccacttacta ctgtcaacag gatcaaagtt atccgtacac gttcggaggg      300
gggaccaagc tgaaaaaaa                                                  319
```

```
<210> SEQ ID NO 151
<211> LENGTH: 345
<212> TYPE: DNA
<213> ORGANISM: Mus sp.

<400> SEQUENCE: 151
caggttcagc tgcagcagtc tgacgctgag ttggtgaaac ctggggcttc agtgaagata      60
tcctgcaagg cctctggcta caccttcact gaccatgcta ttcactgggt gaagcagaag      120
cctgaacagg gcctggaatg gattggatat atttctcccg gaaatgatga tattaagtac      180
aatgagaagt tcaagggcaa ggccacactg actgcagaca atcctccag cactgcctac       240 atgcagctca acagcctgac atctgaggat tctgcagtgt atttctgtaa aagatccatt      300
actacgtctt actggggcca agggactctg gtcactgtct ctgca                     345
```

```
<210> SEQ ID NO 152
<211> LENGTH: 323
<212> TYPE: DNA
<213> ORGANISM: Mus sp.

<400> SEQUENCE: 152
aacattgtaa tgacccaatc tcccaaatcc atgtccatgt cagtaggaga gagggtcacc      60
ttgacctgca aggccagtga aatgtggtt atttatgttt cctggtatca acagaaacca      120
gagcagtctc ctaaactgct gatatacggg gcatccaacc ggtacactgg ggtcccccgat     180 cgcttcacag gcagtggatc tgcaacagat ttcactctga ccatcagcag tgtgcaggct     240
gaagaccttg cagattatca ctgtggacag ggttacagct atccgtacac gttcggaggg    300
gggaccaagc tggaaataaa acg                                             323
```

```
<210> SEQ ID NO 153
<211> LENGTH: 345
<212> TYPE: DNA
<213> ORGANISM: Mus sp.

<400> SEQUENCE: 153
caggttcagt tgcagcagtc tgacgctgag ttggtgaaac ctggggcttc agtgaagata      60
tcctgcaagg cttctggcta caccttcact gaccatgcca ttcattgggt gaagcagaag      120
```

```
cctgaacagg gcctggaatg gattggatat gtttctcccg gaaatggtga tattaagtac    180
aatgagaagt tcaagggcaa ggccacactg actgcagaca aatcctccag cactgcctac    240
atgcagctca acagcctgac atcggaggat tctgcagtgt atttctgtaa aagatcttta    300
attggagact attggggcca aggcaccact ctcacagtct cctca                   345
```

<210> SEQ ID NO 154
<211> LENGTH: 322
<212> TYPE: DNA
<213> ORGANISM: Mus sp.

<400> SEQUENCE: 154

```
gacattgtga tgacccagtc tcaaaaattc atgtcctcat cagtaggaga cagggtcacc    60
atcacctgca aggccagtca gaatgtgggt actgctgtag cctggtatca acagaaacca    120
ggacaatctc ctaaatttct gatttactcg gcatccaatc ggtacactgg agtccctgat    180
cgcttcacag gcagtggatc tgggacagat ttcactctca cgatcagcaa tatgcagtct    240
gaagacctgg cagattattt ctgccagcaa tatagcagct atcgtctgac gttcggtgga    300
ggcaccaagc tggaaatcaa ac                                            322
```

<210> SEQ ID NO 155
<211> LENGTH: 345
<212> TYPE: DNA
<213> ORGANISM: Mus sp.

<400> SEQUENCE: 155

```
caggttcagc tgcagcagtc tgacgctgaa ttggtgaaac ctggggcttc agtgaagata    60
tcctgcaagg cttctggcta caccttcact gaccatgcta ttcactgggt gaagcagaag    120
cctgaacagg gcctggaatg gattggatat ctttctcccg gaaatgatga tattaagtac    180
agtgagaagt tcaaggacaa ggccacactg actgcagaca atcctccag cactgcctac    240 atgcagctca acagcctgac atctgaggat tctgcagtgt atttctgtaa aagatccata    300
gggggggacc actggggcca aggcaccact ctcacagtct cctca                   345
```

<210> SEQ ID NO 156
<211> LENGTH: 323
<212> TYPE: DNA
<213> ORGANISM: Mus sp.

<400> SEQUENCE: 156

```
gacatccaga tgaaccagtc tccatccagt ctgtctgcat cccttggaga cacaattacc    60
atcacttgcc atgccagtca gaacattaat gtttggttaa actggtacca gcagaaacca    120
ggaaatattc ctaaactatt gatctataag gcttccaact tgcacacagg cgtcccatca    180
aggtttagtg gcagtggatc tggaacaggt ttcacattaa ccatcggcag cctgcagcct    240
gaagacattg ccacttacta ctgtcaacag ggtcaaagtt atccgttcac gttcggaggg    300
gggaccaagc tggaaataaa acg                                           323
```

<210> SEQ ID NO 157
<211> LENGTH: 345
<212> TYPE: DNA
<213> ORGANISM: Mus sp.

<400> SEQUENCE: 157

```
caggttcagc tgcagcagtc tgacgctgag ttggtgaaac ctggggcttc agtgaagata    60
```

```
tcctgcaagg cttctggcta caccttcact gaccatgcta ttcactgggt gaaacagaag    120
cctgaacagg gcctggaatg gattggatat atttctcccg gaaatggtga tattaagtat    180
aatgagaagt tcaagggcaa ggccacactg actgcagaca atcctccag cactgcctac     240 atgcagctca acagcctgac atctgaggat tctgcagtgt atttctgtca aagacaactg    300
ggacaaggct actggggcca aggcaccact ctcacagtct cctca                    345
```

<210> SEQ ID NO 158
<211> LENGTH: 338
<212> TYPE: DNA
<213> ORGANISM: Mus sp.

<400> SEQUENCE: 158

```
gatgttgtga tgacccaaac tccactctcc ctgcctgtca gtcttggaga tcaagcctcc    60
atctcttgca gatctagtca gagccttgta cacagttatg gaaacaccta tttacattgg    120
tacctgcaga agccaggcca gtctccaaag ctcctgattt acaaagtttc caaccgattt    180
tctggggtcc cagacaggtt cagtggcagt ggatcaggga cagatttcac actcaagatc    240
agcagagtgg aggctgagga tctgggagtt tatttctgct ctcaaaatac acatgttccg    300
tacacgttcg agggggggac caagctggaa ataaaacg                            338
```

<210> SEQ ID NO 159
<211> LENGTH: 345
<212> TYPE: DNA
<213> ORGANISM: Mus sp.

<400> SEQUENCE: 159

```
caggttcagc tgcagcagtc tgacgctgag ttggggaaac ctggggcttc agtgaagata    60
tcctgcaagg cttctggcta caccttcagt gaccatgcta ttcactgggt gaagcagaag    120
cctgaacagg gcctggaatg gattggatat atctctcccg gaaacgatga tattaagtac    180
aatgagaagt tcaagggcaa ggccacactg actgcagaca atcctccag cactgcctac     240 atgcagctca acagcctgac atctgaggat tctgcagtgt atttctgtga agatcgatg     300 attggggttt actggggcca agggactctg gtcactgtct ctgca                    345
```

<210> SEQ ID NO 160
<211> LENGTH: 337
<212> TYPE: DNA
<213> ORGANISM: Mus sp.

<400> SEQUENCE: 160

```
gatgttgtga tgacccaaac tccactctcc ctgactgtca gtcttggcga tcaagcctcc    60
atctcttgca gatttagtca gagccttgta caaagtaatg gaaataccta tttacagtgg    120
tatctgcaga agccaggcca gtctccaaag ctcctgattt acaaagtctc caaccgattt    180
tgtggggtcc cagacaggtt cagtggcagt ggatcaggga cagatttcac actcaagatc    240
agcagagtgg aggctgagga tctgggagtt tatttctgct ctcaaagtac acatgctccg    300
ctcacgttcg gtgctgggac caagctggag ctgaaac                             337
```

<210> SEQ ID NO 161
<211> LENGTH: 342
<212> TYPE: DNA
<213> ORGANISM: Mus sp.

<400> SEQUENCE: 161

```
caggttcagc tgcagcagtc tgacgctgag ttggtgaaac ctggggcttc agtgaagata    60
```

```
tcctgcaaga cttctggcta caccttcact gaccatgcaa ttcactgggt gaagcagaag    120
cctgaacagg gcctggaatg gattggatat atttctcccg gaaatggtga tattaagtac    180
aatgagaagt tcaagggcaa ggccaccctg actgcagaca atcctccag cactgcctat     240 atgcagctca gcagcctgac acctgaggat tctgcagtgt atttctgtaa aatatcttac    300
tacggtattt ggggccaagg caccactctc acagtctcct ca                       342
```

<210> SEQ ID NO 162
<211> LENGTH: 322
<212> TYPE: DNA
<213> ORGANISM: Mus sp.

<400> SEQUENCE: 162

```
gacatccaga tgactcagtc tccagcctcc ctatctgtat ctgtgggaga gtctgtcacc    60
atcacatgtc gactaagtga agatatttac agtaatttag catggtttca gcagagaccg   120
ggaaaatctc ctcagctcct ggtttataaa gcaacaaact tagcagacgg tgtgccatca   180
aggttcagtg gcagtggatc aggcacacag tattccctca agatcaacag cctgcagtct   240
gaagattttg ggacttatta ctgtcaacat ttttggggta ctccattcac gttcggctcg   300
gggaccaagg tggaaataaa ac                                             322
```

<210> SEQ ID NO 163
<211> LENGTH: 342
<212> TYPE: DNA
<213> ORGANISM: Mus sp.

<400> SEQUENCE: 163

```
caggttcagc tgcagcagtc tgacgctgag ttggtgaaac ctggggcttc agtgaagata    60
tcctgcaagg cttctggcta caccttcact gaccatgcta ttcactgggt gaagcagaag   120
cctgaacagg gcctggaatg gattggatat ttttctcccg gaaatgatga tattaagtat   180
aatgagaagt tcaaggtcaa ggccacactg actgcagaca atcctccag cactgcctac    240 atgcaactca ccagcctgac atctgaagat tctgcagtgt atttctgtaa aagatcttac   300
tacggtgatt ggggccaagg caccactctc acagtctcct ca                       342
```

<210> SEQ ID NO 164
<211> LENGTH: 322
<212> TYPE: DNA
<213> ORGANISM: Mus sp.

<400> SEQUENCE: 164

```
gacatccaga tgactcagtc tccagcctcc ctatctgttt ctgtgggaga actgtcacc    60 atcacatgtc gagcaagtga gaatatttac agtcatttag catggtatca acagaaacag   120
ggaaaatctc ctcaactcct ggtctatggt gcaactaact tagcagatgg tgtgccatca   180
aggttcagtg gcagtggatc aggcacacag ttttccctca agatccacag cctgcagtct   240
gaagattttg ggagttatta ctgtcaacat ttttggggtg ctccattcac gttcggctcg   300
gggacaaagt tggaaataaa ac                                             322
```

<210> SEQ ID NO 165
<211> LENGTH: 345
<212> TYPE: DNA
<213> ORGANISM: Mus sp.

<400> SEQUENCE: 165

```
caaattcagc tgcagcagtc tgacgctgag ttggtgaaac ctgggacttc agtgaagatg    60
tcctgcaagg cttctggcta caccttcact gaccatgcta ttcactgggt gaagcagaag   120
cctgaacagg gcctggaatg gattggatat ttttctcccg gaaatgatga tattaagtat   180
aatgtgaagt tcaagggcaa ggccacactg actgcagaca aatcctccag cactgcctac   240
atgcagctca acagcctgac atctgaagat tctgcagtgt atttctgttc ggtgggatac   300
gcccttgact actggggcct aggcaccact ctcacagtct cctca                   345
```

<210> SEQ ID NO 166
<211> LENGTH: 323
<212> TYPE: DNA
<213> ORGANISM: Mus sp.

<400> SEQUENCE: 166

```
aacattgtaa tgacccaatc tcccaaatcc atgtccatgt cagtaggaga gagggtcacc    60
ttgacctgca aggccagtga gaatgtggtt acttatgttt cctggtatca acagaaacca   120
gagcagtctc ctaaactgct gatatacggg gcatccaacc ggtacactgg ggtccccgat   180
cgcttcacag gcagtggatc tgcaacagat ttcactctga ccatcagcag tgtgcaggct   240
gaagaccttg cagattatca ctgtggacag ggttacagct atccgtacac gttcggaggg   300
gggaccaagc tggaaataaa acg                                           323
```

<210> SEQ ID NO 167
<211> LENGTH: 345
<212> TYPE: DNA
<213> ORGANISM: Mus sp.

<400> SEQUENCE: 167

```
caggttcagc tgcaacagtc tgacgctgag ttggtgaaac ctgggactac agtgaagata    60
tcctgcaagg cttctggcta cactttcact gaccatgcta ttcactgggt gaaggagaag   120
cctgaacagg gcctggaatg gatcggatat atttctcccg gaaatgatga tattaagtac   180
agtgagaagt tcaagggcaa ggccacactg actgcagaca aatcctccag cactgcttac   240
atgcagctca acagcctgac atctgatgat tctgcagtgt atttctgtaa aagatcgctt   300
agtacgcctt actggggcca aggactctg gtcactgtct ctgca                    345
```

<210> SEQ ID NO 168
<211> LENGTH: 477
<212> TYPE: DNA
<213> ORGANISM: Mus sp.

<400> SEQUENCE: 168

```
tttttaatac gactccctat agggcaagca gtggtatcaa tgcagattac aagggggaaa    60
ggcatcagac cagcatgggc atcaaggtgg aatcacagac tctggtcttc atatccatac   120
tgtttgggtt atatggagct gatgggaaca cattaatgac ccaatctccc acatccatgt   180
acatgtcagt aggagagagg gtcacccttga cttgcaaggc cagtgagaat gagattaatt   240
atgtttcctg gtatcaacag aaaccagagc agtctcctaa actgttgata tacggggcat   300
ccaaccggta ctctggggtc cccgatcgct tcacaggcag tggatctgca acagatttca   360
ctctgaccat cagcagtgtg caggctgaag accttgcaga ttatccctgt ggagcaaggg   420
attaactagc tatccgtaca cgttcggagg ggggaccaag ctggaaataa aacgggc     477
```

<210> SEQ ID NO 169
<211> LENGTH: 341

<210> SEQ ID NO 169
<211> LENGTH: 341
<212> TYPE: DNA
<213> ORGANISM: Mus sp.

<400> SEQUENCE: 169

```
gacattgtga tgacacagtc tccatcctcc ctgactgtga cagcaggaga gaaggtcact    60
atgagctgca ggtccagtca gagtctgtta aacagtggaa atcaaaagaa ctacttgacc   120
tggtaccagc agaaaccagg gcagcctcct aaactgttga tctactgggc atccactagg   180
gaatctgggg tccctgatcg cttcacaggc agtggatctg gaacagattt cactctcacc   240
atcagcagtg tgcaggctga agacctggca gtttattact gtcagaatga ttatagttat   300
ccgtacacgt tcggaggggg gaccaagctg gaaataaaac g                      341
```

<210> SEQ ID NO 170
<211> LENGTH: 343
<212> TYPE: DNA
<213> ORGANISM: Mus sp.

<400> SEQUENCE: 170

```
caggttcagc tgcagcagtc tgacgctgag ttggtgaaac ctggggcttc agtgaagata    60
tcctgcaagg cttctggcta caccttcact gaccatgcta ttcactgggt gatgcagatg   120
cctgaacagg gcctggaatg gattggatat atttctcccg gaaatggtga tgttaagtac   180
agtgagaggt tcaagggcag ggccacactg actgcagaca atcctccag ctctgcctac   240
atgcagctca acagcctgac atctgaggat tctgcagttt atttctgtaa aagatcgctt   300
agtacgcctt actggggcca agggactctg gtcactgtct ctg                     343
```

<210> SEQ ID NO 171
<211> LENGTH: 341
<212> TYPE: DNA
<213> ORGANISM: Mus sp.

<400> SEQUENCE: 171

```
gacattgtga tgacacagtc tccatcctcc ctgactgtga cagcaggaga gagggtcact    60
atgagctgca agtccagtca gagtctgtta aacagtggaa atcaaaagag ctacttgacc   120
tggtaccagc agaaaccagg gcagcctcct aaactgttga tctcctgggc atccactagg   180
gattctgggg tccctgatcg cttcacaggc agtggatctg gaacagattt cactctcacc   240
atcagcagtg tgcaggctga agacctggca gtttattact gtcagagtga ttatagttat   300
ccgtacacgt tcggaggggg gaccaagctg gaaataaaac g                      341
```

<210> SEQ ID NO 172
<211> LENGTH: 345
<212> TYPE: DNA
<213> ORGANISM: Mus sp.
<220> FEATURE:
<221> NAME/KEY: modified_base
<222> LOCATION: (26)..(26)
<223> OTHER INFORMATION: a, c, t, g, unknown or other
<220> FEATURE:
<221> NAME/KEY: modified_base
<222> LOCATION: (332)..(332)
<223> OTHER INFORMATION: a, c, t, g, unknown or other

<400> SEQUENCE: 172

```
caggttcagc tgcagcagtc tgacgntgag ttggtgaaac cggggcttc agtgaagata     60
tcctgtaagg cttctggcta caccttcact gaccatgcta ttcactgggt gaagcagaag   120
cctgaacagg gcctggaatg gattggatat ttttctcccg gaaatgatga tattaagtac   180
```

```
aatgagaagt ttaggggcaa ggccacactg actgcagaca aatcctccag cactgcctac      240
atgcagctca acagcctgtc atctgatgat tctgcagtgt atttctgtaa aagatcgctt      300
agtacgcctt actggggcca agggactctg gncactgtct ctgca                     345
```

<210> SEQ ID NO 173
<211> LENGTH: 341
<212> TYPE: DNA
<213> ORGANISM: Mus sp.

<400> SEQUENCE: 173

```
gacattgtga tgacacagtc tccatcctcc ctgactgtga cagcaggaga gaaagtcact      60
atgagctgca agtccagtca gagtctgtta aaccgtggaa atcataagaa ctacttgacc     120
tggtaccggc agaaaccagg gctgcctcct aaactgttga tttactgggc atccactagg     180
gaatctgggg tccctgatcg cttcacaggc agtggatctg gaacagattt cgctctcacc     240
atcagcagtg ttcaggctga agacctggca gtttattact gtcagaatga ttatacttat     300
ccgtacacgt tcggaggggg gaccaagctg gagataaaac g                         341
```

<210> SEQ ID NO 174
<211> LENGTH: 345
<212> TYPE: DNA
<213> ORGANISM: Mus sp.

<400> SEQUENCE: 174

```
caggttcagc tgcagcagtc tgacgctgag ttggtgaaac ctggggcttc aatgaagatt      60
tcctgcaagg cttctggcta caccttcact gaccatgcta ttcactgggt gaagcagaag     120
cctgaacagg gcctggaatg gattggatat atttctcccg gaaatggtga tattaagtac     180
aatgagaagt tcaaggtcaa ggccacactg actgcagaca aatcctccag cactgcctac     240
atgcagctca acagcctgac atctgaggat tctgcagtgt atttctgtaa aagatcgatt     300
actacgcctt actggggcca agggactctg gtcactgtct ctgca                     345
```

<210> SEQ ID NO 175
<211> LENGTH: 341
<212> TYPE: DNA
<213> ORGANISM: Mus sp.

<400> SEQUENCE: 175

```
gacattgtga tgacacagtc tccatcctcc ctgactgtga cagcaggaga gaaggtcact      60
atgagctgca agtccagtca gagtctgtta aacagtggaa aaacaaagaa ctacttgacg     120
tggtaccagc agaaaccagg gcagcctcct aaactgttga tctactgggc atccactagg     180
gaatctgggg tccctgatcg cttcacaggc agtggatctg gaacagattt cactctcacc     240
atcagcagtg tgcaggctga agacctggca gtttattact gtaagaatga ttatagttat     300
ccgtacacgt tcggaggggg gaccaagctg gaaataaaac g                         341
```

<210> SEQ ID NO 176
<211> LENGTH: 345
<212> TYPE: DNA
<213> ORGANISM: Mus sp.

<400> SEQUENCE: 176

```
caggttcagc tgcagcagtc tgacgctgaa ttggtgaagc tgggggcttc agtgaagata      60
tcctgcaaga cttctggcta caccttcact gaccatgcta ttcactgggt gaagcagaag     120
cctgaacagg gcctggaatg gattggatat atctctcccg gaaatgatga tattaagtac     180
```

| | | |
|---|---|---|
| actgagaagt tcaagggcaa ggtcacactg actgcagaca aatcctccag cactgcctac | 240 | |
| atgcagctca acagcctgac atctgaggat tctgcagtct atttctgtaa aagatcgatt | 300 | |
| actacgcctt actggggcca agggactctg gtcactgtct ctgca | 345 | |

<210> SEQ ID NO 177
<211> LENGTH: 480
<212> TYPE: DNA
<213> ORGANISM: Mus sp.
<220> FEATURE:
<221> NAME/KEY: modified_base
<222> LOCATION: (153)..(153)
<223> OTHER INFORMATION: a, c, t, g, unknown or other
<220> FEATURE:
<221> NAME/KEY: modified_base
<222> LOCATION: (285)..(286)
<223> OTHER INFORMATION: a, c, t, g, unknown or other
<220> FEATURE:
<221> NAME/KEY: modified_base
<222> LOCATION: (289)..(289)
<223> OTHER INFORMATION: a, c, t, g, unknown or other
<220> FEATURE:
<221> NAME/KEY: modified_base
<222> LOCATION: (297)..(298)
<223> OTHER INFORMATION: a, c, t, g, unknown or other
<220> FEATURE:
<221> NAME/KEY: modified_base
<222> LOCATION: (332)..(332)
<223> OTHER INFORMATION: a, c, t, g, unknown or other
<220> FEATURE:
<221> NAME/KEY: modified_base
<222> LOCATION: (405)..(405)
<223> OTHER INFORMATION: a, c, t, g, unknown or other
<220> FEATURE:
<221> NAME/KEY: modified_base
<222> LOCATION: (412)..(412)
<223> OTHER INFORMATION: a, c, t, g, unknown or other
<220> FEATURE:
<221> NAME/KEY: modified_base
<222> LOCATION: (429)..(429)
<223> OTHER INFORMATION: a, c, t, g, unknown or other

<400> SEQUENCE: 177

| | | |
|---|---|---|
| tttttatacg ccactttcta atacgcctca ctatagggca agcagtggta tcaacgcaga | 60 | |
| ttacaaaggg gaaaggaatc agaccgactc gcgcatcaag atggaatcac agactctggt | 120 | |
| cttcatatcc agtacgctcg gggactatgg agnggaacag tacattttaa tgacccaatg | 180 | |
| tcccaaaggc aagaacatgt cagtaggaga gagggtcact cagagtgcaa ggccaggaga | 240 | |
| aatcaaaaca cttatgtttc ctggtatcaa cagaaaccag agcannctnt aaaatgnnga | 300 | |
| ttacggggca tccaaccggg aatctggggt cnccgatcgc ttcacaggca gtggatctgg | 360 | |
| aacagatttc actctcacca tcagcagtgt gcaggctgaa gaccnggcag tnttcactgt | 420 | |
| ggacagggnt acagttatcc gtacacgttc ggaggggga ccaagctgaa aaaacgggc | 480 | |

<210> SEQ ID NO 178
<211> LENGTH: 345
<212> TYPE: DNA
<213> ORGANISM: Mus sp.

<400> SEQUENCE: 178

| | | |
|---|---|---|
| caggttcagc tgcagcagtc tgacgctgag ttggtgaaac ctggggcttc agtgaagata | 60 | |
| tcctgcaagg cttctggcta caccttcact gaccatgcta ttcactgggt gaagcagaag | 120 | |
| cctgaacagg gcctggaatg gattggatat atttctcccg gaaatggtga tattaagtac | 180 | |
| gatgagaagt ttaagggcaa ggccacactg actgcagaca aatcctcctc cactgcctac | 240 | |

```
atgcagctca acagcctgac atctgaagat tctgcagtgt atttctgtaa aagatcgatt    300
actacctctt actggggcca agggactctg gtcactgtct ctgca                    345
```

<210> SEQ ID NO 179
<211> LENGTH: 345
<212> TYPE: DNA
<213> ORGANISM: Mus sp.

<400> SEQUENCE: 179

```
caggttcagc tgcagcagtc tgacgctgag ttggtgaaac ctggggcttc agtgaagata     60
tcctgcaagg cttctggcta caccttcact gaccatgcta ttcactgggt gaagcagaag    120
cctgaacagg gcctggaatg gattggatat atttctcccg gaaatgatga tattaagtac    180
aatgagaagt tcaagggcaa ggccacactg actgcagaca gtcctccag cactgcctac     240 atgcagctca acagcctgac atctgaggat tctgcagtgt ttttctgtaa aagatcgatt    300
actacctctt actggggcca agggactctg gtcactgtct ctgca                    345
```

<210> SEQ ID NO 180
<211> LENGTH: 483
<212> TYPE: DNA
<213> ORGANISM: Mus sp.
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (137)..(137)
<223> OTHER INFORMATION: a, c, t, g, unknown or other
<220> FEATURE:
<221> NAME/KEY: modified_base
<222> LOCATION: (193)..(193)
<223> OTHER INFORMATION: a, c, t, g, unknown or other

<400> SEQUENCE: 180

```
ttnataggac tcaatatagg gcaagcagtg gtattaacgc cgagtacatg gggagggcaa     60
gggcagaaag tcactttcag tgaggataca ccatcagcat gagggtcctt gttgagctcc    120 tggggggggct ggtgttntgc tttttaggtg tgagatgtga catccagatg aaccagtctc    180
catccagtct gtntgcatcc tttggagaca caattaccat catttgccat tccagtcaga    240
acattaatgt ttggttaaga tggtaccagc agaaaccagg aaatattcct aaaatattga    300
tatataaggg ttccaacttg tacacaggcg tcccatcaag gtttagtggc agtggatttg    360
gaacaggttt cacattaacc atcagcagcg tgcagcggga agacattgcc acttactact    420
gtcaacagga tcaaagttat ccgtacacgt tcggaggggg gaccaagctg aaataaaacg    480
ggc                                                                   483
```

<210> SEQ ID NO 181
<211> LENGTH: 345
<212> TYPE: DNA
<213> ORGANISM: Mus sp.

<400> SEQUENCE: 181

```
caggttcagc tgcagcagtc tgacgccgag ttggtgaaac ctggggcttc agtgaagata     60
tcctgcaagg cttctggcta catcttcact gaccatgcta ttcactgggt gaagcagaag    120
cctgaacagg gcctggaatg gattggatat atttctcccg gaaatggtga tattaagtac    180
aatgagaagt tcaagggcaa ggccacactg actgcagaca atcctccag cactgcctac     240 atgcatctca acagcctgac atctgaggat tctgcagtgt atttctgtaa aagatcgatt    300
```

```
actacctctt actggggcca agggactctg gtcactgtct ctgca              345
```

<210> SEQ ID NO 182
<211> LENGTH: 323
<212> TYPE: DNA
<213> ORGANISM: Mus sp.

<400> SEQUENCE: 182

```
gacatccaga tgaaccagtc cccatccagt ctgtctgcat cccttggaga cacaattacc    60
atcacttgcc atgccagtca gcacattaat tttttggttaa gctggtacca gcagaaacca   120
ggaaatattc ctaaactctt gatctataag gcttccaact tgcacacagg cgtcccatca   180
aggtttagtg gcagtggatc tggaacaggt ttcacattaa ccatcagcag cctgctgcct   240
gaagacgttg ccacttacta ctgtcaacag gatcaaagtt atccgtatat gttcggaggg   300
gggaccaagc tggaaataaa acg                                            323
```

<210> SEQ ID NO 183
<211> LENGTH: 345
<212> TYPE: DNA
<213> ORGANISM: Mus sp.

<400> SEQUENCE: 183

```
caggttcagc tgcagcagtc tgacgctgag ttggtgaaac ctggggcttc agtgaagata    60
tcctgcaagg cttctggcta caccttcact gaccatgcta ttcactgggt gaagcagaag   120
cctgaacagg gcctggaatg gattggatat atttctcccg gaaatgatga tattaagtac   180
aatgagaagt ttaagggcaa ggccacactg actgcagaca atcctccag cactgcctac   240
atgctgctca acagcctgac atctgaggat tctgcagtgt atttctgtaa aagatcgatt   300
actacctctt actggggcca agggactctg gtcactgtct ctgca                   345
```

<210> SEQ ID NO 184
<211> LENGTH: 323
<212> TYPE: DNA
<213> ORGANISM: Mus sp.

<400> SEQUENCE: 184

```
aacattgtaa tgacccaatc tcccaaatcc atgtccatgt cagtaggaga gagggtcacc    60
ttgacctgca aggccagtga gaatgtggtt acttatgttt cctggtatca acagaaacca   120
gagcagtctc ctaaactgct gatatacggg gcatccaacc ggtacactgg ggtccccgat   180
cgcttcacag gcagtggatc tgcaacagat ttcactttga ccatcagcag tgtgcaggct   240
gaagaccttg cagattatca ctgtggacag ggttacagct atccgtacac gttcggaggg   300
gggaccaagc tggaaataaa acg                                            323
```

<210> SEQ ID NO 185
<211> LENGTH: 345
<212> TYPE: DNA
<213> ORGANISM: Mus sp.

<400> SEQUENCE: 185

```
caggttcaac tgcagcagtc tgacgctgag ttggtgaaac ctggggcttc agtgaagata    60
tcctgcaagg cttctggcta caccttcact gaccatgcta ttcactgggt gaagcagaag   120
cctgaacagg gcctggaatg gattggatat atttctcccg gaaatggtga tattaagtac   180
aatgagaagt tcaagggtaa ggccacactg actgcagaca cttcctccac cactgcctac   240
```

```
atgcagctca acagcctgac atctgaggat tctgcaatgt atttctgtaa aagatccatt    300
actacgtctt actggggcca agggactctg gtcactgtct ctgca                    345
```

<210> SEQ ID NO 186
<211> LENGTH: 321
<212> TYPE: DNA
<213> ORGANISM: Mus sp.

<400> SEQUENCE: 186

```
gacatccaga tgaaccagtc tccatccagt ctgtctgcat cccttggaga cacaattacc    60
atcacttgcc atgccagtca gaacattaat gtttggttaa ctggtacca gcagaaacca    120 ggaaatattc ctaaactatt gatctataag gcttccaatt tgtatacagg cgtcccatca    180
aggtttagtg gcagtggatc tggaacaggt ttcacattaa ccatcagcag cctgcagcct    240
gaagacgttg ccacgtacta ctgtcaacac gatcaaagtt atccgtacac gttcggaggg    300
gggaccaagc tggaaataaa a                                              321
```

<210> SEQ ID NO 187
<211> LENGTH: 345
<212> TYPE: DNA
<213> ORGANISM: Mus sp.

<400> SEQUENCE: 187

```
caggttcagc tgcagcagtc tgacgctgag ttggtgaaac ctggggcttc agtgaagata    60
tcctgcaagg cttctggcta catcttcact gaccatgcaa ttcactgggt gaagcagaag    120
cctgaacagg gcctggaatg gattggatat atttctcccg gaaatggtga tattaagtac    180
attgagaagt tcaggggcaa ggccacactg actgcagaca atcctccag cactgcctac    240 atgcagctca acagcctgac atctgaggat tctgcagtgt atttctgtaa aagatcgctt    300
agtacgcctt actggggcca agggactctg gtcactgtct ctgca                    345
```

<210> SEQ ID NO 188
<211> LENGTH: 329
<212> TYPE: DNA
<213> ORGANISM: Mus sp.

<400> SEQUENCE: 188

```
aacattttaa tgacccaatc tcccaaatcc atgtccatgt cagtaggaga gagggtcacc    60
ttgacctgca aggccagtga gaatgtggtt aattatgttt cctggtatca acagaaacca    120
gagcagtctc ctaaactgct gatattcggg gcatccaacc ggtactctgg ggtccccgat    180
cgcttcacag gcagtggatc tgcaacagat ttcactctga ccatcagcag tgtgcaggct    240
gaagaccttg cagattatca ctgtggaagc aagtggatta ctagctatcc gtacacgttc    300
ggagggggga ccaagctgga aataaaacg                                      329
```

<210> SEQ ID NO 189
<211> LENGTH: 326
<212> TYPE: DNA
<213> ORGANISM: Mus sp.

<400> SEQUENCE: 189

```
aacatttttaa tgacccaatc tcccaaatcc atgtccatgt cagtaggaga gagggtcacc   60
ttgacctgca aggccagtga gaatgtggtt aattatgttt cctggtatca acagaaacca    120
gagcagtctc ctaaactgct gatatacggg gcatccaacc ggtactctgg ggtccccgat    180
cgcttcacag gcagtggatc tgcaacagat ttcactctga ccatcagcag tgtgcaggct    240
```

```
gaagaccttg cagattatca ctgtggagca agggttacta gctatccgta cacgttcgga      300 gggggggacca agctggaaat aaaacg                                          326
```

<210> SEQ ID NO 190
<211> LENGTH: 345
<212> TYPE: DNA
<213> ORGANISM: Mus sp.

<400> SEQUENCE: 190

```
caggttcagc tgcagcagtc tgacgctgag ttggtgaaac ctgggacttc agtgaagata       60
tcctgcaggg cttctggcta caccttcact gaccatgcta ttcactgggt gaagcagaag      120
cctgaacagg gcctggaatg gattggatat atttctcccg gaaatggtga tattaagtac      180
aatgagaagt tcaagggcaa ggccacactg actgcagaca atcctccag cactgcctac       240 atgcagctca acagcctgac atctgacgat tctgcagtgt atttctgtaa aagatccatt      300
actacgcctt actggggcca aggcaccact ctcacagtct cctca                      345
```

<210> SEQ ID NO 191
<211> LENGTH: 315
<212> TYPE: DNA
<213> ORGANISM: Mus sp.

<400> SEQUENCE: 191

```
agttttgtga tgacccagac tcccaaattc ctgcttgtgt cagcaggaga cagggttacc       60
ataacctgca aggccagtca gagtgtgaat aataatgtag cttggtacca acagaagcca      120
gggcagtctc ctaaacagct gatatactat gcatccaatc gctacactgg agtccctgat      180
cgcttcactg gcagtggata tgggacggat ttcactttca ccatctacac tgtgcaggct      240
gaagacctgg cagtttattt ctgtcagcag ggttatagct ctccgtggac gttcggtgga      300
ggcaccaagc tgaaa                                                       315
```

<210> SEQ ID NO 192
<211> LENGTH: 330
<212> TYPE: PRT
<213> ORGANISM: Mus sp.

<400> SEQUENCE: 192

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 193
<211> LENGTH: 107
<212> TYPE: PRT
<213> ORGANISM: Mus sp.

<400> SEQUENCE: 193

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 194
<211> LENGTH: 330
<212> TYPE: PRT
<213> ORGANISM: Homo sapiens

<400> SEQUENCE: 194

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

```
Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 195
<211> LENGTH: 107
<212> TYPE: PRT
<213> ORGANISM: Homo sapiens

<400> SEQUENCE: 195

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
```

```
              65                  70                  75                  80
Lys His Lys Val Tyr Ala Cys Glu Val Thr His Gln Gly Leu Ser Ser
                    85                  90                  95

Pro Val Thr Lys Ser Phe Asn Arg Gly Glu Cys
                100                 105
```

<210> SEQ ID NO 196
<211> LENGTH: 446
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 196

```
Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
                20                  25                  30

Ala Ile His Trp Val Lys Gln Lys Pro Glu Gln Gly Leu Asp Trp Ile
            35                  40                  45

Gly Tyr Ile Ser Pro Gly Asn Gly Asp Ile Lys Tyr Asn Glu Lys Phe
    50                  55                  60

Lys Asp Lys Val Thr Leu Thr Ala Asp Lys Ser Ser Ser Thr Ala Cys
65                  70                  75                  80

Met His Leu Asn Ser Leu Thr Ser Glu Asp Ser Ala Val Tyr Phe Cys
                85                  90                  95

Lys Arg Ser Leu Leu Ala Leu Asp Tyr Trp Gly Gln Gly Thr Thr Leu
                100                 105                 110

Thr Val Ser Ser Ala Lys Thr Thr Ala Pro Ser Val Tyr Pro Leu Ala
            115                 120                 125

Pro Val Cys Gly Asp Thr Thr Gly Ser Ser Val Thr Leu Gly Cys Leu
    130                 135                 140

Val Lys Gly Tyr Phe Pro Glu Pro Val Thr Leu Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Thr Ser Ser Thr Trp Pro
                180                 185                 190

Ser Gln Ser Ile Thr Cys Asn Val Ala His Pro Ala Ser Ser Thr Lys
            195                 200                 205

Val Asp Lys Lys Ile Glu Pro Arg Gly Pro Thr Ile Lys Pro Cys Pro
    210                 215                 220

Pro Cys Lys Cys Pro Ala Pro Asn Leu Leu Gly Gly Pro Ser Val Phe
225                 230                 235                 240

Ile Phe Pro Pro Lys Ile Lys Asp Val Leu Met Ile Ser Leu Ser Pro
                245                 250                 255

Ile Val Thr Cys Val Val Val Asp Val Ser Glu Asp Asp Pro Asp Val
                260                 265                 270

Gln Ile Ser Trp Phe Val Asn Asn Val Glu Val His Thr Ala Gln Thr
            275                 280                 285

Gln Thr His Arg Glu Asp Tyr Asn Ser Thr Leu Arg Val Val Ser Ala
    290                 295                 300

Leu Pro Ile Gln His Gln Asp Trp Met Ser Gly Lys Glu Phe Lys Cys
305                 310                 315                 320
```

```
Lys Val Asn Asn Lys Asp Leu Pro Ala Pro Ile Glu Arg Thr Ile Ser
            325                 330                 335

Lys Pro Lys Gly Ser Val Arg Ala Pro Gln Val Tyr Val Leu Pro Pro
            340                 345                 350

Pro Glu Glu Glu Met Thr Lys Lys Gln Val Thr Leu Thr Cys Met Val
            355                 360                 365

Thr Asp Phe Met Pro Glu Asp Ile Tyr Val Glu Trp Thr Asn Asn Gly
            370                 375                 380

Lys Thr Glu Leu Asn Tyr Lys Asn Thr Glu Pro Val Leu Asp Ser Asp
385                 390                 395                 400

Gly Ser Tyr Phe Met Tyr Ser Lys Leu Arg Val Glu Lys Lys Asn Trp
            405                 410                 415

Val Glu Arg Asn Ser Tyr Ser Cys Ser Val Val His Glu Gly Leu His
            420                 425                 430

Asn His His Thr Thr Lys Ser Phe Ser Arg Thr Pro Gly Lys
            435                 440                 445

<210> SEQ ID NO 197
<211> LENGTH: 1401
<212> TYPE: DNA
<213> ORGANISM: Artificial Sequence
<220> FEATURE:
<223> OTHER INFORMATION: Description of Artificial Sequence: Synthetic
      hybrid polynucleotide

<400> SEQUENCE: 197
atggagaccg acaccctgct gctctgggtg ctgctgctct gggtgcccgg ctccaccgga     60
caggttcagc tgcagcagtc tgacgctgag ttggtgaaac tggggcttc agtgaagata    120 tcctgcaagg cttctggcta caccttcact gaccatgcta ttcactgggt gaagcaaaag    180
cctgaacagg gcctggactg gattggatat atttctcccg aaatggtga tattaagtac    240 aatgagaagt tcaaggacaa ggtcacactg actgcagaca atcctccag cactgcctgc    300 atgcacctca acagcctgac atctgaggat tctgcagtgt atttctgcaa agatccccta    360
ctagctcttg actactgggg ccaaggcacc actctcacag tctcctcagc taaaacaaca    420
gccccatcgg tctatccact ggcccctgtg tgtggagata caactggctc ctcggtgact    480
ctaggatgcc tggtcaaggg ttatttccct gagccagtga ccttgacctg gaactctggt    540
tccctgtcca gtggtgtgca caccttccca gctgtcctgc agtctgacct ctacaccctc    600
agctcaagcg tgactgtaac cagctcgacc tggcccagcc agtccatcac ctgcaatgtg    660
gcccacccgg caagcagcac caaggtggac aagaaaattg agcccagagg ccccacaatc    720
aagccctgtc ctccatgcaa atgcccagca cctaacctct gggtggacc atccgtcttc    780 atcttccctc caaagatcaa ggatgtactc atgatctccc tgagcccat agtcacatgt    840 gtagtcgttg atgtgagcga ggatgaccca gatgtccaga tcagctggtt tgtgaacaac    900
gtggaagtgc acactgctca gacacagacg catagagagg attacaacag tactctccgg    960
gttgtcagtg ccctccccat ccagcaccag gactggatga gtggcaagga gttcaaatgc   1020
aaggtcaaca acaaagacct cccagcgccc atcgagagaa ccatctcaaa acccaagggg   1080
tcagtaagag ctccacaggt atatgtcttg cctccaccag aagaggagat gactaagaaa   1140
caggtcactc tgacctgcat ggtcacagac ttcatgcctg aagacattta cgtggagtgg   1200
accaacaacg ggaaaacaga gctaaactac aagaacactg aaccagtcct ggactctgat   1260
ggttcttact tcatgtacag caagctgaga gtggagaaga gaactgggt ggagagaaat   1320
```

-continued

```
agctactcct gttcagtggt ccacgagggt ctgcacaatc accacacgac taagagcttc    1380
tcccggactc cgggtaaata g                                              1401
```

<210> SEQ ID NO 198
<211> LENGTH: 214
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 198

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Asn
            20                  25                  30

Ile Ala Trp Tyr Gln Gln Lys Pro Gly Arg Ser Pro Lys Val Leu Ile
        35                  40                  45

Tyr Ser Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Thr Asp Tyr Phe Cys Gln Gln Tyr Ser Ser Phe Pro Leu
                85                  90                  95

Thr Phe Gly Val Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 199
<211> LENGTH: 705
<212> TYPE: DNA
<213> ORGANISM: Artificial Sequence
<220> FEATURE:
<223> OTHER INFORMATION: Description of Artificial Sequence: Synthetic
      hybrid polynucleotide

<400> SEQUENCE: 199

```
atggagaccg acaccctgct gctctgggtg ctgctgctct gggtgcccgg ctccaccgga    60
gacattgtga tgacccagtc tcacaaattc atgtccacat cagtaggaga cagggtcagc   120
atcacctgca aggccagtca ggatgtgggc actaatatag cctggtatca acagaaacca   180
ggccgatctc ctaaagtact gatttactcg gcatccaccc ggcacactgg agtccctgat   240
cgcttcacag gcagtggatc tgggacagat ttcactctca ccattagcaa tgtgcagtct   300
gaagacttga cagattattt ctgtcagcaa tatagcagct ttcctctcac gttcggtgtt   360
```

```
gggaccaagc tggagctgaa acgggcagat gctgcaccaa ctgtatccat cttcccacca    420
tccagtgagc agttaacatc tggaggtgcc tcagtcgtgt gcttcttgaa caacttctac    480
cccaaagaca tcaatgtcaa gtggaagatt gatggcagtg aacgacaaaa tggcgtcctg    540
aacagttgga ctgatcagga cagcaaagac agcacctaca gcatgagcag cacccctcacg   600 ttgaccaagg acgagtatga acgacataac agctatacct gtgaggccac tcacaagaca    660
tcaacttcac ccattgtcaa gagcttcaac aggaatgagt gttga                    705

<210> SEQ ID NO 200
<211> LENGTH: 296
<212> TYPE: DNA
<213> ORGANISM: Homo sapiens

<400> SEQUENCE: 200
caggttcagc tggtgcagtc tggagctgag gtgaagaagc ctggggcctc agtgaaggtc    60
tcctgcaagg cttctggtta cacctttacc agctatggta tcagctgggt gcgacaggcc    120
cctggacaag gcttgagtg gatgggatgg atcagcgctt acaatggtaa cacaaactat     180
gcacagaagc tccagggcag agtcaccatg accacagaca catccacgag cacagcctac    240
atggagctga ggagcctgag atctgacgac acggccgtgt attactgtgc gagaga        296

<210> SEQ ID NO 201
<211> LENGTH: 286
<212> TYPE: DNA
<213> ORGANISM: Homo sapiens

<400> SEQUENCE: 201
gacatccaga tgacccagtc tccatcctcc ctgtctgcat ctgtaggaga cagagtcacc    60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta cccctc                   286

<210> SEQ ID NO 202
<211> LENGTH: 305
<212> TYPE: DNA
<213> ORGANISM: Homo sapiens

<400> SEQUENCE: 202
gacatcgtga tgacccagtc tccagactcc ctggctgtgt ctctgggcga gagggccacc    60
atcaactgca gtccagcca gagtgtttta tacagctcca acaataagaa ctacttagct    120
tggtaccagc agaaaccagg acagcctcct aagctgctca tttactgggc atctacccgg    180
gaatccgggg tccctgaccg attcagtggc agcgggtctg ggacagattt cactctcacc    240
atcagcagcc tgcaggctga agatgtggca gtttattact gtcagcaata ttatagtact    300
cctcc                                                                305

<210> SEQ ID NO 203
<211> LENGTH: 98
<212> TYPE: PRT
<213> ORGANISM: Homo sapiens

<400> SEQUENCE: 203

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg

<210> SEQ ID NO 204
<211> LENGTH: 95
<212> TYPE: PRT
<213> ORGANISM: Homo sapiens

<400> SEQUENCE: 204

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 205
<211> LENGTH: 102
<212> TYPE: PRT
<213> ORGANISM: Homo sapiens

<400> SEQUENCE: 205

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Cys
            100

<210> SEQ ID NO 206
<211> LENGTH: 25
<212> TYPE: PRT
<213> ORGANISM: Homo sapiens -continued

<400> SEQUENCE: 206

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 207
<211> LENGTH: 22
<212> TYPE: PRT
<213> ORGANISM: Homo sapiens

<400> SEQUENCE: 207

Ile Gln Met Thr Gln Ser Pro Ser Ser Leu Ser Ala Ser Val Gly Asp
1               5                   10                  15

Arg Val Thr Ile Thr Cys
            20

<210> SEQ ID NO 208
<211> LENGTH: 23
<212> TYPE: PRT
<213> ORGANISM: Homo sapiens

<400> SEQUENCE: 208

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 209
<211> LENGTH: 14
<212> TYPE: PRT
<213> ORGANISM: Homo sapiens

<400> SEQUENCE: 209

Trp Val Arg Gln Ala Pro Gly Gln Gly Leu Glu Trp Met Gly
1               5                   10

<210> SEQ ID NO 210
<211> LENGTH: 15
<212> TYPE: PRT
<213> ORGANISM: Homo sapiens

<400> SEQUENCE: 210

Trp Tyr Gln Gln Lys Pro Gly Lys Ala Pro Lys Leu Leu Ile Tyr
1               5                   10                  15

<210> SEQ ID NO 211
<211> LENGTH: 15
<212> TYPE: PRT
<213> ORGANISM: Homo sapiens

<400> SEQUENCE: 211

Trp Tyr Gln Gln Lys Pro Gly Gln Pro Pro Lys Leu Leu Ile Tyr
1               5                   10                  15

<210> SEQ ID NO 212
<211> LENGTH: 32
<212> TYPE: PRT
<213> ORGANISM: Homo sapiens

<400> SEQUENCE: 212

Arg Val Thr Met Thr Thr Asp Thr Ser Thr Ser Thr Ala Tyr Met Glu
1               5                   10                  15

```
Leu Arg Ser Leu Arg Ser Asp Asp Thr Ala Val Tyr Tyr Cys Ala Arg
            20                  25                  30

<210> SEQ ID NO 213
<211> LENGTH: 32
<212> TYPE: PRT
<213> ORGANISM: Homo sapiens

<400> SEQUENCE: 213

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 214
<211> LENGTH: 32
<212> TYPE: PRT
<213> ORGANISM: Homo sapiens

<400> SEQUENCE: 214

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 215
<211> LENGTH: 11
<212> TYPE: PRT
<213> ORGANISM: Homo sapiens

<400> SEQUENCE: 215

Trp Gly Gln Gly Thr Leu Val Thr Val Ser Ser
1               5                   10

<210> SEQ ID NO 216
<211> LENGTH: 10
<212> TYPE: PRT
<213> ORGANISM: Homo sapiens

<400> SEQUENCE: 216

Phe Gly Gln Gly Thr Lys Val Glu Ile Lys
1               5                   10

<210> SEQ ID NO 217
<211> LENGTH: 107
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 217

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser His
            20                  25                  30

Leu Ala Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln His Phe Trp Gly Ala Pro Phe
                85                  90                  95

Thr Phe Gly Gln Gly Thr Lys Val Glu Ile Lys
            100                 105
```

<210> SEQ ID NO 218
<211> LENGTH: 107
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 218

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser His
            20                  25                  30

Leu Ala Trp Tyr Gln Gln Lys Pro Gly Lys Ala Pro Lys Leu Leu Val
        35                  40                  45

Tyr Gly Ala Thr Asn Leu Ala Ser Gly Val Pro Ser Arg Phe Ser Gly
50                  55                  60

Ser Gly Ser Gly Thr Gln Phe Thr Leu Thr Ile Ser Ser Leu Gln Pro
65                  70                  75                  80

Glu Asp Phe Ala Thr Tyr Tyr Cys Gln His Phe Trp Gly Ala Pro Phe
                85                  90                  95

Thr Phe Gly Gln Gly Thr Lys Val Glu Ile Lys
            100                 105
```

<210> SEQ ID NO 219
<211> LENGTH: 107
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 219

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser His
            20                  25                  30

Leu Ala Trp Tyr Gln Gln Lys Pro Gly Lys Ala Pro Lys Leu Leu Val
        35                  40                  45

Tyr Gly Ala Thr Asn Leu Ala Asp Gly Val Pro Ser Arg Phe Ser Gly
50                  55                  60

Ser Gly Ser Gly Thr Gln Phe Thr Leu Thr Ile Ser Ser Leu Gln Pro
65                  70                  75                  80

Glu Asp Phe Ala Thr Tyr Tyr Cys Gln His Phe Trp Gly Ala Pro Phe
                85                  90                  95

Thr Phe Gly Gln Gly Thr Lys Val Glu Ile Lys
            100                 105
```

<210> SEQ ID NO 220
<211> LENGTH: 114
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 220

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Gly Leu Glu Trp Met
        35                  40                  45

Gly Tyr Phe Ser Pro Gly Asn Asp Asp Ile Lys Tyr Asn Glu Lys Phe
    50                  55                  60

Lys Val Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Tyr Tyr Gly Asp Trp Gly Gln Gly Thr Leu Val Thr Val
            100                 105                 110

Ser Ser

<210> SEQ ID NO 221
<211> LENGTH: 114
<212> TYPE: PRT
<213> ORGANISM: Artificial Sequence
<220> FEATURE:
<223> OTHER INFORMATION: Description of Artificial Sequence: Synthetic hybrid polypeptide

<400> SEQUENCE: 221

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Gly Leu Glu Trp Met
        35                  40                  45

Gly Tyr Phe Ser Pro Gly Asn Asp Asp Ile Lys Tyr Asn Glu Lys Phe
    50                  55                  60

Lys Val Arg Val Thr Met Thr Ala Asp Lys Ser Ser Thr Ala Tyr
65                  70                  75                  80

Met Glu Leu Arg Ser Leu Arg Ser Asp Asp Thr Ala Val Tyr Phe Cys
                85                  90                  95

Lys Arg Ser Tyr Tyr Gly Asp Trp Gly Gln Gly Thr Leu Val Thr Val
            100                 105                 110

Ser Ser

<210> SEQ ID NO 222
<211> LENGTH: 114
<212> TYPE: PRT
<213> ORGANISM: Artificial Sequence
<220> FEATURE:
<223> OTHER INFORMATION: Description of Artificial Sequence: Synthetic hybrid polypeptide

<400> SEQUENCE: 222

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Arg Gln Ala Pro Gly Gln Gly Leu Glu Trp Ile
        35                  40                  45

```
Gly Tyr Phe Ser Pro Gly Asn Asp Asp Ile Lys Tyr Asn Glu Lys Phe
        50                  55                  60

Lys Val Arg Ala Thr Leu Thr Ala Asp Lys Ser Ser Thr Ala Tyr
 65                  70                  75                  80

Met Glu Leu Arg Ser Leu Arg Ser Asp Asp Thr Ala Val Tyr Phe Cys
                    85                  90                  95

Lys Arg Ser Tyr Tyr Gly Asp Trp Gly Gln Gly Thr Leu Val Thr Val
                100                 105                 110

Ser Ser
```

<210> SEQ ID NO 223
<211> LENGTH: 114
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 223

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp His
                20                  25                  30

Ala Ile His Trp Val Arg Gln Ala Pro Gly Gln Gly Leu Glu Trp Met
            35                  40                  45

Gly Tyr Phe Ser Pro Gly Asn Asp Asp Ile Lys Tyr Asn Glu Lys Phe
        50                  55                  60

Lys Val Arg Val Thr Met Thr Ala Asp Lys Ser Ser Thr Ala Tyr
 65                  70                  75                  80

Met Glu Leu Arg Ser Leu Arg Ser Asp Asp Thr Ala Val Tyr Phe Cys
                    85                  90                  95

Lys Arg Ser Tyr Tyr Gly Asp Trp Gly Gln Gly Thr Leu Val Thr Val
                100                 105                 110

Ser Ser
```

<210> SEQ ID NO 224
<211> LENGTH: 114
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 224

```
Glu Val Gln Leu Val Gln Ser Gly Ala Glu Val Lys Lys Pro Gly Ala
 1               5                  10                  15

Ser Val Lys Ile Ser Cys Lys Ala Ser Gly Tyr Thr Phe Thr Asp His
                20                  25                  30

Ala Ile His Trp Val Arg Gln Ala Pro Gly Gln Gly Leu Glu Trp Ile
            35                  40                  45

Gly Tyr Phe Ser Pro Gly Asn Asp Asp Ile Lys Tyr Asn Glu Lys Phe
        50                  55                  60

Lys Val Arg Ala Thr Leu Thr Ala Asp Lys Ser Ser Thr Ala Tyr
 65                  70                  75                  80

Met Glu Leu Arg Ser Leu Arg Ser Asp Asp Thr Ala Val Tyr Phe Cys
                    85                  90                  95

Lys Arg Ser Tyr Tyr Gly Asp Trp Gly Gln Gly Thr Leu Val Thr Val
```

Ser Ser

<210> SEQ ID NO 225
<211> LENGTH: 107
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 225

Asp Ile Gln Met Thr Gln Ser Pro Ser Ser Leu Ser Ala Ser Val Gly
1               5                   10                  15

Asp Arg Val Thr Ile Thr Cys His Ala Ser Gln His Ile Asn Phe Trp
            20                  25                  30

Leu Ser Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Gln Ser Tyr Pro Tyr
                85                  90                  95

Met Phe Gly Gln Gly Thr Lys Val Glu Ile Lys
            100                 105

<210> SEQ ID NO 226
<211> LENGTH: 107
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 226

Asp Ile Gln Met Thr Gln Ser Pro Ser Ser Leu Ser Ala Ser Val Gly
1               5                   10                  15

Asp Arg Val Thr Ile Thr Cys His Ala Ser Gln His Ile Asn Phe Trp
            20                  25                  30

Leu Ser Trp Tyr Gln Gln Lys Pro Gly Lys Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Phe Ala Thr Tyr Tyr Cys Gln Gln Asp Gln Ser Tyr Pro Tyr
                85                  90                  95

Met Phe Gly Gln Gly Thr Lys Val Glu Ile Lys
            100                 105

<210> SEQ ID NO 227
<211> LENGTH: 107
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 227

Asp Ile Gln Met Thr Gln Ser Pro Ser Ser Leu Ser Ala Ser Val Gly
1               5                   10                  15

Asp Arg Ile Thr Ile Thr Cys His Ala Ser Gln His Ile Asn Phe Trp
            20                  25                  30

Leu Ser Trp Tyr Gln Gln Lys Pro Gly Lys Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65              70                  75                  80

Glu Asp Val Ala Thr Tyr Tyr Cys Gln Gln Asp Gln Ser Tyr Pro Tyr
                85                  90                  95

Met Phe Gly Gln Gly Thr Lys Leu Glu Ile Lys
            100                 105

<210> SEQ ID NO 228
<211> LENGTH: 107
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 228

Asp Ile Gln Met Thr Gln Ser Pro Ser Ser Leu Ser Ala Ser Val Gly
1               5                   10                  15

Asp Arg Val Thr Ile Thr Cys His Ala Ser Gln His Ile Asn Phe Trp
            20                  25                  30

Leu Ser Trp Tyr Gln Gln Lys Pro Gly Lys Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65              70                  75                  80

Glu Asp Phe Ala Thr Tyr Tyr Cys Gln Gln Asp Gln Ser Tyr Pro Tyr
                85                  90                  95

Phe Phe Gly Gln Gly Thr Lys Val Glu Ile Lys
            100                 105

<210> SEQ ID NO 229
<211> LENGTH: 107
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 229

Asp Ile Gln Met Thr Gln Ser Pro Ser Ser Leu Ser Ala Ser Val Gly
1               5                   10                  15

Asp Arg Ile Thr Ile Thr Cys His Ala Ser Gln His Ile Asn Phe Trp
            20                  25                  30

Leu Ser Trp Tyr Gln Gln Lys Pro Gly Lys Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65              70                  75                  80

-continued

Glu Asp Val Ala Thr Tyr Tyr Cys Gln Gln Asp Gln Ser Tyr Pro Tyr
                85                  90                  95

Phe Phe Gly Gln Gly Thr Lys Leu Glu Ile Lys
            100                 105

<210> SEQ ID NO 230
<211> LENGTH: 115
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 230

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asp His
                20                  25                  30

Ala Ile His Trp Val Arg Gln Ala Pro Gly Gln Gly Leu Glu Trp Met
            35                  40                  45

Gly Tyr Ile Ser Pro Gly Asn Gly Asp Ile Lys Tyr Asn Glu Lys Phe
        50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Ile Thr Thr Ser Tyr Trp Gly Gln Gly Thr Leu Val Thr
            100                 105                 110

Val Ser Ser
        115

<210> SEQ ID NO 231
<211> LENGTH: 115
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 231

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asp His
                20                  25                  30

Ala Ile His Trp Val Arg Gln Ala Pro Gly Gln Gly Leu Glu Trp Met
            35                  40                  45

Gly Tyr Ile Ser Pro Gly Asn Gly Asp Ile Lys Tyr Asn Glu Lys Phe
        50                  55                  60

Lys Gly Arg Val Thr Met Thr Ala Asp Lys Ser Ser Ser Thr Ala Tyr
65                  70                  75                  80

Met Glu Leu Arg Ser Leu Arg Ser Asp Asp Thr Ala Val Tyr Phe Cys
                85                  90                  95

Lys Arg Ser Ile Thr Thr Ser Tyr Trp Gly Gln Gly Thr Leu Val Thr
            100                 105                 110

Val Ser Ser
        115

<210> SEQ ID NO 232
<211> LENGTH: 115

```
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 232

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ile Phe Thr Asp His
                20                  25                  30

Ala Ile His Trp Val Arg Gln Ala Pro Gly Gln Gly Leu Glu Trp Ile
            35                  40                  45

Gly Tyr Ile Ser Pro Gly Asn Gly Asp Ile Lys Tyr Asn Glu Lys Phe
        50                  55                  60

Lys Gly Arg Ala Thr Leu Thr Ala Asp Lys Ser Ser Ser Thr Ala Tyr
65                  70                  75                  80

Met His Leu Arg Ser Leu Arg Ser Asp Asp Thr Ala Val Tyr Phe Cys
                85                  90                  95

Lys Arg Ser Ile Thr Thr Ser Tyr Trp Gly Gln Gly Thr Leu Val Thr
                100                 105                 110

Val Ser Ser
        115

<210> SEQ ID NO 233
<211> LENGTH: 115
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 233

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asp His
                20                  25                  30

Ala Ile His Trp Val Arg Gln Ala Pro Gly Gln Gly Leu Glu Trp Met
            35                  40                  45

Gly Tyr Ile Ser Pro Gly Ser Gly Asp Ile Lys Tyr Asn Glu Lys Phe
        50                  55                  60

Lys Gly Arg Val Thr Met Thr Ala Asp Lys Ser Ser Ser Thr Ala Tyr
65                  70                  75                  80

Met Glu Leu Arg Ser Leu Arg Ser Asp Asp Thr Ala Val Tyr Phe Cys
                85                  90                  95

Lys Arg Ser Ile Thr Thr Ser Tyr Trp Gly Gln Gly Thr Leu Val Thr
                100                 105                 110

Val Ser Ser
        115

<210> SEQ ID NO 234
<211> LENGTH: 115
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 234

Glu Val Gln Leu Val Gln Ser Gly Ala Glu Val Lys Lys Pro Gly Ala
```

```
                1               5                  10                 15
Ser Val Lys Ile Ser Cys Lys Ala Ser Gly Tyr Ile Phe Thr Asp His
                20                 25                 30

Ala Ile His Trp Val Arg Gln Ala Pro Gly Gln Gly Leu Glu Trp Ile
                35                 40                 45

Gly Tyr Ile Ser Pro Gly Ser Gly Asp Ile Lys Tyr Asn Glu Lys Phe
                50                 55                 60

Lys Gly Arg Ala Thr Leu Thr Ala Asp Lys Ser Ser Thr Ala Tyr
 65                70                 75                 80

Met His Leu Arg Ser Leu Arg Ser Asp Thr Ala Val Tyr Phe Cys
                85                 90                 95

Lys Arg Ser Ile Thr Thr Ser Tyr Trp Gly Gln Gly Thr Leu Val Thr
                100                105                110

Val Ser Ser
        115
```

<210> SEQ ID NO 235
<211> LENGTH: 113
<212> TYPE: PRT
<213> ORGANISM: Artificial Sequence
<220> FEATURE:
<223> OTHER INFORMATION: Description of Artificial Sequence: Synthetic hybrid polypeptide

<400> SEQUENCE: 235

```
Asp Ile Val Met Thr Gln Ser Pro Asp Ser Leu Ala Val Ser Leu Gly
 1               5                  10                 15

Glu Arg Ala Thr Ile Asn Cys Lys Ser Ser Gln Ser Leu Leu Asn Arg
                20                 25                 30

Gly Asn His Lys Asn Tyr Leu Thr Trp Tyr Gln Gln Lys Pro Gly Gln
                35                 40                 45

Pro Pro Lys Leu Leu Ile Tyr Trp Ala Ser Thr Arg Glu Ser Gly Val
                50                 55                 60

Pro Asp Arg Phe Ser Gly Ser Gly Ser Gly Thr Asp Phe Thr Leu Thr
 65                70                 75                 80

Ile Ser Ser Leu Gln Ala Glu Asp Val Ala Val Tyr Tyr Cys Gln Asn
                85                 90                 95

Asp Tyr Thr Tyr Pro Tyr Thr Phe Gly Gln Gly Thr Lys Val Glu Ile
                100                105                110

Lys
```

<210> SEQ ID NO 236
<211> LENGTH: 113
<212> TYPE: PRT
<213> ORGANISM: Artificial Sequence
<220> FEATURE:
<223> OTHER INFORMATION: Description of Artificial Sequence: Synthetic hybrid polypeptide

<400> SEQUENCE: 236

```
Asp Ile Val Met Thr Gln Ser Pro Asp Ser Leu Ala Val Ser Leu Gly
 1               5                  10                 15

Glu Arg Val Thr Met Ser Cys Lys Ser Ser Gln Ser Leu Leu Asn Arg
                20                 25                 30

Gly Asn His Lys Asn Tyr Leu Thr Trp Tyr Gln Gln Lys Pro Gly Gln
                35                 40                 45

Pro Pro Lys Leu Leu Ile Tyr Trp Ala Ser Thr Arg Glu Ser Gly Val
                50                 55                 60
```

```
Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Thr Tyr Pro Tyr Thr Phe Gly Gln Gly Thr Lys Val Glu Ile
            100                 105                 110

Lys

<210> SEQ ID NO 237
<211> LENGTH: 115
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 237

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
                20                  25                  30

Ala Ile His Trp Val Arg Gln Ala Pro Gly Gln Gly Leu Glu Trp Met
            35                  40                  45

Gly Tyr Phe Ser Pro Gly Asn Asp Asp Ile Lys Tyr Asn Glu Lys Phe
    50                  55                  60

Arg Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Leu Ser Thr Pro Tyr Trp Gly Gln Gly Thr Leu Val Thr
            100                 105                 110

Val Ser Ser
        115

<210> SEQ ID NO 238
<211> LENGTH: 115
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 238

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
                20                  25                  30

Ala Ile His Trp Val Arg Gln Ala Pro Gly Gln Gly Leu Glu Trp Met
            35                  40                  45

Gly Tyr Phe Ser Pro Gly Asn Asp Asp Ile Lys Tyr Asn Glu Lys Phe
    50                  55                  60

Arg Gly Arg Val Thr Met Thr Ala Asp Lys Ser Ser Ser Thr Ala Tyr
65                  70                  75                  80

Met Glu Leu Arg Ser Leu Arg Ser Asp Asp Thr Ala Val Tyr Phe Cys
                85                  90                  95

Lys Arg Ser Leu Ser Thr Pro Tyr Trp Gly Gln Gly Thr Leu Val Thr
            100                 105                 110
```

Val Ser Ser
        115

<210> SEQ ID NO 239
<211> LENGTH: 115
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 239

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Arg Gln Ala Pro Gly Gln Gly Leu Glu Trp Ile
        35                  40                  45

Gly Tyr Phe Ser Pro Gly Asn Asp Asp Ile Lys Tyr Asn Glu Lys Phe
    50                  55                  60

Arg Gly Arg Val Thr Leu Thr Ala Asp Lys Ser Ser Ser Thr Ala Tyr
65                  70                  75                  80

Met Glu Leu Arg Ser Leu Arg Ser Asp Asp Thr Ala Val Tyr Phe Cys
                85                  90                  95

Lys Arg Ser Leu Ser Thr Pro Tyr Trp Gly Gln Gly Thr Leu Val Thr
            100                 105                 110

Val Ser Ser
        115

<210> SEQ ID NO 240
<211> LENGTH: 115
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 240

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Gly Leu Glu Trp Met
        35                  40                  45

Gly Tyr Phe Ser Pro Gly Asn Asp Asp Ile Lys Tyr Asn Glu Lys Phe
    50                  55                  60

Arg Gly Arg Val Thr Met Thr Ala Asp Lys Ser Ser Ser Thr Ala Tyr
65                  70                  75                  80

Met Glu Leu Arg Ser Leu Arg Ser Asp Asp Thr Ala Val Tyr Phe Cys
                85                  90                  95

Lys Arg Ser Leu Ser Thr Pro Tyr Trp Gly Gln Gly Thr Leu Val Thr
            100                 105                 110

Val Ser Ser
        115

<210> SEQ ID NO 241
<211> LENGTH: 115
<212> TYPE: PRT
<213> ORGANISM: Artificial Sequence
<220> FEATURE:

-continued

<223> OTHER INFORMATION: Description of Artificial Sequence: Synthetic
      hybrid polypeptide

<400> SEQUENCE: 241

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Arg Gln Ala Pro Gly Gln Gly Leu Glu Trp Ile
        35                  40                  45

Gly Tyr Phe Ser Pro Gly Asn Asp Asp Ile Lys Tyr Asn Glu Lys Phe
    50                  55                  60

Arg Gly Arg Val Thr Leu Thr Ala Asp Lys Ser Ser Ser Thr Ala Tyr
65                  70                  75                  80

Met Glu Leu Arg Ser Leu Arg Ser Asp Asp Thr Ala Val Tyr Phe Cys
                85                  90                  95

Lys Arg Ser Leu Ser Thr Pro Tyr Trp Gly Gln Gly Thr Leu Val Thr
            100                 105                 110

Val Ser Ser
        115

<210> SEQ ID NO 242
<211> LENGTH: 107
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 242

Asp Ile Gln Met Thr Gln Ser Pro Ser Ser Leu Ser Ala Ser Val Gly
1               5                   10                  15

Asp Arg Val Thr Ile Thr Cys Lys Ala Ser Glu Asn Val Val Thr Tyr
            20                  25                  30

Val Ser Trp Tyr Gln Gln Lys Pro Gly Lys Ala Pro Lys Leu Leu Ile
        35                  40                  45

Tyr Gly Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gly Gln Gly Tyr Ser Tyr Pro Tyr
                85                  90                  95

Thr Phe Gly Gln Gly Thr Lys Val Glu Ile Lys
            100                 105

<210> SEQ ID NO 243
<211> LENGTH: 107
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 243

Asn Ile Gln Met Thr Gln Ser Pro Ser Ser Leu Ser Ala Ser Val Gly
1               5                   10                  15

Asp Arg Val Thr Ile Thr Cys Lys Ala Ser Glu Asn Val Val Thr Tyr
            20                  25                  30

Val Ser Trp Tyr Gln Gln Lys Pro Gly Lys Ala Pro Lys Leu Leu Ile

```
                35                  40                  45

Tyr Gly Ala Ser Asn Arg Tyr Thr Gly Val Pro Ser Arg Phe Ser Gly
 50                  55                  60

Ser Gly Ser Ala Thr Asp Phe Thr Leu Thr Ile Ser Ser Leu Gln Pro
65                  70                  75                  80

Glu Asp Phe Ala Thr Tyr Tyr Cys Gly Gln Gly Tyr Ser Tyr Pro Tyr
                85                  90                  95

Thr Phe Gly Gln Gly Thr Lys Val Glu Ile Lys
            100                 105

<210> SEQ ID NO 244
<211> LENGTH: 107
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 244

Asn Ile Val Met Thr Gln Ser Pro Ser Ser Met Ser Met Ser Val Gly
1               5                   10                  15

Asp Arg Val Thr Leu Thr Cys Lys Ala Ser Glu Asn Val Val Thr Tyr
            20                  25                  30

Val Ser Trp Tyr Gln Gln Lys Pro Gly Lys Ser Pro Lys Leu Leu Ile
        35                  40                  45

Tyr Gly Ala Ser Asn Arg Tyr Thr Gly Val Pro Ser Arg Phe Ser Gly
 50                  55                  60

Ser Gly Ser Ala Thr Asp Phe Thr Leu Thr Ile Ser Ser Val Gln Pro
65                  70                  75                  80

Glu Asp Leu Ala Thr Tyr His Cys Gly Gln Gly Tyr Ser Tyr Pro Tyr
                85                  90                  95

Thr Phe Gly Gln Gly Thr Lys Leu Glu Ile Lys
            100                 105

<210> SEQ ID NO 245
<211> LENGTH: 107
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 245

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Val Trp
            20                  25                  30

Leu Ser Trp Tyr Gln Gln Lys Pro Gly Lys Ala Pro Lys Leu Leu Ile
        35                  40                  45

Tyr Lys Ala Ser Asn Leu Tyr Thr Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Asp Gln Ser Tyr Pro Tyr
                85                  90                  95

Thr Phe Gly Gln Gly Thr Lys Val Glu Ile Lys
            100                 105
```

```
<210> SEQ ID NO 246
<211> LENGTH: 107
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 246

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Val Trp
            20                  25                  30

Leu Ser Trp Tyr Gln Gln Lys Pro Gly Lys Ile Pro Lys Leu Leu Ile
        35                  40                  45

Tyr Lys Ala Ser Asn Leu Tyr Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Phe Ala Thr Tyr Tyr Cys Gln His Asp Gln Ser Tyr Pro Tyr
                85                  90                  95

Thr Phe Gly Gln Gly Thr Lys Val Glu Ile Lys
            100                 105

<210> SEQ ID NO 247
<211> LENGTH: 107
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 247

Asp Ile Gln Met Thr Gln Ser Pro Ser Ser Leu Ser Ala Ser Val Gly
1               5                   10                  15

Asp Arg Ile Thr Ile Thr Cys His Ala Ser Gln Asn Ile Asn Val Trp
            20                  25                  30

Leu Ser Trp Tyr Gln Gln Lys Pro Gly Lys Ile Pro Lys Leu Leu Ile
        35                  40                  45

Tyr Lys Ala Ser Asn Leu Tyr Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Phe Ala Thr Tyr Tyr Cys Gln His Asp Gln Ser Tyr Pro Tyr
                85                  90                  95

Thr Phe Gly Gln Gly Thr Lys Leu Glu Ile Lys
            100                 105

<210> SEQ ID NO 248
<211> LENGTH: 107
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 248

Asp Ile Gln Met Asn Gln Ser Pro Ser Ser Leu Ser Ala Ser Val Gly
1               5                   10                  15

Asp Arg Ile Thr Ile Thr Cys His Ala Ser Gln Asn Ile Asn Val Trp
            20                  25                  30
```

Leu Ser Trp Tyr Gln Gln Lys Pro Gly Lys Ile Pro Lys Leu Leu Ile
            35                  40                  45

Tyr Lys Ala Ser Asn Leu Tyr Thr Gly Val Pro Ser Arg Phe Ser Gly
        50                  55                  60

Ser Gly Ser Gly Thr Gly Phe Thr Leu Thr Ile Ser Ser Leu Gln Pro
65                  70                  75                  80

Glu Asp Phe Ala Thr Tyr Tyr Cys Gln His Asp Gln Ser Tyr Pro Tyr
                85                  90                  95

Thr Phe Gly Gln Gly Thr Lys Leu Glu Ile Lys
                100                 105

<210> SEQ ID NO 249
<211> LENGTH: 115
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 249

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
                20                  25                  30

Ala Ile His Trp Val Arg Gln Ala Pro Gly Gln Gly Leu Glu Trp Met
            35                  40                  45

Gly Tyr Ile Ser Pro Gly Asn Gly Asp Ile Lys Tyr Asn Glu Lys Phe
        50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Ile Thr Thr Ser Tyr Trp Gly Gln Gly Thr Leu Val Thr
                100                 105                 110

Val Ser Ser
        115

<210> SEQ ID NO 250
<211> LENGTH: 115
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 250

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
                20                  25                  30

Ala Ile His Trp Val Arg Gln Ala Pro Gly Gln Gly Leu Glu Trp Met
            35                  40                  45

Gly Tyr Ile Ser Pro Gly Asn Gly Asp Ile Lys Tyr Asn Glu Lys Phe
        50                  55                  60

Lys Gly Arg Val Thr Met Thr Ala Asp Lys Ser Ser Thr Thr Ala Tyr
65                  70                  75                  80

Met Glu Leu Arg Ser Leu Arg Ser Asp Asp Thr Ala Val Tyr Phe Cys
                85                  90                  95

```
Lys Arg Ser Ile Thr Thr Ser Tyr Trp Gly Gln Gly Thr Leu Val Thr
                100                 105                 110

Val Ser Ser
        115

<210> SEQ ID NO 251
<211> LENGTH: 115
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 251

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp His
                20                  25                  30

Ala Ile His Trp Val Arg Gln Ala Pro Gly Gln Gly Leu Glu Trp Ile
            35                  40                  45

Gly Tyr Ile Ser Pro Gly Asn Gly Asp Ile Lys Tyr Asn Glu Lys Phe
        50                  55                  60

Lys Gly Arg Ala Thr Leu Thr Ala Asp Lys Ser Ser Thr Thr Ala Tyr
65                  70                  75                  80

Met Glu Leu Arg Ser Leu Arg Ser Asp Asp Thr Ala Met Tyr Phe Cys
                85                  90                  95

Lys Arg Ser Ile Thr Thr Ser Tyr Trp Gly Gln Gly Thr Leu Val Thr
                100                 105                 110

Val Ser Ser
        115

<210> SEQ ID NO 252
<211> LENGTH: 115
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 252

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
                20                  25                  30

Ala Ile His Trp Val Arg Gln Ala Pro Gly Gln Gly Leu Glu Trp Met
            35                  40                  45

Gly Tyr Ile Ser Pro Gly Ser Gly Asp Ile Lys Tyr Asn Glu Lys Phe
        50                  55                  60

Lys Gly Arg Val Thr Met Thr Ala Asp Lys Ser Ser Thr Thr Ala Tyr
65                  70                  75                  80

Met Glu Leu Arg Ser Leu Arg Ser Asp Asp Thr Ala Val Tyr Phe Cys
                85                  90                  95

Lys Arg Ser Ile Thr Thr Ser Tyr Trp Gly Gln Gly Thr Leu Val Thr
                100                 105                 110

Val Ser Ser
        115

<210> SEQ ID NO 253
```

```
<211> LENGTH: 115
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 253

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp His
                20                  25                  30

Ala Ile His Trp Val Arg Gln Ala Pro Gly Gln Gly Leu Glu Trp Ile
            35                  40                  45

Gly Tyr Ile Ser Pro Gly Ser Gly Asp Ile Lys Tyr Asn Glu Lys Phe
    50                  55                  60

Lys Gly Arg Ala Thr Leu Thr Ala Asp Lys Ser Thr Ser Thr Ala Tyr
65                  70                  75                  80

Met Glu Leu Arg Ser Leu Arg Ser Asp Asp Thr Ala Met Tyr Phe Cys
                85                  90                  95

Lys Arg Ser Ile Thr Thr Ser Tyr Trp Gly Gln Gly Thr Leu Val Thr
                100                 105                 110

Val Ser Ser
        115

<210> SEQ ID NO 254
<211> LENGTH: 107
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 254

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Asn
                20                  25                  30

Ile Ala Trp Tyr Gln Gln Lys Pro Gly Lys Ala Pro Lys Leu Leu Ile
            35                  40                  45

Tyr Ser Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Leu
                85                  90                  95

Thr Phe Gly Gln Gly Thr Lys Val Glu Ile Lys
                100                 105

<210> SEQ ID NO 255
<211> LENGTH: 107
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 255

Asp Ile Gln Met Thr Gln Ser Pro Ser Ser Leu Ser Ala Ser Val Gly
1               5                   10                  15
```

Asp Arg Val Thr Ile Thr Cys Lys Ala Ser Gln Asp Val Gly Thr Asn
                20                  25                  30

Ile Ala Trp Tyr Gln Gln Lys Pro Gly Lys Ala Pro Lys Val Leu Ile
            35                  40                  45

Tyr Ser Ala Ser Thr Arg His Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Ser Ser Phe Pro Leu
                85                  90                  95

Thr Phe Gly Gln Gly Thr Lys Val Glu Ile Lys
            100                 105

<210> SEQ ID NO 256
<211> LENGTH: 116
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 256

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
                20                  25                  30

Ala Ile His Trp Val Arg Gln Ala Pro Gly Gln Gly Leu Glu Trp Met
            35                  40                  45

Gly Tyr Ile Ser Pro Gly Asn Gly Asp Ile Lys Tyr Asn Glu Lys Phe
        50                  55                  60

Lys Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Leu Leu Ala Leu Asp Tyr Trp Gly Gln Gly Thr Leu Val
            100                 105                 110

Thr Val Ser Ser
        115

<210> SEQ ID NO 257
<211> LENGTH: 116
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 257

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
                20                  25                  30

Ala Ile His Trp Val Arg Gln Ala Pro Gly Gln Gly Leu Glu Trp Met
            35                  40                  45

Gly Tyr Ile Ser Pro Gly Asn Gly Asp Ile Lys Tyr Asn Glu Lys Phe
        50                  55                  60

Lys Asp Arg Val Thr Met Thr Ala Asp Lys Ser Ser Ser Thr Ala Tyr
65                  70                  75                  80

Met Gln Leu Arg Ser Leu Arg Ser Asp Asp Thr Ala Val Tyr Phe Cys
                 85                  90                  95

Lys Arg Ser Leu Leu Ala Leu Asp Tyr Trp Gly Gln Gly Thr Leu Val
            100                 105                 110

Thr Val Ser Ser
        115

<210> SEQ ID NO 258
<211> LENGTH: 116
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 258

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Arg Gln Ala Pro Gly Gln Gly Leu Glu Trp Ile
        35                  40                  45

Gly Tyr Ile Ser Pro Gly Asn Gly Asp Ile Lys Tyr Asn Glu Lys Phe
    50                  55                  60

Lys Asp Arg Val Thr Leu Thr Ala Asp Lys Ser Ser Ser Thr Ala Ser
65                  70                  75                  80

Met His Leu Arg Ser Leu Arg Ser Asp Asp Thr Ala Val Tyr Phe Cys
                85                  90                  95

Lys Arg Ser Leu Leu Ala Leu Asp Tyr Trp Gly Gln Gly Thr Leu Val
            100                 105                 110

Thr Val Ser Ser
        115

<210> SEQ ID NO 259
<211> LENGTH: 116
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 259

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Gly Leu Glu Trp Met
        35                  40                  45

Gly Tyr Ile Ser Pro Gly Ser Gly Asp Ile Lys Tyr Asn Glu Lys Phe
    50                  55                  60

Lys Asp Arg Val Thr Met Thr Ala Asp Lys Ser Ser Ser Thr Ala Tyr
65                  70                  75                  80

Met Gln Leu Arg Ser Leu Arg Ser Asp Asp Thr Ala Val Tyr Phe Cys
                85                  90                  95

Lys Arg Ser Leu Leu Ala Leu Asp Tyr Trp Gly Gln Gly Thr Leu Val
            100                 105                 110

Thr Val Ser Ser
        115

<210> SEQ ID NO 260
<211> LENGTH: 116
<212> TYPE: PRT
<213> ORGANISM: Artificial Sequence
<220> FEATURE:
<223> OTHER INFORMATION: Description of Artificial Sequence: Synthetic
      hybrid polypeptide

<400> SEQUENCE: 260

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Arg Gln Ala Pro Gly Gln Gly Leu Glu Trp Ile
        35                  40                  45

Gly Tyr Ile Ser Pro Gly Ser Gly Asp Ile Lys Tyr Asn Glu Lys Phe
    50                  55                  60

Lys Asp Arg Val Thr Leu Thr Ala Asp Lys Ser Ser Ser Thr Ala Ser
65                  70                  75                  80

Met His Leu Arg Ser Leu Arg Ser Asp Asp Thr Ala Val Tyr Phe Cys
                85                  90                  95

Lys Arg Ser Leu Leu Ala Leu Asp Tyr Trp Gly Gln Gly Thr Leu Val
            100                 105                 110

Thr Val Ser Ser
        115

<210> SEQ ID NO 261
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Cys Gln Phe Asp Leu Ser Thr Arg Arg Leu Lys Cys
1               5                   10

<210> SEQ ID NO 262
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Cys Gln Tyr Asn Leu Ser Ser Arg Ala Leu Lys Cys
1               5                   10

<210> SEQ ID NO 263
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Met Ala Asn Val Gln Leu Asn Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

```
Ser Tyr Ala Met Ser Trp Val Arg Gln Ala Pro Gly Lys Gly Leu Glu
            35                  40                  45

Trp Val Ser Asp Ile Ser Pro Ser Gly Ala Val Lys Ala Tyr Ser Asp
 50                  55                  60

Ser Val Lys Gly Arg Phe Thr Ile Ser Arg Asp Asn Ala Lys Asn Arg
 65                  70                  75                  80

Leu Tyr Leu Gln Met Asn Ser Leu Thr Pro Glu Asp Thr Gly Glu Tyr
                 85                  90                  95

Phe Cys Thr Lys Val Gln Ser Pro Arg Thr Arg Ile Pro Ala Pro Ser
                100                 105                 110

Ser Gln Gly Thr Gln Val Thr Val Ser Ser
            115                 120
```

<210> SEQ ID NO 264
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

```
Met Ala Asn Val Gln Leu Asn Glu Ser Gly Gly Gly Leu Val Gln Pro
 1               5                  10                  15

Gly Gly Ser Leu Arg Leu Ser Cys Ala Ala Ser Gly Phe Thr Phe Ser
                20                  25                  30

Ser Tyr Ala Met Ser Trp Val Arg Gln Ala Pro Gly Lys Gly Leu Glu
            35                  40                  45

Trp Val Ser Glu Ile Ser Pro Ser Gly Ala Val Lys Ala Tyr Ser Asp
 50                  55                  60

Ser Val Lys Gly Arg Phe Thr Ile Ser Arg Asp Asn Ala Lys Asn Arg
 65                  70                  75                  80

Leu Tyr Leu Gln Met Asn Ser Leu Thr Pro Glu Asp Thr Gly Glu Tyr
                 85                  90                  95

Phe Cys Thr Lys Val Gln Ser Pro Arg Thr Arg Ile Pro Ala Pro Ser
                100                 105                 110

Ser Gln Gly Thr Gln Val Thr Val Ser Ser
            115                 120
```

<210> SEQ ID NO 265
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

```
Glu Gln Lys Leu Ile Ser Glu Glu Asp Leu
 1               5                  10
```

<210> SEQ ID NO 266
<211> LENGTH: 8
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 266

Asp Tyr Lys Asp Asp Asp Asp Lys
1               5
```

GLYCAN-INTERACTING COMPOUNDS AND METHODS OF USE

CROSS-REFERENCE TO RELATED APPLICATIONS

This application claims priority to international application PCT/US2016/061427 entitled GLYCAN-INTERACTING COMPOUNDS AND METHODS OF USE filed Nov. 10, 2016, which claims priority to U.S. application 62/254,278, filed Nov. 12, 2015 entitled GLYCAN-INTERACTING COMPOUNDS AND METHODS OF USE, U.S. application 62/274,572, filed Jan. 4, 2016 entitled GLYCAN-INTERACTING COMPOUNDS AND METHODS OF USE, U.S. application 62/287,666, filed Jan. 27, 2016 entitled GLYCAN-INTERACTING COMPOUNDS AND METHODS OF USE, U.S. application 62/293,989, filed Feb. 11, 2016 entitled GLYCAN-INTERACTING COMPOUNDS AND METHODS OF USE, U.S. application 62/345,515, filed Jun. 3, 2016 entitled GLYCAN-INTERACTING COMPOUNDS AND METHODS OF USE and U.S. application 62/382,835, filed Sep. 2, 2016 entitled GLYCAN-INTERACTING COMPOUNDS AND METHODS OF USE; the contents of each of which are herein incorporated by reference in their entireties.

GOVERNMENT SUPPORT

This invention was made with government support under Grant Nos. HHSN261201400027C and HHSN261201600042C awarded by the Department of Health and Human Services. The United States government may have certain rights in the invention.

REFERENCE TO SEQUENCE LISTING

The instant application contains a Sequence Listing which has been submitted electronically in ASCII format and is hereby incorporated by reference in its entirety. The sequence listing file, entitled 20331021_US371 SEQLIST.txt, was created on May 11, 2018 and is 159,612 bytes in size.

FIELD OF THE INVENTION

This disclosure relates to glycan-interacting compounds, such as antibodies, and methods for the development of such compounds and related compositions for the detection and/or removal of glycosylated matter from an organism. The invention also relates to methods of treating diseases related to aberrant glycosylation, such as cancer, with glycan-interacting compounds and compositions presented herein.

BACKGROUND OF THE INVENTION

Aberrant glycosylation accompanies some of the other mutations commonly observed in carcinomas. It has been estimated that about 80% of all carcinomas express the truncated glycans, the Tn Antigen and the sialylated form, Sialyl Tn (STn). With few exceptions, Tn and STn are not expressed in normal, healthy tissues. Furthermore, the non-human immunogenic sialic acid, N-glycolylneuraminic acid (Neu5Gc), seems to be differentially expressed on carcinomas such as breast cancer in the form of Neu5Gc-STn (GcSTn).

Multiple aberrant glycosylation forms have been described in human cancers, identifying specific glycans as a class of cell surface molecules suitable for specific tumor targeting (Cheever, M. A. et al., Clin Cancer Res. 2009 Sep. 1; 15(17):5323-37). For example, various human cancer types (such as bladder, breast, cervical, colon, lung, and ovarian cancer among others) show high expression of STn antigen, which is rare in normal human tissues (Karlen, P. et al., Gastroenterology. 1998 December; 11 5(6):1395-404; Ohno, S. et al, Anticancer Res. 2006 November-December; 26(6A):4047-53). In addition, the presence of STn on tumor-associated mucins relates to cancer with poor prognosis and is therewith considered an attractive epitope for cancer detection and targeted therapy (Cao, Y. et al., Virchows Arch. 1997 September; 431(3):159-66; Julien, S. et al., Br J Cancer. 2009 Jun. 2; 100(11):1746-54; Itzkowitz, S. H. et al., Cancer. 1990 Nov. 1; 66(9):1960-6; Motoo, Y. et al., Oncology. 1991; 48(4):321-6; Kobayashi, H. et al., J Clin Oncol. 1992 January; 10(1):95-101). Tn and STn formation is associated with somatic mutations in the gene Cosmc that encodes a molecular chaperon required for the formation of the activate T-synthase (Ju, T. et al., Nature. 2005 Oct. 27; 437(7063):1252; Ju, T. et al., Cancer Res. 2008 Mar. 15; 68(6):1636-46). It can also result from increased expression of the sialyl transferase, ST6GalNAc-I (Ikehara, Y. et al., Glycobiology. 1999 November; 9(11):1213-24; Brockhausen, I. et al., Biol Chem. 2001 February; 382(2):219-32). De-novo expression of STn can modulate carcinoma cells, change the malignant phenotype, and lead to more aggressive cell behaviors (Pinho, S. et al., Cancer Lett. 2007 May 8; 249(2):157-70). Although STn is highly expressed in malignant tissues, low levels are also found on healthy human cells (Jass, J. R. et al., J Pathol. 1995 June; 176(2): 143-9; Kirkeby, S. et al., Arch Oral Biol. 2010 November; 55(11):830-41). STn alone has attracted attention as a target for cancer detection and therapy (Cheever, M. A. et al., Clin Cancer Res. 2009 Sep. 1; 15(17):5323-37). STn is also present in mucins associated with cancer stem cells (Engelmann et al., Cancer research, 2008, 68, 2419-2426) and STn is implicated in immune supression (Carrascal, M. A., et al., Molecular Oncology. 2014. 8(3): 753-65).

In addition to the presence of STn, other glycosylation changes have been described in cancer. One of them involves Neu5Gc. N-acetylneuraminic acid (NeuSAc) and Neu5Gc are the two major sialic acids on mammalian cell surfaces. NeuSAc and Neu5Gc differ only in that Neu5Gc includes an additional oxygen atom associated with chemical group attached to carbon 5. Due to the loss of a functional gene, humans can only synthesize sialic acid in the form of NeuSAc, but not Neu5Gc. However Neu5Gc can be metabolically incorporated into humans from animal-derived dietary sources such as red meats (Tangvoranuntakul, P. et al., Proc Natl Acad Sci USA. 2003 Oct. 14; 100(21):12045-50; Nguyen, D. H. et al., J Immunol. 2005 Jul. 1; 175(1):228-36; U.S. Pat. Nos. 7,682,794, and 8,084,219, US2012/0142903, WO2010030666 and WO2010030666). Neu5Gc is significantly abundant among human tumors (Higashi, H. et al., Cancer Res. 1985 August; 45(8):3796-802; Miyoshi I. et al., Mol Immunol. 1986. 23: 631-638; Hirabayashi, Y. et al., Jpn J Cancer Res. 1987. 78: 614-620; Kawachi. S, et al., Int Arch Allergy Appl Immunol. 1988. 85: 381-383; Devine, P. L. et al., Cancer Res. 1991. 51: 5826-5836; Malykh, Y. N. et al, Biochimie. 2001. 83: 623-634 and Inoue, S. et al., 2010. Glycobiology. 20(6): 752-762) and remarkably low in normal human tissues, which had been overlooked for several decades (Diaz, S. L. et al., PLoS One. 2009. 4: e4241; Tangvoranuntakul, P. et al., Proc Natl Acad Sci USA. 2003. 100: 12045-12050; Varki, A. et al., Glycoconj J. 2009. 26: 231-245). The increased metabolic accumulation of diet-derived Neu5Gc in cancer tissue compared to healthy human tissues is likely explained by at least three factors: rapid growth with underproduction of competing endogenous NeuSAc, enhanced macropinocytosis induced by growth factors (Dharmawardhane, S. et al., Mol Biol Cell. 2000 October; 11(10):3341-52; Simonsen, A. et al., Curr Opin Cell Biol. 2001 August; 13(4):485-92; Johannes, L. et al., Traffic. 2002 July; 3(7):443-51; Amyere, M. et al., Int J Med Microbiol. 2002 February; 291(6-7):487-94), and the upregulation of gene expression of the lysosomal sialic acid transporter gene sialin by hypoxia (Yin, J. et al., Cancer Res. 2006 March 15; 66(6):2937-45). In addition, all humans tested to date include a polyclonal antibody reservoir against non-human Neu5Gc, which makes it the first example of a xeno-autoantigen (Padler-Karavani, V. et al., Glycobiology. 2008 October; 18(10):818-30; Varki, N. M. et al., Annu Rev Pathol. 2011; 6:365-93). The accumulation of dietary Neu5Gc in malignant tumors in the face of an anti-Neu5Gc response was shown to facilitate tumor progression by inducing a low-grade chronic inflammation (Hedlund, M. et al., Proc Natl Acad Sci USA. 2008 Dec. 2; 105(48):18936-41). Thus, Neu5Gc containing glycan epitopes on human tumors represent a valuable possibility for drug targeting. A recent study suggests the existence of antibodies against Neu5Gc-containing STn (GcSTn), but not NeuSAc-STn (AcSTn), in cancer patients and explores their potential as a specific biomarker for cancer detection (Padler-Karavani, V. et al., Cancer Res. 2011 May 1; 71(9):3352-63).

There remains a need in the art for therapeutic antibodies capable of binding glycans, including glycans associated with disease and diseased cells and tissues. Further, there remains a need for better methods to develop such antibodies and methods of using these antibodies to target diseased cells and tissues. The present disclosure meets these needs by providing related compounds and methods.

SUMMARY OF THE INVENTION

In some embodiments, the present disclosure provides an antibody having a heavy chain variable domain (VH) with a CDR-H3 complementarity determining region having at least 50% amino acid sequence identity to an amino acid sequence selected from the group consisting of SEQ ID NOs: 114-120, 140, and 141. The VH may include a CDR-H1 having at least 50% sequence identity to an amino acid sequence selected from the group consisting of SEQ ID NOs: 105, 106, and 136 and a CDR-H2 having at least 60% sequence identity to an amino acid sequence selected from the group consisting of SEQ ID NOs: 107-113, and 137-139.

In some embodiments, antibodies include a light chain variable domain (VL) with a CDR-L3 having at least 50% amino acid sequence identity to an amino sequence selected from the group consisting of SEQ ID NOs: 89, 91, 93, 95-98, 101-103, 133-135, and 148. The VL may include a CDR-L1 having at least 50% sequence identity to an amino acid sequence selected from the group consisting of SEQ ID NOs: 121-129, and 142-146 and a CDR-L2 having at least 50% sequence identity to an amino acid sequence selected from the group consisting of SEQ ID NOs: 77, 79-81, 83-86, 88, 130-132, and 147. The antibody may include at least one human framework region having an amino acid sequence with at least 70% sequence identity to an amino acid sequence selected from the group consisting of SEQ ID NOs: 206-216.

In some embodiments, antibodies include a VH having at least 70% sequence identity to an amino acid sequence selected from the group consisting of SEQ ID NOs: 220-224, 230-234, 237-241, 249-253, and 256-260. Antibodies may include a VL having at least 70% sequence identity to an amino acid sequence selected from the group consisting of SEQ ID NOs: 217-219, 225-229, 235, 236, 242-248, 254, and 255. The VH may have at least 95% sequence identity to an amino acid sequence selected from the group consisting of SEQ ID NOs: 220-224 and the VL may have at least 95% sequence identity to an amino acid sequence selected from the group consisting of SEQ ID NOs: 217-219. The VH may have at least 95% sequence identity to an amino acid sequence selected from the group consisting of SEQ ID NOs: 237-241 and the VL may have at least 95% sequence identity to an amino acid sequence selected from the group consisting of SEQ ID NOs: 235 and 236. Antibodies may be an isotype selected from the group consisting IgG1, IgG2a, IgG2b, IgG2c, IgG3, and IgG4. Antibodies may be a human or humanized antibody. The antibodies may be a human IgG1 antibody.

In some embodiments, the present disclosure provides a construct that may encode a described antibody. Further provided are cells that may include the construct. The construct may be included in a vector. In some embodiments, antibodies are provided that are produced from cells including a construct encoding an antibody of the present disclosure.

In some embodiments, antibodies are provided that bind to cell-associated STn with a half maximal effective concentration (EC50) of from about 0.01 nM to about 30 nM.

In some embodiments, antibodies may be conjugated to a therapeutic agent. The therapeutic agent may be a cytotoxic agent selected from the group consisting of monomethyl auristatin E (MMAE) and monomethyl auristatin F (MMAF). The antibody may be capable of killing an STn-associated cell with a half-maximal inhibitory concentration (IC50) of from about 0.1 nM to about 20 nM.

In some embodiments, methods of treating cancer are provided that include administering disclosed antibodies. The cancer may include at least one tumor. The volume of the tumor may be reduced by the treatment. The reduction in tumor size may be at least 20%. The tumor may include at least one tumor cell, which may include at least one tumor-associated carbohydrate antigen (TACA). The TACA may include sialyl($\alpha$2,6)N-acetylgalactosamine (STn). The cancer may include one or more of breast cancer, colon cancer, pancreatic cancer, lung cancer, cervical cancer, ovarian cancer, stomach cancer, prostate cancer, and liver cancer. The antibodies may be administered in combination with a chemotherapeutic agent and/or therapeutic antibody. The chemotherapeutic agent may be selected from at least one of fluoropyrimidine, oxaliplatin, and irinotecan. The therapeutic antibody may be selected from at least one of bevacizumab and anti-epidermal growth factor receptor (EGFR) antibody. The antibodies may be administered at a dose of from about 0.1 mg/kg to about 30 mg/kg. The dose may be from about 2.5 mg/kg to about 5 mg/kg. The antibodies may be detectable in at least one subject sample obtained from about 1 day after treatment to about 1 month after treatment. The antibodies may be conjugated with MMAE. The drug to antibody ratio (DAR) of the MMAE to the antibody in the sample may change by less than 50% in the at least one subject sample.

In some embodiments, a method of screening a cell or sample for the presence of at least one TACA is provided that includes contacting the cell or sample with a disclosed antibody. The at least one TACA may include STn. The sample may be a biological sample. The biological sample may be obtained from a subject. The subject may have or be suspected of having cancer. The biological sample may include one or more of a cell, a tissue, a tissue section, and a body fluid. The antibody may include a detectable label. The antibody may be detected using a detection agent. The detection agent may be a secondary antibody. The secondary antibody may include a detectable label. The method may be used for diagnosing cancer in a subject. The method may be part of a companion diagnostic. The companion diagnostic may be used for one or more of stratifying cancer severity, stratifying cancer risk, selecting a subject for a clinical trial, developing a therapeutic regimen, modulating a therapeutic regimen, increasing treatment safety, and modulating treatment effectiveness. The method may include the use of a protein array. The protein array may include one or more antibodies configured to bind one or more proteins present in the sample.

In some embodiments, the present disclosure provides a kit for carrying out described methods. The kit may include a described antibody. The kit may include a secondary antibody. The secondary antibody may include a detectable label.

In some embodiments, the present disclosure provides a composition that includes one or more of the antibodies described. The composition may include at least one excipient. The composition may include a pharmaceutically acceptable excipient. The composition may include an antibody-coated agent. The antibody-coated agent may include one or more of a particle, a nanoparticle, a protein, a fusion-protein, a lipid, a liposome, and a cell. The antibody may be an antibody fragment. The antibody fragment may be selected from one or more of a Fab fragment and a single chain Fv.

In some embodiments, the present disclosure provides a modified cell having a synthetic construct. The synthetic construct may encode a factor that modulates cellular STn levels. The factor may include at least one factor involved in STn synthesis The factor may be selected from at least one of (Alpha-N-Acetyl-Neuraminyl-2,3-Beta-Galactosyl-1,3)-N-Acetylgalactosaminide, Alpha-2,6-Sialyltransferase I (ST6GalNAc I), T-synthase, and Core 1 Beta3-Galactosyl-transferase-Specific Molecular Chaperone (COSMC). The modified cell may include elevated STn levels when compared with at least one unmodified cell. The factor may reduce expression of ST6GalNAC. The factor may be an inhibitory ribonucleic acid (RNA) molecule. The modified cell may be a modified ovarian tumor cell. The modified ovarian tumor cell may be selected from one or more of a SKOV3 cell, an OVCAR3 cell, an OVCAR4 cell, a BRCA1 mutant tumor cell, and a non-BRCA1 mutant tumor cell.

In some embodiments, a method of characterizing antibody binding is provided. The method may include contacting a glycan array with the antibody. The glycan array may include a plurality of glycans. The plurality of glycans may include a panel of glycans consisting of one or more of each of Neu5Acα6GalNAcαO(CH$_2$)2CH$_2$NH2; Neu5Gcα6GalNAcαO(CH$_2$)2CH$_2$NH2; Neu5Acα6Galβ4GlcNAcαO(CH$_2$)2CH$_2$NH2; Neu5Gcα6Galβ4GlcNAcβO(CH$_2$)2CH$_2$NH2; Neu5Acα6Galf34Glcf30(CH$_2$)2CH$_2$NH2; Neu5Galf34Glcf30(CH$_2$)2CH$_2$NH2; Neu5Acα6GalβO(CH$_2$)2CH$_2$NH2; Neu5Gcα6Galf30(CH$_2$)2CH$_2$NH2; GalNAcαO(CH$_2$)2CH$_2$NH2; Galβ3GalNAcβO(CH$_2$)2CH$_2$NH2; Gal3βGalNAcαO(CH$_2$)2CH$_2$NH2; Neu5Acα3Galβ1-3GalNAcαO(CH$_2$)2CH$_2$NH2; and Neu5Gcα3Gaβ1-3GalNAcαO(CH$_2$)2CH$_2$NH2. Each of the plurality of glycans may be part of a neoglycolipid probe.

BRIEF DESCRIPTION OF THE FIGURES

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

FIG. 2 is a schematic of a variable domain.

DETAILED DESCRIPTION

Introduction

Figure 1A:
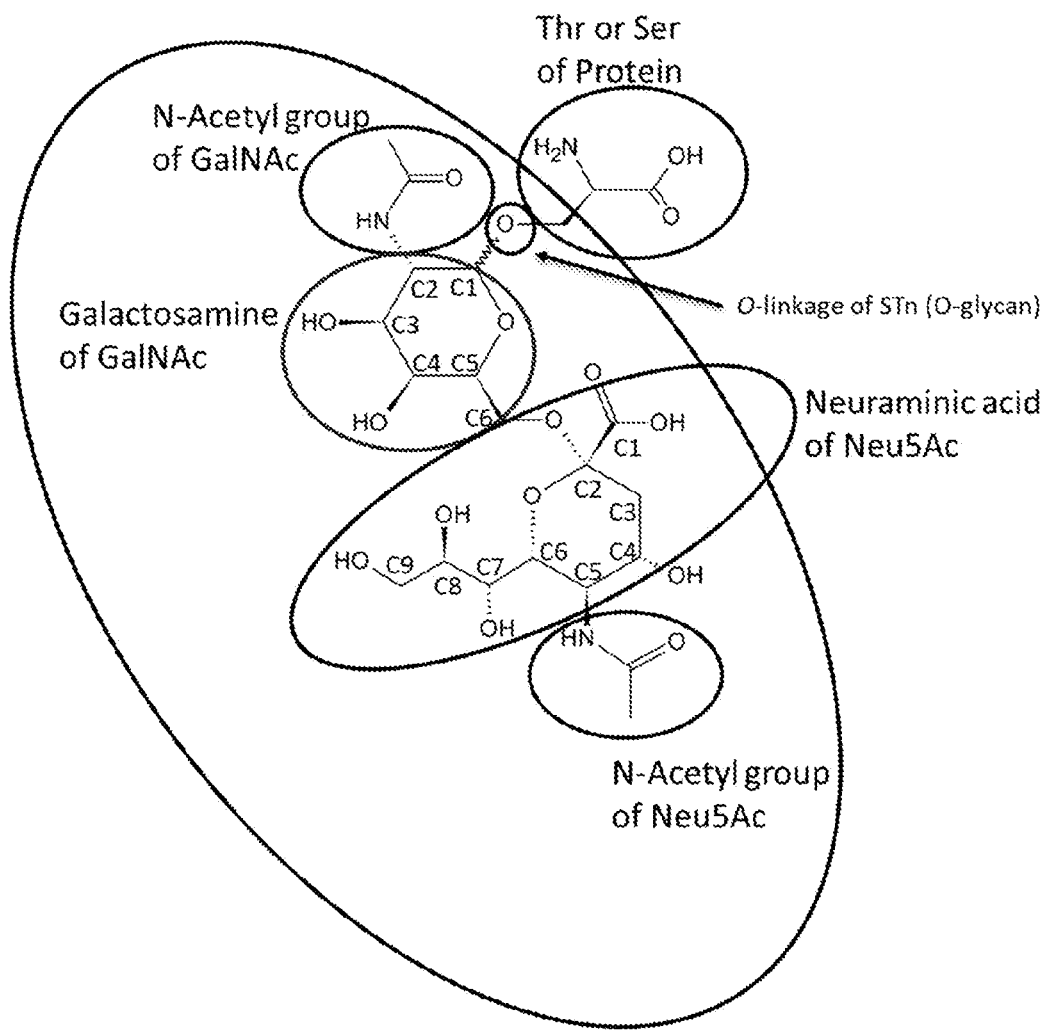
FIGS. 1A-1D are diagrams depicting α2,6-sialylated N-acetylgalactosamine (STn) and indicating putative epitopes involved in anti-STn antibody binding. The largest ellipse in each diagram indicates the specific region of STn targeted by each of 4 antibody groups. These groups include Group 1 antibodies (binding to the large elliptical region indicated in FIG. 1A), Group 2 antibodies (binding to the large elliptical region indicated in FIG. 1B), Group 3 antibodies (binding to the large elliptical region indicated in FIG. 1C) and Group 4 antibodies (binding to the large elliptical region indicated in FIG. 1D).

According to the present invention are antibodies specific for or which interact with epitopes that include carbohydrate groups referred to herein as glycans. Some glycan-interacting antibodies described herein may be used as biotherapeutics. Other embodiments provide methods for generating such glycan-interacting antibodies.

In nature, STns may be sialylated with N-acetylneuraminic acid (Neu5Ac) or N-glycolylneuraminic acid (Neu5Gc). Glycan-interacting antibodies according to the present invention may be directed to glycans having any STns (pan-STn antibodies), glycans having STns that include Neu5Ac specifically (AcSTn) or glycans having STns that include Neu5Gc specifically (GcSTn). In some embodiments, glycan-interacting antibodies of the present invention target cancer-related glycan antigens, such as α2,6-sialylated N-acetylgalactosamine (STn).

In some embodiments, the present disclosure provides methods of producing glycan-interacting antibodies. Such methods may include the use of mice for generating an immune response to one or more antigens, including STn (e.g. AcSTn and/or GcSTn). As described herein, a number of methods may be utilized in order to manipulate the resulting antibodies produced through mouse immunization. Such methods may include varying the strain and/or gender of the mice being immunized, varying the antigen used, varying the type and dose of adjuvant included in antigen administration and time course of immunization before initiation of hybridoma fusion.

In some embodiments, the present disclosure provides methods for eliminating cancer stem cells using glycan-interacting antibodies. In other embodiments, the present invention provides methods for treating cancer in a subject by eliminating cancer stem cells using glycan-interacting antibodies. In some aspects, glycan-interacting antibodies may be used alone. In other aspects, glycan-interacting antibodies are used in combination with chemotherapeutic agents.

Further provided are optimized, humanized and conjugated forms of glycan-interacting antibodies disclosed herein. Additionally, kits, assays and reagents including antibodies and/or methods of the present invention are presented.

Definitions

Adjacent: As used herein, the term "adjacent" refers to something that is adjoining, neighboring or next to a given entity. In some embodiments, "adjacent residues" are sugar residues within a glycan chain that are linked to one another. In some embodiments, "adjacent glycans" are glycan chains that next to each other either in direct contact or within close proximity and without another glycan in between the two.

Administered in combination: As used herein, the term "administered in combination" or "combined administration" means that a subject is simultaneously exposed to two or more agents administered at the same time or within an interval of time such that the subject is at some point in time simultaneously exposed to both and/or such that there may be an overlap in the effect of each agent on the patient. In some embodiments, at least one dose of one or more agents is administered within about 24 hours, 12 hours, 6 hours, 3 hours, 1 hour, 30 minutes, 15 minutes, 10 minutes, 5 minutes, or 1 minute of at least one dose of one or more other agents. In some embodiments, administration occurs in overlapping dosage regimens. As used herein, the term "dosage regimen" refers to a plurality of doses spaced apart in time. Such doses may occur at regular intervals or may include one or more hiatus in administration. In some embodiments, the administration of individual doses of one or more glycan-interacting antibodies, as described herein, are spaced sufficiently closely together such that a combinatorial (e.g., a synergistic) effect is achieved.

Amino acid: As used herein, the terms "amino acid" and "amino acids" refer to all naturally occurring L-alpha-amino acids as well as non-naturally occurring amino acids. Amino acids are identified by either the one-letter or three-letter designations as follows: aspartic acid (Asp:D), isoleucine (Ile:I), threonine (Thr:T), leucine (Leu:L), serine (Ser:S), tyrosine (Tyr:Y), glutamic acid (Glu:E), phenylalanine (Phe:F), proline (Pro:P), histidine (His:H), glycine (Gly:G), lysine (Lys:K), alanine (Ala:A), arginine (Arg:R), cysteine (Cys:C), tryptophan (Trp:W), valine (Val:V), glutamine (Gln:Q) methionine (Met:M), asparagine (Asn:N), where the amino acid is listed first followed parenthetically by the three and one letter codes, respectively.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Antibody: As used herein, the term "antibody" is used in the broadest sense and specifically covers various embodiments including, but not limited to monoclonal antibodies, polyclonal antibodies, multispecific antibodies (e.g. bispecific antibodies formed from at least two intact antibodies), and antibody fragments such as diabodies so long as they exhibit a desired biological activity. Antibodies are primarily amino-acid based molecules but may also include one or more modifications such as with sugar moieties.

Antibody fragment: As used herein, the term "antibody fragment" refers to a portion of an intact antibody, preferably including an antigen binding region thereof. Examples of antibody fragments include Fab, Fab', F(ab')$_2$, and Fv fragments; diabodies; linear antibodies; single-chain antibody molecules; and multispecific antibodies formed from antibody fragments. Papain digestion of antibodies produces two identical antigen-binding fragments, called "Fab" fragments, each with a single antigen-binding site. Also produced is a residual "Fc" fragment, whose name reflects its ability to crystallize readily. Pepsin treatment yields an F(ab')$_2$ fragment that has two antigen-binding sites and is still capable of cross-linking antigen. Glycan-interacting antibodies may include one or more of these fragments. For the purposes herein, an antibody may include a heavy and light variable domain as well as an Fc region.

Antigen-binding region: As used herein, the term "antigen-binding region" refers to the portion of an antibody, antibody fragment, or related molecule that directly interacts with a target molecule or epitope. Antigen-binding regions typically include a variable domain pair, as in the Fab region of an antibody or as linked together in a scFv.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

Bifunctional: As used herein, the term "bifunctional" refers to any substance, molecule or moiety which is capable of or maintains at least two functions. The functions may affect the same outcome or a different outcome. The structure that produces the function may be the same or different.

Biomolecule: As used herein, the term "biomolecule" is any natural molecule which is amino acid-based, nucleic acid-based, carbohydrate-based or lipid-based, and the like.

Bispecific antibody: As used herein, the term "bispecific antibody" refers to an antibody capable of binding two different antigens. Such antibodies typically include regions from at least two different antibodies. Bispecific antibodies may include any of those described in Riethmuller, G. 2012. Cancer Immunity. 12:12-18, Marvin, J. S. et al., 2005. Acta Pharmacologica Sinica. 26(6):649-58 and Schaefer, W. et al., 2011. PNAS. 108(27):11187-92, the contents of each of which are herein incorporated by reference in their entirety.

Branch: As used herein, the term "branch" refers to an entity, moiety or appendage that is linked or extends out from a main entity or source. In some embodiments, a "branch chain" or "branching chain" includes one or more residues (including, but not limted to sugar residues) that extend from a parent chain. As used herein, a "parent chain" is used to refer to a chain of residues (including, but not limited to sugar residues) from which a branching chain is linked. In the case of a glycan with multiple branches, the parent chain may also refer to the source chain from which all such branches are directly or indirectly attached. In the case of a polysaccharide having a chain of hexose residues, parent chain linkages typically occur between carbons 1 and 4 of adjacent residues while branching chains are attached to a parent chain through a linkage between carbon 1 of the branching residue and carbon 3 of the parent residue from which the branch extends. As used herein, the term "branching residue" refers to the residue attached to the parent chain in a branching chain.

Cancer stem cells: As used herein, cancer stem cells (CSCs) refer to a subset of tumor cells that have the ability to self-renew. CSCs may be able to regenerate diverse cell types. In some cases, these cells are difficult or impossible to remove through surgical or chemical treatment of a tumor.

Compound: As used herein, the term "compound," refers to a distinct chemical entity. In some embodiments, a particular compound may exist in one or more isomeric or isotopic forms (including, but not limited to stereoisomers, geometric isomers and isotopes). In some embodiments, a compound is provided or utilized in only a single such form. In some embodiments, a compound is provided or utilized as a mixture of two or more such forms (including, but not limited to a racemic mixture of stereoisomers). Those of skill in the art appreciate that some compounds exist in different such forms, show different properties and/or activities (including, but not limited to biological activities). In such cases it is within the ordinary skill of those in the art to select or avoid particular forms of the compound for use in accordance with the present invention. For example, compounds that contain asymmetrically substituted carbon atoms can be isolated in optically active or racemic forms. Methods on how to prepare optically active forms from optically active starting materials are known in the art, such as by resolution of racemic mixtures or by stereoselective synthesis.

Cyclic or Cyclized: As used herein, the term "cyclic" refers to the presence of a continuous loop. Cyclic molecules need not be circular, only joined to form an unbroken chain of subunits.

Cytidine monphosphate-N-acetylneuraminic acid hydroxylase: As used herein, the term "cytidine monophosphate-N-acetylneuraminic acid hydroxylase" or "CMAH" refers to an enzyme, absent in humans, but present in most other mammals (including, but not limited to mice, pigs and chimpanzees) that catalyzes the formation of N-glycolylneuraminic acid from N-acetylneuraminic acid. The absence of the enzyme in humans is due to a frameshift mutation resulting in the premature termination of the CMAH transcript and the production of a non-functional protein.

Cytotoxic: As used herein, the term "cytotoxic" is used to refer to an agent that kills or causes injurious, toxic, or deadly effects on a cell (e.g., a mammalian cell (e.g., a human cell)), bacterium, virus, fungus, protozoan, parasite, prion, or a combination thereof.

Delivery: As used herein, "delivery" refers to the act or manner of transporting a compound, substance, entity, moiety, cargo or payload to an intended destination.

Delivery Agent: As used herein, "delivery agent" refers to any substance which facilitates, at least in part, the in vivo delivery of a compound, substance, entity, moiety, cargo or payload.

Detectable label: As used herein, "detectable label" refers to one or more markers, signals, or moieties which are attached, incorporated or associated with another entity, which markers, signals or moieties are readily detected by methods known in the art including radiography, fluorescence, chemiluminescence, enzymatic activity, absorbance and the like. Detectable labels include radioisotopes, fluorophores, chromophores, enzymes, dyes, metal ions, ligands such as biotin, avidin, streptavidin and haptens, quantum dots, and the like. Detectable labels may be located at any position in the entity with which they are attached, incorporated or associated. For example, when attached, incorporated in or associated with a peptide or protein, they may be within the amino acids, the peptides, or proteins, or located at the N- or C-termini.

Display library: As used herein, the term "display library" refers to a tool used in scientific discovery to identify biomolecular interactions. Different variations of display libraries exist that include the utilization of bacteriophages, yeast and ribosomes. In each case, proteins within a given library (also referred to herein as "library members") are linked (physically or through association with a host) to the nucleic acid which encodes the protein. When a target molecule is incubated with the members of a display library, any library members that bind to the target may be isolated and the sequences encoding the bound protein may be determined through analysis of the linked nucleic acid. In some embodiments, display libraries are "phage display libraries" wherein the display library is made up of bacteriophage viral particles (also referred to herein as "phage particles") wherein nucleic acids have been incorporated into the phage genome resulting in the production of viral coat proteins that are fused to proteins encoded by the nucleic acids that have been introduced. Such fused proteins are "displayed" on the outer surface of the assembled phage particles where they may interact with a given target.

Distal: As used herein, the term "distal" means situated away from the center or away from a point or region of interest.

Engineered: As used herein, embodiments of the invention are "engineered" when they are designed to have a feature or property, whether structural or chemical, that varies from a starting point, wild type or native molecule. Thus, engineered agents or entities are those whose design and/or production include an act of the hand of man.

Epitope: As used herein, an "epitope" refers to a surface or region on a molecule that is capable of interacting with components of the immune system, including, but not limited to antibodies. In some embodiments, an epitope may include a target site. Epitopes may include a region on an antigen or between two or more antigens that is specifically recognized and bound by a corresponding antibody. Some epitopes may include one or more sugar residues along one or more glycan. Such epitopes may include 1, 2, 3, 4, 5, 6, 7, 8, 9 or at least 10 sugar residues. Epitopes may also include one or more regions of interaction between entities. In some embodiments, epitopes may include a junction between two sugar residues, between a branching chain and a parent chain or between a glycan and a protein.

Ether bond: As used herein, an "ether bond" refers to a chemical bond that includes an oxygen bonded between two carbon atoms. In some embodiments, ether bonds link sugar residues to other entities, including, but not limited to other sugar residues to form a glycan chain. Such bonds are also referred to as "glycosidic bonds" or "glycosidic linkages". In the context of at least one sugar residue, the terms "link" and/or "linkage" are also used herein when referring to a glycosidic linkage. In some embodiments, linkages may link glycans to other entities, including, but not limited to proteins, lipids, phospholipids and sphingolipids. In some embodiments, sugar residues may be linked to protein, typically forming a link between a sugar residue and an amino acid residue. Such amino acid residues include serine and threonine. In some embodiments, ether bonds link glycans to a glycan array through a carbohydrate linker that participates in bond formation. Glycosidic linkages may differ in their stereochemical properties. In some embodiments, alpha oriented glycosidic linkages (also referred to herein as "alpha linkages") result in an axial orientation between the bonded oxygen of the ether bond and the cyclohexane ring of the sugar reside. In some embodiments, beta oriented glycosidic linkages (also referred to herein as "beta linkages") result in an equatorial orientation between the bonded oxygen of the ether bond and the cyclohexane ring of the sugar residue.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; (4) folding of a polypeptide or protein; and (5) post-translational modification of a polypeptide or protein.

Feature: As used herein, a "feature" refers to a characteristic, a property, or a distinctive element.

Formulation: As used herein, a "formulation" refers to a material or mixture prepared according to a formula and which may include at least one antibody, compound, substance, entity, moiety, cargo or payload and a delivery agent, carrier or excipient.

Functional: As used herein, a "functional" biological molecule is a biological entity with a structure and in a form in which it exhibits a property and/or activity by which it is characterized. As used herein, a "functional group" or "chemical group" refers to a characteristic group of atoms or chemical bonds that are part of a larger molecule. In some embodiments, functional groups may be associated with different molecules, but may participate in similar chemical reactions regardless of the molecule of which they are a part. Common functional groups include, but are not limited to carboxyl groups (—COOH), acetyl groups (—COH), amino groups (—NH$_2$), methyl groups (—CH$_3$), sulfate groups (—SO$_3$H) and acyl groups. In some embodiments, the addition of one or more functional group to a molecule may be conveyed using terms that modify the name of the functional group with the ending "-ylated", e.g., acetylated, methylated and sulfated.

Glycan: As used herein, the terms "glycan", "oligosaccharide" and "polysaccharide" are used interchangeably and refer to polymers made up of sugar monomers, typically joined by glycosidic bonds also referred to herein as linkages. In some embodiments, the terms "glycan", "oligosaccharide" and "polysaccharide" may be used to refer to the carbohydrate portion of a glycoconjugate (e.g., glycoprotein, glycolipid or proteoglycan).

Glycan chain: As used herein, the term "glycan chain" refers to a sugar polymer that includes two or more sugars. In some embodiments, glycan chains are covalently linked to proteins through serine or threonine residues on the protein.

Glycan-rich composition: As used herein, the term "glycan-rich composition" refers to a mixture that includes a large percentage of glycans. In some embodiments, glycans within a glycan-rich composition may make up from about 1% to about 10%, from about 5% to about 15%, from about 20% to about 40%, from about 30% to about 50%, from about 60% to about 80%, from about 70% to about 90% or at least 100% of the total weight of the composition.

Glycosidic bond: As used herein, the term "glycosidic bond" refers to a covalent bond formed between a carbohydrate and another chemical group. In some embodiments, glycosidic bonds are formed between the reducing end of one sugar molecule and the non-reducing end of a second sugar molecule or polysaccharide chain. Such glycosidic bonds are also known as O-glycosidic bonds due to the oxygen (or ether bond) between the joined sugars. In some embodiments, a glycosidic bond between two sugars or between a sugar and a linker may also be referred to as a "linkage".

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Isolated: As used herein, the term "isolated" is synonymous with "separated", but carries with it the inference separation was carried out by the hand of man. In one embodiment, an isolated substance or entity is one that has been separated from at least some of the components with which it was previously associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Kit: As used herein, the term "kit" refers to a set that includes one or more components adapted for a cooperative purpose and instructions for use thereof.

Knockout: As used herein, the term "knockout" refers to an organism wherein an existing gene has been inactivated through a process that typically involves the hand of man. In a knockout organism, a gene that has been inactivated is said to have been "knocked out". In some embodiments, the knocked out gene may be inactivated through the insertion of a nucleotide sequence into the gene or through replacement of the gene entirely.

Linker: As used herein, a "linker" refers to a moiety that connects two or more domains, moieties or entities. In one embodiment, a linker may include 10, 11, 12, 13, 14, 15 or more atoms. In a further embodiment, a linker may include a group of atoms, e.g., 10-1,000 atoms. Such atoms or groups thereof may include, but are not limited to, carbon, amino, alkylamino, oxygen, sulfur, sulfoxide, sulfonyl, carbonyl, and imine. In some embodiments, the linker may include an amino acid, peptide, polypeptide or protein. In some embodiments, a moiety bound by a linker may include, but is not limited to an atom, a chemical group, a nucleoside, a nucleotide, a nucleobase, a sugar, a nucleic acid, an amino acid, a peptide, a polypeptide, a protein, a protein complex, a payload (e.g., a therapeutic agent) or a marker (including, but not limited to a chemical, fluorescent, radioactive or bioluminescent marker). The linker can be used for any useful purpose, such as to form multimers or conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers, Other examples include, but are not limited to, cleavable moieties within the linker, such as, for example, a disulfide bond (—S—S—) or an azo bond (—N=N—), which can be cleaved using a reducing agent or photolysis. Non-limiting examples of a selectively cleavable bonds include an amido bond which may be cleaved for example by the use of tris(2-carboxyethyl)phosphine (TCEP), or other reducing agents, and/or photolysis, as well as an ester bond which may be cleaved for example by acidic or basic hydrolysis. In some embodiments, a linker is a carbohydrate moiety used to link glycans to a substrate, such as in a glycan array. Such carbohydrate linkers include, but are not limited to —O(CH$_2$)$_2$CH$_2$HN$_2$ and —O(CH$_2$)$_3$NHCOCH$_2$(OCH$_2$CH$_2$)$_6$NH$_2$.

mRNA: As used herein, the term "mRNA" refers to messenger RNA produced as a result of gene transcription and processing of the generated transcript. In some embodiments, mRNA that has left the nucleus of the cell may be extracted from a cell or set of cells and analyzed to determine which genes have undergone transcription at a given time or under a given set of circumstances.

Mucin: As used herein, the term "mucin" refers to a family of proteins that are heavily glycosylated. In some embodiments mucins are produced by the submaxillary glands and are found in saliva and mucous.

Negative selection: As used herein, the term "negative selection" refers to the selection of library members from a display library based on their ability to bind entities and/or components of a composition that do not include a target antigen. In some embodiments, negative selection is used prior to positive selection to remove elements that might bind non-specifically to the target.

Off-target: As used herein, "off target" refers to any unintended effect on any one or more target, gene, or cellular transcript.

Patient: As used herein, "patient" refers to a subject who may seek or be in need of treatment, requires treatment, is receiving treatment, will receive treatment, or a subject who is under care by a trained (e.g., licensed) professional for a particular disease or condition.

Peptide: As used herein, "peptide" is a protein or polypeptide which is less than or equal to 50 amino acids long, e.g., about 5, 10, 15, 20, 25, 30, 35, 40, 45, or 50 amino acids long.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than active agents (e.g., as described herein) present in a pharmaceutical composition and having the properties of being substantially nontoxic and non-inflammatory in a patient. In some embodiments, a pharmaceutically acceptable excipient is a vehicle capable of suspending or dissolving the active agent. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: Pharmaceutically acceptable salts of the compounds described herein are forms of the disclosed compounds wherein the acid or base moiety is in its salt form (e.g., as generated by reacting a free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Pharmaceutically acceptable salts include the conventional non-toxic salts, for example, from non-toxic inorganic or organic acids. In some embodiments a pharmaceutically acceptable salt is prepared from a parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, *Pharmaceutical Salts: Properties, Selection, and Use,* P. H. Stahl and C.G. Wermuth (eds.), Wiley-VCH, 2008, and Berge et al., *Journal of Pharmaceutical Science,* 66, 1-19 (1977), each of which is incorporated herein by reference in its entirety. *Pharmaceutically acceptable solvate*: The term "pharmaceutically acceptable solvate," as used herein, refers to a crystalline form of a compound wherein molecules of a suitable solvent are incorporated in the crystal lattice. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate." In some embodiments, the solvent incorporated into a solvate is of a type or at a level that is physiologically tolerable to an organism to which the solvate is administered (e.g., in a unit dosage form of a pharmaceutical composition).

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Physicochemical: As used herein, "physicochemical" means of or relating to a physical and/or chemical property.

Positive selection: As used herein, the term "positive selection" refers to the selection of a given entity from a group of unique entities. Such entities and groups thereof may be, for example antibodies. In some cases they may be antibody fragments or antibody fragments expressed is association with an agent capable of expressing such fragments (e.g. library members from a display library). Selection may be based on the ability of selected entities to bind to a desired target or epitope. In some embodiments, positive selection may be used with phage display libraries to identify phage particles expressing scFvs that bind to the desired target. In other embodiments, positive selection may refer to the selection of antibody candidates from among a pool of antibodies. In other cases, entities may be cells, cell lines or clones as in the slection of clones during hybridoma selection. In such cases, positive selection may refer to clonal selection based on one or more features of antibodies (e.g. specificity for one or more desired epitopes) produced by such clones. In some cases, desired epitopes in positive selection methods may include STn (e.g. AcSTn and/or GcSTn).

Conversely, "negative selection," as used herein, included the same principles and examples described for positive selection, but with the distinguishing characteristic that it is used for removal of undesired entities from a group of unique entities.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Prodrug: The present disclosure also includes prodrugs of the compounds described herein. As used herein, "prodrugs" refer to any substance, molecule or entity which is in a form predicate for that substance, molecule or entity to act as a therapeutic upon chemical or physical alteration. Prodrugs may by covalently bonded or sequestered in some way and which release or are converted into the active drug moiety prior to, upon or after administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Preparation and use of prodrugs is discussed in T. Higuchi and V. Stella, "Prodrugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Proximal: As used herein, the term "proximal" means situated nearer to the center or to a point or region of interest.

Region of interaction: As used herein, the term "region of interaction" refers to a region along any of two or more entities where such entities interact or overlap. In some embodiments, a region of interaction may include one or more sugar residues along a glycan chain that contacts a second glycan chain. In some embodiments, the glycan chains are branching chains from the same parent chain. In some embodiments, a region of interaction may occur between two glycan chains wherein one chain is a branching chain and the second chain is a parent chain. In the case of glycan chains, regions of interaction may include 1, 2, 3, 4, 5, 6, 7, 8, 9 or at least 10 sugar residues. In some embodiments, regions of interaction may also occur between glycans and proteins or between glycans and lipids.

Residue: As used herein, the term "residue" refers to a monomer associated with or capable of associating with a polymer. In some embodiments, residues include sugar molecules including, but not limited to glucose, galactose, N-acetylglucosamine, N-acetylgalactosamine, sialic acids. In some embodiments, residues include amino acids.

Sample: As used herein, the term "sample" refers to an aliquot or portion taken from a source and/or provided for analysis or processing. In some embodiments, a sample is from a biological source (also referred to herein as a "biological sample") such as a tissue, cell or component part (e.g. a body fluid, including but not limited to blood, plasma, serum, mucus, lymphatic fluid, synovial fluid, cerebrospinal fluid, saliva, amniotic fluid, amniotic cord blood, urine, vaginal fluid and semen). In some embodiments, a sample may be or include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. In some embodiments, a sample includes a medium, such as a nutrient broth or gel, which may contain cellular components, such as proteins or nucleic acid molecule. In some embodiments, a "primary" sample is an aliquot of the source. In some embodiments, a primary sample is subjected to one or more processing (e.g., separation, purification, etc.) steps to prepare a sample for analysis or other use.

Sialyl: As used herein, the prefix "sialyl" as well as the term "sialylated" describe compounds including sialic acid.

Single unit dose: As used herein, a "single unit dose" is a dose of any therapeutic administered in one dose/at one time/single route/single point of contact, i.e., single administration event. In some embodiments, a single unit dose is provided as a discrete dosage form (e.g., a tablet, capsule, patch, loaded syringe, vial, etc).

Split dose: As used herein, a "split dose" is the division of single unit dose or total daily dose into two or more doses.

Stable: As used herein "stable" refers to a compound or entity that is sufficiently robust to survive isolation to a useful degree of purity from a reaction mixture, and preferably capable of formulation into an efficacious therapeutic agent.

Stabilized: As used herein, the term "stabilize", "stabilized," "stabilized region" means to make or become stable. In some embodiments, stability is measured relative to an absolute value. In some embodiments, stability is measured relative to a reference compound or entity.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans) and/or plants.

Submaxillary glands: As used herein, the term "submaxillary glands" or "submandibular glands" refers to mucous producing glands located beneath the mouth floor. These glands are capable of producing mucins and in some embodiments, may be extracted from mammals as a source of mucin.

Suffering from: An individual who is "suffering from" a disease, disorder, and/or condition has been diagnosed with or displays one or more symptoms of a disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Synthetic: The term "synthetic" means produced, prepared, and/or manufactured by the hand of man. Synthesis of polynucleotides or polypeptides or other molecules of the present invention may be chemical or enzymatic.

Target: As used herein, the term "target" refers to an object or entity to be affected by an action. In some embodiments, targets refer to antigens to be used for the development of antibodies that specifically bind the antigens.

Target screening: As used herein, the term "target screening" refers to the use of a target substance to identify binding partners for that substance.

Target site: As used herein, the term "target site" refers to a region on or within one or more glycans, glycoproteins, biomolecules and/or biostructures on or within a cell, the extracellular space, a tissue, an organ and/or an organism that is recognized by a binding agent or effector molecule (e.g., an antibody). In some embodiments, glycan target sites may reside exclusively on one sugar residue, may be formed by two or more residues, or may include both glycan and non-glycan components. In some embodiments, target sites are formed between two or more glycans or glycoproteins. In some embodiments, target sites are formed between branching chains of the same glycan or between one or more branching chains and a parent chain.

Targeted Cells: As used herein, "targeted cells" refers to any one or more cells of interest. The cells may be found in vitro, in vivo, in situ or in the tissue or organ of an organism. The organism may be an animal, preferably a mammal, more preferably a human and most preferably a patient.

Terminal residue: As used herein, the term "terminal residue" refers to the last residue in a polymeric chain. In some embodiments, terminal residues are sugar residues located at the non-reducing end of a polysaccharide chain.

Therapeutic agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition. In some embodiments, a therapeutically effective amount is provided in a single dose. In some embodiments, a therapeutically effective amount is administered in a dosage regimen that includes a plurality of doses. Those skilled in the art will appreciate that in some embodiments, a unit dosage form may be considered to include a therapeutically effective amount of a particular agent or entity if it includes an amount that is effective when administered as part of such a dosage regimen.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in 24 hr period. It may be administered as a single unit dose.

Transgenic: As used herein, the term "transgenic" refers to an organism that includes one or more genes incorporated within the organisms genome that are not naturally found in that organism.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Variable region: As used herein, the term "variable region" or "variable domain" refers to specific antibody domains that differ extensively in sequence among antibodies and are used in the binding and specificity of each particular antibody for its particular antigen.

Whole IgG: As used herein, the term "whole IgG" refers to a complete IgG molecule. In some embodiments, whole IgG molecules include regions found naturally in two or more other organisms.

Wild type: As used herein, the term "wild type" refers to an organism that includes a natural genome (free from genes derived from other organisms).

I. Compositions of the Invention

In some embodiments, the present invention provides compounds as well as compositions that include at least one glycan-interacting antibody. Within a glycan, monosaccharide monomers may all be the same or they may differ. Common monomers include, but are not limited to trioses, tetroses, pentoses, glucose, fructose, galactose, xylose, arabinose, lyxose, allose, altrose, mannose, gulose, iodose, ribose, mannoheptulose, sedoheptulose and talose. Amino sugars may also be monomers within a glycan. Glycans including such sugars are herein referred to as aminoglycans. Amino sugars, as used herein, are sugar molecules that include an amine group in place of a hydroxyl group, or in some embodiments, a sugar derived from such a sugar. Examples of amino sugars include, but are not limited to glucosamine, galactosamine, N-acetylglucosamine, N-acetylgalactosamine, sialic acids (including, but not limited to, N-acetylneuraminic acid and N-glycolylneuraminic acid) and L-daunosamine.

As used herein the term "glycan-interacting antibody" refers to an antibody that can interact with a glycan moiety. Such antibodies may bind to a glycan moiety alone, to multiple glycan moieties, or to epitopes that include both glycan and non-glycan components. Non-glycan components may include, but are not limited to proteins, protein-associated moieties (such post-translational modifications), cells, and cell-associated molecules/structures. Glycan-interacting antibodies may function to bind to, alter, activate, inhibit, stabilize, degrade and/or modulate a glycan or a glycan-associated molecule or entity. In so doing, glycan-interacting antibodies may function as a therapeutic, whether palliative, prophylactic or as an ongoing treatment composition. In some embodiments, glycan-interacting antibodies may include conjugates or combinations with other molecules. In some embodiments, glycan-interacting antibodies are directed toward glycans having one or more amino sugar. In a further embodiment, one or more amino sugars is a sialic acid. In a further embodiment, one or more sialic acids is N-acetylneuraminic acid and/or N-glycolylneuraminic acid.

Antibodies

Glycan-interacting antibodies may include entire antibodies or fragments thereof. As used herein, the term "antibody" is used in the broadest sense and embraces various formats including, but not limited to monoclonal antibodies, polyclonal antibodies, multispecific antibodies (e.g., bispecific antibodies formed from at least two intact antibodies), antibody conjugates (including, but not limited to antibody-drug conjugates), antibody variants [including, but not limited to antibody mimetics, chimeric antibodies (e.g. antibodies with amino acid sequences derived from more than one species), and synthetic variants], and antibody fragments, so long as they exhibit a desired biological activity (e.g., binding, activating, inhibiting, stabilizing, degrading, and/or modulating one or more targets). Antibodies are primarily amino-acid based molecules but may include one or more post-translational or synthetic modifications. Post-translational modifications may include glycosylation.

As used herein, the term "antibody fragment" refers to a portion of an intact antibody or fusion-protein thereof, in some cases including at least one antigen binding region. Examples of antibody fragments include Fab, Fab', F(ab')$_2$, Fv fragments, single-chain variable fragments (scFvs); diabodies; tri(a)bodies; linear antibodies; single-chain antibody molecules; and multispecific antibodies formed from antibody fragments. Papain digestion of antibodies produces two identical antigen-binding fragments, called "Fab" fragments, each with a single antigen-binding site. Also produced is a residual "Fc" fragment, whose name reflects its ability to crystallize readily. Pepsin treatment yields an F(ab')$_2$ fragment that has two antigen-binding sites and is still capable of cross-linking antigen. Glycan-interacting antibodies may include one or more of these fragments and may, for example, be generated through enzymatic digestion of whole antibodies or through recombinant expression.

"Native antibodies" are usually heterotetrameric glycoproteins of about 150,000 daltons, composed of two identical light (L) chains and two identical heavy (H) chains. Genes encoding antibody heavy and light chains are known and segments making up each have been well characterized and described (Matsuda, F. et al., 1998. The Journal of Experimental Medicine. 188(11); 2151-62 and Li, A. et al., 2004. Blood. 103(12: 4602-9, the content of each of which are herein incorporated by reference in their entirety). Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VII) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain.

As used herein, the term "variable domain" refers to specific antibody domains found on both the antibody heavy and light chains that differ extensively in sequence among antibodies and are used in the binding and specificity of each particular antibody for its particular antigen. Variable domains include hypervariable regions. As used herein, the term "hypervariable region" refers to a region within a variable domain that includes amino acid residues responsible for antigen binding. The amino acids present within the hypervariable regions determine the structure of the complementarity determining regions (CDRs) that become part of the antigen-binding site of the antibody. As used herein, the term "CDR" refers to a region of an antibody that includes a structure that is complimentary to its target antigen or epitope. Other portions of the variable domain, not interacting with the antigen, are referred to as framework (FW) regions. The antigen-binding site (also known as the antigen combining site or paratope) includes the amino acid residues necessary to interact with a particular antigen. The exact residues making up the antigen-binding site are typically elucidated by co-crystallography with bound antigen, however computational assessments can also be used based on comparisons with other antibodies (Strohl, W. R. Therapeutic Antibody Engineering. Woodhead Publishing, Philadelphia Pa. 2012. Ch. 3, p47-54, the contents of which are herein incorporated by reference in their entirety). Determining residues making up CDRs may include the use of numbering schemes including, but not limited to, those taught by Kabat [Wu, T. T. et al., 1970, JEM, 132(2):211-50 and Johnson, G. et al., 2000, Nucleic Acids Res. 28(1): 214-8, the contents of each of which are herein incorporated by reference in their entirety], Chothia [Chothia and Lesk, J. Mol. Biol. 196, 901 (1987), Chothia et al., Nature 342, 877 (1989) and Al-Lazikani, B. et al., 1997, J. Mol. Biol. 273(4):927-48, the contents of each of which are herein incorporated by reference in their entirety], Lefranc (Lefranc, M. P. et al., 2005, Immunome Res. 1:3) and Honegger (Honegger, A. and Pluckthun, A. 2001. J. Mol. Biol. 309(3):657-70, the contents of which are herein incorporated by reference in their entirety).

VH and VL domains have three CDRs each. VL CDRs are referred to herein as CDR-L1, CDR-L2 and CDR-L3, in order of occurance when moving from N- to C-terminus along the variable domain polypeptide. VH CDRs are referred to herein as CDR-H1, CDR-H2 and CDR-H3, in order of occurance when moving from N- to C-terminus along the variable domain polypeptide. Each of CDRs have favored canonical structures with the exception of the CDR-H3, which includes amino acid sequences that may be highly variable in sequence and length between antibodies resulting in a variety of three-dimensional structures in antigen-binding domains (Nikoloudis, D. et al., 2014. PeerJ. 2:e456). In some cases, CDR-H3s may be analyzed among a panel of related antibodies to assess antibody diversity. Various methods of determining CDR sequences are known in the art and may be applied to known antibody sequences (Strohl, W. R. Therapeutic Antibody Engineering. Woodhead Publishing, Philadelphia Pa. 2012. Ch. 3, p47-54, the contents of which are herein incorporated by reference in their entirety).

As used herein, the term "Fv" refers to an antibody fragment that includes the minimum fragment on an antibody needed to form a complete antigen-binding site. These regions consist of a dimer of one heavy chain and one light chain variable domain in tight, non-covalent association. Fv fragments can be generated by proteolytic cleavage, but are largely unstable. Recombinant methods are known in the art for generating stable Fv fragments, typically through insertion of a flexible linker between the light chain variable domain and the heavy chain variable domain [to form a single chain Fv (scFv)] or through the introduction of a disulfide bridge between heavy and light chain variable domains (Strohl, W. R. Therapeutic Antibody Engineering. Woodhead Publishing, Philadelphia Pa. 2012. Ch. 3, p46-47, the contents of which are herein incorporated by reference in their entirety).

Antibody "light chains" from any vertebrate species can be assigned to one of two clearly distinct types, called kappa and lambda based on amino acid sequences of their constant domains. Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2a, IgG2b, IgG2c, IgG3, IgG4, IgA, and IgA2.

As used herein, the term "single chain Fv" or "scFv" refers to a fusion protein of VH and VL antibody domains, wherein these domains are linked together into a single polypeptide chain by a flexible peptide linker. In some embodiments, the Fv polypeptide linker enables the scFv to form the desired structure for antigen binding. In some embodiments, scFvs are utilized in conjunction with phage display, yeast display or other display methods where they may be expressed in association with a surface member (e.g. phage coat protein) and used in the identification of high affinity peptides for a given antigen.

The term "diabodies" refers to small antibody fragments with two antigen-binding sites, which fragments include a heavy chain variable domain Vp connected to a light chain variable domain VL in the same polypeptide chain. By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993), the contents of each of which are incorporated herein by reference in their entirety.

The term "intrabody" referes to a form of antibody that is not secreted from a cell in which it is produced, but instead target one or more intracellular protein. Intrabodies may be used to affect a multitude of cellular processes including, but not limited to intracellular trafficking, transcription, translation, metabolic processes, proliferative signaling and cell division. In some embodiments, methods of the present invention may include intrabody-based therapies. In some such embodiments, variable domain sequences and/or CDR sequences disclosed herein may be incorporated into one or more construct for intrabody-based therapy. In some cases, intrabodies of the invention may target one or more glycated intracellular protein or may modulate the interaction between one or more glycated intracellular protein and an alternative protein.

The term "chimeric antigen receptor" or "CAR" as used herein, refers to artificial receptors that are engineered to be expressed on the surface of immune effector cells resulting in specific targeting of such immune effector cells to cells expressing entities that bind with high affinity to the artificial receptors. CARs may be designed to include one or more segments of an antibody, antibody variable domain and/or antibody CDR, such that when such CARs are expressed on immune effector cells, the immune effector cells bind and clear any cells that are recognized by the antibody portions of the CARs. In some cases, CARs are designed to specifically bind cancer cells, leading to immune-regulated clearance of the cancer cells.

The term "monoclonal antibody" as used herein refers to an antibody obtained from a population of substantially homogeneous cells (or clones), i.e., the individual antibodies making up the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen The modifier "monoclonal" indicates the character of the antibody as being obtained from a substantially homogeneous population of antibodies, and is not to be construed as requiring production of the antibody by any particular method. The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies.

"Humanized" forms of non-human (e.g., murine) antibodies are chimeric antibodies that contain minimal sequences derived from non-human immunoglobulins. For the most part, humanized antibodies are human immunoglobulins (recipient antibody) in which residues from the hypervariable region from an antibody of the recipient are replaced by residues from the hypervariable region from an antibody of a non-human species (donor antibody) such as mouse, rat, rabbit or nonhuman primate having the desired specificity, affinity, and capacity. Humanized antibodies may include one or more back-mutation that include the reversion of one or more amino acids back to amino acids found in a donor antibody. Conversely, residues from donor antibodies included in humanized antibodies may be mutated to match residues present in human recipient antibodies.

In some embodiments, glycan-interacting antibodies of the present invention may be antibody mimetics. The term "antibody mimetic" refers to any molecule which mimics the function or effect of an antibody and which binds specifically and with high affinity to their molecular targets. In some embodiments, antibody mimetics may be monobodies, designed to incorporate the fibronectin type III domain (Fn3) as a protein scaffold (U.S. Pat. Nos. 6,673,901; and 6,348,584). In some embodiments, antibody mimetics may be those known in the art including, but are not limited to affibody molecules, affilins, affitins, anticalins, avimers, DARPins, Fynomers and Kunitz and domain peptides. In other embodiments, antibody mimetics may include one or more non-peptide region.

As used herein, the term "antibody variant" refers to a biomolecule resembling an antibody in structure, sequence and/or function, but including some differences in their amino acid sequence, composition or structure as compared to another antibody or a native antibody.

Antibody Development

Glycan-interacting antibodies of the present invention are developed to bind antigens such as those described herein. As used herein, an "antigen" is an entity which induces or evokes an immune response in an organism. An immune response is characterized by the reaction of the cells, tissues and/or organs of an organism to the presence of a foreign entity. Such an immune response typically leads to the production by the organism of one or more antibodies against the foreign entity, e.g., antigen or a portion of the antigen. In some cases, methods of immunization may be altered based on one or more desired immunization outcomes. As used here, the term "immunization outcome" refers to one or more desired effects of immunization. Examples include high antibody titers and/or increased antibody specificity for a target of interest.

Antigens of the invention may include glycans, glycoconjugates (including, but not limited to glycoproteins and glycolipids), peptides, polypeptides, fusion proteins, or any of the foregoing and may be conjugated or complexed to one or more separate adjuvants or heterologous proteins. In some embodiments, antigens used according to methods of the present invention may include sialylated glycans, such as STn. Antigens having STn may include mucins. Mucins are a family of proteins that are heavily glycosylated. They are a component of many tumors originating from epithelial cells (Ishida, A. et al., 2008. Proteomics. 8: 3342-9, the contents of which are herein incorporated by reference in their entirety). They are highly expressed by submaxillary glands and can be found at high levels in saliva and mucous. Animal-derived submaxillary mucins may be used as antigens to generate anti-STn antibodies in immunogenic hosts. Submaxillary mucin from different species differ in their STn content with regard to AcSTn versus GcSTn forms. Porcine submaxillary mucin (PSM) is particularly rich in GcSTn, which makes up about 90% of total STn. STn from bovine submaxillary mucin (BSM) includes roughly equal percentages of GcSTn and AcSTn. Ovine submaxillary mucin (OSM) is particularly rich in AcSTn, which makes up about 90% of total STn. In some cases, solutions prepared for immunization may be modified to include one or more of PSM, BSM and OSM depending on the desired target of antibodies resulting from such immunization. PSM may be used in immunizations to generate antibodies in immunogenic hosts that are more likely to be specific for GcSTn. PSM is rich in Neu5Gc-containing mucin-type, glycoproteins that are decorated with GcSTn. Among the currently known sources of high Neu5Gc content is red meat; especially submaxillary glands were previously described as a rich source of Neu5Gc due to the high expression of the CMAH enzyme, which catalyzes the reaction to produce the Neu5Gc precursor, CMP-Neu5Ac. In some cases, PSM may be used to prevent a pan-anti-Neu5Gc response and induce a more specific immune response against GcSTn. OSM may be used in immunizations to generate antibodies in immunogenic hosts that are more likely to be specific for AcSTn.

In one embodiment, the present invention provides a glycan-interacting antibody that is GcSTn-specific. The antibody has little cross-reactivity to Neu5Ac-STn or Tn. The antibody can bind GcSTn but has reduced affinity for AcSTn.

In some embodiments, antigens may be subjected to enzymatic digestion prior to immunization to modulate the resulting immune response in immunogenic hosts. In one example, submaxillary mucins may be treated with trypsin or proteinase K enzymes prior to immunization. The activity of such enzymes may help to cleave off and thereby reduce the percentage and variability of non-STn epitopes. Glycan moieties may shield regions of the peptide where they are attached from enzymatic proteolysis and thereby remain intact. Antibody titers resulting from immunizations may have different antibody levels depending on the type and amount of antigen used in such immunizations. In some cases, certain antigens may be selected for use in immunizations based on the expected titer.

As used herein, an "adjuvant" is a pharmacological or immunological agent that modifies the effect of other agents.

Adjuvants according to the present invention include, but are not limited chemical compositions, biomolecules, therapeutics, and/or therapeutic regimens. Adjuvants may include Freund's adjuvant (complete and/or incomplete), immunostimulatory oligonucleotides [e.g. CpG oligodeoxynucleotides (ODNs)], mineral-containing compositions, bacterial ADP-ribosylating toxins, bioadhesives, mucoadhesives, microparticles, lipids, liposomes, muramyl peptides, N-oxidized polyethylene-piperazine derivatives, saponins and/or immune stimulating complexes (ISCOs). In some embodiments, adjuvants may include oil-in-water emulsions (e.g. sub-micron oil-in-water emulsions). Adjuvants according to the present invention may also include any of those disclosed in US Patent Publication No. US20120027813 and/or U.S. Pat. No. 8,506,966, the contents of each of which are herein incorporated by reference in their entirety.

Antibodies of the present invention may be polyclonal or monoclonal or recombinant, produced by methods known in the art or as described in this application. In some embodiments, the antibodies of the present invention may be labeled for purposes of detection with a detectable label known by one of skill in the art. The label can be a radioisotope, fluorescent compound, chemiluminescent compound, enzyme, or enzyme co-factor, or any other labels known in the art. In some aspects, the antibody that binds to a desired antigen is not labeled, but may be detected by binding of a labeled secondary antibody that specifically binds to the primary antibody.

Antibodies of the present invention (e.g., glycan-interacting antibodies) include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), intracellularly made antibodies (i.e., intrabodies), and epitope-binding fragments of any of the above. Antibodies of the present invention (e.g., glycan-interacting antibodies) can be from any animal origin including birds and mammals. Preferably, such antibodies are of human, murine (e.g., mouse and rat), donkey, sheep, rabbit, goat, guinea pig, camel, horse, or chicken origin. The antibodies of the present invention can be monospecific or multispecific (e.g., bispecific, trispecific, or of greater multispecificity). Multispecific antibodies can be specific for different epitopes of a target antigen of the present invention, or can be specific for both a target antigen of the present invention, and a heterologous epitope, such as a heterologous glycan, peptide or solid support material. (See, e.g., WO 93/17715; WO 92/08802; WO 91/00360; WO 92/05793; Tuft, A. et al., *Trispecific F(ab')3 derivatives that use cooperative signaling via the TCR/CD3 complex and CD2 to activate and redirect resting cytotoxic T cells*. J Immunol. 1991 Jul. 1; 147(1):60-9; U.S. Pat. Nos. 4,474,893; 4,714,681; 4,925,648; 5,573,920; 5,601,819; and Kostelny, S. A. et al., *Formation of a bispecific antibody by the use of leucine zippers*. J Immunol. 1992 Mar. 1; 148(5): 1547-53).

Glycan-interacting antibodies of the present disclosure may be prepared using well-established methods known in the art for developing monoclonal antibodies. In one embodiment, the monoclonal antibodies are prepared using hybridoma technology (Kohler, G. et al., *Continuous cultures of fused cells secreting antibody of predefined specificity*. Nature. 1975 Aug. 7; 256(5517):495-7). For hybridoma formations, first, a mouse, hamster, or other appropriate host animal, is typically immunized with an immunizing agent (e.g., a target antigen of the invention) to elicit lymphocytes that produce or are capable of producing antibodies that will specifically bind to the immunizing agent. Alternatively, the lymphocytes may be immunized in vitro. The lymphocytes are then fused with an immortalized cell line using a suitable fusing agent, such as polyethylene glycol, to form a hybridoma cell (Goding, J. W., *Monoclonal Antibodies: Principles and Practice. Academic Press*. 1986; 59-1031). Immortalized cell lines are usually transformed mammalian cells, particularly myeloma cells of rodent, rabbit, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, D. et al., *A human hybrid myeloma for production of human monoclonal antibodies*. J Immunol. 1984 December; 133(6):3001-5; Brodeur, B. et al., Monoclonal Antibody Production Techniques and Applications. Marcel Dekker, Inc., New York. 1987; 33:51-63).

In some embodiments, myeloma cells may be subjected to genetic manipulation. Such manipulation may be carried out using zinc-finger nuclease (ZFN) mutagenesis as described herein. Alternatively, transfection methods known in the art may be used. NSO myeloma cells or other mouse myeloma cell lines may be used. For example, Sp2/0-Ag14 can be an alternative cell line for hybridoma development.

Transcription Activator-Like Effector Nucleases (TALENs)—induced gene editing provides an alternative gene knock out method. TALENs are artificial restriction enzymes generated by fusing the TAL effector DNA binding domain to a DNA cleavage domain. Similar to ZFNs, TALENs induce double-strand breaks at desired loci that can be repaired by error-prone NHEJ to yield insertions/deletions at the break sites (Wood, A. J. et al., Targeted genome editing across species using ZFNs and TALENs. Science. 2011 Jul. 15; 333(6040):307). Cellectis Bioresearch (Cambridge, Mass.) provides the service of TALEN design and plasmid construction. The culture medium in which the hybridoma cells are cultured can then be assayed for the presence of monoclonal antibodies. Preferably, the binding specificity (i.e., specific immunoreactivity) of monoclonal antibodies produced by the hybridoma cells is determined by immunoprecipitation or by an in vitro binding assay, such as radioimmunoassay (RIA) or enzyme-linked immunosorbent assay (ELISA). Such techniques and assays are known by those skilled in the art. The binding specificity of the monoclonal antibody can, for example, be determined by Scatchard analysis (Munson, P. J. et al., *Ligand: a versatile computerized approach for characterization of ligand-binding systems. Anal Biochem*. 1980 Sep. 1; 107(1):220-39). In some cases, antibody specificity for regions of a given antigen may be characterized by chemically modifying the antigens prior to assaying for antibody binding. In one example, periodate treatment may be used to to destroy the C6 side chain of sialic acids. Assays may be conducted with and without periodate treatment to reveal whether or not binding in untreated samples is sialic acid-specific. In some cases, antigens having 9-O-acetylated sialic acid may be subjected to mild base treatment (e.g. with 0.1 M NaOH) to destroy 9-O-acetyl groups. Assays may be conducted with and without mild base treatment to reveal whether or not binding in untreated samples depends on 9-O-acetylation of sialic acid.

After the desired hybridoma cells are identified, the clones may be subcloned by limiting dilution procedures and grown by standard methods. Suitable culture media for this purpose include, for example, Dulbecco's Modified Eagle's Medium or RPMI-1640 medium. Alternatively, the hybridoma cells may be grown in vivo as ascites in a mammal.

Alternative methods to clone hybridomas may include those provided by kits from STEMCELL Technologies (Vancouver, BC, Canada), e.g. ClonaCell™-HY kit, containing methylcellulose-based semi-solid medium and other media and reagents, to support the selection and growth of hybridoma clones. However, the media in this kit contain FCS, which provides an exogenous source for Neu5Gc incorporation. Though the machinery for endogenous Neu5Gc synthesis is destroyed in Cmah$^{-/-}$ hybridoma, Neu5Gc incorporated from the culture media may also pose a problem in some cases (Bardor, M. et al., Mechanism of uptake and incorporation of the non-human sialic acid N-glycolylneuraminic acid into human cells. J Biol Chem. 2005. 280: 4228-4237). In such instances, The culture media may be supplemented with Neu5Ac to eliminate Neu5Gc incorporation by metabolic competition (Ghaderi, D. et al., Implications of the presence of N-glycolylneuraminic acid in recombinant therapeutic glycoproteins. Nat Biotechnol. 2010. 28: 863-867).

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

In another embodiment, the monoclonal antibodies of the present invention can also be made by recombinant DNA methods, such as those described in U.S. Pat. No. 4,816,567, which is hereby incorporated by reference in its entirety. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of DNA. Once isolated, the DNA can be placed into expression vectors, which are then transfected into host cells. Host cells may include, but are not limited to HEK293 cells, HEK293T cells, simian COS cells, Chinese hamster ovary (CHO) cells, and myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

In some embodiments, antibodies of the present invention (e.g., glycan-interacting antibodies) may be produced by various procedures known by those skilled in the art. For the production of polyclonal antibodies in vivo, host animals, such as rabbits, rats, mice, cows, horses, donkeys, chickens, monkeys, sheep or goats, are immunized with either free or carrier-coupled antigens, for example, by intraperitoneal and/or intradermal injection. In some embodiments, injection material may be an emulsion containing about 100 µg of antigen or carrier protein. In some embodiments, injection materials may include a glycan-rich composition such as non-human mammalian submaxillary mucin in solution. Various adjuvants can also be used to increase the immunological response, depending on the host species. Adjuvants include, but are not limited to, Freund's (complete and incomplete), mineral gels such as aluminum hydroxide, surface active substances such as lysolecithin, pluronic polyols, polyanions, peptides, oil emulsions, TITERMAX® (CytRx Corp, Las Angeles, Calif.), keyhole limpet hemocyanins, dinitrophenol, and potentially useful human adjuvants such as BCG (bacille Calmette-Guerin) and *Corynebacterium parvum*. Such adjuvants are also well known in the art. Several booster injections may be needed, for instance, at intervals of about two weeks, to provide a useful titer of antibody which can be detected, for example, by ELISA assay using glycans and/or free peptide adsorbed to a solid surface. The titer of antibodies in serum from an immunized animal can be increased by selection of antibodies, e.g., by adsorption of antigens onto a solid support and elution of the selected antibodies according to methods well known in the art.

Glycan-interacting antibodies, variants and fragments thereof may be selected and produced using high throughput methods of discovery. In one embodiment, glycan-interacting antibodies that include synthetic antibodies, variants and fragments thereof are produced through the use of display libraries. The term "display" as used herein, refers to the expression or "display" of proteins or peptides on the surface of a given host. The term "library" as used herein, refers to a collection of unique cDNA sequences and/or the proteins that are encoded by them. A library may contain from as little as two unique cDNAs to hundreds of billions of unique cDNAs. In some embodiments, glycan-interacting antibodies that are synthetic antibodies are produced using antibody display libraries or antibody fragment display libraries. The term "antibody fragment display library" as used herein, refers to a display library wherein each member encodes an antibody fragment containing at least one variable region of an antibody. Such antibody fragments are preferably Fab fragments, but other antibody fragments such as single-chain variable fragments (scFvs) are contemplated as well. In an Fab antibody fragment library, each Fab encoded may be identical except for the amino acid sequence contained within the variable loops of the complementarity determining regions (CDRs) of the Fab fragment. In an alternative or additional embodiment, amino acid sequences within the individual $V_H$ and/or $V_L$ regions may differ as well.

Display libraries may be expressed in a number of possible hosts including, but not limited to yeast, bacteriophage, bacteria and retroviruses. Additional display technologies that may be used include ribosome-display, microbead-display and protein-DNA linkage techniques. In a preferred embodiment, Fab display libraries are expressed in yeast or in bacteriophages (also referred to herein as "phages" or "phage particles". When expressed, the Fabs decorate the surface of the phage or yeast where they can interact with a given antigen. An antigen that includes a glycan or other antigen from a desired target may be used to select phage particles or yeast cells expressing antibody fragments with the highest affinity for that antigen. The DNA sequence encoding the CDR of the bound antibody fragment can then be determined through sequencing using the bound particle or cell. In one embodiment, positive selection is used in the development of antibodies. In some embodiments, negative selection is utilized in the development of antibodies. In some embodiments, both positive and negative selection methods are utilized during multiple rounds of selection in the development of antibodies using display libraries.

In yeast display, cDNA encoding different antibody fragments are introduced into yeast cells where they are expressed and the antibody fragments are "displayed" on the cell surface as described by Chao et al. (Chao, G. et al., *Isolating and engineering human antibodies using yeast surface display*. Nat Protoc. 2006; 1(2):755-68). In yeast surface display, expressed antibody fragments may contain an additional domain that includes the yeast agglutinin protein, Aga2p. This domain allows the antibody fragment fusion protein to attach to the outer surface of the yeast cell through the formation of disulphide bonds with surface-expressed Aga1p. The result is a yeast cell, coated in a particular antibody fragment. Display libraries of cDNA encoding these antibody fragments are utilized initially in which the antibody fragments each have a unique sequence. These fusion proteins are expressed on the cell surface of millions of yeast cells where they can interact with a desired antigenic target antigen, incubated with the cells. Target antigens may be covalently or otherwise modified with a chemical or magnetic group to allow for efficient cell sorting after successful binding with a suitable antibody fragment takes place. Recovery may be by way of magnetic-activated cell sorting (MACS), fluorescence-activated cell sorting (FACS) or other cell sorting methods known in the art. Once a subpopulation of yeast cells is selected, the corresponding plasmids may be analyzed to determine the CDR sequence.

Bacteriophage display technology typically utilizes filamentous phage including, but not limited to fd, F1 and M13 virions. Such strains are non-lytic, allowing for continued propagation of the host and increased viral titres. Examples of phage display methods that can be used to make the antibodies of the present invention include those disclosed in Miersch et al. (Miersch, S. et al., *Synthetic antibodies: Concepts, potential and practical considerations*. Methods. 2012 August; 57(4):486-98), Bradbury et al. (Bradbury, A. R. et al., *Beyond natural antibodies: the power of in vitro display technologies*. Nat Biotechnol. 2011 March; 29(3): 245-54), Brinkman et al. (Brinkmann, U. et al., *Phage display of disulfide-stabilized Fv fragments*. J Immunol Methods. 1995 May 11; 182(1):41-50); Ames et al. (Ames, R. S. et al., Conversion of murine Fabs isolated from a combinatorial phage display *library to full length immunoglobulins*. J Immunol Methods. 1995 Aug. 18; 184(2):177-86); Kettleborough et al. (Kettleborough, C. A. et al., *Isolation of tumor cell-specific single-chain Fv from immunized mice using phage-antibody libraries and the re-construction of whole antibodies from these antibody fragments*. Eur J Immunol. 1994 April; 24(4):952-8); Persic et al. (Persic, L. et al., *An integrated vector system for the eukaryotic expression of antibodies or their fragments after selection from phage display libraries*. Gene. 1997 Mar. 10; 187(1):9-18); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403, 484; 5,580,717; 5,427,908; 5,750,753; 5,821,047; 5,571, 698; 5,427,908; 5,516,637; 5,780,225; 5,658,727; 5,733,743 and 5, 969,108, each of which is incorporated herein by reference in its entirety. Antibody fragment expression on bacteriophages may be carried out by inserting the cDNA encoding the fragment into the gene expressing a viral coat protein. The viral coat of filamentous bacteriophages is made up of five coat proteins, encoded by a single-stranded genome. Coat protein pIII is the preferred protein for antibody fragment expression, typically at the N-terminus. If antibody fragment expression compromises the function of pIII, viral function may be restored through coexpression of a wild type pIII, although such expression will reduce the number of antibody fragments expressed on the viral coat, but may enhance access to the antibody fragment by the target antigen. Expression of viral as well as antibody fragment proteins may alternatively be encoded on multiple plasmids. This method may be used to reduce the overall size of infective plasmids and enhance the transformation efficiency.

As described above, after selection of a host expressing a high affinity antibody or antibody fragment, (e.g., glycan-interacting antibodies) the coding regions from the antibody or antibody fragment can be isolated and used to generate whole antibodies, including human antibodies, or any other desired antigen binding fragment, and expressed in any desired host, including mammalian cells, insect cells, plant cells, yeast, and bacteria, e.g., as described in detail below.

The DNA sequence encoding a high affinity antibody can be mutated for additional rounds of selection in a process known as affinity maturation. The term "affinity maturation", as used herein, refers to a method whereby antibodies are produced with increasing affinity for a given antigen through successive rounds of mutation and selection of antibody- or antibody fragment-encoding cDNA sequences. In some cases, this process is carried out in vitro. To accomplish this, amplification of CDR coding sequences may be carried out using error-prone PCR to produce millions of copies containing mutations including, but not limited to point mutations, regional mutations, insertional mutations and deletional mutations. As used herein, the term "point mutation" refers to a nucleic acid mutation in which one nucleotide within a nucleotide sequence is changed to a different nucleotide. As used herein, the term "regional mutation" refers to a nucleic acid mutation in which two or more consecutive nucleotides are changed to different nucleotides. As used herein, the term "insertional mutation" refers to a nucleic acid mutation in which one or more nucleotides are inserted into a nucleotide sequence. As used herein, the term "deletional mutation" refers to a nucleic acid mutation in which one or more nucleotides are removed from a nucleotide sequence. Insertional or deletional mutations may include the complete replacement of an entire codon or the change of one codon to another by altering one or two nucleotides of the starting codon.

Mutagenesis may be carried out on CDR-encoding cDNA sequences to create millions of mutants with singular mutations in CDR heavy and light chain regions. In another approach, random mutations are introduced only at CDR residues most likely to improve affinity. These newly generated mutagenic libraries can be used to repeat the process to screen for clones that encode antibody fragments with even higher affinity for the target antigen. Continued rounds of mutation and selection promote the synthesis of clones with greater and greater affinity (Chao, G. et al., *Isolating and engineering human antibodies using yeast surface display*. Nat Protoc. 2006; 1(2):755-68).

Examples of techniques that can be used to produce antibodies and antibody fragments, such as Fabs and scFvs, include those described in U.S. Pat. Nos. 4,946,778 and 5,258, 498; Miersch et al. (Miersch, S. et al., Synthetic antibodies: Concepts, potential and practical considerations. Methods. 2012 August; 57(4):486-98), Chao et al. (Chao, G. et al., Isolating and engineering human antibodies using yeast surface display. Nat Protoc. 2006; 1(2):755-68), Huston et al. (Huston, J. S. et al., *Protein engineering of single-chain Fv analogs and fusion proteins*. Methods Enzymol. 1991; 203:46-88); Shu et al. (Shu, L. et al., *Secretion of a single-gene-encoded immunoglobulin from myeloma cells*. Proc Natl Acad Sci USA. 1993 Sep. 1; 90(17):7995-9); and Skerra et al. (Skerra, A. et al., *Assembly of a functional immunoglobulin Fv fragment in Escherichia coli*. Science. 1988 May 20; 240(4855):1038-41), each of which is incorporated herein by reference in its entirety.

For some uses, including the in vivo use of antibodies (e.g., glycan-interacting antibodies) in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal immunoglobulin and a human immunoglobulin constant region. Methods for producing chimeric antibodies are known in the art. (Morrison, S. L., *Transfectomas provide novel chimeric antibodies*. Science. 1985 Sep. 20; 229 (4719):1202-7; Gillies, S. D. et al., *High-level expression of chimeric antibodies using adapted cDNA variable region cassettes*. J Immunol Methods. 1989 Dec. 20; 125(1-2):191-202.; and U.S. Pat. Nos. 5,807,715; 4,816,567; and 4,816, 397, which are incorporated herein by reference in their entirety).

Humanized antibodies are antibody molecules from non-human species that bind to the desired antigen and have one or more complementarity determining regions (CDRs) from the nonhuman species and framework regions from a human immunoglobulin molecule. Often, framework residues in the human framework regions are substituted with corresponding residues from the CDR and framework regions of the donor antibody to alter, preferably improve, antigen binding. These framework substitutions are identified by methods well known in the art, e.g., by modeling of the interactions of the CDR and framework residues to identify framework residues important for antigen binding, and by sequence comparison to identify unusual framework residues at particular positions. (U.S. Pat. Nos. 5,693,762 and 5,585,089; Riechmann, L. et al., Reshaping human antibodies for therapy. Nature. 1988 Mar. 24; 332(6162):323-7, which are incorporated herein by reference in their entireties). Antibodies can be humanized using a variety of techniques known in the art, including, for example, CDR-grafting (EP 239,400; PCT publication WO 91/09967; U.S. Pat. Nos. 5,225,539; 5,530,101; and 5,585,089); veneering or resurfacing (EP 592,106; EP 519,596; Padlan, E. A., *A possible procedure for reducing the immunogenicity of antibody variable domains while preserving their ligand-binding properties*. Mol Immunol. 1991 April-May; 28(4-5):489-98; Studnicka, G. M. et al., *Human-engineered monoclonal antibodies retain full specific binding activity by preserving non-CDR complementarity-modulating residues*. Protein Eng. 1994 June; 7(6):805-14; Roguska, M. A. et al., *Human-ization of murine monoclonal antibodies through variable domain resurfacing*. Proc Natl Acad Sci USA. 1994 Feb. 1; 91(3):969-73); and chain shuffling (U.S. Pat. No. 5,565, 332); each of which is incorporated herein by reference in their entirety. Humanized antibodies of the present invention may be developed for desired binding specificity, complement-dependent cytotoxicity, and antibody-dependent cellular-mediated cytotoxicity, etc.

In some cases, human frameworks are selected by alignment of donor antibody sequences with human framework sequences to find human framework candidates with the highest level of homology. In some cases, framework regions may be selected from more than one human framework candidate (e.g., framework regions 1-3 may be selected from one candidate and framework region 4 may be selected from an alternative candidate). In some cases, framework regions may be selected from human consensus sequences to avoid the risk of including immunogenic epitopes created by somatic mutations. Consensus sequences are sequences formed by comparing many sequences and adopting most commonly occurring residues at each position. In some cases, human frameworks may be selected from human germline sequences. These may be identified through database searching (e.g., using the NCBI protein database or other databases).

Light and heavy chain human frameworks may be selected from the same or from different clones. Light and heavy chains derived from the same clone have a greater likelihood of associating to form binding sites that are functional; however, the conserved nature of the interface between heavy and light chains typically allows light and heavy chains from different clones to associate and be functional. Frequency of pairing between human light and heavy chain frameworks can be reviewed, for example, in Tiller et al., 2013. MAbs. 5(3): 445-70, the contents of which are herein incorporated by reference in their entirety.

Residues in humanized antibody sequences may be considered for "back-mutation" to improve or restore antibody affinity lost during humanization. Back-mutation involves changing residues altered during humanization back to those present in the original non-human antibody sequence. Residues that are candidates for back-mutation may be identified, for example, by comparison to standard conformations found in canonical antibody structures (see Al-Lazikani, et al., 1997. J. Mol. Biol. 273: 927-48, the contents of which are herein incorporated by reference in their entirety). Unusual canonical residues may be identified and targeted for back-mutation. In some cases, residues that are candidates for back-mutation may be "Vernier residues", a term used to refer to residues in contact with CDRs. These residues have a higher likelihood of impacting CDR positioning and conformation, and therefor antibody affinity and/or specificity (Strohl, W. R. Therapeutic Antibody Engineering. Woodhead Publishing, Philadelphia Pa. 2012. Ch. 6, p117). In some cases, human framework regions are kept constant and CDRs from donor antibodies are back-mutated to fit human CDR regions while maintaining binding through empirical methods.

Completely human antibodies (e.g., glycan-interacting antibodies) are particularly desirable for therapeutic treatment of human patients, so as to avoid or alleviate immune reaction to foreign protein. Human antibodies can be made by a variety of methods known in the art, including the antibody display methods described above, using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies (e.g., glycan-interacting antibodies) can also be produced using transgenic mice which are incapable of expressing functional endogenous immunoglobulins, but which can express human immunoglobulin polynucleotides. For example, the human heavy and light chain immunoglobulin polynucleotide complexes can be introduced randomly, or by homologous recombination, into mouse embryonic stem cells. Alternatively, the human variable region, constant region, and diversity region may be introduced into mouse embryonic stem cells, in addition to the human heavy and light chain polynucleotides. The mouse heavy and light chain immunoglobulin polynucleotides can be rendered nonfunctional separately or simultaneously with the introduction of human immunoglobulin loci by homologous recombination. In particular, homozygous deletion of the Jh region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a glycan, glycoconjugate and/or polypeptide of the invention.

Thus, using such a technique, it is possible to produce useful human IgG, IgA, IgM, IgD and IgE antibodies. For an overview of the technology for producing human antibodies, see Lonberg and Huszar (Lonberg, N. et al., *Human antibodies from transgenic mice*. Int Rev Immunol. 1995; 13(1): 65-93). For a detailed discussion of the technology for producing human antibodies and human monoclonal antibodies and protocols for producing such antibodies, see, e.g., PCT publications WO 98/24893; WO 92/01047; WO 96/34096; WO 96/33735; U.S. Pat. Nos. 5,413,923; 5,625, 126; 5,633,425; 5,569,825; 5,661,016; 5,545,806; 5,814, 318; 5,885,793; 5,916,771; 5,939,598; 6,075,181; and 6,114, 598, each of which are incorporated by reference herein in their entirety. In addition, companies such as Abgenix, Inc. (Fremont, Calif.), Protein Design Labs, Inc. (Mountain View, Calif.) and Genpharm (San Jose, Calif.) can be engaged to provide human antibodies directed against a selected antigen using technology similar to the above described technologies.

Once an antibody molecule of the present invention has been produced by an animal, a cell line, chemically synthesized, or recombinantly expressed, it can be purified (i.e., isolated) by any method known in the art for the purification of an immunoglobulin or polypeptide molecule, for example, by chromatography (e.g., ion exchange, affinity, particularly by affinity for the specific antigen, Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The affinity between an antibody and a target or ligand (such as an antigen used to generate a given antibody) may be measured in terms of $K_D$ using one or more binding assays as described herein. Depending on the desired application for a given antibody, varying $K_D$ values may be desirable. High affinity antibodies typically form ligand bonds with a $K_D$ of about $10^{-5}$ M or less, e.g. about $10^{-6}$ M or less, about $10^{-7}$ M or less, about $10^{-8}$ M or less, about $10^{-9}$ M or less, about $10^{-10}$ M or less, about $10^{-11}$ M or less or about $10^{-12}$ M or less.

In some embodiments, antibodies of the invention may be characterized according to their half maximal effective or inhibitory concentration ($EC_{50}$ or $IC_{50}$, respectively). In some cases, this value may represent the concentration of antibody necessary to inhibit cells expressing STn (e.g. kill, reduce proliferation and/or reduce one or more cell function) at a level equal to half of the maximum inhibition observed with the highest concentrations of antibody. Such $IC_{50}$ values may be from about 0.001 nM to about 0.01 nM, from about 0.005 nM to about 0.05 nM, from about 0.01 nM to about 1 nM, from about 0.05 nM to about 5 nM, from about 0.1 nM to about 10 nM, from about 0.5 nM to about 25 nM, from about 1 nM to about 50 nM, from about 5 nM to about 75 nM, from about 10 nM to about 100 nM, from about 25 nM to about 250 nM, from about 200 nM to about 1000 nM or more than 1000 nM.

In some embodiments, antibodies taught in the present disclosure may be tested for their ability to target patient-derived cancer cells and/or cancer stem cells (CSCs). According to such embodiments, patient-derived cancer cells may be cultured in vitro and antibodies of the present disclosure may be used to target such cells.

In other embodiments, patient-derived cells may be used to produce patient-derived xenograft (PDX) tumors. In some cases, pieces of primary or metastatic solid tumors maintained as tissue structures may be collected by surgery or biopsy procedures. In some cases, fluid drained from malignant ascites or pleural effusions may be used. Tumors may be implanted as pieces or single cell suspensions, either alone or in some studies coated with MATRIGEL® (Corning Life Sciences, Corning, N.Y.) or mixed with human fibroblasts or mesenchymal stem cells. Sites of implantation may include the dorsal region of mice (subcutaneous implantation), although implantation in the same organ as the original tumor may be an option (orthotopic implantation, i.e. pancreas, oral cavity, ovary, mammary fat pad, brain, etc.). In addition, independently of the tumor origin, some approaches may include implanting primary tumors in the renal capsule in an effort to increase engraftment success rates. A variety of mouse strains having different degrees of immunosuppression may be used in such studies. For hormone sensitive tumors, some studies may use hormone supplementation with the intent of increasing engraftment rates. In some embodiments, PDX tumors may be generated in non-obese diabetic/severe combined immunodeficiency (NOD/SCID) mice. Antibodies may be administered to mice with PDX tumors and the effect on tumor volume may be analyzed. In some cases, PDX tumors may be dissected, subjected to cellular dissociation, and the resulting cells grown in culture. The ability of antibodies of the present disclosure to target these cells may be assessed in vitro.

The preparation of antibodies, whether monoclonal or polyclonal, is known in the art. Techniques for the production of antibodies are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999.

Targets

Glycan-interacting antibodies of the present invention may exert their effects via binding (reversibly or irreversibly) to one or more glycan or glycan-associated or glycan-related targets. In some embodiments, glycan-interacting antibodies can be prepared from any region of the targets taught herein. In some embodiments, targets of the present invention include glycans. Glycans used for generating antibodies may include a chain of sugars having at least 2, at least 3, at least 4, at least 5, at least 6, at least 7, at least 8, at least 9, at least 10, at least 11, at least 12, at least 13, at least 14, at least 15, at least 16, at least 17, at least 18, at least 19 or at least 20 residues. Some glycans used for generating antibodies may include from about 2 residue to about 5 residues.

In some embodiments, glycan-interacting antibody target antigens include sialic acids. N-acetylneuraminic acid (Neu5Ac) and N-glycolylneuraminic acid (Neu5Gc) are the major sialic acids on mammalian cell surfaces. Of these, Neu5Ac is naturally produced in humans. Neu5Gc is naturally produced in most mammals with the exception of humans due to a mutation in the cytidine monophosphate (CMP)-N-acetylneuraminic acid hydroxylase (CMAH) gene responsible for CMP-Neu5Gc production from CMP-Neu5Ac. Neu5Gc in humans is in fact immunogenic with nearly all humans expressing anti-Neu5Gc antibodies. Despite a lack of production, most human systems include some level of Neu5Gc due to dietary intake. These foreign products are subsequently incorporated into human glycoproteins. Such glycoproteins are contemplated as targets of the invention. Glycan target antigens of the present invention may include, but are not limited to those listed in the following Table.

TABLE 1

Glycan target antigens
Glycan

GalNAcα-R
Galα1,3Galβ1,4GlcNAcβ-R
Galβ1,3GalNAcβ-R
Galβ1,3GlcNAcα-R
Galβ1,3GlcNAcβ1,3Galβ1,4Glcβ-R
Galβ1,3GlcNAcβ-R
Galβ1,4GlcNAc6Sβ-R
Galβ1,4GlcNAcβ-R
Galβ1,4Glcβ-R
KDNα2,8Neu5Acα2,3Galβ1,4Glcβ-R
KDNα2,8Neu5Gcα2,3Galβ1,4Glcβ-R
Neu5,9Ac2α2,3Galβ1,3GalNAcα-R
Neu5,9Ac2α2,3Galβ1,3GalNAcβ-R
Neu5,9Ac2α2,3Galβ1,3GlcNAcβ-R
Neu5,9Ac2α2,3Galβ1,4GlcNAcβ-R
Neu5,9Ac2α2,3Galβ1,4Glcβ-R
Neu5,9Ac2α2,3Galβ-R
Neu5,9Ac2α2,6GalNAcα-R
Neu5,9Ac2α2,6Galβ1,4GlcNAcβ-R
Neu5,9Ac2α2,6Galβ1,4Glcβ-R
Neu5,9Ac2α2,6Galβ-R
Neu5Acα2,3Galβ1,3GalNAcα-R
Neu5Acα2,3Galβ1,3GalNAcβ-R
Neu5Acα2,3Galβ1,3GlcNAcβ1,3Galβ1,4Glcβ-R
Neu5Acα2,3Galβ1,3GlcNAcβ-R
Neu5Acα2,3Galβ1,4(Fucα1,3)GlcNAc6Sβ-R
Neu5Acα2,3Galβ1,4(Fucα1,3)GlcNAcβ-R
Neu5Acα2,3Galβ1,4GlcNAc6Sβ-R
Neu5Acα2,3Galβ1,4GlcNAcβ-R
Neu5Acα2,3Galβ1,4Glcβ-R
Neu5Acα2,3Galβ-R
Neu5Acα2,6(KDNα2,3)Galβ1,4Glcβ-R
Neu5Acα2,6(Neu5Acα2,3)Galβ1,4Glcβ-R
Neu5Acα2,6(Neu5Gcα2,3)Galβ1,4Glcβ-R
Neu5Acα2,6GalNAcα-R
Neu5Acα2,6Galβ1,4GlcNAcβ-R
Neu5Acα2,6Galβ1,4Glcβ-R
Neu5Acα2,6Galβ-R
Neu5Acα2,8KDNα2,6Galβ1,4Glcβ-R
Neu5Acα2,8Neu5Acα2,3Galβ1,4Glcβ-R
Neu5Acα2,8Neu5Acα2,3Galβ1,4Glcβ-R
Neu5Acα2,8Neu5Acα2,6Galβ1,4Glcβ-R

TABLE 1-continued

Glycan target antigens
Glycan

Neu5Acα2,8Neu5Acα2,8Neu5Acα2,3Galβ1,4Glcβ-R
Neu5Acα2,8Neu5Acα2,8Neu5Acα2,3Galβ1,4Glcβ-R
Neu5Acα2,8Neu5Gcα2,3Galβ1,4Glcβ-R
Neu5Acα2,8Neu5Gcα2,6Galβ1,4Glcβ-R
Neu5Gc9Acα2,3Galβ1,4Glcβ-R
Neu5Gc9Acα2,6Galβ1,4Glcβ-R
Neu5Gc9Acα2,3Galβ1,3GalNAcα-R
Neu5Gc9Acα2,3Galβ1,3GalNAcβ-R
Neu5Gc9Acα2,3Galβ1,3GlcNAcβ-R
Neu5Gc9Acα2,3Galβ1,4GlcNAcβ-R
Neu5Gc9Acα2,3Galβ-R
Neu5Gc9Acα2,6GalNAcα-R
Neu5Gc9Acα2,6Galβ1,4GlcNAcβ-R
Neu5Gc9Acα2,6Galβ-R
Neu5GcOMeα2,8Neu5Acα2,3Galβ1,4Glcβ-R
Neu5Gcα2,3Galβ1,3GalNAcα-R
Neu5Gcα2,3Galβ1,3GalNAcβ-R
Neu5Gcα2,3Galβ1,3GlcNAcβ1,3Galβ1,4Glcβ-R
Neu5Gcα2,3Galβ1,3GlcNAcβ-R
Neu5Gcα2,3Galβ1,4(Fucα1,3)GlcNAc6Sβ-R
Neu5Gcα2,3Galβ1,4(Fucα1,3)GlcNAcβ-R
Neu5Gcα2,3Galβ1,4GlcNAc6Sβ-R
Neu5Gcα2,3Galβ1,4GlcNAcβ-R
Neu5Gcα2,3Galβ1,4Glcβ-R
Neu5Gcα2,3Galβ-R
Neu5Gcα2,6GalNAcα-R
Neu5Gcα2,6Galβ1,4GlcNAcβ-R
Neu5Gcα2,6Galβ1,4Glcβ-R
Neu5Gcα2,6Galβ-R
Neu5Gcα2,8Neu5Acα2,3Galβ1,4Glcβ-R
Neu5Gcα2,8Neu5Gcα2,3Galβ1,4Glcβ-R

The following abbreviations are used herein: Glc—glucose, Gal—galactose, GlcNAc—etylglucosamine, GalNAc—N-acetylgalactosamine, GlcNAc6S—6-Sulfo-N-acetylglucosamine, KDN—2-keto-3-deoxy-D-glycero-D-galactononic acid, Neu5,9Ac2—N-acetyl-9-O-acetylneuraminic acid, Fuc—fucose and Neu5GcOMe—2-O-methyl-N-glycolylneuraminic acid. O-glycosidic bonds are present between each residue in the glycans listed with α and β indicating the relative stoichiometry between the two residues joined by the bond, wherein α indicates an axial orientation and β indicates an equatorial orientation. The numbers following α and/or β, in the format x,x, indicate the carbon number of each of the carbons from each of the adjoined residues that participate in bond formation. While the glycans listed in the previous Table represent individual glycan target antigens contemplated, the present invention also includes embodiments wherein the above presented glycans include different combinations of α and β-oriented O-glycosidic bonds than the ones presented. Also in the previous Table, R represents an entity that the glycan may be coupled with. In some embodiments, R is a protein wherein the glycan is linked typically to a serine or threonine residue. In some embodiments, R is a linker molecule used to join the glycan to a substrate, such as in a glycan array. In some embodiments, R may be a linker with the formula of —(CH$_2$)$_2$CH$_2$NH$_2$ or —(CH$_2$)$_3$NHCOCH$_2$(OCH$_2$CH$_2$)$_6$NH$_2$. In some embodiments, R may be biotin, albumin, ProNH$_2$, —CH—, —OH, —OCH$_3$, —OCH$_2$CH$_3$, —H, hydrido, hydroxy, alkoxyl, oxygen, carbon, sulfur, nitrogen, polyacrylamide, phosphorus, NH$_2$, ProNH$_2$=O (CH$_2$)$_2$CH$_2$NH$_2$, (OCH$_2$CH$_2$)$_6$NH$_2$, O(CH$_2$)$_3$NHCOCH$_2$(OCH$_2$CH$_2$)$_6$NH$_2$, the fluorescent labels 2-aminobenzamide (AB) and/or 2-aminobenzoid acid (AA), 2-aminobenzamide analog that contains an alkyl amine (AEAB), aminooxy-groups, methylaminooxygroups, hydrazide groups, amino lipid 1,2-dihexadecyl-sn-glycero-3-phosphoethanolamine (DHPE), aminooxy (AO) functionalized DHPE and glycosylphosphatidylinositol (GPI). Without intending to limit the source or nature of R, this may include structures that affect the physical spacing of glycan residue. In some embodiments, the R group may include a combination of the R groups presented here, e.g. a biotinylated polyacrylamide. In some embodiments, the R group in combination with underlying substrates effect glycan residue spacing.

Glycan targets of the present invention may include one or more regions of antibody recognition. As used herein, the term "region of antibody recognition" refers to a segment located on any part of the molecule, an attached group or located on a region of interaction between the glycan and another molecule, including, but not limited to another glycan, protein, membrane, cell surface structure, or extracellular matrix component. In some embodiments, regions of antibody recognition are located at interchain target sites, wherein the term "interchain" means within the present polymeric chain. Interchain target sites may include regions of antibody recognition having 1, 2, 3, 4, 5, 6, 7, 8, 9 or at least 10 residues, bonds between residues or combinations of residues and bonds. In some embodiments, regions of antibody recognition are located at regions of interaction between one or more glycan chains. Such regions may be between 2, 3, 4 or at least 5 glycan chains.

In some embodiments, regions of antibody recognition are located at regions of interaction between glycan branch chains connected to a common parent chain. In some embodiments, regions of antibody recognition are located at regions of interaction between a glycan branch chain and a parent chain. In some embodiments, regions of antibody recognition are located at regions of interaction between glycans and proteins. Such regions of interaction may include chemical bonds between the glycan and the protein, including, but not limited to covalent bonds, ionic bonds, hydrostatic bonds, hydrophobic bonds and hydrogen bonds. In some embodiments, regions of antibody recognition are located at regions of interaction between glycans and other biomolecules including, but not limited to lipids and nucleic acids. Such regions of interaction may include chemical bonds between the glycan and the biomolecule, including, but not limited to covalent bonds, ionic bonds, hydrostatic bonds, hydrophobic bonds and hydrogen bonds.

In some embodiments, glycan targets of the present invention are components of glycoconjugates. As used herein, the term "glycoconjugate" refers to any entity joined with a glycan moiety. In some embodiments, glycoconjugates are glycolipids. As used herein, the term "glycolipid" refers to a class of lipids wherein a carbohydrate moiety is covalently attached. In some embodiments, carbohydrate moieties present on glycolipids may be glycans. In some embodiments, lipid components of glycolipids include ceramide moieties. Examples of glycolipids contemplated as targets of the present invention include, but are not limited to glyceroglycolipids (including, but not limited to galactolipids and sulfolipids), glycosphingolipids (including, but not limited to cerebrosides (e.g., galactocerebrosides, glucocerebrosides and sulfatides), gangliosides, globosides and glycophosphosphingolipids) and glycosylphosphatidylinositols. When located within cell membranes, glycan moieties of glycolipids are located on the extracellular side of the membrane where they may interact with other cells as well as cell signaling ligands (Maccioni, H. J. et al., *Organization of the synthesis of glycolipid oligosaccharides in the Golgi complex*. FEBS Lett. 2011 Jun. 6; 585(11):1691-8).

In some embodiments, glycoconjugate targets of the present invention are glycoprotein and/or proteoglycans. Glycoproteins refer to any proteins that are covalently bonded with glycans. Proteoglycans are a class of proteins that are heavily glycosylated with glycans that often carry a negative charge. This property makes them very hydrophilic and important components of connective tissue.

Cancer-Related Targets

In some embodiments, targets of the present invention are cancer-related antigens or epitopes. As used herein, the term "cancer-related" is used to describe entities that may be in some way associated with cancer, cancerous cells and/or cancerous tissues. Many cancer-related antigens or epitopes that include glycans have been identified that are expressed in correlation with tumor cells (Heimburg-Molinaro, J. et al., Cancer vaccines and carbohydrate epitopes. Vaccine. 2011 November 8; 29(48):8802-26). These are referred to herein as "tumor-associated carbohydrate antigens" or "TACAs." TACAs include, but are not limited to mucin-related antigens [including, but not limited to Tn, Sialyl Tn (STn) and Thomsen-Friedenreich antigen], blood group Lewis related antigens [including, but not limited to Lewis$^Y$ (Le$^Y$), Lewis$^X$ (Le$^X$), Sialyl Lewis$^X$ (SLe$^X$) and Sialyl Lewis$^A$ (SLe$^A$)], glycosphingolipid-related antigens [including, but not limited to Globo H, stage-specific embryonic antigen-3 (SSEA-3) and glycosphingolipids that include sialic acid], ganglioside-related antigens [including, but not limited to gangliosides GD2, GD3, GM2, fucosyl GM1 and Neu5GcGM3] and polysialic acid-related antigens. Many of such antigens are described in International Publication No. WO2015054600, the contents of which are herein incorporated by reference in their entirety.

In some embodiments, TACA targets of the present invention include Lewis blood group antigens. Lewis blood group antigens include a fucose residue linked to GlcNAc by an α1-3 linkage or an α1-4 linkage. They may be found on both glycolipids and glycoproteins. Lewis blood group antigens may be found in the body fluid of individuals that are secretors of these antigens. Their appearance on red cells is due to absorption of Lewis antigens from the serum by the red cells.

In some embodiments, TACA targets of the present invention include Le$^Y$. Le$^Y$ (also known as CD174) is made up of Galβ1,4GlcNAC having α1,2- as well as α1,3-linked fucose residues yielding the Fucα(1,2)Galβ(1,4)Fucα(1,3)GlcNAc epitope. It is synthesized from the H antigen by α1,3 fucosyltransferases which attach the α1,3 fucose to the GlcNAc residue of the parent chain. Le$^Y$ may be expressed in a variety of cancers including, but not limited to ovarian, breast, prostate, colon, lung and epithelial. Due to its low expression level in normal tissues and elevated expression level in many cancers, the Le$^Y$ antigen is an attractive target for therapeutic antibodies.

In some embodiments, TACA targets of the present invention include Le$^X$. Le$^X$ includes the epitope Galβ1-4(Fucα1-3)GlcNAcβ-R. It is also known as CD15 and stage-specific embryonic antigen-1 (SSEA-1). This antigen was first recognized as being immunoreactive with sera taken from a mouse subjected to immunization with F9 teratocarcinoma cells. Le$^X$ was also found to correlate with embryonic development at specific stages. It is also expressed in a variety of tissues both in the presence and absence of cancer, but can also be found in breast and ovarian cancers where it is only expressed by cancerous cells.

In some embodiments, TACA targets of the present invention include SLe$^A$ and/or SLe$^X$. SLe$^A$ and SLe$^X$ are made up of structures Neu5Acα2-3Galβ1-3(Fucα1-4)GlcNAcβ-R and Neu5Acα2-3Galβ1-4(Fucα1-3)GlcNAcβ-R, respectively. Their expression is upregulated in cancer cells. The presence of these antigens in serum correlates with malignancy and poor prognosis. SLe$^X$ is mostly found as a mucin terminal epitope. It is expressed in a number of different cancers including breast, ovarian, melanoma, colon, liver, lung and prostate. In some embodiments of the present invention, SLe$^A$ and SLe$^X$ targets include Neu5Gc (referred to herein as GcSLe$^A$ and GcSLe$^X$, respectively).

In some cases, cancer-related targets of the invention may include mucins. Ishida et al demonstrate that interaction of MUC2 with dendritic cells (with anti-tumor activity) leads to dendritic cell apoptosis (Ishida, A. et al., 2008. Proteomics. 8: 3342-9, the contents of which are herein incorporated by reference in their entirety). In some aspects, the present invention provided anti-mucin antibodies to prevent dendritic cell apoptosis and support anti-tumor activity.

In some embodiments, TACA targets of the present invention include glycolipids and/or epitopes present on glycolipids, including, but not limited to glycosphingolipids. Glycosphingolipids include the lipid ceramide linked to a glycan by the ceramide hydroxyl group. On the cell membrane, glycosphingolipids form clusters referred to as "lipid rafts".

In some embodiments, TACA targets of the present invention include Globo H. Globo H is a cancer-related glycosphingolipid first identified in breast cancer cells. The glycan portion of Globo H includes Fucα(1-2)Galβ(1-3)GalNAcβ(1-3)Galα(1-4)Galβ(1-4)Glcβ(1). Although found in a number of normal epithelial tissues, Globo H has been identified in association with many tumor tissues including, but not limited to, small cell lung, breast, prostate, lung, pancreatic, gastric, ovarian and endometrial tumors.

In some embodiments, cancer-related glycosphingolipid targets of the present invention include gangliosides. Gangliosides are glycosphingolipids having one or more sialic acid. According to ganglioside nomenclature, G is used as an abbreviation for ganglioside. This abbreviation is followed by the letters M, D or T referring to the number of sialic acid residues attached (1, 2 or 3 respectively). Finally the numbers 1, 2 or 3 are used to refer to the order of the distance each migrates when analyzed by thin layer chromatography (wherein 3 travels the greatest distance, followed by 2, and then 1). Gangliosides are known to be involved in cancer-related growth and metastasis and may be expressed on the cell surface of tumor cells. Gangliosides expressed on tumor cells may include, but are not limited to GD2, GD3, GM2 and fucosyl GM1 (also referred to herein as Fuc-GM1). In some embodiments of the present invention, glycan-interacting antibodies are directed toward GD3. GD3 is a regulator of cell growth. In some embodiments, GD3-directed antibodies are used to modulate cell growth and/or angiogenesis. In some embodiments, GD3-directed antibodies are used to modulate cell attachment. GD3 associated with some tumor cells may include 9-O-acetylated sialic acid residues (Mukherjee, K. et al., 2008. J Cell Biochem. 105: 724-34 and Mukherjee, K. et al., 2009. Biol Chem. 390: 325-35, the contents of each of which are herein incorporated by reference in their entirety). In some cases, antibodies of the invention are selective for 9-O-acetylated sialic acid residues. Some antibodies may be specific for 9-O-acetylated GD3s. Such antibodies may be used to target tumor cells expressing 9-O-acetylated GD3. In some embodiments of the present invention, glycan interacting antibodies are directed toward GM2. In some embodiments, GM2-directed antibodies are used to modulate cell to cell contact. In some embodiments, ganglioside targets of the present invention include Neu5Gc. In some embodiments, such targets may include a GM3 variant having Neu5Gc (referred to herein as GcGM3). The glycan component of GcGM3 is Neu5Gcα2-3Galβ1-4Glc. GcGM3 is a known component of tumor cells (Casadesus, A. V. et al., 2013. Glycoconj J. 30(7):687-99, the contents of which are herein incorporated by reference in their entirety).

In some embodiments, TACAs of the present disclosure include at least one Neu5Gc residue.

Recombinant Antibodies

Recombinant antibodies (e.g., glycan-interacting antibodies) of the invention may be generated using standard techniques known in the art. In some embodiments, recombinant antibodies may be anti-glycan antibodies. Further antibodies may be anti-STn antibodies (e.g. anti-GcSTn or anti-AcSTn antibodies). Recombinant antibodies of the invention may be produced using variable domains obtained from hybridoma cell-derived antibodies produced according to methods described herein. Heavy and light chain variable region cDNA sequences of antibodies may be determined using standard biochemical techniques. Total RNA may be extracted from antibody-producing hybridoma cells and converted to cDNA by reverse transcriptase (RT) polymerase chain reaction (PCR). PCR amplification may be carried out on resulting cDNA to amplify variable region genes. Such amplification may include the use of primers specific for amplification of heavy and light chain sequences. In other embodiments, recombinant antibodies may be produced using variable domains obtained from other sources. This includes the use of variable domains selected from one or more antibody fragment library, such as an scFv library used in antigen panning. Resulting PCR products may then be subcloned into plasmids for sequence analysis. Once sequenced, antibody coding sequences may be placed into expression vectors. For humanization, coding sequences for human heavy and light chain constant domains may be used to substitute for homologous murine sequences. The resulting constructs may then be transfected into mammalian cells for large scale translation.

Anti-Tn Antibodies

In some embodiments, recombinant antibodies of the invention (e.g., glycan-interacting antibodies) may be anti-Tn antibodies. Such antibodies may bind to targets having Tn. Anti-Tn antibodies may be specific for Tn or may bind other modified forms of Tn, such as Tn linked to other moieties, including, but not limited to additional carbohydrate residues. In some cases anti-Tn antibodies may be anti-sialyl-Tn antibodies. Such antibodies may bind to sialylated Tn that includes Neu5Ac and/or sialylated Tn that include Neu5Gc. Some anti-Tn antibodies may bind specifically to clusters of Tn antigen.

Anti-STn Antibodies

Figure 1B:
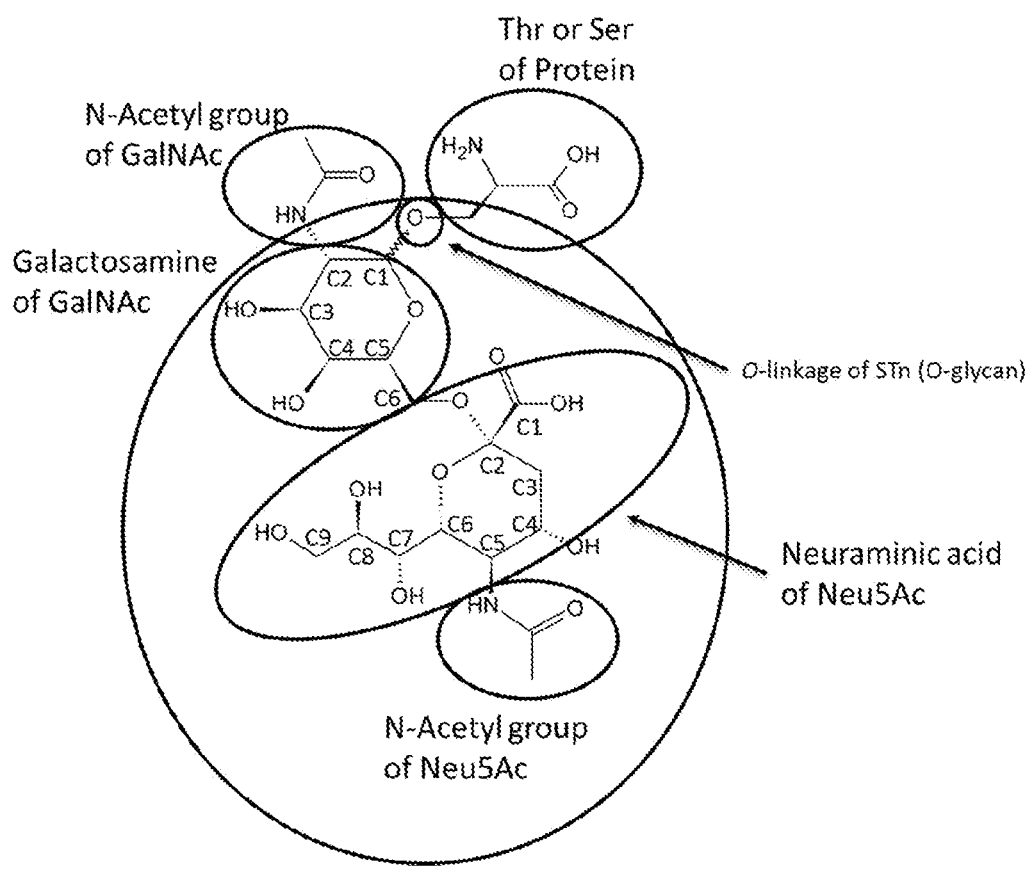
Figure 1C:
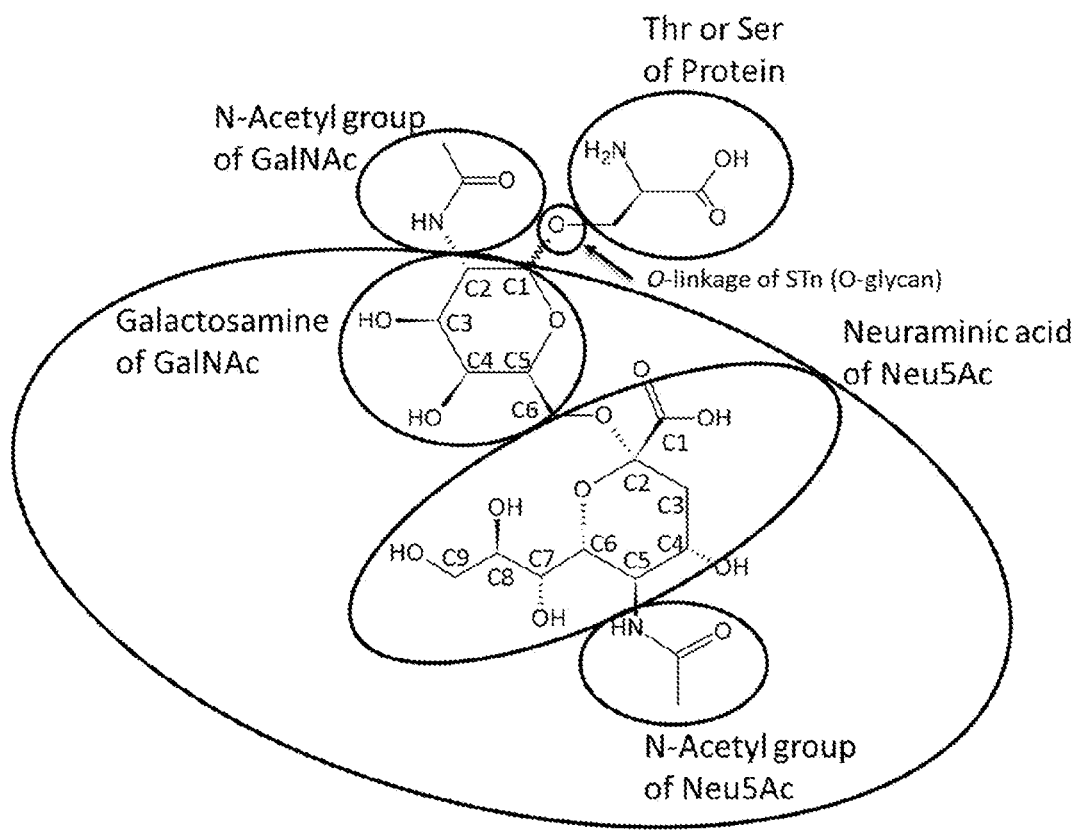
Figure 1D:
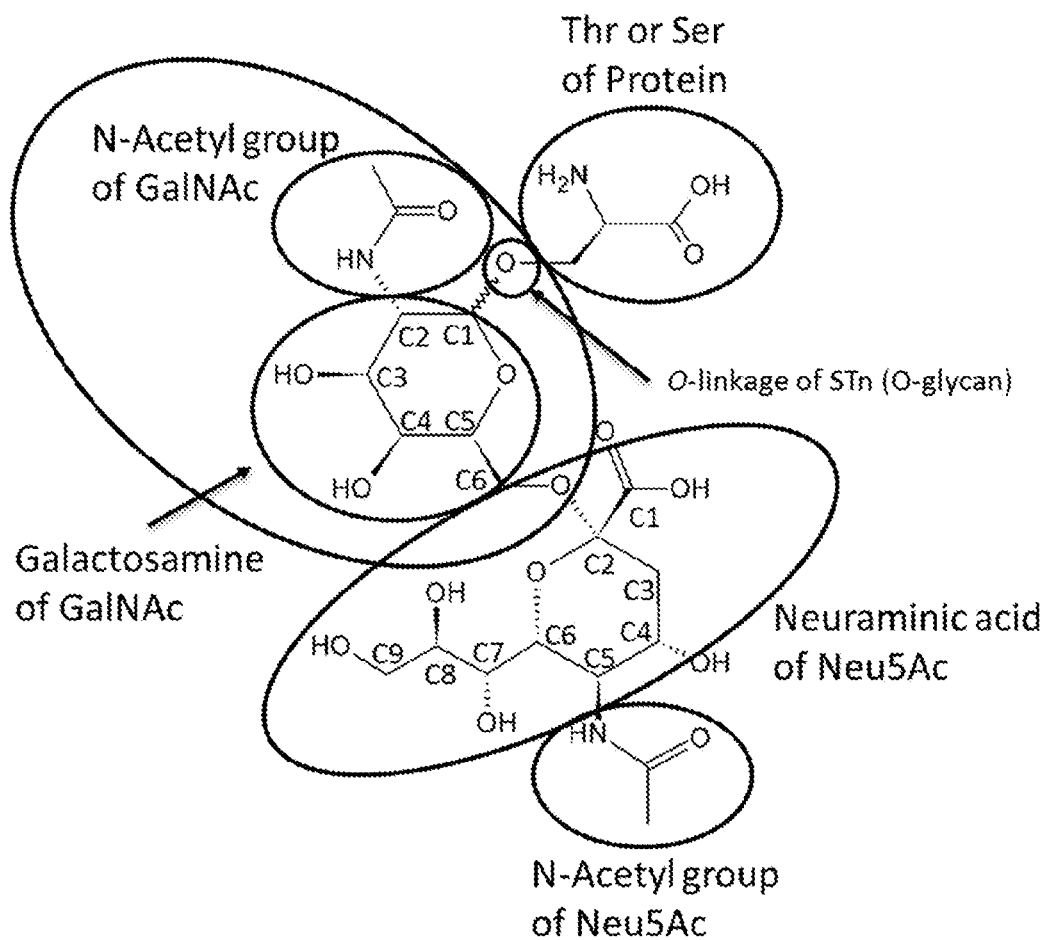

In some embodiments, antibodies of the invention (e.g., glycan-interacting antibodies) may specifically bind to STn. Anti-STn antibodies of the invention may be categorized by their binding to specific portions of STn antigens and/or by their specificity for AcSTn versus GcSTn. In some cases, anti-STn antibodies of the invention are Group 1 antibodies. "Group 1" antibodies according to the invention are antibodies capable of binding AcSTn and GcSTn. Such antibodies may also be referred to herein as pan-STn antibodies due to their ability to associate with a wider range of STn structures. In some embodiments, Group 1 antibodies may associate with the portion of STn indicated by the large oval in FIG. 1A. In some cases, anti-STn antibodies of the invention are Group 2 antibodies. "Group 2" antibodies, accoding to the invention, are antibodies capable of binding STn as well as some related structures that include an O-linkage to serine or threonine. In some embodiments, Group 2 antibodies may associate with glycans that include a sialylated galactose residue. In some cases, Group 2 antibodies may associate with the portion of STn indicated by the large oval in FIG. 1B. Some Group 2 antibodies preferably bind to structures with AcSTn over structures with GcSTn. Further anti-STn antibodies may be Group 3 antibodies. As referred to herein, "Group 3" antibodies are antibodies capable of binding STn, but may also bind a broader set of related structures. Unlike Group 2 antibodies, Group 3 antibodies do not require that such structures have an O-linkage to serine or threonine. In some embodiments, Group 3 antibodies may associate with the portion of STn indicated by the large oval in FIG. 1C. Finally, some anti-STn antibodies of the invention may be Group 4 antibodies. As referred to herein, "Group 4" antibodies are capable of binding to both AcSTn and GcSTn as well as the un-sialylated Tn antigen, and therefore have broader specificity. In some embodiments, Group 4 antibodies may associate with the portion of STn indicated by the large oval in FIG. 1D.

In some cases, anti-STn antibodies of the invention may bind specifically to clusters of STn on a particular antigen or cell surface. Some such antibodies may recognize epitopes formed by the clustering of STn, including epitopes that include areas of contact between neighboring STn structures. Such epitopes may be formed by the clustering of 2, 3, 4, 5, 6, 7, 8, 9, 10 or more STn structures.

In some embodiments, anti-STn antibodies of the present disclosure may be used bind cellular proteins carrying STn. Such antibodies may be useful for targeting cellular proteins associated with cancer cells that are distinguishable from similar proteins in non-cancerous cells by STn expression. In some cases, such proteins may include cell surface proteins. Cancer cell surface proteins carrying STn may be targeted by anti-STn antibodies during cancer treatment and/or diagnosis. Cell surface proteins carrying STn may be identified using mass spectrometry and/or using immunological methods (e.g., FACS analysis, immunoprecipitation, immunoblotting, ELISA, etc.). In some cases, cellular proteins carrying STn may include cancer cell markers, cancer stem cell markers, and/or cancer stem cell signaling proteins. In some embodiments, cellular proteins carrying STn may include, but are not limited to CD44, CD133, CD117, integrins, Notch, and Hedgehog.

Antibody Components

In some cases, antibodies or antigen binding fragments thereof of the invention may include variable domain and/or CDR amino acid sequences provided herein. Some antibodies or antigen binding fragments may include different combinations of such sequences. In some cases, antibodies or antigen binding fragments of the invention may include one or more of the variable domain sequences listed in the following Table. Residues indicated with an "X" may be absent or selected from any amino acid residues. Light chain variable domains presented in the Table may be expressed with or without a C-terminal arginine residue. This residue typically links light chain variable domains with light chain constant domains and may be expressed as part of the light chain constant domain instead of the light chain variable domain. In some cases, antibodies or antigen binding fragments thereof may include an amino acid sequence with from about 50% to about 99.9% sequence identity (e.g. from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 99.9%, from about 95% to about 99.9%, about 97%, about 97.5%, about 98%, about 98.5%, about 99%, about 99.5%, about 99.6%, about 99.7% or about 99.8%) with one or more of the variable domain sequences listed in the following Table. In some cases, antibodies or antigen binding fragments thereof of the invention may include an amino acid sequence having one or more fragments of any of the sequences listed in the following Table.

TABLE 2

Variable domain sequences

| Antibody ID Number | Variable domain | Sequence | SEQ ID NO |
|---|---|---|---|
| 7D3-2C10 | Heavy chain | QVQLLQYDAELVKPGGSVKISCKASGYTFTDHAIHWV KQKPEQGLEWIGYFSPGNDDIKYSEKFKGKATLTADKS SSTAYMQLNSLTSEDSAVYFCKRSITTPYWGQGTLVTV SA | 1 |
| 7D3-2C10 | Light chain | DIQMNQSPSSLSASLGDTITITCHASQNINVWLSWYQQK PGNIPKLLIYKVSNLHTGVPSRFSGSGSGTGFTLTISSLQ PEDIATYYCQQDQSYPYTFGGGTKLKK | 2 |
| A5-2G12 | Heavy chain | QVQLQQSDAELVKPGASVKISCKASGYTFTDHAIHWV KQKPEQGLEWIGYISPGNDDIKYNEKFKGKATLTADKS SSTAYMQLNSLTSEDSAVYFCKRSITTSYWGQGTLVTV SA | 3 |
| A5-2G12 | Light chain | NIVMTQSPKSMSMSVGERVTLTCKASENVVIYVSWYQ QKPEQSPKLLIYGASNRYTGVPDRFTGSGSATDFTLTISS VQAEDLADYHCGQGYSYPYTFGGGTKLEIKR | 4 |
| 1A5-2C9 | Heavy chain | QVQLQQSDAELVKPGASVKISCKASGYTFTDHAIHWV KQKPEQGLEWIGYVSPGNGDIKYNEKFKGKATLTADK SSSTAYMQLNSLTSEDSAVYFCKRSLIGDYWGQGTTLT VSS | 5 |
| 1A5-2C9 | Light chain | DIVMTQSQKFMSSSVGDRVTITCKASQNVGTAVAWYQ QKPGQSPKFLIYSASNRYTGVPDRFTGSGSGTDFTLTIS NMQSEDLADYFCQQYSSYRLTFGGGTKLEIK | 6 |

TABLE 2-continued

Variable domain sequences

| Antibody ID Number | Variable domain | Sequence | SEQ ID NO |
|---|---|---|---|
| 4D9-2C11 | Heavy chain | QVQLQQSDAELVKPGASVKISCKASGYTFTDHAIHWV KQKPEQGLEWIGYLSPGNDDIKYSEKFKDKATLTADKS SSTAYMQLNSLTSEDSAVYFCKRSIGGDHWGQGTTLTV SS | 7 |
| 4D9-2C11 | Light chain | DIQMNQSPSSLSASLGDTITITCHASQNINVWLNWYQQ KPGNIPKLLIYKASNLHTGVPSRFSGSGSGTGFTLTIGSL QPEDIATYYCQQGQSYPFTFGGGTKLEIKR | 8 |
| 2F4-1E2 | Heavy chain | QVQLQQSDAELVKPGASVKISCKASGYTFTDHAIHWV KQKPEQGLEWIGYISPGNGDIKYNEKFKGKATLTADKS SSTAYMQLNSLTSEDSAVYFCQRQLGQGYWGQGTTLT VSS | 9 |
| 2F4-1E2 | Light chain | DVVMTQTPLSLPVSLGDQASISCRSSQSLVHSYGNTYL HWYLQKPGQSPKLLIYKVSNRFSGVPDRFSGSGSGTDF TLKISRVEAEDLGVYFCSQNTHVPYTFGGGTKLEIKR | 10 |
| 2F4-1H8 | Heavy chain | QVQLQQSDAELVKPGASVKISCKASGYTFTDHAIHWV KQKPEQGLEWIGYISPGNGDIKYNEKFKGKATLTADKS SSTAYMQLNSLTSEDSAVYFCQRQLGQGYWGQGTTLT VSS | 9 |
| 2F4-1H8 | Light chain | DVVMTQTPLSLPVSLGDQASISCRSSQSLVHSYGNTYL HWYLQKPGQSPKLLIYKVSNRFSGVPDRFSGSGSGTDF TLKISRVEAEDLGVYFCSQNTHVPYTFGGGTKLEIKR | 10 |
| 2C6-2F11 | Heavy chain | QVQLQQSDAELGKPGASVKISCKASGYTFSDHAIHWV KQKPEQGLEWIGYISPGNDDIKYNEKFKGKATLTADKS SSTAYMQLNSLTSEDSAVYFCERSMIGVYWGQGTLVT VSA | 11 |
| 2C6-2F11 | Light chain | DVVMTQTPLSLTVSLGDQASISCRFSQSLVQSNGNTYL QWYLQKPGQSPKLLIYKVSNRFCGVPDRFSGSGSGTDF TLKISRVEAEDLGVYFCSQSTHAPLTFGAGTKLELK | 12 |
| 2B2-2A7 | Heavy chain | QVQLQQSDAELVKPGASVKISCKTSGYTFTDHAIHWVK QKPEQGLEWIGYISPGNGDIKYNEKFKGKATLTADKSS STAYMQLSSLTPEDSAVYFCKISYYGIWGQGTTLTVSS | 13 |
| 2B2-2A7 | Light chain | DIQMTQSPASLSVSVGESVTITCRLSEDIYSNLAWFQQR PGKSPQLLVYKATNLADGVPSRFSGSGSGTQYSLKINSL QSEDFGTYYCQHFWGTPFTFGSGTKVEIK | 14 |
| 5G2-1B3 | Heavy chain | QVQLQQSDAELVKPGASVKISCKASGYTFTDHAIHWV KQKPEQGLEWIGYFSPGNDDIKYNEKFKVKATLTADKS SSTAYMQLTSLTSEDSAVYFCKRSYYGDWGQGTTLTV SS | 15 |
| 5G2-1B3 | Light chain | DIQMTQSPASLSVSVGETVTITCRASENIYSHLAWYQQ KQGKSPQLLVYGATNLADGVPSRFSGSGSGTQFSLKIH SLQSEDFGSYYCQHFWGAPFTFGSGTKLEIK | 16 |
| 7A6-2A2 | Heavy chain | QIQLQQSDAELVKPGTSVKMSCKASGYTFTDHAIHWV KQKPEQGLEWIGYFSPGNDDIKYNVKFKGKATLTADK SSSTAYMQLNSLTSEDSAVYFCSVGYALDYWGLGTTL TVSS | 17 |
| 7A6-2A2 | Light chain | NIVMTQSPKSMSMSVGERVTLTCKASENVVTYVSWYQ QKPEQSPKLLIYGASNRYTGVPDRFTGSGSATDFTLTISS VQAEDLADYHCGQGYSYPYTFGGGTKLEIKR | 18 |
| 10C9-2G7 | Heavy chain | QVQLQQSDAELVKPGTTVKISCKASGYTFTDHAIHWV KEKPEQGLEWIGYISPGNDDIKYSEKFKGKATLTADKSS STAYMQLNSLTSDDSAVYFCKRSLSTPYWGQGTLVTV SA | 19 |
| 10C9-2G7 | Light chain | Unknown | |
| 1C11-2G9 | Heavy chain | Unknown | |

TABLE 2-continued

Variable domain sequences

| Antibody ID Number | Variable domain | Sequence | SEQ ID NO |
|---|---|---|---|
| 1C11-2G9 | Light chain | DIVMTQSPSSLTVTAGEKVTMSCRSSQSLLNSGNQKNYLTWYQQKPGQPPKLLIYWASTRESGVPDRFTGSGSGTDFTLTISSVQAEDLAVYYCQNDYSYPYTFGGGTKLEIKR | 20 |
| 1F6-1B7 (also sequence of 1F6-1C10) | Heavy chain | QVQLQQSDAELVKPGASVKISCKASGYTFTDHAIHWVMQMPEQGLEWIGYISPGNGDVKYSERFKGRATLTADKSSSSAYMQLNSLTSEDSAVYFCKRSLSTPYWGQGTLVTVS | 21 |
| 1F6-1B7 (also sequence of 1F6-1C10) | Light chain | DIVMTQSPSSLTVTAGERVTMSCKSSQSLLNSGNQKSYLTWYQQKPGQPPKLLISWASTRDSGVPDRFTGSGSGTDFTLTISSVQAEDLAVYYCQSDYSYPYTFGGGTKLEIKR | 22 |
| 2G12-2B2 | Heavy chain | QVQLQQSDXELVKPGASVKISCKASGYTFTDHAIHWVKQKPEQGLEWIGYFSPGNDDIKYNEKFRGKATLTADKSSSTAYMQLNSLSSDDSAVYFCKRSLSTPYWGQGTLXTVSA | 23 |
| 2G12-2B2 | Light chain | DIVMTQSPSSLTVTAGEKVTMSCKSSQSLLNRGNHKNYLTWYRQKPGLPPKLLIYWASTRESGVPDRFTGSGSGTDFALTISSVQAEDLAVYYCQNDYTYPYTFGGGTKLEIKR | 24 |
| 5E6-2E7 | Heavy chain | QVQLQQSDAELVKPGASMKISCKASGYTFTDHAIHWVKQKPEQGLEWIGYISPGNGDIKYNEKFKVKATLTADKSSSTAYMQLNSLTSEDSAVYFCKRSITTPYWGQGTLVTVSA | 25 |
| 5E6-2E7 | Light chain | DIVMTQSPSSLTVTAGEKVTMSCKSSQSLLNSGKTKNYLTWYQQKPGQPPKLLIYWASTRESGVPDRFTGSGSGTDFTLTISSVQAEDLAVYYCKNDYSYPYTFGGGTKLEIKR | 26 |
| 9E5-1A8 | Heavy chain | QVQLQQSDAELVKPGASVKISCKTSGYTFTDHAIHWVKQKPEQGLEWIGYISPGNDDIKYTEKFKGKVTLTADKSSSTAYMQLNSLTSEDSAVYFCKRSITTPYWGQGTLVTVSA | 27 |
| 9E5-1A8 | Light chain | Unknown | |
| 9F11-1F7 | Heavy chain | QVQLQQSDAELVKPGASMKISCKASGYTFTDHAIHWVKQKPEQGLEWIGYISPGNGDIKYNEKFKVKATLTADKSSSTAYMQLNSLTSEDSAVYFCKRSITTPYWGQGTLVTVSA | 25 |
| 9F11-1F7 | Light chain | DIVMTQSPSSLTVTAGEKVTMSCKSSQSLLNSGKTKNYLTWYQQKPGQPPKLLIYWASTRESGVPDRFTGSGSGTDFTLTISSVQAEDLAVYYCKNDYSYPYTFGGGTKLEIKR | 26 |
| 10F4-2F2 | Heavy chain | QVQLQQSDAELVKPGASVKISCKASGYTFTDHAIHWVKQKPEQGLEWIGYISPGNGDIKYDEKFKGKATLTADKSSSTAYMQLNSLTSEDSAVYFCKRSITTSYWGQGTLVTVSA | 28 |
| 10F4-2F2 | Light chain | NIVMTQSPKSMSMSVGERVTLTCKASENVVTYVSWYQQKPEQSPKLLIYGASNRYTGVPDRFTGSGSATDFTLTISSVQAEDLADYHCGQGYSYPYTFGGGTKLEIKR | 18 |
| 2B8-2F10 | Heavy chain | QVQLQQSDAELVKPGASVKISCKASGYTFTDHAIHWVKQKPEQGLEWIGYISPGNDDIKYNEKFKGKATLTADKSSSTAYMQLNSLTSEDSAVFFCKRSITTSYWGQGTLVTVSA | 29 |
| 2B8-2F10 | Light chain | Unknown | |
| 4G8-1E3 | Heavy chain | QVQLQQSDAELVKPGASVKISCKASGYIFTDHAIHWVKQKPEQGLEWIGYISPGNGDIKYNEKFKGKATLTADKSSSTAYMHLNSLTSEDSAVYFCKRSITTSYWGQGTLVTVSA | 30 |
| 4G8-1E3 | Light chain | DIQMNQSPSSLSASLGDTITITCHASQHINFWLSWYQQKPGNIPKLLIYKASNLHTGVPSRFSGSGSGTGFTLTISSLLPEDVATYYCQQDQSYPYMFGGGTKLEIKR | 31 |

TABLE 2-continued

Variable domain sequences

| Antibody ID Number | Variable domain | Sequence | SEQ ID NO |
|---|---|---|---|
| 6B11-2E3 | Heavy chain | QVQLQQSDAELVKPGASVKISCKASGYTFTDHAIHWV KQKPEQGLEWIGYISPGNDDIKYNEKFKGKATLTADKS SSTAYMLLNSLTSEDSAVYFCKRSITTSYWGQGTLVTV SA | 32 |
| 6B11-2E3 | Light chain | NIVMTQSPKSMSMSVGERVTLTCKASENVVTYVSWYQ QKPEQSPKLLIYGASNRYTGVPDRFTGSGSATDFTLTISS VQAEDLADYHCGQGYSYPYTFGGGTKLEIKR | 18 |
| 8C2-2D6 | Heavy chain | QVQLQQSDAELVKPGASVKISCKASGYTFTDHAIHWV KQKPEQGLEWIGYISPGNGDIKYNEKFKGKATLTADTS STTAYMQLNSLTSEDSAMYFCKRSITTSYWGQGTLVTV SA | 33 |
| 8C2-2D6 | Light chain | NIVMTQSPKSMSMSVGERVTLTCKASENVVTYVSWYQ QKPEQSPKLLIYGASNRYTGVPDRFTGSGSATDFTLTISS VQAEDLADYHCGQGYSYPYTFGGGTKLEIKR | 18 |
| 8C2-2D6 | Light chain (V2) | DIQMNQSPSSLSASLGDTITITCHASQNINVWLSWYQQK PGNIPKLLIYKASNLYTGVPSRFSGSGSGTGFTLTISSLQ PEDVATYYCQHDQSYPYTFGGGTKLEIK | 34 |
| 7D4-2A2-2F2 | Heavy chain | QVQLQQSDAELVKPGASVKISCKASGYIFTDHAIHWVK QKPEQGLEWIGYISPGNGDIKYIEKFRGKATLTADKSSS TAYMQLNSLTSEDSAVYFCKRSLSTPYWGQGTLVTVSA | 35 |
| 7D4-2A2-2F2 | Light chain | NILMTQSPKSMSMSVGERVTLTCKASENVVNYVSWYQ QKPEQSPKLLIFGASNRYSGVPDRFTGSGSATDFTLTISS VQAEDLADYHCGSKWITSYPYTFGGGTKLEIKR | 36 |
| 7D4-1H12-2B3 | Heavy chain | QVQLQQSDAELVKPGASVKISCKASGYIFTDHAIHWVK QKPEQGLEWIGYISPGNGDIKYIEKFRGKATLTADKSSS TAYMQLNSLTSEDSAVYFCKRSLSTPYWGQGTLVTVSA | 35 |
| 7D4-1H12-2B3 | Light chain | NILMTQSPKSMSMSVGERVTLTCKASENVVNYVSWYQ QKPEQSPKLLIYGASNRYSGVPDRFTGSGSATDFTLTISS VQAEDLADYHCGARVTSYPYTFGGGTKLEIKR | 37 |
| 2C2-2C5 | Heavy chain | QVQLQQSDAELVKPGTSVKISCRASGYTFTDHAIHWVK QKPEQGLEWIGYISPGNGDIKYNEKFKGKATLTADKSS STAYMQLNSLTSDDSAVYFCKRSITTPYWGQGTTLTVSS | 38 |
| 2C2-2C5 | Light chain | SFVMTQTPKFLLVSAGDRVTITCKASQSVNNNVAWYQ QKPGQSPKQLIYYASNRYTGVPDRFTGSGYGTDFTFTIY TVQAEDLAVYFCQQGYSSPWTFGGGTKLK | 39 |
| 10F4-2A9 | Heavy chain | QVQLQQSDAELVKPGASVKISCKASGYTFTDHAIHWV KQKPEQGLEWIGYISPGNGDIKYDEKFKGKATLTADKS SSTAYMQLNSLTSEDSAVYFCKRSITTSYWGQGTLVTV SA | 28 |
| 3F1 | Heavy chain | QVQLQQSDAELVKPGASVKISCKASGYTFTDHAIHWV KQKPEQGLDWIGYISPGNGDIKYNEKFKDKVTLTADKS SSTACMHLNSLTSEDSAVYFCKRSLLALDYWGQGTTLT VSS | 40 |
| 3F1 | Light chain | DIVMTQSHKFMSTSVGDRVSITCKASQDVGTNIAWYQ QKPGRSPKVLIYSASTRHTGVPDRFTGSGSGTDFTLTIS NVQSEDLTDYFCQQYSSFPLTFGVGTKLELK | 41 |
| 3F1 | Heavy chain (with C80S mutation) | QVQLQQSDAELVKPGASVKISCKASGYTFTDHAIHWV KQKPEQGLDWIGYISPGNGDIKYNEKFKDKVTLTADKS SSTASMHLNSLTSEDSAVYFCKRSLLALDYWGQGTTLT VSS | 42 |

In some cases, antibodies or antigen binding fragments thereof of the invention may include one or more of the CDR amino acid sequences listed in the following Table. Residues indicated with an "X" may be absent or selected from any amino acid residues. In some cases, antibodies or antigen binding fragments thereof may include an amino acid sequence with from about 50% to about 99.9% sequence identity (e.g. from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 99.9%, from about 95% to about 99.9%, about 97%, about 97.5%, about 98%, about 98.5%, about 99%, about 99.5%, about 99.6%, about 99.7% or about 99.8%) with one or more of the CDR sequences listed in the following Table. In some cases, antibodies or antigen binding fragments thereof of the invention may include an amino acid sequence having one or more fragments of any of the sequences listed in the following Table.

TABLE 3

CDR sequences

| Antibody ID Number | CDR | Sequence | SEQ ID NO |
|---|---|---|---|
| 7A6-2A2 | CDR-H1 | GYTFTDHAIHWV | 43 |
| 2B2-2A7 | CDR-H1 | GYTFTDHAIHWV | 43 |
| 5G2-1B3 | CDR-H1 | GYTFTDHAIHWV | 43 |
| 4D9-2C11 | CDR-H1 | GYTFTDHAIHWV | 43 |
| 2F4-1E2 | CDR-H1 | GYTFTDHAIHWV | 43 |
| 2F4-1H8 | CDR-H1 | GYTFTDHAIHWV | 43 |
| 1A5-2C9 | CDR-H1 | GYTFTDHAIHWV | 43 |
| 1F6-1B7 (also sequence of 1F6-1C10) | CDR-H1 | GYTFTDHAIHWV | 43 |
| 2C2-2C5 | CDR-H1 | GYTFTDHAIHWV | 43 |
| 2G12-2B2 | CDR-H1 | GYTFTDHAIHWV | 43 |
| 10C9-2G7 | CDR-H1 | GYTFTDHAIHWV | 43 |
| 2C6-2F11 | CDR-H1 | GYTFSDHAIHWV | 44 |
| 7D4-2A2-2F2 | CDR-H1 | GYIFTDHAIHWV | 45 |
| 7D4-1H12-2B3 | CDR-H1 | GYIFTDHAIHWV | 45 |
| 7D3-2C10 | CDR-H1 | GYTFTDHAIHWV | 43 |
| 8C2-2D6 | CDR-H1 | GYTFTDHAIHWV | 43 |
| 9E5-1A8 | CDR-H1 | GYTFTDHAIHWV | 43 |
| 5E6-2E7 | CDR-H1 | GYTFTDHAIHWV | 43 |
| 9F11-1F7 | CDR-H1 | GYTFTDHAIHWV | 43 |
| 4G8-1E3 | CDR-H1 | GYIFTDHAIHWV | 45 |
| 10F4-2F2 | CDR-H1 | GYTFTDHAIHWV | 43 |
| 10F4-2A9 | CDR-H1 | GYTFTDHAIHWV | 43 |
| 6B11-2E3 | CDR-H1 | GYTFTDHAIHWV | 43 |
| 2B8-2F10 | CDR-H1 | GYTFTDHAIHWV | 43 |
| 7A5-2G12 | CDR-H1 | GYTFTDHAIHWV | 43 |
| 7A6-2A2 | CDR-H2 | FSPGNDDIKY | 46 |
| 2B2-2A7 | CDR-H2 | ISPGNGDIKY | 47 |
| 5G2-1B3 | CDR-H2 | FSPGNDDIKY | 46 |
| 4D9-2C11 | CDR-H2 | LSPGNDDIKY | 48 |
| 2F4-1E2 | CDR-H2 | ISPGNGDIKY | 47 |
| 2F4-1H8 | CDR-H2 | ISPGNGDIKY | 47 |
| 1A5-2C9 | CDR-H2 | VSPGNGDIKY | 49 |
| 1F6-1B7 (also sequence of 1F6-1C10) | CDR-H2 | ISPGNGDVKY | 50 |
| 2C2-2C5 | CDR-H2 | ISPGNGDIKY | 47 |
| 2G12-2B2 | CDR-H2 | FSPGNDDIKY | 46 |
| 10C9-2G7 | CDR-H2 | ISPGNDDIKY | 51 |
| 2C6-2F11 | CDR-H2 | ISPGNDDIKY | 51 |
| 7D4-2A2-2F2 | CDR-H2 | ISPGNGDIKY | 47 |
| 7D4-1H12-2B3 | CDR-H2 | ISPGNGDIKY | 47 |
| 7D3-2C10 | CDR-H2 | FSPGNDDIKY | 46 |
| 8C2-2D6 | CDR-H2 | ISPGNGDIKY | 47 |
| 9E5-1A8 | CDR-H2 | ISPGNDDIKY | 51 |
| 5E6-2E7 | CDR-H2 | ISPGNGDIKY | 47 |
| 9F11-1F7 | CDR-H2 | ISPGNGDIKY | 47 |
| 4G8-1E3 | CDR-H2 | ISPGNGDIKY | 47 |
| 10F4-2F2 | CDR-H2 | ISPGNGDIKY | 47 |
| 10F4-2A9 | CDR-H2 | ISPGNGDIKY | 47 |
| 6B11-2E3 | CDR-H2 | ISPGNDDIKY | 51 |
| 2B8-2F10 | CDR-H2 | ISPGNDDIKY | 51 |
| 7A5-2G12 | CDR-H2 | ISPGNDDIKY | 51 |
| 7A6-2A2 | CDR-H3 | SVGYALDY | 52 |
| 2B2-2A7 | CDR-H3 | KISYYGI | 53 |
| 5G2-1B3 | CDR-H3 | KRSYYGD | 54 |
| 4D9-2C11 | CDR-H3 | KRSIGGDH | 55 |
| 2F4-1E2 | CDR-H3 | QRQLGQGY | 56 |
| 2F4-1H8 | CDR-H3 | QRQLGQGY | 56 |
| 1A5-2C9 | CDR-H3 | KRSLIGDY | 57 |
| 1F6-1B7 (also sequence of 1F6-1C10) | CDR-H3 | KRSLSTPY | 58 |
| 2C2-2C5 | CDR-H3 | KRSITTPY | 59 |
| 2G12-2B2 | CDR-H3 | KRSLSTPY | 58 |
| 10C9-2G7 | CDR-H3 | KRSLSTPY | 58 |
| 2C6-2F11 | CDR-H3 | ERSMIGVY | 60 |
| 7D4-2A2-2F2 | CDR-H3 | KRSLSTPY | 58 |
| 7D4-1H12-2B3 | CDR-H3 | KRSLSTPY | 58 |

TABLE 3-continued

CDR sequences

| Antibody ID Number | CDR | Sequence | SEQ ID NO |
|---|---|---|---|
| 7D3-2C10 | CDR-H3 | KRSITTPY | 59 |
| 8C2-2D6 | CDR-H3 | KRSITTSY | 61 |
| 9E5-1A8 | CDR-H3 | KRSITTPY | 59 |
| 5E6-2E7 | CDR-H3 | KRSITTPY | 59 |
| 9F11-1F7 | CDR-H3 | KRSITTPY | 59 |
| 4G8-1E3 | CDR-H3 | KRSITTSY | 61 |
| 10F4-2F2 | CDR-H3 | KRSITTSY | 61 |
| 10F4-2A9 | CDR-H3 | KRSITTSY | 61 |
| 6B11-2E3 | CDR-H3 | KRSITTSY | 61 |
| 2B8-2F10 | CDR-H3 | KRSITTSY | 61 |
| 7A5-2G12 | CDR-H3 | KRSITTSY | 61 |
| 7A6-2A2 | CDR-L1 | ENVVTY | 62 |
| 2B2-2A7 | CDR-L1 | EDIYSN | 63 |
| 5G2-1B3 | CDR-L1 | ENIYSH | 64 |
| 4D9-2C11 | CDR-L1 | QNINVW | 65 |
| 2F4-1E2 | CDR-L1 | QSLVHSYGNTY | 66 |
| 2F4-1H8 | CDR-L1 | QSLVHSYGNTY | 66 |
| 1A5-2C9 | CDR-L1 | QNVGTA | 67 |
| 1F6-1B7 (also sequence of 1F6-1C10) | CDR-L1 | QSLLNSGNQKSY | 68 |
| 2C2-2C5 | CDR-L1 | QSVNNN | 69 |
| 2G12-2B2 | CDR-L1 | QSLLNRGNHKNY | 70 |
| 2C6-2F11 | CDR-L1 | QSLVQSNGNTY | 71 |
| 7D4-2A2-2F2 | CDR-L1 | ENVVNY | 72 |
| 7D4-1H12-2B3 | CDR-L1 | ENVVNY | 72 |
| 7D3-2C10 | CDR-L1 | QNINVW | 65 |
| 8C2-2D6 | CDR-L1 | ENVVTY | 62 |
| 5E6-2E7 | CDR-L1 | QSLLNSGKTKNY | 73 |
| 9F11-1F7 | CDR-L1 | QSLLNSGKTKNY | 73 |
| 4G8-1E3 | CDR-L1 | QHINFW | 74 |
| 10F4-2F2 | CDR-L1 | ENVVTY | 62 |
| 10F4-2A9 | CDR-L1 | ENVVTY | 62 |
| 6B11-2E3 | CDR-L1 | ENVVTY | 62 |
| 7A5-2G12 | CDR-L1 | ENVVIY | 75 |
| 1C11-2G9 | CDR-L1 | QSLLNSGNQKNY | 76 |
| 7A6-2A2 | CDR-L2 | GASNRYT | 77 |
| 2B2-2A7 | CDR-L2 | KATNLAD | 78 |
| 5G2-1B3 | CDR-L2 | GATNLAD | 79 |
| 4D9-2C11 | CDR-L2 | KASNLHT | 80 |
| 2F4-1E2 | CDR-L2 | KVSNRFS | 81 |
| 2F4-1H8 | CDR-L2 | KVSNRFS | 81 |
| 1A5-2C9 | CDR-L2 | SASNRYT | 82 |
| 1F6-1B7 (also sequence of 1F6-1C10) | CDR-L2 | WASTRDS | 83 |
| 2C2-2C5 | CDR-L2 | YASNRYT | 84 |
| 2G12-2B2 | CDR-L2 | WASTRES | 85 |
| 2C6-2F11 | CDR-L2 | KVSNRFC | 86 |
| 7D4-2A2-2F2 | CDR-L2 | GASNRYS | 87 |
| 7D4-1H12-2B3 | CDR-L2 | GASNRYS | 87 |
| 7D3-2C10 | CDR-L2 | KVSNLHT | 88 |
| 8C2-2D6 | CDR-L2 | GASNRYT | 77 |
| 5E6-2E7 | CDR-L2 | WASTRES | 85 |
| 9F11-1F7 | CDR-L2 | WASTRES | 85 |
| 4G8-1E3 | CDR-L2 | KASNLHT | 80 |
| 10F4-2F2 | CDR-L2 | GASNRYT | 77 |
| 10F4-2A9 | CDR-L2 | GASNRYT | 77 |
| 6B11-2E3 | CDR-L2 | GASNRYT | 77 |
| 7A5-2G12 | CDR-L2 | GASNRYT | 77 |
| 1C11-2G9 | CDR-L2 | WASTRES | 85 |
| 7A6-2A2 | CDR-L3 | GQGYSYPYT | 89 |
| 2B2-2A7 | CDR-L3 | QHFWGTPFT | 90 |
| 5G2-1B3 | CDR-L3 | QHFWGAPFT | 91 |
| 4D9-2C11 | CDR-L3 | QQGQSYPFT | 92 |
| 2F4-1E2 | CDR-L3 | SQNTHVPYT | 93 |
| 2F4-1H8 | CDR-L3 | SQNTHVPYT | 93 |
| 1A5-2C9 | CDR-L3 | QQYSSYRLT | 94 |
| 1F6-1B7 (also sequence of 1F6-1C10) | CDR-L3 | QSDYSYPYT | 95 |
| 2C2-2C5 | CDR-L3 | QQGYSSPWT | 96 |
| 2G12-2B2 | CDR-L3 | QNDYTYPYT | 97 |

TABLE 3-continued

CDR sequences

| Antibody ID Number | CDR | Sequence | SEQ ID NO |
|---|---|---|---|
| 2C6-2F11 | CDR-L3 | SQSTHAPLT | 98 |
| 7D4-2A2-2F2 | CDR-L3 | GSKWITSYPYT | 99 |
| 7D4-1H12-2B3 | CDR-L3 | GARVTSYPYT | 100 |
| 7D3-2C10 | CDR-L3 | QQDQSYPYT | 101 |
| 8C2-2D6 | CDR-L3 | GQGYSYPYT | 89 |
| 5E6-2E7 | CDR-L3 | KNDYSYPYT | 102 |
| 9F11-1F7 | CDR-L3 | KNDYSYPYT | 102 |
| 4G8-1E3 | CDR-L3 | QQDQSYPYM | 103 |
| 10F4-2F2 | CDR-L3 | GQGYSYPYT | 89 |
| 10F4-2A9 | CDR-L3 | GQGYSYPYT | 89 |
| 6B11-2E3 | CDR-L3 | GQGYSYPYT | 89 |
| 7A5-2G12 | CDR-L3 | GQGYSYPYT | 89 |
| 1C11-2G9 | CDR-L3 | QNDYSYPYT | 104 |

In some cases, antibodies of the present disclosure may include heavy chain variable domains having one or more CDR amino acid sequences from the CDR sequence groups listed in the following Table. Residues indicated with an "X" may be absent or selected from any amino acid residues. In some cases, antibodies or antigen binding fragments thereof may include an amino acid sequence with from about 50% to about 99.9% sequence identity (e.g. from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 99.9%, from about 95% to about 99.9%, about 97%, about 97.5%, about 98%, about 98.5%, about 99%, about 99.5%, about 99.6%, about 99.7% or about 99.8%) with one or more of the CDR sequences listed in the following Table. In some cases, antibodies may include an amino acid sequence having one or more fragments of any of the sequences listed in the following Table.

TABLE 4

VH CDR sequence groups

| Clone ID | CDR-H1 | SEQ ID NO | CDR-H2 | SEQ ID NO | CDR-H3 | SEQ ID NO |
|---|---|---|---|---|---|---|
| 8C2-2D6 | GYTFTDHAIH | 105 | YISPGNGDIKYNEKFKG | 107 | SITTSY | 114 |
| 4G8-1E3 | GYIFTDHAIH | 106 | YISPGNGDIKYNEKFKG | 107 | SITTSY | 114 |
| 2G12-2B2 | GYTFTDHAIH | 105 | YFSPGNDDIKYNEKFRG | 108 | SLSTPY | 115 |
| 5G2-1B3 | GYTFTDHAIH | 105 | YFSPGNDDIKYNEKFKV | 109 | SYYGD | 116 |
| 5E6-2E7 | GYTFTDHAIH | 105 | YISPGNGDIKYNEKFKV | 110 | SITTPY | 117 |
| 2C2-2C5 | GYTFTDHAIH | 105 | YISPGNGDIKYNEKFKG | 107 | SITTPY | 117 |
| 9F11-1F7 | GYTFTDHAIH | 105 | YISPGNGDIKYNEKFKV | 110 | SITTPY | 117 |
| 1F6-1C10 | GYTFTDHAIH | 105 | YISPGNGDVKYSERFKG | 137 | SLSTPY | 115 |
| 7D3-2C10 | GYTFTDHAIH | 105 | YFSPGNDDIKYSEKFKG | 138 | SITTPY | 117 |
| 7A5-2G12 | GYTFTDHAIH | 105 | YFSPGNDDIKYNEKFKG | 113 | SITTSY | 114 |
| 10F4-2A9 | GYTFTDHAIH | 105 | YISPGNGDIKYDEKFKG | 139 | SITTSY | 114 |
| 2F4-1E2 | GYTFTDHAIH | 105 | YISPGNGDIKYNEKFKG | 107 | QLGQGY | 140 |
| 2C6-2F11 | GYTFSDHAIH | 136 | YISPGNDDIKYNEKFKG | 113 | SMIGVY | 141 |
| 6B11-2E3 | GYTFTDHAIH | 105 | YISPGNDDIKYNEKFKG | 113 | SITTSY | 114 |
| 3F1 | GYTFTDHAIH | 105 | YISPGNGDIKYNEKFKD | 111 | SLLALDY | 118 |
| CC49 | GYTFTDHAIH | 105 | YFSPGNDDFKYNEKFKG | 112 | SLNMAY | 119 |
| B72.3 | GYTFTDHAIH | 105 | YISPGNDDIKYNEKFKG | 113 | SYYGH | 120 |
| Consensus | GYTFTDHAIH | 105 | YISPGNGDIKYNEKFKG | 107 | SITTSY | 114 |

In some cases, antibodies of the present disclosure may include light chain variable domains having one or more CDR amino acid sequences from the CDR sequence groups listed in the following Table. Residues indicated with an "X" may be absent or selected from any amino acid residues. In some cases, antibodies or antigen binding fragments thereof may include an amino acid sequence with from about 50% to about 99.9% sequence identity (e.g. from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 99.9%, from about 95% to about 99.9%, about 97%, about 97.5%, about 98%, about 98.5%, about 99%, about 99.5%, about 99.6%, about 99.7% or about 99.8%) with one or more of the CDR sequences listed in the following Table. In some cases, antibodies may include an amino acid sequence having one or more fragments of any of the sequences listed in the following Table.

TABLE 5

| | VL CDR sequence groups | | | | | |
|---|---|---|---|---|---|---|
| Clone ID | CDR-L1 | SEQ ID NO | CDR-L2 | SEQ ID NO | CDR-L3 | SEQ ID NO |
| 8C2-2D6 | KASENVVTYVS | 121 | GASNRYT | 77 | GQGYSYPYT | 89 |
| 8C2-2D6(V2) | HASQNINVWLS | 142 | KASNLYT | 147 | QHDQSYPTY | 148 |
| 4G8-1E3 | HASQHINFWLS | 122 | KASNLHT | 80 | QQDQSYPYM | 103 |
| 2G12-2B2 | KSSQSLLNRGNHKNYLT | 123 | WASTRES | 85 | QNDYTYPYT | 97 |
| 5G2-1B3 | RASENIYSHLA | 124 | GATNLAD | 79 | QHFWGAPFT | 91 |
| 5E6-2E7 | KSSQSLLNSGKTKNYLT | 125 | WASTRES | 85 | KNDYSYPYT | 102 |
| 2C2-2C5 | KASQSVNNNVA | 126 | YASNRYT | 84 | QQGYSSPWT | 96 |
| 1F6-1C10 | KSSQSLLNSGNQKSYLT | 143 | WASTRDS | 83 | QSDYSYPYT | 95 |
| 7D3-2C10 | HASQNINVWLS | 142 | KVSNLHT | 88 | QQDQSYPYT | 101 |
| 7A5-2G12 | KASENVVIYVS | 144 | GASNRYT | 77 | GQGYSYPYT | 89 |
| 10F4-2A9 | KASENVVTYVS | 121 | GASNRYT | 77 | GQGYSYPYT | 89 |
| 2F4-1E2 | RSSQSLVHSYGNTYLH | 145 | KVSNRFS | 81 | SQNTHVPYT | 93 |
| 2C6-2F11 | RFSQSLVQSNGNTYLQ | 146 | KVSNRFC | 86 | SQSTHAPLT | 98 |
| 6B11-2E3 | KASENVVTYVS | 121 | GASNRYT | 77 | GQGYSYPYT | 89 |
| 3F1 | KASQDVGTNIA | 127 | SASTRHT | 130 | QQYSSFPLT | 133 |
| CC49 | KSSQSLLYSGNQKNYLA | 128 | WASARES | 131 | QQYYSYPLT | 134 |
| B72.3 | RASENIYSNLA | 129 | AATNLAD | 132 | QHFWGTPYT | 135 |

In some cases, antibodies or antigen binding fragments of the invention may be encoded by a nucleotide sequence that includes one or more of the variable domain sequences listed in the following Table. Residues labeled "N" may be absent or selected from nucleotides A, C, G or T. In some cases, antibodies or antigen binding fragments thereof may be encoded by a nucleotide sequence that includes a sequence with from about 50% to about 99.9% sequence identity (e.g. from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 99.9%, from about 95% to about 99.9%, about 97%, about 97.5%, about 98%, about 98.5%, about 99%, about 99.5%, about 99.6%, about 99.7% or about 99.8%) with one or more of the variable domain sequences listed in the following Table. In some cases, antibodies or antigen binding fragments thereof of the invention may be encoded by a nucleotide sequence that includes one or more fragments of any of the sequences listed in the following Table.

TABLE 6

Variable domain nucleotide sequences

| Antibody ID Number | Variable chain | Sequence | SEQ ID NO |
|---|---|---|---|
| 7D3-2C10 | Heavy chain | CAGGTTCAGTTGCTGCAGTATGACGCTGAGTTGGTGAAACCTGGGGGGTCAGTGAAGATATCGTGCAAGGCCTCTGGCTACACCTTCACTGACCATGCTATTCACTGGGTGAAGCAGAAGCCTGAACAGGGCCTGGAATGGATTGGATATTTTCTCCCGGAAATGATGATATTAAGTACAGTGAGAAGTTCAAGGGCAAGGCCACACTGACTGCAGACAAGTCCTCCAGCACTGCCTACATGCAGCTCAACAGCCTGACATCTGAGGATTCTGCAGTGTATTTCTGTAAAAGATCCATTACTACGCCTTACTGGGGCCAAGGGACTCTGGTCACTGTCTCTGCA | 149 |
| 7D3-2C10 | Light chain | GACATCCAGATGAACCAGTCTCCATCCAGTCTGTCTGCATCCCTTGGAGACACAATTACCATCACTTGCCATGCCAGTCAGAACATTAATGTTTGGTTAAGCTGGTACCAGCAGAAACCAGGAAATATTCCTAAACTATTGATCTATAAGGTTTCCAACTTGCACACAGGCGTCCCATCAAGGTTTAGTGGCAGTGGATCTGGAACAGGTTTCACATTAACCATCAGCAGCCTGCAGCCTGAAGACATTGCCACTTACTACTGTCAACAGGATCAAAGTTATCCGTACACGTTCGGAGGGGGGACCAAGCTGAAAAAAA | 150 |
| 7A5-2G12 | Heavy chain | CAGGTTCAGCTGCAGCAGTCTGACGCTGAGTTGGTGAAACCTGGGGCTTCAGTGAAGATATCCTGCAAGGCCTCTGGCTACACCTTCACTGACCATGCTATTCACTGGGTGAAGCAGAAGCCTGAACAGGGCCTGGAATGGATTGGATATATTTCTCCCGGAAATGATGATATTAAGTACAATGAGAAGTTCAAGGGCAAGGCCACACTGACTGCAGACAAATCCTCCAGCACTGCCTACATGCAGCTCAACAGCCTGACATCTGAGGATTCTGCAGTGTATTTCTGTAAAAGATCCATTACTACGTCTTACTGGGGCCAAGGGACTCTGGTCACTGTCTCTGCA | 151 |
| 7A5-2G12 | Light chain | AACATTGTAATGACCCAATCTCCCAAATCCATGTCCATGTCAGTAGGAGAGAGGGTCACCTTGACCTGCAAGGCCAGTGAGAATGTGGTTATTTATGTTTCCTGGTATCAACAGAAACCAGAGCAGTCTCCTAAACTGCTGATATACGGGGCATCCAACCGGTACACTGGGGTCCCCGATCGCTTCACAGGCAGTGGATCTGCAACAGATTTCACTCTGACCATCAGCAGTGTGCAGGCTGAAGACCTTGCAGATTATCACTGTGGACAGGGTTACAGCTATCCGTACACGTTCGGAGGGGGGACCAAGCTGGAAATAAAACG | 152 |
| 1A5-2C9 | Heavy chain | CAGGTTCAGTTGCAGCAGTCTGACGCTGAGTTGGTGAAACCTGGGGCTTCAGTGAAGATATCCTGCAAGGCTTCTGGCTACACCTTCACTGACCATGCCATTCATTGGGTGAAGCAGAAGCCTGAACAGGGCCTGGAATGGATTGGATATGTTTCTCCCGGAAATGGTGATATTAAGTACAATGAGAAGTTCAAGGGCAAGGCCACACTGACTGCAGACAAATCCTCCAGCACTGCCTACATGCAGCTCAACAGCCTGACATCGGAGGATTCTGCAGTGTATTTCTGTAAAAGATCTTTAATTGGAGACTATTGGGGCCAAGGCACCACTCTCACAGTCTCCTCA | 153 |
| 1A5-2C9 | Light chain | GACATTGTGATGACCCAGTCTCAAAAATTCATGTCCTCATCAGTAGGAGACAGGGTCACCATCACCTGCAAGGCCAGTCAGAATGTGGGTACTGCTGTAGCCTGGTATCAACAGAAACCAGGACAATCTCCTAAATTTCTGATTTACTCGGCATCCAATCGGTACACTGGAGTCCCTGATCGCTTCACAGGCAGTGGATCTGGGACAGATTTCACTCTCACGATCAGCAATATGCAGTCTGAAGACCTGGCA | 154 |

TABLE 6-continued

Variable domain nucleotide sequences

| Antibody ID Number | Variable chain | Sequence | SEQ ID NO |
|---|---|---|---|
| | | GATTATTTCTGCCAGCAATATAGCAGCTATCGTCTG ACGTTCGGTGGAGGCACCAAGCTGGAAATCAAAC | |
| 4D9-2C11 | Heavy chain | CAGGTTCAGCTGCAGCAGTCTGACGCTGAATTGGTG AAACCTGGGGCTTCAGTGAAGATATCCTGCAAGGCT TCTGGCTACACCTTCACTGACCATGCTATTCACTGG GTGAAGCAGAAGCCTGAACAGGGCCTGGAATGGAT TGGATATCTTTCTCCCGGAAATGATGATATTAAGTA CAGTGAGAAGTTCAAGGACAAGGCCACACTGACTG CAGACAAATCCTCCAGCACTGCCTACATGCAGCTCA ACAGCCTGACATCTGAGGATTCTGCAGTGTATTTCT GTAAAAGATCCATAGGGGGGGACCACTGGGGCCAA GGCACCACTCTCACAGTCTCCTCA | 155 |
| 4D9-2C11 | Light chain | GACATCCAGATGAACCAGTCTCCATCCAGTCTGTCT GCATCCCTTGGAGACACAATTACCATCACTTGCCAT GCCAGTCAGAACATTAATGTTTGGTTAAACTGGTAC CAGCAGAAACCAGGAAATATTCCTAAACTATTGATC TATAAGGCTTCCAACTTGCACACAGGCGTCCCATCA AGGTTTAGTGGCAGTGGATCTGGAACAGGTTTCACA TTAACCATCGGCAGCCTGCAGCCTGAAGACATTGCC ACTTACTACTGTCAACAGGGTCAAAGTTATCCGTTC ACGTTCGGAGGGGGGACCAAGCTGGAAATAAAACG | 156 |
| 2F4-1E2 | Heavy chain | CAGGTTCAGCTGCAGCAGTCTGACGCTGAGTTGGTG AAACCTGGGGCTTCAGTGAAGATATCCTGCAAGGCT TCTGGCTACACCTTCACTGACCATGCTATTCACTGG GTGAAACAGAAGCCTGAACAGGGCCTGGAATGGAT TGGATATATTTCTCCCGGAAATGGTGATATTAAGTA TAATGAGAAGTTCAAGGGCAAGGCCACACTGACTG CAGACAAATCCTCCAGCACTGCCTACATGCAGCTCA ACAGCCTGACATCTGAGGATTCTGCAGTGTATTTCT GTCAAAGACAACTGGGACAAGGCTACTGGGGCCAA GGCACCACTCTCACAGTCTCCTCA | 157 |
| 2F4-1E2 | Light chain | GATGTTGTGATGACCCAAACTCCACTCTCCCTGCCT GTCAGTCTTGGAGATCAAGCCTCCATCTCTTGCAGA TCTAGTCAGAGCCTTGTACACAGTTATGGAAACACC TATTTACATTGGTACCTGCAGAAGCCAGGCCAGTCT CCAAAGCTCCTGATTTACAAAGTTTCCAACCGATTT TCTGGGGTCCCAGACAGGTTCAGTGGCAGTGGATCA GGGACAGATTTCACACTCAAGATCAGCAGAGTGGA GGCTGAGGATCTGGGAGTTTATTTCTGCTCTCAAAA TACACATGTTCCGTACACGTTCGGAGGGGGGACCAA GCTGGAAATAAAACG | 158 |
| 2F4-1H8 | Heavy chain | CAGGTTCAGCTGCAGCAGTCTGACGCTGAGTTGGTG AAACCTGGGGCTTCAGTGAAGATATCCTGCAAGGCT TCTGGCTACACCTTCACTGACCATGCTATTCACTGG GTGAAACAGAAGCCTGAACAGGGCCTGGAATGGAT TGGATATATTTCTCCCGGAAATGGTGATATTAAGTA TAATGAGAAGTTCAAGGGCAAGGCCACACTGACTG CAGACAAATCCTCCAGCACTGCCTACATGCAGCTCA ACAGCCTGACATCTGAGGATTCTGCAGTGTATTTCT GTCAAAGACAACTGGGACAAGGCTACTGGGGCCAA GGCACCACTCTCACAGTCTCCTCA | 157 |
| 2F4-1H8 | Light chain | GATGTTGTGATGACCCAAACTCCACTCTCCCTGCCT GTCAGTCTTGGAGATCAAGCCTCCATCTCTTGCAGA TCTAGTCAGAGCCTTGTACACAGTTATGGAAACACC TATTTACATTGGTACCTGCAGAAGCCAGGCCAGTCT CCAAAGCTCCTGATTTACAAAGTTTCCAACCGATTT TCTGGGGTCCCAGACAGGTTCAGTGGCAGTGGATCA GGGACAGATTTCACACTCAAGATCAGCAGAGTGGA GGCTGAGGATCTGGGAGTTTATTTCTGCTCTCAAAA TACACATGTTCCGTACACGTTCGGAGGGGGGACCAA GCTGGAAATAAAACG | 158 |
| 2C6-2F11 | Heavy chain | CAGGTTCAGCTGCAGCAGTCTGACGCTGAGTTGGGG AAACCTGGGGCTTCAGTGAAGATATCCTGCAAGGCT TCTGGCTACACCTTCAGTGACCATGCTATTCACTGG GTGAAGCAGAAGCCTGAACAGGGCCTGGAATGGAT TGGATATATCTCTCCCGGAAACGATGATATTAAGTA CAATGAGAAGTTCAAGGGCAAGGCCACACTGACTG | 159 |

TABLE 6-continued

Variable domain nucleotide sequences

| Antibody ID Number | Variable chain | Sequence | SEQ ID NO |
|---|---|---|---|
| | | CAGACAAATCCTCCAGCACTGCCTACATGCAGCTCA ACAGCCTGACATCTGAGGATTCTGCAGTGTATTTCT GTGAAAGATCGATGATTGGGGTTTACTGGGGCCAAG GGACTCTGGTCACTGTCTCTGCA | |
| 2C6-2F11 | Light chain | GATGTTGTGATGACCCAAACTCCACTCTCCCTGACT GTCAGTCTTGGCGATCAAGCCTCCATCTCTTGCAGA TTTAGTCAGAGCCTTGTACAAAGTAATGGAAATACC TATTTACAGTGGTATCTGCAGAAGCCAGGCCAGTCT CCAAAGCTCCTGATTTACAAAGTCTCCAACCGATTT TGTGGGGTCCCAGACAGGTTCAGTGGCAGTGGATCA GGGACAGATTTCACACTCAAGATCAGCAGAGTGGA GGCTGAGGATCTGGGAGTTTATTTCTGCTCTCAAAG TACACATGCTCCGCTCACGTTCGGTGCTGGGACCAA GCTGGAGCTGAAAC | 160 |
| 2B2-2A7 | Heavy chain | CAGGTTCAGCTGCAGCAGTCTGACGCTGAGTTGGTG AAACCTGGGGCTTCAGTGAAGATATCCTGCAAGACT TCTGGCTACACCTTCACTGACCATGCAATTCACTGG GTGAAGCAGAAGCCTGAACAGGGCCTGGAATGGAT TGGATATATTTCTCCCGGAAATGGTGATATTAAGTA CAATGAGAAGTTCAAGGGCAAGGCCACCCTGACTG CAGACAAATCCTCCAGCACTGCCTATATGCAGCTCA GCAGCCTGACACCTGAGGATTCTGCAGTGTATTTCT GTAAAATATCTTACTACGGTATTTGGGGCCAAGGCA CCACTCTCACAGTCTCCTCA | 161 |
| 2B2-2A7 | Light chain | GACATCCAGATGACTCAGTCTCCAGCCTCCCTATCT GTATCTGTGGGAGAGTCTGTCACCATCACATGTCGA CTAAGTGAAGATATTTACAGTAATTTAGCATGGTTT CAGCAGAGACCGGGAAAATCCTCAGCTCCTGGTT TATAAAGCAACAAACTTAGCAGACGGTGTGCCATCA AGGTTCAGTGGCAGTGGATCAGGCACACAGTATTCC CTCAAGATCAACAGCCTGCAGTCTGAAGATTTTGGG ACTTATTACTGTCAACATTTTTGGGGTACTCCATTCA CGTTCGGCTCGGGGACCAAGGTGGAAATAAAAC | 162 |
| 5G2-1B3 | Heavy chain | CAGGTTCAGCTGCAGCAGTCTGACGCTGAGTTGGTG AAACCTGGGGCTTCAGTGAAGATATCCTGCAAGGCT TCTGGCTACACCTTCACTGACCATGCTATTCACTGG GTGAAGCAGAAGCCTGAACAGGGCCTGGAATGGAT TGGATATTTTTCTCCCGGAAATGATGATATTAAGTA TAATGAGAAGTTCAAGGTCAAGGCCACACTGACTGC AGACAAATCCTCCAGCACTGCCTACATGCAACTCAC CAGCCTGACATCTGAAGATTCTGCAGTGTATTTCTG TAAAAGATCTTACTACGGTGATTGGGGCCAAGGCAC CACTCTCACAGTCTCCTCA | 163 |
| 5G2-1B3 | Light chain | GACATCCAGATGACTCAGTCTCCAGCCTCCCTATCT GTTTCTGTGGGAGAAACTGTCACCATCACATGTCGA GCAAGTGAGAATATTTACAGTCATTTAGCATGGTAT CAACAGAAACAGGGAAAATCTCCTCAACTCCTGGTC TATGGTGCAACTAACTTAGCAGATGGTGTGCCATCA AGGTTCAGTGGCAGTGGATCAGGCACACAGTTTTCC CTCAAGATCCACAGCCTGCAGTCTGAAGATTTTGGG AGTTATTACTGTCAACATTTTTGGGGTGCTCCATTCA CGTTCGGCTCGGGGACAAAGTTGGAAATAAAAC | 164 |
| 7A6-2A2 | Heavy chain | CAAATTCAGCTGCAGCAGTCTGACGCTGAGTTGGTG AAACCTGGGACTTCAGTGAAGATGTCCTGCAAGGCT TCTGGCTACACCTTCACTGACCATGCTATTCACTGG GTGAAGCAGAAGCCTGAACAGGGCCTGGAATGGAT TGGATATTTTTCTCCCGGAAATGATGATATTAAGTA TAATGTGAAGTTCAAGGGCAAGGCCACACTGACTGC AGACAAATCCTCCAGCACTGCCTACATGCAGCTCAA CAGCCTGACATCTGAAGATTCTGCAGTGTATTTCTG TTCGGTGGGATACGCCCTTGACTACTGGGGCCTAGG CACCACTCTCACAGTCTCCTCA | 165 |
| 7A6-2A2 | Light chain | AACATTGTAATGACCCAATCTCCCAAATCCATGTCC ATGTCAGTAGGAGAGAGGGTCACCTTGACCTGCAA GGCCAGTGAGAATGTGGTTACTTATGTTTCCTGGTA TCAACAGAAACCAGAGCAGTCTCCTAAACTGCTGAT ATACGGGGCATCCAACCGGTACACTGGGGTCCCCGA | 166 |

TABLE 6-continued

Variable domain nucleotide sequences

| Antibody ID Number | Variable chain | Sequence | SEQ ID NO |
|---|---|---|---|
| | | TCGCTTCACAGGCAGTGGATCTGCAACAGATTTCAC TCTGACCATCAGCAGTGTGCAGGCTGAAGACCTTGC AGATTATCACTGTGGACAGGGTTACAGCTATCCGTA CACGTTCGGAGGGGGACCAAGCTGGAAATAAAACG | |
| 10C9-2G7 | Heavy chain | CAGGTTCAGCTGCAACAGTCTGACGCTGAGTTGGTG AAACCTGGGACTACAGTGAAGATATCCTGCAAGGCT TCTGGCTACACTTTCACTGACCATGCTATTCACTGGG TGAAGGAGAAGCCTGAACAGGGCCTGGAATGGATC GGATATATTTCTCCCGGAAATGATGATATTAAGTAC AGTGAGAAGTTCAAGGGCAAGGCCACACTGACTGC AGACAAATCCTCCAGCACTGCTTACATGCAGCTCAA CAGCCTGACATCTGATGATTCTGCAGTGTATTTCTGT AAAAGATCGCTTAGTACGCCTTACTGGGGCCAAGGG ACTCTGGTCACTGTCTCTGCA | 167 |
| 10C9-2G7 | Light chain | TTTTTAATACGACTCCCTATAGGGCAAGCAGTGGTA TCAATGCAGATTACAAGGGGGAAAGGCATCAGACC AGCATGGGCATCAAGGTGGAATCACAGACTCTGGTC TTCATATCCATACTGTTTGGGTTATATGGAGCTGATG GGAACACATTAATGACCCAATCTCCCACATCCATGT ACATGTCAGTAGGAGAGAGGGTCACCTTGACTTGCA AGGCCAGTGAGAATGAGATTAATTATGTTTCCTGGT ATCAACAGAAACCAGAGCAGTCTCCTAAACTGTTGA TATACGGGGCATCCAACCGGTACTCTGGGGTCCCCG ATCGCTTCACAGGCAGTGGATCTGCAACAGATTTCA CTCTGACCATCAGCAGTGTGCAGGCTGAAGACCTTG CAGATTATCCCTGTGGAGCAAGGGATTAACTAGCTA TCCGTACACGTTCGGAGGGGGGACCAAGCTGGAAA TAAAACGGGC | 168 |
| 1C11-2G9 | Heavy chain | Unknown | |
| 1C11-2G9 | Light chain | GACATTGTGATGACACAGTCTCCATCCTCCCTGACT GTGACAGCAGGAGAAGGTCACTATGAGCTGCAG GTCCAGTCAGAGTCTGTTAAACAGTGGAAATCAAAA GAACTACTTGACCTGGTACCAGCAGAAACCAGGGC AGCCTCCTAAACTGTTGATCTACTGGGCATCCACTA GGGAATCTGGGGTCCCTGATCGCTTCACAGGCAGTG GATCTGGAACAGATTTCACTCTCACCATCAGCAGTG TGCAGGCTGAAGACCTGGCAGTTTATTACTGTCAGA ATGATTATAGTTATCCGTACACGTTCGGAGGGGGGA CCAAGCTGGAAATAAAACG | 169 |
| 1F6-1B7 (also sequence of 1F6-1C10) | Heavy chain | CAGGTTCAGCTGCAGCAGTCTGACGCTGAGTTGGTG AAACCTGGGGCTTCAGTGAAGATATCCTGCAAGGCT TCTGGCTACACCTTCACTGACCATGCTATTCACTGG GTGATGCAGATGCCTGAACAGGGCCTGGAATGGATT GGATATATTTCTCCCGGAAATGGTGATGTTAAGTAC AGTGAGAGGTTCAAGGGCAGGGCCACACTGACTGC AGACAAATCCTCCAGCTCTGCCTACATGCAGCTCAA CAGCCTGACATCTGAGGATTCTGCAGTTTATTTCTGT AAAAGATCGCTTAGTACGCCTTACTGGGGCCAAGGG ACTCTGGTCACTGTCTCTG | 170 |
| 1F6-1B7 (also sequence of 1F6-1C10) | Light chain | GACATTGTGATGACACAGTCTCCATCCTCCCTGACT GTGACAGCAGGAGAGAGGGTCACTATGAGCTGCAA GTCCAGTCAGAGTCTGTTAAACAGTGGAAATCAAAA GAGCTACTTGACCTGGTACCAGCAGAAACCAGGGC AGCCTCCTAAACTGTTGATCTCCTGGGCATCCACTA GGGATTCTGGGGTCCCTGATCGCTTCACAGGCAGTG GATCTGGAACAGATTTCACTCTCACCATCAGCAGTG TGCAGGCTGAAGACCTGGCAGTTTATTACTGTCAGA GTGATTATAGTTATCCGTACACGTTCGGAGGGGGGA CCAAGCTGGAAATAAAACG | 171 |
| 2G12-2B2 | Heavy chain | CAGGTTCAGCTGCAGCAGTCTGACGNTGAGTTGGTG AAACCGGGGGCTTCAGTGAAGATATCCTGTAAGGCT TCTGGCTACACCTTCACTGACCATGCTATTCACTGG GTGAAGCAGAAGCCTGAACAGGGCCTGGAATGGAT TGGATATTTTTCTCCCGGAAATGATGATATTAAGTA CAATGAGAAGTTTAGGGGCAAGGCCACACTGACTG CAGACAAATCCTCCAGCACTGCCTACATGCAGCTCA | 172 |

TABLE 6-continued

Variable domain nucleotide sequences

| Antibody ID Number | Variable chain | Sequence | SEQ ID NO |
|---|---|---|---|
| | | ACAGCCTGTCATCTGATGATTCTGCAGTGTATTTCTG TAAAAGATCGCTTAGTACGCCTTACTGGGGCCAAGG GACTCTGGNCACTGTCTCTGCA | |
| 2G12-2B2 | Light chain | GACATTGTGATGACACAGTCTCCATCCTCCCTGACT GTGACAGCAGGAGAGAAAGTCACTATGAGCTGCAA GTCCAGTCAGAGTCTGTTAAACCGTGGAAATCATAA GAACTACTTGACCTGGTACCGGCAGAAACCAGGGCT GCCTCCTAAACTGTTGATTTACTGGGCATCCACTAG GGAATCTGGGGTCCCTGATCGCTTCACAGGCAGTGG ATCTGGAACAGATTTCGCTCTCACCATCAGCAGTGT TCAGGCTGAAGACCTGGCAGTTTATTACTGTCAGAA TGATTATACTTATCCGTACACGTTCGGAGGGGGGAC CAAGCTGGAGATAAAACG | 173 |
| 5E6-2E7 | Heavy chain | CAGGTTCAGCTGCAGCAGTCTGACGCTGAGTTGGTG AAACCTGGGGCTTCAATGAAGATTTCCTGCAAGGCT TCTGGCTACACCTTCACTGACCATGCTATTCACTGG GTGAAGCAGAAGCCTGAACAGGGCCTGGAATGGAT TGGATATATTTCTCCCGGAAATGGTGATATTAAGTA CAATGAGAAGTTCAAGGTCAAGGCCACACTGACTG CAGACAAATCCTCCAGCACTGCCTACATGCAGCTCA ACAGCCTGACATCTGAGGATTCTGCAGTGTATTTCT GTAAAAGATCGATTACTACGCCTTACTGGGGCCAAG GGACTCTGGTCACTGTCTCTGCA | 174 |
| 5E6-2E7 | Light chain | GACATTGTGATGACACAGTCTCCATCTCCCTGACT GTGACAGCAGGAGAGAAGGTCACTATGAGCTGCAA GTCCAGTCAGAGTCTGTTAAACAGTGGAAAACAAA AGAACTACTTGACGTGGTACCAGCAGAAACCAGGG CAGCCTCCTAAACTGTTGATCTACTGGGCATCCACT AGGGAATCTGGGGTCCCTGATCGCTTCACAGGCAGT GGATCTGGAACAGATTTCACTCTCACCATCAGCAGT GTGCAGGCTGAAGACCTGGCAGTTTATTACTGTAAG AATGATTATAGTTATCCGTACACGTTCGGAGGGGGG ACCAAGCTGGAAATAAAACG | 175 |
| 9E5-1A8 | Heavy chain | CAGGTTCAGCTGCAGCAGTCTGACGCTGAATTGGTG AAGCCTGGGGCTTCAGTGAAGATATCCTGCAAGACT TCTGGCTACACCTTCACTGACCATGCTATTCACTGG GTGAAGCAGAAGCCTGAACAGGGCCTGGAATGGAT TGGATATATCTCTCCCGGAAATGATGATATTAAGTA CACTGAGAAGTTCAAGGGCAAGGTCACACTGACTG CAGACAAATCCTCCAGCACTGCCTACATGCAGCTCA ACAGCCTGACATCTGAGGATTCTGCAGTCTATTTCT GTAAAAGATCGATTACTACGCCTTACTGGGGCCAAG GGACTCTGGTCACTGTCTCTGCA | 176 |
| 9E5-1A8 | Light chain | TTTTTATACGCCACTTTCTAATACGCCTCACTATAGG GCAAGCAGTGGTATCAACGCAGATTACAAAGGGGA AAGGAATCAGACCGACTCGCGCATCAAGATGGAAT CACAGACTCTGGTCTTCATATCCAGTACGCTCGGGG ACTATGGAGNGGAACAGTACATTTTAATGACCCAAT GTCCCAAAGGCAAGAACATGTCAGTAGGAGAGAGG GTCACTCAGAGTGCAAGGCCAGGAGAAATCAAAAC ACTTATGTTTCCTGGTATCAACAGAAACCAGAGCAN NCTNTAAAATGNNGATTACGGGGCATCCAACCGGG AATCTGGGGTCNCCGATCGCTTCACAGGCAGTGGAT CTGGAACAGATTTCACTCTCACCATCAGCAGTGTGC AGGCTGAAGACCNGGCAGTNTTCACTGTGGACAGG GNTACAGTTATCCGTACACGTTCGGAGGGGGGACCA AGCTGAAAAAAACGGGC | 177 |
| 9F11-1F7 | Heavy chain | CAGGTTCAGCTGCAGCAGTCTGACGCTGAGTTGGTG AAACCTGGGGCTTCAATGAAGATTTCCTGCAAGGCT TCTGGCTACACCTTCACTGACCATGCTATTCACTGG GTGAAGCAGAAGCCTGAACAGGGCCTGGAATGGAT TGGATATATTTCTCCCGGAAATGGTGATATTAAGTA CAATGAGAAGTTCAAGGTCAAGGCCACACTGACTG CAGACAAATCCTCCAGCACTGCCTACATGCAGCTCA ACAGCCTGACATCTGAGGATTCTGCAGTGTATTTCT GTAAAAGATCGATTACTACGCCTTACTGGGGCCAAG GGACTCTGGTCACTGTCTCTGCA | 174 |

TABLE 6-continued

Variable domain nucleotide sequences

| Antibody ID Number | Variable chain | Sequence | SEQ ID NO |
|---|---|---|---|
| 9F11-1F7 | Light chain | GACATTGTGATGACACAGTCTCCATCCTCCCTGACT GTGACAGCAGGAGAAGGTCACTATGAGCTGCAA GTCCAGTCAGAGTCTGTTAAACAGTGGAAAAACAA AGAACTACTTGACGTGGTACCAGCAGAAACCAGGG CAGCCTCCTAAACTGTTGATCTACTGGGCATCCACT AGGGAATCTGGGGTCCCTGATCGCTTCACAGGCAGT GGATCTGGAACAGATTTCACTCTCACCATCAGCAGT GTGCAGGCTGAAGACCTGGCAGTTTATTACTGTAAG AATGATTATAGTTATCCGTACACGTTCGGAGGGGGG ACCAAGCTGGAAATAAAACG | 175 |
| 10F4-2F2 | Heavy chain | CAGGTTCAGCTGCAGCAGTCTGACGCTGAGTTGGTG AAACCTGGGGCTTCAGTGAAGATATCCTGCAAGGCT TCTGGCTACACCTTCACTGACCATGCTATTCACTGG GTGAAGCAGAAGCCTGAACAGGGCCTGGAATGGAT TGGATATATTTCTCCCGGAAATGGTGATATTAAGTA CGATGAGAAGTTTAAGGGCAAGGCCACACTGACTG CAGACAAATCCTCCTCCACTGCCTACATGCAGCTCA ACAGCCTGACATCTGAAGATTCTGCAGTGTATTTCT GTAAAAGATCGATTACTACCTCTTACTGGGGCCAAG GGACTCTGGTCACTGTCTCTGCA | 178 |
| 10F4-2F2 | Light chain | AACATTGTAATGACCCAATCTCCCAAATCCATGTCC ATGTCAGTAGGAGAGAGGGTCACCTTGACCTGCAA GGCCAGTGAGAATGTGGTTACTTATGTTTCCTGGTA TCAACAGAAACCAGAGCAGTCTCCTAAACTGCTGAT ATACGGGGCATCCAACCGGTACACTGGGGTCCCCGA TCGCTTCACAGGCAGTGGATCTGCAACAGATTTCAC TCTGACCATCAGCAGTGTGCAGGCTGAAGACCTTGC AGATTATCACTGTGGACAGGGTTACAGCTATCCGTA CACGTTCGGAGGGGGGACCAAGCTGGAAATAAAACG | 166 |
| 2B8-2F10 | Heavy chain | CAGGTTCAGCTGCAGCAGTCTGACGCTGAGTTGGTG AAACCTGGGGCTTCAGTGAAGATATCCTGCAAGGCT TCTGGCTACACCTTCACTGACCATGCTATTCACTGG GTGAAGCAGAAGCCTGAACAGGGCCTGGAATGGAT TGGATATATTTCTCCCGGAAATGATGATATTAAGTA CAATGAGAAGTTCAAGGGCAAGGCCACACTGACTG CAGACAAGTCCTCCAGCACTGCCTACATGCAGCTCA ACAGCCTGACATCTGAGGATTCTGCAGTGTTTTTCT GTAAAAGATCGATTACTACCTCTTACTGGGGCCAAG GGACTCTGGTCACTGTCTCTGCA | 179 |
| 2B8-2F10 | Light chain | TTNATAGGACTCAATATAGGGCAAGCAGTGGTATTA ACGCCGAGTACATGGGGAGGGCAAGGGCAGAAAGT CACTTTCAGTGAGGATACACCATCAGCATGAGGGTC CTTGTTGAGCTCCTGGGGGGCTGGTGTTNTGCTTTT TAGGTGTGAGATGTGACATCCAGATGAACCAGTCTC CATCCAGTCTGTNTGCATCCTTTGGAGACACAATTA CCATCATTTGCCATTCCAGTCAGAACATTAATGTTTG GTTAAGATGGTACCAGCAGAAACCAGGAAATATTC CTAAAATATTGATATATAAGGGTTCCAACTTGTACA CAGGCGTCCCATCAAGGTTTAGTGGCAGTGGATTTG GAACAGGTTTCACATTAACCATCAGCAGCGTGCAGC GGGAAGACATTGCCACTTACTACTGTCAACAGGATC AAAGTTATCCGTACACGTTCGGAGGGGGGACCAAG CTGAAATAAAACGGGC | 180 |
| 4G8-1E3 | Heavy chain | CAGGTTCAGCTGCAGCAGTCTGACGCCGAGTTGGTG AAACCTGGGGCTTCAGTGAAGATATCCTGCAAGGCT TCTGGCTACATCTTCACTGACCATGCTATTCACTGGG TGAAGCAGAAGCCTGAACAGGGCCTGGAATGGATT GGATATATTTCTCCCGGAAATGGTGATATTAAGTAC AATGAGAAGTTCAAGGGCAAGGCCACACTGACTGC AGACAAATCCTCCAGCACTGCCTACATGCATCTCAA CAGCCTGACATCTGAGGATTCTGCAGTGTATTTCTG TAAAAGATCGATTACTACCTCTTACTGGGGCCAAGG GACTCTGGTCACTGTCTCTGCA | 181 |
| 4G8-1E3 | Light chain | GACATCCAGATGAACCAGTCCCCATCCAGTCTGTCT GCATCCCTTGGAGACACAATTACCATCACTTGCCAT GCCAGTCAGCACATTAATTTTTGGTTAAGCTGGTAC CAGCAGAAACCAGGAAATATTCCTAAACTCTTGATC TATAAGGCTTCCAACTTGCACACAGGCGTCCCATCA | 182 |

TABLE 6-continued

Variable domain nucleotide sequences

| Antibody ID Number | Variable chain | Sequence | SEQ ID NO |
|---|---|---|---|
| | | AGGTTTAGTGGCAGTGGATCTGGAACAGGTTTCACA TTAACCATCAGCAGCCTGCTGCCTGAAGACGTTGCC ACTTACTACTGTCAACAGGATCAAAGTTATCCGTAT ATGTTCGGAGGGGGGACCAAGCTGGAAATAAAACG | |
| 6B11-2E3 | Heavy chain | CAGGTTCAGCTGCAGCAGTCTGACGCTGAGTTGGTG AAACCTGGGGCTTCAGTGAAGATATCCTGCAAGGCT TCTGGCTACACCTTCACTGACCATGCTATTCACTGG GTGAAGCAGAAGCCTGAACAGGGCCTGGAATGGAT TGGATATATTTCTCCCGGAAATGATGATATTAAGTA CAATGAGAAGTTTAAGGGCAAGGCCACACTGACTG CAGACAAATCCTCCAGCACTGCCTACATGCTGCTCA ACAGCCTGACATCTGAGGATTCTGCAGTGTATTTCT GTAAAAGATCGATTACTACCTCTTACTGGGGCCAAG GGACTCTGGTCACTGTCTCTGCA | 183 |
| 6B11-2E3 | Light chain | AACATTGTAATGACCCAATCTCCCAAATCCATGTCC ATGTCAGTAGGAGAGAGGGTCACCTTGACCTGCAA GGCCAGTGAGAATGTGGTTACTTATGTTTCCTGGTA TCAACAGAAACCAGAGCAGTCTCCTAAACTGCTGAT ATACGGGGCATCCAACCGGTACACTGGGGTCCCCGA TCGCTTCACAGGCAGTGGATCTGCAACAGATTTCAC TTTGACCATCAGCAGTGTGCAGGCTGAAGACCTTGC AGATTATCACTGTGGACAGGGTTACAGCTATCCGTA CACGTTCGGAGGGGGGACCAAGCTGGAAATAAAACG | 184 |
| 8C2-2D6 | Heavy chain | CAGGTTCAACTGCAGCAGTCTGACGCTGAGTTGGTG AAACCTGGGGCTTCAGTGAAGATATCCTGCAAGGCT TCTGGCTACACCTTCACTGACCATGCTATTCACTGG GTGAAGCAGAAGCCTGAACAGGGCCTGGAATGGAT TGGATATATTTCTCCCGGAAATGGTGATATTAAGTA CAATGAGAAGTTCAAGGGTAAGGCCACACTGACTG CAGACACTTCCTCCACCACTGCCTACATGCAGCTCA ACAGCCTGACATCTGAGGATTCTGCAATGTATTTCT GTAAAAGATCCATTACTACGTCTTACTGGGGCCAAG GGACTCTGGTCACTGTCTCTGCA | 185 |
| 8C2-2D6 | Light chain | AACATTGTAATGACCCAATCTCCCAAATCCATGTCC ATGTCAGTAGGAGAGAGGGTCACCTTGACCTGCAA GGCCAGTGAGAATGTGGTTACTTATGTTTCCTGGTA TCAACAGAAACCAGAGCAGTCTCCTAAACTGCTGAT ATACGGGGCATCCAACCGGTACACTGGGGTCCCCGA TCGCTTCACAGGCAGTGGATCTGCAACAGATTTCAC TCTGACCATCAGCAGTGTGCAGGCTGAAGACCTTGC AGATTATCACTGTGGACAGGGTTACAGCTATCCGTA CACGTTCGGAGGGGGGACCAAGCTGGAAATAAAACG | 152 |
| 8C2-2D6 | Light chain (V2) | GACATCCAGATGAACCAGTCTCCATCCAGTCTGTCT GCATCCCTTGGAGACACAATTACCATCACTTGCCAT GCCAGTCAGAACATTAATGTTTGGTTAAGCTGGTAC CAGCAGAAACCAGGAAATATTCCTAAACTATTGATC TATAAGGCTTCCAATTTGTATACAGGCGTCCCATCA AGGTTTAGTGGCAGTGGATCTGGAACAGGTTTCACA TTAACCATCAGCAGCCTGCAGCCTGAAGACGTTGCC ACGTACTACTGTCAACACGATCAAAGTTATCCGTAC ACGTTCGGAGGGGGGACCAAGCTGGAAATAAAA | 186 |
| 7D4-2A2-2F2 | Heavy chain | CAGGTTCAGCTGCAGCAGTCTGACGCTGAGTTGGTG AAACCTGGGGCTTCAGTGAAGATATCCTGCAAGGCT TCTGGCTACATCTTCACTGACCATGCAATTCACTGG GTGAAGCAGAAGCCTGAACAGGGCCTGGAATGGAT TGGATATATTTCTCCCGGAAATGGTGATATTAAGTA CATTGAGAAGTTCAGGGGCAAGGCCACACTGACTG CAGACAAATCCTCCAGCACTGCCTACATGCAGCTCA ACAGCCTGACATCTGAGGATTCTGCAGTGTATTTCT GTAAAAGATCGCTTAGTACGCCTTACTGGGGCCAAG GGACTCTGGTCACTGTCTCTGCA | 187 |
| 7D4-2A2-2F2 | Light chain | AACATTTTAATGACCCAATCTCCCAAATCCATGTCC ATGTCAGTAGGAGAGAGGGTCACCTTGACCTGCAA GGCCAGTGAGAATGTGGTTAATTATGTTTCCTGGTA TCAACAGAAACCAGAGCAGTCTCCTAAACTGCTGAT ATTCGGGGCATCCAACCGGTACTCTGGGGTCCCCGA TCGCTTCACAGGCAGTGGATCTGCAACAGATTTCAC | 188 |

TABLE 6-continued

Variable domain nucleotide sequences

| Antibody ID Number | Variable chain | Sequence | SEQ ID NO |
|---|---|---|---|
| | | TCTGACCATCAGCAGTGTGCAGGCTGAAGACCTTGC AGATTATCACTGTGGAAGCAAGTGGATTACTAGCTA TCCGTACACGTTCGGAGGGGGGACCAAGCTGGAAA TAAAACG | |
| 7D4-1H12-2B3 | Heavy chain | CAGGTTCAGCTGCAGCAGTCTGACGCTGAGTTGGTG AAACCTGGGGCTTCAGTGAAGATATCCTGCAAGGCT TCTGGCTACATCTTCACTGACCATGCAATTCACTGG GTGAAGCAGAAGCCTGAACAGGGCCTGGAATGGAT TGGATATATTTCTCCCGGAAATGGTGATATTAAGTA CATTGAGAAGTTCAGGGGCAAGGCCACACTGACTG CAGACAAATCCTCCAGCACTGCCTACATGCAGCTCA ACAGCCTGACATCTGAGGATTCTGCAGTGTATTTCT GTAAAAGATCGCTTAGTACGCCTTACTGGGGCCAAG GGACTCTGGTCACTGTCTCTGCA | 187 |
| 7D4-1H12-2B3 | Light chain | AACATTTTAATGACCCAATCTCCCAAATCCATGTCC ATGTCAGTAGGAGAGAGGGTCACCTTGACCTGCAA GGCCAGTGAGAATGTGGTTAATTATGTTTCCTGGTA TCAACAGAAACCAGAGCAGTCTCCTAAACTGCTGAT ATACGGGGCATCCAACCGGTACTCTGGGGTCCCCGA TCGCTTCACAGGCAGTGGATCTGCAACAGATTTCAC TCTGACCATCAGCAGTGTGCAGGCTGAAGACCTTGC AGATTATCACTGTGGAGCAAGGGTTACTAGCTATCC GTACACGTTCGGAGGGGGGACCAAGCTGGAAATAA AACG | 189 |
| 2C2-2C5 | Heavy chain | CAGGTTCAGCTGCAGCAGTCTGACGCTGAGTTGGTG AAACCTGGGACTTCAGTGAAGATATCCTGCAGGGCT TCTGGCTACACCTTCACTGACCATGCTATTCACTGG GTGAAGCAGAAGCCTGAACAGGGCCTGGAATGGAT TGGATATATTTCTCCCGGAAATGGTGATATTAAGTA CAATGAGAAGTTCAAGGGCAAGGCCACACTGACTG CAGACAAATCCTCCAGCACTGCCTACATGCAGCTCA ACAGCCTGACATCTGACGATTCTGCAGTGTATTTCT GTAAAAGATCCATTACTACGCCTTACTGGGGCCAAG GCACCACTCTCACAGTCTCCTCA | 190 |
| 2C2-2C5 | Light chain | AGTTTTGTGATGACCCAGACTCCCAAATTCCTGCTT GTGTCAGCAGGAGACAGGGTTACCATAACCTGCAA GGCCAGTCAGAGTGTGAATAATAATGTAGCTTGGTA CCAACAGAAGCCAGGGCAGTCTCCTAAACAGCTGA TATACTATGCATCCAATCGCTACACTGGAGTCCCTG ATCGCTTCACTGGCAGTGGATATGGGACGGATTTCA CTTTCACCATCTACACTGTGCAGGCTGAAGACCTGG CAGTTTATTTCTGTCAGCAGGGTTATAGCTCTCCGTG GACGTTCGGTGGAGGCACCAAGCTGAAA | 191 |
| 10F4-2A9 | Heavy chain | CAGGTTCAGCTGCAGCAGTCTGACGCTGAGTTGGTG AAACCTGGGGCTTCAGTGAAGATATCCTGCAAGGCT TCTGGCTACACCTTCACTGACCATGCTATTCACTGG GTGAAGCAGAAGCCTGAACAGGGCCTGGAATGGAT TGGATATATTTCTCCCGGAAATGGTGATATTAAGTA CGATGAGAAGTTTAAGGGCAAGGCCACACTGACTG CAGACAAATCCTCCTCCACTGCCTACATGCAGCTCA ACAGCCTGACATCTGAAGATTCTGCAGTGTATTTCT GTAAAAGATCGATTACTACCTCTTACTGGGGCCAAG GGACTCTGGTCACTGTCTCTGCA | 178 |
| 10F4-2A9 | Light chain | AACATTGTAATGACCCAATCTCCCAAATCCATGTCC ATGTCAGTAGGAGAGAGGGTCACCTTGACCTGCAA GGCCAGTGAGAATGTGGTTACTTATGTTTCCTGGTA TCAACAGAAACCAGAGCAGTCTCCTAAACTGCTGAT ATACGGGGCATCCAACCGGTACACTGGGGTCCCCGA TCGCTTCACAGGCAGTGGATCTGCAACAGATTTCAC TCTGACCATCAGCAGTGTGCAGGCTGAAGACCTTGC AGATTATCACTGTGGACAGGGTTACAGCTATCCGTA CACGTTCGGAGGGGGGACCAAGCTGGAAATAAAACG | 152 |

In some cases, antibodies or antigen binding fragments of the invention may include any of the IgG framework regions presented in the following Table. In some cases, antibodies or fragments thereof may include an amino acid sequence with from about 50% to about 99.9% sequence identity (e.g. from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 99.9%, from about 95% to about 99.9%, about 97%, about 97.5%, about 98%, about 98.5%, about 99%, about 99.5%, about 99.6%, about 99.7% or about 99.8%) with one or more of the constant domain sequences listed in the following Table. In some cases, antibodies or fragments thereof of the invention may include an amino acid sequence having one or more fragments of any of the sequences listed in the following Table.

TABLE 7

IgG Constant domain sequences

| Domain | Sequence | SEQ ID NO |
|---|---|---|
| Murine IgG2a heavy chain constant domain regions | AKTTAPSVYPLAPVCGDTTGSSVTLGCLVKGYFPEPVTLT WNSGSLSSGVHTFPAVLQSDLYTLSSSVTVTSSTWPSQSIT CNVAHPASSTKVDKKIEPRGPTIKPCPPCKCPAPNLLGGPS VFIFPPKIKDVLMISLSPIVTCVVVDVSEDDPDVQISWFVN NVEVHTAQTQTHREDYNSTLRVVSALPIQHQDWMSGKEF KCKVNNKDLPAPIERTISKPKGSVRAPQVYVLPPPEEEMT KKQVTLTCMVTDFMPEDIYVEWTNNGKTELNYKNTEPVL DSDGSYFMYSKLRVEKKNWVERNSYSCSVVHEGLHNHH TTKSFSRTPGK | 192 |
| Murine IgG2a kappa light chain constant region | RADAAPTVSIFPPSSEQLTSGGASVVCFLNNFYPKDINVKW KIDGSERQNGVLNSWTDQDSKDSTYSMSSTLTLTKDEYER HNSYTCEATHKTSTSPIVKSFNRNEC | 193 |
| Human IgG1 heavy chain constant regions | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPELLGG PSVFLFPPKPKDTLMISRTPEVTCVVVDVSHEDPEVKFNW YVDGVEVHNAKTKPREEQYNSTYRVVSVLTVLHQDWLN GKEYKCKVSNKALPAPIEKTISKAKGQPREPQVYTLPPSRD ELTKNQVSLTCLVKGFYPSDIAVEWESNGQPENNYKTTPP VLDSDGSFFLYSKLTVDKSRWQQGNVFSCSVMHEALHNH YTQKSLSLSPGK | 194 |
| Human IgG1 light chain constant regions | RTVAAPSVFIFPPSDEQLKSGTASVVCLLNNFYPREAKVQ WKVDNALQSGNSQESVTEQD SKDSTYSLSSTLTLSKADYEKHKVYACEVTHQGLSSPVTK SFNRGEC | 195 |

In some cases, antibodies may include one or both of the amino acid sequences in the following table and/or be encoded by one or both of the nucleotide sequences presented in the following Table or optimized versions thereof.

TABLE 8

| | | 3F1 antibody sequences | |
|---|---|---|---|
| Antibody | Domain | Sequence | SEQ ID NO |
| 3F1 | Heavy chain full length, amino acids | QVQLQQSDAELVKPGASVKISCKASGYTFTDHAIHW VKQKPEQGLDWIGYISPGNGDIKYNEKFKDKVTLTA DKSSSTACMHLNSLTSEDSAVYFCKRSLLALDYWG QGTTLTVSSAKTTAPSVYPLAPVCGDTTGSSVTLGCL VKGYFPEPVTLTWNSGSLSSGVHTFPAVLQSDLYTL SSSVTVTSSTWPSQSITCNVAHPASSTKVDKKIEPRGP TIKPCPPCKCPAPNLLGGPSVFIFPPKIKDVLMISLSPI VTCVVVDVSEDDPDVQISWFVNNVEVHTAQTQTHR EDYNSTLRVVSALPIQHQDWMSGKEFKCKVNNKDL PAPIERTISKPKGSVRAPQVYVLPPPEEEMTKKQVTL TCMVTDFMPEDIYVEWTNNGKTELNYKNTEPVLDS DGSYFMYSKLRVEKKNWVERNSYSCSVVHEGLHNH HTTKSFSRTPGK | 196 |
| 3F1 | Heavy chain full length, nucleotide | ATGGAGACCGACACCCTGCTGCTCTGGGTGCTGCT GCTCTGGGTGCCCGGCTCCACCGGACAGGTTCAGC TGCAGCAGTCTGACGCTGAGTTGGTGAAACCTGG GGCTTCAGTGAAGATATCCTGCAAGGCTTCTGGCT ACACCTTCACTGACCATGCTATTCACTGGGTGAAG CAAAAGCCTGAACAGGGCCTGGACTGGATTGGAT ATATTTCTCCCGGAAATGGTGATATTAAGTACAAT GAGAAGTTCAAGGACAAGGTCACACTGACTGCAG ACAAATCCTCCAGCACTGCCTGCATGCACCTCAAC AGCCTGACATCTGAGGATTCTGCAGTGTATTTCTG CAAAAGATCCCTACTAGCTCTTGACTACTGGGGCC AAGGCACCACTCTCACAGTCTCCTCAGCTAAAACA ACAGCCCCATCGGTCTATCCACTGGCCCCTGTGTG TGGAGATACAACTGGCTCCTCGGTGACTCTAGGAT GCCTGGTCAAGGGTTATTTCCCTGAGCCAGTGACC TTGACCTGGAACTCTGGTTCCCTGTCCAGTGGTGT GCACACCTTCCCAGCTGTCCTGCAGTCTGACCTCT ACACCCTCAGCTCAAGCGTGACTGTAACCAGCTCG ACCTGGCCCAGCCAGTCCATCACCTGCAATGTGGC CCACCCGGCAAGCAGCACCAAGGTGGACAAGAAA ATTGAGCCCAGAGGGCCCACAATCAAGCCCTGTC CTCCATGCAAATGCCCAGCACCTAACCTCTTGGGT GGACCATCCGTCTTCATCTTCCCTCCAAAGATCAA GGATGTACTCATGATCTCCCTGAGCCCCATAGTCA CATGTGTAGTCGTTGATGTGAGCGAGGATGACCCA GATGTCCAGATCAGCTGGTTTGTGAACAACGTGGA AGTGCACACTGCTCAGACACAGACGCATAGAGAG GATTACAACAGTACTCTCCGGGTTGTCAGTGCCCT CCCCATCCAGCACCAGGACTGGATGAGTGGCAAG GAGTTCAAATGCAAGGTCAACAACAAAGACCTCC CAGCGCCCATCGAGAGAACCATCTCAAAACCCAA AGGGTCAGTAAGAGCTCCACAGGTATATGTCTTGC CTCCACCAGAAGAGGAGATGACTAAGAAACAGGT CACTCTGACCTGCATGGTCACAGACTTCATGCCTG AAGACATTTACGTGGAGTGGACCAACAACGGGAA AACAGAGCTAAACTACAAGAACACTGAACCAGTC CTGGACTCTGATGGTTCTTACTTCATGTACAGCAA GCTGAGAGTGGAGAAGAAGAACTGGGTGGAGAG AAATAGCTACTCCTGTTCAGTGGTCCACGAGGGTC TGCACAATCACCACACGACTAAGAGCTTCTCCCGG ACTCCGGGTAAATAG | 197 |
| 3F1 | Light chain full length, amino acids | DIVMTQSHKFMSTSVGDRVSITCKASQDVGTNIAWY QQKPGRSPKVLIYSASTRHTGVPDRFTGSGSGTDFTL TISNVQSEDLTDYFCQQYSSFPLTFGVGTKLELKRAD AAPTVSIFPPSSEQLTSGGASVVCFLNNFYPKDINVK WKIDGSERQNGVLNSWTDQDSKDSTYSMSSTLTLT KDEYERHNSYTCEATHKTSTSPIVKSFNRNEC | 198 |
| 3F1 | Light chain full length, nucleotide | ATGGAGACCGACACCCTGCTGCTCTGGGTGCTGCT GCTCTGGGTGCCCGGCTCCACCGGAGACATTGTGA TGACCCAGTCTCACAAATTCATGTCCACATCAGTA GGAGACAGGGTCAGCATCACCTGCAAGGCCAGTC AGGATGTGGGCACTAATATAGCCTGGTATCAACA GAAACCAGGCCGATCTCCTAAAGTACTGATTTACT CGGCATCCACCCGGCACACTGGAGTCCCTGATCGC TTCACAGGCAGTGGATCTGGGACAGATTTCACTCT CACCATTAGCAATGTGCAGTCTGAAGACTTGACAG ATTATTTCTGTCAGCAATATAGCAGCTTTCCTCTCA CGTTCGGTGTTGGGACCAAGCTGGAGCTGAAACG | 199 |

TABLE 8-continued

3F1 antibody sequences

| AntibodyDomain | Sequence | SEQ ID NO |
|---|---|---|
| | GGCAGATGCTGCACCAACTGTATCCATCTTCCCAC<br>CATCCAGTGAGCAGTTAACATCTGGAGGTGCCTCA<br>GTCGTGTGCTTCTTGAACAACTTCTACCCCAAAGA<br>CATCAATGTCAAGTGGAAGATTGATGGCAGTGAA<br>CGACAAAATGGCGTCCTGAACAGTTGGACTGATC<br>AGGACAGCAAAGACAGCACCTACAGCATGAGCAG<br>CACCCTCACGTTGACCAAGGACGAGTATGAACGA<br>CATAACAGCTATACCTGTGAGGCCACTCACAAGA<br>CATCAACTTCACCCATTGTCAAGAGCTTCAACAGG<br>AATGAGTGTTGA | |

In some cases, antibodies or fragments thereof may include an amino acid sequence with from about 50% to about 99.9% sequence identity (e.g., from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 99.9%, from about 95% to about 99.9%, about 97%, about 97.5%, about 98%, about 98.5%, about 99%, about 99.5%, about 99.6%, about 99.7% or about 99.8%) with one or more of the amino acid sequences presented in the previous Table. In some cases, antibodies or fragments thereof may be encoded by a nucleotide sequence with from about 50% to about 99.9% sequence identity (e.g. from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 99.9%, from about 95% to about 99.9%, about 97%, about 97.5%, about 98%, about 98.5%, about 99%, about 99.5%, about 99.6%, about 99.7% or about 99.8%) with one or more of the nucleotide sequences presented in the previous Table.

In some embodiments, the disclosure includes antibody fragments produced using one or more of the antibody sequences or related variants described above. Such antibody fragments may include scFvs, Fab fragments, or any other antibody fragments, including any of those described herein.

Humanized Antibodies

"Humanized" forms of non-human (e.g., murine) antibodies are chimeric antibodies that contain minimal sequences derived from non-human immunoglobulin. For the most part, humanized antibodies are human immunoglobulins (recipient antibody) in which residues from the hypervariable region from an antibody of the recipient are replaced by residues from the hypervariable region from an antibody of a non-human species (donor antibody) such as mouse, rat, rabbit or nonhuman primate having the desired specificity, affinity, and capacity.

In some embodiments, fully humanized heavy and light chains may be designed from antibody sequences and/or with CDRs presented herein. Protein models of antibody variable regions may be generated using existing antibody structures as templates. Segments of starting heavy and light chain variable region amino acid sequences may be compared with human sequences to identify human germline antibodies with similar sequences. Series of humanized heavy and light chain variable regions may be designed using human variable domain framework region sequences with the objective that T cell epitopes be avoided. Variant human sequence segments with significant incidence of potential T cell epitopes as determined by in silico technologies may then be discarded. In some cases, some of the amino acid residues in resulting variable domains may be mutated back to amino acids present in the original mouse variable domain. In some cases, some of the mouse residues in the resulting variable domains may be mutated to match residues present in human germline sequences.

Humanized heavy and light chain variable region genes may be constructed from overlapping oligonucleotides assembled into full length genes using the ligase chain reaction (LCR). LCR products may be amplified and suitable restriction sites may be added for cloning into expression vectors. PCR products may be cloned into intermediate vectors and confirmed by sequencing.

For construction of expression plasmids encoding fully humanized antibodies with human constant regions, DNA sequences encoding antibody variable region may be inserted into expression vectors (e.g., mammalian expression vectors) between an upstream promoter/enhancer, for example, cytomegalovirus immediate/early promoter/enhancer (CMV TE), plus the immunoglobulin signal sequence and a downstream immunoglobulin constant region gene. DNA samples may then be prepared for transfection into mammalian cells.

For generation of cell lines and selection of fully humanized antibodies, heavy and light chain plasmid DNA pairs may be transfected into cells for expression. In some embodiments, mammalian NSO cells may be used. Cell lines producing humanized antibodies may be expanded for expression antibodies that may be harvested and purified from cell culture media.

In some embodiments, antibodies of the present disclosure may be prepared according to humanization methods known in the art. Such methods may include, but are not limited to CDR grafting, resurfacing, superhumanization, and human string content optimization (see, for example, Almagro, et al., 2008. Front. Biosci. 13:1619-33). In some embodiments, empirical methods are used. Such methods may include the generation of large combinatorial libraries and selecting desired variants by enrichment technoloiges, such as phage display, yeast display, ribosomal display, or other high throughput screening techniques. These methods may be utilized alone or in combination with framework libraries, guided selection, framework shuffling, and humaneering.

In some embodiments, humanized antibodies may be prepared by utilizing one or more of the human variable domains presented in the following Table. Such antibodies may include one or more of any of the CDR sequences presented herein or fragments or variants thereof that are substituted for the CDR sequences present in the human variable domains. In some cases, variants of the human variable domain sequences are utilized, wherein such variants have at least 50%, at least 60%, at least 70%, at least 75%, at least 80%, at least 85%, at least 90%, at least 95%, at least 96%, at least 97%, at least 98%, at least 99%, at least 99.5%, or at least 99.9% sequence identity to any of the human variable domain sequences presented in the following Table.

TABLE 9

Human variable domains

| Variable domain | Kabat Germline | Sequence | SEQ ID NO |
|---|---|---|---|
| VH | IGHV1-18*01, nucleotide | CAGGTTCAGCTGGTGCAGTCTGGAGCTGAGGTG AAGAAGCCTGGGGCCTCAGTGAAGGTCTCCTGC AAGGCTTCTGGTTACACCTTTACCAGCTATGGTA TCAGCTGGGTGCGACAGGCCCCTGGACAAGGGC TTGAGTGGATGGGATGGATCAGCGCTTACAATG GTAACACAAACTATGCACAGAAGCTCCAGGGCA GAGTCACCATGACCACAGACACATCCACGAGCA CAGCCTACATGGAGCTGAGGAGCCTGAGATCTG ACGACACGGCCGTGTATTACTGTGCGAGAGA | 200 |
| VL | IGKV1-39*01, nucleotide | GACATCCAGATGACCCAGTCTCCATCCTCCCTGT CTGCATCTGTAGGAGACAGAGTCACCATCACTT GCCGGGCAAGTCAGAGCATTAGCAGCTATTTAA ATTGGTATCAGCAGAAACCAGGGAAAGCCCCTA AGCTCCTGATCTATGCTGCATCCAGTTTGCAAAG TGGGGTCCCATCAAGGTTCAGTGGCAGTGGATC TGGGACAGATTTCACTCTCACCATCAGCAGTCTG CAACCTGAAGATTTTGCAACTTACTACTGTCAAC AGAGTTACAGTACCCCTC | 201 |
| VL | IGKV4-1*01, nucleotide | GACATCGTGATGACCCAGTCTCCAGACTCCCTGG CTGTGTCTCTGGGCGAGAGGGCCACCATCAACT GCAAGTCCAGCCAGAGTGTTTTATACAGCTCCA ACAATAAGAACTACTTAGCTTGGTACCAGCAGA AACCAGGACAGCCTCCTAAGCTGCTCATTTACTG GGCATCTACCCGGGAATCCGGGGTCCCTGACCG ATTCAGTGGCAGCGGGTCTGGGACAGATTTCAC TCTCACCATCAGCAGCCTGCAGGCTGAAGATGT GGCAGTTTATTACTGTCAGCAATATTATAGTACT CCTCC | 202 |
| VH | IGHV1-18*01, amino acids | QVQLVQSGAEVKKPGASVKVSCKASGYTFTSYGIS WVRQAPGQGLEWMGWISAYNGNTNYAQKLQGR VTMTTDTSTSTAYMELRSLRSDDTAVYYCAR | 203 |
| VL | IGKV1-39*01, amino acids | DIQMTQSPSSLSASVGDRVTITCRASQSISSYLNWY QQKPGKAPKLLIYAASSLQSGVPSRFSGSGSGTDFT LTISSLQPEDFATYYCQQSYSTP | 204 |
| VL | IGKV4-1*01, amino acids | DIVMTQSPDSLAVSLGERATINCKSSQSVLYSSNNK NYLAWYQQKPGQPPKLLIYWASTRESGVPDRFSG SGSGTDFTLTISSLQAEDVAVYYCQQYYSTPC | 205 |

In some embodiments, humanized antibodies of the present disclosure may include one or more of the human framework regions presented in the following Table. Some antibodies may include framework regions with at least 50%, at least 60%, at least 70%, at least 75%, at least 80%, at least 85%, at least 90%, at least 95%, or at least 98% sequence identity to any of the framework regions presented in the following Table.

TABLE 10

Human framework regions

| Framework region, Variable domain | Kabat Germline | Amino Acid Sequence | SEQ ID NO |
|---|---|---|---|
| FR1, VH | IGHV1-18*01 | QVQLVQSGAEVKKPGASVKVSCKAS | 206 |
| FR1, VL | IGKV1-39*01 | IQMTQSPSSLSASVGDRVTITC | 207 |
| FR1, VL | IGKV4-1*01 | DIVMTQSPDSLAVSLGERATINC | 208 |
| FR2, VH | IGHV1-18*01 | WVRQAPGQGLEWMG | 209 |
| FR2, VL | IGKV1-39*01 | WYQQKPGKAPKLLIY | 210 |
| FR2, VL | IGKV4-1*01 | WYQQKPGQPPKLLIY | 211 |
| FR3, VH | IGHV1-18*01 | RVTMTTDTSTSTAYMELRSLRSDDTAVYYCAR | 212 |
| FR3, VL | IGKV1-39*01 | GVPSRFSGSGSGTDFTLTISSLQPEDFATYYC | 213 |
| FR3, VL | IGKV4-1*01 | GVPDRFSGSGSGTDFTLTISSLQAEDVAVYYC | 214 |
| FR4, VH | Human consensus sequence 1 | WGQGTLVTVSS | 215 |
| FR4, VL | Human consensus sequence 1 | FGQGTKVEIK | 216 |

In some embodiments, one or more residues of humanized antibodies may be back-crossed to improve antibody binding or other properties.

In some embodiments, humanized variable domains present in antibodies of the present disclosure may include any of the variable domains presented in the following Table. In some cases, antibodies include one or more variants of these variable domains with at least 70%, at least 75%, at least 85%, at least 90%, at least 95%, at least 96%, at least 97%, at least 98%, at least 99%, or at least 99.5% sequence identity.

TABLE 11

Humanized variable domains

| mAb | Chain | Sequence | SEQ ID NO |
|---|---|---|---|
| 5G2-1B3 | VL0 | DIQMTQSPSSLSASVGDRVTITCRASENIYSHLAWYQQKPGKAPKLLIYGATNLADGVPSRFSGSGSGTDFTLTISSLQPEDFATYYCQHFWGAPFTFGQGTKVEIK | 217 |
| 5G2-1B3 | VL1 | DIQMTQSPSSLSASVGDRVTITCRASENIYSHLAWYQQKPGKAPKLLVYGATNLASGVPSRFSGSGSGTQFTLTISSLQPEDFATYYCQHFWGAPFTFGQGTKVEIK | 218 |
| 5G2-1B3 | VL2 | DIQMTQSPSSLSASVGDRVTITCRASENIYSHLAWYQQKPGKAPKLLVYGATNLADGVPSRFSGSGSGTQFTLTISSLQPEDFATYYCQHFWGAPFTFGQGTKVEIK | 219 |
| 5G2-1B3 | VH0 | QVQLVQSGAEVKKPGASVKVSCKASGYTFTDHAIHWVRQAPGQGLEWMGYFSPGNDDIKYNEKFKVRVTMTTDTSTSTAYMELRSLRSDDTAVYYCARSYYGDWGQGTLVTVSS | 220 |
| 5G2-1B3 | VH1 | QVQLVQSGAEVKKPGASVKVSCKASGYTFTDHAIHWVRQAPGQGLEWMGYFSPGNDDIKYNEKFKVRVTMTADKSSSTAYMELRSLRSDDTAVYFCKRSYYGDWGQGTLVTVSS | 221 |
| 5G2-1B3 | VH2 | QVQLVQSGAEVKKPGASVKISCKASGYTFTDHAIHWVRQAPGQGLEWIGYFSPGNDDIKYNEKFKVRATLTADKSSSTAYMELRSLRSDDTAVYFCKRSYYGDWGQGTLVTVSS | 222 |

TABLE 11-continued

Humanized variable domains

| mAb | Chain | Sequence | SEQ ID NO |
|---|---|---|---|
| 5G2-1B3 | VH3 | EVQLVQSGAEVKKPGASVKVSCKASGYTFTDHAIH WVRQAPGQGLEWMGYFSPGNDDIKYNEKFKVRVT MTADKSSSTAYMELRSLRSDDTAVYFCKRSYYGDW GQGTLVTVSS | 223 |
| 5G2-1B3 | VH4 | EVQLVQSGAEVKKPGASVKISCKASGYTFTDHAIHW VRQAPGQGLEWIGYFSPGNDDIKYNEKFKVRATLTA DKSSSTAYMELRSLRSDDTAVYFCKRSYYGDWGQG TLVTVSS | 224 |
| 4G8-1E3 | VL0 | DIQMTQSPSSLSASVGDRVTITCHASQHINFWLSWY QQKPGKAPKLLIYKASNLHTGVPSRFSGSGSGTDFTL TISSLQPEDFATYYCQQDQSYPYMFGQGTKVEIK | 225 |
| 4G8-1E3 | VL1 | DIQMTQSPSSLSASVGDRVTITCHASQHINFWLSWY QQKPGKIPKLLIYKASNLHTGVPSRFSGSGSGTGFTL TISSLQPEDFATYYCQQDQSYPYMFGQGTKVEIK | 226 |
| 4G8-1E3 | VL2 | DIQMTQSPSSLSASVGDRITITCHASQHINFWLSWYQ QKPGKIPKLLIYKASNLHTGVPSRFSGSGSGTGFTLTI SSLQPEDVATYYCQQDQSYPYMFGQGTKLEIK | 227 |
| 4G8-1E3 | VL3 | DIQMTQSPSSLSASVGDRVTITCHASQHINFWLSWY QQKPGKIPKLLIYKASNLHTGVPSRFSGSGSGTGFTL TISSLQPEDFATYYCQQDQSYPYFFGQGTKVEIK | 228 |
| 4G8-1E3 | VL4 | DIQMTQSPSSLSASVGDRITITCHASQHINFWLSWYQ QKPGKIPKLLIYKASNLHTGVPSRFSGSGSGTGFTLTI SSLQPEDVATYYCQQDQSYPYFFGQGTKLEIK | 229 |
| 4G8-1E3 | VH0 | QVQLVQSGAEVKKPGASVKVSCKASGYIFTDHAIH WVRQAPGQGLEWMGYISPGNGDIKYNEKFKGRVT MTTDTSTSTAYMELRSLRSDDTAVYYCARSITTSYW GQGTLVTVSS | 230 |
| 4G8-1E3 | VH1 | QVQLVQSGAEVKKPGASVKVSCKASGYIFTDHAIH WVRQAPGQGLEWMGYISPGNGDIKYNEKFKGRVT MTADKSSSTAYMELRSLRSDDTAVYFCKRSITTSYW GQGTLVTVSS | 231 |
| 4G8-1E3 | VH2 | QVQLVQSGAEVKKPGASVKISCKASGYIFTDHAIHW VRQAPGQGLEWIGYISPGNGDIKYNEKFKGRATLTA DKSSSTAYMHLRSLRSDDTAVYFCKRSITTSYWGQG TLVTVSS | 232 |
| 4G8-1E3 | VH3 | EVQLVQSGAEVKKPGASVKVSCKASGYIFTDHAIHW VRQAPGQGLEWMGYISPGSGDIKYNEKFKGRVTMT ADKSSSTAYMELRSLRSDDTAVYFCKRSITTSYWGQ GTLVTVSS | 233 |
| 4G8-1E3 | VH4 | EVQLVQSGAEVKKPGASVKISCKASGYIFTDHAIHW VRQAPGQGLEWIGYISPGSGDIKYNEKFKGRATLTA DKSSSTAYMHLRSLRSDDTAVYFCKRSITTSYWGQG TLVTVSS | 234 |
| 2G12-2B2 | VL0 | DIVMTQSPDSLAVSLGERATINCKSSQSLLNRGNHK NYLTWYQQKPGQPPKLLIYWASTRESGVPDRFSGSG SGTDFTLTISSLQAEDVAVYYCQNDYTYPYTFGQGT KVEIK | 235 |
| 2G12-2B2 | VL2 | DIVMTQSPDSLAVSLGERVTMSCKSSQSLLNRGNHK NYLTWYQQKPGQPPKLLIYWASTRESGVPDRFSGSG SGTDFTLTISSLQAEDVAVYYCQNDYTYPYTFGQGT KVEIK | 236 |
| 2G12-2B2 | VH0 | QVQLVQSGAEVKKPGASVKVSCKASGYTFTDHAIH WVRQAPGQGLEWMGYFSPGNDDIKYNEKFRGRVT MTTDTSTSTAYMELRSLRSDDTAVYYCARSLSTPYW GQGTLVTVSS | 237 |
| 2G12-2B2 | VH1 | QVQLVQSGAEVKKPGASVKVSCKASGYTFTDHAIH WVRQAPGQGLEWMGYFSPGNDDIKYNEKFRGRVT MTADKSSSTAYMELRSLRSDDTAVYFCKRSLSTPYW GQGTLVTVSS | 238 |

TABLE 11-continued

Humanized variable domains

| mAb | Chain | Sequence | SEQ ID NO |
|---|---|---|---|
| 2G12-2B2 | VH2 | QVQLVQSGAEVKKPGASVKISCKASGYTFTDHAIHW VRQAPGQGLEWIGYFSPGNDDIKYNEKFRGVTLTA DKSSSTAYMELRSLRSDDTAVYFCKRSLSTPYWGQG TLVTVSS | 239 |
| 2G12-2B2 | VH3 | EVQLVQSGAEVKKPGASVKVSCKASGYTFTDHAIH WVRQAPGQGLEWMGYFSPGNDDIKYNEKFRGRVT MTADKSSSTAYMELRSLRSDDTAVYFCKRSLSTPYW GQGTLVTVSS | 240 |
| 2G12-2B2 | VH4 | EVQLVQSGAEVKKPGASVKISCKASGYTFTDHAIHW VRQAPGQGLEWIGYFSPGNDDIKYNEKFRGVTLTA DKSSSTAYMELRSLRSDDTAVYFCKRSLSTPYWGQG TLVTVSS | 241 |
| 8C2-2D6 | VL0 | DIQMTQSPSSLSASVGDRVTITCKASENVVTYVSWY QQKPGKAPKLLIYGASNRYTGVPSRFSGSGSGTDFTL TISSLQPEDFATYYCGQGYSYPYTFGQGTKVEIK | 242 |
| 8C2-2D6 | VL1 | NIQMTQSPSSLSASVGDRVTITCKASENVVTYVSWY QQKPGKAPKLLIYGASNRYTGVPSRFSGSGSATDFTL TISSLQPEDFATYYCGQGYSYPYTFGQGTKVEIK | 243 |
| 8C2-2D6 | VL2 | NIVMTQSPSSMSMSVGDRVTLTCKASENVVTYVSW YQQKPGKSPKLLIYGASNRYTGVPSRFSGSGSATDFT LTISSVQPEDLATYHCGQGYSYPYTFGQGTKLEIK | 244 |
| 8C2-2D6(V2) | VL0 | DIQMTQSPSSLSASVGDRVTITCHASQNINVWLSWY QQKPGKAPKLLIYKASNLYTGVPSRFSGSGSGTDFTL TISSLQPEDFATYYCQHDQSYPYTFGQGTKVEIK | 245 |
| 8C2-2D6(V2) | VL1 | DIQMTQSPSSLSASVGDRVTITCHASQNINVWLSWY QQKPGKIPKLLIYKASNLYTGVPSRFSGSGSGTGFTL TISSLQPEDFATYYCQHDQSYPYTFGQGTKVEIK | 246 |
| 8C2-2D6(V2) | VL2 | DIQMTQSPSSLSASVGDRITITCHASQNINVWLSWYQ QKPGKIPKLLIYKASNLYTGVPSRFSGSGSGTGFTLTI SSLQPEDFATYYCQHDQSYPYTFGQGTKLEIK | 247 |
| 8C2-2D6(V2) | VL3 | DIQMNQSPSSLSASVGDRITITCHASQNINVWLSWYQ QKPGKIPKLLIYKASNLYTGVPSRFSGSGSGTGFTLTI SSLQPEDFATYYCQHDQSYPYTFGQGTKLEIK | 248 |
| 8C2-2D6 | VH0 | QVQLVQSGAEVKKPGASVKVSCKASGYTFTDHAIH WVRQAPGQGLEWMGYISPGNGDIKYNEKFKGRVT MTTDTSTSTAYMELRSLRSDDTAVYYCARSITTSYW GQGTLVTVSS | 249 |
| 8C2-2D6 | VH1 | QVQLVQSGAEVKKPGASVKVSCKASGYTFTDHAIH WVRQAPGQGLEWMGYISPGNGDIKYNEKFKGRVT MTADKSSTTAYMELRSLRSDDTAVYFCKRSITTSYW GQGTLVTVSS | 250 |
| 8C2-2D6 | VH2 | QVQLVQSGAEVKKPGASVKISCKASGYTFTDHAIHW VRQAPGQGLEWIGYISPGNGDIKYNEKFKGRATLTA DKSSTTAYMELRSLRSDDTAMYFCKRSITTSYWGQG TLVTVSS | 251 |
| 8C2-2D6 | VH3 | EVQLVQSGAEVKKPGASVKVSCKASGYTFTDHAIH WVRQAPGQGLEWMGYISPGSGDIKYNEKFKGRVTM TADKSSTTAYMELRSLRSDDTAVYFCKRSITTSYWG QGTLVTVSS | 252 |
| 8C2-2D6 | VH4 | EVQLVQSGAEVKKPGASVKISCKASGYTFTDHAIHW VRQAPGQGLEWIGYISPGSGDIKYNEKFKGRATLTA DKSSTTAYMELRSLRSDDTAMYFCKRSITTSYWGQG TLVTVSS | 253 |
| 3F1 | VL0 | DIQMTQSPSSLSASVGDRVTITCKASQDVGTNIAWY QQKPGKAPKLLIYSASTRHTGVPSRFSGSGSGTDFTL TISSLQPEDFATYYCQQYSSFPLTFGQGTKVEIK | 254 |

TABLE 11-continued

Humanized variable domains

| mAb | Chain | Sequence | SEQ ID NO |
|---|---|---|---|
| 3F1 | VL1 | DIQMTQSPSSLSASVGDRVTITCKASQDVGTNIAWYQQKPGKAPKVLIYSASTRHTGVPSRFSGSGSGTDFTLTISSLQPEDFATYFCQQYSSFPLTFGQGTKVEIK | 255 |
| 3F1 | VH0 | QVQLVQSGAEVKKPGASVKVSCKASGYTFTDHAIHWVRQAPGQGLEWMGYISPGNGDIKYNEKFKDRVTMTTDTSTSTAYMELRSLRSDDTAVYYCARSLLALDYWGQGTLVTVSS | 256 |
| 3F1 | VH1 | QVQLVQSGAEVKKPGASVKVSCKASGYTFTDHAIHWVRQAPGQGLEWMGYISPGNGDIKYNEKFKDRVTMTADKSSSTAYMQLRSLRSDDTAVYFCKRSLLALDYWGQGTLVTVSS | 257 |
| 3F1 | VH2 | QVQLVQSGAEVKKPGASVKISCKASGYTFTDHAIHWVRQAPGQGLEWIGYISPGNGDIKYNEKFKDRVTLTADKSSSTASMHLRSLRSDDTAVYFCKRSLLALDYWGQGTLVTVSS | 258 |
| 3F1 | VH3 | EVQLVQSGAEVKKPGASVKVSCKASGYTFTDHAIHWVRQAPGQGLEWMGYISPGSGDIKYNEKFKDRVTMTADKSSSTAYMQLRSLRSDDTAVYFCKRSLLALDYWGQGTLVTVSS | 259 |
| 3F1 | VH4 | EVQLVQSGAEVKKPGASVKISCKASGYTFTDHAIHWVRQAPGQGLEWIGYISPGSGDIKYNEKFKDRVTLTADKSSSTASMHLRSLRSDDTAVYFCKRSLLALDYWGQGTLVTVSS | 260 |

Antibody Sequence Optimization

Variable domain sequences may be analyzed for sequence characteristics that may impact antibody function, expression, stability, and/or immunogenicity. In some cases, such characteristics may include NG residue pairs. NG residue pairs may be susceptible to asparagine deamidation, with possible conversion to glutamate and pyroglutamate in a 3:1 ratio over time. These residue pairs may be mutated, for example, to SG or QG pairs to prevent deamidation at these sites. Alternatively, these antibodies may be formulated to reduce deamidation.

In some embodiments, aspartate isomerization sites may be identified and altered. Aspartate isomerization sites include DG amino acid residue pairs. Aspartic acid at these sites can convert to glutamate and pyroglutamate in a 3:1 ratio over time. DG residue pairs may be mutated to SG or QG residue pairs to prevent isomerization at these sites. Alternatively, these antibodies may be formulated to reduce deamidation.

In some embodiments, N-terminal glutamine residues may be converted to N-terminal glutamate residues. This may prevent N-terminal pyrolization.

In some embodiments, one or more aggregation-prone patch of amino acid residues may be mutated. These may include patches having amino acids with bulky side chains, for example, histidine, phenylalanine, and tryptophan.

In some embodiments, one or more cysteine residues may be mutated to prevent the presence of unpaired cysteines. Unpaired cysteines may be reactive, for example, when accessible to solvent as part of an antibody. In some cases, unpaired cysteine residues may be mutated to serine.

In some embodiments, one or more glycosylation sites (e.g., N-linked NXS/T sites), acid cleavage sites, and amino acid oxidation sites are mutated to improve antibody production, stability, binding, and/or activity.

IgG Synthesis

IgG antibodies (e.g. IgG1, IgG2, IgG3 or IgG4) including one or more variable domain and/or CDR amino acid sequences presented herein (or fragment or variants thereof) may be synthesized for further testing and/or product development. Such antibodies may be produced by insertion of one or more segments of cDNA encoding desired amino acid sequences into expression vectors suited for IgG production. Expression vectors may include mammalian expression vectors suitable for IgG expression in mammalian cells. Mammalian expression of IgGs may be carried out to ensure that antibodies produced include modifications (e.g. glycosylation) characteristic of mammalian proteins and/or to ensure that antibody preparations lack endotoxin and/or other contaminants that may be present in protein preparations from bacterial expression systems.

Immunogenic Hosts

In some embodiments, glycan-interacting antibodies of the present invention may be developed through the use of non-human animals as hosts for immunization, referred to herein as "immunogenic hosts". In some embodiments, immunogenic hosts are mammals. In some embodiments, immunogenic hosts are transgenic knockout mice. Antigens having target sites and/or epitope targets of glycan-interacting antibodies may be used to contact immunogenic hosts in order to stimulate an immune response and produce antibodies in the immunogenic host that specifically bind the target sites and/or epitope targets present on the antigens introduced.

According to some methods of the present invention, the development of anti-STn antibodies may include immunizing mice that have had the Cmah gene disrupted. Such mutations may result in more human-like physiology in that Neu5Gc, the immunogenic, non-human form of sialic acid, is no longer produced in such mice. Also provided is a Cmah$^{-/-}$ myeloma cell for producing a hybridoma that is free of Neu5Gc expression, for production of a GcSTn monoclonal antibody either by reducing the amount of recoverable anti-GcSTn or the hybridoma will begin to die due to antibody binding back to the hybridoma. Other genes can be knocked out in the background of Cmah$^{-/-}$ myeloma cells. For example, the alpha1,3-galactosyltransferase gene, which encodes an enzyme critical for the formation of an epitope highly-immunogenic to humans (Chung, C. H. et al., Cetuximab-induced anaphylaxis and IgE specific for galactose-alpha-1,3-galactose. N Engl J Med. 2008 Mar. 13; 358(11):1109-17), can be knocked out in the background of Cmah$^{-/-}$ myeloma cells.

According to other methods of the present invention, wild type mice may be used for immunization. Such methods may sometimes be favorable for the production of antibodies that interact with AcSTn or pan-STn epitopes. In some cases, immune responses in wild type mice may be more robust.

Antibodies produced through immunization may be isolated from serum of the immunogenic hosts. Antibody producing cells from the immunogenic hosts may also be used to generate cell lines that produce the desired antibody. In some embodiments, screening for antibodies and/or antibody producing cells from the immunogenic host may be carried out through the use of enzyme-linked immunosorbent assays (ELISAs) and/or glycan arrays.

Adjuvants

Immunization of immunogenic hosts with antigens described herein may include the use of one or more adjuvants. Adjuvants may be used to elicit a higher immune response in such immunogenic hosts. As such, adjuvants used according to the present invention may be selected based on their ability to affect antibody titers.

In some embodiments, water-in-oil emulsions may be useful as adjuvants. Water-in-oil emulsions may act by forming mobile antigen depots, facilitating slow antigen release and enhancing antigen presentation to immune components. Freund's adjuvant may be used as complete Freund's adjuvant (CFA), which includes mycobacterial particles that have been dried and inactivated, or as incomplete Freund's adjuvant (IFA), lacking such particles. Other water-in-oil-based adjuvants may include EMULSIGEN® (MVP Technologies, Omaha, Nebr.). EMULSIGEN® includes micron sized oil droplets that are free from animal-based components. It may be used alone or in combination with other adjuvants, including, but not limited to aluminum hydroxide and CARBIGEN™ (MVP Technologies, Omaha, Nebr.).

In some embodiments, TITERMAX® adjuvant may be used. TITERMAX® is another water-in-oil emulsion that includes squalene as well as sorbitan monooleate 80 (as an emulsifier) and other components. In some cases, TITERMAX® may provide higher immune responses, but with decreased toxicity toward immunogenic hosts.

Immunostimmulatory oligonucleotides may also be used as adjuvants. Such adjuvants may include CpG oligodeoxynucleotide (ODN). CpG ODNs are recongnized by Toll-like receptor 9 (TLR9) leading to strong immunostimulatory effects. Type C CpG ODNs induce strong IFN-α production from plasmacytoid dendritic cell (pDC) and B cell stimulation as well as IFN-γ production from T-helper (T$_H$) cells. CpG ODN adjuvant has been shown to significantly enhance pneumococcal polysaccharide (19F and type 6B)-specific IgG2a and IgG3 in mice. CpG ODN also enhanced antibody responses to the protein carrier CRM197, particularly CRM197-specific IgG2a and IgG3 (Chu et al., Infection Immunity 2000, vol 68(3):1450-6). Additionally, immunization of aged mice with pneumococcal capsular polysaccharide serotype 14 (PPS14) combined with a CpG-ODN restored IgG anti-PPS14 responses to young adult levels (Sen et al., Infection Immunity, 2006, 74(3):2177-86). CpG ODNs used according to the present invention may include class A, B or C ODNs. In some embodiments, ODNs may include any of those available commercially, such as ODN-1585, ODN-1668, ODN-1826, ODN-2006, ODN-2007, ODN-2216, ODN-2336, ODN-2395 and/or ODN-M362, each of wich may be purchased, for example, from Invivo-Gen, (San Diego, Calif.). In some cases, ODN-2395 may be used. ODN-2395 is a class C CpG ODN that specifically stimulated human as well as mouse TLR9. These ODNs include phosphorothioate backbones and CpG palindromic motifs.

In some embodiments, immune stimulating complexes (ISCOMs) may be used as adjuvants. ISCOMs are spherical open cage-like structures (typically 40 nm in diameter) that are spontaneously formed when mixing together cholesterol, phospholipids and Quillaia saponins under a specific stoichiometry. ISCOM technology is proven for a huge variety of antigens from large glycoproteins such as gp340 from Epstein-Barr virus (a 340 kDa antigen consisting of 80% carbohydrates) down to carrier-conjugated synthetic peptides and small haptens such as biotin. Some ISCOMs are capable of generating a balanced immune response with both T$_{H1}$ and T$_{H2}$ characteristics. Immune response to ISCOMs is initiated in draining lymph nodes, but is efficiently relocated to the spleen, which makes it particularly suitable for generating monoclonal antibodies as well. In some embodiments, the ISCOM adjuvant AbISCO-100 (Isconova, Uppsala, Sweden) may used. AbISCO-100 is a saponin-based adjuvant specifically developed for use in immunogenic hosts, such as mice, that may be sensitive to other saponins.

According to embodiments of the present invention, adjuvant components of immunization solutions may be varied in order to achieve desired results. Such results may include modulating the overall level of immune response and/or level of toxicitiy in immunogenic hosts.

Antibody Sequence and Structural Analysis and Optimization

In some embodiments, antibodies of the present invention may be subjected to sequence analysis and/or structural analysis wherein they are analyzed for characteristics that may affect antibody chemistry, affinity, specificity, protein folding, stability, manufacturing, expression, and/or immunogenicity (i.e., immune reactions in subjects being treated with such antibodies). Such analysis may include comparisons between antibodies binding to the same or similar epitopes.

Antibodies sequences of antibodies binding to the same epitope may be analyzed for variation in light and/or heavy chain sequences. Such analysis may include germline sequences and/or CDR sequences. Information obtained from such analysis may be used to identify (and optionally to modify, delete, replace or repair) conserved amino acid residues; conserved segments of amino acids; amino acid positions with conserved side chain characteristics; conserved CDR lengths; and other features conserved among antibodies binding to the same epitope. This information may be used to design variants or to inform antibody optimization procedures to improve antibody affinity, specificity, protein folding, stability, manufacturing, expression and/or immunogenicity.

Sequence analysis may include aligning two or more antibodies that bind to the same or similar epitopes to identify similarities. Such analysis may compare the sequence and/or length of antibody regions (e.g., CDRs, variable domains, germline segments). Amino acid insertions, amino acid deletions, and substitutions may be identified and assessed. Sequence differences may be compared against antibody affinity and/or specificity.

In some cases, sequence analyses are conducted to identify (and optionally to modify, delete, replace or repair) one or more of unpaired cysteines or irregular disulfides; glycosylation sites (e.g., N-linked NXS/T sites); acid cleavage sites, amino acid oxidation sites, conformity with mouse germline sequences; asparagine deamidation sites; aspartate isomerization sites; N-terminal pyroglutamate formation sites; and aggregation-prone patches in CDRs.

In some cases, the present invention provides sequence analysis-informed variants of antibodies presented herein. As used herein, the term "sequence analysis-informed variant" refers to an antibody variant that has been modified based on one or more conclusions derived from antibody sequence analysis. In some cases, antibodies of the invention may be modified to produce antibody variants that include modifications to one or more of antibody affinity, specificity, protein folding, stability, manufacturing, expression and/or immunogenicity.

Some sequence analysis-informed variants include one or more CDR length modification. CDR length modified antibodies may include one or more added or deleted amino acids in one or more CDRs relative to an original antibody sequence. In some cases, sequence analysis-informed variants may include a substitution of one or more CDRs with one or more CDRs derived from another antibody (e.g., an antibody binding to the same or similar epitope). In some cases, sequence analysis-informed variants may include a substitution of a heavy or light chain variable domain from another antibody (e.g., an antibody binding to the same or similar epitope). Sequence analysis-informed variants may include modifications to one or more germline genes that the antibody is expressed from. Such modifications may include point mutations, regional mutations, insertional mutations or deletional mutations. In some case, germline gene modifications are carried out to move CDRs from one known germline gene to another. Sequence analysis-informed variants may include other variants described herein, including, but not limited to scFvs, monobodies, diabodies, intrabodies, CARs, antibody mimetics, etc.

In some embodiments, sequence and/or structural analysis may be used to inform the construction of antibody fragment display libraries (including, but not limited to scFv libraries, phage display libraries, and yeast display libraries). In one example, sequence alignment may be carried out to align two or more antibodies with a common antigen or epitope and amino acid residues may be identified that are conserved among the aligned antibodies or that are variable among the aligned antibodies. In such cases, antibody fragment display libraries may be constructed such that variability among library members is primarily limited to the variable amino acids identified in the sequence analysis. In some cases, such libraries may be used to identify variants with altered affinity and/or specificity for a target antigen (e.g., STn) or a specific epitope of the target antigen (e.g., the epitopes recognized by Group 1, 2, 3 and 4 antibodies as described in Example 1, hereinbelow).

In some embodiments, antibodies of the invention may be modified to remove, replace or otherwise eliminate one or more unpaired cysteine residues. In some cases, unpaired cysteine residues may be reactive and in some cases may affect antibody affinity and/or specificity. Accordingly, some antibodies of the invention have been modified to eliminate unpaired cysteine residues. In some cases, such variants may have modified epitope specificity and/or affinity. In some cases, modification of unpaired cysteine residues may alter antibody folding. In some cases, these variants include a substitution or deletion of one or more cysteine residues. In some cases, these variants include one or more additional amino acid residues (including, but not limited to, the addition of one or more cysteine residues) to prevent or reduce undesired effects from unpaired cysteine residues. In some cases, cysteine residues are replaced with an amino acid having a hydrophobic side chain (e.g., tyrosine, alanine, valine, isoleucine, leucine, methionine, phenylalanine or tryptophan).

Antibody Testing and Characterization

Antibodies described herein may be tested and/or characterized using a variety of methods. Such methods may be used to determine a variety of characteristics that may include, but are not limited to, antibody affinity; specificity; and activity (e.g., activation or inhibition of cellular signaling pathways or other cellular or biological activities). Antibody testing may further include testing in vivo (e.g., in animal and/or human studies) for one or more of toxicity, therapeutic effect, pharmacodynamics, pharmacokinetics, absorption, deposition, metabolism, and excretion. Testing in animals may include, but is not limited to, testing in mice, rats, rabbits, guinea pigs, pigs, primates (e.g., cynomolgus monkeys), sheep, goats, horses, and cattle.

Cell-Based Assays

In some embodiments, antibodies of the present invention may be tested or characterized through the use of one or more cell-based assays. Such cell-based assays may be carried out in vitro with cells in culture. In some cases, cell-based assays may be carried out in vivo. Examples of cell-based in vivo assays include tumor models in which tumor cells are injected or otherwise introduced into a host.

In some cases, cells used in cell-based assays may express one or more target glycans recognized by one or more antibodies of the invention. Such glycans may be naturally expressed by such cells or, alternatively, cells may be induced to express one or more glycans desired for purposes of a particular assay. Induced expression may be through one or more treatments that upregulate expression of glycosylated proteins or enzymes that regulate glycosylation. In other cases, induced expression may include transfection, transduction, or other form of introduction of one or more genes or transcripts for the endogenous expression of one or more glycosylated proteins or enzymes involved in regulation of glycosylation.

In some cases, cell-based assays used herein may include the use of cancer cells. Many cancer cell lines are available for experiments to test antibodies of the invention. Such cells may express target glycan or may be induced to express target glycans. Additionally, cancer cell lines may be used to test antibodies of the invention, where the cancer cell lines are representative of cancer stem cells. Cancer stem cell (CSC) cell lines may be isolated or differentiated from cancer cells grown in culture (e.g., through sorting based on markers specific for cancer stem cells). Cell lines used in cell-based assays may include, but are not limted to breast, colon, ovary, lymphocyte, bone marrow, and skin cell lines. Specific cell lines may include, but are not limited to SNU-16 cells, LS-174T cells, MC38 cells, TOV-112D cells, TOV-21G cells, Jurkate E6.1 cells, K-562 cells, B16-F0 cells, B16-F10 cells, LS180 cells, COL0205 cells, TB4 cells, HT29 cells, Panc1 cells, HPAC cells, HPAFII cells, RKO cells, SW480 cells, and SNU-C2A cells.

In some embodiments, ovarian cancer cell lines may be used. Such cell lines may include, but are not limited to SKOV3, OVCAR3, OV90 and A2870 cell lines. In some cases, CSC cells may be isolated from these cell lines by isolating cells expressing CD44 and/or CD133 cell markers.

OVCAR3 cells were first established using malignant ascites obtained from a patient suffering from progressive ovarian adenocarcinoma (Hamilton, T. C. et al., 1983. Cancer Res. 43: 5379-89). Cancer stem cell populations may be isolated from OVCAR3 cell cultures through selection based on specific cell surface markers such as CD44 (involved in cell adhesion and migration), CD133 and CD117 (Liang, D. et al., 2012. BMC Cancer. 12: 201, the contents of which are herein incorporated by reference in their entirety). OV90 cells are epithelial ovarian cancer cells that were similarly derived from human ascites (see U.S. Pat. No. 5,710,038). OV-90 cells may also express CD44 when activated (Meunier, L. et al., 2010. Transl Oncol. 3(4): 230-8).

In some embodiments, cell lines derived from gastric cancers may be used. Such cell lines may include, but are not limited to SNU-16 cells (see description in Park J. G. et al., 1990. Cancer Res. 50: 2773-80, the contents of which are herein incorporated by reference in their entirety). SNU-16 cells express STn naturally, but at low levels.

In some embodiments, methods of the present disclosure include methods of characterizing glycan-interacting antibodies by contacting colorectal cells with glycan-interacting antibodies and evaluating antibody binding to the cells, antibody internalization into the cells, and/or antibody killing of the cells. According to some such methods, the colorectal cells may be derived from a colorectal cell line grown in vitro (e.g., propagated through cell culture). In some cases, colorectal cell lines are derived from a tumor. In other embodiments, colorectal cell lines may be derived from a tumor formed using a xenograft animal model (e.g., a xenograft mouse model). Colorectal cells used for characterizing glycan-interacting antibodies may be from a patient (e.g., a patient tumor). Methods of characterizing glycan-interacting antibodies may include the use of tissue micro arrays, including those having one or more colorectal cells.

Characterizing glycan-interacting antibodies with colorectal cells may include evaluating binding between such antibodies and cells by determining the EC50 of binding of the glycan-interacting antibody to the colorectal cell. The $EC_{50}$ may be determined by using one or more of flow cytometry analysis and ELISA analysis. In some embodiments, characterizing glycan-interacting antibodies with colorectal cells may include evaluating the killing of such cells by glycan-interacting antibodies. This may be carried out by treating colorectal cells with glycan-interacting antibodies and using a cell viability assay to determine the percentage of cells killed by the treatment. In some cases, evaluating killing of colorectal cells by glycan-interacting antibodies includes determining the $IC_{50}$ for glycan-interacting antibody killing of colorectal cells. In some cases, the antibodies may be conjugated with a cytotoxic agent (e.g., MMAE or MMAF).

Glycan Arrays

In some embodiments, glycan-interacting antibodies of the present invention may be developed through the use of glycan arrays. As used herein, the term "glycan array" refers to a tool used to identify agents that interact with any of a number of different glycans linked to the array substrate. In some embodiments, glycan arrays include a number of chemically-synthesized glycans, referred to herein as "glycan probes". In some embodiments, glycan arrays include at least 2, at least 5, at least 10, at least 20, at least 30, at least 40, at least 50, at least 60, at least 70, at least 80, at least 90, at least 100, at least 150, at least 350, at least 1000 or at least 1500 glycan probes. In some embodiments, glycan arrays may be customized to present a desired set of glycan probes. In some embodiments, glycan probes may be attached to the array substrate by a linker molecule. Such linkers may include molecules including, but not limited to —O(CH$_2$)$_2$CH$_2$)NH$_2$ and O(CH$_2$)$_3$NHCOCH$_2$(OCH$_2$CH$_2$)6NH$_2$.

In some embodiments, a glycan array has more than 70 chemically-synthesized glycans, most of which are presented as Neu5Ac and Neu5Gc-containing glycan pairs. Some examples of glycan probes may include: Neu5Ac-α-2-6-GalNAc (AcSTn); Neu5Gc-α-2-6-GalNAc (GcSTn); Neu5,9Ac2-α-2,6-GalNAc; Neu9Ac5Gc-α-2,6-GalNAc, and GalNAc (Tn). The antibody binding specificity to AcSTn vs. GcSTn can be determined using the array or other methods of determining specificity known in the art. In addition, the binding profile of antibodies to O-acetylated STn can be determined. The loss of O-acetylation on STn is relevant to cancer as cancer-associated expression correlates with increased STn recognition by antibodies (Ogata, S. et al., Tumor-associated sialylated antigens are constitutively expressed in normal human colonic mucosa. Cancer Res. 1995 May 1; 55(9):1869-74) In some cases, glycan arrays may be used to determine recognition of STn vs. Tn.

Antibody Fragment Display Library Screening Techniques

In some embodiments, antibodies of the present invention may be produced and/or optimized using high throughput methods of discovery. Such methods may include any of the display techniques (e.g. display library screening techniques) disclosed in International Patent Application No. WO2014074532, the contents of which are herein incorporated by reference in their entirety. In some embodiments, synthetic antibodies may be designed, selected or optimized by screening target antigens using display technologies (e.g. phage display technologies). Phage display libraries may include millions to billions of phage particles, each expressing unique antibody fragments on their viral coats. Such libraries may provide richly diverse resources that may be used to select potentially hundreds of antibody fragments with diverse levels of affinity for one or more antigens of interest (McCafferty, et al., 1990. Nature. 348:552-4; Edwards, B. M. et al., 2003. J M B. 334: 103-18; Schofield, D. et al., 2007. Genome Biol. 8, R254 and Pershad, K. et al., 2010. Protein Engineering Design and Selection. 23:279-88; the contents of each of which are herein incorporated by reference in their entirety). Often, the antibody fragments present in such libraries include scFv antibody fragments that include a fusion protein of $V_H$ and $V_L$ antibody domains joined by a flexible linker. In some cases, scFvs may contain the same sequence with the exception of unique sequences encoding variable loops of the complementarity determining regions (CDRs). In some cases, scFvs are expressed as fusion proteins, linked to viral coat proteins (e.g. the N-terminus of the viral pIII coat protein). $V_L$ chains may be expressed separately for assembly with $V_H$ chains in the periplasm prior to complex incorporation into viral coats. Precipitated library members may be sequenced from the bound phage to obtain cDNA encoding desired scFvs. Such sequences may be directly incorporated into antibody sequences for recombinant antibody production, or mutated and utilized for further optimization through in vitro affinity maturation.

Development of Cytotoxic Anibodies

In some embodiments, antibodies of the present invention may be capable of inducing antibody-dependent cell-mediated cytotoxicity (ADCC) and/or antibody-dependent cell phagocytosis (ADCP). ADCC is an immune mechanism whereby cells are lysed as a result of immune cell attack. Such immune cells may include CD56+ cells, CD3− natural killer (NK) cells, monocytes and neutrophills (Strohl, W. R. Therapeutic Antibody Engineering. Woodhead Publishing, Philadelphia Pa. 2012. Ch. 8, p186, the contents of which are herein incorporated by reference in their entirety).

In some cases, antibodies of the present invention may be engineered to include a given isotype depending on whether or not ADCC or ADCP is desired upon antibody binding. Such antibodies, for example, may be engineered according to any of the methods disclosed by Alderson, K. L. et al., J Biomed Biotechnol. 2011. 2011:379123). In the case of mouse antibodies, different isotypes of antibodies are more effective at promoting ADCC. IgG2a, for example, is more effective at inducing ADCC than is IgG2b. Some antibodies of the present invention, including mouse IgG2b antibodies may be reengineered to be IgG2a antibodies. Such reengineered antibodies may be more effective at inducing ADCC upon binding cell-associated antigens. In some embodiments, antibodies are reengineered by modifying or introducing one or more post-translational modifications to improve ADCC and/or CDC biological activity.

In some embodiments, genes encoding variable regions of antibodies developed according to methods of the present invention may be cloned into mammalian expression vectors encoding human Fc regions. Such Fc regions may be Fc regions from human IgG1κ. IgG1κ Fc regions may include amino acid mutations known to enhance Fc-receptor binding and antibody-dependent cell-mediated cytotoxicity (ADCC).

In some embodiments, antibodies of the invention may be developed for antibody-drug conjugate (ADC) therapeutic applications. ADCs are antibodies in which one or more cargo (e.g., therapeutic agents) are attached [e.g. directly or via linker (e.g. a cleavable linker or a non-cleavable linker)]. ADCs are useful for delivery of therapeutic agents (e.g., drugs or cytotoxic agents) to one or more target cells or tissues (Panowski, S. et al., 2014. mAbs 6:1, 34-45). In some cases, ADCs may be designed to bind to a surface antigen on a targeted cell. Upon binding, the entire antibody-antigen complex may be internalized and directed to a cellular lysosome. ADCs may then be degraded, releasing the bound cargo. Where the cargo is a cytotoxic agent, the target cell will be killed or otherwise disabled. Cytotoxic agents may include, but are not limited to cytoskeletal inhibitors [e.g. tubulin polymerization inhibitors such as maytansines or auristatins (e.g. monomethyl auristatin E [MMAE] and monomethyl auristatin F [MMAF])] and DNA damaging agents (e.g. DNA polymerization inhibitors such as calcheamicins and duocarmycins).

In some embodiments, antibodies of the invention may be tested for their ability to promote cell death when developed as ADCs. Cell viability assays may be performed in the presence and absence of secondary antibody-drug conjugates. Antibodies with potent cell growth inhibition may then be used to design direct antibody-drug conjugates (ADCs). The use of such secondary antibody-drug conjugates in cell-based cytotoxic assays may allow for quick pre-screening of many ADC candidates. Based on such assays, an unconjugated antibody candidate is directly added to cells in the presence of a secondary antibody that is conjugated to one or more cytotoxic agents (referred to herein as a 2° ADC). Internalization of the antibody/2° ADC complex into cells that express a high density of the targeted antigen can achieve a dose-dependent drug release within the cells, causing a cytotoxic effect to kill the cells (e.g., tumor cells), while cells expressing a low density of the targeted antigen are not affected (e.g., normal cells).

ADCs of the invention may be designed to target cancer cells. Such ADCs may include antibodies directed to one or more tumor-associated carbohydrate antigen (TACA). In some cases, ADCs of the invention are anti-STn antibodies.

Development of Chimeric Antigen Receptors

In some embodiments, antibody sequences of the invention may be used to develop a chimeric antigen receptor (CAR). CARs are transmembrane receptors expressed on immune cells that facilitate recognition and killing of target cells (e.g. tumor cells). CARs typically include three basic parts. These include an ectodomain (also known as the recognition domain), a transmembrane domain and an intracellular (signaling) domain. Ectodomains facilitate binding to cellular antigens on target cells, while intracellular domains typically include cell signaling functions to promote the killing of bound target cells. Further, they may have an extracellular domain with one or more antibody variable domains described herein or fragments thereof. CARs of the invention also include a transmembrane domain and cytoplasmic tail. CARs may be designed to include one or more segments of an antibody, antibody variable domain and/or antibody CDR, such that when such CARs are expressed on immune effector cells, the immune effector cells bind and clear any cells that are recognized by the antibody portions of the CARs.

Characteristics of CARs include their ability to redirect T-cell specificity and reactivity toward a selected target in a non-MHC-restricted manner, exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

CARs engineered to target tumors may have specificity for one or more tumor associated carbohydrate antigens (TACAs). In some embodiments, ectodomains of these CARs may include one or more antibody variable domains or a fragment thereof. In some embodiments, CARs are expressed in T cells, and may be referred to as "CAR-engineered T cells" or "CAR-Ts". CAR-Ts may be engineered with CAR ectodomains having one or more antibody variable domains.

Structural Features of Chimeric Antigen Receptors

With gene-transfer technology, T cells can be engineered to stably express antibodies on their surface, conferring a desired antigen specificity. Chimeric antigen receptors (CARs) combine an antigen-recognition domain of a specific antibody with an intracellular domain of the CD3-zeta chain or FcγRI protein having T cell activating properties into a single chimeric fusion protein. CAR technology provides MHC-unrestricted recognition of target cells by T cells. Removal of the MHC restriction of T cells facilitates the use of these molecules in any patient, and also, in both CD8$^+$ and CD4$^+$ T cells, usually restricted to MHC class I or II epitopes, respectively. The use of Ab-binding regions allows T cells to respond to epitopes formed not only by protein, but also carbohydrate and lipid. This chimeric receptor approach is especially suited to immunotherapy of cancer, being able to bypass many of the mechanisms by which tumors avoid immunorecognition, such as MHC down-regulation, lack of expression of costimulatory molecules, CTL resistance, and induction of T cell suppression, and where the use of both CD8+ CTL and CD4+ T cells are best combined for optimum antitumor efficacy. This approach has been demonstrated to be applicable to a wide range of tumor antigens, in addition to viruses such as HIV (Finney, et al., *J. Immunology,* 2004, 172:104-113).

Although chimeric antigen receptors can trigger T-cell activation in a manner similar to that of endogenous T-cell receptors, in practice, the clinical application of CAR technology has been impeded by inadequate in vivo expansion of chimeric antigen receptor T cells. For example, first generation CARs included as their signaling domain the cytoplasmic region of the CD3ζ or Fc receptor γ chain. These first generation CARs were tested in phase I clinical studies in patients with ovarian cancer, renal cancer, lymphoma, and neuroblastoma, and were found to induce modest responses, effectively redirecting T cell cytotoxicity but failing to enable T cell proliferation and survival upon repeated antigen exposure. The prototypes for second generation CARs involved receptors encompassing both CD28 and CD3ζ, and second generation CARs have been tested for treatment of B cell malignancies and other cancers (Sadelain, et al., (2009) *Current Opinion in Immunology,* 21(2):215-223). Thus, CARs have rapidly expanded into a diverse array of receptors with different functional properties.

More recently, it was discovered that CAR-mediated T-cell responses can be enhanced with the addition of a costimulatory domain. In preclinical models, the inclusion of the CD137 (4-1BB) signaling domain was found to significantly increase antitumor activity and in vivo persistence of chimeric antigen receptors as compared with inclusion of the CD3-zeta chain alone (Porter, et al., *N Engl. J. Med.* 2011, 365:725-733).

Thus, in some embodiments of the present disclosure, antibody sequences of the invention may be used to develop a chimeric antigen receptor (CAR). In some embodiments, CARs are transmembrane receptors expressed on immune cells that facilitate recognition and killing of target cells (e.g. tumor cells).

In many cancers, tumor-specific antigens for targeting have not been defined, but in B-cell neoplasms, CD19 is an attractive target. Expression of CD19 is restricted to normal and malignant B cells and B-cell precursors. A pilot clinical trial of treatment with autologous T cells expressing an anti-CD19 chimeric antigen receptor (CART19) was performed in patients with advanced, p53-deficient chronic lymphoid leukemia (CLL). The generation of a CD19-specific immune response in bone marrow was demonstrated by temporal release of cytokines and ablation of leukemia cells that coincided with peak infiltration of chimeric antigen receptor T cells. (Porter, et al., *N. Engl. J. Med.* 2011, 365:725-733).

Further structural features of CARs may include any of those disclosed in several PCT Publications assigned to City of Hope and having the common inventor Michael Jensen. For example, PCT Publication WO 00/23573 describes genetically engineered, CD20-specific redirected T cells expressing a cell surface protein having an extracellular domain that includes a receptor specific for CD20, an intracellular signaling domain, and a transmembrane domain. Use of such cells for cellular immunotherapy of CD20+ malignancies and for abrogating any untoward B cell function. In one embodiment, the cell surface protein is a single chain FvFc:ζ receptor where FAT designates the VH and VL chains of a single chain monoclonal antibody to CD20 linked by peptide, Fc represents a hinge-$CH_2$-$CH_3$ region of a human IgG1, and ζ represents the intracellular signaling domain of the zeta chain of human CD3. A method of making a redirected T cell expressing a chimeric T cell receptor by electroporation using naked DNA encoding the receptor. Similarly, PCT Publication WO 02/077029 describes genetically engineered, CD19-specific redirected immune cells expressing a cell surface protein having an extracellular domain that includes a receptor which is specific for CD19, an intracellular signaling domain, and a transmembrane domain. Use of such cells for cellular immunotherapy of CD19+ malignancies and for abrogating any untoward B cell function. In one embodiment, the immune cell is a T cell and the cell surface protein is a single chain svFvFc:ζ receptor where scFc designates the VH and VL chains of a single chain monoclonal antibody to CD19, Fc represents at least part of a constant region of an IgG1, and zeta represents the intracellular signaling domain of the T cell antigen receptor complex zeta chain (zeta chain of human CD3). The extracellular domain scFvFc and the intracellular domain zeta are linked by a transmembrane domain such as the transmembrane domain of CD4. A method of making a redirected T cell expressing a chimeric T cell receptor by electroportion using naked DNA encoding the receptor. These chimeric antigen receptors have the ability, when expressed in T cells, to redirect antigen recognition based on the monoclonal antibody's specificity. The design of scFvFc: receptors with target specificities for tumor cell-surface epitopes is a conceptually attractive strategy to generate antitumor immune effector cells for adoptive therapy as it does not rely on pre-existing anti-tumor immunity. These receptors are "universal" in that they bind antigen in a MHC independent fashion, thus, one receptor construct can be used to treat a population of patients with antigen positive tumors. City of Hope PCT Publications WO 02/088334, WO 2007/059298 and WO 2010/065818 describe "zetakines" made up of an extracellular domain that includes a soluble receptor ligand linked to a support region capable of tethering the extracellular domain to a cell surface, a transmembrane region and an intracellular signalling domain. Zetakines, when expressed on the surface of T lymphocytes, direct T cell activity to those specific cells expressing a receptor for which the soluble receptor ligand is specific.

Additional features of CARs may include any of those disclosed in two PCT Publications assigned to University of Texas and having a common inventor Lawrence Cooper. PCT Publication No. WO 2009/091826 describes compositions that include a human CD19-specific chimeric T cell receptor (or chimeric antigen receptor, CAR) polypeptide (designated hCD19CAR) that includes an intracellular signaling domain, a transmembrane domain and an extracellular domain, the extracellular domain including a human CD 19 binding region. In another aspect, the CD 19 binding region is an F(ab')2, Fab', Fab, Fv or scFv. The intracellular domain may include an intracellular signaling domain of human CD3ζ and may further include human CD28 intracellular segment. In certain aspects the transmembrane domain is a CD28 transmembrane domain. PCT Publication No. WO 2013/074916 describes methods and compositions for immunotherapy employing CAR+ T cells genetically modified to eliminate expression of T cell receptor and/or HLA. In particular embodiments, the T cell receptor-negative and/or HLA-negative T cells are generated using zinc finger nucleases, for example. The CAR+ T cells from allogeneic healthy donors can be administered to any patient without causing graft versus host disease (GVHD), acting as universal reagents for off-the-shelf treatment of medical conditions such as cancer, autoimmunity, and infection.

PCT Publication WO 2011/041093 assigned to the U.S. Department of Health and Human Services describes anti-vascular endothelial growth factor receptor-2 chimeric antigen receptors that include an antigen binding domain of a KDR-1121 or DC101 antibody, an extracellular hinge domain, a T cell receptor transmembrane domain, and an intracellular T cell receptor signaling domain, and their use in the treatment of cancer.

PCT Publications WO 2012/079000 and WO 2013/040557, the contents of each of which are herein incorporated by reference in their entirety, are assigned to University of Pennsylvania and share the common inventor Carl H. June; these publications describe CARs comprising an antigen binding domain, a transmembrane domain, a costimulatory signaling region, and a CD3 zeta signaling domain, and methods for generating RNA Chimeric Antigen Receptor (CAR) transfected T cells, respectively.

PCT Publication WO2013/126712, also assigned to University of Pennsylvania and sharing the common inventor Carl H. June, describes compositions and methods for generating a persisting population of T cells exhibiting prolonged exponential expansion in culture that is ligand independent and independent of the addition of exogenous cytokines or feeder cells, which are useful for the treatment of cancer. In some embodiments, the antigen binding domain is an anti-cMet binding domain. In some embodiments, the antigen binding domain is an anti-mesothelin binding domain. In some embodiments, the antigen binding domain is an anti-CD 19 binding domain. The hinge domain is IgG4, the transmembrane domain is a CD28 transmembrane domain. In some embodiments, the costimulatory signaling region is a CD28 signaling region. Also provided is a vector comprising a nucleic acid sequence encoding a chimeric antigen receptor (CAR), and the CAR comprising an antigen binding domain, a hinge domain, a transmembrane domain, a costimulatory signaling region, and a CD3 zeta signaling domain.

PCT Publication WO 2014/039513 assigned to University of Pennsylvania describes compositions and methods for inhibiting one or more diacylglycerol kinase (DGK) isoform in a cell in order to enhance the cytolytic activity of the cell. The cells may be used in adoptive T cell transfer in which, the cell is modified to express a chimeric antigen receptor (CAR). Inhibition of DGK in T cells used in adoptive T cell transfer increases cytolytic activity of the T cells and thus may be used in the treatment of a variety of conditions, including cancer, infection, and immune disorders.

PCT Publication WO 2014/055771 assigned to University of Pennsylvania describes compositions and methods for treating ovarian cancer. Specifically, the invention relates to administering a genetically modified T cell having alpha-folate receptor (FR-alpha) binding domain and CD27 costimulatory domain to treat ovarian cancer. In one embodiment, the FR-alpha binding domain is said to be fully human, thereby preventing a host immune response.

In some embodiments, CARs of the invention may be engineered to target tumors. Such CARs may have specificity for one or more TACAs. In some case, ectodomains of these CARs may comprise one or more antibody variable domain presented herein or a fragment thereof. In some embodiments, CARs of the invention are expressed in T cells, referred to herein as "CAR-engineered T cells" or "CAR-Ts". CAR-Ts may be engineered with CAR ectodomains having one or more antibody variable domain presented herein.

Multispecific Antibodies

In some embodiments, antibodies of the present invention may bind more than one epitope. As used herein, the terms "multibody" or "multispecific antibody" refer to an antibody wherein two or more variable regions bind to different epitopes. The epitopes may be on the same or different targets. In certain embodiments, a multi-specific antibody is a "bispecific antibody," which recognizes two different epitopes on the same or different antigens.

Bispecific Antibodies

Bispecific antibodies are capable of binding two different antigens. Such antibodies typically comprise antigen-binding regions from at least two different antibodies. For example, a bispecific monoclonal antibody (BsMAb, BsAb) is an artificial protein composed of fragments of two different monoclonal antibodies, thus allowing the BsAb to bind to two different types of antigen. One common application for this technology is in cancer immunotherapy, where BsMAbs are engineered to simultaneously bind to a cytotoxic cell (using a receptor like CD3) and a target like a tumor cell to be destroyed.

Bispecific antibodies may include any of those described in Riethmuller, G., 2012. *Cancer Immunity.* 12:12-18; Marvin, J. S. et al., 2005. *Acta Pharmacologica Sinica.* 26(6): 649-58; and Schaefer, W. et al., 2011. *PNAS.* 108(27):11187-92, the contents of each of which are herein incorporated by reference in their entirety.

New generations of BsMAb, called "trifunctional bispecific" antibodies, have been developed. These consist of two heavy and two light chains, one each from two different antibodies, where the two Fab regions (the arms) are directed against two antigens, and the Fc region (the foot) comprises the two heavy chains and forms the third binding site.

Of the two paratopes that form the tops of the variable domains of a bispecific antibody, one can be directed against a target antigen and the other against a T-lymphocyte antigen like CD3. In the case of trifunctional antibodies, the Fc region may additionally binds to a cell that expresses Fc receptors, like a mactrophage, a natural killer (NK) cell or a dendritic cell. In sum, the targeted cell is connected to one or two cells of the immune system, which subsequently destroy it.

Other types of bispecific antibodies have been designed to overcome certain problems, such as short half-life, immunogenicity and side-effects caused by cytokine liberation. They include chemically linked Fabs, consisting only of the Fab regions, and various types of bivalent and trivalent single-chain variable fragments (scFvs), fusion proteins mimicking the variable domains of two antibodies. The furthest developed of these newer formats are the bi-specific T-cell engagers (BiTEs) and mAb2's, antibodies engineered to contain an Fcab antigen-binding fragment instead of the Fc constant region.

A bispecific, single-chain antibody Fv fragment (Bs-scFv) was successfully used to kill cancer cells. Some human cancers are caused by functional defects in p53 that are restored by gene therapy with wild-type p53. Weisbart, et al., describe the construction and expression of a bispecific single-chain antibody that penetrates living colon cancer cells, binds intracellular p53, and targets and restores its wild type function (Weisbart, et al., *Int. J. Oncol.* 2004 October; 25(4):1113-8; and Weisbart, et al., *Int. J. Oncol.* 2004 December; 25(6):1867-73). In these studies, a bispecific, single-chain antibody Fv fragment (Bs-scFv) was constructed from (i) a single-chain Fv fragment of mAb 3E10 that penetrates living cells and localizes in the nucleus, and (ii) a single-chain Fv fragment of a non-penetrating antibody, mAb PAb421 that binds the C-terminal of p53. PAb421 binding restores wild-type functions of some p53 mutants, including those of SW480 human colon cancer cells. The Bs-scFv penetrated SW480 cells and was cytotoxic, suggesting an ability to restore activity to mutant p53. COS-7 cells (monkey kidney cells with wild-type p53) served as a control since they are unresponsive to PAb421 due to the presence of SV40 large T antigen that inhibits binding of PAb421 to p53. Bs-scFv penetrated COS-7 cells but was not cytotoxic, thereby eliminating non-specific toxicity of Bs-scFv unrelated to binding p53. Fv fragments alone were not cytotoxic, indicating that killing was due to transduction of p53. A single mutation in CDR1 of PAb421 VH eliminated binding of the Bs-scFv to p53 and abrogated cytotoxicity for SW480 cells without altering cellular penetration, further supporting the requirement of PAb421 binding to p53 for cytotoxicity (Weisbart, et al., *Int. J. Oncol.* 2004 October; 25(4):1113-8; and Weisbart, et al., *Int. J. Oncol.* 2004 December; 25(6):1867-73).

In some embodiments, antibodies of the present invention may be diabodies. Diabodies are functional bispecific single-chain antibodies (bscAb). These bivalent antigen-binding molecules are composed of non-covalent dimers of scFvs, and can be produced in mammalian cells using recombinant methods. (See, e.g., Mack et al, *Proc. Natl. Acad. Sci.,* 92: 7021-7025, 1995). Few diabodies have entered clinical development. An iodine-123-labeled diabody version of the anti-CEA chimeric antibody cT84.66 has been evaluated for pre-surgical immunoscintigraphic detection of colorectal cancer in a study sponsored by the Beckman Research Institute of the City of Hope (Clinicaltrials.gov NCT00647153) (Nelson, A. L., *MAbs.* 2010. January-February; 2(1):77-83).

Using molecular genetics, two scFvs can be engineered in tandem into a single polypeptide, separated by a linker domain, called a "tandem scFv" (tascFv). TascFvs have been found to be poorly soluble and require refolding when produced in bacteria, or they may be manufactured in mammalian cell culture systems, which avoids refolding requirements but may result in poor yields. Construction of a tascFv with genes for two different scFvs yields a "bispecific single-chain variable fragments" (bis-scFvs). Only two tascFvs have been developed clinically by commercial firms; both are bispecific agents in active early phase development by Micromet for oncologic indications, and are described as "Bispecific T-cell Engagers (BiTE)." Blinatumomab is an anti-CD19/anti-CD3 bispecific tascFv that potentiates T-cell responses to B-cell non-Hodgkin lymphoma in Phase 2. MT110 is an anti-EP-CAM/anti-CD3 bispecific tascFv that potentiates T-cell responses to solid tumors in Phase 1. Bispecific, tetravalent "TandAbs" are also being researched by Affimed (Nelson, A. L., *MAbs.* 2010. January-February; 2(1):77-83).

Also included are maxibodies (bivalent scFV fused to the amino terminus of the Fc ($CH_2$-$CH_3$ domains) of IgG.

Bispecific T-cell-engager (BiTE) antibodies are designed to transiently engage cytotoxic T-cells for lysis of selected target cells. These typically include two scFvs (one binding to CD3 on Tcells and one binding to a target antigen on the surface of a cell being targeted for destruction). In some embodiments, the two scFvs are joined by a linker. In other embodiments, the two scFvs are different regions on an antibody. The clinical activity of BiTE antibodies corroborates findings that ex vivo expanded, autologous T-cells derived from tumor tissue, or transfected with specific T-cell receptors, have shown therapeutic potential in the treatment of solid tumors. While these personalized approaches prove that T-cells alone can have considerable therapeutic activity, even in late-stage cancer, they are cumbersome to perform on a broad basis. This is different for cytotoxic T-lymphocyte antigen 4 (CTLA-4) antibodies, which facilitate generation of tumor-specific T-cell clones, and also for bi- and tri-specific antibodies that directly engage a large proportion of patients' T-cells for cancer cell lysis. The potential of global T-cell engagement for human cancer therapy by T-cell-engaging antibodies is under active investigation (Baeuerle P A, et al., *Current Opinion in Molecular Therapeutics.* 2009, 11(1):22-30 and Baeuerle P A and Reinhardt C, Cancer Res. 2009, 69(12): 4941-4, the contents of each of which are herein incorporated by reference in their entirety).

Third generation molecules include "miniaturized" antibodies. Among the best examples of mAb miniaturization are the small modular immunopharmaceuticals (SMIPs) from Trubion Pharmaceuticals. These molecules, which can be monovalent or bivalent, are recombinant single-chain molecules containing one $V_L$, one $V_H$ antigen-binding domain, and one or two constant "effector" domains, all connected by linker domains. Presumably, such a molecule might offer the advantages of increased tissue or tumor penetration claimed by fragments while retaining the immune effector functions conferred by constant domains. At least three "miniaturized" SMIPs have entered clinical development. TRU-015, an anti-CD20 SMIP developed in collaboration with Wyeth, is the most advanced project, having progressed to Phase 2 for rheumatoid arthritis (RA). Earlier attempts in systemic lupus erythrematosus (SLE) and B cell lymphomas were ultimately discontinued. Trubion and Facet Biotechnology are collaborating in the development of TRU-016, an anti-CD37 SMIP, for the treatment of CLL and other lymphoid neoplasias, a project that has reached Phase 2. Wyeth has licensed the anti-CD20 SMIP SBI-087 for the treatment of autoimmune diseases, including RA, SLE and possibly multiple sclerosis, although these projects remain in the earliest stages of clinical testing. (Nelson, A. L., *MAbs.* 2010. January-February; 2(1):77-83).

Genmab is researching application of their "Unibody" technology, in which the hinge region has been removed from IgG4 molecules. While IgG4 molecules are unstable and can exchange light-heavy chain heterodimers with one another, deletion of the hinge region prevents heavy chain-heavy chain pairing entirely, leaving highly specific monovalent light/heavy heterodimers, while retaining the Fc region to ensure stability and extended half-life in vivo. This configuration may minimize the risk of immune activation or oncogenic growth, as IgG4 interacts poorly with FcRs and monovalent unibodies fail to promoteintracellular signaling complex formation. These contentions are, however, largely supported by laboratory, rather than clinical, evidence. Biotecnol is also developing a "miniaturized" mAb, CAB051, which is a "compacted" 100 kDa anti-HER2 antibody in preclinical research (Nelson, A. L., *MAbs.* 2010. January-February; 2(1):77-83).

Recombinant therapeutics composed of single antigen-binding domains have also been developed, although they currently account for only 4% of the clinical pipeline. These molecules are extremely small, with molecular weights approximately one-tenth of those observed for full-sized mAbs. Arana and Domantis engineer molecules composed of antigen-binding domains of human immunoglobulin light or heavy chains, although only Arana has a candidate in clinical testing, ART-621, an anti-TNFα molecule in Phase 2 study for the treatment of psoriasis and rheumatoid arthritis. Ablynx produces "nanobodies" derived from the antigen-binding variable heavy chain regions (VHHs) of heavy chain antibodies found in camels and llamas, which lack light chains. Two Ablynx anti-von Willebrand Factor nanobodies have advanced to clinical development, including ALX-0081, in Phase 2 development as an intravenous therapy to prevent thrombosis in patients undergoing percutaneous coronary intervention for acute coronary syndrome, and ALX-0681, a Phase 1 molecule for subcutaneous administration intended for both patients with acute coronary syndrome and thrombotic thrombocytopenic purpura (Nelson, A. L., *MAbs*.2010. January-February; 2(1):77-83).

Development of Multispecific Antibodies

In some embodiments, antibody sequences of the invention may be used to develop multispecific antibodies (e.g., bispecific, trispecific, or of greater multispecificity). Multispecific antibodies can be specific for different epitopes of a target antigen of the present invention, or can be specific for both a target antigen of the present invention, and a heterologous epitope, such as a heterologous glycan, peptide or solid support material. (See, e.g., WO 93/17715; WO 92/08802; WO 91/00360; WO 92/05793; Tutt, A. et al., *Trispecific F(ab')3 derivatives that use cooperative signaling via the TCR/CD3 complex and CD2 to activate and redirect resting cytotoxic T cells. J Immunol.* 1991 Jul. 1; 147(1):60-9; U.S. Pat. Nos. 4,474,893; 4,714,681; 4,925,648; 5,573,920; 5,601,819; and Kostelny, S. A. et al., *Formation of a bispecific antibody by the use of leucine zippers. J. Immunol.* 1992 Mar. 1; 148(5):1547-53); U.S. Pat. No. 5,932,448.

Disclosed and claimed in PCT Publication WO2014144573 to Memorial Sloan-Kettering Cancer Center are multimerization technologies for making dimeric multispecific binding agents (e.g., fusion proteins comprising antibody components) with improved properties over multispecific binding agents without the capability of dimerization.

Disclosed and claimed in PCT Publication WO2014144357 to Merck Patent GMBH are tetravalent bispecific antibodies (TetBiAbs), and methods of making and methods of using TetBiAbs for diagnostics and for the treatment of cancer or immune disorders. TetBiAbs feature a second pair of Fab fragments with a second antigen specificity attached to the C-terminus of an antibody, thus providing a molecule that is bivalent for each of the two antigen specificities. The tetravalent antibody is produced by genetic engineering methods, by linking an antibody heavy chain covalently to a Fab light chain, which associates with its cognate, co-expressed Fab heavy chain.

Disclosed and claimed in PCT Publication WO2014028560 to IBC Pharmaceuticals, Inc. are T cell redirecting bispecific antibodies (bsAb), with at least one binding site for a T-cell antigen and at least one binding site for an antigen on a diseased cell or pathogen, for treatment of disease. Preferably, this bsAb is an anti-CD3×anti-CD19 bispecific antibody, although antibodies against other T-cell antigens and/or disease-associated antigens may be used. The complex is capable of targeting effector T cells to induce T-cell-mediated cytotoxicity of cells associated with a disease, such as cancer, autoimmune disease or infectious disease. The cytotoxic immune response is enhanced by co-administration of interfon-based agents that comprise interferon-α, interferon-bgr; interferon-λ1, interferon-λ2 or interferon-λ3.

Disclosed and claimed in PCT Publication WO2013092001 to Synimmune GMBH is a bispecific antibody molecule, as well as a method for producing the same, its use and a nucleic acid molecule encoding the bispecific antibody molecule. In particular is provided an antibody molecule that is capable of mediating target cell restricted activation of immune cells.

Disclosed and claimed in PCT Publication WO2012007167 is a multispecific modular antibody specifically binding to at least a glycoepitope and a receptor of the erbB class on the surface of a tumor cell, thereby crosslinking the glycoepitope and the receptor, which antibody has apoptotic activity effecting cytolysis independent of NK cells.

Disclosed and claimed in PCT Publications WO2012048332 and WO2013055404 are meditopes, meditope-binding antibodies, meditope delivery systems, as well as a monoclonal antibody framework binding interface for meditopes, and methods for their use. Specifically, two antibody binding peptides, C-QFDLSTRRLK-C ("cQFD"; sequence identification number 1 therein; SEQ ID NO: 261 herein) and C-QYNLSSRALK-C ("cQYN"; sequence identification number 2 therein; SEQ ID NO: 262 herein) were shown to have novel mAb binding properties. Also called "meditopes," cQFD and cQYN were shown to bind to a region of the Fab framework of the anti-EGFR mAb cetuximab and not to bind the complementarity determining regions (CDRs) that bind antigen. The binding region on the Fab framework is distinct from other framework-binding antigens, such as the superantigens *Staphylococcal* protein A (SpA) (Graille et al., 2000) and *Peptostreptococcus magnus* protein L (PpL) (Graille et al., 2001). Accordingly, one embodiment disclosed is a framework binding interface comprising a framework region of a unique murine-human antibody or functional fragment thereof that binds a cyclic meditope.

Exemplary patents and patent publications of interest are: U.S. Pat. Nos. 5,585,089; 5,693,761; and 5,693,762, all filed Jun. 7, 1995 and U.S. Pat. No. 6,180,370, all assigned to Protein Design Labs, Inc., describe methods for producing, and compositions of, humanized immunoglobulins having one or more complementarity determining regions (CDR's) and possible additional amino acids from a donor immunoglobulin and a framework region from an accepting human immunoglobulin. Each humanized immunoglobulin chain is said to usually comprise, in addition to the CDR's, amino acids from the donor immunoglobulin framework that are, e.g., capable of interacting with the CDRs to effect binding affinity, such as one or more amino acids which are immediately adjacent to a CDR in the donor immunoglobulin or those within about about 3 Å as predicted by molecular modeling. The heavy and light chains may each be designed by using any one or all of various position criteria. When combined into an intact antibody, the humanized immunoglobulins of the present invention is said to be substantially non-immunogenic in humans and retain substantially the same affinity as the donor immunoglobulin to the antigen, such as a protein or other compound containing an epitope.

U.S. Pat. No. 5,951,983, assigned to Universite Catholique De Louvain and Bio Transplant, Inc., describes a humanized antibody against T-lymphocytes. Framework regions from a human V kappa gene designated as HUM5400 (EMBL accession X55400) and from the human antibody clone Amu 5-3 (GenBank accession number U00562) are set forth therein.

U.S. Pat. No. 5,091,513, to Creative Biomolecules, Inc., describes a family of synthetic proteins having affinity for a preselected antigen. The proteins are characterized by one or more sequences of amino acids constituting a region which behaves as a biosynthetic antibody binding site (BABS). The sites comprise 1) non-covalently associated or disulfide bonded synthetic $V_H$ and $V_L$ dimers, 2) $V_H$-$V_L$ or $V_L$-$V_H$ single chains wherein the $V_H$ and $V_L$ are attached by a polypeptide linker, or 3) individuals $V_H$ or $V_L$ domains. The binding domains comprise linked CDR and FR regions, which may be derived from separate immunoglobulins. The proteins may also include other polypeptide sequences which function, e.g., as an enzyme, toxin, binding site, or site of attachment to an immobilization media or radioactive atom. Methods are disclosed for producing the proteins, for designing BABS having any specificity that can be elicited by in vivo generation of antibody, and for producing analogs thereof.

U.S. Pat. No. 8,399,625, to ESBATech, an Alcon Biomedical Research Unit, LLC, describes antibody acceptor frameworks and methods for grafting non-human antibodies, e.g., rabbit antibodies, using a particularly well suited antibody acceptor framework.

Intrabodies

In some embodiments, antibodies of the present invention may be intrabodies. Intrabodies are a form of antibody that is not secreted from a cell in which it is produced, but instead targets one or more intracellular proteins. Intrabodies are expressed and function intracellularly, and may be used to affect a multitude of cellular processes including, but not limited to intracellular trafficking, transcription, translation, metabolic processes, proliferative signaling and cell division. In some embodiments, methods described herein include intrabody-based therapies. In some such embodiments, variable domain sequences and/or CDR sequences disclosed herein are incorporated into one or more constructs for intrabody-based therapy. For example, intrabodies may target one or more glycated intracellular proteins or may modulate the interaction between one or more glycated intracellular proteins and an alternative protein.

More than two decades ago, intracellular antibodies against intracellular targets were first described (Biocca, Neuberger and Cattaneo *EMBO J.* 9: 101-108, 1990). The intracellular expression of intrabodies in different compartments of mammalian cells allows blocking or modulation of the function of endogenous molecules (Biocca, et al., *EMBO J.* 9: 101-108, 1990; Colby et al., *Proc. Natl. Acad. Sci. U.S.A.* 101: 17616-21, 2004). Intrabodies can alter protein folding, protein-protein, protein-DNA, protein-RNA interactions and protein modification. They can induce a phenotypic knockout and work as neutralizing agents by direct binding to the target antigen, by diverting its intracellular traffic or by inhibiting its association with binding partners. They have been largely employed as research tools and are emerging as therapeutic molecules for the treatment of human diseases as viral pathologies, cancer and misfolding diseases. The fast growing bio-market of recombinant antibodies provides intrabodies with enhanced binding specificity, stability and solubility, together with lower immunogenicity, for their use in therapy (Biocca, abstract in *Antibody Expression and Production Cell Engineering* Volume 7, 2011, pp. 179-195).

In some embodiments, intrabodies have advantages over interfering RNA (iRNA); for example, iRNA has been shown to exert multiple non-specific effects, whereas intrabodies have been shown to have high specificity and affinity of to target antigens. Furthermore, as proteins, intrabodies possess a much longer active half-life than iRNA. Thus, when the active half-life of the intracellular target molecule is long, gene silencing through iRNA may be slow to yield an effect, whereas the effects of intrabody expression can be almost instantaneous. Lastly, it is possible to design intrabodies to block certain binding interactions of a particular target molecule, while sparing others.

Development of Intrabodies

Intrabodies are often single chain variable fragments (scFvs) expressed from a recombinant nucleic acid molecule and engineered to be retained intracellularly (e.g., retained in the cytoplasm, endoplasmic reticulum, or periplasm). Intrabodies may be used, for example, to ablate the function of a protein to which the intrabody binds. The expression of intrabodies may also be regulated through the use of inducible promoters in the nucleic acid expression vector comprising the intrabody. Intrabodies may be produced using methods known in the art, such as those disclosed and reviewed in: (Marasco et al., 1993 *Proc. Natl. Acad. Sci. USA,* 90: 7889-7893; Chen et al., 1994, *Hum. Gene Ther.* 5:595-601; Chen et al., 1994, *Proc. Natl. Acad. Sci. USA,* 91: 5932-5936; Maciejewski et al., 1995, *Nature Med.,* 1: 667-673; Marasco, 1995, *Immunotech,* 1: 1-19; Mhashilkar, et al., 1995, *EMBO J.* 14: 1542-51; Chen et al., 1996, Hum. Gene Therap., 7: 1515-1525; Marasco, Gene Ther. 4:11-15, 1997; Rondon and Marasco, 1997, *Annu. Rev. Microbiol.* 51:257-283; Cohen, et al., 1998, *Oncogene* 17:2445-56; Proba et al., 1998, *J. Mol. Biol.* 275:245-253; Cohen et al., 1998, *Oncogene* 17:2445-2456; Hassanzadeh, et al., 1998, *FEBS Lett.* 437:81-6; Richardson et al., 1998, *Gene Ther.* 5:635-44; Ohage and Steipe, 1999, *J. Mol. Biol.* 291:1119-1128; Ohage et al., 1999, *J. Mol. Biol.* 291:1129-1134; Wirtz and Steipe, 1999, *Protein Sci.* 8:2245-2250; Zhu et al., 1999, *J. Immunol. Methods* 231:207-222; Arafat et al., 2000, *Cancer Gene Ther.* 7:1250-6; der Maur et al., 2002, *J. Biol. Chem.* 277:45075-85; Mhashilkar et al., 2002, *Gene Ther.* 9:307-19; and Wheeler et al., 2003, *FASEB J.* 17: 1733-5; and references cited therein). In particular, a CCRS intrabody has been produced by Steinberger et al., 2000, *Proc. Natl. Acad. Sci. USA* 97:805-810). See generally Marasco, Wash., 1998, "Intrabodies: Basic Research and Clinical Gene Therapy Applications" Springer:New York; and for a review of scFvs, see Pluckthun in "The Pharmacology of Monoclonal Antibodies," 1994, vol. 113, Rosenburg and Moore eds. Springer-Verlag, New York, pp. 269-315.

In some embodiments, antibody sequences are used to develop intrabodies. Intrabodies are often recombinantly expressed as single domain fragments such as isolated VH and VL domains or as a single chain variable fragment (scFv) antibody within the cell. For example, intrabodies are often expressed as a single polypeptide to form a single chain antibody comprising the variable domains of the heavy and light chain joined by a flexible linker polypeptide. Intrabodies typically lack disulfide bonds and are capable of modulating the expression or activity of target genes through their specific binding activity. Single chain antibodies can also be expressed as a single chain variable region fragment joined to the light chain constant region.

As is known in the art, an intrabody can be engineered into recombinant polynucleotide vectors to encode sub-cellular trafficking signals at its N or C terminus to allow expression at high concentrations in the sub-cellular compartments where a target protein is located. For example, intrabodies targeted to the endoplasmic reticulum (ER) are engineered to incorporate a leader peptide and, optionally, a C-terminal ER retention signal, such as the KDEL amino acid motif. Intrabodies intended to exert activity in the nucleus are engineered to include a nuclear localization signal. Lipid moieties are joined to intrabodies in order to tether the intrabody to the cytosolic side of the plasma membrane. Intrabodies can also be targeted to exert function in the cytosol. For example, cytosolic intrabodies are used to sequester factors within the cytosol, thereby preventing them from being transported to their natural cellular destination.

There are certain technical challenges with intrabody expression. In particular, protein conformational folding and structural stability of the newly-synthesized intrabody within the cell is affected by reducing conditions of the intracellular environment. In human clinical therapy, there are safety concerns surrounding the application of transfected recombinant DNA, which is used to achieve intrabody expression within the cell. Of particular concern are the various viral-based vectors commonly-used in genetic manipulation. Thus, one approach to circumvent these problems is to fuse protein transduction domains (PTD) to scFv antibodies, to create a 'cell-permeable' antibody or 'Transbody.' Transbodies are cell-permeable antibodies in which a protein transduction domain (PTD) is fused with single chain variable fragment (scFv) antibodies (Heng and Cao, 2005, *Med Hypotheses*. 64:1105-8).

Upon interaction with a target gene, an intrabody modulates target protein function and/or achieves phenotypic/functional knockout by mechanisms such as accelerating target protein degradation and sequestering the target protein in a non-physiological sub-cellular compartment. Other mechanisms of intrabody-mediated gene inactivation can depend on the epitope to which the intrabody is directed, such as binding to the catalytic site on a target protein or to epitopes that are involved in protein-protein, protein-DNA, or protein-RNA interactions.

In one embodiment, intrabodies are used to capture a target in the nucleus, thereby preventing its activity within the nucleus. Nuclear targeting signals are engineered into such intrabodies in order to achieve the desired targeting. Such intrabodies are designed to bind specifically to a particular target domain. In another embodiment, cytosolic intrabodies that specifically bind to a target protein are used to prevent the target from gaining access to the nucleus, thereby preventing it from exerting any biological activity within the nucleus (e.g., preventing the target from forming transcription complexes with other factors).

In order to specifically direct the expression of such intrabodies to particular cells, the transcription of the intrabody is placed under the regulatory control of an appropriate tumor-specific promoter and/or enhancer. In order to target intrabody expression specifically to prostate, for example, the PSA promoter and/or promoter/enhancer can be utilized (See, for example, U.S. Pat. No. 5,919,652 issued 6 Jul. 1999).

Protein transduction domains (PTDs) are short peptide sequences that enable proteins to translocate across the cell membrane and be internalized within the cytosol, through atypical secretory and internalization pathways. There are a number of distinct advantages that a 'Transbody' would possess over conventional intrabodies expressed within the cell. For a start, 'correct' conformational folding and disulfide bond formation can take place prior to introduction into the target cell. More importantly, the use of cell-permeable antibodies or 'Transbodies' would avoid the overwhelming safety and ethical concerns surrounding the direct application of recombinant DNA technology in human clinical therapy, which is required for intrabody expression within the cell. 'Transbodies' introduced into the cell would possess only a limited active half-life, without resulting in any permanent genetic alteration. This would allay any safety concerns with regards to their application in human clinical therapy (Heng and Cao 2005, *Med Hypotheses*. 64:1105-8).

Intrabodies are promising therapeutic agents for the treatment of misfolding diseases, including Alzheimer's, Parkinson's, Huntington's and prion diseases, because of their virtually infinite ability to specifically recognize the different conformations of a protein, including pathological isoforms, and because they can be targeted to the potential sites of aggregation (both intra- and extracellular sites). These molecules can work as neutralizing agents against amyloidogenic proteins by preventing their aggregation, and/or as molecular shunters of intracellular traffic by rerouting the protein from its potential aggregation site (Cardinale, and Biocca, *Curr. Mol. Med.* 2008, 8:2-11).

Exemplary Patent Publications describing intracellular antibodies or intrabodies are set forth hereinbelow, each of which is incorporated by reference in its entirety.

PCT Publication WO03014960 and U.S. Pat. No. 7,608,453 granted to Cattaneo, et al., describe an intracellular antibody capture technology method of identifying at least one consensus sequence for an intracellular antibody (ICS) comprising the steps of: creating a database comprising sequences of validated intracellular antibodies (VIDA database) and aligning the sequences of validated intracellular antibodies according to Kabat; determining the frequency with which a particular amino acid occurs in each of the positions of the aligned antibodies; selecting a frequency threshold value (LP or consensus threshold) in the range from 70% to 100%; identifying the positions of the alignment at which the frequency of a particular amino acid is greater than or equal to the LP value; and identifying the most frequent amino acid, in the position of said alignment.

PCT Publications WO0054057; WO03077945; WO2004046185; WO2004046186; WO2004046187; WO2004046188; WO2004046189; US Patent Application Publications US2005272107; US2005276800; US2005288492; US2010143939; granted U.S. Pat. Nos. 7,569,390 and 7,897,347 and granted European Patents EP1560853; and EP1166121 all assigned to the Medical Research Council and including inventors Cattaneo, et al., describe intracellular intracellular single domain immunoglobulins, and a method for determining the ability of a immunoglobulin single domain to bind to a target in an intracellular environment, as well as methods for generating intracellular antibodies.

PCT Publication WO0235237; US Patent Application Publication 2003235850 and granted European Patent EP1328814 naming Catteneo as an inventor and assigned to S.I.S.S.A. Scuola Internazionale Superiore describe a method for the in vivo identification of epitopes of an intracellular antigen.

PCT Publication WO2004046192 and European Patent EP1565558 assigned to Lay Line Genomics SPA and naming Catteneo as an inventor describe a method for isolating intracellular antibodies that disrupt and neutralize an interaction between a protein ligand x and a protein ligand y inside a cell. Also disclosed are a method to identify a protein ligand x able to bind to a known y ligand using intracellular antibodies able to the interaction between x and y; and a method for the isolation of a set of antibody fragments against a significant proportion of the protein-protein interactions of a given cell (interactome) or against the protein interactions that constitute an intracellular pathway or network.

US Patent Application Publication 2006034834 and PCT Publication WO9914353 entitled "Intrabody-mediated control of immune reactions" and assigned to Dana Farber Cancer Institute Inc. name inventors Marasco and Mhashilkar are directed to methods of altering the regulation of the immune system, e.g., by selectively targeting individual or classes of immunomodulatory receptor molecules (IRMs) on cells comprising transducing the cells with an intracellularly expressed antibody, or intrabody, against the IRMs. In a preferred embodiment the intrabody comprises a single chain antibody against an IRM, e.g, MHC-1 molecules.

PCT Publication WO2013033420 assigned to Dana Farber Cancer Institute Inc. and Whitehead Biomedical Institute, and naming inventors Bradner, Rahl and Young describes methods and compositions useful for inhibiting interaction between a bromodomain protein and an immunoglobulin (Ig) regulatory element and downregulating expression of an oncogene translocated with an Ig locus, as well as for treating a cancer (e.g., hematological malignancy) characterized by increased expression of an oncogene which is translocated with an Ig locus. Intrabodies are generally described.

PCT Publication WO02086096 and US Patent Application Publication 2003104402 entitled "Methods of producing or identifying intrabodies in eukaryotic cells," assigned to University of Rochester Medical Center and naming inventors Zauderer, Wei and Smith describe a high efficiency method of expressing intracellular immunoglobulin molecules and intracellular immunoglobulin libraries in eukaryotic cells using a trimolecular recombination method. Further provided are methods of selecting and screening for intracellular immunoglobulin molecules and fragments thereof, and kits for producing, screening and selecting intracellular immunoglobulin molecules, as well as the intracellular immunoglobulin molecules and fragments produced using these methods.

PCT Publication WO2013023251 assigned to Affinity Biosciences PTY LTD and naming inventors Beasley, Niven and Kiefel describes polypeptides, such as antibody molecules and polynucleotides encoding such polypeptides, and libraries thereof, wherein the expressed polypeptides that demonstrate high stability and solubility. In particular, polypeptides comprising paired VL and VH domains that demonstrate soluble expression and folding in a reducing or intracellular environment are described, wherein a human scFv library was screened, resulting in the isolation of soluble scFv genes that have identical framework regions to the human germline sequence as well as remarkable thermostability and tolerance of CDR3 grafting onto the scFv scaffold.

European Patent Application EP2314622 and PCT Publications WO03008451 and WO03097697 assigned to Esbatech AG and University of Zuerich and naming inventors Ewert, Huber, Honneger and Plueckthun describe the modification of human variable domains and provide compositions useful as frameworks for the creation of very stable and soluble single-chain FAT antibody fragments. These frameworks have been selected for intracellular performance and are thus ideally suited for the creation of scFv antibody fragments or scFv antibody libraries for applications where stability and solubility are limiting factors for the performance of antibody fragments, such as in the reducing environment of a cell. Such frameworks can also be used to identify highly conserved residues and consensus sequences which demonstrate enhanced solubility and stability.

PCT Publication WO02067849 and US Patent Application Publication 2004047891 entitled "Systems devices and methods for intrabody targeted delivery and reloading of therapeutic agents" describe systems, devices and methods for intrabody targeted delivery of molecules. More particularly, some embodiments relate to a reloadable drug delivery system, which enables targeted delivery of therapeutic agents to a tissue region of a subject, in a localized and timely manner.

PCT Publication WO2005063817 and U.S. Pat. No. 7,884,054 assigned to Amgen Inc. and naming inventors Zhou, Shen and Martin describe methods for identifying functional antibodies, including intrabodies. In particular, a homodimeric intrabody is described, wherein each polypeptide chain of the homodimer comprises an Fc region, an scFv, and an intracellular localization sequence. The intracellular localization sequence may cause the intrabody to be localized to the ER or the Golgi. Optionally, each polypeptide chain comprises not more than one scFv.

PCT Publication WO2013138795 by Vogan, et al. and assigned to Permeon Biologics Inc. describes cell penetrating compositions for delivery of intracellular antibodies and antibody-like moieties and methods for delivering them (referred to herein as "AAM moieties" or "an AAM moiety") into a cell. Without being bound by theory, the present disclosure is based, at least in part, on the discovery that an AAM moiety can be delivered into a cell by complexing the AAM moiety with a cell penetrating polypeptide having surface positive charge (referred to herein as a "Surf+ Penetrating Polypeptide"). Examples of some applications of intraphilin technology are also provided.

PCT Publication WO2010004432 assigned to the Pasteur Institute describes immunoglobulins from camelidae (camels, dromedaries, llamas and alpacas), about 50% of which are antibodies devoid of light chain. These heavy-chain antibodies interact with the antigen by the virtue of only one single variable domain, referred to as VHH(s), VHH domain (s) or VHH antibody (ies). Despite the absence of light chain, these homodimeric antibodies exhibit a broad antigen-binding repertoire by enlarging their hypervariable regions, and can act as a transbody and/or intrabody in vitro as well as in vivo, when the VHH domain is directed against an intracellular target.

PCT Publication WO2014106639 describes a method for identifying a cellular target involved in a cell phenotype by identifying an intrabody that can modify a cell phenotype and identifying a direct or indirect cellular target of the intrabody. In particular, intrabodies 3H2-1, 3H2-VH and 5H4 are capable of inhibiting the degranulation reaction in mast cells triggered by an allergic stimulus; furthermore, intrabodies 3H2-1 and 5H4 directly or indirectly targeted a protein of the ABCF1 family and C120RF4 family, respectively. These ABCF1 and C120RF4 inhibitors are said to be useful in therapy, in particular for treating allergic and/or inflammatory conditions.

PCT Publication WO0140276 assigned to Urogenesis Inc. generally describes the possibility of inhibition of STEAP (Six Transmembrane Epithelial Antigen of the Prostate) proteins using intracellular antibodies (intrabodies).

PCT Publication WO02086505 assigned to University of Manchester and US Patent Application Publication US2004115740 naming inventors Simon and Benton describe a method for the intracelular analysis of a target molecule, wherein intrabodies are said to be preferred. In one embodiment, a vector (designated pScFv-ECFP) capable of expressing an anti-MUC1 intrabody coupled to CFP is described.

PCT Publication WO03095641 and WO0143778 assigned to Gene Therapy Systems Inc. describe compositions and methods for intracellular protein delivery, and intrabodies are generally described.

PCT Publication WO03086276 assigned to Selective Genetics Inc. describes a platform technology for the treatment of intracellular infections. Compositions and methods described therein include non-target specific vectors that target infectable cells via linked ligands that bind and internalize through cell surface receptors/moieties associated with infection. The vectors comprise exogenous nucleic acid sequences that are expressed upon internalization into a target cell. Vector associated ligands and nucleic acid molecules may be altered to target different infectious agents. In addition, the invention provides methods of identifying epitopes and ligands capable of directing internalization of a vector and capable of blocking viral entry.

PCT Publication WO03062415 assigned to Erasmus University describes a transgenic organism comprising a polynucleotide construct encoding an intracellular antibody which disrupts the catalysis of the production of the xenoantigen galactose alpha 1,3 galactose and/or a polynucleotide construct which encodes an intracellular antibody which binds specifically to a retrovirus protein, such as a PERV particle protein. Cells, tissues and organs of the transgenic organism may be used in xenotransplantation.

PCT Publication WO2004099775 entitled "Means for detecting protein conformation and applications thereof" describes the use of scFv fragments as conformation-specific antibodies for specifically detecting a conformational protein state, said to have applications as sensors for following in livings cells, upon intracellular expression, the behavior of endogeneous proteins.

PCT Publication WO2008070363 assigned to Imclone Systems Inc. describes a single domain intrabody that binds to an intracellular protein or to an intracellular domain of an intracellular protein, such as Etk, the endothelial and epithelial tyrosine kinase, which is a member of the Tec family of non-receptor tyrosine kinases. Also provided is a method of inhibiting an intracellular enzyme, and treating a tumor in a patient by administering the intrabody or a nucleic acid expressing the intrabody.

PCT Publication WO2009018438 assigned to Cornell Research Foundation Inc. describes a method of identifying a protein that binds to a target molecule and has intracellular functionality, by providing a construct comprising a DNA molecule encoding the protein which binds to the target molecule, with the DNA molecule being coupled to a stall sequence. A host cell is transformed with the construct and then cultured under conditions effective to form, within the host cell, a complex of the protein whose translation has been stalled, the mRNA encoding the protein, and ribosomes. The protein in the complex is in a properly folded, active form and the complex is recovered from the cell. This method can be carried out with a cell-free extract preparation containing ribosomes instead of a host cell. The present invention also relates to a construct which includes a DNA molecule encoding a protein that binds to a target molecule and an SecM stalling sequence coupled to the DNA molecule. The DNA molecule and the SecM stalling sequence are coupled with sufficient distance between them to permit expression of their encoded protein, within the cell, in a properly folded, active form. The use of intrabodies is generally described.

PCT Publication WO2014030780 assigned to Mogam Biotech Research Institute describes a method named Tat-associated protein engineering (TAPE), for screening a target protein having higher solubility and excellent thermostability, in particular, an immunoglobulin variable domain (VH or VL) derived from human germ cells, by preparing a gene construct where the target protein and an antibiotic-resistant protein are linked to a Tat signal sequence, and then expressing this within E. coli. Also disclosed are human or engineered VH and VL domain antibodies and human or engineered VH and VL domain antibody scaffolds having solubility and excellent thermostability, which are screened by the TAPE method. Also provided is a library including random CDR sequences in the human or engineered VH or VL domain antibody scaffold screened by the TAPE method, a preparing method thereof, a VH or VL domain antibody having binding ability to the target protein screened by using the library, and a pharmaceutical composition including the domain antibody.

European Patent Application EP2422811 describes an antibody that binds to an intracellular epitope; such intrabodies comprise at least a portion of an antibody that is capable of specifically binding an antigen and preferably does not contain operable sequences coding for its secretion and thus remains within the cell. In one embodiment, the intrabody comprises a scFv. The scFv polypeptide further comprises a polypeptide linker between the VH and VL domains which enables the scFv to form the desired structure for antigen binding. Also described is a specific embodiment in which the intrabody binds to the cytoplasmic domain of an Eph receptor and prevents its signaling (e.g., autophosphorylation). In another specific embodiment, an intrabody binds to the cytoplasmic domain of a B-type Ephrin (e.g., EphrinB1, EphrinB2 or EphrinB3).

PCT Publication WO2011003896 and European Patent Application EP2275442 describe intracellular functional PCNA-Chromobodies made using nucleic acid molecule encoding a polypeptide specifically binding to proliferating cell nuclear antigen (PCNA). Examples of such polypeptides comprising conservative substitutions of one or more amino acids in one or two framework regions include MANVQLNESGGGLVQPGGSLRLS-CAASGFTFSSYAMSWVRQAPGKGLEWVSDISPS GAVKAYSDSVKGRFTISRDNAKNRLYLQMNSLT-PEDTGEYFCTKVQSPRTRIPAPSS QGTQVTVSS (SEQ ID NO: 263) and MANVQLNESGGGLVQPGGSLRLS-CAASGFTFSSYAMSWVRQAPGKGLEWVSEISPS GAVKAYSDSVKGRFTISRDNAKNRLYLQMNSLT-PEDTGEYFCTKVQSPRTRIPAPSS QGTQVTVSS (SEQ ID NO: 264), including the framework regions of the polypeptides. In the examples, the framework regions as well as the CDR regions involved in the binding of PCNA have been determined.

European Patent Application EP2703485 describes a method for selecting plasma cells or plasmablasts, as well as for producing target antigen specific antibodies, and novel monoclonal antibodies. In one embodiment, cells expressing intracellular immunoglobulin were identified.

Antibody-Coated Agents

In some embodiments, antibodies or antibody fragments described herein may be used to prepare a composition that includes an antibody-coated agent. As used herein, the term "antibody-coated agent" refers to any particle, nanoparticle, molecule, protein, fusion-protein, lipid, liposome, cell membrane, cell, or other structure that includes one or more surface-associated antibodies or antibody fragments. Antibody-coated agents may target one or more glycans, proteins, cells, tissues, and/or organs based on the specificity of the antibody or antibody fragments used for coating.

Antibody-coated agents may include associated, enclosed, or embedded cargo. The cargo may be a detectable label. Some cargo may include one or more therapeutic agent. Such therapeutic agents may include, but are not limited to drugs, chemotherapeutic agents, and cytotoxic agents. Cytotoxic agents may be used to kill or otherwise disable a cell. Cytotoxic agents may include, but are not limited to cytoskeletal inhibitors [e.g. tubulin polymerization inhibitors such as maytansines or auristatins (e.g. monomethyl auristatin E [MMAE] and monomethyl auristatin F [MMAF])] and DNA damaging agents (e.g. DNA polymerization inhibitors such as calcheamicins and duocarmycins).

In some embodiments, antibody-coated agents may include nanoparticles coated with one or more antibodies or antibody fragments described herein. Such antibody-coated agents may target one or more glycan, including, but not limited to cell-associated glycans. Some such antibody-coated agents include one or more cytoxic agents.

Proteins and Variants

Glycan-interacting antibodies of the present invention may exist as a whole polypeptide, a plurality of polypeptides or fragments of polypeptides, which independently may be encoded by one or more nucleic acids, a plurality of nucleic acids, fragments of nucleic acids or variants of any of the aforementioned. As used herein, "polypeptide" means a polymer of amino acid residues (natural or unnatural) linked together most often by peptide bonds. The term, as used herein, refers to proteins, polypeptides, and peptides of any size, structure, or function. In some instances the polypeptide encoded is smaller than about 50 amino acids and the polypeptide is then termed a peptide. If the polypeptide is a peptide, it will be at least about 2, 3, 4, or at least 5 amino acid residues long. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer or tetramer. They may also include single chain or multichain polypeptides and may be associated or linked. The term polypeptide may also apply to amino acid polymers in which one or more amino acid residues are an artificial chemical analogue of a corresponding naturally occurring amino acid.

The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. Ordinarily, variants will possess at least about 50% identity (homology) to a native or reference sequence, and preferably, they will be at least about 80%, more preferably at least about 90% identical (homologous) to a native or reference sequence.

In some embodiments "variant mimics" are provided. As used herein, the term "variant mimic" is one which contains one or more amino acids which would mimic an activated sequence. For example, glutamate may serve as a mimic for phosphoro-threonine and/or phosphoro-serine. Alternatively, variant mimics may result in deactivation or in an inactivated product containing the mimic, e.g., phenylalanine may act as an inactivating substitution for tyrosine; or alanine may act as an inactivating substitution for serine. The amino acid sequences of the glycan-interacting antibodies of the invention may include naturally occurring amino acids and as such may be considered to be proteins, peptides, polypeptides, or fragments thereof.

Alternatively, the glycan-interacting antibodies may include both naturally and non-naturally occurring amino acids.

The term "amino acid sequence variant" refers to molecules with some differences in their amino acid sequences as compared to a native or starting sequence. The amino acid sequence variants may possess substitutions, deletions, and/or insertions at certain positions within the amino acid sequence. "Native" or "starting" sequence should not be confused with a wild type sequence. As used herein, a native or starting sequence is a relative term referring to an original molecule against which a comparison may be made. "Native" or "starting" sequences or molecules may represent the wild-type (that sequence found in nature) but do not have to be the wild-type sequence.

Ordinarily, variants will possess at least 70%, at least 75%, at least 80%, at least 85%, at least 90%, at least 95%, at least 96%, at least 97%, at least 98%, at least 99%, at least 99.5% at least 99.8%, or at least 99.9% sequence identity as compared to a native sequence. "Sequence identity" as it applies to amino acid sequences or nucleotide sequences is defined as the percentage of residues in the candidate sequence that are identical with the residues in the second sequence after aligning the sequences and taking gaps and fragments into consideration, if necessary, to achieve the maximum percent sequence identity. Calculation of the percent identity of two polymeric sequences, for example, can be performed by aligning the two sequences for optimal comparison purposes (e.g., gaps can be introduced in one or both of a first and a second polymeric sequence for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The residues at corresponding positions are then compared. When a position in the first sequence is occupied by the same residue as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, N.J., 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and FASTA Altschul, S. F. et al., J. Molec. Biol., 215, 403 (1990)).

By "homologs" as it applies to amino acid sequences is meant the corresponding sequence of other species having substantial identity to a second sequence of a second species.

"Analogs" is meant to include polypeptide variants which differ by one or more amino acid alterations, e.g., substitutions, additions or deletions of amino acid residues that still maintain the properties of the parent polypeptide.

The present invention contemplates several types of glycan-interacting antibodies which are amino acid based including variants and derivatives. These include substitutional, insertional, deletion and covalent variants and derivatives. As such, included within the scope of this invention are glycan-interacting antibody molecules containing substitutions, insertions and/or additions, deletions and covalently modifications. For example, sequence tags or amino acids, such as one or more lysines, can be added to the peptide sequences of the invention (e.g., at the N-terminal or C-terminal ends). Sequence tags can be used for peptide purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

"Substitutional variants" when referring to proteins are those that have at least one amino acid residue in a native or starting sequence removed and a different amino acid inserted in its place at the same position. The substitutions may be single, where only one amino acid in the molecule has been substituted, or they may be multiple, where two or more amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Insertional variants" when referring to proteins are those with one or more amino acids inserted immediately adjacent to an amino acid at a particular position in a native or starting sequence. "Immediately adjacent" to an amino acid means connected to either the alpha-carboxy or alpha-amino functional group of the amino acid.

"Deletional variants" when referring to proteins, are those with one or more amino acids in the native or starting amino acid sequence removed. Ordinarily, deletional variants will have one or more amino acids deleted in a particular region of the molecule.

As used herein, the term "derivative" is used synonymously with the term "variant" and refers to a molecule that has been modified or changed in any way relative to a reference molecule or starting molecule. In some embodiments, derivatives include native or starting proteins that have been modified with an organic proteinaceous or non-proteinaceous derivatizing agent, and post-translational modifications. Covalent modifications are traditionally introduced by reacting targeted amino acid residues of the protein with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays, or for the preparation of anti-protein antibodies for immunoaffinity purification of the recombinant glycoprotein. Such modifications are within the ordinary skill in the art and are performed without undue experimentation.

Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be present in the proteins used in accordance with the present invention.

Other post-translational modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W.H. Freeman & Co., San Francisco, pp. 79-86 (1983)).

Covalent derivatives specifically include fusion molecules in which proteins of the invention are covalently bonded to a non-proteinaceous polymer. The non-proteinaceous polymer ordinarily is a hydrophilic synthetic polymer, i.e. a polymer not otherwise found in nature. However, polymers which exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. Particularly useful are polyvinylalkylene ethers such a polyethylene glycol, polypropylene glycol. The proteins may be linked to various non-proteinaceous polymers, such as polyethylene glycol, polypropylene glycol or polyoxyalkylenes, in the manner set forth in U.S. Pat. No. 4,640,835; 4,496,689; 4,301,144; 4,670,417; 4,791,192 or 4,179,337.

"Features" when referring to proteins are defined as distinct amino acid sequence-based components of a molecule. Features of the proteins of the present invention include surface manifestations, local conformational shape, folds, loops, half-loops, domains, half-domains, sites, termini or any combination thereof.

As used herein when referring to proteins the term "surface manifestation" refers to a polypeptide based component of a protein appearing on an outermost surface.

As used herein when referring to proteins the term "local conformational shape" means a polypeptide based structural manifestation of a protein which is located within a definable space of the protein.

As used herein when referring to proteins the term "fold" means the resultant conformation of an amino acid sequence upon energy minimization. A fold may occur at the secondary or tertiary level of the folding process. Examples of secondary level folds include beta sheets and alpha helices. Examples of tertiary folds include domains and regions formed due to aggregation or separation of energetic forces. Regions formed in this way include hydrophobic and hydrophilic pockets, and the like.

As used herein the term "turn" as it relates to protein conformation means a bend which alters the direction of the backbone of a peptide or polypeptide and may involve one, two, three or more amino acid residues.

As used herein when referring to proteins the term "loop" refers to a structural feature of a peptide or polypeptide which reverses the direction of the backbone of a peptide or polypeptide and includes four or more amino acid residues. Oliva et al. have identified at least 5 classes of protein loops (J. Mol Biol 266 (4): 814-830; 1997).

As used herein when referring to proteins the term "half-loop" refers to a portion of an identified loop having at least half the number of amino acid resides as the loop from which it is derived. It is understood that loops may not always contain an even number of amino acid residues. Therefore, in those cases where a loop contains or is identified to include an odd number of amino acids, a half-loop of the odd-numbered loop will include the whole number portion or next whole number portion of the loop (number of amino acids of the loop/2+/−0.5 amino acids). For example, a loop identified as a 7 amino acid loop could produce half-loops of 3 amino acids or 4 amino acids (7/2=3.5+/−0.5 being 3 or 4).

As used herein when referring to proteins the term "domain" refers to a motif of a polypeptide having one or more identifiable structural or functional characteristics or properties (e.g., binding capacity, serving as a site for protein-protein interactions.

As used herein when referring to proteins the term "half-domain" means portion of an identified domain having at least half the number of amino acid resides as the domain from which it is derived. It is understood that domains may not always contain an even number of amino acid residues. Therefore, in those cases where a domain contains or is identified to include an odd number of amino acids, a half-domain of the odd-numbered domain will include the whole number portion or next whole number portion of the domain (number of amino acids of the domain/2+/−0.5 amino acids). For example, a domain identified as a 7 amino acid domain could produce half-domains of 3 amino acids or 4 amino acids (7/2=3.5+/−0.5 being 3 or 4). It is also understood that sub-domains may be identified within domains or half-domains, these subdomains possessing less than all of the structural or functional properties identified in the domains or half domains from which they were derived. It is also understood that the amino acids of any of the domain types herein need not be contiguous along the backbone of the polypeptide (i.e., nonadjacent amino acids may fold structurally to produce a domain, half-domain or subdomain).

As used herein when referring to proteins the terms "site" as it pertains to amino acid based embodiments is used synonymous with "amino acid residue" and "amino acid side chain". A site represents a position within a peptide or polypeptide that may be modified, manipulated, altered, derivatized or varied within the polypeptide based molecules of the present invention.

As used herein the terms "termini or terminus" when referring to proteins refers to an extremity of a peptide or polypeptide. Such extremity is not limited only to the first or final site of the peptide or polypeptide but may include additional amino acids in the terminal regions. The polypeptide based molecules of the present invention may be characterized as having both an N-terminus (terminated by an amino acid with a free amino group (NH2)) and a C-terminus (terminated by an amino acid with a free carboxyl group (COOH)). Proteins of the invention are in some cases made up of multiple polypeptide chains brought together by disulfide bonds or by non-covalent forces (multimers, oligomers). These sorts of proteins will have multiple N- and C-termini. Alternatively, the termini of the polypeptides may be modified such that they begin or end, as the case may be, with a non-polypeptide based moiety such as an organic conjugate.

Once any of the features have been identified or defined as a component of a molecule of the invention, any of several manipulations and/or modifications of these features may be performed by moving, swapping, inverting, deleting, randomizing or duplicating. Furthermore, it is understood that manipulation of features may result in the same outcome as a modification to the molecules of the invention. For example, a manipulation which involved deleting a domain would result in the alteration of the length of a molecule just as modification of a nucleic acid to encode less than a full length molecule would.

Modifications and manipulations can be accomplished by methods known in the art such as site directed mutagenesis. The resulting modified molecules may then be tested for activity using in vitro or in vivo assays such as those described herein or any other suitable screening assay known in the art.

Isotopic Variations

The glycan-interacting antibodies of the present invention may contain one or more atoms that are isotopes. As used herein, the term "isotope" refers to a chemical element that has one or more additional neutron. In one embodiment, compounds of the present invention may be deuterated. As used herein, the term "deuterated" refers to a substance that has had one or more hydrogen atoms replaced by deuterium isotopes. Deuterium isotopes are isotopes of hydrogen. The nucleus of hydrogen contains one proton while deuterium nuclei contain both a proton and a neutron. The glycan-interacting antibodies may be deuterated in order to change a physical property of the compound, such as stability, or to allow the compounds to be used in diagnostic and experimental applications.

Conjugates and Combinations

It is contemplated by the present invention that the glycan-interacting antibodies of the present invention may be complexed, conjugated or combined with one or more homologous or heterologous molecules. As used herein, "homologous molecule" means a molecule which is similar in at least one of structure or function relative to a starting molecule while a "heterologous molecule" is one that differs in at least one of structure or function relative to a starting molecule. Structural homologs are therefore molecules which are substantially structurally similar. They can be identical. Functional homologs are molecules which are substantially functionally similar. They can be identical.

Glycan-interacting antibodies of the invention may include conjugates. Such conjugates of the invention may include a naturally occurring substance or ligand, such as a protein (e.g., human serum albumin (HSA), low-density lipoprotein (LDL), high-density lipoprotein (HDL), or globulin); a carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly(L-lactide-co-gly-colied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

The conjugates can also include targeting groups, e.g., a cell or tissue targeting agent or group, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Targeting groups can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Targeting groups may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, multivalent fucose, or aptamers.

The targeting group can be any ligand that is capable of targeting a specific receptor. Examples include, without limitation, folate, GalNAc, galactose, mannose, mannose-6P, apatamers, integrin receptor ligands, chemokine receptor ligands, transferrin, biotin, serotonin receptor ligands, PSMA, endothelin, GCPII, somatostatin, LDL, and HDL ligands. In particular embodiments, the targeting group is an aptamer. The aptamer can be unmodified or have any combination of modifications disclosed herein.

In still other embodiments, glycan-interacting antibodies are covalently conjugated to a cell penetrating polypeptide. The cell-penetrating peptide may also include a signal sequence. The conjugates of the invention can be designed to have increased stability; increased cell transfection; and/or altered biodistribution (e.g., targeted to specific tissues or cell types).

Conjugating moieties may be added to glycan-interacting antibodies such that they allow labeling or flagging targets for clearance. Such tagging/flagging molecules include, but are not limited to ubiquitin, fluorescent molecules, human influenza hemaglutinin (HA), c-myc [a 10 amino acid segment of the human protooncogene myc with sequence EQKLISEEDL (SEQ ID NO: 265)], histidine (His), flag [a short peptide of sequence DYKDDDDK (SEQ ID NO: 266)], glutathione S-transferase (GST), V5 (a paramyxovirus of simian virus 5 epitope), biotin, avidin, streptavidin, horse radish peroxidase (HRP) and digoxigenin.

In some embodiments, glycan-interacting antibodies may be combined with one another or other molecule in the treatment of a disease or condition.

Nucleic Acids

The present invention embraces nucleic acid molecules. In some embodiments, nucleic acids encode antibodies of the invention (including, but not limited to antibodies, antibody fragments, intrabodies and chimeric receptor antigens). Such nucleic acid molecules include, without limitation, DNA molecules, RNA molecules, polynucleotides, oligonucleotides, mRNA molecules, vectors, plasmids and other constructs. As used herein, the term "construct" refers to any recombinant nucleic acid molecule including, but not limited to plasmids, cosmids, autonomously replicating polynucleotide molecules or linear or circular single-stranded or double-stranded DNA or RNA polynucleotide molecules. The present invention also embraces cells programmed or generated to express nucleic acid molecules encoding glycan-interacting antibodies. Such cells may be generated throught the use of transfection, electroporation, viral delivery and the like. Viruses engineered with constructs of the invention may include, but are not limited to lentiviruses, adenoviruses, adeno-associated viruses and phages. In some cases, nucleic acids of the invention include codon-optimized nucleic acids. Methods of generating codon-optimized nucleic acids are known in the art and may include, but are not limited to those described in U.S. Pat. Nos. 5,786,464 and 6,114,148, the contents of each of which are herein incorporated by reference in their entirety. In some embodiments, nucleic acid sequence are codon optimized to improve protein expression or to remove cryptic splice sites.

II. Methods and Uses

Methods of the present disclosure include, but are not limited to, methods of utilizing one or more glycan-interacting antibody for therapeutic, diagnostic, quantitative, bioprocessing, experimental, and/or investigative purposes. Such glycan-interacting antibodies may include anti-STn antibodies.

Therapeutics

Cancer-Related Applications

Aberrant glycosylation is a hallmark of cancer cell transformation. Multiple aberrant glycosylation forms have been described in human cancers, identifying specific tumor-associated carbohydrate antigens (TACAs) as a class of cell surface molecules suitable for specific tumor targeting (Cheever, M. A. et al., Clin Cancer Res. 2009 September 1; 15(17):5323-37). TACA antigen expression has been found in epithelial cancers including, but not limited to, breast, colon, lung, bladder, cervical, ovarian, stomach, prostate, and liver. TACA antigen expression has been found in embryonal cancers including, but not limited to, yolk sac tumors and seminomas. In addition, TACA antigen expression has been found in many melanomas, carcinomas, and leukemias of various tissues (Heimburg-Molinaro et al., Vaccine. 2011 November 8: 29(48):8802-8826). Antibodies of the present invention that target one or more TACA are referred to herein as "anti-TACA antibodies."

MUC1 is a key cell surface glycoprotein that is normally extensively glycosylated but is underglycosylated in tumor cells. Sparse glycosylation of MUC1 leads to exposure of immunogenic antigens. These may be along the MUC1 core peptide sequence or along core carbohydrate residues. These TACAs include, but are not limited to N-acetylgalactosamine (Tn), sialyl($\alpha$2,6)N-acetylgalactosamine (STn) and galactose($\beta$1-3)N-acetylgalactosamine (also known as Thomsen-Friedenreich antigen or TF). It has been estimated that about 80% of all carcinomas express Tn among the core carbohydrates of MUC1 with STn being strongly expressed on human carcinoma cells and linked to cancer progression and metastasis. With few exceptions, Tn and STn are not expressed in normal healthy tissues. Sialic acid forms a prominent epitope on STn. The invention takes advantage of the fact that aberrant Neu5Gc-STn (GcSTn) glycan expression appears to be highly specific to various carcinomas.

In the case of MUC1, Neu5Gc incorporation into STn yields a tumor-specific target, a site that is an attractive target for antibody-based therapies to treat tumor tissue. In some embodiments of the present invention, glycan-interacting antibodies target MUC1 expressing cancer cells that include Neu5Gc. To date, Neu5Gc has been detected in glycoconjugates from a number of human cancer tissues including, but not limited to colon cancer, retinoblastoma tissue, melanoma, breast cancer and yolk sac tumor tissue. In some embodiments of the present invention, methods are contemplated for glycan-interacting antibody treatment of these forms of cancer as well as other forms of cancer, not specifically listed here, characterized by the presence of cancer cells that include Neu5Gc.

Additional antigens that include glycans have been identified that are expressed in correlation with cancer (Heimburg-Molinaro, J. et al., Cancer vaccines and carbohydrate epitopes. Vaccine. 2011 Nov. 8; 29(48):8802-26). These tumor-associated carbohydrate antigens include, but are not limited to blood group Lewis related antigens [including, but not limited to Lewis$^Y$ (Le$^Y$), Lewis$^X$ (Le$^X$), Sialyl Lewis$^X$ (SLe$^X$) and Sialyl Lewis$^A$ (SLe$^A$)], glycosphingolipid-related antigens [including, but not limited to Globo H, stage-specific embryonic antigen-3 (SSEA-3) and glycosphingolipids that include sialic acid], ganglioside-related antigens [including, but not limited to gangliosides GD2, GD3, GM2, fucosyl GM1 and Neu5GcGM3] and polysialic acid-related antigens.

In some embodiments, therapeutics of the present invention may be directed toward Lewis blood group antigens. Lewis blood group antigens include a fucose residue linked to GlcNAc by an $\alpha$1-3 linkage or an $\alpha$1-4 linkage. They may be found on both glycolipids and glycoproteins. Lewis blood group antigens may be found in the body fluid of individuals that are secretors of these antigens. Their appearance on red cells is due to absorption of Lewis antigens from the serum by the red cells.

In some embodiments, therapeutics of the present invention may be directed toward Le$^Y$. Le$^Y$ (also known as CD174) is made up of Gal$\beta$1,4GlcNAC and includes $\alpha$1,2- as well as $\alpha$1,3-linked fucose residues yielding the Fuc$\alpha$(1, 2)Gal$\beta$(1,4)Fuc$\alpha$(1,3)GlcNAc epitope. It is synthesized from the H antigen by $\alpha$1,3 fucosyltransferases which attach the $\alpha$1,3 fucose to the GlcNAc residue of the parent chain. Le$^Y$ may be expressed in a variety of cancers including, but not limited to ovarian, breast, prostate, colon, lung and epithelial. Due to its low expression level in normal tissues and elevated expression level in many cancers, the Le$^Y$ antigen is an attractive target for therapeutic antibodies.

In some embodiments, therapeutics of the present invention may be directed toward Le$^X$. Le$^X$ includes the epitope Gal$\beta$1-4(Fuc$\alpha$1-3)GlcNAc$\beta$-R. It is also known as CD15 and stage-specific embryonic antigen-1 (SSEA-1). This antigen was first recognized as being immunoreactive with sera taken from a mouse subjected to immunization with F9 teratocarcinoma cells. Le$^X$ was also found to correlate with embryonic development at specific stages. It is also expressed in a variety of tissues both in the presence and absence of cancer, but can also be found in breast and ovarian cancers where it is only expressed by cancerous cells.

In some embodiments, therapeutics of the present invention may be directed toward SLe$^A$ and/or SLe$^X$. SLe$^A$ and SLe$^X$ include the structures Neu5Ac$\alpha$2-3Gal$\beta$1-3(Fuc$\alpha$1-4)GlcNAc$\beta$-R and Neu5Ac$\alpha$2-3Gal$\beta$1-4(Fuc$\alpha$1-3)GlcNAc$\beta$-R respectively. Their expression is upregulated in cancer cells. The presence of these antigens in serum correlates with malignancy and poor prognosis. SLe$^X$ is mostly found as a mucin terminal epitope. It is expressed in a number of different cancers including breast, ovarian, melanoma, colon, liver, lung and prostate. In some embodiments of the present invention, SLe$^A$ and SLe$^X$ targets include Neu5Gc (referred to herein as GcSLe$^A$ and GcSLe$^X$, respectively).

In some embodiments, therapeutics of the present invention may be directed toward glycolipids and/or epitopes present on glycolipids, including, but not limited to glycosphingolipids. Glycosphingolipids include the lipid ceramide linked to a glycan by the ceramide hydroxyl group. On the cell membrane, glycosphingolipids form clusters referred to as "lipid rafts".

In some embodiments, therapeutics of the present invention may be directed toward Globo H. Globo H is a cancer-related glycosphingolipid first identified in breast cancer cells. The glycan portion of Globo H includes Fuc$\alpha$(1-2)Gal$\beta$(1-3)GalNAc$\beta$(1-3)Gal$\alpha$(1-4)Gal$\beta$(1-4)Glc$\beta$(1). Although found in a number of normal epithelial tissues, Globo H has been identified in association with many tumor tissues including, but not limited to, small cell lung, breast, prostate, lung, pancreatic, gastric, ovarian and endometrial tumors.

In some embodiments, therapeutics of the present invention may be directed toward gangliosides. Gangliosides are glycosphingolipids that include one or more sialic acid. According to ganglioside nomenclature, G is used as an abbreviation for ganglioside. This abbreviation is followed by the letters M, D, or T referring to the number of sialic acid residues attached (1, 2 or 3 respectively). Finally the numbers 1, 2 or 3 are used to refer to the order of the distance each migrates when analyzed by thin layer chromatography (wherein 3 travels the greatest distance, followed by 2, and then 1). Gangliosides are known to be involved in cancer-related growth and metastasis and may be expressed on the cell surface of tumor cells. Gangliosides expressed on tumor cells may include, but are not limited to GD2, GD3, GM2 and fucosyl GM1 (also referred to herein as Fuc-GM1). In some embodiments of the present invention, glycan-interacting antibodies are directed toward GD3. GD3 is a regulator of cell growth. In some embodiments, GD3-directed antibodies are used to modulate cell growth and/or angiogenesis. In some embodiments, GD3-directed antibodies are used to modulate cell attachment. In some embodiments of the present invention, glycan interacting antibodies are directed toward GM2. In some embodiments, GM2-directed antibodies are used to modulate cell to cell contact. In some embodiments, ganglioside targets of the present invention include one or more Neu5Gc residue. In some embodiments, such targets may include a GM3 variant having Neu5Gc (referred to herein as GcGM3). The glycan component of GcGM3 is Neu5Gcα2-3Galβ1-4Glc. GcGM3 is a known component of tumor cells.

In some embodiments, TACAs targeted by anti-TACA antibodies of the present invention may include, but are not limited to any of those listed in US Publication Nos. US2013/0236486A1, US2013/0108624A1, US2010/0178292A1, US2010/0104572A1, US2012/0039984A1, US2009/0196916A1, and US2009/0041836A1, the contents of each of which are herein incorporated by reference in their entirety.

In some embodiments, the present invention provides methods of treating cancer that include the administration of anti-glycan antibodies taught herein or the administration of compositions of such antibodies (e.g., compositions of anti-glycan antibodies having at least one excipient).

In some embodiments, methods of the disclosure include completely eradicating tumor cells to induce durable initial remission through administration of one or more glycan-interacting antibodies. Other methods include inhibition of tumor resurgence for a period of time, in some cases without excessive toxicity. Such periods of time may be from about 1 month to about 18 months, from about 1 year to about 5 years, from about 2 years to about 10 years, or greater than 10 years.

STn in Cancer

The immune system has multiple mechanisms for promoting anti-tumor cell immune activity including both innate and adaptive immune activity. As used herein, the term "anti-tumor cell immune activity" refers to any activity of the immune system that kills or prevents growth and/or proliferation of tumor cells. In some cases, anti-tumor immune activity includes recognition and tumor cell killing by natural killer (NK) cells and phagocytosis by macrophages. Adaptive anti-tumor immune responses include tumor antigen uptake and presentation by antigen presenting cells (APCs,) such as dendritic cells (DCs,) leading to modulation of T cell anti-tumor activity and/or expansion of B cells with secretion of tumor-specific antibodies. The binding of tumor-specific antibodies to tumors can lead to antibody-dependent cellular cytotoxicity (ADCC) and complement-dependent cytotoxicity (CDC) mechanisms of tumor cell death.

As used herein, the term "immune-resistant tumor cell" refers to a tumor cell that reduces or evades anti-tumor cell immune activity. Some studies indicate that the expression of STn (a known TACA) on tumor cell surfaces or secreted into the tumor cell microenvironment can promote tumor cell evasion of anti-tumor immune activity. As used herein, the term "tumor cell microenvironment" refers to any area adjacent to or surrounding a tumor cell. Such areas include, but are not limited to areas between tumor cells, between tumor and non-tumor cells, surrounding fluids and surrounding components of the extracellular matrix.

Sialylated mucins having STn were demonstrated by Ogata et al to reduce NK cell targeting of tumor cells (Ogata, S. et al., 1992. Canc. Res. 52:4741-6, the contents of which are herein incorporated by reference in their entirety). This study found that the presence of ovine, bovine and porcine submaxillary mucin (OSM, BSM and PSM, respectively) led to nearly one hundred percent inhibition of cytotoxicity (see Table 2 of Ogata et al). Further studies by Jandus et al, demonstrate that some tumor cells can evade NK destruction due to the expression of sialoglycan ligands that can interact with NK cell siglec receptors, leading to NK inhibition (Jandus, C. et al., 2014. JCI. pii: 65899, the contents of which are herein incorporated by reference in their entirety).

Studies by Toda et al., demonstrate that STn may bind CD22 receptors on B cells, leading to decreased signal transduction and reduced B cell activation (Toda, M. et al., 2008. Biochem Biophys Res Commun. 372(1):45-50, the contents of which are herein incorporated by reference in their entirety). Dendritic cells (DCs) can affect adaptive immune activity by modulating T cell activity. Studies by Carrascal et al found that STn expression by bladder cancer cells induced tolerance in DCs, reducing their ability to induce anti-tumor cell immune activity in T cells (Carrascal, M A et al., 2014. Mol Oncol. pii: 51574-7891(14)00047-7, the contents of which are herein incorporated by reference in their entirety). These studies revealed that DCs coming into contact with STn-positive bladder cancer cells displayed a tolorigenic expression profile with low expression of CD80, CD86, IL-12 and TNF-α. Further, DCs were found to modulate regulatory T cells such that the T cells had low expression of IFNγ and high expression of FoxP3. Other studies by van Vliet and others, indicate that DC surface expression of macrophage galactose-type lectin (MGL) can lead to targeting of those cells to tumor tissues (van Vliet, SJ., 2007. Amsterdam: Vrije Universiteit. p1-232 and van Vliet, S J. et al., 2008. J Immunol. 181(5):3148-55, Nollau, P. et al., 2013. J Histochem Cytochem. 61(3):199-205, the contents of each of which are herein incorporated by reference in their entirety). DCs arriving at tissues due to MGL interactions may influence T helper (Th) cells in one of three ways. DCs can induce T cell tolerance, T cell immune activity or downregulation of effector T cells. MGL has been shown to bind to both AcSTn and GcSTn and the affinity has been analyzed in depth (Mortezai, N. et al., 2013. Glycobiology. 23(7):844-52, the contents of which are herein incorporated by reference in their entirety). Interestingly, MUC1 expression on tumors has been shown to lead to T cell tolerance, protecting tumor cells from immune eradication.

In some embodiments, glycan-interacting antibodies (including, but not limited to anti-STn antibodies) of the present invention may be used to treat subjects having one or more tumor cells expressing one or more TACAs. In some cases, glycan-interacting antibodies (including, but not limited to anti-STn antibodies) of the invention may be used to increase anti-tumor cell immune activity toward tumor cells expressing STn. Such antibodies may increase the adaptive immune response and/or the innate immune response toward immune-resistant tumor cells. Some glycan-interacting antibodies may be used to increase NK anti-tumor cell activity. Such glycan-interacting antibodies may, in some cases, block the interaction between glycan receptors expressed on NK cells and STn glycans on cancer cells or in surrounding tissues.

In some embodiments, glycan-interacting antibodies (including, but not limited to anti-STn antibodies) of the invention may be used to increase B cell anti-tumor cell activity. Such antibodies may reduce the interaction between CD22 receptors on B cells and STn glycans on cancer cells or in surrounding tissues. A study by Sjoberg et al. demonstrates that 9-O-acetylation of α2,6-linked sialic acids on glycoproteins also reduced interaction between B cell CD22 receptors and such glycoproteins (Sjoberg, E. R. et al. 1994. JCB. 126(2): 549-562). Another study by Shi et al. reveals that higher levels of 9-O-acetylated sialic acid residues on murine erythroleukemia cells makes these cells more susceptible to complement-mediated lysis (Shi, W-X. et al., 1996. J of Biol Chem. 271(49): 31526-32, the contents of which are herein incorporated by reference in their entirety).

In some embodiments, anti-STn antibodies of the invention are capable of selectively binding non-9-O-acetylated STn, reducing overall STn binding, but reducing tumor cell growth and/or proliferation. (e.g. through increased B cell anti-tumor activity and increased complement-mediated tumor cell destruction). In some embodiments, glycan-interacting antibodies (including, but not limited to anti-STn antibodies) of the invention may be used to increase DC anti-tumor activity. Such antibodies may be used to reduce DC tolerance to tumor cells. Reduced DC tolerance may include increasing DC expression of CD80, CD86, IL-12 and/or TNF-$\alpha$. In some cases, DC anti-tumor cell activity may include promotion of T cell anti-tumor cell activity. Such antibodies may prevent binding between DC MGL and glycans expressed on or around cancer cells.

A study by Ibrahim et al. suggests that high levels of anti-STn antibodies along with endocrine therapy may increase overall survival and time to progression (TTP) in women with metastatic breast cancer (Ibrahim, N. K. et al., 2013. 4(7): 577-584, the contents of which are herein incorporated by reference in their entirety). In this study, anti-STn antibody levels were elevated after vaccination with STn linked to keyhole-limpet Hemocyanin (KLH). In some embodiments, anti-STn antibodies of the invention may be used in combination with endocrine therapy (e.g. tamoxifen and/or an aromatase inhibitor).

In some embodiments, glycan-interacting antibodies of the invention may be used to reduce or eliminate cancerous cells and/or cells expressing STn. Such cells include cells that may be part of a tumor.

In some cases, the present invention provides methods of reducing tumor volumes by administering anti-glycan antibodies of the invention to subjects with one or more tumors. Reduction in tumor volumes may be determined by comparing tumor volumes in a subject before and after treatment, or by comparing tumor volumes between anti-glycan antibody-treated and control treated subjects.

In some cases, anti-glycan antibodies of the invention may be administered to achieve a desired percent reduction in tumor volume in a subject. This may assessed by determining the volume of one or more tumors (e.g., through the use of calipers or imaging techniques like CT scan) in a subject before and after treatment with an anti-glycan antibody and then calculating the percent reduction in tumor volume from the two values. In some embodiments, tumor volume in subjects treated with anti-glycan antibodies may be reduced by from about 0.1% to about 2%, from about 1% to about 5%, from about 3% to about 12%, from about 10% to about 30%, from about 20% to about 50%, from about 40% to about 60%, from about 50% to about 75%, from about 60% to about 85%, or from about 80% to about 99%. In some cases, tumor volume in subjects treated with anti-glycan antibodies may be reduced by at least 1%, by at least 5%, by at least 10%, by at least 20%, by at least 40%, by at least 50%, by at least 60%, by at least 80%, by at least 85%, by at least 90%, by at least 95%, by at least 98%, by at least 99%, or by 100%.

In some cases, anti-glycan antibodies of the invention may be administered to achieve a desired percent tumor growth inhibition (% T/C). % T/C is calculated by determining tumor volumes in treated subjects and comparing them to tumor volumes in non-treated or placebo-treated subjects. In some embodiments, the present invention provides methods of reducing tumor volume in a subject by administering an anti-glycan antibody, wherein the % T/C is from about 0.1% to about 1%, from about 0.5% to about 5%, from about 2% to about 20%, from about 3% to about 16%, from about 10% to about 30%, from about 20% to about 60%, or from about 40% to about 80%. In some cases the % T/C is at least 80%. In some cases the % T/C is less than 0.1%.

In some embodiments, antibodies used to reduce tumor volumes in subjects may be selected based on their ability to bind cell surface glycans (e.g., STn) and/or their ability to kill cancerous cells. In some instances, antibodies may be selected based on their half-maximal effective concentration (EC50) for binding cells having cell surface STn. ECso values for such antibodies may be determined, e.g., through flow cytometry analysis with cells having cell surface STn. Such antibodies may have EC50 values of from about 0.1 nM to about 2 nM, from about 0.5 nM to about 5 nM, from about 1 nM to about 10 nM, from about 5 nM to about 20 nM, or from about 10 nM to about 30 nM.

In some embodiments, the present invention provides methods of killing cancer cells, such as tumor cells, by administering one or more antibodies presented herein.

In some embodiments, the present disclosure provides a method of identifying a subject in need of anti-STn antibody treatment by isolating cancer cells (including, but not limited to cancer stem cells) and/or obtaining biopsy material from a subject and screening the cancer cells and/or biopsy material for STn expression. According to such methods, subjects with cancer cells and/or biopsy material expressing STn are deemed to likely benefit from anti-STn antibody treatment or to be in need of anti-STn antibody treatment (e.g., treatment with one or more antibody described herein). In some cases, antibodies described herein may be used for screening of cancer cells and/or biopsy material. Cancer cells may be screened in vitro by culturing the cancer cells and detecting STn expression using standard immunological assays (e.g., ELISA, Western blot, or other standard immunological assays). In some cases, cancer cells may be screened for STn expression using flow cytometry techniques. In other embodiments, cancer cells may be grown in culture and tested for viability after treatment with anti-STn antibodies that are antibody-drug conjugates (ADCs). Such ADCs may include a cytotoxic agent, including, but not limited to those described herein. Cytotoxic agents may include MMAE. Anti-STn antibodies may include humanized antibodies, including, but not limited to, those described herein. In other embodiments, cancer cells may be screened by using the cancer cells to form tumors in mice (e.g., NOD/SCID mice). The tumors developed in mice may be screened by preparing tissue sections from such tumors and subjecting the tissue sections to immunohistochemical analysis using anti-STn antibodies, including, but not limited to anti-STn antibodies described herein. In some cases, the tumors formed in mice may be assessed for changes in tumor volume after treatment of the mice with anti-STn antibodies, including, but not limited to anti-STn antibodies described herein. Such anti-STn antibodies may include ADCs. ADCs may include one or more cytotoxic agent, including, but not limited to any of those described herein (e.g., MMAE). Subjects with cancer cells that demonstrate STn expression after screening may be determined to be in need of anti-STn antibody treatment.

In some embodiments, the present disclosure provides a method of identifying an antibody suitable for treating cancer by isolating cancer cells (including, but not limited to cancer stem cells) from a subject, screening the cancer cells for STn expression, and contacting STn-expressing cancer cells with one or more candidate antibodies specific for STn to determine whether any of the one or more candidate antibodies are able to bind the cancer cells. As used herein, the term "candidate antibody" refers to an antibody or one of a group of antibodies that are being evaluated for one or more purposes. Subject cancer cells may be screened in vitro by culturing the cancer cells and detecting STn expression using STn-detecting antibodies with standard immunological assays (e.g., ELISA, Western blot, or other standard immunological assays) or using flow cytometry techniques. As used herein, the term "STn-detecting antibody" refers to an antibody that binds STn and that allows for observation of such binding either through the presence of an incorporated detectable label or through the use of a secondary antibody having a detectable label. In other embodiments, screening the cancer cells may involve using them to form tumors in mice (e.g., NOD/SCID mice). Screening may be carried out by assessing the mouse tumors for expression of STn or for reduction in volume after administration of anti-STn antibodies, including, but not limited to ADCs.

In some embodiments, the present invention includes methods of evaluating the suitability of an antibody for treating cancer in a subject by obtaining cancer cells from a subject, using the cancer cells to form tumors in mice (e.g., NOD/SCID mice), administering an anti-STn antibody to the mice, and measuring changes in tumor volume in the mice, wherein if the tumor volume in the mice is decreased, the anti-STn antibody is determined to be suitable for treating cancer in the subject. In some cases, the anti-STn antibodies are administered multiple times. According to such methods, antibodies may be administered hourly, daily, weekly, monthly, and/or yearly. In some cases, antibodies are administered weekly for a period of from about 2 to about 12 weeks. In some cases, antibodies are administered weekly for a period of at least 12 weeks.

STn expression has been implicated in contributing to the metastatic potential of cancer cells. According to some methods of the disclosure, glycan-interacting antibodies may be used to reduce metastasis. Such methods may include the reduction of metastasis by from about 1% to about 15%, from about 5% to about 25%, from about 10% to about 50%, from about 20% to about 60%, from about 30% to about 70%, from about 40% to about 80%, from about 50% to about 90%, from about 75% to about 95%, or at least 95%.

Cancer Stem Cells as Therapy Targets

Cancer stem cells or CSCs (also called tumor initiating cells) are a subset of cancer cells within a heterogeneous tumor population that drive the initiation, growth, dissemination, and recurrence of primary and metastatic tumors (Karsten and Goletz, SpringerPlus, 2013, 2, 301), which can occur in varying proportions of the total population depending on tumor type. CSCs are distinguished from terminally differentiated cells by their capacity to self-renew and give rise to non-CSC, differentiated progeny (Gupta et al., Nature medicine, 2009, 15, 1010-1012). These properties are akin to those of normal stem cells. Such distinctions between normal stem cells and CSCs have important implications for therapy.

An increasing number of cell-surface biomarkers have been identified that purport to differentiate CSCs from their non-CSC counterparts (Medema et al., Nature cell biology, 2013, 15, 338-344; Zoller, Cancer, 2011, 11, 254-267). These may include, but are not limited to CD44, CD133, CD117, and aldehyde dehydrogenase isoform 1 (ALDH1). Although some of these derive from studies of mouse tumors and human cell lines, others have been validated using primary human tumor samples. One of these, the membrane-spanning CD44 glycoprotein, or hyaluronan receptor, which is a well-known constituent of a variety of tumor types, has also more recently found acceptance as a bona fide CSC marker in human cancers, and in fact is the one most frequently observed (Lobo et al., 2007, 23, 675-699).

CD44 exists in several variant isoforms generated by alternative splicing events occurring among the 20 exons and 19 introns of the full-length CD44 gene (Williams et al, Experimental biology and medicine, 2013, 238, 324-338). Growing experimental evidence points to the supporting role of CD44 and its variants in contributing to the innate metastatic and drug resistant phenotype of CSCs (Negi et al., Journal of drug targeting, 2012, 20, 561-573), in part due to modulation of intracellular signal transduction pathways (Williams et al, Experimental biology and medicine, 2013, 238, 324-338). Additionally, patients with triple negative breast cancer, along with several other cancer types, that display high levels of CD44 cells are known to have a poor prognosis and higher mortality (Negi et al., Journal of drug targeting, 2012, 20, 561-573). These observations support the notion that targeting CD44 offers a means of treating cancer through inhibition or elimination of CSCs, in addition to mature cancer cells. Indeed, numerous approaches to targeting CD44 have been attempted experimentally with varying degrees of success. These include a wide range of technologies that include the use of conjugated and unconjugated antibodies, nano-carrier drug systems, and hyaluronan-conjugated drugs (Negi et al., Journal of drug targeting, 2012, 20, 561-573). In several instances, however, toxic effects were observed in in vivo studies; these untoward side effects may be attributable to the widespread occurrence of CD44 and variants on the membranes of most vertebrate cells (Naor et al., Seminars in cancer biology, 2008, 18, 260-267), in addition to its presence on the surface of the targeted CSCs and mature tumor cells. Targeting CD44 protein, which is a constituent of normal human stem cells (Williams et al, Experimental biology and medicine, 2013, 238, 324-338), can also harm normal stem cell function (Leth-Larsen et al., Molecular medicine, 2012, 18, 1109-1121). Although a large body of research points to the desirability of targeting CD44 protein on CSCs, as well as on mature tumor cells, the intrinsic problem with this approach remains the present difficulty in designing inhibitors that will spare normal tissue as well as normal stem cells.

Another well-known tumor antigen with implications to CSC biology is the epithelial mucin MUC1, a membrane tethered glycoprotein that is differentially expressed at high levels on the majority of adenocarcinomas but at low levels or not at all on normal epithelial cells. MUC1 has recently been identified as a CSC biomarker on a variety of neoplasias including breast (Engelmann et al., Cancer research, 2008, 68, 2419-2426), and pancreatic cancers, where its expression is correlated with high metastasis and poor prognosis. As a constituent of CSCs, MUC1 has been shown to function in cell adhesion, proliferation, survival, and signaling (Engelmann et al., Cancer research, 2008, 68, 2419-2426) and may also be co-expressed with CD44 (Leth-Larsen et al., Molecular medicine, 2012, 18, 1109-1121). Immunotherapeutic approaches for targeting MUC1 in cancer are being pursued using vaccines as well as other approaches, but primarily in the context of mature cancer cell therapy (Julien et al., Biomolecules, 2012, 2, 435-466; Acres et al., Expert review of vaccines, 2005, 4, 493-502).

Cancer stem cells have been hypothesized to be generated through the epithelial-to-mesenchymal (EMT) transition (Gupta et al., Nature medicine, 2009, 15, 1010-1012), and/or reversely the mesenchymal-to-epithelial (MET) transition that occurs at the site of metastasis (Leth-Larsen et al., Molecular medicine, 2012, 18, 1109-1121) (also called CSCs plasticity where non-CSCs can give rise to CSCs). This discovery further underscores the need to eliminate both CSCs and non-CSCs in a tumor population.

Recent studies with enriched CSC populations has revealed that these cells, unlike the bulk of the tumor, are relatively quiescent and are preferentially resistant to many types of current therapies, including chemotherapy and radiation (Leth-Larsen et al., Molecular medicine, 2012, 18, 1109-1121). Thus current therapeutic strategies target non-CSC components of the tumor, leaving CSCs largely unaffected only to re-emerge after appropriate cues to reform recurrent primary tumors at the initial site or to disseminate to distant sites, colonize, and create metastatic disease, the major cause of cancer mortality.

Current understanding of the properties of cancer stem cells clearly emphasized the need not only to target the bulk of cells present in tumors, as is current practice, but also the CSC compartment in order to potentially effect complete cures.

As discussed above, strategies that have been developed based on tumor (including CSCs) associated biomarkers face a challenge that most cancer biomarkers are also present in normal cells including normal stem cells. A therapy that targets a protein biomarker to eliminate CSCs, may also target normal stem cells, causing elimination of normal cells.

Tumor-Specific Glycans in CSCs

Aberrant forms of glycosylation, including appearance of the Thomsen-nouveau (Tn) antigen (GalNAc-O-Ser/Thr), have been described in numerous human cancers, identifying glycans as an entirely novel class of tumor-associated carbohydrate antigens suitable for specific tumor targeting (Rabu et al., Future oncology, 2012, 8, 943-960). The formation of the sialyl derivative of Tn (STn) is mediated by the sialyl transferase ST6GalNAc-I which adds sialic acid in an $\alpha 2,6$ linkage to the Tn antigen. The sialylation of STn prevents further sugar additions, thus truncating further glycan extensions (Schultz et al., Cancer metastasis reviews, 2012, 31, 501-518).

While the presence of STn in normal adult human tissues is rare, STn occurs in various human cancers, including ovarian, bladder, breast, cervical, colon, and lung cancer, among others (Ferreira et al., Molecular oncology, 2013, 7, 719-731; Kinney et al., Cancer, 1997, 80, 2240-2249). Further, the presence of STn in tumors is associated with metastatic disease, poor prognosis, and reduced overall survival (Ferreira et al., Molecular oncology, 2013, 7, 719-731; Kinney et al., Cancer, 1997, 80, 2240-2249); therefore, STn is considered a highly attractive target for cancer detection and therapy. There are two distinct forms of sialic acid—Neu5Ac and Neu5Gc—located at the terminal position of STn. The Neu5Ac-sialylated form is predominant in humans since humans cannot synthesize Neu5Gc due to an inactive CMP-Neu5Ac hydroxylase (CMAH) gene. However, consumption of Neu5Gc-rich foods leads to foreign Neu5Gc incorporation into human cells, especially in carcinomas. Previous studies have shown that solid tumors take up and express the Neu5Gc form of sialic acid (Inoue et al., Glycobiology, 2010, 20, 752-762; Malykh et al., Biochimie, 2001, 83, 623-634; Padler-Karavani et al., Cancer research, 2011, 71, 3352-3363). mAbs that bind to both glyco-isoforms of STn that are potential cancer targets: Neu5Ac-STn (AcSTn) and Neu5Gc-STn (GcSTn) (i.e., designated as pan-STn antibodies).

STn accumulation is associated with specific somatic mutations observed repeatedly in solid tumors and with the inactivation of the gene that encodes the molecular chaperone Core 1 Beta3-Galactosyltransferase-Specific Molecular Chaperone (COSMC), which is required for the formation of active T-synthase (Ju et al., Nature, 2005, 437, 125). T-synthase competes with ST6GalNAc-I for the GalNAc substrate and therefore when inactivated by mutation results in elevated STn synthesis. Additionally, STn accumulation can also result from increased expression of ST6GalNAc-I, which is often observed (Brockhausen et al., Biological chemistry, 2001, 382, 219-232; Ikehara et al., Glycobiology, 1999, 9, 1213-1224). De novo expression of STn can modulate carcinoma cells, change the malignant phenotype, and lead to more aggressive cell behaviors (Pinho et al., Cancer letters, 2007, 249, 157-170). As such, STn is not only an interesting cancer biomarker and therapeutic target, but interfering with STn function offers the intriguing potential to have significant functional, anti-metastatic therapeutic benefits.

Although it is well-known that glycosylation of cellular glycoproteins is altered in cancer, it appears that aberrant glycosylation is selective with respect to both the glycoprotein and glycan in question. In fact, in human tumor CSCs only CD44 and MUC1 are major carriers of the STn antigen (Cazet et al., Breast cancer research: BCR,2010, 12,204; Julien et al., Glycobiology, 2006, 16, 54-64), immediately suggesting a selective approach for targeting not only mature tumor cells but also CSCs. Whereas MUC1 is a normal surface constituent of some epithelial cells where it serves a barrier function, tumor-associated MUC1 is characterized by hypoglycosylation and increased sialylation on CSCs in the same fashion as observed in mature cancer cells, with STn appearing as a specific marker for both CSCs and mature tumor cells (Curry et al., Journal of surgical oncology,2013, 107, 713-722). The aberrant oligosaccharide profile of MUC1 gives rise to the expression of neomarkers such as sialyl-Lea (used in the CA19-9 test), sialyl-Le', and sialyl-Tn (TAG-72), as well as the cryptic epitopes such as Tn in cancer cells (e.g., CSCs). In addition, because of underglycosylation, the peptide core of the mucin becomes exposed such that epitopes within the core (not accessible within normal tissue-derived MUC1) may serve as potential antigens.

Clinical approaches targeting STn have thus far consisted solely of STn vaccines. The most advanced clinical candidate is Theratope, a therapeutic vaccine consisting of STn coupled to keyhole limpet hemocyanin. In in vivo mouse studies Theratope immunization induced a potent antibody response that was shown to mediate a delay in the growth of injected STn-expressing mammary carcinoma cells (Julien et al., British journal of cancer, 2009, 100, 1746-1751). However, Theratope failed to meet its primary endpoint in a phase III clinical trial in metastatic breast cancer. A leading hypothesis for why the Theratope trial missed its primary endpoint is that the patient population was not evaluated for STn expression prior to enrollment. Since STn expression in breast cancer is highly heterogeneous between patients, ranging from 25%-80% depending on the study and detection method, lack of ability to correlate STn expression with response may have masked any benefit from Theratope. Importantly, a subset of patients receiving hormonal therapy showed a significant 7.5 month increase in median overall survival when treated with Theratope compared to hormone therapy alone (Ibrahim et al., Journal of clinical oncology: official journal of the American Society of Clinical Oncology, 2004, 22, 2547; and Miles et al., The oncologist, 2011, 16, 1092-1100), validating the therapeutic potential of targeting STn in particular patient populations. Additionally, since the immune response often varies considerably between vaccinated patients, vaccine approaches lack the ability to control or modulate antibody titer, resulting in wide ranges of therapeutic antibody exposure among patients. Nonetheless, Theratope was well tolerated with minimal toxicity, demonstrating the safety of targeting STn for cancer therapy.

The growing understanding of the molecular basis of STn expression in cancer cells strongly suggests that cells that express STn on any cell surface protein will also express STn on many (if not all) other O-glycosylated cell surface proteins, rendering it an excellent widely-distributed cancer-associated therapeutic target. Thus, STn positive cancer cell populations may be enriched for CSCs. In addition, recent data demonstrate that abrogation of STn expression renders cancers less aggressive with significant reductions in metastatic behavior (Gill et al., Proceedings of the National Academy of Sciences of the United States of America 2013, 110, E3152-3161).

Anti-STn Antibodies Targeting CSCs as Cancer Treatment

Several anti-STn antibodies have been described in the field, but some demonstrate low specificity towards the STn antigen or sialylated isoforms. For example, the commercial B72.3 anti-STn antibody has been shown to bind not only to STn but also to the Tn antigen (Bapat, S. A. (2010) Human ovarian cancer stem cells. Reproduction 140, 33-41). The availability of monoclonal antibodies (mAbs) targeting STn, engineered to induce antibody-dependent cellular cytotoxicity (ADCC) and/or complement-dependent cytotoxicity (CDC), or conjugated with a cytotoxic payload [e.g. antibody drug conjugate (ADC)], offers the potential of a significant therapeutic benefit for cancer patients with STn-expressing tumors. In addition, such antibodies would also allow for the development of a companion diagnostic to pre-select patients most likely to respond to therapy.

STn is often present on one or more of CSC surface antigens, and together they serve to promote the stemness and chemoresistance properties associated with CSCs. Thus, anti-STn antibodies offer a CSC-associated cancer targeting agent with the potential not only to directly kill CSCs via direct engagement and/or ADCC, but also offer a unique opportunity to bind to a wide array of cell-surface proteins and interfere with their associated functions essential for CSC viability, self-renewal, and replication.

As discuss herein, the rationale and advantages of targeting STn on CSCs may include: (1) many tumor-specific truncated glycoproteins carry STn in cancer; (2) STn is a unique glycan target expressed preferentially on CD44, MUC1, and potentially other important cell-surface markers, on both CSCs and mature tumor cells, irrespective of proliferation status, allowing for targeting of both of these tumor components by a single therapeutic agent; (3) STn is also a component of CA-125, a biomarker of ovarian cancer and others; (4) STn is a component of the ovarian CSC marker CD44. Therefore, the use of pan-STn murine mAbs, targeting an epitope that encompasses both the Neu5Ac and Neu5Gc forms of sialic acid linked to Tn, will bind to and kill or impair the function of CSCs and, by virtue of the common epitope, non-CSC tumor cells.

In some embodiments, the present invention provides new anti-pan STn mAb(s) for specific elimination of human CSCs as well as mature tumor cells. In one aspect of the present invention, the anti-STn antibody will target the validated STn glycan itself—not a particular glycopeptide or carrier protein, which should offer the broad potential of binding to CD44, MUC1, or other STn-glycosylated markers on both CSC and non-CSC tumor populations. In some embodiments, glycan-interacting antibodies of the present disclosure may be used to target stem cell-related proteins that have one or more associated glycans. As used herein, the term "stem cell-related protein" refers to any protein that is associated with one or more stem cells. Such proteins may include, but are not limited to, cell surface proteins, markers, intracellular proteins, transcription factors, and proteins involved in cellular signaling that affect stem cell survival, growth, replication, and/or maintenance. In some cases, such glycans include STn. Stem cell-related proteins may include, but are not limited to, Notch, Hedgehog, CD44, CD117, CD133, and integrin.

Given the exceptional specificity in targeting tumor-associated STn, the present invention may spare normal tissues, including normal adult stem cells, thereby allowing for an excellent therapeutic window.

In accordance with the present invention, provided herein is a unique immunotherapeutic solution aimed at eradicating human neoplasias by eliminating both CSCs and mature cancer cells contained within the tumor compartment. The present invention provides therapies and methods specifically targeting tumors, which now include targeting CSCs, and hence expanding the therapeutic window by targeting associated tumor-specific carbohydrate moieties of these potential targets. The elimination is specifically conferred through targeting tumor associated cell-surface sialylated Tn antigen (STn) structures that are uniquely present in cancer tissue, including cancer stem cells Ovarian CSCs Ovarian cancer is the leading gynecological cancer effecting women in the U.S. During 2013. It is estimated that 22,240 women will be diagnosed with and 14,030 will die of this disease, making it the fifth leading cause of female-related cancer deaths and the most lethal gynecologic malignancy in the U.S. (Siegel et al., Cancer statistics, 2013. CA: a cancer journal for clinicians 63, 11-30). This high mortality can be ascribed to non-symptomatic onset, late-stage initial diagnosis, aggressiveness of this type of cancer, and a general lack of therapeutically targetable genetic changes. The current standard of care is tumor debulking followed by taxane and platinum based chemotherapy. While this initial treatment results in ~70% of patients achieving an initial complete clinical response, a majority of these patients will unfortunately relapse with chemoresistant disease (Foster et al., Cancer letters, 2013, 338, 147-157; and McCann et al., PloS one, 2011,6, e28077). In part, recurrent disease has been attributable, as with other cancer types, to the presence of CSCs within the total tumor population. Indeed, ovarian CSCs have been identified and shown to be resistant to chemo- and radiotherapy (Burgos-Ojeda et al., Cancer letters, 2012, 322, 1-7). Thus, again as the case with other forms of cancer, eliminating CSCs along with mature cells in the tumor population offers the best hope to manage recurrent disease and ideally effect cures.

In some embodiments of the present invention, ovarian CSCs may be targeted for ovarian cancer treatment. Although CD133 is the most widely studied of putative ovarian CSC markers, it is recognized that CD44, a known carrier of STn as discussed above, is associated with ovarian cancer and is included in the set of markers that identify ovarian CSCs (Zhang et al., Cancer research, 2008, 68, 4311-4320; Foster et al., Cancer letters, 2013, 338, 147-157; and Zoller, Cancer, 2011, 11, 254-267). Further, STn is expressed on the well-known ovarian cancer biomarker CA-125 (MUC16), as well as on MUC1, where the levels of these STn-associated mucins in serum have been used recently as further differentiators of cancerous versus benign ovarian disease. Elevated serum levels of STn occur in ~50% of ovarian cancer patients and correlate with a lower 5-year survival rate (Kobayashi et al., Journal of clinical oncology: official journal of the American Society of Clinical Oncology, 1991, 9, 983-987; Kobayashi et al., Journal of clinical oncology: official journal of the American Society of Clinical Oncology,1992, 10, 95-101; and Chen et al., Journal of proteome research, 2013, 12, 1408-1418). Finally, Vathipadiekal et al. in a study of differential gene expression between human primary ovarian carcinoma CSCs and non-CSC populations found that the expression of STn-generating sialyl transferase ST6GalNAc-I did not differ among cells from the two compartments.

In some embodiments, the present invention provides antibodies for targeting CSCs to prevent control or cure cancer related to CSCs. Such antibodies may include anti-STn antibodies, including, but not limited to any of those described (or derived from any of those described) in international application number PCT/US14/60079, the contents of which are herein incorporated by reference in their entirety. Further anti-STn antibodies may include antibody 3F1 (SBH Sciences, Natick, Mass.) or derivatives thereof, including recombinant antibodies with CDRs from 3F1 and/or humanized derivatives.

In some embodiments, antibodies of the invention may be used to target ovarian cancer stem cells that are resistant to other forms of treatment. Such treatments may include chemotherapy. Chemotherapy treatments may include any of those described herein and may include, but are not limited to treatment with carboplatin and/or paclitaxel. Methods of targeting chemotherapy-resistant ovarian cancer stem cells may take advantage of changes in cell surface glycan expression in ovarian cancer stem cells occurring after chemotherapy treatment. In some cases, chemotherapy-resistant ovarian cancer stem cells express STn before and/or after chemotherapy treatment. After chemotherapy treatments, some chemotherapy-resistant ovarian cancer stem cells may proliferate resulting in a population of tumor cells that express one or more cell surface glycans (e.g., STn) that distinguish these cells from surrounding cells. Anti-glycan antibodies, including, but not limited to those presented herein, may be used to kill such populations of ovarian cancer stem cells by targeting these distinguishing glycans. In some cases, anti-STn antibodies may be provided. Such antibodies may include, but are not limited to any of the antibodies described herein. In some cases, such antibodies may have at least one variable domain that is human or humanized. In some embodiments, subjects having one or more chemotherapy-resistant ovarian cancer stems cells may be treated with anti-STn antibodies of the invention after treatment with carboplatin and/or paclitaxel.

Colorectal Cancer

Colorectal cancer (CRC) has the $4^{th}$ largest incidence, and is currently the third leading cause of cancer-related death in the US. Currently, 20% of patients are diagnosed with metastatic disease and roughly 50% of patients with CRC will eventually develop metastases. For those diagnosed with metastatic disease, the 5-year survival rate is 13.1%. In patients with metastatic colon cancer (mCRC), there is precedence for use of therapeutic antibodies (e.g., monoclonal antibodies), such as anti-epidermal growth factor receptor (EGFR) monoclonal antibodies and anti-VEGF monoclonal antibodes.

In some embodiments, glycan-interacting antibodies of the present disclosure may be used to treat CRC and/or mCRC. In some cases, such glycan-interacting antibodies are anti-STn antibodies, including, but not limited to any of those described herein. Glycan-interacting antibodies used to treat CRC and/or mCRC may be conjugated with a cytotoxic agent (e.g., MMAE and MMAF). Glycan-interacting antibodies may be used in combination with other therapies such as therapies with a chemotherapeutic agent (e.g., fluoropyrimidine, oxaliplatin, and/or irinotecan) and/or with a therapeutic antibody (e.g., bevacizumab and/or anti-EGFR).

According to some embodiments, glycan-interacting antibodies used to treat colorectal cancer may be administered at a dose of from about 0.5 mg/kg to about 20 mg/kg. For example, antibodies may be administered at doses of from about 0.5 mg/kg to about 2 mg/kg, from about 1 mg/kg to about 5 mg/kg, from about 2.5 mg/kg to about 10 mg/kg, or from about 5 mg/kg to about 20 mg/kg.

Combined Cancer Therapies

In some embodiments, compounds and compositions of the invention may be combined with one or more additional forms of cancer treatment. In some cases, such additional forms may include chemotherapeutic treatments. Accordingly, some methods of the invention include methods of treating cancer by administering at least one chemotherapeutic agent to a subject having cancer and administering a glycan-interacting antibody. Such antibodies may include anti-STn antibodies described herein.

As used herein, the term, "chemotherapy" refers to a form of treatment using chemical substances. Such chemical substances are referred to herein as "chemotherapeutic agents." In the treatment of cancer, chemotherapeutic agents are agents that slow or prohibit the proliferation of cancer cells.

In some embodiments, chemotherapeutic agents of the invention may be nucleic acid antagonistic agents. Such agents primarily affect proliferating cells, such as cancer cells, and typically function by disrupting DNA repair and/or synthesis. In some cases, nucleic acid antagonistic agents are alkylating agents (e.g., bifunctional alkylators or monofunctional alkylators). Alkylating agents are reactive compounds that may be used to disrupt DNA synthesis in dividing cells. Alklyating agents of the invention may include, but are not limited to, cyclophosphamide, mechlorethamine, chlorambucil, melphalan, decarbazine, nitrosoureas, and temozolomide.

In other embodiments, nucleic acid antagonistic agents of the invention may include anthracyclines. Anthracyclines are bacterial derived compounds that disrupt nucleic acid synthesis. Anthracyclines of the invention may include, but are not limited to daunorubicin, doxorubicin, epirubicin, idarubicin, mitoxantrone, and valrubicin. In some embodiments, anthracyclines may be liposomally encapsulated.

In further embodiments, nucleic acid antagonistic agents may be histone deacetylase inhibitors and/or topoisomerase inhibitors. These inhibitors prevent changes in DNA supercoiling that are necessary for DNA synthesis and repair. Inhibitors of topoisomerase I may include, but are not limited to irinotecan and topotecan. Inhibitors of topoisomerase II may include, but are not limited to etoposide, teniposide, and tafluposide. Histone deacetylase inhibitors may include, but are not limited to vorinostat and romidepsin.

In some embodiments, nucleic acid antagonistic agents of the invention may include nucleotide analogs and/or nucleotide precursor analogs. Proliferating cells require nucleotides for incorporation into nucleic acids in resulting daughter cells. Nucleotide analogs may disrupt the formation of such nucleic acids or render them non-functional. Nucleotide analogs of the invention may include, but are not limited to azacitidine, azathioprine, capecitabine, doxifluridine, fluorouracil, gemcitabine, hydroxyurea, mercaptopurine, methotrexate, and tioguanine. In some embodiments, leucovorin as administered along with nucleotide analogs to enhance their effects and/or reduce harmful side effects.

In some embodiments, nucleic acid antagonistic agents of the invention are platinum-based agents. These agents disrupt nucleic acids by cross-linking them. Platinum-based agents of the invention may include, but are not limited to oxaliplatin, cisplatin, and carboplatin.

In some cases, chemotherapeutic agents of the invention include cytoskeletal disrupting agents. Actively dividing cells undergo major cytoskeletal changes that may be disrupted by these compounds. Cytoskeletal disrupting agents of the invention may include, but are not limited to vinca alkaloids, epothilones, paclitaxel, ABRAXANE® (paclitaxel protein-bound particles for injectable suspension), and docetaxel.

Although effective at targeting proliferating cancer cells, chemotherapeutic agents often affect some non-cancerous cells as well. Because of this, their administration is typically limited by dose, length of treatment, or area of treatment. Further, because chemotherapeutic agents primarily affect proliferating cells, non-proliferating cancer stem cells may remain viable after treatment and capable of reforming cancerous cells. Accordingly, in some embodiments, method of the invention include methods of treating cancer in which at least one chemotherapeutic agent is first administered to a subject having cancer, followed by administration of a glycan-interacting antibody. In some cases, the glycan-interacting antibody is selected to target a specific cell surface glycan associated with chemotherapy-resistant cells. As used herein, the term "chemotherapy-resistant" is used to refer to cells that are unaffected by or that have limited susceptibility to chemotherapy treatment.

Methods of targeting chemotherapy-resistant cells (e.g., chemotherapy-resistant cancer stem cells) may take advantage of changes in STn expression in these cells occurring after chemotherapy treatment. In some cases, chemotherapy-resistant cells express STn before and/or after chemotherapy treatment. In some cases, cell surface STn expression in chemoresistant cells may be increased following chemotherapy treatment [e.g., due to altered expression of factors involved in STn synthesis (e.g., STnGalNAc I, T-synthase, or Cosmc), decreased degradation, or other mechanisms leading to increased cell surface STn expression]. After chemotherapy treatments, some chemotherapy-resistant cells expressing cell surface STn may proliferate resulting in a population of STn-expressing tumor cells that are chemotherapy-resistant. In some embodiments, anti-STn antibodies may be used to target chemotherapy-resistant cells. In some cases, these cells are cancer stem cells. Accordingly, methods of the invention may include methods of administering an anti-STn antibody to target STn-expressing chemotherapy-resistant cells present after administration of one or more chemotherapeutic agent.

The identification of cell surface glycans on chemotherapy-resistant cells may be carried out by analyzing chemotherapy-resistant cells after chemotherapy treatment for the identity of cell surface glycans that distinguish these cells from surrounding cells. In some embodiments, such cell surface glycans may include, but are not limited to mucin-related antigens (including, but not limited to Tn, STn and Thomsen-Friedenreich antigen), blood group Lewis related antigens [including, but not limited to Lewis$^Y$ (Le$^Y$), Lewis$^X$ (Le$^X$), Sialyl Lewis$^X$ (SLe$^X$) and Sialyl Lewis$^A$ (SLe$^A$)], glycosphingolipid-related antigens [including, but not limited to Globo H, stage-specific embryonic antigen-3 (SSEA-3) and glycosphingolipids having sialic acid], ganglioside-related antigens [including, but not limited to gangliosides GD2, GD3, GM2, fucosyl GM1 and Neu5GcGM3] and polysialic acid-related antigens. Many of such antigens are described in International Publication No. WO2015054600, the contents of which are herein incorporated by reference in their entirety. Analyses carried out to identify cell surface glycans expressed on cancer stem cells remaining after chemotherapy may be carried out according to any methods known in the art. In some cases, such analyses are carried out by obtaining a tissue sample and assessing the expression of cell surface glycans in the tissue sample using one or more immunological assay (e.g., immunohistochemical analysis, ELISA analysis, flow cytometric analysis, antibody array, or mass spectrometry).

In some embodiments, chemotherapy-resistant cells are analyzed to assess the expression level of cell surface STn. This may be carried out by obtaining a tissue sample and analyzing the sample for expression of cell surface STn [for example, using one or more immunological assay (e.g., immunohistochemical analysis, ELISA analysis, flow cytometric analysis, antibody array, or mass spectrometry)]. Where chemotherapy-resistant cells express STn, anti-STn antibodies may be administered to a subject after administration of chemotherapeutic agents.

In some embodiments, one or more tumors are primed for treatment with one or more glycan-interacting antibodies by contacting the tumors with at least one chemotherapeutic agent. According to such embodiments, priming a tumor for glycan-interacting antibody treatment refers to reducing proliferating cells in a tumor, leaving one or more chemotherapy-resistant tumor cells behind. According to such methods, glycan-interacting antibodies may be used to further reduce tumor volumes by eliminating chemotherapy-resistant cells that remain after treatment with one or more chemotherapeutic agents.

Administration of glycan-interacting antibodies after administration of one or more chemotherapeutic agent may be carried out from about 1 day to about one year after treatment with one or more chemotherapeutic agents (e.g., from about 1 day to about 10 days, from 1 week to about 4 weeks, from about 2 weeks to about 10 weeks, from about 1 month to about 3 months, from about 2 months to about 6 months, or from about 3 months to about 12 months). In some cases, administration of glycan-interacting antibodies may be carried out at least 1 year after treatment with one or more chemotherapeutic agents.

In some embodiments, multiple rounds of administration with one or more chemotherapeutic agents may be followed by administration of glycan-interacting antibodies (e.g., 2 rounds, 3 rounds, 4 rounds, 5 rounds, 6 rounds, 7 rounds, 8 rounds, 9 rounds, 10 rounds, or at least 10 rounds). In some cases, rounds of treatment are repeated until tissue analyses reveal that cancerous cells and/or chemotherapy-resistant cells are reduced or eliminated.

The dose of chemotherapeutic agents may be adjusted based on the size of the subject receiving treatment. In some embodiments, doses include those described by Calvo et al. 2014 (Calvo, E. et al., 2014. Chemotherapeutic agents and their uses, dosages, and toxicities. Cancer Network. p1-12). In some cases, doses are adjusted based on the surface area of the subject being treated [typically measured in square meters ($m^2$)]. Chemotherapeutic agents of the invention may be administered at doses of from about 0.01 mg/m$^2$ to about 1 mg/m$^2$, from about 0.1 mg/m$^2$ to about 5 mg/m$^2$, from about 1 mg/m$^2$ to about 20 mg/m$^2$, from about 10 mg/m$^2$ to about 100 mg/m², from about 50 mg/m² to about 500 mg/m², from about 200 mg/m² to about 2000 mg/m², or from about 1000 mg/m² to about 10000 mg/m². In some cases, chemotherapeutic agents of the invention are administered at a dose of at least 10000 mg/m². According to some methods, chemotherapeutic agents are administered intravenously.

In some embodiments, administration of chemotherapeutic agents includes administration of carboplatin. According to some methods, carboplatin is administered at a dose of from about 200 mg/m² to about 400 mg/m². In some embodiments, administration of chemotherapeutic agents includes administration of paclitaxel. According to some methods, paclitaxel is administered at a dose of from about 20 mg/m² to about 300 mg/m².

In some embodiments, glycan-interacting antibodies of the present disclosure are administered in combination with anti-angiogenic therapies (e.g., bevacizumab). According to some embodiments, methods of treating cancer are provided that include identifying a subject in need of cancer treatment, wherein the subject has cancer that is not fully responsive to treatment with at least one poly-ADP-ribose polymerase inhibitor, and administering an anti-STn antibody to the subject. Such anti-STn antibodies may include any of those known in the art or described herein.

Immune-Related Targets

In some embodiments, glycan-interacting antibodies of the invention may be immunomodulatory antibodies. As used herein, an immunomodulatory antibody is an antibody that enhances or suppresses one or more immune function or pathway.

Many bacterial glycans are known to include sialic acid. In some cases, such glycans allow bacteria to evade the innate immune system of hosts, including, but not limited to humans. In one example, bacterial glycans inhibit alternate complement pathway activation through factor H recognition. In another example, bacterial glycans mask underlying residues that may be antigenic. Some bacterial glycans participate in cell signaling events through activation of inhibitory sialic acid binding Ig-like lectins (Siglecs) that dampen the immune response to entities including certain sialylated moieties (Chen, X. et al., Advances in the biology and chemistry of sialic acids. ACS Chem Biol. 2010 Feb. 19; 5(2):163-76). In some embodiments, glycan-interacting antibodies of the present invention may be used to treat immune complications related to bacterial glycans.

Due to the foreign nature of Neu5Gc as described herein, some Neu5Gc glycans are immunogenic resulting in immune related destruction of cells and other entities where these glycans may be expressed. Such autoimmune destruction may be pathogenic. In some embodiments, glycan-interacting antibodies may be used to treat patients suffering from autoimmune disorders related to Neu5Gc glycans.

In some embodiments, immunomodulatory antibodies of the invention may be used to promote or suppress T cell-mediated immunity. Such antibodies may interact with one or more glycans present on T cells, T cell-related proteins and/or on one or more other cell types that interact with T cells. Immunomodulatory antibodies that enhance T cell mediated immunity may be used to stimulate T cell mediated targeting of cancer cells.

In some tumors, infiltration by tumor-associated macrophages (TAMs) may lead to immunosuppression promoting tumor cell viability and growth. This is thought to be due to immunosuppressive cell signaling that occurs through interactions between myeloid C-type lectin receptors (CLRs) present on TAMs and tumor-associated mucins (Allavena, P. et al., Clin Dev Immunol. 2010; 2010:547179). In some embodiments, binding of immunomodulatory antibodies of the invention to one or more tumor-associated mucin or TACA prevents immunosuppressive cell signaling in TAMs.

Anti-Viral Applications

In some embodiments, glycan-interacting antibodies of the invention may target viruses. Viral coat proteins and viral envelopes often include glycans, referred to herein as viral surface glycans. Such glycans may be targets of glycan-interacting antibodies. In some embodiments, viral surface glycans include sialyl-STn. In a further embodiment, viral surface glycans may include GcSTn. Viruses that may be targeted by glycan-interacting antibodies include, but are not limited to HIV, influenza, rhinovirus, varicella-zoster, rotavirus, herpes (e.g. types 1 and 2), hepatitis (e.g. types A, B, C, D and E), yellow fever and human papillomavirus.

Other Therapeutic Applications

In some embodiments, glycan-interacting antibodies of the invention may act to alter or control proteolytic events. In some embodiments, glycan-interacting antibodies of the present invention may be internalized into cells prior to binding to targets.

Veterinary Applications

It is contemplated that glycan-interacting antibodies of the invention will find utility in the area of veterinary care including the care and treatment of non-human vertebrates. As described herein, the term "non-human vertebrate" includes all vertebrates with the exception of Homo sapiens, including wild and domesticated species such as companion animals and livestock. Non-human vertebrates include mammals, such as alpaca, banteng, bison, camel, cat, cattle, deer, dog, donkey, gayal, goat, guinea pig, horse, llama, mule, pig, rabbit, reindeer, sheep water buffalo, and yak. Livestock includes domesticated animals raised in an agricultural setting to produce materials such as food, labor, and derived products such as fiber and chemicals. Generally, livestock includes all mammals, avians and fish having potential agricultural significance. In particular, four-legged slaughter animals include steers, heifers, cows, calves, bulls, cattle, swine and sheep.

Bioprocessing

In some embodiments of the invention are methods for producing biological products in host cells by contacting the cells with one or more glycan-interacting antibody (such as an antibody or fusion protein) capable of modulating gene expression, or altering levels and/or types of glycans produced wherein such modulation or alteration enhances production of biological products. According to the present invention, bioprocessing methods may be improved by using one or more of the glycan-interacting antibodies of the present invention. They may also be improved by supplementing, replacing or adding one or more glycan-interacting antibodies.

Diagnostics

In some embodiments, compounds and compositions of the invention may be used as diagnostics. In some cases, antibodies of the invention may be used to identify, label or stain cells, tissues, organs, etc. expressing target antigens. In further embodiments, antibodies of the invention may be used to identify STn present in tissue sections (i.e., histological tissue sections), including tissue known or suspected of having cancerous cells. Such methods of using antibodies of the invention may in some cases be used to identify cancerous cells or tumors in tissue sections. Tissue sections may be from any tissue or organ including, but not limited to breast, colon, pancreatic, ovarian, brain, liver, kidney, spleen, lung, skin, stomach, intestine, esophagous, or bone.

In some embodiments, diagnostic methods of the invention may include the analysis of one or more cells or tissues using immunohistochemical techniques. Such methods may include the use of one or more of any of the glycan-interacting antibodies described herein. Immunohistochemical methods of the invention may include staining tissue sections to determine the presence and/or level of one or more glycosylated proteins or other markers. Tissue sections may be derived from subject tumors (e.g., patient tumors and animal tumors such as animal model tumors). Tissue sections may come from formalin-fixed or unfixed fresh frozen tissues. In some case, tissue section come from formalin fixed paraffin-embedded (FFPE) tissues. Glycan-interacting antibodies described herein may be used as primary antibodies. Primary antibodies are used to contact tissue sections directly and bind to target epitopes. Primary antibodies may be directly conjugated with a detectable label or may be detected through the use of a detection agent such as a secondary antibody. In some embodiments, primary antibodies or detection agents include an enzyme that can be used to react with a substrate to generate a visible product (e.g., precipitate). Such enzymes may include, but are not limited to horse raddish peroxidase, alkaline phosphatase, beta-galactosidase, and catalase.

Anti-STn antibodies described herein may be used according to immunohistochemical methods of the present disclosure to detect STn-glycosylated proteins in tissues or cells. In some cases, these antibodies are used to detect and/or determine the level of STn in tumor tissues. Such tumor tissues may include tumor tissues included in tumor microarrays. Suitable tumor types include, but are not limitd to breast, colon, ovarian, pancreatic, skin, intestinal, lung, and brain tumors. Levels of anti-STn antibodies used in immunohistochemical staining techniques may be varied to increase visible staining or to decrease background levels of staining. In some embodiments, antibody concentrations of from about 0.01 µg/ml to about 50 µg/ml are used. For example, antibody concentrations of from about 0.01 µg/ml to about 1 µg/ml, from about 0.05 µg/ml to about 5 µg/ml, from about 0.1 µg/ml to about 3 µg/ml, from about 1 µg/ml to about 10 µg/ml, from about 2 µg/ml to about 20 µg/ml, from about 3 µg/ml to about 25 µg/ml, from about 4 µg/ml to about 30 µg/ml, or from about 5 µg/ml to about 50 µg/ml may be used.

In some embodiments, diagnostic methods of the invention include methods of generating an STn-linked glycoprotein profile. As used herein the term "STn-linked glycoprotein profile" refers to a set of information indicating the level and/or identity of STn-linked glycoproteins in a sample or subject. Methods of generating an STn-linked glycoprotein profile may be carried out on a sample obtained from a subject. Such samples may be biological samples including, but not limited to, any of those described herein. Biological samples may be cellular samples. In some cases, cellular samples may include at least one tumor cell. In some embodiments, tumor cell samples may include BRCA1 mutant or non-BRCA1 mutant tumor cells.

Glycoproteins included in STn-linked glycoprotein profiles may include, but are not limited to, cancer cell markers, stem cell markers, cancer stem cell markers, and stem cell-related proteins. In some embodiments, glycoproteins identified and/or quantitated as part of a STn-linked glycoprotein profile may include, but are not limited to CD44, CD133, CD117, integrin, Notch, and Hedgehog.

Levels and/or identities of STn-linked glycoproteins in STn-linked glycoprotein profiles may be determined according to any methods known in the art for identifying proteins and/or quantitating protein levels. In some embodiments, such methods may include, but are not limited to mass spectrometry, array analysis (e.g., antibody array or protein array), Western blotting, flow cytometry, immunoprecipitation, and ELISA. STn-linked glycoproteins may in some cases be immunoprecipitated from a sample prior to analysis. Such immunoprecipitation may be carried out using an anti-STn antibody. Anti-STn antibodies used for immunoprecipitation of STn-linked glyocproteins may include any of those known in the art or described herein. In some embodiments, STn-glycoproteins are immunoprecipitated from biological samples using an anti-STn antibody and then identified and/or quantitated using mass spectrometry.

In some embodiments, cancer treatments are informed by STn-linked glycoprotein profile information. Accordingly, the present disclosure provides methods of treating cancer that include obtaining a sample from a subject in need of cancer treatment, generating an STn-linked glycoprotein profile from the sample, selecting a glycan-interacting antibody that binds to an STn-glycosylated protein from the STn-linked glycoprotein profile, and administering the glycan-interacting antibody to the subject. Glycan-interacting antibodies administered according to such methods may include one or more CDRs or variable domains taught herein.

In some embodiments, methods of the present disclosure may be used as companion diagnostics. As used herein, the term "companion diagnostic" refers to an assay, the results of which aid in the diagnosis or treatment of subjects. Companion diagnostics may be useful for stratifying patient disease, disorder or condition severity levels, allowing for modulation of treatment regimen and dose to reduce costs, shorten the duration of clinical trial, increase safety and/or increase effectiveness. Companion diagnostics may be used to predict the development of a disease, disorder or condition and aid in the prescription of preventative therapies. Some companion diagnostics may be used to select subjects for one or more clinical trials. In some cases, companion diagnostic assays may go hand-in-hand with a specific treatment to facilitate treatment optimization.

In some embodiments, methods of the present disclosure may be useful as companion diagnostics for diseases, disorders and/or conditions related to cancer. Some companion diagnostics of the present invention may be useful for predicting and/or determining the severity of one or more forms of cancer. Some companion diagnostics of the present invention may be used to stratify subjects by risk of developing one or more forms of cancer. Some companion diagnostics of the present invention may be used to facilitate and expedite drug development for cancer therapeutics.

STn Expression-Modified Cells

In some embodiments, the present disclosure provides modified cells having altered STn levels. Such cells may may be used for various purposes (e.g., experimental, therapeutic, antibody testing etc.). In some cases, methods of the present disclosure include methods of enhancing the expression of ST6GalNAc I in one or more cells or tissues. This may result in the generation of one or more cells having increased expression of cellular STn (e.g., surface-expressed STn). Expression of ST6GalNAc I may be enhanced, for example, by introducing one or more vectors carrying a ST6GalNAc I expression construct. Such expression constructs may be designed with the natural ST6GalNAc I promoter or with a promoter to enhance gene expression. Promoters configured for enhancement of gene expression may have constitutively or overly active promoter elements. In some cases, promoters may be configured for inducible gene expression. Such promoters may become active or have elevated activity when contacted with factors that activate inducible elements of the promoter. STn expression constructs may include hST6GalNAc I pRc-CMV as described in Julien, S. et al., 2001. Glycoconj J, 18: 883-93, the contents of which are herein incorporated by reference in their entirety. In some embodiments, expression constructs may encode other factors involved in STn synthesis and/or expression. Such factors may include, but are not limited to, T-synthase, and Core 1 Beta3-Galactosyltransferase-Specific Molecular Chaperone (COSMC). In some embodiments, cells with minimal STn expression are converted to STn-expressing cells. Such cells may include, but are not limited to, SKOV3 cells, BRCA1 mutant cells, and non-mutant BRCA1 cells.

Also provided are modified cells having decreased STn expression relative to unmodified cells. Accordingly, methods of the present disclosure include methods of repressing STn expression. Such methods may include reducing ST6GalNAc I expression. In some embodiments, such methods may include the administration of one or more nucleic acid molecules that repress ST6GalNAc I expression. Such nucleic acid molecules may include, but are not limited to inhibitory RNA (e.g., RNAi or silencer siRNA). In some embodiments, other factors involved in STn synthesis and/or expression may be reduced. Such factors may include, but are not limited to T-synthase and COSMC. In some embodiments, cells naturally expressing STn are converted to STn-deficient cells. Such cells may include, but are not limited to, OVCAR3 cells and OVCAR4 cells.

III. Pharmaceutical Compositions

In some embodiments, the present disclosure includes pharmaceutical compositions. Such pharmaceutical compositions may include antibodies of the present disclosure and/or fragments, peptides, or proteins derived from such antibodies. Pharmaceutical compositions may be characterized by one or more of bioavailability, therapeutic window and/or volume of distribution.

Bioavailability

Glycan-interacting antibodies, when formulated into a composition with a delivery/formulation agent or vehicle as described herein, can exhibit an increase in bioavailability as compared to a composition lacking a delivery agent as described herein. As used herein, the term "bioavailability" refers to the systemic availability of a given amount of glycan-interacting antibodies administered to a mammal. Bioavailability can be assessed by measuring the area under the curve (AUC) or the maximum serum or plasma concentration (Cmax) of the unchanged form of a compound following administration of the compound to a mammal. AUC is a determination of the area under the curve plotting the serum or plasma concentration of a compound along the ordinate (Y-axis) against time along the abscissa (X-axis). Generally, the AUC for a particular compound can be calculated using methods known to those of ordinary skill in the art and as described in G. S. Banker, Modern Pharmaceutics, Drugs and the Pharmaceutical Sciences, v. 72, Marcel Dekker, New York, Inc., 1996, herein incorporated by reference.

The Cmax value is the maximum concentration of the compound achieved in the serum or plasma of a mammal following administration of the compound to the mammal. The Cmax value of a particular compound can be measured using methods known to those of ordinary skill in the art. The phrases "increasing bioavailability" or "improving the pharmacokinetics," as used herein mean that the systemic availability of a glycan-interacting antibody, measured as AUC, $C_{max}$, or $C_{min}$ in a mammal is greater, when co-administered with a delivery agent as described herein, than when such co-administration does not take place. In some embodiments, the bioavailability of the glycan-interacting antibody can increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%.

Therapeutic window

Glycan-interacting antibodies, when formulated into a composition with a delivery agent as described herein, can exhibit an increase in the therapeutic window of the administered glycan-interacting antibody composition as compared to the therapeutic window of the administered glycan-interacting antibody composition lacking a delivery agent as described herein. As used herein "therapeutic window" refers to the range of plasma concentrations, or the range of levels of therapeutically active substance at the site of action, with a high probability of eliciting a therapeutic effect. In some embodiments, the therapeutic window of the glycan-interacting antibody when co-administered with a delivery agent as described herein can increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%.

In some embodiments, glycan-interacting antibodies are detectable in subject samples for at least 1 days, at least 2 days, at least 5 days, at least 10 days, at least 14 days, at least 1 month, at least 2 months, at least 6 months, or at least a year after administration. Where antibodies are conjugated with cytotoxic agents (e.g., MMAE), the drug to antibody ratio (DAR) may remain stable. In some cases, the DAR may change by less than 1%, by less than 5%, by less than 10%, by less than 20%, by less than 30%, by less than 40%, by less than 50%, by less than 60%, or by less than 75% over a given period of time (e.g., the period of time in which antibody levels are detectable in subject samples).

Volume of Distribution

Glycan-interacting antibodies, when formulated into a composition with a delivery agent as described herein, can exhibit an improved volume of distribution (Vdist), e.g., reduced or targeted, relative to a composition lacking a delivery agent as described herein. The volume of distribution ($V_{distant}$) relates the amount of the drug in the body to the concentration of the drug in the blood or plasma. As used herein, the term "volume of distribution" refers to the fluid volume that would be required to contain the total amount of the drug in the body at the same concentration as in the blood or plasma: V&A equals the amount of drug in the body/concentration of drug in blood or plasma. For example, for a 10 mg dose and a plasma concentration of 10 mg/L, the volume of distribution would be 1 liter. The volume of distribution reflects the extent to which the drug is present in the extravascular tissue. A large volume of distribution reflects the tendency of a compound to bind to the tissue components compared with plasma protein binding. In a clinical setting, $V_{dist}$ can be used to determine a loading dose to achieve a steady state concentration. In some embodiments, the volume of distribution of the glycan-interacting antibody when co-administered with a delivery agent as described herein can decrease at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%.

In some embodiments, glycan-interacting antibodies are included in compositions and/or complexes with one or more pharmaceutically acceptable excipients. Pharmaceutical compositions may optionally include one or more additional active substances, e.g. therapeutically and/or prophylactically active substances. General considerations in the formulation and/or manufacture of pharmaceutical agents may be found, for example, in Remington: The Science and Practice of Pharmacy 21$^{st}$ ed., Lippincott Williams & Wilkins, 2005 (incorporated herein by reference).

In some embodiments, compositions are administered to humans, human patients or subjects. For the purposes of the present disclosure, the phrase "active ingredient" generally refers to glycan-interacting antibodies to be delivered as described herein.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition that includes a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may include between 0.1% and 100%, e.g., between 0.5 and 50%, between 1-30%, between 5-80%, or at least 80% (w/w) active ingredient. In one embodiment, active ingredients are antibodies directed toward cancer cells.

Formulation

Glycan-interacting antibodies of the invention can be formulated using one or more excipients to: (1) increase stability; (2) increase cell permeability; (3) permit the sustained or delayed release (e.g., from a formulation of the glycan-interacting antibody); and/or (4) alter the biodistribution (e.g., target the glycan-interacting antibody to specific tissues or cell types). In addition to traditional excipients such as any and all solvents, dispersion media, diluents, or other liquid vehicles, dispersion or suspension aids, surface active agents, isotonic agents, thickening or emulsifying agents, preservatives, formulations of the present invention can include, without limitation, liposomes, lipid nanoparticles, polymers, lipoplexes, core-shell nanoparticles, peptides, proteins, cells transfected with the glycan-interacting antibodies (e.g., for transplantation into a subject) and combinations thereof.

Excipients

As used herein, the term "excipient" refers to any substance combined with a compound and/or composition of the invention before use. In some embodiments, excipients are inactive and used primarily as a carrier, diluent or vehicle for a compound and/or composition of the present invention. Various excipients for formulating pharmaceutical compositions and techniques for preparing the composition are known in the art (see Remington: The Science and Practice of Pharmacy, 21st Edition, A. R. Gennaro, Lippincott, Williams & Wilkins, Baltimore, Md., 2006; incorporated herein by reference).

The use of a conventional excipient medium is contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

Formulations of the pharmaceutical compositions described herein may be prepared by any method known or hereafter developed in the art of pharmacology. In general, such preparatory methods include the step of associating the active ingredient with an excipient and/or one or more other accessory ingredients.

A pharmaceutical composition in accordance with the present disclosure may be prepared, packaged, and/or sold in bulk, as a single unit dose, and/or as a plurality of single unit doses.

Relative amounts of the active ingredient, the pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical compositions.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM®), sodium lauryl sulfate, quaternary ammonium compounds, etc., and/or combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and VEEGUM® [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [TWEEN®20], polyoxyethylene sorbitan [TWEENn®60], polyoxyethylene sorbitan monooleate [TWEEN®80], sorbitan monopalmitate [SPAN®40], sorbitan monostearate [Span®60], sorbitan tristearate [Span®65], glyceryl monooleate, sorbitan monooleate [SPAN®80]), polyoxyethylene esters (e.g. polyoxyethylene monostearate [MYRJ®45], polyoxyethylene hydrogenated castor oil, polyethoxylated castor oil, polyoxymethylene stearate, and SOLUTOL®), sucrose fatty acid esters, polyethylene glycol fatty acid esters (e.g. CREMOPHOR®), polyoxyethylene ethers, (e.g. polyoxyethylene lauryl ether [BRIJ®30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, PLUORINC®F 68, POLOXAMER®188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include, but are not limited to, antioxidants, chelating agents, antimicrobial preservatives, antifungal preservatives, alcohol preservatives, acidic preservatives, and/or other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL®115, GERMABEN®II, NEOLONE™, KATHON™, and/or EUXYL®.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof.

Excipients such as cocoa butter and suppository waxes, coloring agents, coating agents, sweetening, flavoring, and/or perfuming agents can be present in the composition, according to the judgment of the formulator.

In some embodiments, anti-glycan antibodies of the invention are formulated with an excipient that includes citrate and/or NaCl. Such composition may include from about 1 mM to about 10 mM, from about 2 mM to about 20 mM, from about 5 mM to about 50 mM, from about 10 mM to about 100 mM, from about 50 mM to about 200 mM, or from about 100 mM to about 1,000 mM citrate. Further compositions may include from about 1 mM to about 10 mM, from about 5 mM to about 20 mM, from about 15 mM to about 50 mM, from about 30 mM to about 60 mM, from about 50 mM to about 200 mM, from about 100 mM to about 300 mM, or from about 250 mM to about 1000 mM NaCl.

Vehicles

Liposomes, Lipoplexes and Lipid Nanoparticles

Glycan-interacting antibodies of the present invention may be formulated using one or more liposomes, lipoplexes, or lipid nanoparticles. In one embodiment, pharmaceutical compositions including glycan-interacting antibodies further include liposomes. Liposomes are artificially-prepared vesicles which may include one or more lipid bilayers and may be used as a delivery vehicle for the administration of nutrients and pharmaceutical formulations. Liposomes can be of different sizes such as, but not limited to, a multilamellar vesicle (MLV) which may be hundreds of nanometers in diameter and may contain a series of concentric bilayers separated by narrow aqueous compartments, a small unicellular vesicle (SUV) which may be smaller than 50 nm in diameter, and a large unilamellar vesicle (LUV) which may be between 50 and 500 nm in diameter. Liposome design may include, but is not limited to, opsonins or ligands in order to improve the attachment of liposomes to unhealthy tissue or to activate events such as, but not limited to, endocytosis. Liposomes may contain a low or a high pH in order to improve the delivery of the pharmaceutical formulations.

The formation of liposomes may depend on the physicochemical characteristics such as, but not limited to, the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimization size, polydispersity and the shelf-life of the vesicles for the intended application, and the batch-to-batch reproducibility and possibility of large-scale production of safe and efficient liposomal products.

In one embodiment such formulations may also be constructed or compositions altered such that they passively or actively are directed to different cell types in vivo.

Formulations can also be selectively targeted through expression of different ligands on their surface as exemplified by, but not limited by, folate, transferrin, N-acetylgalactosamine (GalNAc), and antibody targeted approaches.

Liposomes, lipoplexes, or lipid nanoparticles may be used to improve the efficacy of glycan-interacting antibody function as these formulations may be able to increase cell transfection with glycan-interacting antibodies. The liposomes, lipoplexes, or lipid nanoparticles may also be used to increase the stability of glycan-interacting antibodies.

Liposomes that are specifically formulated for antibody cargo are prepared according to techniques known in the art, such as described by Eppstein et al. (Eppstein, D. A. et al., Biological activity of liposome-encapsulated murine interferon gamma is mediated by a cell membrane receptor. Proc Natl Acad Sci USA. 1985 June; 82(11):3688-92); Hwang et al. (Hwang, K. J. et al., Hepatic uptake and degradation of unilamellar sphingomyelin/cholesterol liposomes: a kinetic study. Proc Natl Acad Sci USA. 1980 July; 77(7):4030-4); U.S. Pat. Nos. 4,485,045 and 4,544,545. Production of liposomes with sustained circulation time is also described in U.S. Pat. No. 5,013,556.

Liposomes that include glycan-interacting antibodies of the present invention may be generated using reverse phase evaporation utilizing lipids such as phosphatidylcholine, cholesterol as well as phosphatidylethanolamine that has been polyethylene glycol-derivatized. Filters with defined pore size are used to extrude liposomes of the desired diameter. In another embodiment, glycan-interacting antibodies of the present invention can be conjugated to the external surface of liposomes by disulfide interchange reaction as is described by Martin et al. (Martin, F. J. et al., *Irreversible coupling of immunoglobulin fragments to preformed vesicles. An improved method for liposome targeting*. J Biol Chem. 1982 Jan. 10; 257(1):286-8).

Polymers and Nanoparticles

Glycan-interacting antibodies of the invention can be formulated using natural and/or synthetic polymers. Non-limiting examples of polymers which may be used for delivery include, but are not limited to DMRI/DOPE, poloxamer, chitosan, cyclodextrin, and poly(lactic-co-glycolic acid) (PLGA) polymers. These may be biodegradable.

The polymer formulation can permit the sustained or delayed release of glycan-interacting antibodies (e.g., following intramuscular or subcutaneous injection). The altered release profile for glycan-interacting antibodies can result in, for example, release of the glycan-interacting antibodies over an extended period of time. The polymer formulation may also be used to increase the stability of glycan-interacting antibodies.

Polymer formulations can also be selectively targeted through expression of different ligands as exemplified by, but not limited by, folate, transferrin, and N-acetylgalactosamine (GalNAc) (Benoit et al., Biomacromolecules. 2011 12:2708-2714; Rozema et al., Proc Natl Acad Sci USA. 2007 104:12982-12887; Davis, Mol Pharm. 2009 6:659-668; Davis, Nature 2010 464:1067-1070; herein incorporated by reference in its entirety).

Glycan-interacting antibodies of the invention can also be formulated as nanoparticles using a combination of polymers, lipids, and/or other biodegradable agents, such as, but not limited to, calcium phosphate. Components may be combined in a core-shell, hybrid, and/or layer-by-layer architecture, to allow for fine-tuning of the nanoparticle so delivery of glycan-interacting antibodies may be enhanced. For glycan-interacting antibodies, systems based on poly(2-(methacryloyloxy)ethyl phosphorylcholine)-block-(2-(diisopropylamino)ethyl methacrylate), (PMPC-PDPA), a pH sensitive diblock copolymer that self-assembles to form nanometer-sized vesicles, also known as polymersomes, at physiological pH may be used. These polymersomes have been shown to successfully deliver relatively high antibody payloads within live cells. (Massignani, et al, Cellular delivery of antibodies: effective targeted subcellular imaging and new therapeutic tool. Nature Proceedings, May, 2010).

In one embodiment, a PEG-charge-conversional polymer (Pitella et al., Biomaterials. 2011 32:3106-3114) may be used to form a nanoparticle to deliver glycan-interacting antibodies of the present invention. The PEG-charge-conversional polymer may improve upon the PEG-polyanion block copolymers by being cleaved into a polycation at acidic pH, thus enhancing endosomal escape.

The use of core-shell nanoparticles has additionally focused on a high-throughput approach to synthesize cationic cross-linked nanogel cores and various shells (Siegwart et al., Proc Natl Acad Sci USA. 2011 108:12996-13001). The complexation, delivery, and internalization of the polymeric nanoparticles can be precisely controlled by altering the chemical composition in both the core and shell components of the nanoparticle.

In one embodiment, matrices of poly(ethylene-co-vinyl acetate), are used to deliver glycan-interacting antibodies of the invention. Such matrices are described in Nature Biotechnology 10, 1446-1449 (1992).

Antibody Formulations

Glycan-interacting antibodies of the invention may be formulated for intravenous administration or extravascular administration (Daugherty, et al., *Formulation and delivery issues for monoclonal antibody therapeutics.* Adv Drug Deliv Rev. 2006 Aug. 7; 58(5-6):686-706, US patent publication number 2011/0135570, all of which are incorporated herein in their entirety). Extravascular administration routes may include, but are not limited to subcutaneous administration, intraperitoneal administration, intracerebral administration, intraocular administration, intralesional administration, topical administration and intramuscular administration.

Antibody structures may be modified to improve their effectiveness as therapeutics. Improvements may include, but are not limited to improved thermodynamic stability, reduced Fc receptor binding properties and improved folding efficiency. Modifications may include, but are not limited to amino acid substitutions, glycosylation, palmitoylation and protein conjugation.

Glycan-interacting antibodies may be formulated with antioxidants to reduce antibody oxidation. glycan-interacting antibodies may also be formulated with additives to reduce protein aggregation. Such additives may include, but are not limited to albumin, amino acids, sugars, urea, guanidinium chloride, polyalchohols, polymers (such as polyethylene glycol and dextrans), surfactants (including, but not limited to polysorbate 20 and polysorbate 80) or even other antibodies.

Glycan-interacting antibodies of the present invention may be formulated to reduce the impact of water on antibody structure and function. Antibody preparations in such formulations may be may be lyophilized. Formulations subject to lyophilization may include carbohydrates or polyol compounds to protect and stabilize antibody structure. Such compounds include, but are not limited to sucrose, trehalose and mannitol.

Glycan-interacting antibodies of the present invention may be formulated with polymers. In one embodiment, polymer formulations may contain hydrophobic polymers. Such polymers may be microspheres formulated with polylactide-co-glycolide through a solid-in-oil-in-water encapsulation method. Microspheres that include ethylene-vinyl acetate copolymer are also contemplated for antibody delivery and may be used to extend the time course of antibody release at the site of delivery. In another embodiment, polymers may be aqueous gels. Such gels may, for example, include carboxymethylcellulose. Aqueous gels may also include hyaluronic acid hydrogel. Antibodies may be covalently linked to such gels through a hydrazone linkage that allows for sustained delivery in tissues, including but not limited to the tissues of the central nervous system.

Peptide and Protein Formulations

Glycan-interacting antibodies of the invention may be formulated with peptides and/or proteins. In one embodiment, peptides such as, but not limited to, cell penetrating peptides and proteins and peptides that enable intracellular delivery may be used to deliver pharmaceutical formulations. A non-limiting example of a cell penetrating peptide which may be used with the pharmaceutical formulations of the present invention includes a cell-penetrating peptide sequence attached to polycations that facilitates delivery to the intracellular space, e.g., HIV-derived TAT peptide, penetratins, transportans, or hCT derived cell-penetrating peptides (see, e.g., Caron et al., Mol. Ther. 3(3):310-8 (2001); Langel, Cell-Penetrating Peptides: Processes and Applications (CRC Press, Boca Raton Fla., 2002); El-Andaloussi et al., Curr. Pharm. Des. 11(28):3597-611 (2003); and Deshayes et al., Cell. Mol. Life Sci. 62(16):1839-49 (2005), all of which are incorporated herein by reference). The compositions can also be formulated to include a cell penetrating agent, e.g., liposomes, which enhance delivery of the compositions to the intracellular space. Glycan-interacting antibodies of the invention may be complexed to peptides and/or proteins such as, but not limited to, peptides and/or proteins from Aileron Therapeutics (Cambridge, Mass.) and Permeon Biologics (Cambridge, Mass.) in order to enable intracellular delivery (Cronican et al., ACS Chem. Biol. 2010 5:747-752; McNaughton et al., Proc. Natl. Acad. Sci. USA 2009 106:6111-6116; Sawyer, Chem Biol Drug Des. 2009 73:3-6; Verdine and Hilinski, Methods Enzymol. 2012; 503:3-33; all of which are herein incorporated by reference in their entirety).

In one embodiment, cell-penetrating polypeptides may include a first domain and a second domain. The first domain may include a supercharged polypeptide. The second domain may include a protein-binding partner. As used herein, "protein-binding partner" includes, but are not limited to, antibodies and functional fragments thereof, scaffold proteins, or peptides. The cell-penetrating polypeptide may further include an intracellular binding partner for the protein-binding partner. The cell-penetrating polypeptide may be capable of being secreted from a cell where glycan-interacting antibodies may be introduced.

In formulations of the present invention, peptides or proteins may be incorporated to increase cell transfection by glycan-interacting antibodies or alter the biodistribution of glycan-interacting antibodies (e.g., by targeting specific tissues or cell types).

Cell Formulations

Cell-based formulations of glycan-interacting antibody compositions of the invention may be used to ensure cell transfection (e.g., in the cellular carrier) or alter the biodistribution of the compositions (e.g., by targeting the cell carrier to specific tissues or cell types).

Cell Transfer Methods

A variety of methods are known in the art and are suitable for introduction of nucleic acids or proteins, such as glycan-interacting antibodies, into a cell, including viral and non-viral mediated techniques. Examples of typical non-viral mediated techniques include, but are not limited to, electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like) or cell fusion.

The technique of sonoporation, or cellular sonication, is the use of sound (e.g., ultrasonic frequencies) for modifying the permeability of the cell plasma membrane. Sonoporation methods are known to those in the art and are used to deliver nucleic acids in vivo (Yoon and Park, Expert Opin Drug Deliv. 2010 7:321-330; Postema and Gilja, Curr Pharm Biotechnol. 2007 8:355-361; Newman and Bettinger, Gene Ther. 2007 14:465-475; all herein incorporated by reference in their entirety). Sonoporation methods are known in the art and are also taught for example as it relates to bacteria in US Patent Publication 20100196983 and as it relates to other cell types in, for example, US Patent Publication 20100009424, each of which are incorporated herein by reference in their entirety.

Electroporation techniques are also well known in the art and are used to deliver nucleic acids in vivo and clinically (Andre et al., Curr Gene Ther. 2010 10:267-280; Chiarella et al., Curr Gene Ther. 2010 10:281-286; Hojman, Curr Gene Ther. 2010 10:128-138; all herein incorporated by reference in their entirety). In one embodiment, glycan-interacting antibodies may be delivered by electroporation.

Administration and Delivery

The compositions of the present invention may be administered by any of the standard methods or routes known in the art.

Glycan-interacting antibodies of the present invention may be administered by any route which results in a therapeutically effective outcome. These include, but are not limited to enteral, gastroenteral, epidural, oral, transdermal, epidural (peridural), intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection, (into the base of the penis), intravaginal administration, intrauterine, extra-amniotic administration, transdermal (diffusion through the intact skin for systemic distribution), transmucosal (diffusion through a mucous membrane), insufflation (snorting), sublingual, sublabial, enema, eye drops (onto the conjunctiva), or in ear drops. In specific embodiments, compositions may be administered in a way which allows them cross the blood-brain barrier, vascular barrier, or other epithelial barrier. Non-limiting routes of administration for glycan-interacting antibodies of the present invention are described below.

Parenteral and Injectable Administration

Liquid dosage forms for oral and parenteral administration include, but are not limited to, pharmaceutically acceptable emulsions, microemulsions, solutions, suspensions, syrups, and/or elixirs. In addition to active ingredients, liquid dosage forms may include inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such as CREMOPHOR®, alcohols, oils, modified oils, glycols, polysorbates, cyclodextrins, polymers, and/or combinations thereof. In other embodiments, surfactants are included such as hydroxypropylcellulose.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are prepared by entrapping the drug in liposomes or microemulsions which are compatible with body tissues.

Rectal and Vaginal Administration

Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the active ingredient.

Oral Administration

Solid dosage forms for oral administration include capsules, tablets, pills, powders, and granules. In such solid dosage forms, an active ingredient is mixed with at least one inert, pharmaceutically acceptable excipient such as sodium citrate or dicalcium phosphate and/or fillers or extenders (e.g. starches, lactose, sucrose, glucose, mannitol, and silicic acid), binders (e.g. carboxymethylcellulose, alginates, gelatin, polyvinylpyrrolidinone, sucrose, and acacia), humectants (e.g. glycerol), disintegrating agents (e.g. agar, calcium carbonate, potato or tapioca starch, alginic acid, certain silicates, and sodium carbonate), solution retarding agents (e.g. paraffin), absorption accelerators (e.g. quaternary ammonium compounds), wetting agents (e.g. cetyl alcohol and glycerol monostearate), absorbents (e.g. kaolin and bentonite clay), and lubricants (e.g. talc, calcium stearate, magnesium stearate, solid polyethylene glycols, sodium lauryl sulfate), and mixtures thereof. In the case of capsules, tablets and pills, the dosage form may include buffering agents.

Topical or Transdermal Administration

As described herein, compositions containing glycan-interacting antibodies of the invention may be formulated for administration topically. The skin may be an ideal target site for delivery as it is readily accessible. Gene expression may be restricted not only to the skin, potentially avoiding nonspecific toxicity, but also to specific layers and cell types within the skin.

The site of cutaneous expression of the delivered compositions will depend on the route of nucleic acid delivery. Three routes are commonly considered to deliver glycan-interacting antibodies to the skin: (i) topical application (e.g. for local/regional treatment and/or cosmetic applications); (ii) intradermal injection (e.g. for local/regional treatment and/or cosmetic applications); and (iii) systemic delivery (e.g. for treatment of dermatologic diseases that affect both cutaneous and extracutaneous regions). glycan-interacting antibodies can be delivered to the skin by several different approaches known in the art.

In one embodiment, the invention provides for a variety of dressings (e.g., wound dressings) or bandages (e.g., adhesive bandages) for conveniently and/or effectively carrying out methods of the present invention. Dressings or bandages may include sufficient amounts of pharmaceutical compositions and/or glycan-interacting antibodies described herein to allow a user to perform multiple treatments of a subject(s).

In one embodiment, the invention provides for compositions that include glycan-interacting antibodies to be delivered in more than one injection.

Dosage forms for topical and/or transdermal administration of a composition may include ointments, pastes, creams, lotions, gels, powders, solutions, sprays, inhalants and/or patches. Generally, an active ingredient is admixed under sterile conditions with a pharmaceutically acceptable excipient and/or any needed preservatives and/or buffers as may be required.

Additionally, the present invention contemplates the use of transdermal patches, which often have the added advantage of providing controlled delivery of a compound to the body. Such dosage forms may be prepared, for example, by dissolving and/or dispensing the compound in the proper medium. Alternatively or additionally, rate may be controlled by either providing a rate controlling membrane and/or by dispersing the compound in a polymer matrix and/or gel.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions.

Topically-administrable formulations may, for example, include from about 1% to about 10% (w/w) active ingredient, although the concentration of active ingredient may be as high as the solubility limit of the active ingredient in the solvent. Formulations for topical administration may further include one or more of the additional ingredients described herein.

Depot Administration

As described herein, in some embodiments, compositions of the present invention are formulated in depots for extended release. Generally, a specific organ or tissue (a "target tissue") is targeted for administration.

In some aspects of the invention, glycan-interacting antibodies are spatially retained within or proximal to a target tissue. Provided are methods of providing compositions to one or more target tissue of a mammalian subject by contacting the one or more target tissue (including one or more target cells) with compositions under conditions such that the compositions, in particular glycan-interacting antibody component(s) of the compositions, are substantially retained in the target tissue, meaning that at least 10, 20, 30, 40, 50, 60, 70, 80, 85, 90, 95, 96, 97, 98, 99, 99.9, 99.99 or greater than 99.99% of the composition is retained in the target tissue. Advantageously, retention is determined by measuring the level of glycan-interacting antibodies present in the compositions entering the target tissues and/or cells. For example, at least 1, 5, 10, 20, 30, 40, 50, 60, 70, 80, 85, 90, 95, 96, 97, 98, 99, 99.9, 99.99 or greater than 99.99% of glycan-interacting antibodies administered to the subject are present intracellularly at a period of time following administration. For example, intramuscular injection to a mammalian subject may be performed using an aqueous composition including one or more glycan-interacting antibody and a transfection reagent, and retention of the composition may be determined by measuring the level of glycan-interacting antibodies present in the muscle cells.

Certain aspects of the invention are directed to methods of providing compositions to target tissues of mammalian subjects, by contacting the target tissues (containing one or more target cells) with compositions under conditions such that the compositions are substantially retained in the target tissue. Compositions contain an effective amount of glycan-interacting antibodies such that the effect of interest is produced in at least one target cell. Compositions generally contain cell penetration agents and a pharmaceutically acceptable carrier, although "naked" glycan-interacting antibodies (such as glycan-interacting antibodies without cell penetration agents or other agents) are also contemplated.

In some embodiments, compositions include a plurality of different glycan-interacting antibodies, where one or more than one of the glycan-interacting antibodies targets a glycan of interest. Optionally, compositions also contain cell penetration agents to assist in the intracellular delivery of compositions. A determination is made of the composition dose required to target glycans of interest in a substantial percentage of cells contained within a predetermined volume of the target tissue (generally, without targeting glycans in tissue adjacent to the predetermined volume, or distally to target tissues). Subsequent to this determination, the determined dose may be introduced directly into the tissue of the mammalian subject.

In one embodiment, the invention provides for glycan-interacting antibodies to be delivered in more than one injection or by split dose injections.

Pulmonary Administration

Pharmaceutical compositions may be prepared, packaged, and/or sold in formulations suitable for pulmonary administration via the buccal cavity. Such formulations may include dry particles further including active ingredients and having a diameter in the range from about 0.5 nm to about 7 nm or from about 1 nm to about 6 nm. Such compositions may be suitably in the form of dry powders for administration using a device that includes a dry powder reservoir to which a stream of propellant may be directed to disperse the powder and/or using a self-propelling solvent/powder dispensing container such as a device including the active ingredient dissolved and/or suspended in a low-boiling propellant in a sealed container. Such powders may include particles wherein at least 98% of the particles by weight have a diameter greater than 0.5 nm and at least 95% of the particles by number have a diameter less than 7 nm. Alternatively, at least 95% of the particles by weight have a diameter greater than 1 nm and at least 90% of the particles by number have a diameter less than 6 nm. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50% to 99.9% (w/w) of the composition, and active ingredient may constitute 0.1% to 20% (w/w) of the composition. A propellant may further include additional ingredients such as a liquid non-ionic and/or solid anionic surfactant and/or a solid diluent (which may have a particle size of the same order as particles that include the active ingredient).

Pharmaceutical compositions formulated for pulmonary delivery may provide an active ingredient in the form of droplets of a solution and/or suspension. Such formulations may be prepared, packaged, and/or sold as aqueous and/or dilute alcoholic solutions and/or suspensions, optionally sterile, that include active ingredient, and may conveniently be administered using any nebulization and/or atomization device. Such formulations may further include one or more additional ingredients including, but not limited to, a flavoring agent such as saccharin sodium, a volatile oil, a buffering agent, a surface active agent, and/or a preservative such as methylhydroxybenzoate. Droplets provided by this route of administration may have an average diameter in the range from about 0.1 nm to about 200 nm.

Intranasal, Nasal and buccal Administration

Formulations described herein as being useful for pulmonary delivery are useful for intranasal delivery of a pharmaceutical composition. Another formulation suitable for intranasal administration is a coarse powder comprising the active ingredient and having an average particle from about 0.2 µm to 500 µm. Such a formulation is administered in the manner in which snuff is taken, i.e. by rapid inhalation through the nasal passage from a container of the powder held close to the nose.

Formulations suitable for nasal administration may, for example, comprise from about as little as 0.1% (w/w) and as much as 100% (w/w) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, 0.1% to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising active ingredient. Such powdered, aerosolized, and/or aerosolized formulations, when dispersed, may have an average particle and/or droplet size in the range from about 0.1 nm to about 200 nm, and may further comprise one or more of any additional ingredients described herein.

Ophthalmic or Otic Administration

Pharmaceutical compositions may be prepared, packaged, and/or sold in a formulation suitable for ophthalmic or otic administration. Such formulations may, for example, be in the form of eye or ear drops including, for example, a 0.1/1.0% (w/w) solution and/or suspension of the active ingredient in an aqueous or oily liquid excipient. Such drops may further comprise buffering agents, salts, and/or one or more other of any additional ingredients described herein. Other ophthalmically-administrable formulations which are useful include those which comprise the active ingredient in microcrystalline form and/or in a liposomal preparation. Subretinal inserts may also be used as a form of administration.

Payload Administration

Glycan-interacting antibodies described herein may be used in a number of different scenarios in which delivery of a substance (the "payload") to a biological target is desired, for example delivery of detectable substances for detection of the target, or delivery of a therapeutic or diagnostic agent. Detection methods can include, but are not limited to, both imaging in vitro and in vivo imaging methods, e.g., immunohistochemistry, bioluminescence imaging (BLI), Magnetic Resonance Imaging (MRI), positron emission tomography (PET), electron microscopy, X-ray computed tomography, Raman imaging, optical coherence tomography, absorption imaging, thermal imaging, fluorescence reflectance imaging, fluorescence microscopy, fluorescence molecular tomographic imaging, nuclear magnetic resonance imaging, X-ray imaging, ultrasound imaging, photoacoustic imaging, lab assays, or in any situation where tagging/staining/imaging is required.

Glycan-interacting antibodies can be designed to include both a linker and a payload in any useful orientation. For example, a linker having two ends is used to attach one end to the payload and the other end to the glycan-interacting antibody. The glycan-interacting antibodies of the invention can include more than one payload as well as a cleavable linker. In another example, a drug that may be attached to glycan-interacting antibodies via a linker and may be fluorescently labeled can be used to track the drug in vivo, e.g. intracellularly.

Other examples include, but are not limited to, the use of glycan-interacting antibodies in reversible drug delivery into cells.

Glycan-interacting antibodies described herein can be used in intracellular targeting of a payload, e.g., detectable or therapeutic agents, to specific organelles. In addition, glycan-interacting antibodies described herein may be used to deliver therapeutic agents to cells or tissues, e.g., in living animals. For example, glycan-interacting antibodies described herein may be used to deliver chemotherapeutic agents to kill cancer cells. glycan-interacting antibodies attached to therapeutic agents through linkers can facilitate member permeation allowing the therapeutic agent to travel into a cell to reach an intracellular target.

In some embodiments, the payload may be a therapeutic agent such as a cytotoxin, radioactive ion, chemotherapeutic, or other therapeutic agent. A cytotoxin or cytotoxic agent includes any agent that may be detrimental to cells. Examples include, but are not limited to, taxol, cytochalasin B, gramicidin D, ethidium bromide, emetine, mitomycin, etoposide, teniposide, vincristine, vinblastine, colchicine, doxorubicin, daunorubicin, dihydroxyanthracinedione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020 incorporated herein in its entirety), rachelmycin (CC-1065, see U.S. Pat. Nos. 5,475,092, 5,585,499, and 5,846,545, all of which are incorporated herein by reference), and analogs or homologs thereof. Radioactive ions include, but are not limited to iodine (e.g., iodine 125 or iodine 131), strontium 89, phosphorous, palladium, cesium, iridium, phosphate, cobalt, yttrium 90, samarium 153, and praseodymium. Other therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thiotepa chlorambucil, rachelmycin (CC-1065), melphalan, carmustine (BSNU), lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). In the case of anti-STn antibodies of the present invention, tumor killing may be boosted by the conjugation of a toxin to such anti-STn antibodies.

In some embodiments, the payload may be a detectable agent, such as various organic small molecules, inorganic compounds, nanoparticles, enzymes or enzyme substrates, fluorescent materials, luminescent materials (e.g., luminol), bioluminescent materials (e.g., luciferase, luciferin, and aequorin), chemiluminescent materials, radioactive materials (e.g., $^{18}$F, $^{67}$Ga, $^{81m}$Kr, $^{82}$Rb, $^{111}$In, $^{123}$I, $^{133}$Xe, $^{201}$Tl, $^{125}$I, $^{35}$X, $^{14}$C, $^{3}$H, or $^{99m}$Tc (e.g., as pertechnetate (technetate(VII), TcO$_4^-$)), and contrast agents (e.g., gold (e.g., gold nanoparticles), gadolinium (e.g., chelated Gd), iron oxides (e.g., superparamagnetic iron oxide (SPIO), monocrystalline iron oxide nanoparticles (MIONs), and ultrasmall superparamagnetic iron oxide (USPIO)), manganese chelates (e.g., Mn-DPDP), barium sulfate, iodinated contrast media (iohexol), microbubbles, or perfluorocarbons). Such optically-detectable labels include for example, without limitation, 4-acetamido-4'-isothiocyanatostilbene-2,2'disulfonic acid; acridine and derivatives (e.g., acridine and acridine isothiocyanate); 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives (e.g., coumarin, 7-amino-4-methylcoumarin (AMC, Coumarin 120), and 7-amino-4-trifluoromethylcoumarin (Coumarin 151)); cyanine dyes; cyanosine; 4',6-diaminidino-2-phenylindole (DAPI); 5' 5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]-naphthalene-1-sulfonyl chloride (DNS, dansylchloride); 4-dimethylaminophenylazophenyl-4'-isothiocyanate (DABITC); eosin and derivatives (e.g., eosin and eosin isothiocyanate); erythrosin and derivatives (e.g., erythrosin B and erythrosin isothiocyanate); ethidium; fluorescein and derivatives (e.g., 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, X-rhodamine-5-(and-6)-isothiocyanate (QFITC or XRITC), and fluorescamine); 2-[2-[3-[[1,3-dihydro-1,1-dimethyl-3-(3-sulfopropyl)-2H-benz[e]indol-2-ylidene]ethylidene1-2-[4-(ethoxycarbonyl)-1-piperazinyl]-1-cyclopenten-1-yl]ethenyl]-1,1-dimethyl-3-(3-sulforpropyl)-1H-benz[e]indolium hydroxide, inner salt, compound with n,n-diethylethanamine(1:1) (IR144); 5-chloro-2-[2-[3-[(5-chloro-3-ethyl-2(3H)-benzothiazol-ylidene)ethylidene]-2-(diphenylamino)-1-cyclopenten-1-yl] ethenyl]-3-ethyl benzothiazolium perchlorate (IR140); Malachite Green isothiocyanate; 4-methylumbelliferone orthocresolphthalein; nitrotyrosine; pararosaniline; Phenol Red; B-phycoerythrin; o-phthaldialdehyde; pyrene and derivatives(e.g., pyrene, pyrene butyrate, and succinimidyl 1-pyrene); butyrate quantum dots; Reactive Red 4 (CIBA-CRON™ Brilliant Red 3B-A); rhodamine and derivatives (e.g., 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'tetramethyl-6-carboxyrhodamine (TAMRA) tetramethyl rhodamine, and tetramethyl rhodamine isothiocyanate (TRITC)); riboflavin; rosolic acid; terbium chelate derivatives; Cyanine-3 (Cy3); Cyanine-5 (Cy5); cyanine-5.5 (Cy5.5), Cyanine-7 (Cy7); IRD 700; IRD 800; Alexa 647; La Jolta Blue; phthalo cyanine; and naphthalo cyanine.

In some embodiments, the detectable agent may be a non-detectable precursor that becomes detectable upon activation (e.g., fluorogenic tetrazine-fluorophore constructs (e.g., tetrazine-BODIPY FL, tetrazine-Oregon Green 488, or tetrazine-BODIPY TMR-X) or enzyme activatable fluorogenic agents (e.g., PROSENSE® (VisEn Medical))). In vitro assays in which the enzyme labeled compositions can be used include, but are not limited to, enzyme linked immunosorbent assays (ELISAs), immunoprecipitation assays, immunofluorescence, enzyme immunoassays (EIA), radioimmunoassays (RIA), and Western blot analysis.

Combinations

Glycan-interacting antibodies may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of pharmaceutical, prophylactic, diagnostic, and/or imaging compositions in combination with agents that may improve their bioavailability, reduce and/or modify their metabolism, inhibit their excretion, and/or modify their distribution within the body.

Dosage

The present disclosure encompasses delivery of glycan-interacting antibodies for any of therapeutic, pharmaceutical, diagnostic or imaging by any appropriate route taking into consideration likely advances in the sciences of drug delivery. Delivery may be naked or formulated.

Naked Delivery

Glycan-interacting antibodies of the present invention may be delivered to cells, tissues, organs or organisms in naked form. As used herein in, the term "naked" refers to glycan-interacting antibodies delivered free from agents or modifications which promote transfection or permeability. Naked glycan-interacting antibodies may be delivered to cells, tissues, organs and/or organisms using routes of administration known in the art and described herein. Naked delivery may include formulation in a simple buffer such as saline or PBS.

Formulated Delivery

Glycan-interacting antibodies of the present invention may be formulated, using methods described herein. Formulations may include glycan-interacting antibodies which may be modified and/or unmodified. Formulations may further include, but are not limited to, cell penetration agents, pharmaceutically acceptable carriers, delivery agents, bioerodible or biocompatible polymers, solvents, and sustained-release delivery depots. Formulated glycan-interacting antibodies may be delivered to cells using routes of administration known in the art and described herein.

Compositions may also be formulated for direct delivery to organs or tissues in any of several ways in the art including, but not limited to, direct soaking or bathing, via a catheter, by gels, powder, ointments, creams, gels, lotions, and/or drops, by using substrates such as fabric or biodegradable materials coated or impregnated with compositions, and the like.

Dosing

In some embodiments, the present disclosure provides methods that include administering one or more glycan-interacting antibodies in accordance with the invention to a subject in need thereof. Nucleic acids encoding glycan-interacting antibodies, proteins or complexes that include glycan-interacting antibodies, or pharmaceutical, imaging, diagnostic, or prophylactic compositions thereof, may be administered to a subject using any amount and any route of administration effective for preventing, treating, diagnosing, or imaging a disease, disorder, and/or condition. The exact amount required will vary from subject to subject, depending on the species, age, and general condition of the subject, the severity of the disease, the particular composition, its mode of administration, its mode of activity, and the like. Compositions in accordance with the invention are typically formulated in dosage unit form for ease of administration and uniformity of dosage. It will be understood, however, that the total daily usage of the compositions of the present invention will be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In certain embodiments, compositions in accordance with the present invention may be administered at dosage levels sufficient to deliver from about 0.0001 mg/kg to about 100 mg/kg, from about 0.01 mg/kg to about 50 mg/kg, from about 0.1 mg/kg to about 40 mg/kg, from about 0.5 mg/kg to about 20 mg/kg, 0.5 mg/kg to about 30 mg/kg, from about 0.01 mg/kg to about 10 mg/kg, from about 0.1 mg/kg to about 10 mg/kg, from about 2.5 mg/kg to about 5.0 mg/kg, or from about 1 mg/kg to about 25 mg/kg, of subject body weight per day, one or more times a day, to obtain the desired therapeutic, diagnostic, prophylactic, or imaging effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

According to the present invention, glycan-interacting antibodies may be administered in split-dose regimens. As used herein, a "split dose" is the division of single unit dose or total daily dose into two or more doses, e.g., two or more administrations of the single unit dose. As used herein, a "single unit dose" is a dose of any therapeutic administered in one dose/at one time/single route/single point of contact, i.e., single administration event. As used herein, a "total daily dose" is an amount given or prescribed in a 24 hr period. It may be administered as a single unit dose. In one embodiment, glycan-interacting antibodies of the present invention are administered to a subject in split doses. Glycan-interacting antibodies may be formulated in buffer only or in a formulation described herein. Pharmaceutical compositions including glycan-interacting antibodies as described herein may be formulated into a dosage form described herein, such as a topical, intranasal, intratracheal, or injectable (e.g., intravenous, intraocular, intravitreal, intramuscular, intracardiac, intraperitoneal or subcutaneous). General considerations in the formulation and/or manufacture of pharmaceutical agents may be found, for example, in Remington: The Science and Practice of Pharmacy 21$^{st}$ ed., Lippincott Williams & Wilkins, 2005 (incorporated herein by reference).

In some embodiments, dosage of glycan-interacting antibodies may be adjusted to reduce bystander effects. As used herein the "bystander effect" refers to any negative effects on non-target cells or cells neighboring target cells (also referred to herein as bystander cells). According to such methods, antibody doses or conjugate types may be adjusted to reduce bystander effects. Such adjustments may lead to the treatments with greater than 95%, greater than 90%, greater than 85%, greater than 80%, greater than 75%, greater than 70%, greater than 65%, greater than 60%, greater than 55%, greater than 50%, greater than 45%, greater than 40%, greater than 35%, greater than 30%, or greater than 25% of bystander cells remaining viable.

Coatings or Shells

Solid dosage forms of tablets, dragees, capsules, pills, and granules can be prepared with coatings and shells such as enteric coatings and other coatings well known in the pharmaceutical formulating art. They may optionally include opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

IV. Kits and Devices

Kits

Any of the compositions described herein may be included in a kit. In a non-limiting example, reagents for generating glycan-interacting antibodies, including antigen molecules are included in a kit. The kit may further include reagents or instructions for creating or synthesizing glycan-interacting antibodies. It may also include one or more buffers. Other kits of the invention may include components for making glycan-interacting antibody protein or nucleic acid arrays or libraries and thus, may include, for example, a solid support.

In some embodiments, the present disclosure includes kits for screening, monitoring, and/or diagnosis of a subject that include one or more glycan-interacting antibodies. Such kits may be used alone or in combination with one or more other methods of screening, monitoring, and/or diagnosis (e.g., as a companion diagnostic). Some kits include one or more of a buffer, a biological standard, a secondary antibody, a detection reagent, and a composition for sample pre-treatment (e.g., for antigen retrieval, blocking, etc.).

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit (labeling reagent and label may be packaged together), the kit also will generally contain a second, third or other additional container into which the additional components may be separately placed. The kits may also include a second container means for containing a sterile, pharmaceutically acceptable buffer and/or other diluent. However, various combinations of components may be included in a vial. The kits of the present invention also will typically include a means for containing the glycan-interacting antibodies, e.g., proteins, nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means. In some embodiments, labeling dyes are provided as a dried powder. It is contemplated that 10, 20, 30, 40, 50, 60, 70, 80, 90, 100, 120, 120, 130, 140, 150, 160, 170, 180, 190, 200, 300, 400, 500, 600, 700, 800, 900, 1000 micrograms or at least 1000 micrograms or at most 10 g of dried dye are provided in kits of the invention. The dye may then be resuspended in any suitable solvent, such as DMSO.

A kit may include instructions for employing the kit components as well the use of any other reagent not included in the kit. Instructions may include variations that can be implemented.

Devices

Any of the compositions described herein may be combined with, coated onto or embedded in a device. Devices include, but are not limited to, dental implants, stents, bone replacements, artificial joints, valves, pacemakers or other implantable therapeutic devices.

V. Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc). can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Example 1

Glycan Array Analysis

Optimized glycan arrays are utilized to test antibody affinity and specificity for multiple glycans in a single experiment. Glycan arrays include 71 chemically synthesized and well-defined glycans, most of which are Neu5Ac and Neu5Gc glycan pairs. Array slides are obtained commercially (Arraylt Corp, Sunnyvale, Calif.) and include the glycans listed in the following Table.

TABLE 12

Array glycans

| Glycan ID No. | Glycan |
|---|---|
| 1 | Neu5,9Acα2,3Galβ1,4GlcNAcβO(CH2)2CH2NH2 |
| 2 | Neu5Gc9Acα2,3Galβ1,4GlcNAcβO(CH2)2CH2NH2 |
| 3 | Neu5,9Acα2,6Galβ1,4GlcNAcβO(CH2)2CH2NH2 |
| 4 | Neu5Gc9Acα2,6Galβ1,4GlcNAcβO(CH2)2CH2NH2 |
| 5 | Neu5Acα2,6GalNAcαO(CH2)2CH2NH2 |
| 6 | Neu5Gcα2,6GalNAcαO(CH2)2CH2NH2 |
| 7 | Neu5,9Acα2,3Galβ1,3GlcNAcβO(CH2)2CH2NH2 |
| 8 | Neu5Gc9Acα2,3Galβ1,3GlcNAcβO(CH2)2CH2NH2 |
| 9 | Neu5,9Acα2,3Galβ1,3GalNAcαO(CH2)2CH2NH2 |
| 10 | Neu5Gc9Acα2,3Galβ1,3GalNAcαO(CH2)2CH2NH2 |
| 11 | Neu5Acα2,3Galβ1,4GlcNAcβO(CH2)2CH2NH2 |
| 12 | Neu5Gcα2,3Galβ1,4GlcNAcβO(CH2)2CH2NH2 |
| 13 | Neu5Acα2,3Galβ1,3GlcNAcβO(CH2)2CH2NH2 |
| 14 | Neu5Gcα2,3Galβ1,3GlcNAcβO(CH2)2CH2NH2 |
| 15 | Neu5Acα2,3Galβ1,3GalNAcαO(CH2)2CH2NH2 |
| 16 | Neu5Gcα2,3Galβ1,3GalNAcαO(CH2)2CH2NH2 |
| 17 | Neu5Acα2,6Galβ1,4GlcNAcβO(CH2)2CH2NH2 |
| 18 | Neu5Gcα2,6Galβ1,4GlcNAcβO(CH2)2CH2NH2 |
| 19 | Neu5Acα2,6Galβ1,4GlcβO(CH2)2CH2NH2 |
| 20 | Neu5Gcα2,6Galβ1,4GlcβO(CH2)2CH2NH2 |
| 21 | Neu5Acα2,3Galβ1,4GlcβO(CH2)2CH2NH2 |
| 22 | Neu5Gcα2,3Galβ1,4GlcβO(CH2)2CH2NH2 |
| 23 | Neu5,9Acα2,6GalNAcαO(CH2)2CH2NH2 |
| 24 | Neu5Gc9Acα2,6GalNAcαO(CH2)2CH2NH2 |
| 25 | Neu5Acα2,3GalβO(CH2)2CH2NH2 |
| 26 | Neu5Gcα2,3GalβO(CH2)2CH2NH2 |
| 27 | Neu5Acα2,6GalβO(CH2)2CH2NH2 |
| 28 | Neu5Gcα2,6GalβO(CH2)2CH2NH2 |
| 29 | Neu5,9Acα2,3GalβO(CH2)2CH2NH2 |
| 30 | Neu5Gc9Acα2,3GalβO(CH2)2CH2NH2 |
| 31 | Neu5,9Acα2,6GalβO(CH2)2CH2NH2 |
| 32 | Neu5Gc9Acα2,6GalβO(CH2)2CH2NH2 |
| 33 | Neu5Acα2,3Galβ1,3GalNAcβO(CH2)2CH2NH2 |
| 34 | Neu5Gcα2,3Galβ1,3GalNAcβO(CH2)2CH2NH2 |
| 35 | Neu5,9Acα2,3Galβ1,3GalNAcβO(CH2)2CH2NH2 |
| 36 | Neu5Gc9Acα2,3Galβ1,3GalNAcβO(CH2)2CH2NH2 |
| 37 | Neu5,9Acα2,6Galβ1,4GlcβO(CH2)2CH2NH2 |
| 38 | Neu5Gc9Acα2,6Galβ1,4GlcβO(CH2)2CH2NH2 |
| 39 | Neu5,9Acα2,3Galβ1,4GlcβO(CH2)2CH2NH2 |
| 40 | Neu5Gc9Acα2,3Galβ1,4GlcβO(CH2)2CH2NH2 |
| 41 | Neu5Acα2,8Neu5Acα2,3Galβ1,4GlcβO(CH2)2CH2NH2 |
| 42 | Neu5Acα2,8Neu5Acα2,8Neu5Acα2,3Galβ1,4GlcβO(CH2)2CH2NH2 |
| 43 | Galβ1,4GlcβO(CH2)2CH2NH2 |
| 45 | Galβ1,4GlcNAcβO(CH2)2CH2NH2 |
| 47 | GalNAcαO(CH2)2CH2NH2 |
| 51 | Galβ1,3GalNAcβO(CH2)2CH2NH2 |
| 52 | Galβ1,3GlcNAcαO(CH2)2CH2NH2 |
| 53 | Galβ1,3GlcNAcβO(CH2)2CH2NH2 |
| 54 | Galβ1,4GlcNAc6SβO(CH2)2CH2NH2 |
| 55 | Neu5Acα2,3Galβ1,4(Fucα1,3)GlcNAcβO(CH2)2CH2NH2 |
| 56 | Neu5Gcα2,3Galβ1,4(Fucα1,3)GlcNAcβO(CH2)2CH2NH2 |
| 57 | Neu5Acα2,3Galβ1,4(Fucα1,3)GlcNAc6SβO(CH2)2CH2NH2 |
| 58 | Neu5Gcα2,3Galβ1,4(Fucα1,3)GlcNAc6SβO(CH2)2CH2NH2 |
| 59 | Galβ1,3GlcNAcβ1,3Galβ1,4GlcβO(CH2)2CH2NH2 |
| 60 | Neu5Acα2,3Galβ1,3GlcNAcβ1,3Galβ1,4GlcβO(CH2)2CH2NH2 |
| 61 | Neu5Gcα2,3Galβ1,3GlcNAcβ1,3Galβ1,4GlcβO(CH2)2CH2NH2 |
| 62 | Neu5Acα2,3Galβ1,4GlcNAc6SβO(CH2)2CH2NH2 |
| 63 | Neu5Gcα2,3Galβ1,4GlcNAc6SβO(CH2)2CH2NH2 |
| 64 | Neu5Acα2,8Neu5Acα2,3Galβ1,4GlcβO(CH2)3NHCOCH2(OCH2CH2)6NH2 |
| 65 | Neu5Acα2,8Neu5Acα2,8Neu5Acα2,3Galβ1,4GlcβO(CH2)3NHCOCH2(OCH2CH2)6NH2 |
| 66 | Neu5Acα2,6(Neu5Acα2,3)Galβ1,4GlcβO(CH2)2CH2NH2 |
| 67 | Neu5Acα2,6(Neu5Gcα2,3)Galβ1,4GlcβO(CH2)2CH2NH2 |
| 68 | Neu5Acα2,6(KDNα2,3)Galβ1,4GlcβO(CH2)2CH2NH2 |
| 69 | Neu5Gcα2,6Neu5Acα2,3Galβ1,4GlcβO(CH2)2CH2NH2 |
| 70 | KDNα2,8Neu5Acα2,3Galβ1,4GlcβO(CH2)2CH2NH2 |
| 71 | Neu5Acα2,8Kdnα2,6Galβ1,4GlcβO(CH2)2CH2NH2 |
| 72 | Neu5Acα2,8Neu5Gcα2,3Galβ1,4GlcβO(CH2)2CH2NH2 |
| 73 | Neu5Acα2,8Neu5Gcα2,6Galβ1,4GlcβO(CH2)2CH2NH2 |
| 74 | KDNα2,8Neu5Gcα2,3Galβ1,4GlcβO(CH2)2CH2NH2 |
| 75 | Neu5Gcα2,8Neu5Gcα2,3Galβ1,4GlcβO(CH2)2CH2NH2 |
| 76 | Neu5Acα2,8Neu5Acα2,6Galβ1,4GlcβO(CH2)2CH2NH2 |

300 ml of epoxy blocking buffer is prepared by combining 15 ml of 2 M Tris buffer (pH 8) with 0.9 ml of 16.6 M ethanolamine and 284.1 ml of distilled water. The solution is brought to a final pH of 9.0 with HCl. The solution is filtered using a 0.2 µM nitrocellulose membrane. The epoxy buffer solution as well as 1 L of distilled water are pre-warmed to 50° C. Glass slides are arranged in a slide holder and quickly submerged in a staining tub with the warmed epoxy blocking buffer. Slides are incubated in the epoxy blocking buffer for 1 hour at 50° C. with periodic shaking to deactivate epoxy binding sites. Next, slides are rinsed and blocked with PBS with 1% OVA at 25° C. for one hour. Serum samples with polyclonal antibodies (1:1000) or purified monoclonal antibodies (1 ug/mL), are diluted in PBS with 1% OVA and added to the glycan array for one hour at 25° C. After extensive washing, binding of antibodies are detected by incubating glycan microarray slides with Cy3-conjugated anti-mouse IgG (Jackson Immunoresearch, West Grove, Pa.) for one hour. Slides are then washed extensively, dried and scanned with a Genepix 4000B scanner (Laser at 100%; gain at 350; 10 µm pixels). Raw data from scanned images are extracted using the Genepix software and analysis of raw data is carried out. Antibodies are considered to be highly specific for AcSTn and GcSTn if they demonstrate binding to both molecules, but not to Tn or any other glycans on the array.

Based on array analysis, antibodies are classified according to array glycan binding profile. Antibodies are classified as "Group 1" antibodies, capable of binding AcSTn and GcSTn, if they bind to glycans 5, 6, 23 and 24. Such antibodies are referred to as Pan-STn antibodies due to their ability to associate with a wider range of STn structures and the portion of STn indicated by the large oval in FIG. 1A. Antibodies are classified as "Group 2" antibodies, capable of binding STn as well as some related structures that include an O-linkage to serine or threonine, if they bind to glycans 5, 6, 23, 24, 27 and 31. These antibodies are thought to associate with the portion of STn indicated by the large oval in FIG. 1B. Some Group 2 antibodies preferably bind to structures with AcSTn over structures with GcSTn. Antibodies are classified as "Group 3" antibodies (capable of binding STn, but may also bind a broader set of related structures) if they bind glycans 5, 6, 23, 24, 17, 3, 19, 37, 27 and 31. Unlike Group 2 antibodies, Group 3 antibodies do not require that such structures have an O-linkage to serine or threonine. Group 3 antibodies are thought to associate with the portion of STn indicated by the large oval in FIG. 1C. Finally, antibodies are "Group 4" antibodies, capable of binding to both AcSTn and GcSTn as well as the un-sialylated Tn antigen (therefore having broader specificity) if they bind to glycans 5, 6, 23, 24 and 47. Group 4 antibodies are thought to associate with the portion of STn indicated by the large oval in FIG. 1D.

Example 2

Flow Cytometry-Based Analysis of Antibody Binding

Flow cytometry-based analysis is carried out to elucidate the dose-response curve for binding of antibodies to cell surface antigens. For these analyses, various cell lines are employed.

MDA-MB-231 cells are human breast cancer cells. They are grown in Earle's Minimum Essential Medium supplemented with 10% fetal calf serum (FCS), 100 µg/ml penicillin, 100 UI/ml streptomycin and 45 µg/ml gentamycin. MCF-7 cells are also human breast cancer cells and are grown under the same conditions as MDA-MB-231 cells. Stably transfected versions of MDA-MB-231 (MDA-MB-231-STn, clone TAH3.P10) and MCF-7 cells (clone A12.1 for MCF-7 cells) that over express (Alpha-N-Acetyl-Neuraminyl-2,3-Beta-Galactosyl-1,3)-N-Acetylgalactosaminide Alpha-2,6-Sialyltransferase I (GalNAc α2,6-sialyltransferase I or ST6GalNAc I), are also cultured under the same conditions with the exception of an added 1 mg/ml of G418 to support cells expressing the transgene. ST6GalNAc I is an enzme capable of sialylating GalNAc. As a result of over expression, transfected cells express high levels of Neu5Ac-STn (see Julien, S. et al., Glycoconjugate journal. 2001. 18, 883-93; the contents of which are herein incorporated by reference in their entirety).

E3 cells are murine breast cancer cells. They are cultured in Dulbecco's E4 medium with 10% FCS. Stably transfected versions of E3 cells expressing high levels of Neu5Gc-STn (E3-STn) are cultured with 600 µg/ml of G418 and 200 µg/ml hygromycin. During growth and maintenance of experimental cells, trypsin is not used for cell passaging.

OV90 and OVCAR3 cells are also used. These are human ovarian cancer cell lines, described previously.

SNU-16 cells are also used. These are gastric cancer cell lines that express low levels of STn.

For analysis, cells are harvested using StemPro Accutase (Life Technologies, Carlsbad, Calif.) and washed with PBS including 5% FBS before pelleting by light centrifugation. Cell numbers and viability are determined by trypan blue dye exclusion analysis and cell concentrations are adjusted to $5 \times 10^6$ cells/ml in PBS with 5% FBS. 50 µl of cells are added to each well of an assay plate. Cells are combined with 50 µl solutions of antibody being analyzed or control antibodies and incubated for 1 hour at 4° C. Cells are washed and pelleted twice with PBS with 5% FBS before being treated with 100 µl of PBS with 5% FBS including a 1:1, 500 dilution of anti-mouse IgG (Southern Biotech, Birmingham, Ala.) conjugated to allophycocyanin (APC). Cells are incubated for 30 min at 4° C. before washing and resuspending in 200 µl of propidium iodide (PI) diluted 1:1000 in PBS with 5% FBS. Treated cells are then subjected to flow cytometry analysis and 10,000 events are acquired for each sample.

Example 3

Antibody Humanization

Fully humanized heavy and light chains are designed with CDRs presented herein. Protein models of the variable regions are generated using existing antibody structures as templates. Segments of starting heavy and light chain variable region amino acid sequences are compared with human sequences for possible inclusion in the fully humanized sequences. Series of humanized heavy and light chain variable regions are designed entirely from segments of human variable region sequences with the objective that T cell epitopes be avoided. Variant human sequence segments with significant incidence of potential T cell epitopes as determined by in silico technologies are discarded.

Humanized heavy and light chain variable region genes are constructed from overlapping oligonucleotides assembled into full length genes using the ligase chain reaction (LCR). LCR products are amplified and suitable restriction sites are added for cloning into expression vectors. PCR products are cloned into intermediate vectors and confirmed by sequencing.

For construction of expression plasmids encoding fully humanized antibodies with human constant regions, DNA sequences for each variable region are inserted into mammalian expression vectors between an upstream cytomegalovirus immediate/early promoter/enhancer (CMV IE) plus the immunoglobulin signal sequence and a downstream immunoglobulin constant region gene. DNA samples are prepared for transfection into mammalian cells.

For generation of cell lines and selection of lead fully humanized antibodies, heavy and light chain plasmid DNA pairs are transfected into mammalian cells (NSO). Cell lines producing humanized antibodies are expanded and antibody samples are purified. Antibodies are tested in primary and secondary binding assays to determine leading antibody candidates. The 3 leading candidates are used for further analysis.

Example 4

Immunogenicity Testing

Lead antibodies are subjected to EpiScreen (Antitope, Paradise Valley, Ariz.) whole antibody human T cell assays using a minimum of 20 blood samples from healthy volunteer donors. Immunogenicity of lead antibodies is compared with control chimeric antibodies with starting antibody variable regions and matched human constant regions. Data are benchmarked against EpiScreen whole protein data for clinical-stage biologics.

Example 5

Antibody Sequence Analysis

Anti-glycan antibody variable domain sequences were analyzed for sequence similarities as well as for characteristics that may impact antibody function, expression, stability or immunogenicity. The antibodies used were commercially available or developed previously as described in U.S. Publication Numbers US2016/0264684 and US2016/0130356, the contents of which are herein incorporated by reference in their entirety. Analysis revealed far more variability in the light chain variable domains as compared to the heavy chain variable domains. Additionally, it was determined that heavy chain variable domains of the anti-glycan antibodies originated from one germline gene, muIGHV1S53, a germline gene that is shared with anti-STn antibodies known in the art: antibody 3F1 (SBH Sciences, Natick, Mass.), antibody B72.3 (see Colcher, D. et al., 1981. PNAS. 78(5): 3199-203), and antibody CC49 (see Muraro, R. et al., 1988. Cancer Res. 48: 4588-96). A comparative view of heavy chain CDR sequences based on the analysis is presented in the following Table.

TABLE 13

CDR sequence heavy chain comparison

| Clone ID | CDR-H1 | SEQ ID NO | CDR-H2 | SEQ ID NO | CDR-H3 | SEQ ID NO |
|---|---|---|---|---|---|---|
| 8C2-2D6 | GYTFTDHAIH | 105 | YISPGNGDIKYNEKFKG | 107 | SITTSY | 114 |
| 4G8-1E3 | GYIFTDHAIH | 106 | YISPGNGDIKYNEKFKG | 107 | SITTSY | 114 |
| 2G12-2B2 | GYTFTDHAIH | 105 | YFSPGNDDIKYNEKFRG | 108 | SLSTPY | 115 |
| 5G2-1B3 | GYTFTDHAIH | 105 | YFSPGNDDIKYNEKFKV | 109 | SYYGD | 116 |
| 5E6-2E7 | GYTFTDHAIH | 105 | YISPGNGDIKYNEKFKV | 110 | SITTPY | 117 |
| 2C2-2C5 | GYTFTDHAIH | 105 | YISPGNGDIKYNEKFKG | 107 | SITTPY | 117 |
| 9F11-1F7 | GYTFTDHAIH | 105 | YISPGNGDIKYNEKFKV | 110 | SITTPY | 117 |
| 1F6-1C10 | GYTFTDHAIH | 105 | YISPGNGDVKYSERFKG | 137 | SLSTPY | 115 |
| 7D3-2C10 | GYTFTDHAIH | 105 | YFSPGNDDIKYSEKFKG | 138 | SITTPY | 117 |
| 7A5-2G12 | GYTFTDHAIH | 105 | YISPGNDDIKYNEKFKG | 113 | SITTSY | 114 |
| 10F4-2A9 | GYTFTDHAIH | 105 | YISPGNGDIKYDEKFKG | 139 | SITTSY | 114 |
| 2F4-1E2 | GYTFTDHAIH | 105 | YISPGNGDIKYNEKFKG | 107 | QLGQGY | 140 |
| 2C6-2F11 | GYTFSDHAIH | 136 | YISPGNDDIKYNEKFKG | 113 | SMIGVY | 141 |
| 6B11-2E3 | GYTFTDHAIH | 105 | YISPGNDDIKYNEKFKG | 113 | SITTSY | 114 |
| 3F1 | GYTFTDHAIH | 105 | YISPGNGDIKYNEKFKD | 111 | SLLALDY | 118 |
| CC49 | GYTFTDHAIH | 105 | YFSPGNDDFKYNEKFKG | 112 | SLNMAY | 119 |
| B72.3 | GYTFTDHAIH | 105 | YISPGNDDIKYNEKFKG | 113 | SYYGH | 120 |
| Consensus | GYTFTDHAIH | 105 | YISPGNGDIKYNEKFKG | 107 | SITTSY | 114 |

CDR-H3 sequences varied by plus or minus one amino acid relative to the median length.

Interestingly, target-specific light chains were found to be derived from 5 light chain germline families: IGKV6, IGKV15, IGKV8, IGKV1 and IGKV12. Of these, all had the same CDR-L2 and CDR-L3 sequence lengths. Two classes of CDR-L1 sequences were found to persist [long (IGKV8 and IGKV1) and short (IGKV6, IGKV15, and IGKV12)], potentially presenting unified topology in each class.

A comparison of light chain CDR sequences is presented in the following Table.

TABLE 14

CDR sequence light chain comparison

| Clone ID | CDR-L1 | SEQ ID NO | CDR-L2 | SEQ ID NO | CDR-L3 | SEQ ID NO |
|---|---|---|---|---|---|---|
| 8C2-2D6 | KASENVVTYVS | 121 | GASNRYT | 77 | GQGYSYPYT | 89 |
| 8C2-2D6(V2) | HASQNINVWLS | 142 | KASNLYT | 147 | QHDQSYPTY | 148 |
| 4G8-1E3 | HASQHINFWLS | 122 | KASNLHT | 80 | QQDQSYPYM | 103 |
| 2G12-2B2 | KSSQSLLNRGNHKNYLT | 123 | WASTRES | 85 | QNDYTYPYT | 97 |
| 5G2-1B3 | RASENIYSHLA | 124 | GATNLAD | 79 | QHFWGAPFT | 91 |
| 5E6-2E7 | KSSQSLLNSGKTKNYLT | 125 | WASTRES | 85 | KNDYSYPYT | 102 |
| 2C2-2C5 | KASQSVNNNVA | 126 | YASNRYT | 84 | QQGYSSPWT | 96 |
| 1F6-1C10 | KSSQSLLNSGNQKSYLT | 143 | WASTRDS | 83 | QSDYSYPYT | 95 |
| 7D3-2C10 | HASQNINVWLS | 142 | KVSNLHT | 88 | QQDQSYPYT | 101 |
| 7A5-2G12 | KASENVVIYVS | 144 | GASNRYT | 77 | GQGYSYPYT | 89 |
| 10F4-2A9 | KASENVVTYVS | 121 | GASNRYT | 77 | GQGYSYPYT | 89 |
| 2F4-1E2 | RSSQSLVHSYGNTYLH | 145 | KVSNRFS | 81 | SQNTHVPYT | 93 |
| 2C6-2F11 | RFSQSLVQSNGNTYLQ | 146 | KVSNRFC | 86 | SQSTHAPLT | 98 |
| 6B11-2E3 | KASENVVTYVS | 121 | GASNRYT | 77 | GQGYSYPYT | 89 |
| 3F1 | KASQDVGTNIA | 127 | SASTRHT | 130 | QQYSSFPLT | 133 |
| CC49 | KSSQSLLYSGNQKNYLA | 128 | WASARES | 131 | QQYYSYPLT | 134 |
| B72.3 | RASENIYSNLA | 129 | AATNLAD | 132 | QHFWGTPYT | 135 |

Taken together, the sequence analysis suggests distinct patterns of CDR-H3 diversity that correspond with specific light chain germline pairings. Three sequence groups [Group A (with subgroups A1 and A2), Group B (with subgroups B1 and B2), and Group C] were identified based on these pairings. A listing of antibodies falling into each group are presented in the following Table.

TABLE 15

Antibody sequence groups

| Clone ID | Light Chain Murine Germline | Sequence Group |
|---|---|---|
| 8C2-2D6 | IGKV6-20 | Group A1 |
| 7A5-2G12 | IGKV6-20 | Group A1 |
| 10F4-2A9 | IGKV6-20 | Group A1 |
| 6B11-2E3 | IGKV6-20 | Group A1 |

TABLE 15-continued

Antibody sequence groups

| Clone ID | Light Chain Murine Germline | Sequence Group |
|---|---|---|
| 2C2-2C5 | IGKV6-32 | Group A1 |
| 3F1 | IGKV6-32 | Group A1 |
| 4G8-1E3 | IGKV15-103 | Group A2 |
| 7D3-2C10 | IGKV15-103 | Group A2 |
| 8C2-2D6(V2) | IGKV15-103 | Group A2 |
| 2G12-2B2 | IGKV8-19 | Group B1 |

TABLE 15-continued

Antibody sequence groups

| Clone ID | Light Chain Murine Germline | Sequence Group |
|---|---|---|
| 5E6-2E7 | IGKV8-19 | Group B1 |
| 1F6-1C10 | IGKV8-19 | Group B1 |
| CC49 | IGKV8-30 | Group B1 |
| 2F4-1E2 | IGKV1-110 | Group B2 |
| 2C6-2F11 | IGKV1-110 | Group B2 |
| 5G2-1B3 | IGKV12-46 | Group C |
| B72.3 | IGKV12-46 | Group C |

Group A includes antibodies 8C2-2D6, 4G8-1E3 and 3F1. These antibodies have similar CDR-H3 sequences, with the exception of 3F1, which is distinct from all other antibodies in terms of CDR-H3 length (having an extra amino acid, creating a longer loop). Group A antibodies also have light chain CDRs with similarities, especially in CDR residue lengths.

Group B includes antibodies 2G12-2B2 and CC49. Among the similarities in heavy chain sequences, these antibodies have conserved F and D residues in the CDR-H2 and a conserved L residue in the CDR-H3. Additionally, Group B antibodies have highly similar light chain sequences.

Group C antibodies include 5G2-1B3 and B72.3. Among the similarities between their heavy chain sequences, these antibodies have conserved D residues in their CDR-H2 sequences as well as a YYG motif in their CDR-H3 sequences. Group C antibodies also have highly similar light chain sequences.

The limited number of groups identified highlights the relatively rare sequence specificity necessary for anti-STn binding. Antibody grouping facilitates the identification of relevant intra-group sequence-based contributions to epitope binding. Notably, within Group A, 3F1 uniquely contains an extended CDR-H3 loop that may contribute to a novel binding profile. Interestingly, immunohistochemistry data indicates that 3F1 may bind to a broader range of targets, including undesired binding to endothelial cells.

Example 6

Antibody Variants

Variable domain sequences for anti-glycan antibodies of the invention were analyzed for sequence characteristics that may impact antibody function, expression, stability and/or immunogenicity.

Many of the antibodies analyzed had CDR-H2 sequences containing NG residue pairs, making them susceptible to asparagine deamidation, with possible conversion to glutamate and pyroglutamate in a 3:1 ratio over time. These sequences may be subjected to mutagenesis to convert NG residue pairs to SG or QG pairs to prevent deamidation at these sites. Alternatively, these antibodies may be formulated to reduce deamidation.

Antibodies 2B2-2A7 and 5G2-1B3 had aspartate isomerization sites (identified by DG amino acid residue pairs) in their light chain variable domains. Aspartic acid at these sites can convert into glutamate and pyroglutamate in a 3:1 ratio over time. These sequences may be subjected to mutagenesis to convert DG residue pairs to SG or QG to prevent isomerization at these sites. Alternatively, these antibodies may be formulated to reduce isomerization.

Many of the antibodies have heavy chains with N-terminal glutamine residues. These sequences may be subjected to mutagenesis to convert N-terminal glutamine residues to glutamate residues.

Sequence analysis for aggregation-prone patches revealed an HFW segment in the CDR-L3 of 5G2-1B3, which carries some risk of increasing antibody aggregation. Aggregation stability studies may be carried out with variants of this motif to identify less aggregation-prone antibodies.

Example 7

Antibody Humanization

Humanized versions of lead antibodies were developed using sequence and structural analysis. First, mouse germline antibody sequences were identified for each antibody (see the following Table).

TABLE 16

| Antibody mouse germline sequences | | |
|---|---|---|
| Antibody | VH mouse germline | VL mouse germline |
| 4G8-1E3 | muIGHV1S53 | muIGKV15-103 |
| 5G2-1B3 | muIGHV1S53 | muIGKV12-46 |
| 2G12-2B2 | muIGHV1S53 | muIGKV8-19 |
| 8C2-2D6 | muIGHV1S53 | muIGKV6-20 |
| 3F1 | muIGHV1S53 | muIGKV6-23 |

Antibody variable domain sequences were then compared to human framework sequences and human framework sequences suitable for CDR grafting were identified by homology. A schematic of a variable domain is shown in FIG. 2, demonstrating the layout of antibody variable domain framework regions [framework region 1 (FR1), framework region 2 (FR2), framework region 3 (FR3) and framework region 4 (FR4)] in relation to CDRs. The following Table indicates the human framework or human consensus sequence selected to replace the corresponding framework region of antibodies 4G8-1E3, 5G2-1B3, 2G12-2B2, 8C2-2D6, and 3F1. FR4 of human consensus 1 heavy chain corresponds to the amino acid sequence WGQGTLVTVSS (SEQ ID NO: 215) and FR4 of human consensus 1 light chain corresponds to the amino acid sequence FGQGTKVEIK (SEQ ID NO: 216).

TABLE 17

| | | | | CDR1 (SEQ ID NO) | | CDR2 (SEQ ID NO) | | CDR3 (SEQ ID NO) | |
|---|---|---|---|---|---|---|---|---|---|
| mAb | Chain | FR1 | | FR2 | | FR3 | | FR4 | |
| 4G8-1E3 | VH | IGHV1-18*01 | 106 | IGHV1-18*01 | 107 | IGHV1-18*01 | 114 | Human Consensus 1, Heavy Chain | |
| 4G8-1E3 | VL | IGKV1-39*01 | 122 | IGKV1-39*01 | 80 | IGKV1-39*01 | 103 | Human Consensus 1, Light Chain | |
| 5G2-1B3 | VH | IGHV1-18*01 | 105 | IGHV1-18*01 | 109 | IGHV1-18*01 | 116 | Human Consensus 1, Heavy Chain | |

TABLE 17-continued

Selected human framework regions

| mAb | Chain | FR1 | CDR1 (SEQ ID NO) | FR2 | CDR2 (SEQ ID NO) | FR3 | CDR3 (SEQ ID NO) | FR4 |
|---|---|---|---|---|---|---|---|---|
| 5G2-1B3 | VL | IGKV1-39*01 | 124 | IGKV1-39*01 | 79 | IGKV1-39*01 | 91 | Human Consensus 1, Light Chain |
| 2G12-2B2 | VH | IGHV1-18*01 | 105 | IGHV1-18*01 | 108 | IGHV1-18*01 | 115 | Human Consensus 1, Heavy Chain |
| 2G12-2B2 | VL | IGKV4-1*01 | 123 | IGKV4-1*01 | 85 | IGKV4-1*01 | 97 | Human Consensus 1, Light Chain |
| 8C2-2D6 | VH | IGHV1-18*01 | 105 | IGHV1-18*01 | 107 | IGHV1-18*01 | 114 | Human Consensus 1, Heavy Chain |
| 8C2-2D6 | VL | IGKV1-39*01 | 121 | IGKV1-39*01 | 77 | IGKV1-39*01 | 89 | Human Consensus 1, Light Chain |
| 8C2-2D6 | VL (V2) | IGKV1-39*01 | 142 | IGKV1-39*01 | 147 | IGKV1-39*01 | 148 | Human Consensus 1, Light Chain |
| 3F1 | VH | IGHV1-18*01 | 105 | IGHV1-18*01 | 111 | IGHV1-18*01 | 118 | Human Consensus 1, Heavy Chain |
| 3F1 | VL | IGKV1-39*01 | 127 | IGKV1-39*01 | 130 | IGKV1-39*01 | 133 | Human Consensus 1, Light Chain |

Additional analysis was conducted to identify residues that may be back-crossed to improve antibody binding or other properties. Based on this analysis, several humanized VL and VH sequences were designed for synthesis and testing. These include the variable domain sequences presented in the following Table. In the Table, VH or VL domains are indicated, followed by a digit to show the variant number. Domains with the digit "0" represent the humanized sequence without any back-mutation.

TABLE 18

Humanized variable domains

| mAb | Chain | Sequence | SEQ ID NO |
|---|---|---|---|
| 5G2-1B3 | VL0 | DIQMTQSPSSLSASVGDRVTITCRASENIYSHLAWYQQKPGKAPKLLIYGATNLADGVPSRFSGSGSGTDFTLTISSLQPEDFATYYCQHFWGAPFTFGQGTKVEIK | 217 |
| 5G2-1B3 | VL1 | DIQMTQSPSSLSASVGDRVTITCRASENIYSHLAWYQQKPGKAPKLLVYGATNLASGVPSRFSGSGSGTQFTLTISSLQPEDFATYYCQHFWGAPFTFGQGTKVEIK | 218 |
| 5G2-1B3 | VL2 | DIQMTQSPSSLSASVGDRVTITCRASENIYSHLAWYQQKPGKAPKLLVYGATNLADGVPSRFSGSGSGTQFTLTISSLQPEDFATYYCQHFWGAPFTFGQGTKVEIK | 219 |
| 5G2-1B3 | VH0 | QVQLVQSGAEVKKPGASVKVSCKASGYTFTDHAIHWVRQAPGQGLEWMGYFSPGNDDIKYNEKFKVRVTMTTDTSTSTAYMELRSLRSDDTAVYYCARSYYGDWGQGTLVTVSS | 220 |
| 5G2-1B3 | VH1 | QVQLVQSGAEVKKPGASVKVSCKASGYTFTDHAIHWVRQAPGQGLEWMGYFSPGNDDIKYNEKFKVRVT | 221 |

TABLE 18-continued

Humanized variable domains

| mAb | Chain | Sequence | SEQ ID NO |
|---|---|---|---|
| | | MTADKSSSTAYMELRSLRSDDTAVYFCKRSYYGDW GQGTLVTVSS | |
| 5G2-1B3 | VH2 | QVQLVQSGAEVKKPGASVKISCKASGYTFTDHAIHW VRQAPGQGLEWIGYFSPGNDDIKYNEKFKVRATLTA DKSSSTAYMELRSLRSDDTAVYFCKRSYYGDWGQG TLVTVSS | 222 |
| 5G2-1B3 | VH3 | EVQLVQSGAEVKKPGASVKVSCKASGYTFTDHAIH WVRQAPGQGLEWMGYFSPGNDDIKYNEKFKVRVT MTADKSSSTAYMELRSLRSDDTAVYFCKRSYYGDW GQGTLVTVSS | 223 |
| 5G2-1B3 | VH4 | EVQLVQSGAEVKKPGASVKISCKASGYTFTDHAIHW VRQAPGQGLEWIGYFSPGNDDIKYNEKFKVRATLTA DKSSSTAYMELRSLRSDDTAVYFCKRSYYGDWGQG TLVTVSS | 224 |
| 4G8-1E3 | VL0 | DIQMTQSPSSLSASVGDRVTITCHASQHINFWLSWY QQKPGKAPKLLIYKASNLHTGVPSRFSGSGSGTDFTL TISSLQPEDFATYYCQQDQSYPYMFGQGTKVEIK | 225 |
| 4G8-1E3 | VL1 | DIQMTQSPSSLSASVGDRVTITCHASQHINFWLSWY QQKPGKIPKLLIYKASNLHTGVPSRFSGSGSGTGFTL TISSLQPEDFATYYCQQDQSYPYMFGQGTKVEIK | 226 |
| 4G8-1E3 | VL2 | DIQMTQSPSSLSASVGDRITITCHASQHINFWLSWYQ QKPGKIPKLLIYKASNLHTGVPSRFSGSGSGTGFTLTI SSLQPEDVATYYCQQDQSYPYMFGQGTKLEIK | 227 |
| 4G8-1E3 | VL3 | DIQMTQSPSSLSASVGDRVTITCHASQHINFWLSWY QQKPGKIPKLLIYKASNLHTGVPSRFSGSGSGTGFTL TISSLQPEDFATYYCQQDQSYPYFFGQGTKVEIK | 228 |
| 4G8-1E3 | VL4 | DIQMTQSPSSLSASVGDRITITCHASQHINFWLSWYQ QKPGKIPKLLIYKASNLHTGVPSRFSGSGSGTGFTLTI SSLQPEDVATYYCQQDQSYPYFFGQGTKLEIK | 229 |
| 4G8-1E3 | VH0 | QVQLVQSGAEVKKPGASVKVSCKASGYIFTDHAIH WVRQAPGQGLEWMGYISPGNGDIKYNEKFKGRVT MTTDTSTSTAYMELRSLRSDDTAVYYCARSITTSYW GQGTLVTVSS | 230 |
| 4G8-1E3 | VH1 | QVQLVQSGAEVKKPGASVKVSCKASGYIFTDHAIH WVRQAPGQGLEWMGYISPGNGDIKYNEKFKGRVT MTADKSSSTAYMELRSLRSDDTAVYFCKRSITTSYW GQGTLVTVSS | 231 |
| 4G8-1E3 | VH2 | QVQLVQSGAEVKKPGASVKISCKASGYIFTDHAIHW VRQAPGQGLEWIGYISPGNGDIKYNEKFKGRATLTA DKSSSTAYMHLRSLRSDDTAVYFCKRSITTSYWGQG TLVTVSS | 232 |
| 4G8-1E3 | VH3 | EVQLVQSGAEVKKPGASVKVSCKASGYIFTDHAIHW VRQAPGQGLEWMGYISPGSGDIKYNEKFKGRVTMT ADKSSSTAYMELRSLRSDDTAVYFCKRSITTSYWGQ GTLVTVSS | 233 |
| 4G8-1E3 | VH4 | EVQLVQSGAEVKKPGASVKISCKASGYIFTDHAIHW VRQAPGQGLEWIGYISPGSGDIKYNEKFKGRATLTA DKSSSTAYMHLRSLRSDDTAVYFCKRSITTSYWGQG TLVTVSS | 234 |
| 2G12-2B2 | VL0 | DIVMTQSPDSLAVSLGERATINCKSSQSLLNRGNHK NYLTWYQQKPGQPPKLLIYWASTRESGVPDRFSGSG SGTDFTLTISSLQAEDVAVYYCQNDYTYPYTFGQGT KVEIK | 235 |
| 2G12-2B2 | VL2 | DIVMTQSPDSLAVSLGERVTMSCKSSQSLLNRGNHK NYLTWYQQKPGQPPKLLIYWASTRESGVPDRFSGSG SGTDFTLTISSLQAEDVAVYYCQNDYTYPYTFGQGT KVEIK | 236 |
| 2G12-2B2 | VH0 | QVQLVQSGAEVKKPGASVKVSCKASGYTFTDHAIH WVRQAPGQGLEWMGYFSPGNDDIKYNEKFRGRVT | 237 |

TABLE 18-continued

Humanized variable domains

| mAb | Chain | Sequence | SEQ ID NO |
|---|---|---|---|
| | | MTTDTSTSTAYMELRSLRSDDTAVYYCARSLSTPYW GQGTLVTVSS | |
| 2G12-2B2 | VH1 | QVQLVQSGAEVKKPGASVKVSCKASGYTFTDHAIH WVRQAPGQGLEWMGYFSPGNDDIKYNEKFRGRVT MTADKSSSTAYMELRSLRSDDTAVYFCKRSLSTPYW GQGTLVTVSS | 238 |
| 2G12-2B2 | VH2 | QVQLVQSGAEVKKPGASVKISCKASGYTFTDHAIHW VRQAPGQGLEWIGYFSPGNDDIKYNEKFRGRVTLTA DKSSSTAYMELRSLRSDDTAVYFCKRSLSTPYWGQG TLVTVSS | 239 |
| 2G12-2B2 | VH3 | EVQLVQSGAEVKKPGASVKVSCKASGYTFTDHAIH WVRQAPGQGLEWMGYFSPGNDDIKYNEKFRGRVT MTADKSSSTAYMELRSLRSDDTAVYFCKRSLSTPYW GQGTLVTVSS | 240 |
| 2G12-2B2 | VH4 | EVQLVQSGAEVKKPGASVKISCKASGYTFTDHAIHW VRQAPGQGLEWIGYFSPGNDDIKYNEKFRGRVTLTA DKSSSTAYMELRSLRSDDTAVYFCKRSLSTPYWGQG TLVTVSS | 241 |
| 8C2-2D6 | VL0 | DIQMTQSPSSLSASVGDRVTITCKASENVVTYVSWY QQKPGKAPKLLIYGASNRYTGVPSRFSGSGSGTDFTL TISSLQPEDFATYYCGQGYSYPYTFGQGTKVEIK | 242 |
| 8C2-2D6 | VL1 | NIQMTQSPSSLSASVGDRVTITCKASENVVTYVSWY QQKPGKAPKLLIYGASNRYTGVPSRFSGSGSATDFTL TISSLQPEDFATYYCGQGYSYPYTFGQGTKVEIK | 243 |
| 8C2-2D6 | VL2 | NIVMTQSPSSMSMSVGDRVTLTCKASENVVTYVSW YQQKPGKSPKLLIYGASNRYTGVPSRFSGSGSATDFT LTISSVQPEDLATYHCGQGYSYPYTFGQGTKLEIK | 244 |
| 8C2-2D6(V2) | VL0 | DIQMTQSPSSLSASVGDRVTITCHASQNINVWLSWY QQKPGKAPKLLIYKASNLYTGVPSRFSGSGSGTDFTL TISSLQPEDFATYYCQHDQSYPYTFGQGTKVEIK | 245 |
| 8C2-2D6(V2) | VL1 | DIQMTQSPSSLSASVGDRVTITCHASQNINVWLSWY QQKPGKIPKLLIYKASNLYTGVPSRFSGSGSGTGFTL TISSLQPEDFATYYCQHDQSYPYTFGQGTKVEIK | 246 |
| 8C2-2D6(V2) | VL2 | DIQMTQSPSSLSASVGDRITITCHASQNINVWLSWYQ QKPGKIPKLLIYKASNLYTGVPSRFSGSGSGTGFTLTI SSLQPEDFATYYCQHDQSYPYTFGQGTKLEIK | 247 |
| 8C2-2D6(V2) | VL3 | DIQMNQSPSSLSASVGDRITITCHASQNINVWLSWYQ QKPGKIPKLLIYKASNLYTGVPSRFSGSGSGTGFTLTI SSLQPEDFATYYCQHDQSYPYTFGQGTKLEIK | 248 |
| 8C2-2D6 | VH0 | QVQLVQSGAEVKKPGASVKVSCKASGYTFTDHAIH WVRQAPGQGLEWMGYISPGNGDIKYNEKFKGRVT MTTDTSTSTAYMELRSLRSDDTAVYYCARSITTSYW GQGTLVTVSS | 249 |
| 8C2-2D6 | VH1 | QVQLVQSGAEVKKPGASVKVSCKASGYTFTDHAIH WVRQAPGQGLEWMGYISPGNGDIKYNEKFKGRVT MTADKSSTAYMELRSLRSDDTAVYFCKRSITTSYW GQGTLVTVSS | 250 |
| 8C2-2D6 | VH2 | QVQLVQSGAEVKKPGASVKISCKASGYTFTDHAIHW VRQAPGQGLEWIGYISPGNGDIKYNEKFKGRATLTA DKSSTTAYMELRSLRSDDTAMYFCKRSITTSYWGQG TLVTVSS | 251 |
| 8C2-2D6 | VH3 | EVQLVQSGAEVKKPGASVKVSCKASGYTFTDHAIH WVRQAPGQGLEWMGYISPGSGDIKYNEKFKGRVTM TADKSSTTAYMELRSLRSDDTAVYFCKRSITTSYWG QGTLVTVSS | 252 |

TABLE 18-continued

Humanized variable domains

| mAb | Chain | Sequence | SEQ ID NO |
|---|---|---|---|
| 8C2-2D6 | VH4 | EVQLVQSGAEVKKPGASVKISCKASGYTFTDHAIHW VRQAPGQGLEWIGYISPGSGDIKYNEKFKGRATLTA DKSSTTAYMELRSLRSDDTAMYFCKRSITTSYWGQG TLVTVSS | 253 |

Variable domain pairs were selected for initial expression of full antibodies and testing. Among the pairs selected for 5G2-1B3 were VL0 and VH0 (no back-mutation); VL1 and VH1; VL1 and VH2; VL2 and VH1; VL2 and VH2; and VL1 and VH3. Among the pairs selected for 4G8-1E3 were VL0 and VH0 (no back-mutation); VL1 and VH1; VL1 and VH2; VL2 and VH1; VL2 and VH2; VL1 and VH3; VL3 and VH1; and VL3 and VH3. Among the pairs selected for 2G12-2B2 were VL0 and VH0 (no back-mutation); VL0 and VH1; VL0 and VH2; VL2 and VH1; VL2 and VH2; and VL0 and VH3. Among the pairs selected for 8C2-2D6 were VL0 and VH0 (no back-mutation); VL1 and VH1; VL1 and VH2; VL2 and VH1; VL2 and VH2; and VL1 and VH3. Among the pairs selected for 8C2-2D6(V2) were VL0 and VH0 (no back-mutation); VL1 and VH1; VL1 and VH2; VL2 and VH1; VL2 and VH2; VL3 and VH2; and VL1 and VH3.

3F1 full length heavy chain amino acid sequence (SEQ ID NO: 40) was assessed for the presence of unpaired cysteine residues. Residue 80 of the heavy chain was identified as a cysteine that would be unpaired when part of an IgG. The cysteine was determined to be accessible to solvent when in solution and therefore reactive. A murine 3F1 VH variant was designed to substitute this residue (residue 80 of SEQ ID NO: 40) with a serine residue (QVQLQQSDAELVKP-GASVKISCKASGYTFTDHAIHWVKQKPEQGLDWI-GYISPGNG DIKYNEKFKDKVTLTADKSSS-TASMHLNSLTSEDSAVYFCKRSLLALDYWGQGTTLT VSS; SEQ ID NO: 42).

Humanized 3F1 antibody variable domains were also designed and are presented in the following Table. In the Table, VH or VL domains are indicated, followed by a digit to show the variant number. Domains with the digit "0" represent the humanized sequence without any back-mutation. All VH variants presented were designed with substitution of the unpaired cysteine residue (residue 80 of SEQ ID NO: 40) with a serine residue or with an amino acid having a hydrophobic side chain (e.g., tyrosine).

TABLE 19

3F1 variant variable domains

| mAb Chain | Sequence | SEQ ID NO |
|---|---|---|
| 3F1 VL0 | DIQMTQSPSSLSASVGDRVTITCKASQDVGTNIAWYQQKPG KAPKLLIYSASTRHTGVPSRFSGSGSGTDFTLTISSLQPEDFA TYYCQQYSSFPLTFGQGTKVEIK | 254 |
| 3F1 VL1 | DIQMTQSPSSLSASVGDRVTITCKASQDVGTNIAWYQQKPG KAPKVLIYSASTRHTGVPSRFSGSGSGTDFTLTISSLQPEDFA TYFCQQYSSFPLTFGQGTKVEIK | 255 |
| 3F1 VH0 | QVQLVQSGAEVKKPGASVKVSCKASGYTFTDHAIHWVRQ APGQGLEWMGYISPGNGDIKYNEKFKDRVTMTTDTSTSTA YMELRSLRSDDTAVYYCARSLLALDYWGQGTLVTVSS | 256 |
| 3F1 VH1 | QVQLVQSGAEVKKPGASVKVSCKASGYTFTDHAIHWVRQ APGQGLEWMGYISPGNGDIKYNEKFKDRVTMTADKSSSTA YMQLRSLRSDDTAVYFCKRSLLALDYWGQGTLVTVSS | 257 |
| 3F1 VH2 | QVQLVQSGAEVKKPGASVKISCKASGYTFTDHAIHWVRQA PGQGLEWIGYISPGNGDIKYNEKFKDRVTLTADKSSSTASM HLRSLRSDDTAVYFCKRSLLALDYWGQGTLVTVSS | 258 |
| 3F1 VH3 | EVQLVQSGAEVKKPGASVKVSCKASGYTFTDHAIHWVRQ APGQGLEWMGYISPGSGDIKYNEKFKDRVTMTADKSSSTA YMQLRSLRSDDTAVYFCKRSLLALDYWGQGTLVTVSS | 259 |
| 3F1 VH4 | EVQLVQSGAEVKKPGASVKISCKASGYTFTDHAIHWVRQA PGQGLEWIGYISPGSGDIKYNEKFKDRVTLTADKSSSTASM HLRSLRSDDTAVYFCKRSLLALDYWGQGTLVTVSS | 260 |

Variable domain pairs were selected for initial expression of full antibodies and testing. Among the pairs selected for 3F1 were VL0 and VH0, VL1 and VH1, VL1 and VH2, VL1 and VH3, VL1 and VH4, VL0 and VH3.

Example 8

Characterization of Humanized Antibodies

Humanized IgG1 antibodies having variable domains as described in the previous example were expressed and subjected to characterization analysis including flow cytometry-based binding analysis with MDA-MB-231-STn cells; binding analysis by BSM ELISA; and glycan array analysis.

In flow cytometry-based binding studies, antibodies were screened over a concentration range of 0 to 300 nM, comparing binding to MDA-MB-231 cells with or without transfection-induced STn expression. Binding was determined using an anti-human APC conjugated secondary antibody and only live cells were considered (based on propidium iodide negative gating). 5,000 events were collected per sample on average. Data were analyzed using FlowJo software (Asland, Oreg.) and resulting APC means and % APC were obtained. These data were log transformed then fit to a nonlinear regression model to obtain a dose response curve and $EC_{50}$ binding information. Human isotype IgG1 antibody was used as an isotype negative control. Epidermal growth factor receptor (LA22, EMD Millipore, Billerica, Mass.) was used as a positive control.

For BSM ELISA analysis, antibodies were screened over a concentration range of 0 to 100 nM on bovine submaxillary mucin (BSM) coated wells. A subset of wells were treated with mild periodate solution before antibody binding to remove the side chain on terminal sialic acid residues (destroying the STn antigen). Optical densities of periodate and non-periodate-treated wells were determined and log transformed then fit to a nonlinear regression model to obtain a dose response curve. Optical density values obtained from periodate-treated wells were subtracted from non-periodate treated wells to obtain a periodate-sensitive STn binding curve and corresponding $EC_{50}$ values.

Glycan array analysis was carried out as described previously and antibodies were assigned array glycan binding profiles according to the parameters described therein.

Results from flow cytometry, ELISA, and glycan array analysis are presented in the following Table.

TABLE 20

Antibody characterization results

| Clone ID | Humanized variable domain pair | MDA-MB-231-STn cell binding [$EC_{50}$ (nM)] | BSM ELISA [$EC_{50}$ (nM)] | Array glycan binding profile |
| --- | --- | --- | --- | --- |
| 3F1 | VL1,VH1 | 0.3 | 1.8 | Group 1 |
| 3F1 | VL1,VH2 | 0.7 | 1.4 | Group 1 |
| 3F1 | VL1,VH4 | 9.8 | 6.5 | Group 1 |
| 3F1 | VL1,VH3 | 20.1 | 12.2 | Group 1 |
| 2G12-2B2 | VL0,VH3 | 2.0 | 4.2 | Group 1 |
| 2G12-2B2 | VL2,VH2 | 0.6 | 2.9 | Group 1 |
| 2G12-2B2 | VL0,VH2 | 0.8 | 1.8 | Group 1 |
| 2G12-2B2 | VL2,VH1 | 1.4 | 4.4 | Group 1 |
| 2G12-2B2 | VL0,VH1 | 2.1 | 4.5 | Group 1 |
| 5G2-1B3 | VL1,VH2 | 0.1 | Not Determined | Group 4 |
| 5G2-1B3 | VL1,VH3 | 0.2 | Not Determined | Group 4 |
| 5G2-1B3 | VL2,VH2 | 0.2 | Not Determined | Group 4 |
| 5G2-1B3 | VL2,VH1 | 0.3 | Not Determined | Group 4 |
| 5G2-1B3 | VL1,VH1 | 0.1 | Not Determined | Group 4 |

All antibodies tested demonstrated binding to cell- and BSM-associated STn. No binding was observed with human IgG1 isotype control (Southern Biotech, Birmingham, Ala.). Humanized 5G2-1B3 binding was not periodate sensitive in ELISA assays, so a reliable $EC_{50}$ could not be determined by BSM ELISA.

Based on the results of characterization experiments, two antibodies from each clone group were selected for one liter expression and resulting antibodies were tested again according to the same procedures (see results presented in the following Table).

TABLE 21

Antibody characterization results after one liter production

| Clone ID | Humanized variable domain pair | MDA-MB-231-STn cell binding [$EC_{50}$ (nM)] | BSM ELISA [$EC_{50}$ (nM)] |
| --- | --- | --- | --- |
| 3F1 | VL1, VH1 | 0.48 | 0.86 |
| 3F1 | VL1, VH2 | 0.67 | 0.57 |
| 2G12-2B2 | VL0, VH3 | 1.20 | 0.80 |
| 2G12-2B2 | VL2, VH2 | 0.45 | 1.82 |
| 5G2-1B3 | VL1, VH2 | 0.34 | Not Determined |
| 5G2-1B3 | VL1, VH3 | 1.57 | Not Determined |

All antibodies expressed demonstrated an $EC_{50}$ of less than 2 nM for both cell-associated and BSM-associated STn binding.

Example 9

Analysis of Humanized Antibodies with Antibody-Drug Conjugates

Antibody-drug conjugate (ADC) versions of humanized antibodies described in the previous example were developed by conjugation with monomethyl auristatin E (MMAE). This was carried out by contacting antibodies with maleimidocaproyl-valine-citruline-p-aminobenzyloxy-carbonyl-monomethyl auristatin E (MC-γc-PAB-MMAE, referred to herein as CL-MMAE). The resulting conjugation is maleimide-cysteine based, where the antibody interchain disulfide bonds are reduced with TCEP and then linked to the maleimide moiety of the drug.

Conjugated antibodies were desalted on Sephadex G50 columns to remove residual unreactive toxins and then dialyzed in 30 mM HEPES pH 7.7 with 150 mM NaCl.

ADC antibodies were then assessed in an ADC cytotoxicity assay using MDA-MB-231 cells (parental or transfected for enhanced expression of STn). Parental cells were grown in Eagle's Minimum Essential Medium (EMEM) supplemented with 10% FBS, 1× Pen/Strep and 45 µg/mL gentamycin. STn positive cells were grown in the same media except with the addition of 1 mg/mL G418 for antibiotic selection. Cells were seeded separately (4,000 cells/well for parental cells or 2,000/well for STn positive cells) in 96 well plates using proper media described above. Cells were grown overnight. After 16-20 hours, cells were treated with varying concentratinos of test antibodies in triplicate (50 nM to 0.012 nM) for 72 hours. Then, cells were analyzed using an ADC CELLTITER-GLO® luminescent cell viability assay kit (Promega, Madison, Wis.) to determine the amount of ATP present, an indicator of metabolically active cells. The assay uses a single reagent that is added directly to the cultured cells in serum-supplemented medium. The reagent lyses the cells and generates a luminescent signal proportional to the amount of ATP present. Luminescent signals were analyzed and used to calculate $IC_{50}$ values for each antibody used based on their ability to kill STn positive cells (see the following Table).

TABLE 22

$IC_{50}$ values for humanized ADC antibodies

| Humanized Antibody | $IC_{50}$ (nM) |
|---|---|
| 3F1, VL1, VH1 | 1.30 |
| 3F1, VL1, VH2 | 1.04 |
| 5G12-1B3, VL1, VH2 | 2.58 |
| 5G12-1B3, VL1, VH3 | 7.89 |
| 2G12-2B2, VL0, VH3 | 7.55 |
| 2G12-2B2, VL2, VH2 | 5.17 |

All antibodies tested demonstrated $IC_{50}$ values in the single nanomolar range indicating a strong capability for each to kill STn expressing cells.

Example 10

MDA-MB-231 Xenograft Model Studies

Xenograft model studies are carried out to test humanized ADC antibodies in vivo. Tumors are induced in mice through subcutaneous injection of cancerous cells. Cancerous cells used for injection are selected from: (1) cells transfected to induce expression of STn (MDA-MB-231 STn+ cells), (2) cancer cell lines that naturally express STn on their surface, and (3) patient-derived tumor cells, taken from primary human patient tumors.

Models using patient tumor cells may more faithfully replicate human tumor biology and better predict drug response than other models. In some experiments, patient tumor cells are derived from colorectal cancer patients. In some experiments, patient tumor cells are selected after searching RNA sequence databases to identify cells expressing ST6GalNAc I. In some experiments, patient tumor cells are selected based on expression of STn, as assessed by immunostaining or flow cytometry analysis using anti-STn antibodies.

Once tumor cells are injected into study mice, tumors are allowed to develop until a desired tumor volume (typically between about 175 mm³ to about 225 mm³) is reached. At this point, mice are segregated into treatment groups. Mice are then treated with compositions that include humanized MMAE-conjugated antibodies, irrelevant control antibodies or naked (non-conjugated) antibody controls. Doses are sufficient to deliver from about 1 to about 20 mg of antibody per kilogram of mouse body weight. Mice receive either a single dose or multiple doses (e.g., once per week for three weeks). During treatment, mice are monitored for changes in weight and tumor volume. Tumor volumes in mice treated with humanized ADC antibodies are reduced by about 20 to 100%.

Example 11

Tissue Studies

Humanized antibodies are directly labeled with biotin or pre-complexed with anti-human IgG biotin labeled secondary antibodies. Formalin-fixed paraffin embedded tissue microarray tissue sections are de-paraffinzed, rehydrated, and subjected to antigen retrieval before treatment with biotinylated antibodies or antibody complexes. Antibody binding to the tissues is detected using the VECTASTAIN™ ABC kit (Vector Laboratories, Burlingame, Calif.) to produce a visual precipitate. Following counterstaining with hematoxylin, slides are scored microscopically in a blinded fashion for staining intensity, frequency, and localization. For each candidate antibody, normal tissue microarrays (AC1, Super Bio Chips, Seoul, Korea) containing 60 samples (2 human donors each for 30 organs or subregions of organs) are used to assess normal tissue binding. Human cancer tissue microarrays (MA2 and MA4, Super Bio Chips, Seoul, Korea) containing 118 donor tumor samples are tested to assess antibody binding to cancerous cells. A total of 13 different common tumor types are tested overall, with numerous subclassification annotations captured for each tumor type. Humanized antibodies bind to cancerous cells (including pancreatic and colorectal cancer cells) in human cancer tissue sections with minimal or no binding to cells in normal tissue sections.

Example 12

In Vitro Viability Assays

Experiments are carried out to identify cancer cell lines (e.g., pancreatic and colorectal cell lines) that express STn intrinsically. Among those tested are colorectal cancer cell lines [e.g., LS180 (CL-187), COL0205 (CL-222), TB4 (CCL-248), HT29 (HTB-38), RKO (CRL-2577), SW480 (CCL-228) and SNU-C2A (CCL-250.1) cell lines] and pancreatic cell lines [e.g., Panc-1 (CRL-1469), CFPAC1 (CRL-1918), HPAC (CRL-2119), ASPC1 (CRL-1682), BXPC3 (CRL-1687), CPAN1 (HTB-79), and HPAFII (CRL-1997) cell lines].

Flow cytometry is utilized to assess STn expression. Anti-STn antibodies are combined with cells from the cell line being tested. Binding is determined using an APC conjugated secondary antibody and only live cells are considered (dead cells filtered out using a propidium iodide negative gate). 5,000 events are collected per sample on average. Data are analyzed using FlowJo software (Ashland, Oreg.) and resulting APC means and % APC are obtained. Normal IgG1 antibody is utilized as an isotype control. Cell lines are identified that express STn. Flow cytometry is repeated with humanized antibodies using cell lines found to express STn. Humanized antibodies are found to bind to STn-expressing cancer cell lines.

Cell viability studies are carried out with STn-expressing cancer cell lines identified. Humanized antibodies are used to form ADC antibodies conjugated with MMAE. Cells are treated with the humanized ADC antibodies and $IC_{50}$ values are calculated for each cell line. Humanized ADC antibodies tested are effective in killing STn-expressing cancer cells lines tested.

Example 13

Tissue Cross-Reactivity Study

Tissue cross-reactivity (TCR) studies are carried out to assess the binding profile (both on- and potential off-target binding) of antibodies to human and relevant species used in nonclinical safety testing. For initial characterization and optimization, a preliminary TCR study is conducted to assess the staining pattern of the humanized lead ADC antibodies in human tissues (normal versus cancerous). Lead candidates demonstrate an optimal staining profile with specific cancer cell staining and no or minimal staining of normal tissues.

Cryosections of human, mouse, rat, and cynomolgus monkey normal tissue panel (e.g., brain, colon, heart, liver, lung, pancreas, small intestine, spleen, and stomach) are probed for anti-STn antibody binding. Carcinoma cells within human pancreatic neoplasm are used as positive control tissues and stromal cells within the same tissue are used as negative controls. Detection utilizes an indirect immunoperoxidase technique followed by an ABC tertiary system where the anti-STn humanized antibodies are pre-complexed with biotinylated secondary antibody before tissue incubation. Validation staining runs are undertaken with a limited panel of tissues to determine proper antibody concentrations and conditions before staining the entire tissue panel.

Example 14

Toxicology and Pharmacokinetic Studies

Toxicology studies are carried out in rats using humanized ADC antibodies to identify antibodies with toxic effects and to determine no-observed-adverse-effect-level (NOAEL) for each antibody. Rats are a suitable model because mice are resistant to auristatin, the cytotoxic component of the ADC antibodies. Both single dose and multiple dose studies are undertaken using either 1 mg/kg, 2.5 mg/kg, or 5 mg/kg doses. Multiple rats are included in each treatment group. For single dose studies, animal health and body weights are monitored and rats are sacrificed at different time points after intraperitoneal (IP) antibody administration, including 72 hours after treatment and 2 weeks after treatment. For multiple dose studies, rats receive IP antibody injections at day 0, at week 2 and at week 4. In these studies, rat health and body weights are monitored and rats are sacrificed at different time points after administration, including 24 hours after the last dose and 2 weeks after the last dose.

After sacrifice, organs (adrenal gland, brain, colon, intestine, heart, kidney, lung, mandibular salivary gland, pancrease, spleen, stomach, and thyroid gland) are harvested, formalin-fixed and paraffin-embedded for hematoxylin and eosin (H&E) staining and pathological evaluation.

Rats subjected to single and multiple dose administration of humanized ADC antibodies tested do not show any signs of weight loss or adverse health effects. Organs also appear normal at all time points tested.

In rats utilized for pharmacokinetic analysis, blood samples are obtained before and throughout the study period to quantify serum concentration levels of study antibodies and to conduct pharmacokinetic modeling. Blood is obtained at least 24 hours prior to dosing, at day 1 (approximately 1, 4, and 8 hours post-dose), at day 2 (at approximately 24 hours post-dose), at day 3 (at approximately 48 hours post-dose), at day 4 (at approximately 72 hours post-dose), and at various times post-dose based on single dose results and multiple dose study designs.

Blood samples are allowed to clot and the sera is separated by centrifugation. Resulting samples are subjected to clinical pathological evaluations (clinical chemistry, hematology, and coagulation). Clinical chemistry evaluation includes analysis of sodium creatinine, total protein, potassium, alkaline phosphatase, triglycerides, chloride, alanine aminotransferase, total bilirubin, calcium aspartate aminotransferase, albumin, inorganic phosphorus, glucose, globulin, urea, nitrogen, cholesterol, and albumin/globulin ratio. Hematology evaluation includes evaluation of hematocrit, mean corpuscular hemoglobin concentration, hemoglobin, reticulocyte count (absolute and relative), platelet count, erythrocyte count, mean platelet volume, total white blood cell count, mean corpuscular hemoglobin, differential white blood cell count (absolute & relative), mean corpuscular volume, and red blood cell distribution width. For coagulation analysis, prothrombin time and activated partial thromboplastin time are determined. Clinical pathological evaluations indicate no adverse effects from treatment with humanized ADC antibodies.

Example 15

Evaluation of Patient-Derived Tumor Cells

Experiments are conducted to characterize the STn expression profile of patient-derived xenograft (PDX) cells. Patient-derived cancer cells are used to generate tumors in NOD/SCID mice as described previously. Cells from resulting PDX tumors are removed, dissociated and screened for STn expression. Screening is carried out initially by immunohistochemistry (IHC), then confirmed by flow cytometry analysis. Cells from PDX tumors with the best expression of STn are selected for continued studies.

In one continued study, cells from the selected PDX tumors are cultured in vitro. Some cultures are treated with humanized anti-STn antibodies, described herein, that are conjugated with a cytotoxic agent, MMAE, to form antibody-drug conjugates (ADCs). The ability of these ADCs to kill the cultured cells is determined using cell viability assays. Studies are carried out to compare treatment of these cultures with or without chemotherapeutic agents. Humanized anti-STn ADCs are able to kill cells from PDX tumors that express STn. When cells are first treated with chemotherapeutic agents, the ability of humanized anti-STn ADCs to kill these cells is enhanced.

In another continued study, cells from the selected PDX tumors are cultured in vitro and treated with or without chemotherapeutic agents. STn expression before and after chemotherapeutic agent treatment is evaluated. STn expression in the cells evaluated is increased after chemotherapeutic agent treatment.

Example 16

Antibody Testing Using OVCAR3 Xenograft Model

The effectiveness of humanized anti-STn antibodies to reduce cancer cells in an in vivo tumor model is evaluated. NOD/SCID mice are injected with $5\times10^5$ OVCAR3 cells in a MATRIGEL® (Corning Life Sciences, Corning, N.Y.) suspension to induce OVCAR3 tumor formation. Once mice exhibit tumor volumes ranging from 175-225 $mm^3$, they are randomized into groups with essentially equivalent group mean tumor volumes. Humanized anti-STn antibodies with MMAE conjugates, isotype control antibodies, or vehicle control [20 mM citrate (pH 5.5) and 150 mM NaCl] are administered at a dose of 2.5 mg/kg and mice are monitored for changes in tumor volume and body weight twice weekly for 4 weeks after treatment (or until tumor size reaches an endpoint volume of ≥1000 mm³). Tumors are then extracted and evaluated for the presence of viable tumor cells and STn expression. Antibodies capable of inhibiting or reducing tumor volume; reducing cancer cell numbers; and/or STn expression in tumors are identified and used in further studies.

Example 17

Evaluation of PDX Samples After Single Antibody Treatment

Experiments are carried out to compare responsiveness of PDX models with differing characteristics to anti-STn antibody therapy at different antibody doses. Slow frozen tissue from a passaged ovarian carcinoma PDX tumor is implanted into NOD/SCID mice to generate PDX tumors in those mice over 16 weeks. Tumors are harvested and reinjected into 25 NOD/SCID mice to generate PDX tumors over 12 weeks. Resulting tumors are again harvested and reinjected into 52 NOD/SCID mice and tumors are allowed to form for 12 weeks. These mice are then treated with intraperitoneal injections of humanized anti-STn antibodies (conjugated with MMAE) at 2.5 mg/kg or 5 mg/kg doses; isotype control antibody; or vehicle control [20 mM citrate (pH 5.5) and 150 mM NaCl]. Changes in mouse weight and tumor volume are monitored twice weekly after treatment (or until tumor size reaches an endpoint volume of ≥1000 mm³). Tumors are then extracted and evaluated using flow cytometry for tumor cell viability and STn expression. PDX tumors responsive to anti-STn antibody treatment are identified.

Example 18

Multi-Dose Treatment of PDX Tumors

Cells from PDX tumors with demonstrated responsiveness to humanized anti-STn treatment are selected for use in a multi-dose antibody treatment study. Slow frozen tissue from a passaged ovarian carcinoma PDX tumor is implanted into NOD/SCID mice to generate PDX tumors in those mice over 16 weeks. Tumors are harvested and reinjected into 25 NOD/SCID mice to generate PDX tumors over 12 weeks. Resulting tumors are again harvested and reinjected into 52 NOD/SCID mice and tumors are allowed to form for 12 weeks. These mice are then treated weekly, for 4 weeks, with intraperitoneal injections of humanized anti-STn antibodies (conjugated with MMAE) at a dose of 5 mg/kg; isotype control antibody; or vehicle control [20 mM citrate (pH 5.5) and 150 mM NaCl]. Changes in mouse weight and tumor volume are monitored twice weekly after treatment (or until tumor size reaches an endpoint volume of ≥1000 mm³). Tumors are then extracted and evaluated using flow cytometry for tumor cell viability and STn expression. PDX tumors responsive to anti-STn antibody treatment are identified. MMAE-conjugated humanized anti-STn antibodies are most effective at reducing tumor volume.

Example 19

Cross-Reactivity, Toxicology

Cross-reactivity studies are carried out to determine cross-reactivity of humanized anti-STn antibodies between human, cyno, and rat subjects by immunohistochemical staining using a tissue panel. Humanized anti-STn antibodies are found to cross react with both cyno and rat subjects.

Further toxicological studies are carried out in rats to assess toxicity of humanized anti-STn antibodies. Assessments include in life assessments such as mortality/morbidity, clinical observations, body weight, food consumption, body temperature, local irritation, and ophthalmology. Humanized anti-STn antibodies are not found to be toxic at doses of 10 mg/kg and under.

Example 20

Pharmacokinetic Studies

Humanized anti-STn antibodies conjugated with MMAE are administered to rodent (e.g., rat) or primate study models at a dose of 2.5 mg/kg or 5 mg/kg to evaluate antibody half-life and clinical pathology (e.g., clinical chemistry, hematology, and coagulation). Assessments are made at 72 hour, 2 week and 4 week time points.

For half-life analysis, antibody body fluid concentrations are determined after 1 hour, after 4 hours, after 8 hours, after 24 hours, after 48 hours and after 72 hours from antibody administration.

For clinical pathology, blood samples are collected from study subjects prior to dosing (pretest), and at multiple time points after dosing. For clinical chemistry, sodium creatine, total protein, potassium, alkaline phosphatase, triglycerides, chloride, alanine aminotransferase, total bilirubin, calcium aspartate aminotransferase, albumin, inorganic phosphorus, glucose, globulin, urea, nitrogen, cholesterol, and albumin/globulin ratio are measured. For hematology, hematocrit, mean corpuscular hemoglobin concentration, hemoglobin, reticulocyte count (absolute and relative), platelet count, erythrocyte count, mean platelet volume, total white blood cell count, mean corpuscular hemoglobin, differential white blood cell count (absolute and relative), mean corpuscular volume, and red blood cell distribution width are determined. For coagulation, prothrombin time and activated partial thromboplastin time are evaluated.

Finally, study animals are euthanized and organs (adrenal gland, brain, colon, intestine, heart, kidney, lung, mandibular salivary gland, pancreas, spleen, stomach and thyroid gland) are harvested, formalin-fixed and paraffin-embedded for H&E staining and pathological evaluation by a board-certified pathologist. No adverse effects are observed with humanized antibodies tested.

Example 21

Stable Cell Line Producing Humanized Anti-STn Antibody

Stable cells lines suitable for transition to a GMP facility for production are generated to produce humanized anti-STn antibodies. FREEDOM® pCHO 1.0 vectors (Thermo Fisher Scientific, Waltham, Mass.) are used to generate constructs expressing humanized antibodies having one or more of the variable domains presented in herein. Constructs are introduced by transfection into Chinese Hamster Ovary (CHO) suspension cells using the Gibco FREEDOM® CHO-S® kit (Thermo Fisher Scientific, Waltham, Mass.) and cells are cultured according to kit instructions to select puromycin-resistant cells exhibiting stable expression of the integrated constructs. Resulting stable cell lines are grown for antibody production and storage.

Example 22

Generation of SKOV3 Cell Lines with Enhanced ST6GalNAc I Expression

SKOV3 cells were transduced with lentiviral vectors delivering ST6GalNAc I expression constructs (hST6GalNAc I_pRc-CMV). Stable cell pools were generated and 6 clones with varying expression of ST6GalNAc I [as determined by quantitative polymerase chain reaction (qPCR) analysis] were selected (see the following Table).

TABLE 23

Expression levels of ST6GalNAc I in selected clones

| Clone ID | ST6GalNAc mRNA expression level (fold expression level over control) |
|---|---|
| Clone 7 | 165 |
| Clone 8 | 105 |
| Clone 10 | 15 |
| Clone 13 | 125 |
| Clone 15 | 20 |
| Clone 16 | 30 |

Clones 7, 8, and 13 demonstrated the highest level of ST6GalNAc I mRNA when compared to levels in non-transduced cell lines.

Example 23

Xenograft Tumor Model Studies Using Cells with Varying STn Expression Levels Experiments are carried out to compare responsiveness of xenograft tumors with varying levels of STn expression to humanized anti-STn antibody treatment. Tumor cells with varying levels of STn expression (i.e., cells with no STn expression, cells with low levels of STn expression, cells with intermediate levels of STn expression, and cells with high levels of STn expression) are obtained. These include cells that have been modified to over-express ST6GalNAC I; cells with knockdown of ST6GalNAc I expression; and non-modified cells that have no STn expression, low expression level, intermediate expression level, or high expression level. The tumor cells are implanted into NOD/SCID mice to generate tumors.

Mice are then treated with intraperitoneal injections of humanized anti-STn antibodies (with or without conjugated MMAE); isotype control antibody; or vehicle control [20 mM citrate (pH 5.5) and 150 mM NaCl] for 8 weeks. Changes in mouse weight and tumor volume are monitored twice weekly after treatment. After 8 weeks, mice receiving anti-STn antibody treatments are randomized to either continue 8 more weeks of the initial therapy or to be treated with vehicle control for 8 weeks. At the end of the 16-week period, serum samples are obtained and tumors are extracted for evaluation using flow cytometry for tumor cell viability and STn expression.

Anti-STn antibodies conjugated with MMAE yield the highest level of anti-tumor activity. Discontinuation of anti-STn-MMAE treatment upon randomization promotes tumor resurgence while prolonged therapy with anti-STn-MMAE antibodies prevents tumor resurgence.

Example 24

Screening of Cell Lines for Expression of STn

Breast, colon, ovary, lymphocyte, bone marrow, gastric, paneratic, colorectal, skin cell and other oncological indication cell lines are screened for STn expression. Cell lines tested include SNU-16 cells, LS-174T cells, MC38 cells, COL0205, RKO, HT29, Panc1, HPAC, HPAFII, TOV-112D cells, TOV-21G cells, Jurkate E6.1 cells, K-562 cells, B16-F0 cells, and B16-F10 cells.

Colorectal cell lines [for example, LS180 (CL-187), COL0205 (CL-222), TB4 (CCL-248), HT29 (HTB-38), RKO (CRL-2577), SW480 (CCL-228), and SNU-C2A (CCL-250.1)] are selected for screening based upon ST6GalNAcI expression and desirable characteristics (e.g., doubling time, tumorigenic properties, chemo-resistance and antigen expression). STn expression is tested on both cells grown in vitro and in vivo given that surface and enzymatic expression may be different based on cell growth conditions during development and differentiation.

Cell lines are subjected to STn expression analysis by flow cytometry. Humanized anti-STn antibodies are used to probe for STn expression and a human isotype control is utilized as a negative control.

Each cell line is propagated in culture and distributed among different growth formats. For in vivo formats, cells are injected into NOD/SCID mice in a MATRIGEL™ (Corning Life Sciences, Corning, N.Y.) suspension [$5\times10^6$ cells at a ratio of 1:1 (v/v) with MATRIGELTm] to generate a xenograft model. Mice with mean tumor volumes of 200 $mm^3$, 400 $mm^3$, 600 $mm^3$, or 1000 $mm^3$ are sacrificed and tumors are extracted for STn expression analysis by flow cytometry and for formalin-fixed paraffin embedding for immunohistochemical analysis.

Cells demonstrating STn expression are used for further studies including selection, characterization, and testing of anti-STn antibodies. Some cells demonstrating low or no STn expression are transfected to express STn before use in further studies (e.g., selection, characterization, and testing of anti-STn antibodies).

Example 25

Testing Humanized Anti-STn Antibodies in STn-Expressing Colorectal Cell Lines Humanized anti-STn antibodies are assessed for their capacity for being internalized into STn-expressing colorectal cell lines. Anti-CEA antibodies are used as a positive control. CEA is known to be expressed on the surface of many types of colon cancer cells and may be internalized in colorectal cells, along with other cell types expressing CEA. Anti-STn antibodies as well as controls are covalently labeled with ALEXA FLUOR™ 488 (Thermo Fisher, Waltham, Mass.) according to manufacturer's directions. Surface bound antibody signal is blocked using anti-ALEXA FLUOR™ 488 antibody before assessing internalization via flow cytometry. Results indicate that anti-STn antibodies are internalized by STn-expressing colorectal cell lines.

Example 26

Bystander Killing Assay

STn-positive cells are seeded into a transwell where STn-low or -negative expressors are seeded onto the bottom of the plate. Wells with only STn-positive or only STn-negative cells are included as controls. Doses of 0 to 300 nM of anti-STn antibodies with MMAE conjugates are added to the cultures (as well as free MMAE in some wells as a toxic control) and viability of the STn-low or -negative expressing cells is determined using the Promega (Madison, Wis.) ADC CELLTITER-GLO® luminescent cell viability assay kit, which determines the amount of ATP present as an indicator of metabolically active cells.

Results indicate that STn expressing cells internalize the anti-STn MMAE-conjugated antibodies. The dying cells release cleaved free MMAE which migrates across the transwell membrane and little to no bystander killing is observed by way of toxicity in the non/low-STn expressing cells.

Example 27

Plasma Stability Study

The plasma stability of humanized anti-STn antibodies is evaluated in human, cynomolgus monkey, rat and mouse plasmas. Antibodies are spiked into human, cynomolgus monkey, rat and mouse plasmas in vitro and then incubated at 37° C. for up to 14 days. The concentrations of total humanized antibodies, humanized antibody MMAE conjugtes, and free MMAE in the plasma samples are quantified at different days using immunoassays and LC-MS-based methods. The drug antibody ratio (DAR) is also assessed in the same samples. Antibodies remain relatively stable in plasma and DAR demonstrate little variation over the course of the study.

Example 28

Identification of STn Containing Proteins Using Antibody Microarrays

Cancer cells (MDA MB 231) with or without transfection to induce STn expression were used to identify proteins carrying STn glycosylation. Crude cell lysate from MDA-MB-231 STn+/− were combined with printed antibody microarrays (Rho et. Al, 2013). Each array contains approximately 3500 human-protein specific antibodies, targeting approximately 2100 unique proteins, in triplicate, that are covalently immobilized via N-hydroxysuccinimide (NHS)-ester reactive 3-D thin film surface slides (Nexterion H slide, Schott). Targets of printed antibodies were selected from proteins related to cancer, signaling proteins, and previously identified plasma cancer proteins.

Frozen microarray slides were equilibrated to room temperature for 30 minutes and hydrated in 0.5% Tween20 in phosphate buffered saline (PBS) and then rinsed with distilled/deionized water (dd $H_2O$). The slides were then blocked by incubation for 30 min with 0.3% (v/v) ethanolamine in 50 mM sodium borate, pH 8, followed by 30 min with 1% BSA (w/v), 0.5% Tween 20 in PBS. Next, the arrays were washed with 0.5% Tween 20 in PBS, followed by dd $H_2O$. Then, the arrays were dried by centrifugation at 500 rpm for 8 min in a swinging bucket rotor with a slide rack holder (Sorvall Legend RT). The antibody-printed area of the arrays was covered with a coverslip (mSeries Lifter Slips, 22×25×1 mm, Thermo Scientific).

To detect the presence of STn containing proteins, STn+/− cells were cultured and crude cell lysate was collected in 3 biological replicates to obtain samples (N=3 for STn+ and N=3 for STn−). Lysate was pipetted onto the slide at the microarray/coverslip junction and incubated for 60 min at room temperature. The slides were then washed two times for 5 min with 0.5% Tween 20 in PBS. STn containing glycoproteins were detected after incubation with Siamab's STn antibodies (Hu3F1,L1H1; Hu2G12-2B2,L2H2; Hu5G2-1B3,L1H2 and Hu3F1,L1H1) conjugated to fluorescent Cyanine5 dye. The arrays were washed two times for 5 min with 0.5% Tween 20 in PBS, followed by two times with PBS (5 min each) and once with dd $H_2O$ water followed by drying by centrifugation. To determine background levels of signal, the arrays were incubated with just STn antibody (no cell lysate added) and the resulting signals were used for background subtraction. The slides were then scanned on a GenePix 4200A microarray scanner (Axon Instruments) to produce red (Cy5) images. Spot fluorescent intensities of the scanned array images were obtained using Genepix Pro 6.0 image analysis software.

Differences in Fluorescence intensity (FI) between STn+ and STn− conditions was analyzed by 3 statistical methods: (1) Effect size (((Mean FI STn+ cells−Mean FI STn− cells))/Standard deviation of STn− cells). An effect size >3 is considered desirable in this assay. (2) p-value. A p value <0.25 is desirable in this assay. (3) Ratio ($2^{(Log\ mean\ FI\ STn+\ cells)-Log\ mean\ FI\ STn-\ cells)}$). A ratio >1.2 indicates a protein is increased in STn+ cells and a ratio <0.8 suggests a protein is decreased in STn+ cells.

Each antibody was seen to have different binding properties, but confirmation of certain protein binding between the different antibodies was strong proof of overall upregulation of Sialyl Tn content in cancer. Additionally, known STn carriers MUC16 and MUC1 were detected in this assay. The top 35 hits consisted of proteins located in: plasma membrane (7), extracellular space (8), nucleus (6) and cytoplasm (17). Overall, Hu3F1,L1H1 had the broadest specificity, detecting upregulation in 63 of the total 86 proteins detected. An example of some proteins with STn glycosylation detected using Hu3F1,L1H1, Hu2G12-2B2, L2H2, Hu5G2-1B3,L1H2 in this assay are listed in table below.

TABLE 24

| | | Proteins with increased STn glycosylation | | | | | |
|---|---|---|---|---|---|---|---|
| Gene | Cellular location | Hu3F1 L1H1 p value | Hu3F1 L1H1 effect size | Hu2G12-2B2 L2H2 p value | Hu2G12-2B2 L2H2 effect size | Hu5G2-1B3 L1H2 p value | Hu5G2-1B3 L1H2 effect size |
| IL10 | Extracellular Space | 0.01 | 4.11 | 0.01 | 6.90 | 0.00 | 2.23 |
| SPP1 | Extracellular Space | 0.03 | 13.76 | 0.10 | 2.78 | N/D | N/D |
| LY6D | Plasma Membrane | 0.32 | 2.63 | 0.24 | 1.96 | 0.02 | 13.19 |

TABLE 24-continued

Proteins with increased STn glycosylation

| Gene | Cellular location | Hu3F1 L1H1 p value | Hu3F1 L1H1 effect size | Hu2G12-2B2 L2H2 p value | Hu2G12-2B2 L2H2 effect size | Hu5G2-1B3 L1H2 p value | Hu5G2-1B3 L1H2 effect size |
|---|---|---|---|---|---|---|---|
| MUC16 | Cell membrane, secreted | 0.04 | 2.64 | N/D | N/D | 0.07 | 79.10 |
| F5 | Secreted, Plasma Membrane | 0.02 | 5.69 | 0.04 | 2.89 | 0.20 | 1.59 |
| PDPK1 | Cell membrane-peripheral membrane protein, Cytoplasm | 0.08 | 12.38 | 0.40 | 1.36 | 0.03 | 7.05 |
| Ihh | Extracellular space | 0.15 | 24.84 | 0.54 | 0.93 | 0.83 | 0.07 |
| IHH | Extracellular Space | 0.35 | 1.32 | 0.05 | 3.95 | N/D | N/D |
| IHH | Extracellular Space | N/D | N/D | N/D | N/D | 0.05 | 12.07 |
| SMS | Cytoplasm | 0.10 | 3.11 | 0.13 | 30.82 | 0.03 | 7.22 |
| MAPK3 | Cytoplasm | 0.01 | 6.73 | 0.11 | 3.07 | 0.04 | 11.96 |
| OAS1 | Cytoplasm | 0.01 | 4.69 | 0.05 | 32.20 | 0.89 | 0.28 |
| CRADD | Cytoplasm | 0.13 | 1.26 | 0.17 | 1.68 | 0.06 | 28.19 |
| GRB2 | Cytoplasm | 0.01 | 5.38 | 0.14 | 6.83 | 0.07 | 7.23 |
| PRDX6 | Cytoplasm | 0.06 | 2.48 | 0.25 | 9.99 | 0.19 | 2.35 |
| PCNA | Nucleus | 0.05 | 2.95 | 0.19 | 2.79 | 0.11 | 21.73 |
| CUX1 | Nucleus | 0.06 | 2.35 | 0.00 | 6.74 | N/D | N/D |

All proteins listed showed affinity for at least one STn antibody suggesting the presence of STn glycosylation. IHH appears on the list as three separate entries. These are captured by three unique antibodies to IHH. The following proteins showed binding with two different antibody clones: IL10, SPP1, LY6D, MUC16, F5, PDPK1, SMS, MAPK3, OAS1, CRADD, GRB2, PRDX6, PCNA and CUX1, strongly demonstrating their STn glycosylation.

Among these IL10, SPP1, LY6D and MUC16 have extracellular or cell membrane localization and have been previously implicated as cancer biomarkers.

IL10: Interleukin-10 inhibits the synthesis of a number of cytokines, including IFN-gamma, IL-2, IL-3, TNF and GM-CSF that are produced by activated macrophages and by helper T-cells.

SPP1: Osteopontin is activated by ligand, sialic acid, and is essential for Type I immunity. It can interact with CD44. SPP1 acts as a cytokine and enhances production of interferon-gamma and interleukin-12 and decreases production of interleukin-10.

MUC16: Mucin-16 or CA-125, is a known cancer biomarker for ovarian cancer.

LY6D: Lymphocyte antigen 6D acts as a B cell specification marker at the specification stage of lymphocytes between B- and T-cell development.

Some of the proteins identified by the screen were unique to only one STn antibody clone. Proteins showing glycosylation with Hu3F1,L1H1 are represented in the table below.

TABLE 25

Proteins recognized by Hu3F1, L1H1

| Gene | Location | Hu3F1 L1H1 p value | Hu3F1 L1H1 effect size |
|---|---|---|---|
| TLN1 | Plasma Membrane/Cytoplasmic side | 0.06 | 25.27 |

TABLE 25-continued

Proteins recognized by Hu3F1, L1H1

| Gene | Location | Hu3F1 L1H1 p value | Hu3F1 L1H1 effect size |
|---|---|---|---|
| MUC1 | Plasma Membrane | 0.03 | 9.00 |
| LIMK2 | Cytoplasm | 0.02 | 8.78 |
| MAPRE1 | Cytoplasm | 0.03 | 7.91 |

TLN1: Talin-1 is a part of the connection between cytoskeletal structures and plasma membrane. TLN1 was previously identified in mouse insertional mutagenesis experiments suggesting a causal role in cancer. TLN1 expression correlates with invasion and migration of cancer cells.

MUC1: The beta subunit of Mucin-1 contains a C-terminal domain which is involved in cell signaling, through phosphorylation and protein-protein interactions, through which it can promote tumor growth. In B cells, Mucl modulates ERK, SRC and NF-Kappa-B signaling pathways. While in activated T-cells, it modulates the Ras/MAPK pathway.

Proteins showing glycosylation with Hu2G12-2B2,L2H2 are represented in the table below.

TABLE 26

Proteins recognized by 2G12-2B2, L2H2

| Gene | Location | Hu2G12-2B2, L2H2 p value | Hu2G12-2B2, L2H2 effect size |
|---|---|---|---|
| ALDH1A1 | Cytoplasm | 0.01 | 12.70 |
| ANO1 | Plasma Membrane | 0.02 | 6.67 |

ALDH1A1: Retinal dehydrogenase is a cancer stem cell marker. It has also been implicated in chemoresistance.

ANO1: Anoctamin-1 is a calcium-activated chloride channel which plays a role in trans epithelial anion transport.

ANO1 is amplified and highly expressed in breast cancer cell lines and primary tumors.

Proteins showing glycosylation with Hu5G2-1B3,L1H2 are represented in the table below.

TABLE 27

Proteins recognized by Hu5G2-1B3, L1H2

| Gene | Location | Hu5G2-1B3, L1H2 p value | Hu5G2-1B3, L1H2 effect size |
|---|---|---|---|
| GPC3 | Plasma Membrane | 0.026 | 8.69 |
| HAPLN1 | Extracellular Space | 0.003 | 5.53 |

GPC3: Glypican-3 is a cell surface proteoglycan that bears heparan sulfate. It is involved in the suppression of growth in the predominantly mesodermal tissues and organs. An anti-GPC3 monoclonal antibody has been shown to have anti-cancer activity in mice.

Proteins showing STn glycosylation with Hu3F1,L1H1 antibody were compared with proteins showing glycosylation using the Mu3F1. Results are presented in the following Table.

TABLE 28

3F1 Antibody comparison

| Gene | Location | Hu3F1, L1H1 p value | Hu3F1, L1H1 effect size | Ratio Mu3F1 |
|---|---|---|---|---|
| COL4A3 | Extracellular Space | 0.062 | 22.63 | 1.09 |
| CCR5 | Plasma Membrane | 0.104 | 20.55 | 1.17 |
| SLC30A8 | Cytoplasm vesicle and cell membrane protein | 0.006 | 8.26 | 1.03 |
| CNN1 | Cytoskeleton | 0.015 | 6.42 | 1.06 |
| ITSN1 | Endomembrane system | 0.007 | 5.74 | 1.04 |
| PKM2 | Cytoplasm, plasma membrane, and extracellular space | 0.348 | 6.59 | 1.06 |
| LAMB3 | Extracellular Space | 0.116 | 5.28 | 1.12 |
| F5 | Secreted and Plasma Membrane | 0.022 | 5.69 | 1.14 |
| MUC1 | Plasma Membrane | 0.028 | 9.00 | 1.00 |
| TK1 | Cytoplasm | 0.032 | 7.59 | 1.07 |
| SMS | Cytoplasm | 0.098 | 3.11 | 1.04 |
| PRDX6 | Cytoplasm | 0.060 | 2.48 | 1.05 |
| CUX1 | Nucleus | 0.057 | 2.35 | 1.07 |
| MEF2C | Nucleus | 0.015 | 8.92 | 1.04 |
| CCNE2 | Nucleus | 0.001 | 10.30 | 1.05 |
| PCNA | Nucleus | 0.050 | 2.95 | 1.03 |

Example 29

Humanized Antibody Testing Using Alternative Glycan Array

All proteins listed showed affinity for both STn antibodies, indicating the presence of STn glycosylation. Among these COL4A3, CCR5, and MUC1 have extracellular or cell membrane localization and have been previously implicated as cancer biomarkers.

COL4A3: Collagen alpha-3(IV) chain. Type IV collagen is the major structural component of glomerular basement membranes (GBM), forming a 'chicken-wire' meshwork together with laminins, proteoglycans and entactin/nidogen. Tumstatin, a cleavage fragment corresponding to the collagen alpha 3(IV) NC1 domain, possesses both anti-angiogenic and anti-tumor cell activity CCR5: C—C chemokine receptor type 5 is a receptor for a number of inflammatory CC-chemokines. CCR5 has been implicated in the recruitment of T-reglulatory cells (Treg) from blood into tumor sites in human colorectal cancer. Tumor growth is delayed in CCR5−/− mice and associated with reduced tumor Treg infiltration.

Alternative glycan arrays with 13 chemically synthesized and well-defined glycans were also utilized to test antibody affinity and specificity for multiple glycans in a single experiment. The alternative glycan array includes Neu5Ac and Neu5Gc glycan pairs listed in the following table.

TABLE 29

Array glycans in alternative array

| Glycan ID No. | Glycan |
|---|---|
| 1 | Neu5Acα6GalNAcαO(CH2)2CH2NH2 |
| 2 | Neu5Gcα6GalNAcαO(CH2)2CH2NH2 |
| 3 | Neu5Acα6Galβ4GlcNAcβO(CH2)2CH2NH2 |
| 4 | Neu5Gcα6Galβ4GlcNAcβO(CH2)2CH2NH2 |
| 5 | Neu5Acα6Galβ4GlcβO(CH2)2CH2NH2 |
| 6 | Neu5Gcα6Galβ4GlcβO(CH2)2CH2NH2 |
| 7 | Neu5Acα6GalβO(CH2)2CH2NH2 |
| 8 | Neu5Gcα6GalβO(CH2)2CH2NH2 |

TABLE 29-continued

Array glycans in alternative array

| Glycan ID No. | Glycan |
|---|---|
| 9 | GalNAcαO(CH2)2CH2NH2 |
| 10 | Galβ3GalNAcβO(CH2)2CH2NH2 |
| 11 | Gal3βGalNAcαO(CH2)2CH2NH2 |
| 12 | Neu5Acα3Galβ1-3GalNAcαO(CH2)2CH2NH2 |
| 13 | Neu5Gcα3Galβ1-3GalNAcαO(CH2)2CH2NH2 |

Polyacrylamide (PAA) conjugated, human serum albumin (HAS)-conjugated or amine conjugated glycoconjugates were utilized for glycan probe preparation. Glycoconjugates were synthesized chemoenzymatically according to methods described in Yu, H. et al., 2007. Org Biomol Chem. 5:2458-63, the contents of which are herein incorporated by reference in their entirety. Sialoglycans are synthesized using the "one-pot three-enzyme" approach as described by Yu et al (Yu, H. et al., Nat Protoc. 2006. 1(5): 2485-92, Yu, H. et al., J Am Chem Soc. 2005. 127:17618-9 and Yu, H. et al., 2006. Angew Chem Int Ed Engl. 45:3938-44, the contents of each of which are herein incorporated by reference in their entirety). The compound structure was confirmed by HRMS (ESI) mass spectrometry. Purity of each synthesized glycan was assessed by HPLC analysis and only glycan preparations with greater than 95% purity were used.

Arrays were printed on epoxide-derivatized slides (Corning, N.Y.) with NanoPrint LM-60 Microarrayer equipped with 946MP3 Microarray Printing Pins (Arrayit Corporation, Sunnyvale, Calif.) with 16 sub-array blocks on each slide. Glycan probes were distributed into 384-well source plates using four replicate wells per sample and 8 µL per well. Glycan probes were prepared at a concentration of 100 µM per glycan in print buffer (300 mM Phosphate buffer, pH 8.4). Additionally, the linker (O(CH2)2CH2NH2) alone and buffer alone (300 mM phosphate buffer, pH 8.4) were printed on the array in four replicates. To monitor printing quality, murine IgG and human IgG were also printed on each slide (40 and 20 ng/uL in PBS containing 10% glycerol, Jackson ImmunoResearch Laboratories, WestGrove, Pa.). The arrays were printed with four 946MP3 pins (5 µm tip, 0.25 L sample channel, approximately 100 µm spot diameter, Arrayit Corporation). Each block (sub-array) had 10 rows, 8 columns with spot to spot spacing of 275 µm. The humidity level in the arraying chamber was maintained at about 70% during printing. Printed slides were left on the arrayer deck overnight, allowing humidity to drop to ambient levels (40-45%). The slides were then packed, vacuum sealed and stored at room temperature.

The glycan array was assayed using: Hu2G12-2B2,L0H2, Hu8C2-2D6,L1H1, Hu5G2-1B3,L1H2, Mu2G12-2B2, and Mu3F1.

Additionally, control antibodies and lectins were also tested on the array to determine if the glycans in the array can be recognized by known glycan binding agents. These included: (a) Anti-Gc antibody, which binds to Gc containing glycans, Neu5Gcα6GalNAcαO(CH2)2CH2NH2 (Gc-STn) (Glycan ID No. 2), Neu5Gcα6Galβ4GlcNAcβO(CH2)2CH2NH2 (Glycan ID No. 4), Neu5Gcα6Galβ4GlcβO(CH2)2CH2NH2 (Glycan ID No. 6), Neu5Gcα6GalβO(CH2)2CH2NH2 (Glycan ID No. 8) and Neu5Gcα3Galβ1-3GalNAcαO(CH2)2CH2NH2 (Glycan ID No. 13); (b)MAL-II (Maackia Amurensis Lectin II) which binds to glycans containing (2,3)-linked sialic acid such as Neu5Acα3Galβ1-3GalNAcαO(CH2)2CH2NH2 (Glycan ID No. 12) and Neu5Gcα3Galβ1-3GalNAcαO(CH2)2CH2NH2 (Glycan ID No. 13); (c) SNA (Sambucus Nigra Lectin) which preferentially binds to glycans containing (2, 6) sialic acid linked to a terminal galactose such as Neu5Acα6Galβ4GlcNAcβO(CH2)2CH2NH2 (Glycan ID No. 3), Neu5Gcα6Galβ4GlcNAcβO(CH2)2CH2NH2(Glycan ID No. 4), Neu5Acα6Galβ4GlcβO(CH2)2CH2NH2 (Glycan ID No. 5) and Neu5Gcα6Galβ4GlcβO(CH2)2CH2NH2(Glycan ID No. 6); and (d) Palivizuamab as an isotype negative control and bound no glycans nor linker/buffer printed controls as expected.

An epoxy blocking buffer (300 ml) was prepared by combining 15 ml of 2 M Tris buffer (pH 8) with 0.9 ml of 16.6 M ethanolamine and 284.1 ml of distilled water. The solution was filtered using a 0.2 µM nitrocellulose membrane. The epoxy buffer solution as well as 1 L of distilled water were pre-warmed to 50° C. Glass slides were arranged in a slide holder and quickly submerged in a staining tub with the warmed epoxy blocking buffer. Slides were incubated in the epoxy blocking buffer for 1 hour at 50° C. with periodic shaking to deactivate epoxy binding sites. Next, slides were rinsed with distilled water, placed into ProPlate slide holders (Grace Bio-Labs #204862 16 square 7×7 mm chambers) and then blocked with PBS with 1% OVA at 25° C. for one hour. Test antibodies and isotype control antibodies were tested at 1 and 2.5 ug/mL. Control antibody anti-Gc was tested at 0.5 ug/mL and 1 ug/mL. Control biotin tagged lectins were tested at 40 ug/mL for MALII and 20 ug/mL for SNA. All antibodies/lectins were diluted in blocking buffer (1% OVA/PBS) and incubated with the glycan array for one hour at 25° C. After extensive washing, binding of polyclonal serum antibodies was detected by incubating glycan microarray slides with Cy3-conjugated anti-SA, anti-mouse IgG or antihuman IgG (Jackson Immunoresearch, West Grove, Pa.) for one hour. Slides were then washed extensively, dried and scanned with a Genepix 4000B scanner (Laser at 100%; gain at 350; 10 µm pixels). Raw fluorescence intensity data from scanned images were extracted using the Genepix software and analysis of raw data was carried out. Antibodies were considered to be highly specific for AcSTn and GcSTn if they demonstrated binding to both molecules, but not to Tn or any other glycans on the array.

Antibodies Hu2G12-2B2,L0H2, Hu8C2-2D6,L1H1, Hu5G2-1B3,L1H2, Mu2G12-2B2, and Mu3F1 demonstrated binding to AcSTn and GcSTn (Glycan ID No 1 and 2) but not to other glycans in the array demonstrating that these antibodies have an affinity specifically for STn glycans only. As expected, the anti-Gc antibody, bound to all glycans in the array containing Gc, MALII bound to glycans in the array containing (2,3)-linked sialic acid, SNA bound to glycans in the array containing (2, 6) sialic acid linked to a terminal galactose and the Palivizuamab control showed no binding to the glycans. These results demonstrated that the glycan array contains glycans that can be recognized by antibodies and proteins that are specific to the printed glycans.

Example 30

Neoglycolipid Array Analysis

Neoglycolipid probes are prepared from chemically synthesized glycans described in table below.

TABLE 30

| Glycan ID No | Glycan |
|---|---|
| 1 | Neu5Acα6GalNAcαO(CH2)2CH2NH2 (AcSTn) |
| 2 | Neu5Gcα6GalNAcαO(CH2)2CH2NH2 (GcSTn) |
| 3 | Neu5Acα6Galβ4GlcNAcβO(CH2)2CH2NH2 |
| 4 | Neu5Gcα6Galβ4GlcNAcβO(CH2)2CH2NH2 |
| 5 | Neu5Acα6Galβ4GlcβO(CH2)2CH2NH2 |
| 6 | Neu5Gcα6Galβ4GlcβO(CH2)2CH2NH2 |
| 7 | Neu5Acα6GalβO(CH2)2CH2NH2 |
| 8 | Neu5Gcα6GalβO(CH2)2CH2NH2 |
| 9 | GalNAcαO(CH2)2CH2NH2 |
| 10 | Galβ3GalNAcβO(CH2)2CH2NH2 |
| 11 | Gal3βGalNAcαO(CH2)2CH2NH2 |
| 12 | Neu5Acα3Galβ1-3GalNAcαO(CH2)2CH2NH2 |
| 13 | Neu5Gcα3Galβ1-3GalNAcαO(CH2)2CH2NH2 |

Neoglycolipids are prepared by conjugating the glycans to amino phospholipid N-aminoacetyl-N-(9-anthracenyl methyl)-1,2-dihexadecyl-sn-glycero-3-phosphoethanolamine (ADHP) to generate fluoresecent probes or with L-1,2-dihexadecyl-sn-glycero-3-phosphoethanolamine (DHPE) by reductive amination or N-aminooxyacetyl-1,2-dihexadecyl-sn-glycero-3-phosphoethanolamine (AOPE) by oxime ligation to generate non fluoresecent probes. The conjugation reaction allows the NGLs to be immobilized on solid matrices. Glycans that have been reductively released from glycoproteins are subject to mild periodate reaction prior to conjugation. After conjugation, the NGL products are purified to remove excess lipids and salts, analyzed by mass spectrophotometry and quantified on High Performance thin layer chromatography by densitometry.

Neoglycolipid arrays are produced by robitically dispensing the neoglycolipid probes onto nitrocellulose-coated glass slides in a liposome formulation. Probes are printed at multiple concentrations and densities to determine the optimal hybridization conditions.

Slides are probed with purified anti-STn antibody solutions or polyclonal serum containing anti-STn antibodies. Antibody binding is detected using biotinylated secondary antibody followed by a fluorescently labeled streptavidin. Slides are scanned using a ProScanArray (Perkin Elmer Life Sciences), and Fluorescent binding signals are quantified using ScanArray Express software (PerkinElmer Life Sciences). Purified antibodies or sera are considered to be highly specific for AcSTn and GcSTn if they demonstrate binding to both molecules, but not to Tn or any other glycans on the array.

What is claimed is:

1. An isolated antibody that binds to sialyl($\alpha$2,6)N-acetylgalactosamine (STn), wherein the antibody comprises a heavy chain variable domain (VH) comprising an amino acid sequence selected from SEQ ID NOs: 237-241, and a light chain variable domain (VL) comprising an amino acid sequence selected from SEQ ID NOs: 235 and 236.

2. The isolated antibody of claim 1, wherein the VH comprises the amino acid sequence of SEQ ID NO: 240 and the VL comprises the amino acid sequence of SEQ ID NO: 235.

3. The isolated antibody of claim 1, wherein the antibody comprises a human IgG1, IgG2, IgG3, or IgG4 constant region.

4. The isolated antibody of claim 1, wherein the antibody comprises a human IgG1 constant region.

5. The isolated antibody of claim 2, wherein the antibody comprises a human IgG1 constant region.

6. The isolated antibody of claim 2, wherein the antibody binds to cell-associated STn with a half maximal effective concentration (EC50) of from about 0.01 nM to about 30 nM.

7. A pharmaceutical composition comprising the antibody of claim 1 and at least one pharmaceutically acceptable excipient.

8. An isolated nucleic acid that encodes an antibody that binds to sialyl($\alpha$2,6)N-acetylgalactosamine (STn), wherein the antibody comprises a heavy chain variable domain (VH) comprising an amino acid sequence selected from SEQ ID NOs: 237-241, and a light chain variable domain (VL) comprising an amino acid sequence selected from SEQ ID NOs: 235 and 236.

9. The isolated nucleic acid of claim 8, wherein the VH comprises the amino acid sequence of SEQ ID NO: 240 and the VL comprises the amino acid sequence of SEQ ID NO: 235.

10. The isolated nucleic acid of claim 8, wherein the antibody comprises a human IgG1, IgG2, IgG3, or IgG4 constant region.

11. The isolated nucleic acid of claim 8, wherein the antibody comprises a human IgG1 constant region.

12. The isolated nucleic acid of claim 9, wherein the antibody comprises a human IgG1 constant region.

13. An isolated host cell that comprises the nucleic acid of claim 8.

14. An isolated host cell that comprises the nucleic acid of claim 9.

15. An isolated host cell that expresses the antibody of claim 1.

16. An isolated host cell that expresses the antibody of claim 2.

17. A method of producing an antibody that binds to sialyl($\alpha$2,6)N-acetylgalactosamine (STn), comprising culturing the host cell of claim 15 under conditions suitable for expressing the antibody.

18. The method of claim 17, further comprising isolating the antibody.

19. A method of producing an antibody that binds to sialyl($\alpha$2,6)N-acetylgalactosamine (STn), comprising culturing the host cell of claim 16 under conditions suitable for expressing the antibody.

20. The method of claim 19, further comprising isolating the antibody.

21. A method of treating cancer comprising administering to a subject with cancer a therapeutically effective amount of an antibody that binds to sialyl($\alpha$2,6)N-acetylgalactosamine (STn), wherein the antibody comprises a heavy chain variable domain (VH) comprising an amino acid sequence selected from SEQ ID NOs: 237-241, and a light chain variable domain (VL) comprising an amino acid sequence selected from SEQ ID NOs: 235 and 236, wherein the antibody comprises an IgG1 or IgG3 constant region, and wherein the cancer comprises STn-positive cancer cells.

22. The method of claim 21, wherein the VH comprises the amino acid sequence of SEQ ID NO: 240 and the VL comprises the amino acid sequence of SEQ ID NO: 235.

23. The method of claim 21, wherein the antibody comprises a human IgG1 constant region.

24. The method of claim 22, wherein the antibody comprises a human IgG1 constant region.

25. The method of claim 22, wherein the antibody binds to cell-associated STn with a half maximal effective concentration (EC50) of from about 0.01 nM to about 30 nM.

26. The method of claim 21, wherein the cancer is breast cancer, colon cancer, pancreatic cancer, lung cancer, cervical cancer, ovarian cancer, stomach cancer, prostate cancer, or liver cancer.

27. A method of selecting a subject with cancer for treatment with an anti-STn antibody, comprising contacting a sample from the subject with an antibody that binds to sialyl($\alpha$2,6)N-acetylgalactosamine (STn) and comprises a heavy chain variable domain (VH) comprising an amino acid sequence selected from SEQ ID NOs: 237-241, and a light chain variable domain (VL) comprising an amino acid sequence selected from SEQ ID NOs: 235 and 236; and detecting binding of the antibody to STn-expressing cancer cells.

28. The method of claim 27, further comprising administering an anti-STn antibody to the subject.

29. The method of claim 27, wherein the sample is a cell, a tissue, a tissue section, a body fluid, serum, or a combination thereof.

30. A kit for screening a biological sample for the presence of STn-expressing cancer cells, comprising the isolated antibody of claim 1.

31. An antibody-drug conjugate comprising an antibody conjugated to a therapeutic agent, wherein the antibody binds to sialyl($\alpha$2,6)N-acetylgalactosamine (STn) and comprises a heavy chain variable domain (VH) comprising an amino acid sequence selected from SEQ ID NOs: 237-241, and a light chain variable domain (VL) comprising an amino acid sequence selected from SEQ ID NOs: 235 and 236.

32. The antibody-drug conjugate of claim 31, wherein said therapeutic agent is a cytotoxic agent.

33. The antibody-drug conjugate of claim 32, wherein said cytotoxic agent is monomethyl auristatin E (MMAE) or monomethyl auristatin F (MMAF).

34. The antibody-drug conjugate of claim 33, wherein the cytotoxic agent is MMAE.

35. The antibody-drug conjugate of claim 31, wherein the VH comprises the amino acid sequence of SEQ ID NO: 240 and the VL comprises the amino acid sequence of SEQ ID NO: 235.

36. The antibody-drug conjugate of claim 32, wherein the VH comprises the amino acid sequence of SEQ ID NO: 240 and the VL comprises the amino acid sequence of SEQ ID NO: 235.

37. The antibody-drug conjugate of claim 33, wherein the VH comprises the amino acid sequence of SEQ ID NO: 240 and the VL comprises the amino acid sequence of SEQ ID NO: 235.

38. The antibody-drug conjugate of claim 34, wherein the VH comprises the amino acid sequence of SEQ ID NO: 240 and the VL comprises the amino acid sequence of SEQ ID NO: 235.

39. A pharmaceutical composition comprising the antibody-drug conjugate of claim 31 and at least one pharmaceutically acceptable excipient.

40. A method of treating cancer comprising administering to a subject with cancer a therapeutically effective amount of an antibody-drug conjugate comprising an antibody conjugated to a cytotoxic agent, wherein the antibody binds to sialyl(α2,6)N-acetylgalactosamine (STn) and comprises a heavy chain variable domain (VH) comprising an amino acid sequence selected from SEQ ID NOs: 237-241, and a light chain variable domain (VL) comprising an amino acid sequence selected from SEQ ID NOs: 235 and 236, and wherein the cancer comprises STn-positive cancer cells.

41. The method of claim 40, wherein said cytotoxic agent is monomethyl auristatin E (MMAE) or monomethyl auristatin F (MMAF).

42. The method of claim 41, wherein the cytotoxic agent is MMAE.

43. The method of claim 40, wherein the VH comprises the amino acid sequence of SEQ ID NO: 240 and the VL comprises the amino acid sequence of SEQ ID NO: 235.

44. The method of claim 41, wherein the VH comprises the amino acid sequence of SEQ ID NO: 240 and the VL comprises the amino acid sequence of SEQ ID NO: 235.

45. The method of claim 42, wherein the VH comprises the amino acid sequence of SEQ ID NO: 240 and the VL comprises the amino acid sequence of SEQ ID NO: 235.

46. The method of claim 40, wherein the cancer is breast cancer, colon cancer, pancreatic cancer, lung cancer, cervical cancer, ovarian cancer, stomach cancer, prostate cancer, or liver cancer.

47. The method of claim 45, wherein the cancer is breast cancer, colon cancer, pancreatic cancer, lung cancer, cervical cancer, ovarian cancer, stomach cancer, prostate cancer, or liver cancer.

48. A method of killing a STn-expressing cell, comprising contacting the cell with the antibody-drug conjugate of claim 31.

49. A method of making an antibody-drug conjugate, comprising contacting an antibody that binds to sialyl(α2,6)N-acetylgalactosamine (STn) with maleimidocaproyl-valine-citruline-p-aminobenzyloxycarbonyl-monomethyl auristatin E (MC-γc-PAB-MMAE), wherein the antibody comprises a heavy chain variable domain (VH) comprising an amino acid sequence selected from SEQ ID NOs: 237-241, and a light chain variable domain (VL) comprising an amino acid sequence selected from SEQ ID NOs: 235 and 236.

50. The method of claim 49, wherein the VH comprises the amino acid sequence of SEQ ID NO: 240 and the VL comprises the amino acid sequence of SEQ ID NO: 235.

51. The method of claim 21, wherein the cancer is endometrial cancer, gastric cancer, or colorectal cancer.

52. The method of claim 40, wherein the cancer is endometrial cancer, gastric cancer, or colorectal cancer.

53. The method of claim 45, wherein the cancer is endometrial cancer, gastric cancer, or colorectal cancer.

54. The isolated antibody of claim 1, wherein the antibody binds to cell-associated STn with a half maximal effective concentration (EC50) of from about 0.01 nM to about 30 nM.

55. A pharmaceutical composition comprising the antibody of claim 2 and at least one pharmaceutically acceptable excipient.

56. An isolated nucleic acid that encodes a heavy chain variable domain of an antibody that binds to sialyl(α2,6)N-acetylgalactosamine (STn), wherein the heavy chain variable domain (VH) comprises an amino acid sequence selected from SEQ ID NOs: 237-241.

57. The isolated nucleic acid of claim 52, wherein the VH comprises the amino acid sequence of SEQ ID NO: 240.

58. An isolated nucleic acid that encodes a light chain variable domain of an antibody that binds to sialyl(α2,6)N-acetylgalactosamine (STn), wherein the light chain variable domain (VL) comprises an amino acid sequence selected from SEQ ID NOs: 235 and 236.

59. The isolated nucleic acid of claim 54, wherein the VL comprises the amino acid sequence of SEQ ID NO: 235.

60. The isolated nucleic acid of claim 56, wherein the antibody comprises a human IgG1, IgG2, IgG3, or IgG4 constant region.

61. The isolated nucleic acid of claim 52, wherein the antibody comprises a human IgG1 constant region.

62. The isolated nucleic acid of claim 53, wherein the antibody comprises a human IgG1 constant region.

63. An isolated host cell that comprises a first nucleic acid that encodes a heavy chain variable domain (VH) of an antibody that binds to sialyl(α2,6)N-acetylgalactosamine (STn), wherein the VH comprises an amino acid sequence selected from SEQ ID NOs: 237-241, and a second nucleic acid that encodes a light chain variable domain (VL) of the antibody that binds to sialyl(α2,6)N-acetylgalactosamine (STn), wherein the VL comprises an amino acid sequence selected from SEQ ID NOs: 235 and 236.

64. The isolated host cell of claim 63, wherein the VH comprises the amino acid sequence of SEQ ID NO: 240 and the VL comprises the amino acid sequence of SEQ ID NO: 235.

65. The isolated host cell of claim 63, wherein the antibody comprises a human IgG1, IgG2, IgG3, or IgG4 constant region.

66. The isolated host cell of claim 63, wherein the antibody comprises a human IgG1 constant region.

67. The isolated host cell of claim 64, wherein the antibody comprises a human IgG1 constant region.

68. A method of producing an antibody that binds to sialyl(α2,6)N-acetylgalactosamine (STn), comprising culturing the host cell of claim 63 under conditions suitable for expressing the antibody.

69. The method of claim 68, further comprising isolating the antibody.

70. A method of producing an antibody that binds to sialyl(α2,6)N-acetylgalactosamine (STn), comprising culturing the host cell of claim 64 under conditions suitable for expressing the antibody.

71. The method of claim 70, further comprising isolating the antibody.

72. The antibody-drug conjugate of claim 31, further comprising a linker attaching the therapeutic agent to the antibody.

73. The antibody-drug conjugate of claim 34, further comprising a linker attaching the therapeutic agent to the antibody.

74. The antibody-drug conjugate of claim 35, further comprising a linker attaching the therapeutic agent to the antibody.

75. The antibody-drug conjugate of claim 38, further comprising a linker attaching the therapeutic agent to the antibody.

76. The antibody-drug conjugate of claim 72, wherein the linker is a cleavable linker.

77. The antibody-drug conjugate of claim 73, wherein the linker is a cleavable linker.

78. The antibody-drug conjugate of claim 74, wherein the linker is a cleavable linker.

79. The antibody-drug conjugate of claim 75, wherein the linker is a cleavable linker.

80. The method of claim 40, wherein the antibody-drug conjugate comprises a linker attaching the cytotoxic agent to the antibody.

81. The method of claim 42, wherein the antibody-drug conjugate comprises a linker attaching the cytotoxic agent to the antibody.

82. The method of claim 43, wherein the antibody-drug conjugate comprises a linker attaching the cytotoxic agent to the antibody.

83. The method of claim 45, wherein the antibody-drug conjugate comprises a linker attaching the cytotoxic agent to the antibody.

84. The method of claim 47, wherein the antibody-drug conjugate comprises a linker attaching the cytotoxic agent to the antibody.

85. The method of claim 80, wherein the linker is a cleavable linker.

86. The method of claim 81, wherein the linker is a cleavable linker.

87. The method of claim 82, wherein the linker is a cleavable linker.

88. The method of claim 83, wherein the linker is a cleavable linker.

89. The method of claim 84, wherein the linker is a cleavable linker.

90. The method of claim 82, wherein the cancer is endometrial cancer, gastric cancer, or colorectal cancer.

91. The method of claim 83, wherein the cancer is endometrial cancer, gastric cancer, or colorectal cancer.

92. The method of claim 87, wherein the cancer is endometrial cancer, gastric cancer, or colorectal cancer.

93. The method of claim 88, wherein the cancer is endometrial cancer, gastric cancer, or colorectal cancer.

* * * * *